US011207298B2

(12) United States Patent
Chrovian et al.

(10) Patent No.: US 11,207,298 B2
(45) Date of Patent: Dec. 28, 2021

(54) SUBSTITUTED 1H-IMIDAZO[4,5-B]PYRIDIN-2(3H)-ONES AND THEIR USE AS GLUN2B RECEPTOR MODULATORS

(71) Applicant: JANSSEN PHARMACEUTICA NV, Beerse (BE)

(72) Inventors: Christa C. Chrovian, La Jolla, CA (US); Michael A. Letavic, San Diego, CA (US); Jason C. Rech, Ann Arbor, MI (US); Dale A. Rudolph, San Diego, CA (US); Akinola Soyode-Johnson, San Diego, CA (US); Brice M. Stenne, La Jolla, CA (US); Jessica L. Wall, San Diego, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

(21) Appl. No.: 16/807,385

(22) Filed: Mar. 3, 2020

(65) Prior Publication Data
US 2021/0069155 A1    Mar. 11, 2021

Related U.S. Application Data

(63) Continuation of application No. 15/725,500, filed on Oct. 5, 2017, now Pat. No. 10,617,676.

(60) Provisional application No. 62/404,798, filed on Oct. 6, 2016.

(51) Int. Cl.
| | |
|---|---|
| *A61K 31/4188* | (2006.01) |
| *A61P 25/24* | (2006.01) |
| *A61K 31/12* | (2006.01) |
| *C07D 401/02* | (2006.01) |
| *C07D 205/02* | (2006.01) |
| *C07D 207/08* | (2006.01) |

(52) U.S. Cl.
CPC .......... *A61K 31/4188* (2013.01); *A61K 31/12* (2013.01); *A61P 25/24* (2018.01); *C07D 401/02* (2013.01); *C07D 205/02* (2013.01); *C07D 207/08* (2013.01)

(58) Field of Classification Search
None
See application file for complete search history.

(56) References Cited

U.S. PATENT DOCUMENTS

| | | |
|---|---|---|
| 7,622,486 B2 | 11/2009 | Pal et al. |
| 8,765,784 B2 | 7/2014 | Arrington et al. |
| 8,785,438 B2 | 7/2014 | Ohtsuka et al. |
| 8,877,772 B2 | 11/2014 | Gelbard et al. |
| 9,434,743 B2 | 9/2016 | Cheruvallath et al. |
| 9,963,447 B2 | 5/2018 | Chrovian et al. |
| 9,981,950 B2 | 5/2018 | Schindler et al. |
| 10,071,988 B2 | 9/2018 | Chen et al. |
| 10,155,727 B2 | 12/2018 | Schindler et al. |
| 10,233,173 B2 | 3/2019 | Chen et al. |
| 10,323,021 B2 | 6/2019 | Schindler et al. |
| 10,377,753 B2 | 8/2019 | Chrovian et al. |
| 10,617,676 B2 | 4/2020 | Chrovian et al. |
| 2007/0275965 A1 | 11/2007 | Thomas et al. |
| 2008/0300239 A1 | 12/2008 | Adams et al. |
| 2011/0130384 A1 | 6/2011 | Setoh et al. |
| 2014/0275011 A1 | 9/2014 | Mastracchio et al. |
| 2015/0210681 A1 | 7/2015 | Bourque et al. |
| 2016/0024087 A1 | 1/2016 | Gelbard et al. |
| 2018/0125826 A1 | 5/2018 | Chrovian et al. |
| 2019/0135791 A1 | 5/2019 | Chen et al. |
| 2019/0308950 A1 | 10/2019 | Ziff et al. |
| 2020/0392113 A1 | 12/2020 | Dvorak et al. |
| 2020/0392130 A1 | 12/2020 | Stenne et al. |
| 2020/0392154 A1 | 12/2020 | Stenne et al. |
| 2020/0392155 A1 | 12/2020 | Gelin et al. |
| 2021/0017168 A1 | 1/2021 | Soyode-Johnson et al. |
| 2021/0017169 A1 | 1/2021 | Stenne et al. |

FOREIGN PATENT DOCUMENTS

| | | |
|---|---|---|
| EP | 0 928 789 A1 | 7/1999 |
| EP | 2194045 A1 | 6/2010 |
| JP | 2012-188363 A | 4/2012 |
| KR | 2004-501901 A | 1/2004 |
| WO | 95/28400 | 10/1995 |
| WO | 2002/060877 A1 | 8/2002 |
| WO | 2003/082868 A1 | 10/2003 |
| WO | 2003/097637 A1 | 11/2003 |
| WO | 2003/101968 A1 | 12/2003 |
| WO | 2005/080379 A1 | 9/2005 |
| WO | 2008/145616 A1 | 12/2008 |
| WO | 2009/004430 A1 | 1/2009 |
| WO | 2009/058261 A1 | 5/2009 |
| WO | 2009/118187 A1 | 10/2009 |
| WO | 2009/157196 A1 | 12/2009 |
| WO | 2010/043396 A1 | 4/2010 |
| WO | 2010/108187 A1 | 9/2010 |
| WO | 2011/140202 A1 | 11/2011 |
| WO | 2013/060029 A1 | 5/2013 |
| WO | 2013130855 A1 | 9/2013 |
| WO | 2014124651 A1 | 8/2014 |
| WO | 2014145051 A1 | 9/2014 |
| WO | 2015/002754 A2 | 1/2015 |
| WO | 2015017502 A1 | 2/2015 |
| WO | 2016025917 A1 | 2/2016 |
| WO | 2016/081649 A1 | 5/2016 |
| WO | 2016/15097 A1 | 9/2016 |
| WO | 2018/231745 A1 | 12/2018 |
| WO | 110294756 A | 12/2018 |

(Continued)

OTHER PUBLICATIONS

International Search Report for International Application No. PCT/US2015/045412, dated Nov. 10, 2015.

(Continued)

*Primary Examiner* — Samantha L Shterengarts
(74) *Attorney, Agent, or Firm* — Biospark Intellectual Property Law

(57) ABSTRACT

Substituted 1H-imidazo[4,5-b]pyridin-2(3H)-ones as NR2B receptor ligands. Such compounds may be used in NR2B receptor modulation and in pharmaceutical compositions and methods for the treatment of disease states, disorders, and conditions mediated by NR2B receptor activity.

32 Claims, No Drawings

(56) References Cited

FOREIGN PATENT DOCUMENTS

| WO | 2020249785 A1 | 12/2020 |
|---|---|---|
| WO | 2020249791 A1 | 12/2020 |
| WO | 2020249792 A1 | 12/2020 |
| WO | 2020249796 A1 | 12/2020 |
| WO | 2020249799 A1 | 12/2020 |
| WO | 2020249802 A1 | 12/2020 |

OTHER PUBLICATIONS

International Search Report for International Application No. PCT/US2015/045413, dated Nov. 27, 2015.
International Search Report for International Application No. PCT/US2016/041339 dated Sep. 27, 2016.
International Search Report for International Application No. PCT/US2017/017093, dated Apr. 7, 2017.
International Search Report issued in connection with PCT/US2017/055278, dated Mar. 9, 2018.
PCT ISR PCT/US2017/017093, dated Mar. 20, 2017.
Addy, et al., Single-Dc3e Administration of MK-0657, an N112B-Selective NMDA Antagonist, Does Not Result in Clinically Meaningful Improvement in Motor Function in Patients 127ith Moderate II'arkinson's Disease, Journal of Clinical Pharmacology, 2009, pp. 856-864, vol. 49.
Andreas Straube., Pharmacology of vertigo/nystagmus/oscillopsia, Current Opinion in Neurology, 2005, pp. 11-14, vol. 18 Issue 1.
Arnold, et al., Glutamate receptor gene (GRIN2B) associated with reduced anterior cingulate glutamatergic concentration in pediatric obsessive-compulsive disorder, Psychiatry Research: Neuroimaging, Feb. 19, 2009, pp. 136-139, vol. 172 Issue 2.
Bagshawe, Kenneth D., 1995, "Antibody-Directed Enzyme prodrug Therapy : A Review," Drug Development Research, 34:220-230.
Berberich, et al., The role of NMDAR subtypes and charge transfer during hippocampal LTP induction, Neuropharmacology, 2007, pp. 77-86, vol. 52 Issue 1.
Berge, et al., Pharmaceutical Salts, Journal of Pharmaceutical Sciences, 1977, pp. 1-19, vol. 66, No. 1.
Berge, et al., Pharmaceutical Salts, Journal of Pharmaceutical Sciences, 1997, pp. 1-19, vol. 66, No. 1.
Bertolini, et al., A New Rational Hypothesis for the Pharmacophore of the Active Metabolite of Leflunomide, a Potent Immunosuppressive Drug, Journal of Medicinal Chemistry, Jan. 17, 1997, pp. 2011-2016, vol. 40 Issue 13.
Bodor, Nicholas, 1984, "Novel Approaches to the Design of Safer Drugs: Soft Drugs and Site-Specific Chemical Delivery Systems," Advances in Drug Research, 13:256-331.
Bullock, et al., An Open-Label Study of CP-101,606 in Subjects with a Severe Traumatic Head Injury or Spontaneous Intracerebral Hemorrhage, Annals New York Academy of Sciences, 1999, pp. 51-58, vol. 890.
Buonarati, et al., Role of sulfation and acetylation in the activation of 2-hydroxyamino-1-methyl-6-phenylimidazo[4,5-b]pyridine to intermediates which bind DNA, Mutation Research, Jun. 21, 1990, pp. 185-190, vol. 245.
Chattopadhyay, et al., Fused Tetrazoles as Azide Surrogates in Click Reaction: Efficient Synthesis of N-Heterocycle-Substituted 1,2,3-Triazoles, Organic Letters, Mar. 30, 2010, pp. 2166-2169, vol. 12 Issue 9.
Chemical Abstract Service (CAS), Database Registry [Online], Database Registry [Online], STN Sep. 18, 2012, pp. 1-1, Database Accession No. 1394745_67_5.
Cull-Candy, et al., NMDA receptor subunits: diversity, development and disease, Current Opinion in Neurobiology, 2001, pp. 327-335, vol. 11 Issue 3.
Dalmau, et al., Anti-NMDA-receptor encephalitis: case series and analysis of the effects of antibodies, Lancet Neurol, Dec. 2008, pp. 1091-1098, vol. 7 Issue 12.

Dorval, et al., Association of the glutamate receptor subunit gene GRIN2B with attention-deficit/hyperactivity disorder, Genes, Brain and Behavior, 2007, pp. 444-452, vol. 6 Issue 5.
Duty, Susan, 2012, "Targeting Glutamate Receptors to Tackle the Pathogenesis, Clinical Symptoms and Levodopa-Induced Dyskinesia Associated with Parkinson's Disease," CNS Drugs, 26(12):1017-1032.
Farjam, et al., Inhibition of NR2B-Containing N-methyl-D-Aspartate Receptors (NMDARs) in Experimental Autoimmune Encephalomyelitis, a Model of Multiple Sclerosis, Iranian Journal of Pharmaceutical Research, 2014, pp. 695-705, vol. 13 Issue 2.
Fleisher, et al., Improved oral drug delivery: solubility limitations overcome by the use of prodrugs, Advanced Drug Delivery Reviews, 1996, pp. 115-130, vol. 19.
Fuller, et al., Differential expression of the NMDA NR2B receptor subunit in motoneuron populations susceptible and resistant to amyotrophic lateral sclerosis, Neuroscience Letters, Jan. 26, 2006, pp. 157-161, vol. 399 Issue (1-2).
Glenn D. Considine, Van Nostrand's Encyclopedia of Chemistry Encyclopedia of Chemistry, 2005, pp. 261, Chapter 5.
Grasselli, et al., Abnormal NMDA receptor function exacerbates experimental autoimmune encephalomyelitis, British Journal of Pharmacology, 2013, pp. 502-517, vol. 168 Issue 2.
Grimwood, et al., NR2B-containing NMDA receptors are upregulated in temporal cortex in schizophrenia, NeuroReport, Feb. 25, 1999, pp. 461-465, vol. 10 Issue 3.
Guitton, et al., Blockade of Cochlear NMDA Receptors Prevents Long-Term Tinnitus during a Brief Consolidation Window after Acoustic Trauma, Neural Plasticity, Dec. 12, 2007, pp. 1-11, Article ID 80904.
Haller, et al., NR2B subunit-specific NMDA antagonist Ro25-6981 inhibits the expression of conditioned fear: a comparison with the NMDA antagonist MK-801 and fluoxetine, Behavioural Pharmacology, 2011, pp. 113-121, vol. 22 Issue 2.
Hanson, et al., Altered GluN2B NMDA receptor function and synaptic plasticity during early pathology in the PS2APP mouse model of Alzheimer's disease, Neurobiology of Disease, 2015, pp. 254-262, vol. 74.
Hu, et al., Expression of immediate-early genes in the dorsal cochlear nucleus in salicylate-induced tinnitus, Eur Arch Otorhinolaryngol, 2016, pp. 325-332, vol. 273 Issue 2.
Ito, et al., A Medium-term rat liver bioassay for rapid in vivo detection of carcinogenic potential of chemicals, Cancer Sci, 2003, pp. 3-8, vol. 94 Issue 1.
Jozsef Nagy, The NR2B Subtype of NMDA Receptor: A Potential Target for the Treatment of Alcohol Dependence, Current Drug Targets—CNS & Neurological Disorders, 2004, pp. 169-179, vol. 3 Issue 3.
Jun Wu, et al., Targeting the NMDA Receptor Subunit NR2B for the Treatment of Neuropathic Pain, Neurotherapeutics:, 2009, pp. 693-702, vol. 6 Issue 4.
Kolb, et al., Click Chemistry: Diverse Chemical Function from a Few Good Reactions, Angew. Chem. Int. Ed, 2001, pp. 2004-2021, vol. 40.
Kowal, et al., Human lupus autoantibodies against NMDA receptors mediate cognitive impairment, PNAS, Dec. 26, 2006, pp. 19854-19859, vol. 103 Issue 52.
Layton, et al., Discovery of 5-aryl-1,3-dihydro-2H-imidazo[4,5-b]pyridin-2-ones as positive allosteric modulators of metabotropic glutamate subtype-2(mGlu2) receptors with efficacy in a preclinical model of psychosis, Bioorganic & Medicinal Chemistry Letters, Feb. 15, 2016, pp. 1260-1264, vol. 26.
Leaderbrand, et al., Co-activation of NR2A and NR2B subunits induces resistance to fear extinction, Neurobiol Learn Mem, 2013, pp. 35-40, vol. 113.
Leaver, et al., Neuroprotective Effects of a Selective N-Methyl-d-Aspartate NR2B Receptor Antagonist in the 6-Hydroxydopamine Rat Model of Parkinson's Disease, Clinical and Experimental Pharmacology and Physiology, May 27, 2008, pp. 1388-1394, vol. 35 Issue 11.
Leyva, et al., Photochemistry of Fluorinated Aryl Azides in Toluene Solution and in Frozen Polycrystals, J. Org. Chem, May 8, 1989, pp. 5938-5945, vol. 54 Issue 25, American Chemical Society.

(56) References Cited

OTHER PUBLICATIONS

Li, et al., Enhanced Striatal NR2B-Containing N-Methyl-D-Aspartate Receptor-Mediated Synaptic Currents in a Mouse Model of Huntington Disease, J Neurophysiol, Jun. 3, 2004, pp. 2738-2746, vol. 92 Issue 5.
Li, et al., Glutamate N-methyl-D-aspartate Receptor Antagonists Rapidly Reverse Behavioral and Synaptic Deficits Caused by Chronic Stress Exposure, Biol Psychiatry, 2011, pp. 754-761, vol. 69 Issue 8.
Li, et al., Soluble Ab Oligomers Inhibit Long-Term Potentiation through a Mechanism Involving Excessive Activation of Extrasynaptic NR2B-Containing NMDA Receptors, The Journal of Neuroscience, May 4, 2011, pp. 6627-6638, vol. 31 Issue 18.
Lima-Ojeda, et al., Pharmacological blockade of GluN2B-containing NMDA receptors induces antidepressant-like effects lacking psychotomimetic action and neurotoxicity in the perinatal and adult rodent brain, Progress in Neuro-Psychopharmacology & Biological Psychiatry, Apr. 30, 2013, pp. 28-33, vol. 45.
Martucci, et al., N-methyl-d-aspartate receptor NR2B subunit gene GRIN2B in schizophrenia and bipolar disorder: Polymorphisms and mRNA levels, Schizophrenia Research, Mar. 20, 2006, pp. 214-221, vol. 84 Issue (2-3).
Massey, et al., Differential Roles of NR2A and NR2B-Containing NMDA Receptors in Cortical Long-Term Potentiation and Long-Term Depression, The Journal of Neuroscience, Sep. 8, 2004, pp. 7821-7828, vol. 24 Issue 36.
Miller, et al., GluN2B-containing NMDA receptors regulate depression-like behavior and are critical for the rapid antidepressant actions of ketamine, eLife, Oct. 23, 2014, pp. 1-22, vol. 3.
Morissette, et al., Prevention of Levodopa-Induced Dyskinesias by a Selective NR1A/2B N-Methyl-D-aspartate Receptor Antagonist in Parkinsonian Monkeys: Implication of Preproenkephalin, Movement Disorders, 2006, pp. 9-17, vol. 21 Issue 1.
Naskar, et al., Saving the Nerve from Glaucoma: Memantine to Caspaces, Seminars in Ophthalmology, Sep. 1999, pp. 152-158, vol. 14 Issue 3.
Naspolini, et al., Traxoprodil decreases pentylenetetrazol-induced seizures, Epilepsy Research, Jan. 24, 2012, pp. 12-19, vol. 100 Issue (1-2).
Nutt, et al., Effects of a NR2B Selective NMDA Glutamate Antagonist, CP-101,606, on Dyskinesia and Parkinsonism, Movement Disorders, Aug. 29, 2008, pp. 1860-1866, vol. 23 Issue 13.
Orgogozo, et al., Efficacy and Safety of Memantine in Patients With Mild to Moderate Vascular Dementia a Randomized, Placebo-Controlled Trial (MMM 300), Stroke, 2002, pp. 1834-1839, vol. 33.
Paoletti, et al., NMDA receptor subunit diversity: impact on receptor properties, synaptic plasticity and disease, Nature Reviews | Neuroscience, 2013, pp. 383-400, vol. 14 Issue 6.
Paulekuhn, et al., Trends in Active Pharmaceutical Ingredient Salt Selection based on Analysis of the Orange Book Database, Journal of Medicinal Chemistry, Aug. 20, 2007, pp. 6665-6672, vol. 50 Issue 26.
Peeters, et al., Effects of Pan- and Subtype-Selective N-Methyl-D-aspartate Receptor Antagonists on Cortical Spreading Depression in the Rat: Therapeutic Potential for Migraine, The Journal of Pharmacology and Experimental Therapeutics, Jan. 24, 2007, pp. 564-572, vol. 321 Issue 2.
Porsolt, et al., Behavioural Despair in Mice: A Primary Screening Test for Antidepressants, Arch int Pharmacodyn, 1977, pp. 327-336, vol. 229.
Preskorn, et al., An Innovative Design to Establish Proof of Concept of the Antidepressant Effects of the NR2B Subunit Selective N-Methyl-D-Aspartate Antagonist, CP-101,606, in Patients With Treatment-Refractory Major Depressive Disorder, Journal of Clinical Psychopharmacology, Dec. 2008, pp. 631-637, vol. 28 Issue 6.
Remington, Remington Pharmaceutical Sciences., Pharmaceutical Sciences., 1985, pp. 1418, vol. 76.
Robinson, et al., Discovery of the Hemifumarate and (r-L-Alanyloxy)methyl Ether as Prodrugs of an Antirheumatic Oxindole: Prodrugs for the Enolic OH Group, Journal of Medicinal Chemistry, 1996, pp. 10-18, vol. 39 Issue 1.
Shan, et al., Prodrug Strategies Based on Intramolecular Cyclization Reactions, Journal of Pharmaceutical Sciences, Jul. 1977, pp. 765-767, vol. 86 Issue 7.
Shen, et al., Heroin relapse requires long-term potentiation-like plasticity mediated by NMDA2b-containing receptors, PNAS, Nov. 29, 2011, pp. 19407-19412, vol. 108 Issue 48.
Starck, et al., Drug therapy for acquired pendular nystagmus in multiple sclerosis, J Neurol, 1997, pp. 9-16, vol. 244 Issue 1.
Steece-Collier, et al., Antiparkinsonian Actions of CP-101,606, an Antagonist of NR2B Subunit-Containing N-Methyl-D-Aspartate Receptors, Experimental Neurology, Feb. 4, 2000, pp. 239-243, vol. 163 Issue 1.
STN Registry database entry for CAS RN 1394745-67-5, entered STN Sep. 18, 2012, Accessed Sep. 8, 2017.
STN Registry database entry for CAS RN 1493474-46-6, 1491341-24-2, 1479235-62-5, and 1477636-42-2, Accessed Apr. 10, 2019.
Tang, et al., 2005, "Disturbed Ca2+ signaling and apoptosis of medium spiny neurons in Huntington's disease," PNAS, 102(7):2602-2607.
Tang, et al., Genetic enchancement of learning and memory in mice, Nature, Sep. 2, 1999, pp. 63-69, vol. 401 Issue 6748.
Traynelis, et al., Glutamate Receptor Ion Channels: Structure, Regulation, and Function, Pharmacol Rev, 2010, pp. 405-496, vol. 62 Issue 3.
Wang, et al., Targeting the NMDA receptor subunit NR2B for treating or preventing age-related memory decline, Expert Opin. Ther. Targets, 2014, pp. 1121-1130, vol. 18 Issue 10.
Watanabe, et al., Distinct Distributions of Five N-Methyl-D-Aspartate Receptor Channel Subunit mRNAs in the Forebrain, The Journal of Comparative Neurology, Jul. 30, 1993, pp. 377-390, vol. 338 Issue 3.
Weickert, et al., Molecular evidence of N-methyl-D-aspartate receptor hypofunction in schizophrenia, Molecular Psychiatry, 2013, pp. 1185-1192, vol. 18.
Won, et al., Autistic-like social behaviour in Shank2-mutant mice improved by restoringNMDA receptor function, Nature, Jun. 14, 2012, pp. 261-265, vol. 486.
Yang, et al., Reduced brain infarct volume and improved neurological outcome by inhibition of the NR2B subunit of NMDA receptors by using CP101,606-27 alone and in combination with rt-PA in a thromboembolic stroke model in rats, J. Neurosurg, Feb. 2003, pp. 397-403, vol. 98 Issue 2.
Yuan, et al., Context-Dependent GluN2B-Selective Inhibitors of NMDA Receptor Function Are Neuroprotective with Minimal Side Effects, Neuron, Mar. 18, 2015, pp. 1305-1318, vol. 85 Issue 6.
Zarate, et al., A Randomized Trail of an N-methyl_D-aspartate Antagonist in Treatment-Resistant Major Depression, Arch Gen Psychiatry, 2006, pp. 856-864, vol. 63.
International Search Report for International Application No. PCT/IB2019/052731, dated Nov. 1, 2019.
Written Opinion of the International Searching Authority for International Application No. PCT/IB2019/052731, dated Nov. 1, 2019.
Kamalesh B. Ruppa, et al., Chapter 7: NMDA Antagonists of GluN2b Subtype and Modulators of GluN2A, GluN2C, and GluN2d Subtypes-Recent Results and Developments, Annual Reports in Medicinal Chemistry, Jan. 1, 2012, pp. 89-103, vol. 47.
Park et al., 2001, "Metabolism of Fluorine-containing drugs" Annu. Rev. Pharmacol. Toxicol, 41: 443-470.
Pubchem-CID-90046926, Create Date: Feb. 13, 2015, entire document.
International Search Report for International Application No. PCT/EP2020/066400, dated Jul. 28, 2020.
International Search Report for International Application No. PCT/EP2020/066384, dated Jul. 28, 2020.
International Search Report for International Application No. PCT/EP2020/066396, dated Jul. 29, 2020.
International Search Report for International Application No. PCT/EP2020/066391, dated Jul. 29, 2020.

(56) References Cited

OTHER PUBLICATIONS

International Search Report for International Application No. PCT/EP2020/066405, dated Jul. 29, 2020.
International Search Report for International Application No. PCT/EP2020/066392, dated Sep. 21, 2020.
First Examination Report dated Nov. 30, 2020 in connection with European application No. 17859165.7.
Chrovian, et al., "1H-Pyrrolo[3,2-b]pyridine GluN2B-Selective Negative Allosteric Modulators", ACS Med. Chem. Lett, 2019, vol. 10, pp. 261-266.
Collingridge, et al., "A nomenclature for ligand-gated ion channels" Neuropharmacology, 2009, vol. 56, pp. 2-5.
Houston, et al., "Methods for Predicting In Vivo Pharmacokinetics Using Data from In Vitro Assays" Current Drug Metabolism, 2008, vol. 9, pp. 940-951.
Iadarola et al., 2015, Therapeutic Advances in Chronic Disease, vol. 6 (3), p. 97-114.
Machado-Vieira et al., 2017 "New Targets for Rapid Antidepressant Action" Prog. Neurobiol. 152-21-37.
Youssif, S. "Recent trends in the chemistry of pyridine N-oxides" ARKIVOC, 2001, pp. 242-268.
Sun et al., 2020, "Synthesis and preliminary evaluation of novel C-labled GluN2B-selective NMDA receptor negative allosteric modulators" Acta Pharmacologica Sinica, 0:1-8.
Mao et al. 2014 "Phosphorylation and regulation of glutamate receptors by CaMKII" Acta Physiologica Sinica, 66(3): 365-372.
Communication pursuant to Article 94(3) EPC dated Sep. 13, 2021 in connection with EP application No. 17 859 167.7.
Davies et al., 2012 "A novel series of benzimidazole NR2B-selective NDMA receptor antagonists," Bioorganic & Medicinal Chemistry Letters 22:2620-2623.

SUBSTITUTED 1H-IMIDAZO[4,5-B]PYRIDIN-2(3H)-ONES AND THEIR USE AS GLUN2B RECEPTOR MODULATORS

CROSS-REFERENCE TO RELATED APPLICATIONS

This application is a continuation of U.S. application Ser. No. 15/725,500, filed Oct. 5, 2017, the contents of which are incorporated herein in their entireties by reference thereto, which claims the benefit of U.S. provisional application No. 62/404,798, filed Oct. 6, 2016.

FIELD OF THE INVENTION

The present invention is related to compounds having NR2B modulating properties, pharmaceutical compositions comprising these compounds, chemical processes for preparing these compounds and their use in the treatment of diseases associated with NR2B receptor activity in animals, in particular humans.

BACKGROUND OF THE INVENTION

Glutamate is one of the major excitatory neurotransmitters that is widely spread in the brain. First indication of its role as an excitatory messenger was in the 1950's when it was observed that intravenous administration of glutamate induces convulsions. However, the detection of the whole glutamatergic neurotransmitter system with its various receptors did not take place before the 1970's and 1980's when numerous antagonists were developed or, as in the case of PCP and ketamine, were identified as antagonists. Finally, in the 1990's molecular biology provided the tools for the classification of the glutamatergic receptors.

N-methyl-D-aspartate (NMDA) receptors are a subtype of ionotropic glutamate receptors that mediate excitatory synaptic transmission in the brain. NMDA receptors are ubiquitously distributed throughout the brain and play a key role in synaptic plasticity, synaptogenesis, excitotoxicity, memory acquisition and learning. NMDA receptors are distinct from other major subtypes of ionotropic glutamate receptors (AMPA and kainate receptors) in that they are blocked by $Mg^{2+}$ at resting membrane potentials, are highly $Ca^{2+}$ permeable, and require co-activation by two distinct neurotransmitters: glutamate and glycine (or D-serine) (Traynelis S F et al., *Pharmacol Rev.* 2010; 62(3):405-96). The influx of $Ca^{2+}$ through NMDA receptors triggers signaling cascades and regulates gene expression that is critical for different forms of synaptic plasticity including both long-term potentiation of synapse efficacy (LTP) (Berberich S et al., *Neuropharmacology* 2007; 52(1):77-86) and long-term depression (LTD) (Massey, P V et al., *J Neurosci.* 2004 Sep. 8; 24(36):7821-8).

The vast majority of the mammalian NMDA receptors form a heterotetramer made of two obligatory GluN1 units and two variable GluN2 receptor subunits encoded by the GRIN1 gene and one of four GRIN2 genes, respectively. One or both GluN2 subunits can be potentially replaced by a GluN3A or a GluN3B subunit. The GRIN1 gene product has 8 splice variants while there are 4 different GRIN2 genes (GRIN2A-D) encoding four distinct GluN2 subunits. The glycine binding site is present on the GluN1 subunit and the glutamate binding site is present on the GluN2 subunit.

The GluNR2 subunits play a dominant role in determining the functional and pharmacological properties of the NMDA receptor assembly and exhibit distinct distribution in different areas of the brain. For instance, GluN2B subunits are expressed primarily in the forebrain in the adult mammalian brain (Paoletti P et al., *Nat Rev Neurosci.* 2013; 14(6):383-400; Watanabe M et al., *J Comp Neurol.* 1993; 338(3):377-90) and are implicated in learning, memory processing, mood, attention, emotion and pain perception (Cull-Candy S et al., *Curr Opin Neurobiol.* 2001; 11(3):327-35).

Compounds that modulate GluN2B-containing NMDA receptor function can be useful in treatment of many neurological and psychiatric disorders including but not limited to bipolar disorder (Martucci L et al., *Schizophrenia Res,* 2006; 84(2-3):214-21), major depressive disorder (Miller O H et al., *eLife.* 2014; 3:e03581; Li N et al., *Biol Psychiatry.* 2011; 69(8):754-61), treatment-resistant depression (Preskorn S H et al. *J Clin Psychopharmacol.* 2008; 28(6): 631-7) and their mood disorders (including schizophrenia (Grimwood S et al., *Neuroreport.* 1999; 10(3):461-5; Weickert C S et al. *Molecular Psychiatry* (2013) 18, 1185-1192), ante- and postpartum depression, seasonal affective disorder and the like), Alzheimer's disease (Hanson J E et al., *Neurobiol Dis.* 2015; 74:254-62; Li S et al., *J Neurosci.* 2011; 31(18):6627-38) and other dementias (Orgogozo J M et al. *Stroke* 2002, 33: 1834-1839), Parkinson's disease (Duty S, *CNS Drugs.* 2012; 26(12):1017-32; Steece-Collier K et al., *Exp Neurol.* 2000; 163(1):239-43; Leaver K R et al. *Clin Exp Pharmacol Physiol.* 2008; 35(11): 1388-94), Huntington's chorea (Tang T S et al., *Proc Natl Acad Sci USA.* 2005; 102(7):2602-7; Li L et al., *J Neurophysiol.* 2004; 92(5):2738-46), multiple sclerosis (Grasselli G et al., *Br J Pharmacol.* 2013; 168(2):502-17; Farjam M et al., *Iran J Pharm Res.* 2014; 13(2):695-705), cognitive impairment (Wang D et al. 2014, *Expert Opin Ther Targets Expert Opin Ther Targets.* 2014; 18(10):1121-30), head injury (Bullock M R et al., *Ann NY Acad Sci.* 1999; 890:51-8), spinal cord injury, stroke (Yang Y et al., *J Neurosurg.* 2003; 98(2):397-403), epilepsy (Naspolini A P et al., *Epilepsy Res.* 2012 June; 100(1-2):12-9), movement disorders (e.g. dyskinesias) (Morissette M et al., *Mov Disord.* 2006; 21(1):9-17), various neurodegenerative diseases (e.g. amyotrophic lateral sclerosis (Fuller P I et al., *Neurosci Lett.* 2006; 399(1-2):157-61) or neurodegeneration associated with bacterial or chronic infections), glaucoma (Naskar R et al. *Semin Ophthalmol.* 1999 September; 14(3):152-8), pain (e.g. chronic, cancer, post-operative and neuropathic pain (Wu L J and Zhuo M, *Neurotherapeutics.* 2009; 6(4):693-702), diabetic neuropathy, migraine (Peeters M et al., *J Pharmacol Exp Ther.* 2007; 321(2):564-72), cerebral ischemia (Yuan H et al., *Neuron.* 2015; 85(6):1305-18), encephalitis (Dalmau J. et al., *Lancet Neurol.* 2008; 7(12):1091-8.), autism and autism spectrum disorders (Won H. et al., *Nature.* 2012; 486(7402):261-5), memory and learning disorders (Tang, Y. P. et al., *Nature.* 1999; 401(6748):63-9), obsessive compulsive disorder (Arnold P D et al., *Psychiatry Res.* 2009; 172(2):136-9.), attention deficit hyperactivity disorder (ADHD) (Dorval K M et al., *Genes Brain Behav.* 2007; 6(5):444-52), PTSD (Haller J et al. *Behav Pharmacol.* 2011; 22(2):113-21; Leaderbrand K et al. *Neurobiol Learn Mem.* 2014; 113:35-40), tinnitus (Guitton M J, and Dudai Y, *Neural Plast.* 2007; 80904; Hu S S et al. 2016; 273(2): 325-332), sleep disorders (like narcolepsy or excessive daytime sleepiness, patent WO 2009058261 A1), vertigo and nystagmus (Straube A. et al., *Curr Opin Neurol.* 2005; 18(1): 11-4; Starck M et al. *J Neurol.* 1997 January; 244(1):9-16), anxiety autoimmunological disorders like neuropsychiatric systemic lupus erythematosus (Kowal C et al. *Proc. Natl. Acad. Sci. U.S.A.* 2006; 103, 19854-19859) and addictive illnesses (e.g. alcohol addiction, drug addiction) (Nagy J, 2004, *Curr Drug Targets CNS Neurol Disord.* 2004; 3(3):169-79; Shen H et al., *Proc Natl Acad Sci USA.* 2011; 108(48):19407-12).

In view of the clinical importance of NR2B, the identification of compounds that modulate NR2B receptor function represents an attractive avenue into the development of new therapeutic agents. Such compounds are provided herein.

SUMMARY OF THE INVENTION

The invention is directed to the general and preferred embodiments defined, respectively, by the independent and dependent claims appended hereto, which are incorporated by reference herein. One aspect of this invention concerns compounds of Formula (I):

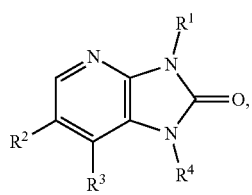

(I)

wherein
$R^1$ is H; $CH_2F$; or $CH_3$; $R^2$ is selected from the group consisting of: phenyl; phenyl substituted with one, two, or three members each independently selected from the group consisting of: halo, $C_{1-6}$alkyl, $C_{1-6}$haloalkyl, CN, $OC_{1-6}$alkyl, $OC_{1-6}$haloalkyl, $N(CH_3)_2$, and cyclopropyl; pyridinyl; pyridinyl substituted with F, $C_{1-4}$alkyl, or $C_{1-4}$haloalkyl; thiazolyl; thiazolyl substituted with $C_{1-6}$alkyl or $C_{1-6}$haloalkyl; thienyl; and thienyl substituted with one or two members each independently selected from the group consisting of: halo, $C_{1-6}$alkyl, $C_{1-6}$haloalkyl, $CH_2OH$, $CH_2OCH_3$, and cyclopropyl;

$R^3$ is H;

$R^4$ is selected from the group consisting of:
(a)

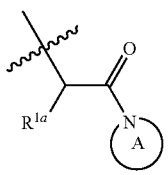

wherein ring A is a 4-6 membered heterocycle optionally containing an additional oxygen heteroatom selected from the group consisting of: azetidinyl; azetidinyl substituted with one or two members independently selected from the group consisting of: F, OH, $C_{1-4}$alkyl, $C_{1-4}$haloalkyl, $CH_2OCH_3$, CN, and $OCH_3$; pyrrolidinyl; pyrrolidinyl substituted two F members; morpholinyl; piperidinyl; piperazinyl substituted with $C_{1-6}$alkyl; and (2,6-diazaspiro[3.3]heptan-6-yl);

(b)

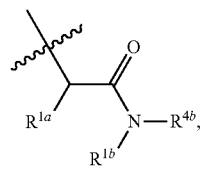

wherein $R^{4b}$ is selected from the group consisting of: H; $C_{1-6}$alkyl; $CH_2CH_2OCH_3$; $C_{3-6}$cycloalkyl; $C_{3-6}$cycloalkyl substituted with two or three members independently selected from the group consisting of F or $CH_3$; oxetanyl; oxetanyl substituted with $CH_3$; and pyridinyl;

(c)

wherein $R^{4c}$ is selected from the group consisting of: cyclopropyl; cyclopropyl substituted with one or two F members; CH(OH)cyclopropyl; azetidinyl; $CH_2$-azetidinyl; $CH_2$-azetidinyl substituted with one or two members independently selected from: F, OH, $OCH_3$, and $CF_3$; oxetanyl; oxetanyl substituted with F or $CH_3$; tetrahydrofuranyl; tetrahydropyranyl; $CH_2$pyrrolidinyl; $CH_2$pyrrolidinyl substituted with $CH_3$, OH, or $OCH_3$; $CH_2$piperidinyl; $CH_2$piperidinyl substituted with OH, or F; morpholinyl; pyrazolyl substituted with one or two $CH_3$ members; triazolyl substituted with $CH_3$; tetrazolyl; isoxazolyl substituted with one or two $CH_3$ members; oxadiazolyl substituted with $CH_3$, or $CH_2OCH_3$; thiadiazolyl; pyridinyl; pyridinyl substituted with one or two members independently selected from the group consisting of: Cl, F, $CH_3$, $OCH_3$, and $CF_3$; (2-oxo-1H-pyridin-3-yl); 6-oxo-1H-pyridin-3-yl; pyrimidinyl; pyrimidinyl substituted with F or $CH_3$; pyrazinyl; pyridazinyl; pyridazinyl substituted with $OCH_3$; phenyl; phenyl substituted with one or two members independently selected from the group consisting of: halo, CN, $OCH_3$, $C_{1-6}$alkyl, and $CF_3$;

(d)

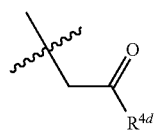

wherein $R^{4d}$ is selected from the group consisting of: OH, $C_{1-6}$alkyl, O—$C_{1-6}$alkyl, $C_{3-6}$cycloalkyl, thienyl, and thiazolyl; and (e) $C_{2-6}$alkyl substituted with one or two members independently selected from OH, $OC_{1-6}$alkyl, or cyclopropyl; $CH_2CH_2NH(C_{1-6}$alkyl); $CH_2CH_2NH$ ($CH_2CH_2OH$); $CH_2CH_2NH(C_{3-6}$cycloalkyl); and difluoro(3-pyridyl)methyl; and $R^{1a}$ and $R^{1b}$ are each independently H or $CH_3$;

and pharmaceutically acceptable salts, stereoisomers, isotopic variants, N-oxides, or solvates of compounds of Formula (I).

Further embodiments are provided by pharmaceutically acceptable salts of compounds of Formulas (I), pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula (I), as well as the pharmaceutically acceptable salts.

In a further aspect, the invention relates to pharmaceutical compositions for treating a disease, disorder, or medical condition mediated by NR2B receptor activity, comprising an effective amount of at least one compound selected from compounds of Formula (I), pharmaceutically acceptable salts of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as NR2B receptor modulators. Thus, the invention is directed to a method for modulating NR2B receptor activity, including when such receptor is in a subject, comprising exposing NR2B receptor to an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by NR2B receptor activity, comprising administering to the subject in need of such treatment an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the method of studying isotopically labeled compounds in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. For example, an $^{18}F$ or $^{11}C$ labeled compound may be particularly preferred for PET or SPECT studies.

Additional embodiments of this invention include methods of making compounds of Formula (I), pharmaceutically acceptable salts of compounds of Formula (I), pharmaceutically acceptable prodrugs of compounds of Formula (I), and pharmaceutically active metabolites of compounds of Formula (I).

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION OF INVENTION

In one aspect, provided herein are compounds of Formula (I), and pharmaceutically acceptable salts, stereoisomers, isotopic variants, N-oxides, or solvates thereof,

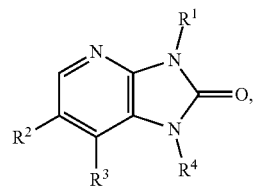

wherein
$R^1$ is H; $CH_2F$; or $CH_3$;
$R^2$ is selected from the group consisting of: phenyl; phenyl substituted with one, two, or three members each independently selected from the group consisting of: halo, $C_{1-6}$alkyl, $C_{1-6}$haloalkyl, CN, $OC_{1-6}$alkyl, $OC_{1-6}$haloalkyl, $N(CH_3)_2$, and cyclopropyl; pyridinyl; pyridinyl substituted with F, $C_{1-4}$alkyl, or $C_{1-4}$haloalkyl; thiazolyl; thiazolyl substituted with $C_{1-6}$alkyl or $C_{1-6}$haloalkyl; thienyl; and thienyl substituted with one or two members each independently selected from the group consisting of: halo, $C_{1-6}$alkyl, $C_{1-6}$haloalkyl, $CH_2OH$, $CH_2OCH_3$, and cyclopropyl;
$R^3$ is H;
$R^4$ is selected from the group consisting of:
(a)

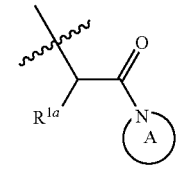

wherein ring A is a 4-6 membered heterocycle optionally containing an additional oxygen heteroatom selected from the group consisting of: azetidinyl; azetidinyl substituted with one or two members independently selected from the group consisting of: F, OH, $C_{1-4}$alkyl, $C_{1-4}$haloalkyl, $CH_2OCH_3$, CN, and $OCH_3$; pyrrolidinyl; pyrrolidinyl substituted two F members; morpholinyl; piperidinyl; piperazinyl substituted with $C_{1-6}$alkyl; and (2,6-diazaspiro[3.3]heptan-6-yl);
(b)

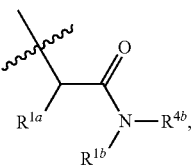

where $R^{4b}$ is selected from the group consisting of: H; $C_{1-6}$alkyl; $CH_2CH_2OCH_3$; $C_{3-6}$cycloalkyl; $C_{3-6}$cycloalkyl substituted with two or three members independently selected from the group consisting of F or $CH_3$; oxetanyl; oxetanyl substituted with $CH_3$; and pyridinyl;
(c)

wherein $R^{4c}$ is selected from the group consisting of: cyclopropyl; cyclopropyl substituted with one or two F members; CH(OH)cyclopropyl; azetidinyl; $CH_2$-azetidinyl; $CH_2$-azetidinyl substituted with one or two members independently selected from: F, OH, $OCH_3$, and $CF_3$; oxetanyl; oxetanyl substituted with F or $CH_3$; tetrahydrofuranyl; tetrahydropyranyl; $CH_2$pyrrolidinyl; $CH_2$pyrrolidinyl substituted with $CH_3$, OH, or $OCH_3$; $CH_2$piperidinyl; $CH_2$piperidinyl substituted with OH, or F; morpholinyl; pyrazolyl substituted with one or two $CH_3$ members; triazolyl substituted with $CH_3$; tetrazolyl; isoxazolyl substituted with one or two $CH_3$ members; oxadiazolyl substituted with $CH_3$, or $CH_2OCH_3$; thiadiazolyl; pyridinyl; pyridinyl substituted with one or two members independently selected from the group consisting of: Cl, F, $CH_3$, $OCH_3$, and $CF_3$; (2-oxo-1H-pyridin-3-yl); 6-oxo-1H-pyridin-3-yl; pyrimidinyl; pyrimidinyl substituted with F or $CH_3$; pyrazinyl; pyridazinyl; pyridazinyl substituted with $OCH_3$; phenyl; phenyl substituted with one or two members independently selected from the group consisting of: halo, CN, $OCH_3$, $C_{1-6}$alkyl, and $CF_3$;

(d)

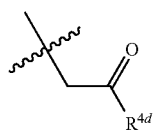

wherein $R^{4d}$ is selected from the group consisting of: OH, $C_{1-6}$alkyl, O—$C_{1-6}$alkyl, $C_{3-6}$cycloalkyl, thienyl, and thiazolyl; and (e) $C_{2-6}$alkyl substituted with one or two members independently selected from OH, $OC_{1-6}$alkyl, or cyclopropyl; $CH_2CH_2NH(C_{1-6}$alkyl); $CH_2CH_2NH(CH_2CH_2OH)$; $CH_2CH_2NH(C_{3-6}$cycloalkyl); and difluoro(3-pyridyl)methyl and $R^{1a}$ and $R^{1b}$ are each independently H or $CH_3$.

An additional embodiment of the invention is a compound of Formula (I) wherein $R^1$ is H.

An additional embodiment of the invention is a compound of Formula (I) wherein $R^1$ is $CH_3$.

An additional embodiment of the invention is a compound of Formula (I) wherein $R^{1a}$ is H.

An additional embodiment of the invention is a compound of Formula (I) wherein $R^2$ is phenyl; phenyl substituted with one, two, or three members each independently selected from the group consisting of: Cl, F, $C_{1-6}$alkyl, $C_{1-6}$haloalkyl, CN, $OC_{1-6}$alkyl, $OC_{1-6}$haloalkyl, $N(CH_3)_2$, and cyclopropyl; pyridinyl; or pyridinyl substituted with $CF_3$.

An additional embodiment of the invention is a compound of Formula (I) wherein $R^2$ is thiazolyl substituted with $C_{1-6}$alkyl or $CF_3$; thienyl; or thienyl substituted with one or two members each independently selected from the group consisting of: Cl, F, $C_{1-6}$alkyl, $C_{1-6}$haloalkyl, $CH_2OH$, $CH_2OCD_3$, and cyclopropyl.

An additional embodiment of the invention is a compound of Formula (I) wherein $R^1$ is H or $CH_3$, $R^2$ is phenyl, wherein the phenyl is optionally substituted with one, two or three members independently selected from: halo, $C_{1-6}$alkyl, and $C_{1-6}$haloalkyl; or thienyl, wherein the thienyl is optionally substituted with one or two members independently selected from: halo, $C_{1-6}$alkyl, and $C_{1-6}$haloalkyl; $R^3$ is H, and $R^4$ is

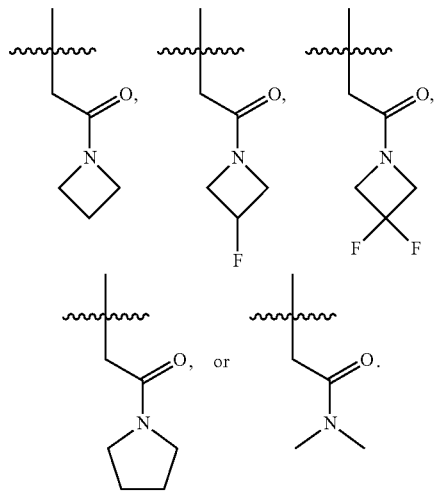

An additional embodiment of the invention is a compound of Formula (I) wherein $R^2$ is phenyl; o-tolyl; m-tolyl; p-tolyl; 4-tert-butylphenyl; 3-(trifluoromethyl)phenyl; 4-fluorophenyl; 3-fluorophenyl; 3-cyanophenyl; 3-chlorophenyl; 4-chlorophenyl; 3-(difluoromethyl)phenyl; 3-methoxyphenyl; 3-(difluoromethoxy)phenyl; 4-methoxyphenyl; 3-(trifluoromethoxy)phenyl; 2-ethoxyphenyl; 3-ethoxyphenyl; 3-cyclopropylphenyl; 3-(dimethylamino)phenyl; 2,3-dichlorophenyl; 2,3-difluorophenyl; 2,3-dimethylphenyl; 2-fluoro-3-(trifluoromethyl)phenyl; 2,4-dimethoxyphenyl; 2,3-dimethoxyphenyl; 2,4-difluorophenyl; 3,4-difluorophenyl; 3,4-dichlorophenyl; 3-(difluoromethyl)-4-fluoro-phenyl; 5-(difluoromethyl)-2-fluorophenyl; 2,6-dimethylphenyl; 3,5-dimethylphenyl; 3,5-difluorophenyl; 3-fluoro-5-(trifluoromethyl)phenyl; 2-methyl-5-(trifluoromethyl)phenyl; 2-methyl-3-(trifluoromethyl)phenyl; 4-chloro-3-methyl-phenyl; 4-fluoro-3-(trifluoromethyl)phenyl; 4-chloro-3-(trifluoromethyl)phenyl; 2-ethoxy-5-fluoro-phenyl; 3-chloro-2-fluoro-phenyl; 3-chloro-4-fluoro-phenyl; 2-chloro-4-methoxy-phenyl; 4-fluoro-2-methyl-phenyl; 4-fluoro-2-methoxy-phenyl; 2-fluoro-6-methoxy-phenyl; 3-fluoro-4-methoxy-phenyl; 3-fluoro-5-methyl-phenyl; 2-fluoro-3-methyl-phenyl; 4-fluoro-3-methyl-phenyl; 4-methoxy-3-methyl-phenyl; 4-fluoro-2,3-dimethyl-phenyl; 2,4-difluoro-3-methyl-phenyl; 2,3,4-trifluorophenyl; 3,4,5-trifluorophenyl; 3,4-difluoro-5-(trifluoromethyl)phenyl; 3-pyridyl; 2-(trifluoromethyl)-4-pyridyl; 2-thienyl; 5-methyl-2-thienyl; 5-ethyl-2-thienyl; 4-methyl-2-thienyl; 5-(trideuteriomethoxymethyl; 5-(hydroxymethyl)-2-thienyl; 5-fluoro-2-thienyl; 5-chloro-2-thienyl; 5-cyclopropyl-2-thienyl; 5-chloro-4-methyl-2-thienyl; 5-(difluoromethyl)-2-thienyl; 5-(difluoromethyl)-3-thienyl; 5-(trifluoromethyl)-2-thienyl; 5-(trifluoromethyl)-3-thienyl; 2-(trifluoromethyl)-3-thienyl; 4-(difluoromethyl)-2-thienyl; 5-(1,1,2,2,2-pentafluoroethyl)-2-thienyl; 4-methylthiazol-2-yl; 2-methylthiazol-5-yl; 2-(trifluoromethyl)thiazol-5-yl; or 2-(trifluoromethyl)thiazol-4-yl.

An additional embodiment of the invention is a compound of Formula (I) wherein $R^3$ is H.

An additional embodiment of the invention is a compound of Formula (I) wherein $R^3$ is D or T.

An additional embodiment of the invention is a compound of Formula (I) wherein $R^4$ is

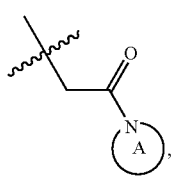
wherein ring A is
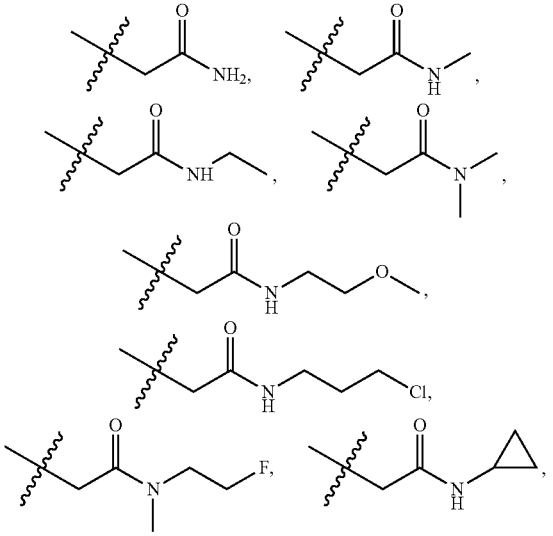
or
An additional embodiment of the invention is a compound of Formula (I) wherein R⁴ is
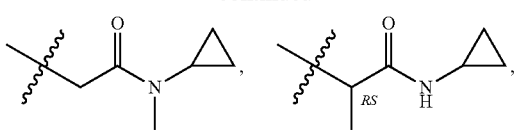
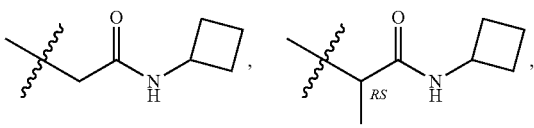
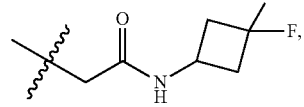
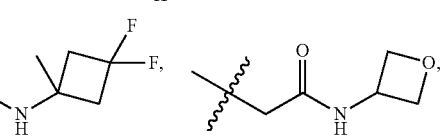
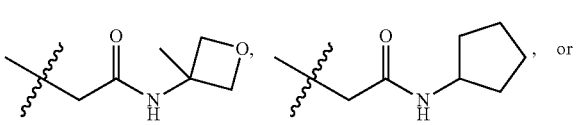
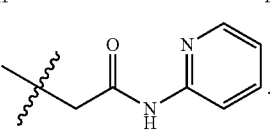
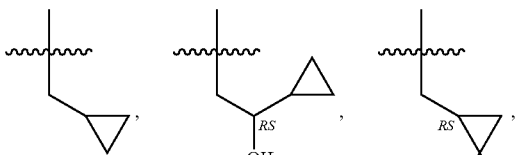
An additional embodiment of the invention is a compound of Formula (I) wherein R⁴ is
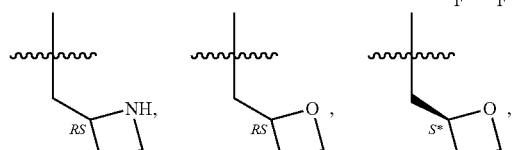
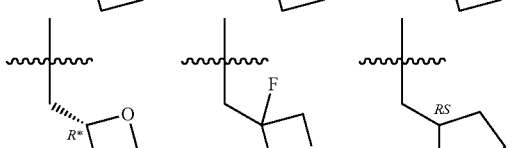
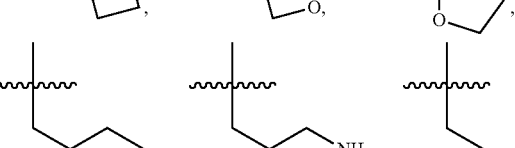
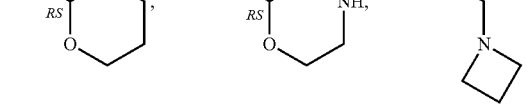

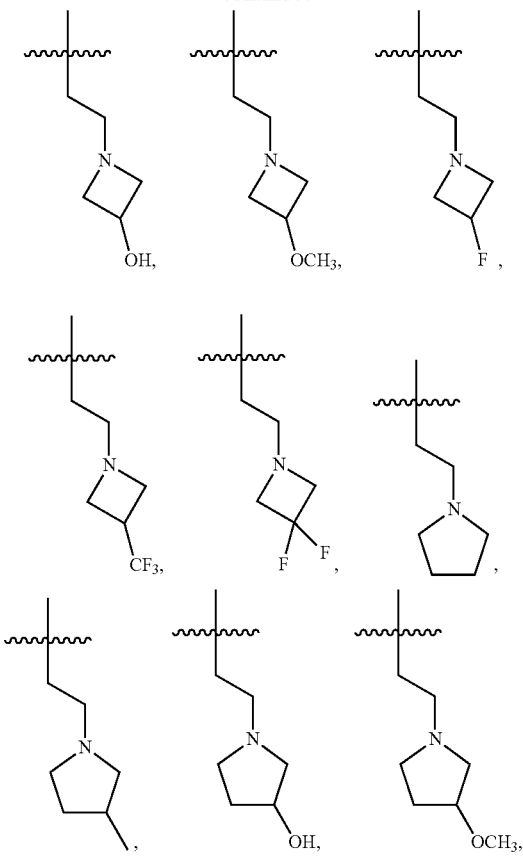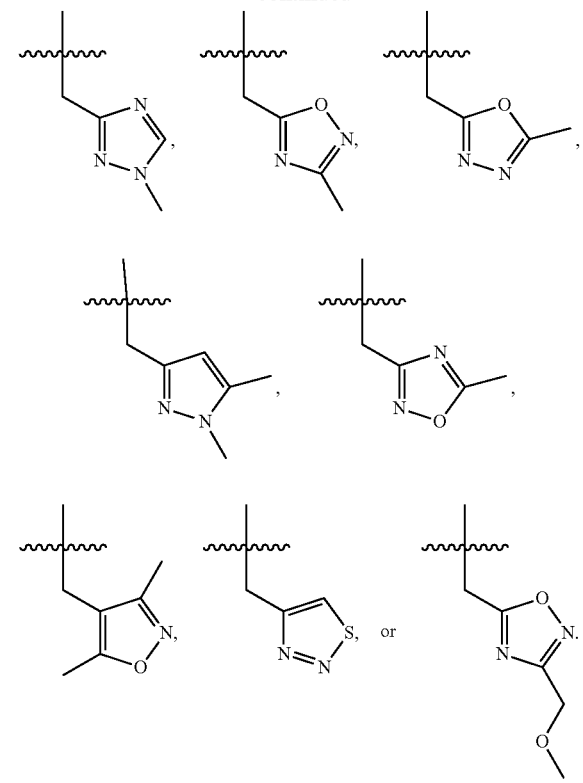
An additional embodiment of the invention is a compound of Formula (I) wherein R⁴ is
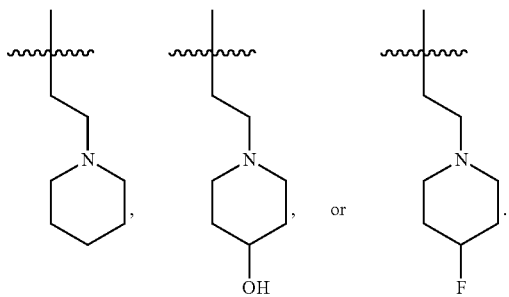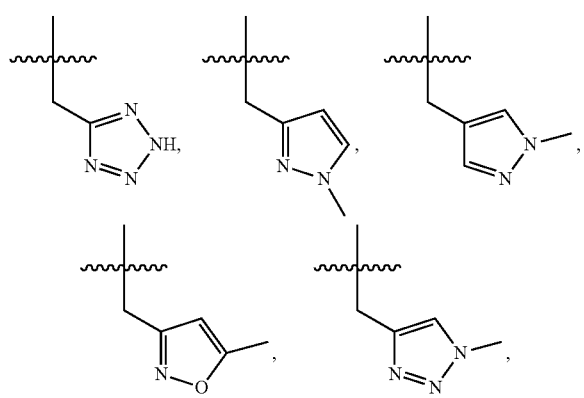
An additional embodiment of the invention is a compound of Formula (I) wherein R⁴ is
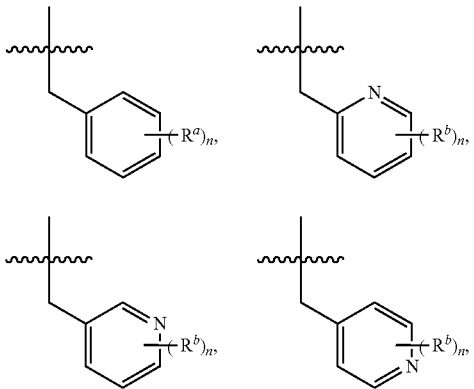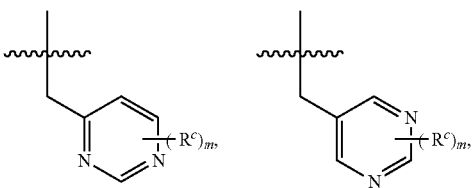

-continued

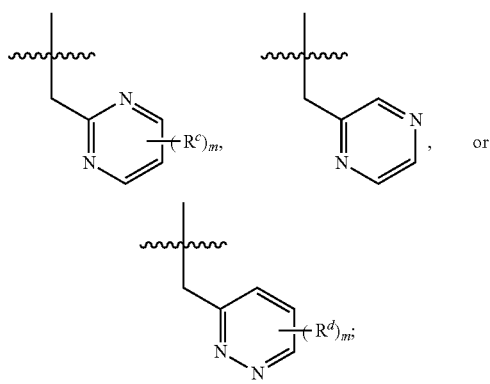

wherein
- $R^a$ is independently selected from: halo, CN, OCH$_3$, C$_{1-6}$alkyl, and CF$_3$;
- $R^b$ is independently selected from: Cl, F, CH$_3$, OCH$_3$, and CF$_3$;
- $R^c$ is F or CH$_3$;
- $R^d$ is OCH$_3$;
- m is 0 or 1; and
- n is 0, 1, or 2.

An additional embodiment of the invention is a compound of Formula (I) wherein
- $R^1$ is H or CH$_3$;
- $R^2$ is phenyl substituted with one, two, or three members each independently selected from the group consisting of: halo, C$_{1-6}$alkyl, C$_{1-6}$haloalkyl, and OC$_{1-6}$alkyl;
- $R^3$ is H; and
- $R^4$ is

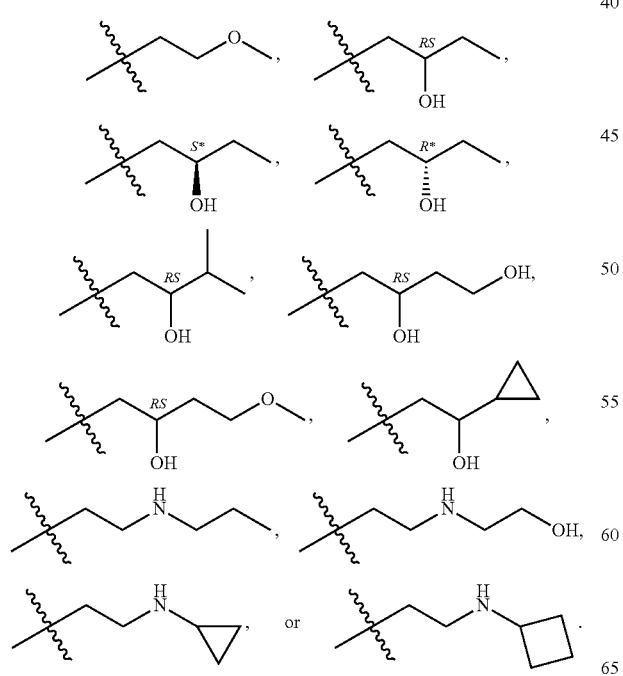

An additional embodiment of the invention is a compound of Formula (I) having the Formula (IA):

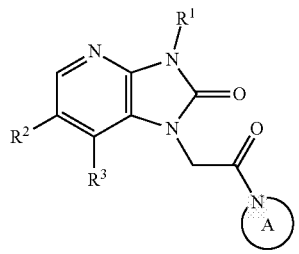

(IA)

wherein $R^1$ is H; CH$_2$F; or CH$_3$;
- $R^2$ is phenyl substituted with one, two, or three members each independently selected from the group consisting of: halo, C$_{1-6}$alkyl, C$_{1-6}$haloalkyl, OC$_{1-6}$alkyl; thiazolyl substituted with C$_{1-6}$alkyl; and thienyl substituted with one or two members each independently selected from the group consisting of: halo, C$_{1-6}$alkyl, C$_{1-6}$haloalkyl, CH$_2$OH, CH$_2$OCD$_3$, and cyclopropyl;
- $R^3$ is H or T; and
- ring A is

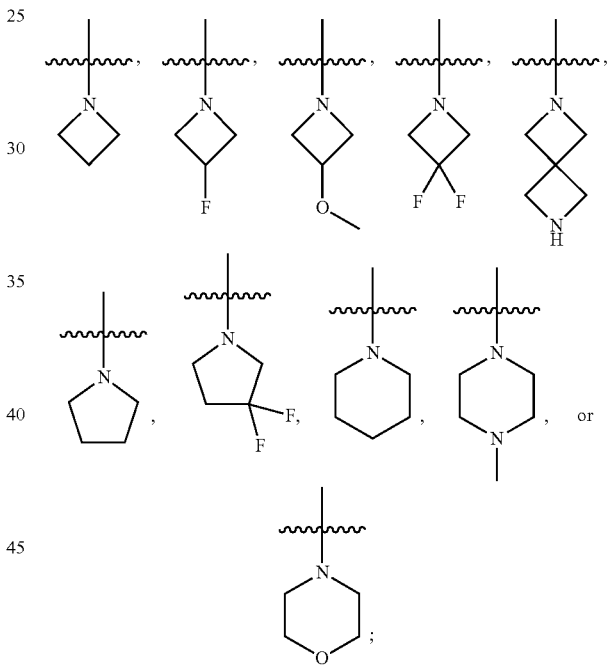

and pharmaceutically acceptable salts, N-oxides or solvates of compounds of Formula (IA).

An additional embodiment of the invention is a compound of Formula (I) having the Formula (IA):

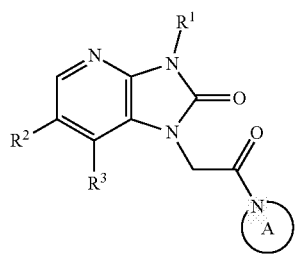

(IA)

wherein
R¹ is H; CH₂F; or CH₃;
R² is 3-(trifluoromethyl)phenyl, 4-fluoro-3-methyl-phenyl, 2,4-difluoro-3-methyl-phenyl, 5-(trifluoromethyl)-2-thienyl, 5-(difluoromethyl)-2-thienyl, or 5-chloro-4-methyl-2-thienyl;
R³ is H; and
ring A is

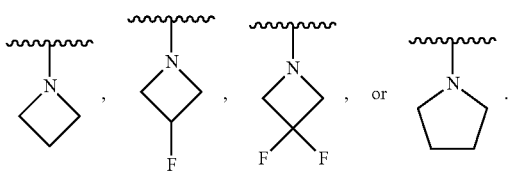

An additional embodiment of the invention is a compound of Formula (I) having the Formula (IA):

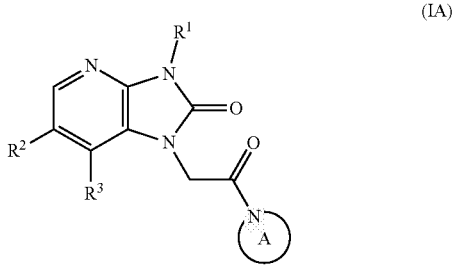

(IA)

wherein R² is m-tolyl, 3-fluorophenyl, 3-chlorophenyl, 3-(trifluoromethyl)phenyl, 5-methyl-2-thienyl, 5-ethyl-2-thienyl, 5-(hydroxymethyl)-2-thienyl, 5-cyclopropyl-2-thienyl, 5-(trideuteriomethoxymethyl)-2-thienyl, 5-(trifluoromethyl)-2-thienyl, 5-(trifluoromethyl)-3-thienyl, 2-(trifluoromethyl)-3-thienyl, 5-(1,1,2,2,2-pentafluoroethyl)-2-thienyl, 5-(trifluoromethyl)thiophen-2-yl, 5-fluoro-2-thienyl, 5-chloro-4-methyl-2-thienyl, 5-(difluoromethyl)-2-thienyl, 4-(difluoromethyl)-2-thienyl, 5-(difluoromethyl)-3-thienyl, 4-methylthiazol-2-yl, 2-methylthiazol-5-yl, 4-methoxyphenyl, 4-fluoro-2-methyl-phenyl, 2-fluoro-3-methyl-phenyl, 4-fluoro-3-methyl-phenyl, 3,5-difluorophenyl, 3,4-difluorophenyl, 2,4-difluoro-3-methyl-phenyl, 3,4,5-trifluorophenyl, 2-(trifluoromethyl)thiazol-5-yl, 2-(trifluoromethyl)thiazol-4-yl, 2-methyl-5-(trifluoromethyl)phenyl, 2-methyl-3-(trifluoromethyl)phenyl, 2-fluoro-3-(trifluoromethyl)phenyl, or 4-fluoro-3-(trifluoromethyl)phenyl.

An additional embodiment of the invention is a compound of Formula (I) having the Formula (IB):

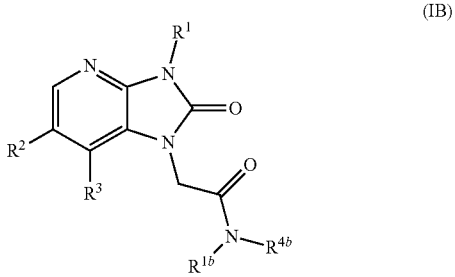

(IB)

wherein R¹ and R¹ᵇ are each independently H or CH₃;
R² is selected from the group consisting of: phenyl substituted with one, two, or three members each independently selected from the group consisting of: halo, $C_{1-6}$alkyl, $C_{1-6}$haloalkyl, $OC_{1-6}$alkyl; pyridinyl; thiazolyl substituted with $C_{1-6}$alkyl; and thienyl substituted with one or two members each independently selected from the group consisting of: halo, $C_{1-6}$alkyl, $C_{1-6}$haloalkyl, $CH_2OH$, and cyclopropyl;
R³ is H; and
R⁴ᵇ is H, $C_{1-6}$alkyl, 2-methoxyethyl, $C_{3-6}$cycloalkyl, 3,3-difluorocyclobutyl, 3,3-difluoro-1-methyl-cyclobutyl, cyclopentyl, oxetan-3-yl, 3-methyloxetan-3-yl, or 2-pyridyl;
and pharmaceutically acceptable salts, N-oxides or solvates of compounds of Formula (IB).

An additional embodiment of the invention is a compound of Formula (I) having the Formula (IB):

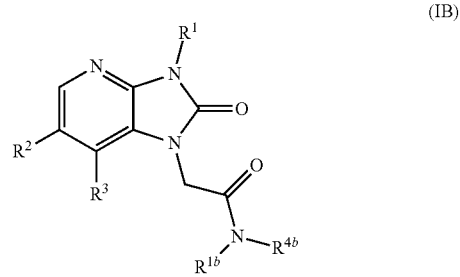

(IB)

wherein
R¹ is H; CH₂F; or CH₃;
R¹ᵇ is CH₃;
R² is 3-(trifluoromethyl)phenyl, 4-fluoro-3-methyl-phenyl, 2,4-difluoro-3-methyl-phenyl, 5-(trifluoromethyl)-2-thienyl, 5-(difluoromethyl)-2-thienyl, or 5-chloro-4-methyl-2-thienyl;
R³ is H; and
R⁴ᵇ is CH₃.

An additional embodiment of the invention is a compound of Formula (I) having the Formula (IB):

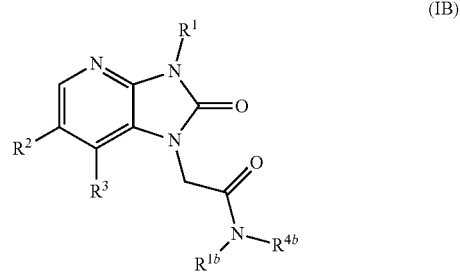

(IB)

wherein R² is 3-pyridyl, 5-methyl-2-thienyl, 4-methyl-2-thienyl, 5-cyclopropyl-2-thienyl, 5-ethyl-2-thienyl, 5-chloro-2-thienyl, 5-(hydroxymethyl)-2-thienyl, 5-(trifluoromethyl)-2-thienyl, 5-(trifluoromethyl)-3-thienyl, 2-(trifluoromethyl)-3-thienyl, 5-(difluoromethyl)-2-thienyl, 5-(difluoromethyl)-3-thienyl, 5-chloro-4-methyl-2-thienyl, 5-fluoro-2-thienyl, 5-fluoro-2-thienyl, 2-methylthiazol-5-yl, 3,5-dimethylphenyl, 3-methoxyphenyl, 4-methoxyphenyl, 4-fluoro-2-methyl-phenyl, 2-fluoro-3-methyl-phenyl, 4-fluoro-3-methyl-phenyl, 4-chlorophenyl, 2,3-difluorophenyl, 3,5-difluorophenyl, 3,4-difluorophenyl, 2-ethoxyphenyl, 3-ethoxyphenyl, 4-methoxy-3-methyl-phenyl, 4-fluoro-2-methoxy-phenyl, 2-fluoro-6-methoxy-phenyl, 2,4-difluoro-3-methyl-phenyl, 3-(difluoromethyl)phenyl, 3-chloro-4-fluoro-phenyl, 2,4-dimethoxyphenyl, 2-ethoxy-5-fluoro-phenyl, 2-chloro-4- methoxy-phenyl, 3-(trifluoromethyl)phenyl, 2-(trifluoromethyl)thiazol-5-yl, 2-(trifluoromethyl)thiazol-4-yl, 2-fluoro-3-(trifluoromethyl)phenyl, or 3,4-difluoro-5-(trifluoromethyl)phenyl.

An additional embodiment of the invention is a compound of Formula (I) having the Formula (IC):

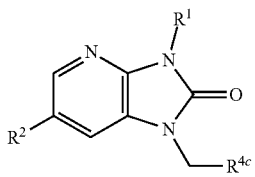
(IC)

wherein $R^1$ is H or $CH_3$;
$R^2$ is selected from the group consisting of: phenyl; phenyl substituted with one, two, or three members each independently selected from the group consisting of: halo, $C_{1-6}$alkyl, $C_{1-6}$haloalkyl, CN, $OC_{1-6}$alkyl, $OC_{1-6}$haloalkyl, and $N(CH_3)_2$; pyridinyl substituted with $CF_3$; and thienyl substituted with one or two members each independently selected from the group consisting of: halo, $C_{1-6}$alkyl, and $C_{1-6}$haloalkyl; and
$R^{4c}$ is selected from the group consisting of: cyclopropyl; cyclopropyl substituted with one or two F members; CH(OH)cyclopropyl; azetidinyl; $CH_2$-azetidinyl; $CH_2$-azetidinyl substituted with one or two members independently selected from: F, OH, $OCH_3$, and $CF_3$; oxetanyl; oxetanyl substituted with F or $CH_3$; tetrahydrofuranyl; tetrahydropyranyl; $CH_2$pyrrolidinyl; $CH_2$pyrrolidinyl substituted with $CH_3$, OH, or $OCH_3$; $CH_2$piperidinyl; $CH_2$piperidinyl substituted with OH, or F; morpholinyl; pyrazolyl substituted with one or two $CH_3$ members; triazolyl substituted with $CH_3$; tetrazolyl; isoxazolyl substituted with one or two $CH_3$ members; oxadiazolyl substituted with $CH_3$, or $CH_2OCH_3$; thiadiazolyl; pyridinyl; pyridinyl substituted with one or two members independently selected from the group consisting of: Cl, F, $CH_3$, $OCH_3$, and $CF_3$; (2-oxo-1H-pyridin-3-yl); 6-oxo-1H-pyridin-3-yl; pyrimidinyl; pyrimidinyl substituted with F or $CH_3$; pyrazinyl; pyridazinyl; pyridazinyl substituted with $OCH_3$; phenyl; phenyl substituted with one or two members independently selected from the group consisting of: halo, CN, $OCH_3$, $C_{1-6}$alkyl, and $CF_3$;
and pharmaceutically acceptable salts, N-oxides or solvates of compounds of Formula (IC).

An additional embodiment of the invention is a compound of Formula (I) having the Formula (ID):

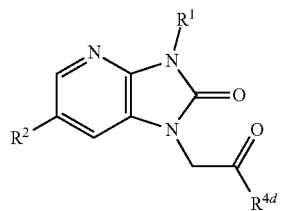
(ID)

wherein $R^1$ is H or $CH_3$;
$R^2$ is m-tolyl, 3-(trifluoromethyl)phenyl, 4-chlorophenyl, 2,4-difluoro-3-methyl-phenyl, 3,4-difluorophenyl, 4-fluoro-3-methyl-phenyl, 3-cyclopropylphenyl, 3-fluoro-4-methoxy-phenyl, 2-ethoxyphenyl, 3-ethoxyphenyl, 4-methoxyphenyl, 2-ethoxy-5-fluoro-phenyl, 4-fluoro-2-methoxy-phenyl, or 3-chloro-4-fluoro-phenyl; and
$R^{4d}$ is OH, $C_{1-6}$alkyl, $C_{3-6}$cycloalkyl, $OC_{1-6}$alkyl, 2-thienyl, or thiazol-2-yl;
and pharmaceutically acceptable salts, N-oxides or solvates of compounds of Formula (ID).

A further embodiment of the current invention is a compound as shown below in Table 1.

| Ex # | Compound Name |
|---|---|
| 1 | 6-(4-Methoxyphenyl)-1-(2-morpholino-2-oxo-ethyl)-3H-imidazo[4,5-b]pyridin-2-one; |
| 2 | 6-(4-Fluoro-2-methyl-phenyl)-1-(2-methoxyethyl)-3H-imidazo[4,5-b]pyridin-2-one; |
| 3 | N-Ethyl-2-[6-(4-fluoro-2-methyl-phenyl)-2-oxo-3H-imidazo[4,5-b]pyridin-1-yl]acetamide; |
| 4 | (S*)-1-(2-Hydroxybutyl)-6-(4-methoxyphenyl)-3H-imidazo[4,5-b]pyridin-2-one; |
| 5 | (R*)-1-(2-Hydroxybutyl)-6-(4-methoxyphenyl)-3H-imidazo[4,5-b]pyridin-2-one; |
| 6 | 6-(4-Fluoro-3-methyl-phenyl)-3-methyl-1-(2-pyridylmethyl)imidazo[4,5-b]pyridin-2-one; |
| 7 | 6-(3-Fluorophenyl)-3-methyl-1-(pyrimidin-4-ylmethyl)imidazo[4,5-b]pyridin-2-one; |
| 8 | 6-(3,4-Difluorophenyl)-3-methyl-1-[(5-methylisoxazol-3-yl)methyl]imidazo[4,5-b]pyridin-2-one; |
| 9 | 2-[6-(5-Chloro-2-thienyl)-3-methyl-2-oxo-imidazo[4,5-b]pyridin-1-yl]-N,N-dimethyl-acetamide; |
| 10 | 6-[5-(Difluoromethyl)-2-thienyl]-1-[2-(3-fluoroazetidin-1-yl)-2-oxo-ethyl]-3-methyl-imidazo[4,5-b]pyridin-2-one; |
| 11 | 1-[(5-Methylisoxazol-3-yl)methyl]-6-phenyl-3H-imidazo[4,5-b]pyridin-2-one; |
| 12 | 6-(4-Fluorophenyl)-1-[(5-methylisoxazol-3-yl)methyl]-3H-imidazo[4,5-b]pyridin-2-one; |
| 13 | 6-(4-Fluorophenyl)-1-[(5-methyl-1,3,4-oxadiazol-2-yl)methyl]-3H-imidazo[4,5-b]pyridin-2-one; |
| 14 | 3-Methyl-1-[(5-methylisoxazol-3-yl)methyl]-6-(4-methyl-2-thienyl)imidazo[4,5-b]pyridin-2-one; |
| 15 | 6-(4-Fluorophenyl)-1-[(1-methylpyrazol-4-yl)methyl]-3H-imidazo[4,5-b]pyridin-2-one; |

-continued

| Ex # | Compound Name |
|---|---|
| 16 | 1-[(1,5-Dimethylpyrazol-3-yl)methyl]-6-(4-fluorophenyl)-3H-imidazo[4,5-b]pyridin-2-one; |
| 17 | 1-[2-(Azetidin-1-yl)ethyl]-6-[3-(trifluoromethyl)phenyl]-3H-imidazo[4,5-b]pyridin-2-one; |
| 18 | 1-[2-(Azetidin-1-yl)ethyl]-3-methyl-6-[3-(trifluoromethyl)phenyl]imidazo[4,5-b]pyridin-2-one; |
| 19 | 1-[(5-Methylisoxazol-3-yl)methyl]-6-[3-(trifluoromethyl)phenyl]-3H-imidazo[4,5-b]pyridin-2-one; |
| 20 | N-Cyclopropyl-2-[2-oxo-6-[3-(trifluoromethyl)phenyl]-3H-imidazo[4,5-b]pyridin-1-yl]acetamide; |
| 21 | 1-[(3-Chlorophenyl)methyl]-6-[3-(trifluoromethyl)phenyl]-3H-imidazo[4,5-b]pyridin-2-one; |
| 22 | 1-[(2-Methoxy-3-pyridyl)methyl]-6-[3-(trifluoromethyl)phenyl]-3H-imidazo[4,5-b]pyridin-2-one; |
| 23 | 1-(Pyrimidin-4-ylmethyl)-6-[3-(trifluoromethyl)phenyl]-3H-imidazo[4,5-b]pyridin-2-one; |
| 24 | (R/S)-1-(Tetrahydrofuran-2-ylmethyl)-6-[3-(trifluoromethyl)phenyl]-3H-imidazo[4,5-b]pyridin-2-one; |
| 25 | 1-[2-(Azetidin-1-yl)-2-oxo-ethyl]-6-[3-(trifluoromethyl)phenyl]-3H-imidazo[4,5-b]pyridin-2-one; |
| 26 | N,N-Dimethyl-2-[2-oxo-6-[5-(trifluoromethyl)-2-thienyl]-3H-imidazo[4,5-b]pyridin-1-yl]acetamide; |
| 27 | 1-[2-(Azetidin-1-yl)-2-oxo-ethyl]-3-methyl-6-[5-(trifluoromethyl)-2-thienyl]imidazo[4,5-b]pyridin-2-one; |
| 28 | N,N-Dimethyl-2-[3-methyl-2-oxo-6-[5-(trifluoromethyl)-2-thienyl]imidazo[4,5-b]pyridin-1-yl]acetamide; |
| 29 | 1-[2-(Azetidin-1-yl)-2-oxo-ethyl]-6-[2-methyl-5-(trifluoromethyl)phenyl]-3H-imidazo[4,5-b]pyridin-2-one; |
| 30 | 6-(2,4-Difluoro-3-methyl-phenyl)-1-(2-oxobutyl)-3H-imidazo[4,5-b]pyridin-2-one; |
| 31 | (R/S)-1-(2-Cyclopropyl-2-hydroxy-ethyl)-6-[3-(trifluoromethyl)phenyl]-3H-imidazo[4,5-b]pyridin-2-one; |
| 32 | 1-[(2-Oxo-1H-pyridin-3-yl)methyl]-6-[3-(trifluoromethyl)phenyl]-3H-imidazo[4,5-b]pyridin-2-one; |
| 33 | (R/S)-6-(4-Fluoro-2-methyl-phenyl)-3-methyl-1-(oxetan-2-ylmethyl)imidazo[4,5-b]pyridin-2-one; |
| 34 | 1-[2-(3-Fluoroazetidin-1-yl)-2-oxo-ethyl]-3-methyl-6-[3-(trifluoromethyl)phenyl]imidazo[4,5-b]pyridin-2-one; |
| 35 | 6-(4-Methoxyphenyl)-1-(2-oxo-2-pyrrolidin-1-yl-ethyl)-3H-imidazo[4,5-b]pyridin-2-one; |
| 36 | N-Cyclopropyl-2-[6-(4-fluoro-2-methyl-phenyl)-2-oxo-3H-imidazo[4,5-b]pyridin-1-yl]acetamide; |
| 37 | 2-[6-(2-Chloro-4-methoxy-phenyl)-2-oxo-3H-imidazo[4,5-b]pyridin-1-yl]-N-cyclopropyl-acetamide; |
| 38 | N-Cyclopropyl-2-[6-(4-methoxyphenyl)-2-oxo-3H-imidazo[4,5-b]pyridin-1-yl]acetamide; |
| 39 | N-Cyclopropyl-2-[6-(3,5-dimethylphenyl)-2-oxo-3H-imidazo[4,5-b]pyridin-1-yl]acetamide; |
| 40 | N-Cyclopropyl-2-[6-(4-fluoro-2-methyl-phenyl)-2-oxo-3H-imidazo[4,5-b]pyridin-1-yl]-N-methyl-acetamide; |
| 41 | N-Cyclopropyl-2-[6-(4-methoxyphenyl)-2-oxo-3H-imidazo[4,5-b]pyridin-1-yl]-N-methyl-acetamide; |
| 42 | N-Cyclopropyl-2-[6-(4-fluoro-2-methyl-phenyl)-3-methyl-2-oxo-imidazo[4,5-b]pyridin-1-yl]acetamide; |
| 43 | (R*)-6-(4-Fluoro-2-methyl-phenyl)-1-(2-hydroxybutyl)-3H-imidazo[4,5-b]pyridin-2-one; |
| 44 | (S*)-6-(4-Fluoro-2-methyl-phenyl)-1-(2-hydroxybutyl)-3H-imidazo[4,5-b]pyridin-2-one; |
| 45 | 6-(4-Fluoro-3-methyl-phenyl)-3-methyl-1-(3-pyridylmethyl)imidazo[4,5-b]pyridin-2-one; |
| 46 | 6-(4-Fluoro-3-methyl-phenyl)-3-methyl-1-(4-pyridylmethyl)imidazo[4,5-b]pyridin-2-one; |
| 47 | 6-(4-Fluoro-3-methyl-phenyl)-3-methyl-1-(pyrazin-2-ylmethyl)imidazo[4,5-b]pyridin-2-one; |
| 48 | 6-(4-Fluoro-3-methyl-phenyl)-3-methyl-1-(pyrimidin-5-ylmethyl)imidazo[4,5-b]pyridin-2-one; |
| 49 | 6-(4-Fluoro-3-methyl-phenyl)-3-methyl-1-(pyrimidin-2-ylmethyl)imidazo[4,5-b]pyridin-2-one; |
| 50 | 6-(4-Fluoro-3-methyl-phenyl)-3-methyl-1-(pyridazin-3-ylmethyl)imidazo[4,5-b]pyridin-2-one; |
| 51 | 6-(3-Fluorophenyl)-3-methyl-1-(3-pyridylmethyl)imidazo[4,5-b]pyridin-2-one; |
| 52 | 6-(3-Fluorophenyl)-3-methyl-1-(4-pyridylmethyl)imidazo[4,5-b]pyridin-2-one; |
| 53 | 6-(3-Fluorophenyl)-3-methyl-1-(2-pyridylmethyl)imidazo[4,5-b]pyridin-2-one; |

| Ex # | Compound Name |
|---|---|
| 54 | 6-(3-Fluorophenyl)-3-methyl-1-(pyrimidin-5-ylmethyl)imidazo[4,5-b]pyridin-2-one; |
| 55 | 6-(3-Fluorophenyl)-3-methyl-1-(pyrazin-2-ylmethyl)imidazo[4,5-b]pyridin-2-one; |
| 56 | 6-(3-Fluorophenyl)-3-methyl-1-(pyrimidin-2-ylmethyl)imidazo[4,5-b]pyridin-2-one; |
| 57 | 6-(3-Fluorophenyl)-3-methyl-1-(pyridazin-3-ylmethyl)imidazo[4,5-b]pyridin-2-one; |
| 58 | 6-(3,4-Difluorophenyl)-3-methyl-1-(4-pyridylmethyl)imidazo[4,5-b]pyridin-2-one; |
| 59 | 6-(3,4-Difluorophenyl)-3-methyl-1-(3-pyridylmethyl)imidazo[4,5-b]pyridin-2-one; |
| 60 | 6-(3,4-Difluorophenyl)-3-methyl-1-(pyrimidin-5-ylmethyl)imidazo[4,5-b]pyridin-2-one; |
| 61 | 6-(3,4-Difluorophenyl)-3-methyl-1-(pyridazin-3-ylmethyl)imidazo[4,5-b]pyridin-2-one; |
| 62 | 6-(3,4-difluorophenyl)-3-methyl-1-(2-pyridylmethyl)imidazo[4,5-b]pyridin-2-one; |
| 63 | 6-(3,4-Difluorophenyl)-3-methyl-1-(pyrazin-2-ylmethyl)imidazo[4,5-b]pyridin-2-one; |
| 64 | 6-(3,4-Difluorophenyl)-3-methyl-1-(pyrimidin-2-ylmethyl)imidazo[4,5-b]pyridin-2-one; |
| 65 | 6-(2,4-Difluoro-3-methyl-phenyl)-3-methyl-1-(pyrimidin-2-ylmethyl)imidazo[4,5-b]pyridin-2-one; |
| 66 | 6-(2,4-Difluoro-3-methyl-phenyl)-3-methyl-1-(4-pyridylmethyl)imidazo[4,5-b]pyridin-2-one; |
| 67 | 6-(2,4-Difluoro-3-methyl-phenyl)-3-methyl-1-(pyridazin-3-ylmethyl)imidazo[4,5-b]pyridin-2-one; |
| 68 | 6-(2,4-Difluoro-3-methyl-phenyl)-3-methyl-1-(2-pyridylmethyl)imidazo[4,5-b]pyridin-2-one; |
| 69 | 6-(2,4-Difluoro-3-methyl-phenyl)-3-methyl-1-(pyrimidin-5-ylmethyl)imidazo[4,5-b]pyridin-2-one; |
| 70 | 6-(3,4-Difluorophenyl)-3-methyl-1-(pyrimidin-4-ylmethyl)imidazo[4,5-b]pyridin-2-one; |
| 71 | 6-(4-Fluoro-3-methyl-phenyl)-3-methyl-1-(pyrimidin-4-ylmethyl)imidazo[4,5-b]pyridin-2-one; |
| 72 | 6-(2,4-Difluoro-3-methyl-phenyl)-3-methyl-1-(pyrimidin-4-ylmethyl)imidazo[4,5-b]pyridin-2-one; |
| 73 | 6-(3,4-Difluorophenyl)-3-methyl-1-[(5-methyl-1,3,4-oxadiazol-2-yl)methyl]imidazo[4,5-b]pyridin-2-one; |
| 74 | 3-Methyl-1-[(5-methylisoxazol-3-yl)methyl]-6-[3-(trifluoromethyl)phenyl]imidazo[4,5-b]pyridin-2-one; |
| 75 | 3-Methyl-1-[(5-methyl-1,3,4-oxadiazol-2-yl)methyl]-6-[3-(trifluoromethyl)phenyl]imidazo[4,5-b]pyridin-2-one; |
| 76 | 3-Methyl-1-[(3-methyl-1,2,4-oxadiazol-5-yl)methyl]-6-[3-(trifluoromethyl)phenyl]imidazo[4,5-b]pyridin-2-one; |
| 77 | 6-(3,4-Difluorophenyl)-3-methyl-1-[(3-methyl-1,2,4-oxadiazol-5-yl)methyl]imidazo[4,5-b]pyridin-2-one; |
| 78 | N,N-Dimethyl-2-[3-methyl-6-(5-methyl-2-thienyl)-2-oxo-imidazo[4,5-b]pyridin-1-yl]acetamide; |
| 79 | 2-[6-(5-Ethyl-2-thienyl)-3-methyl-2-oxo-imidazo[4,5-b]pyridin-1-yl]-N,N-dimethyl-acetamide; |
| 80 | N,N-Dimethyl-2-[3-methyl-6-(4-methyl-2-thienyl)-2-oxo-imidazo[4,5-b]pyridin-1-yl]acetamide; |
| 81 | 1-[2-(Azetidin-1-yl)-2-oxo-ethyl]-6-(5-fluoro-2-thienyl)-3-methyl-imidazo[4,5-b]pyridin-2-one; |
| 82 | 2-[6-(5-Fluoro-2-thienyl)-3-methyl-2-oxo-imidazo[4,5-b]pyridin-1-yl]-N,N-dimethyl-acetamide; |
| 83 | 1-[2-(3-Fluoroazetidin-1-yl)-2-oxo-ethyl]-6-(5-fluoro-2-thienyl)-3-methyl-imidazo[4,5-b]pyridin-2-one; |
| 84 | 3-Methyl-1-(pyridazin-3-ylmethyl)-6-[5-(trifluoromethyl)-2-thienyl]imidazo[4,5-b]pyridin-2-one; |
| 85 | 6-(5-Fluoro-2-thienyl)-3-methyl-1-(pyridazin-3-ylmethyl)imidazo[4,5-b]pyridin-2-one; |
| 86 | 1-[2-(3-Fluoroazetidin-1-yl)-2-oxo-ethyl]-3-methyl-6-(4-methylthiazol-2-yl)imidazo[4,5-b]pyridin-2-one; |
| 87 | 1-[2-(Azetidin-1-yl)-2-oxo-ethyl]-6-(5-ethyl-2-thienyl)-3-methyl-imidazo[4,5-b]pyridin-2-one; |
| 88 | 6-(5-Ethyl-2-thienyl)-1-[2-(3-fluoroazetidin-1-yl)-2-oxo-ethyl]-3-methyl-imidazo[4,5-b]pyridin-2-one; |
| 89 | 1-[2-(Azetidin-1-yl)-2-oxo-ethyl]-6-[5-(hydroxymethyl)-2-thienyl]-3-methyl-imidazo[4,5-b]pyridin-2-one; |
| 90 | 1-[2-(3-Fluoroazetidin-1-yl)-2-oxo-ethyl]-6-[5-(hydroxymethyl)-2-thienyl]-3-methyl-imidazo[4,5-b]pyridin-2-one; |
| 91 | 2-[6-[5-(Hydroxymethyl)-2-thienyl]-3-methyl-2-oxo-imidazo[4,5-b]pyridin-1-yl]-N,N-dimethyl-acetamide; |

| Ex # | Compound Name |
|---|---|
| 92 | 1-[2-(3-Fluoroazetidin-1-yl)-2-oxo-ethyl]-3-methyl-6-[2-(trifluoromethyl)-3-thienyl]imidazo[4,5-b]pyridin-2-one; |
| 93 | 1-[2-(Azetidin-1-yl)-2-oxo-ethyl]-6-[5-(difluoromethyl)-2-thienyl]-3-methyl-imidazo[4,5-b]pyridin-2-one; |
| 94 | 2-[6-[5-(Difluoromethyl)-2-thienyl]-3-methyl-2-oxo-imidazo[4,5-b]pyridin-1-yl]-N,N-dimethyl-acetamide; |
| 95 | 1-[2-(Azetidin-1-yl)-2-oxo-ethyl]-3-methyl-6-[2-(trifluoromethyl)-3-thienyl]imidazo[4,5-b]pyridin-2-one; |
| 96 | N,N-Dimethyl-2-[3-methyl-2-oxo-6-[2-(trifluoromethyl)-3-thienyl]imidazo[4,5-b]pyridin-1-yl]acetamide; |
| 97 | 2-[6-[5-(Difluoromethyl)-3-thienyl]-3-methyl-2-oxo-imidazo[4,5-b]pyridin-1-yl]-N,N-dimethyl-acetamide; |
| 98 | 1-[2-(Azetidin-1-yl)-2-oxo-ethyl]-6-[5-(difluoromethyl)-3-thienyl]-3-methyl-imidazo[4,5-b]pyridin-2-one; |
| 99 | 6-[5-(Difluoromethyl)-3-thienyl]-1-[2-(3-fluoroazetidin-1-yl)-2-oxo-ethyl]-3-methyl-imidazo[4,5-b]pyridin-2-one; |
| 100 | 6-[5-(Difluoromethyl)-2-thienyl]-3-methyl-1-(pyridazin-3-ylmethyl)imidazo[4,5-b]pyridin-2-one; |
| 101 | N,N-Dimethyl-2-[3-methyl-2-oxo-6-[5-(trifluoromethyl)-3-thienyl]imidazo[4,5-b]pyridin-1-yl]acetamide; |
| 102 | 1-[2-(3-Fluoroazetidin-1-yl)-2-oxo-ethyl]-3-methyl-6-[5-(trifluoromethyl)-3-thienyl]imidazo[4,5-b]pyridin-2-one; |
| 103 | 3-Methyl-1-(pyridazin-3-ylmethyl)-6-[5-(trifluoromethyl)-3-thienyl]imidazo[4,5-b]pyridin-2-one; |
| 104 | 1-[2-(Azetidin-1-yl)-2-oxo-ethyl]-3-methyl-6-[5-(trifluoromethyl)-3-thienyl]imidazo[4,5-b]pyridin-2-one; |
| 105 | 1-[2-(Azetidin-1-yl)-2-oxo-ethyl]-6-(5-cyclopropyl-2-thienyl)-3-methyl-imidazo[4,5-b]pyridin-2-one; |
| 106 | 6-(5-Cyclopropyl-2-thienyl)-1-[2-(3-fluoroazetidin-1-yl)-2-oxo-ethyl]-3-methyl-imidazo[4,5-b]pyridin-2-one; |
| 107 | 1-[2-(Azetidin-1-yl)-2-oxo-ethyl]-3-methyl-6-[2-(trifluoromethyl)thiazol-4-yl]imidazo[4,5-b]pyridin-2-one; |
| 108 | N,N-Dimethyl-2-[3-methyl-2-oxo-6-[2-(trifluoromethyl)thiazol-4-yl]imidazo[4,5-b]pyridin-1-yl]acetamide; |
| 109 | 1-[2-(3-Fluoroazetidin-1-yl)-2-oxo-ethyl]-3-methyl-6-[2-(trifluoromethyl)thiazol-4-yl]imidazo[4,5-b]pyridin-2-one; |
| 110 | 2-[6-(5-Cyclopropyl-2-thienyl)-3-methyl-2-oxo-imidazo[4,5-b]pyridin-1-yl]-N,N-dimethyl-acetamide; |
| 111 | 1-[2-(Azetidin-1-yl)-2-oxo-ethyl]-3-methyl-6-[5-(1,1,2,2,2-pentafluoroethyl)-2-thienyl]imidazo[4,5-b]pyridin-2-one; |
| 112 | 1-[2-(Azetidin-1-yl)-2-oxo-ethyl]-3-methyl-6-(2-methylthiazol-5-yl)imidazo[4,5-b]pyridin-2-one; |
| 113 | 1-[2-(3-Fluoroazetidin-1-yl)-2-oxo-ethyl]-3-methyl-6-(2-methylthiazol-5-yl)imidazo[4,5-b]pyridin-2-one; |
| 114 | N,N-Dimethyl-2-[3-methyl-6-(2-methylthiazol-5-yl)-2-oxo-imidazo[4,5-b]pyridin-1-yl]acetamide; |
| 115 | 1-[2-(Azetidin-1-yl)-2-oxo-ethyl]-3-methyl-6-[2-(trifluoromethyl)thiazol-5-yl]imidazo[4,5-b]pyridin-2-one; |
| 116 | 1-[2-(3-Fluoroazetidin-1-yl)-2-oxo-ethyl]-3-methyl-6-[2-(trifluoromethyl)thiazol-5-yl]imidazo[4,5-b]pyridin-2-one; |
| 117 | 1-[2-(Azetidin-1-yl)-2-oxo-ethyl]-6-[4-(difluoromethyl)-2-thienyl]-3-methyl-imidazo[4,5-b]pyridin-2-one; |
| 118 | 6-[4-(Difluoromethyl)-2-thienyl]-1-[2-(3-fluoroazetidin-1-yl)-2-oxo-ethyl]-3-methyl-imidazo[4,5-b]pyridin-2-one; |
| 119 | N,N-Dimethyl-2-[3-methyl-2-oxo-6-[2-(trifluoromethyl)thiazol-5-yl]imidazo[4,5-b]pyridin-1-yl]acetamide; |
| 120 | 1-(2-(Azetidin-1-yl)-2-oxoethyl)-3-methyl-6-(5-(trifluoromethyl)thiophen-2-yl)-1,3-dihydro-2H-imidazo[4,5-b]pyridin-2-one-7-D; |
| 121 | N,N-Dimethyl-2-[3-methyl-2-oxo-6-[5-(trideuteriomethoxymethyl)-2-thienyl]imidazo[4,5-b]pyridin-1-yl]acetamide; |
| 122 | 1-[2-(Azetidin-1-yl)-2-oxo-ethyl]-3-methyl-6-[5-(trideuteriomethoxymethyl)-2-thienyl]imidazo[4,5-b]pyridin-2-one; |
| 123 | 1-[2-(3-Fluoroazetidin-1-yl)-2-oxo-ethyl]-3-methyl-6-[5-(trideuteriomethoxymethyl)-2-thienyl]imidazo[4,5-b]pyridin-2-one; |
| 124 | 1-(2-(Azetidin-1-yl)-2-oxoethyl)-3-methyl-6-(5-(trifluoromethyl)thiophen-2-yl)-1,3-dihydro-2H-imidazo[4,5-b]pyridin-2-one-7-T; |
| 125 | 1-[(5-Methylisoxazol-3-yl)methyl]-6-(4-methyl-2-thienyl)-3H-imidazo[4,5-b]pyridin-2-one; |
| 126 | 1-[(5-Methylisoxazol-3-yl)methyl]-6-(o-tolyl)-3H-imidazo[4,5-b]pyridin-2-one; |
| 127 | 1-[(3-Methyl-1,2,4-oxadiazol-5-yl)methyl]-6-(4-methyl-2-thienyl)-3H-imidazo[4,5-b]pyridin-2-one; |
| 128 | 6-(4-Fluorophenyl)-1-[(1-methylpyrazol-3-yl)methyl]-3H-imidazo[4,5-b]pyridin-2-one; |
| 129 | 6-(4-Fluoro-3-methyl-phenyl)-1-[(1-methylpyrazol-3-yl)methyl]-3H-imidazo[4,5-b]pyridin-2-one; |

| Ex # | Compound Name |
| --- | --- |
| 130 | 6-(3-Chloro-4-fluoro-phenyl)-1-[(1-methylpyrazol-3-yl)methyl]-3H-imidazo[4,5-b]pyridin-2-one; |
| 131 | 6-(3,4-Difluorophenyl)-1-[(1-methylpyrazol-3-yl)methyl]-3H-imidazo[4,5-b]pyridin-2-one; |
| 132 | 6-(2,4-Difluorophenyl)-1-[(1-methylpyrazol-3-yl)methyl]-3H-imidazo[4,5-b]pyridin-2-one; |
| 133 | (R/S)-3-methyl-1-(oxetan-2-ylmethyl)-6-[3-(trifluoromethyl)phenyl]imidazo[4,5-b]pyridin-2-one; |
| 134 | Ethyl 2-[2-oxo-6-[3-(trifluoromethyl)phenyl]-3H-imidazo[4,5-b]pyridin-1-yl]acetate; |
| 135 | 2-[2-Oxo-6-[3-(trifluoromethyl)phenyl]-3H-imidazo[4,5-b]pyridin-1-yl]acetic acid; |
| 136 | Ethyl 2-[3-methyl-2-oxo-6-[3-(trifluoromethyl)phenyl]imidazo[4,5-b]pyridin-1-yl]acetate; |
| 137 | 2-[3-Methyl-2-oxo-6-[3-(trifluoromethyl)phenyl]imidazo[4,5-b]pyridin-1-yl]acetic acid; |
| 138 | 1-[2-(3,3-difluoroazetidin-1-yl)-2-oxo-ethyl]-3-methyl-6-[3-(trifluoromethyl)phenyl]imidazo[4,5-b]pyridin-2-one; |
| 139 | 6-(2,4-Difluoro-3-methyl-phenyl)-3-methyl-1-(pyrazin-2-ylmethyl)imidazo[4,5-b]pyridin-2-one; |
| 140 | 6-(4-Fluorophenyl)-1-[(3-methyl-1,2,4-oxadiazol-5-yl)methyl]-3H-imidazo[4,5-b]pyridin-2-one; |
| 141 | 6-(4-Fluorophenyl)-1-[(1-methyl-1,2,4-triazol-3-yl)methyl]-3H-imidazo[4,5-b]pyridin-2-one; |
| 142 | 6-(4-Fluorophenyl)-1-[(1-methyltriazol-4-yl)methyl]-3H-imidazo[4,5-b]pyridin-2-one; |
| 143 | 6-(3,4-Difluorophenyl)-1-[(3-methyl-1,2,4-oxadiazol-5-yl)methyl]-3H-imidazo[4,5-b]pyridin-2-one; |
| 144 | 6-(3,4-Difluorophenyl)-1-[(5-methyl-1,2,4-oxadiazol-3-yl)methyl]-3H-imidazo[4,5-b]pyridin-2-one; |
| 145 | 6-(3,4-Difluorophenyl)-1-[[3-(methoxymethyl)-1,2,4-oxadiazol-5-yl]methyl]-3H-imidazo[4,5-b]pyridin-2-one; |
| 146 | 1-(2-Pyrrolidin-1-ylethyl)-6-[3-(trifluoromethyl)phenyl]-3H-imidazo[4,5-b]pyridin-2-one; |
| 147 | 1-[2-(3-Hydroxyazetidin-1-yl)ethyl]-6-[3-(trifluoromethyl)phenyl]-3H-imidazo[4,5-b]pyridin-2-one; |
| 148 | 1-[2-(Cyclopropylamino)ethyl]-6-[3-(trifluoromethyl)phenyl]-3H-imidazo[4,5-b]pyridin-2-one; |
| 149 | 1-[2-(3-Methoxyazetidin-1-yl)ethyl]-6-[3-(trifluoromethyl)phenyl]-3H-imidazo[4,5-b]pyridin-2-one; |
| 150 | 1-[2-(Cyclobutylamino)ethyl]-6-[3-(trifluoromethyl)phenyl]-3H-imidazo[4,5-b]pyridin-2-one; |
| 151 | 1-[2-(Azetidin-1-yl)ethyl]-6-(4-fluoro-2-methyl-phenyl)-3H-imidazo[4,5-b]pyridin-2-one; |
| 152 | 1-[2-(Azetidin-1-yl)ethyl]-6-(o-tolyl)-3H-imidazo[4,5-b]pyridin-2-one; |
| 153 | 1-[2-(Azetidin-1-yl)ethyl]-6-phenyl-3H-imidazo[4,5-b]pyridin-2-one; |
| 154 | 1-[2-(Azetidin-1-yl)ethyl]-6-(m-tolyl)-3H-imidazo[4,5-b]pyridin-2-one; |
| 155 | 1-[2-(Azetidin-1-yl)ethyl]-6-[2-(trifluoromethyl)-4-pyridyl]-3H-imidazo[4,5-b]pyridin-2-one; |
| 156 | 1-[2-(Azetidin-1-yl)ethyl]-6-(4-fluoro-3-methyl-phenyl)-3H-imidazo[4,5-b]pyridin-2-one; |
| 157 | 1-[2-(Azetidin-1-yl)ethyl]-6-(2,6-dimethylphenyl)-3H-imidazo[4,5-b]pyridin-2-one; |
| 158 | 1-[2-(Azetidin-1-yl)ethyl]-6-(3-chlorophenyl)-3H-imidazo[4,5-b]pyridin-2-one; |
| 159 | 1-[2-(Azetidin-1-yl)ethyl]-6-(3,5-difluorophenyl)-3H-imidazo[4,5-b]pyridin-2-one; |
| 160 | 1-[2-(Azetidin-1-yl)ethyl]-6-[3-(trifluoromethoxy)phenyl]-3H-imidazo[4,5-b]pyridin-2-one; |
| 161 | 1-[2-(1-Piperidyl)ethyl]-6-[3-(trifluoromethyl)phenyl]-3H-imidazo[4,5-b]pyridin-2-one; |
| 162 | 1-[2-(4-Fluoro-1-piperidyl)ethyl]-6-[3-(trifluoromethyl)phenyl]-3H-imidazo[4,5-b]pyridin-2-one; |
| 163 | 1-[2-(3-Fluoroazetidin-1-yl)ethyl]-6-[3-(trifluoromethyl)phenyl]-3H-imidazo[4,5-b]pyridin-2-one; |
| 164 | 1-[2-(3-Methylpyrrolidin-1-yl)ethyl]-6-[3-(trifluoromethyl)phenyl]-3H-imidazo[4,5-b]pyridin-2-one; |
| 165 | 1-[2-(4-Hydroxy-1-piperidyl)ethyl]-6-[3-(trifluoromethyl)phenyl]-3H-imidazo[4,5-b]pyridin-2-one; |
| 166 | 1-[2-[3-(Trifluoromethyl)azetidin-1-yl]ethyl]-6-[3-(trifluoromethyl)phenyl]-3H-imidazo[4,5-b]pyridin-2-one; |
| 167 | 1-[2-(3,3-Difluoroazetidin-1-yl)ethyl]-6-[3-(trifluoromethyl)phenyl]-3H-imidazo[4,5-b]pyridin-2-one; |
| 168 | 1-[2-(Azetidin-1-yl)ethyl]-6-[2-methyl-3-(trifluoromethyl)phenyl]-3H-imidazo[4,5-b]pyridin-2-one; |
| 169 | 1-[2-(Azetidin-1-yl)ethyl]-6-(2,3-dimethylphenyl)-3H-imidazo[4,5-b]pyridin-2-one; |

| Ex # | Compound Name |
|---|---|
| 170 | 1-[2-(Azetidin-1-yl)ethyl]-6-(3,5-dimethylphenyl)-3H-imidazo[4,5-b]pyridin-2-one; |
| 171 | 1-[2-(Azetidin-1-yl)ethyl]-6-(4-fluoro-2,3-dimethyl-phenyl)-3H-imidazo[4,5-b]pyridin-2-one; |
| 172 | 1-[2-(Azetidin-1-yl)ethyl]-6-[2-methyl-5-(trifluoromethyl)phenyl]-3H-imidazo[4,5-b]pyridin-2-one; |
| 173 | 6-(3,5-Difluorophenyl)-1-[2-(2-hydroxyethylamino)ethyl]-3H-imidazo[4,5-b]pyridin-2-one; |
| 174 | 6-(3,5-Difluorophenyl)-1-(2-pyrrolidin-1-ylethyl)-3H-imidazo[4,5-b]pyridin-2-one; |
| 175 | 6-(3,5-Difluorophenyl)-1-[2-(3-hydroxypyrrolidin-1-yl)ethyl]-3H-imidazo[4,5-b]pyridin-2-one; |
| 176 | 6-(3,5-Difluorophenyl)-1-[2-(3-methoxypyrrolidin-1-yl)ethyl]-3H-imidazo[4,5-b]pyridin-2-one; |
| 177 | 6-(4-Fluoro-2-methyl-phenyl)-1-(2-pyrrolidin-1-ylethyl)-3H-imidazo[4,5-b]pyridin-2-one; |
| 178 | 6-(2,6-Dimethylphenyl)-1-(2-pyrrolidin-1-ylethyl)-3H-imidazo[4,5-b]pyridin-2-one; |
| 179 | 6-(o-Tolyl)-1-(2-pyrrolidin-1-ylethyl)-3H-imidazo[4,5-b]pyridin-2-one; |
| 180 | 6-Phenyl-1-(2-pyrrolidin-1-ylethyl)-3H-imidazo[4,5-b]pyridin-2-one; |
| 181 | 1-[2-(3-Fluoroazetidin-1-yl)ethyl]-6-[2-methyl-3-(trifluoromethyl)phenyl]-3H-imidazo[4,5-b]pyridin-2-one; |
| 182 | 6-(2,3-Dimethylphenyl)-1-[2-(3-fluoroazetidin-1-yl)ethyl]-3H-imidazo[4,5-b]pyridin-2-one; |
| 183 | 6-(3,5-Dimethylphenyl)-1-[2-(3-fluoroazetidin-1-yl)ethyl]-3H-imidazo[4,5-b]pyridin-2-one; |
| 184 | 1-[2-(3-Fluoroazetidin-1-yl)ethyl]-6-(4-fluoro-2,3-dimethyl-phenyl)-3H-imidazo[4,5-b]pyridin-2-one; |
| 185 | 1-[2-(3-Fluoroazetidin-1-yl)ethyl]-6-[2-methyl-5-(trifluoromethyl)phenyl]-3H-imidazo[4,5-b]pyridin-2-one; |
| 186 | 1-[2-(3-Fluoroazetidin-1-yl)ethyl]-6-(o-tolyl)-3H-imidazo[4,5-b]pyridin-2-one; |
| 187 | 1-[2-(3-Fluoroazetidin-1-yl)ethyl]-6-(4-fluoro-2-methyl-phenyl)-3H-imidazo[4,5-b]pyridin-2-one; |
| 188 | 1-[2-(3-Fluoroazetidin-1-yl)ethyl]-6-phenyl-3H-imidazo[4,5-b]pyridin-2-one; |
| 189 | 6-(3,5-Difluorophenyl)-1-[2-(propylamino)ethyl]-3H-imidazo[4,5-b]pyridin-2-one; |
| 190 | N-Cyclobutyl-2-[2-oxo-6-[3-(trifluoromethyl)phenyl]-3H-imidazo[4,5-b]pyridin-1-yl]acetamide; |
| 191 | 1-[2-(3-Methoxyazetidin-1-yl)-2-oxo-ethyl]-6-[3-(trifluoromethyl)phenyl]-3H-imidazo[4,5-b]pyridin-2-one; |
| 192 | N-(Oxetan-3-yl)-2-[2-oxo-6-[3-(trifluoromethyl)phenyl]-3H-imidazo[4,5-b]pyridin-1-yl]acetamide; |
| 193 | 1-[2-(4-Methylpiperazin-1-yl)-2-oxo-ethyl]-6-[3-(trifluoromethyl)phenyl]-3H-imidazo[4,5-b]pyridin-2-one; |
| 194 | 1-[2-(3,3-Difluoroazetidin-1-yl)-2-oxo-ethyl]-6-[3-(trifluoromethyl)phenyl]-3H-imidazo[4,5-b]pyridin-2-one; |
| 195 | N-(3,3-Difluorocyclobutyl)-2-[2-oxo-6-[3-(trifluoromethyl)phenyl]-3H-imidazo[4,5-b]pyridin-1-yl]acetamide; |
| 196 | 1-[2-(3,3-Difluoropyrrolidin-1-yl)-2-oxo-ethyl]-3-methyl-6-[3-(trifluoromethyl)phenyl]imidazo[4,5-b]pyridin-2-one; |
| 197 | 3-Methyl-1-(2-oxo-2-pyrrolidin-1-yl-ethyl)-6-[3-(trifluoromethyl)phenyl]imidazo[4,5-b]pyridin-2-one; |
| 198 | N-(3,3-Difluoro-1-methyl-cyclobutyl)-2-[3-methyl-2-oxo-6-[3-(trifluoromethyl)phenyl]imidazo[4,5-b]pyridin-1-yl]acetamide; |
| 199 | N-(3-Methyloxetan-3-yl)-2-[3-methyl-2-oxo-6-[3-(trifluoromethyl)phenyl]imidazo[4,5-b]pyridin-1-yl]acetamide; |
| 200 | N-(3,3-Difluorocyclobutyl)-2-[3-methyl-2-oxo-6-[3-(trifluoromethyl)phenyl]imidazo[4,5-b]pyridin-1-yl]acetamide; |
| 201 | 1-(2-Oxo-2-pyrrolidin-1-yl-ethyl)-6-[3-(trifluoromethyl)phenyl]-3H-imidazo[4,5-b]pyridin-2-one; |
| 202 | (R/S)—N-Cyclopropyl-2-[2-oxo-6-[3-(trifluoromethyl)phenyl]-3H-imidazo[4,5-b]pyridin-1-yl]propanamide; |
| 203 | (R/S)-1-[2-(Azetidin-1-yl)-1-methyl-2-oxo-ethyl]-6-[3-(trifluoromethyl)phenyl]-3H-imidazo[4,5-b]pyridin-2-one; |
| 204 | 1-(2-Morpholino-2-oxo-ethyl)-6-[3-(trifluoromethyl)phenyl]-3H-imidazo[4,5-b]pyridin-2-one; |
| 205 | N-Cyclopentyl-2-[2-oxo-6-[3-(trifluoromethyl)phenyl]-3H-imidazo[4,5-b]pyridin-1-yl]acetamide; |
| 206 | 1-[2-Oxo-2-(1-piperidyl)ethyl]-6-[3-(trifluoromethyl)phenyl]-3H-imidazo[4,5-b]pyridin-2-one; |
| 207 | 1-[2-(2,6-Diazaspiro[3.3]heptan-6-yl)-2-oxo-ethyl]-6-[3-(trifluoromethyl)phenyl]-3H-imidazo[4,5-b]pyridin-2-one; |
| 208 | 2-[2-Oxo-6-[3-(trifluoromethyl)phenyl]-3H-imidazo[4,5-b]pyridin-1-yl]-N-(2-pyridyl)acetamide; |
| 209 | N-(3,3-Difluoro-1-methyl-cyclobutyl)-2-[2-oxo-6-[3-(trifluoromethyl)phenyl]-3H-imidazo[4,5-b]pyridin-1-yl]acetamide; |

-continued

| Ex # | Compound Name |
|---|---|
| 210 | 1-[(6-Methoxy-3-pyridyl)methyl]-6-[3-(trifluoromethyl)phenyl]-3H-imidazo[4,5-b]pyridin-2-one; |
| 211 | 1-(Cyclopropylmethyl)-6-[3-(trifluoromethyl)phenyl]-3H-imidazo[4,5-b]pyridin-2-one; |
| 212 | 3-[[2-Oxo-6-[3-(trifluoromethyl)phenyl]-3H-imidazo[4,5-b]pyridin-1-yl]methyl]benzonitrile; |
| 213 | 2-[[2-Oxo-6-[3-(trifluoromethyl)phenyl]-3H-imidazo[4,5-b]pyridin-1-yl]methyl]benzonitrile; |
| 214 | 1-[2-Oxo-2-(2-thienyl)ethyl]-6-[3-(trifluoromethyl)phenyl]-3H-imidazo[4,5-b]pyridin-2-one; |
| 215 | 1-(2-Oxo-2-thiazol-2-yl-ethyl)-6-[3-(trifluoromethyl)phenyl]-3H-imidazo[4,5-b]pyridin-2-one; |
| 216 | (R/S)-1-(Oxetan-2-ylmethyl)-6-[3-(trifluoromethyl)phenyl]-3H-imidazo[4,5-b]pyridin-2-one; |
| 217 | (R/S)-1-(Morpholin-2-ylmethyl)-6-[3-(trifluoromethyl)phenyl]-3H-imidazo[4,5-b]pyridin-2-one; |
| 218 | (R/S)-1-(Tetrahydropyran-2-ylmethyl)-6-[3-(trifluoromethyl)phenyl]-3H-imidazo[4,5-b]pyridin-2-one; |
| 219 | 6-[3-(Trifluoromethyl)phenyl]-1-[[4-(trifluoromethyl)phenyl]methyl]-3H-imidazo[4,5-b]pyridin-2-one; |
| 220 | 1-[(3-Fluoro-4-methoxy-phenyl)methyl]-6-[3-(trifluoromethyl)phenyl]-3H-imidazo[4,5-b]pyridin-2-one; |
| 221 | 1-[(4-Fluoro-3-methyl-phenyl)methyl]-6-[3-(trifluoromethyl)phenyl]-3H-imidazo[4,5-b]pyridin-2-one; |
| 222 | 1-[(3-Fluorophenyl)methyl]-6-[3-(trifluoromethyl)phenyl]-3H-imidazo[4,5-b]pyridin-2-one; |
| 223 | (R*)-1-(Oxetan-2-ylmethyl)-6-[3-(trifluoromethyl)phenyl]-3H-imidazo[4,5-b]pyridin-2-one; |
| 224 | (S*)-1-(Oxetan-2-ylmethyl)-6-[3-(trifluoromethyl)phenyl]-3H-imidazo[4,5-b]pyridin-2-one; |
| 225 | (R/S)-1-[(2,2-Difluorocyclopropyl)methyl]-6-[3-(trifluoromethyl)phenyl]-3H-imidazo[4,5-b]pyridin-2-one; |
| 226 | 1-[(3-Fluorooxetan-3-yl)methyl]-6-[3-(trifluoromethyl)phenyl]-3H-imidazo[4,5-b]pyridin-2-one; |
| 227 | 1-(Pyrimidin-2-ylmethyl)-6-[3-(trifluoromethyl)phenyl]-3H-imidazo[4,5-b]pyridin-2-one; |
| 228 | 1-(2-Pyridylmethyl)-6-[3-(trifluoromethyl)phenyl]-3H-imidazo[4,5-b]pyridin-2-one; |
| 229 | 1-(4-Pyridylmethyl)-6-[3-(trifluoromethyl)phenyl]-3H-imidazo[4,5-b]pyridin-2-one; |
| 230 | 1-(3-Pyridylmethyl)-6-[3-(trifluoromethyl)phenyl]-3H-imidazo[4,5-b]pyridin-2-one; |
| 231 | 1-[(2-Methylpyrimidin-5-yl)methyl]-6-[3-(trifluoromethyl)phenyl]-3H-imidazo[4,5-b]pyridin-2-one; |
| 232 | 1-(Pyridazin-3-ylmethyl)-6-[3-(trifluoromethyl)phenyl]-3H-imidazo[4,5-b]pyridin-2-one; |
| 233 | 1-[(3-Methoxy-2-pyridyl)methyl]-6-[3-(trifluoromethyl)phenyl]-3H-imidazo[4,5-b]pyridin-2-one; |
| 234 | 1-[(3-Fluoro-5-methyl-2-pyridyl)methyl]-6-[3-(trifluoromethyl)phenyl]-3H-imidazo[4,5-b]pyridin-2-one; |
| 235 | 1-[(6-Methyl-3-pyridyl)methyl]-6-[3-(trifluoromethyl)phenyl]-3H-imidazo[4,5-b]pyridin-2-one; |
| 236 | 1-(2H-Tetrazol-5-ylmethyl)-6-[3-(trifluoromethyl)phenyl]-3H-imidazo[4,5-b]pyridin-2-one; |
| 237 | 1-[Difluoro(3-pyridyl)methyl]-6-[3-(trifluoromethyl)phenyl]-3H-imidazo[4,5-b]pyridin-2-one; |
| 238 | 1-[(6-Fluoro-3-pyridyl)methyl]-6-[3-(trifluoromethyl)phenyl]-3H-imidazo[4,5-b]pyridin-2-one; |
| 239 | 1-(2-Cyclopropyl-2-oxo-ethyl)-6-[3-(trifluoromethyl)phenyl]-3H-imidazo[4,5-b]pyridin-2-one; |
| 240 | 1-(2-Oxobutyl)-6-[3-(trifluoromethyl)phenyl]-3H-imidazo[4,5-b]pyridin-2-one; |
| 241 | 1-(3-Methyl-2-oxo-butyl)-6-[3-(trifluoromethyl)phenyl]-3H-imidazo[4,5-b]pyridin-2-one; |
| 242 | 1-[(5-Methyl-3-pyridyl)methyl]-6-[3-(trifluoromethyl)phenyl]-3H-imidazo[4,5-b]pyridin-2-one; |
| 243 | 1-(Thiadiazol-4-ylmethyl)-6-[3-(trifluoromethyl)phenyl]-3H-imidazo[4,5-b]pyridin-2-one; |
| 244 | 1-[(6-Oxo-1H-pyridin-3-yl)methyl]-6-[3-(trifluoromethyl)phenyl]-3H-imidazo[4,5-b]pyridin-2-one; |
| 245 | (R/S)-1-(Azetidin-2-ylmethyl)-3-methyl-6-[3-(trifluoromethyl)phenyl]imidazo[4,5-b]pyridin-2-one; |
| 246 | 3-Methyl-1-(pyrimidin-4-ylmethyl)-6-[3-(trifluoromethyl)phenyl]imidazo[4,5-b]pyridin-2-one; |
| 247 | 3-Methyl-1-(pyrimidin-5-ylmethyl)-6-[3-(trifluoromethyl)phenyl]imidazo[4,5-b]pyridin-2-one; |

| Ex # | Compound Name |
|---|---|
| 248 | 3-Methyl-1-[(2-methylpyrimidin-4-yl)methyl]-6-[3-(trifluoromethyl)phenyl]imidazo[4,5-b]pyridin-2-one; |
| 249 | 3-Methyl-1-(pyrazin-2-ylmethyl)-6-[3-(trifluoromethyl)phenyl]imidazo[4,5-b]pyridin-2-one; |
| 250 | 3-Methyl-1-(4-pyridylmethyl)-6-[3-(trifluoromethyl)phenyl]imidazo[4,5-b]pyridin-2-one; |
| 251 | 3-Methyl-1-(2-pyridylmethyl)-6-[3-(trifluoromethyl)phenyl]imidazo[4,5-b]pyridin-2-one; |
| 252 | 1-[(6-Methoxypyridazin-3-yl)methyl]-6-[3-(trifluoromethyl)phenyl]-3H-imidazo[4,5-b]pyridin-2-one; |
| 253 | 1-(Pyrazin-2-ylmethyl)-6-[3-(trifluoromethyl)phenyl]-3H-imidazo[4,5-b]pyridin-2-one; |
| 254 | 1-[(2-Methylpyrimidin-4-yl)methyl]-6-[3-(trifluoromethyl)phenyl]-3H-imidazo[4,5-b]pyridin-2-one; |
| 255 | 1-(Pyrimidin-5-ylmethyl)-6-[3-(trifluoromethyl)phenyl]-3H-imidazo[4,5-b]pyridin-2-one; |
| 256 | 1-[(5-Fluoropyrimidin-2-yl)methyl]-6-[3-(trifluoromethyl)phenyl]-3H-imidazo[4,5-b]pyridin-2-one; |
| 257 | 6-[3-(Trifluoromethyl)phenyl]-1-[[6-(trifluoromethyl)-3-pyridyl]methyl]-3H-imidazo[4,5-b]pyridin-2-one; |
| 258 | 1-[(5-Fluoro-3-pyridyl)methyl]-6-[3-(trifluoromethyl)phenyl]-3H-imidazo[4,5-b]pyridin-2-one; |
| 259 | 6-[3-(Trifluoromethyl)phenyl]-1-[[5-(trifluoromethyl)-3-pyridyl]methyl]-3H-imidazo[4,5-b]pyridin-2-one; |
| 260 | 6-[3-(Trifluoromethyl)phenyl]-1-[[4-(trifluoromethyl)-3-pyridyl]methyl]-3H-imidazo[4,5-b]pyridin-2-one; |
| 261 | 3-Methyl-1-(pyrimidin-2-ylmethyl)-6-[3-(trifluoromethyl)phenyl]imidazo[4,5-b]pyridin-2-one; |
| 262 | 1-(2-cyclobutyl-2-oxo-ethyl)-6-[3-(trifluoromethyl)phenyl]-3H-imidazo[4,5-b]pyridin-2-one; |
| 263 | (R/S)-1-(Azetidin-2-ylmethyl)-6-[3-(trifluoromethyl)phenyl]-3H-imidazo[4,5-b]pyridin-2-one; |
| 264 | (R/S)-1-(Azetidin-2-ylmethyl)-6-[2-fluoro-3-(trifluoromethyl)phenyl]-3H-imidazo[4,5-b]pyridin-2-one; |
| 265 | (R/S)-1-(Azetidin-2-ylmethyl)-6-phenyl-3H-imidazo[4,5-b]pyridin-2-one; |
| 266 | (R/S)-1-(Azetidin-2-ylmethyl)-6-(4-fluorophenyl)-3H-imidazo[4,5-b]pyridin-2-one; |
| 267 | (R/S)-1-(Azetidin-2-ylmethyl)-6-[4-fluoro-3-(trifluoromethyl)phenyl]-3H-imidazo[4,5-b]pyridin-2-one; |
| 268 | (R/S)-1-(Azetidin-2-ylmethyl)-6-(2,3-dichlorophenyl)-3H-imidazo[4,5-b]pyridin-2-one; |
| 269 | 6-(4-Fluoro-3-methyl-phenyl)-1-[(5-methyl-3-pyridyl)methyl]-3H-imidazo[4,5-b]pyridin-2-one; |
| 270 | 6-(2,4-Difluoro-3-methyl-phenyl)-1-[(5-methyl-3-pyridyl)methyl]-3H-imidazo[4,5-b]pyridin-2-one; |
| 271 | (R/S)-6-[4-Fluoro-3-(trifluoromethyl)phenyl]-1-(oxetan-2-ylmethyl)-3H-imidazo[4,5-b]pyridin-2-one; |
| 272 | 6-(3,4-Difluorophenyl)-1-[(5-methyl-3-pyridyl)methyl]-3H-imidazo[4,5-b]pyridin-2-one; |
| 273 | 6-(3-Chlorophenyl)-1-[(5-methyl-3-pyridyl)methyl]-3H-imidazo[4,5-b]pyridin-2-one; |
| 274 | 6-(3-Fluorophenyl)-1-[(5-methyl-3-pyridyl)methyl]-3H-imidazo[4,5-b]pyridin-2-one; |
| 275 | 6-(3,4-Difluorophenyl)-1-[(4-methyl-3-pyridyl)methyl]-3H-imidazo[4,5-b]pyridin-2-one; |
| 276 | 6-(3-Fluorophenyl)-1-[(4-methyl-3-pyridyl)methyl]-3H-imidazo[4,5-b]pyridin-2-one; |
| 277 | 6-(4-Fluoro-3-methyl-phenyl)-1-[(4-methyl-3-pyridyl)methyl]-3H-imidazo[4,5-b]pyridin-2-one; |
| 278 | 6-(2,4-Difluoro-3-methyl-phenyl)-1-[(4-methyl-3-pyridyl)methyl]-3H-imidazo[4,5-b]pyridin-2-one; |
| 279 | 6-(3,4-Difluorophenyl)-1-(2-pyridylmethyl)-3H-imidazo[4,5-b]pyridin-2-one; |
| 280 | 6-(2,4-Difluoro-3-methyl-phenyl)-1-(2-pyridylmethyl)-3H-imidazo[4,5-b]pyridin-2-one; |
| 281 | 6-(3-Fluorophenyl)-1-(2-pyridylmethyl)-3H-imidazo[4,5-b]pyridin-2-one; |
| 282 | 6-(3-Chlorophenyl)-1-(2-pyridylmethyl)-3H-imidazo[4,5-b]pyridin-2-one; |
| 283 | 6-(4-Fluoro-3-methyl-phenyl)-1-(2-pyridylmethyl)-3H-imidazo[4,5-b]pyridin-2-one; |
| 284 | 6-(3,4-Difluorophenyl)-1-[(3-methyl-2-pyridyl)methyl]-3H-imidazo[4,5-b]pyridin-2-one; |
| 285 | 6-(3-Fluorophenyl)-1-[(3-methyl-2-pyridyl)methyl]-3H-imidazo[4,5-b]pyridin-2-one; |
| 286 | 6-(4-Fluorophenyl)-1-(2-pyridylmethyl)-3H-imidazo[4,5-b]pyridin-2-one; |
| 287 | 6-[3-(Difluoromethyl)phenyl]-1-(2-pyridylmethyl)-3H-imidazo[4,5-b]pyridin-2-one; |
| 288 | 6-(3-Methoxyphenyl)-1-(2-pyridylmethyl)-3H-imidazo[4,5-b]pyridin-2-one; |
| 289 | 6-(p-Tolyl)-1-(2-pyridylmethyl)-3H-imidazo[4,5-b]pyridin-2-one; |

-continued

| Ex # | Compound Name |
|---|---|
| 290 | 6-(3-fluorophenyl)-1-(3-pyridylmethyl)-3H-imidazo[4,5-b]pyridin-2-one; |
| 291 | 6-[3-(Difluoromethyl)phenyl]-1-(3-pyridylmethyl)-3H-imidazo[4,5-b]pyridin-2-one; |
| 292 | 6-(3,4-Difluorophenyl)-1-(3-pyridylmethyl)-3H-imidazo[4,5-b]pyridin-2-one; |
| 293 | 6-(2,4-Difluoro-3-methyl-phenyl)-1-(3-pyridylmethyl)-3H-imidazo[4,5-b]pyridin-2-one; |
| 294 | 6-(4-Fluoro-3-methyl-phenyl)-1-(3-pyridylmethyl)-3H-imidazo[4,5-b]pyridin-2-one; |
| 295 | 6-(4-Fluorophenyl)-1-(3-pyridylmethyl)-3H-imidazo[4,5-b]pyridin-2-one; |
| 296 | 6-(3-Chlorophenyl)-1-(3-pyridylmethyl)-3H-imidazo[4,5-b]pyridin-2-one; |
| 297 | 6-(m-Tolyl)-1-(3-pyridylmethyl)-3H-imidazo[4,5-b]pyridin-2-one; |
| 298 | 6-(3,4-Difluorophenyl)-1-[(5-fluoro-3-pyridyl)methyl]-3H-imidazo[4,5-b]pyridin-2-one; |
| 299 | 6-(4-Fluoro-3-methyl-phenyl)-1-[(5-fluoro-3-pyridyl)methyl]-3H-imidazo[4,5-b]pyridin-2-one; |
| 300 | 6-[3-(Difluoromethoxy)phenyl]-1-(3-pyridylmethyl)-3H-imidazo[4,5-b]pyridin-2-one; |
| 301 | 6-(2,4-Difluoro-3-methyl-phenyl)-1-[(5-fluoro-3-pyridyl)methyl]-3H-imidazo[4,5-b]pyridin-2-one; |
| 302 | 6-[3-(Difluoromethyl)phenyl]-1-[(5-fluoro-3-pyridyl)methyl]-3H-imidazo[4,5-b]pyridin-2-one; |
| 303 | 6-(2,3-Difluorophenyl)-1-[(5-fluoro-3-pyridyl)methyl]-3H-imidazo[4,5-b]pyridin-2-one; |
| 304 | 6-[3-(Difluoromethoxy)phenyl]-1-[(5-fluoro-3-pyridyl)methyl]-3H-imidazo[4,5-b]pyridin-2-one; |
| 305 | 6-(3-Chlorophenyl)-1-[(5-fluoro-3-pyridyl)methyl]-3H-imidazo[4,5-b]pyridin-2-one; |
| 306 | 6-(4-Chloro-3-methyl-phenyl)-1-[(5-fluoro-3-pyridyl)methyl]-3H-imidazo[4,5-b]pyridin-2-one; |
| 307 | 1-[(5-Fluoro-3-pyridyl)methyl]-6-[3-(trifluoromethoxy)phenyl]-3H-imidazo[4,5-b]pyridin-2-one; |
| 308 | 1-[(5-Methyl-3-pyridyl)methyl]-6-(3,4,5-trifluorophenyl)-3H-imidazo[4,5-b]pyridin-2-one; |
| 309 | 6-[4-Fluoro-3-(trifluoromethyl)phenyl]-1-[(5-methyl-3-pyridyl)methyl]-3H-imidazo[4,5-b]pyridin-2-one; |
| 310 | 6-(2,3-Difluorophenyl)-1-[(5-methyl-3-pyridyl)methyl]-3H-imidazo[4,5-b]pyridin-2-one; |
| 311 | 6-(3,5-Difluorophenyl)-1-[(5-methyl-3-pyridyl)methyl]-3H-imidazo[4,5-b]pyridin-2-one; |
| 312 | 1-[(4-Methyl-3-pyridyl)methyl]-6-(3,4,5-trifluorophenyl)-3H-imidazo[4,5-b]pyridin-2-one; |
| 313 | 1-[(4-Methyl-3-pyridyl)methyl]-6-[3-(trifluoromethyl)phenyl]-3H-imidazo[4,5-b]pyridin-2-one; |
| 314 | 6-[4-Fluoro-3-(trifluoromethyl)phenyl]-1-[(4-methyl-3-pyridyl)methyl]-3H-imidazo[4,5-b]pyridin-2-one; |
| 315 | 1-[(3-Methyl-2-pyridyl)methyl]-6-[3-(trifluoromethyl)phenyl]-3H-imidazo[4,5-b]pyridin-2-one; |
| 316 | 6-(4-Fluoro-3-methyl-phenyl)-1-[(3-methyl-2-pyridyl)methyl]-3H-imidazo[4,5-b]pyridin-2-one; |
| 317 | 6-(2,4-Difluoro-3-methyl-phenyl)-1-[(3-methyl-2-pyridyl)methyl]-3H-imidazo[4,5-b]pyridin-2-one; |
| 318 | 6-(3,5-Difluorophenyl)-1-[(3-methyl-2-pyridyl)methyl]-3H-imidazo[4,5-b]pyridin-2-one; |
| 319 | 6-(2,3-Difluorophenyl)-1-[(3-methyl-2-pyridyl)methyl]-3H-imidazo[4,5-b]pyridin-2-one; |
| 320 | 1-[2-(Azetidin-1-yl)-2-oxo-ethyl]-6-(4-fluoro-2-methyl-phenyl)-3H-imidazo[4,5-b]pyridin-2-one; |
| 321 | 2-[6-(5-Chloro-4-methyl-2-thienyl)-2-oxo-3H-imidazo[4,5-b]pyridin-1-yl]-N,N-dimethyl-acetamide; |
| 322 | 2-[6-(5-Chloro-4-methyl-2-thienyl)-3-methyl-2-oxo-imidazo[4,5-b]pyridin-1-yl]-N,N-dimethyl-acetamide; |
| 323 | 1-[2-(Azetidin-1-yl)-2-oxo-ethyl]-6-[5-(trifluoromethyl)-2-thienyl]-3H-imidazo[4,5-b]pyridin-2-one; |
| 324 | 1-[2-(Azetidin-1-yl)-2-oxo-ethyl]-6-(5-chloro-4-methyl-2-thienyl)-3H-imidazo[4,5-b]pyridin-2-one; |
| 325 | 1-[2-(Azetidin-1-yl)-2-oxo-ethyl]-6-(5-chloro-4-methyl-2-thienyl)-3-methyl-imidazo[4,5-b]pyridin-2-one; |
| 326 | 1-[2-(Azetidin-1-yl)-2-oxo-ethyl]-3-methyl-6-(5-methyl-2-thienyl)imidazo[4,5-b]pyridin-2-one; |
| 327 | 1-[2-(3-Fluoroazetidin-1-yl)-2-oxo-ethyl]-3-methyl-6-[5-(trifluoromethyl)-2-thienyl]imidazo[4,5-b]pyridin-2-one; |
| 328 | 3-Methyl-1-(2-oxo-2-pyrrolidin-1-yl-ethyl)-6-[5-(trifluoromethyl)-2-thienyl]imidazo[4,5-b]pyridin-2-one; |
| 329 | 1-[2-(Azetidin-1-yl)-2-oxo-ethyl]-6-[2-methyl-3-(trifluoromethyl)phenyl]-3H-imidazo[4,5-b]pyridin-2-one; |
| 330 | 6-(3,4-Difluorophenyl)-1-(2-oxobutyl)-3H-imidazo[4,5-b]pyridin-2-one; |

-continued

| Ex # | Compound Name |
|---|---|
| 331 | 6-(4-Fluoro-3-methyl-phenyl)-1-(2-oxobutyl)-3H-imidazo[4,5-b]pyridin-2-one; |
| 332 | 6-(m-Tolyl)-1-(2-oxobutyl)-3H-imidazo[4,5-b]pyridin-2-one; |
| 333 | (R/S)-6-(3,4-Difluorophenyl)-1-(2-hydroxybutyl)-3-methyl-imidazo[4,5-b]pyridin-2-one; |
| 334 | (R/S)-6-(4-Fluoro-3-methyl-phenyl)-1-(2-hydroxybutyl)-3H-imidazo[4,5-b]pyridin-2-one; |
| 335 | (R/S)-1-(2-Hydroxybutyl)-6-(m-tolyl)-3H-imidazo[4,5-b]pyridin-2-one; |
| 336 | (R/S)-6-(2,4-difluoro-3-methyl-phenyl)-1-(2-hydroxybutyl)-3H-imidazo[4,5-b]pyridin-2-one; |
| 337 | (R/S)-1-(2-Hydroxybutyl)-6-[3-(trifluoromethyl)phenyl]-3H-imidazo[4,5-b]pyridin-2-one; |
| 338 | (R/S)-1-(2-Hydroxy-3-methyl-butyl)-6-[3-(trifluoromethyl)phenyl]-3H-imidazo[4,5-b]pyridin-2-one; |
| 339 | 6-(2,4-Difluoro-3-methyl-phenyl)-3-methyl-1-(3-pyridylmethyl)imidazo[4,5-b]pyridin-2-one; |
| 340 | 6-(4-Fluoro-3-methyl-phenyl)-1-[(5-fluoro-3-pyridyl)methyl]-3-methyl-imidazo[4,5-b]pyridin-2-one; |
| 341 | 6-(2,4-Difluoro-3-methyl-phenyl)-1-[(5-fluoro-3-pyridyl)methyl]-3-methyl-imidazo[4,5-b]pyridin-2-one; |
| 342 | 6-[3-(Difluoromethoxy)phenyl]-1-[(5-fluoro-3-pyridyl)methyl]-3-methyl-imidazo[4,5-b]pyridin-2-one; |
| 343 | 6-(3,4-Difluorophenyl)-1-[(5-fluoro-3-pyridyl)methyl]-3-methyl-imidazo[4,5-b]pyridin-2-one; |
| 344 | 1-[(5-Fluoro-3-pyridyl)methyl]-3-methyl-6-(3,4,5-trifluorophenyl)imidazo[4,5-b]pyridin-2-one; |
| 345 | 1-[(5-Fluoro-3-pyridyl)methyl]-3-methyl-6-[3-(trifluoromethoxy)phenyl]imidazo[4,5-b]pyridin-2-one; |
| 346 | 6-(2,3-Difluorophenyl)-1-[(5-fluoro-3-pyridyl)methyl]-3-methyl-imidazo[4,5-b]pyridin-2-one; |
| 347 | 1-[(5-Fluoro-3-pyridyl)methyl]-3-methyl-6-(2,3,4-trifluorophenyl)imidazo[4,5-b]pyridin-2-one; |
| 348 | 6-(3-Chlorophenyl)-1-[(5-fluoro-3-pyridyl)methyl]-3-methyl-imidazo[4,5-b]pyridin-2-one; |
| 349 | 6-(3-Chloro-2-fluoro-phenyl)-1-[(5-fluoro-3-pyridyl)methyl]-3-methyl-imidazo[4,5-b]pyridin-2-one; |
| 350 | 1-[(5-Fluoro-3-pyridyl)methyl]-3-methyl-6-(m-tolyl)imidazo[4,5-b]pyridin-2-one; |
| 351 | 6-(3,4-Dichlorophenyl)-1-[(5-fluoro-3-pyridyl)methyl]-3-methyl-imidazo[4,5-b]pyridin-2-one; |
| 352 | 6-(2-Fluoro-3-methyl-phenyl)-1-[(5-fluoro-3-pyridyl)methyl]-3-methyl-imidazo[4,5-b]pyridin-2-one; |
| 353 | 3-Methyl-1-(3-pyridylmethyl)-6-(3,4,5-trifluorophenyl)imidazo[4,5-b]pyridin-2-one; |
| 354 | 6-(3,5-Difluorophenyl)-3-methyl-1-(3-pyridylmethyl)imidazo[4,5-b]pyridin-2-one; |
| 355 | 6-(3-Chloro-4-fluoro-phenyl)-3-methyl-1-(3-pyridylmethyl)imidazo[4,5-b]pyridin-2-one; |
| 356 | 3-Methyl-6-(m-tolyl)-1-(3-pyridylmethyl)imidazo[4,5-b]pyridin-2-one; |
| 357 | 6-(2-Fluoro-3-methyl-phenyl)-3-methyl-1-(3-pyridylmethyl)imidazo[4,5-b]pyridin-2-one; |
| 358 | 6-[2-Fluoro-3-(trifluoromethyl)phenyl]-3-methyl-1-(3-pyridylmethyl)imidazo[4,5-b]pyridin-2-one; |
| 359 | 6-(3-Chloro-2-fluoro-phenyl)-3-methyl-1-(3-pyridylmethyl)imidazo[4,5-b]pyridin-2-one; |
| 360 | 6-[4-Fluoro-3-(trifluoromethyl)phenyl]-3-methyl-1-(3-pyridylmethyl)imidazo[4,5-b]pyridin-2-one; |
| 361 | 3-Methyl-1-(3-pyridylmethyl)-6-(2,3,4-trifluorophenyl)imidazo[4,5-b]pyridin-2-one; |
| 362 | 3-Methyl-1-(3-pyridylmethyl)-6-[3-(trifluoromethyl)phenyl]imidazo[4,5-b]pyridin-2-one; |
| 363 | 6-[3-(Difluoromethyl)phenyl]-3-methyl-1-(3-pyridylmethyl)imidazo[4,5-b]pyridin-2-one; |
| 364 | 3-Methyl-1-(3-pyridylmethyl)-6-[5-(trifluoromethyl)-2-thienyl]imidazo[4,5-b]pyridin-2-one; |
| 365 | 6-(5-Chloro-4-methyl-2-thienyl)-3-methyl-1-(3-pyridylmethyl)imidazo[4,5-b]pyridin-2-one; |
| 366 | 1-[(5-Chloro-3-pyridyl)methyl]-3-methyl-6-[3-(trifluoromethyl)phenyl]imidazo[4,5-b]pyridin-2-one; |
| 367 | 1-[(5-Chloro-3-pyridyl)methyl]-6-(4-fluoro-3-methyl-phenyl)-3-methyl-imidazo[4,5-b]pyridin-2-one; |
| 368 | 1-[(5-Chloro-3-pyridyl)methyl]-6-(2,4-difluoro-3-methyl-phenyl)-3-methyl-imidazo[4,5-b]pyridin-2-one; |
| 369 | 1-[(5-Chloro-3-pyridyl)methyl]-6-(3,4-difluorophenyl)-3-methyl-imidazo[4,5-b]pyridin-2-one; |
| 370 | 1-[(5-Chloro-3-pyridyl)methyl]-3-methyl-6-(3,4,5-trifluorophenyl)imidazo[4,5-b]pyridin-2-one; |

| Ex # | Compound Name |
|---|---|
| 371 | 1-[(5-Chloro-3-pyridyl)methyl]-6-(2-fluoro-3-methyl-phenyl)-3-methyl-imidazo[4,5-b]pyridin-2-one; |
| 372 | 6-(5-Chloro-4-methyl-2-thienyl)-1-[(5-chloro-3-pyridyl)methyl]-3-methyl-imidazo[4,5-b]pyridin-2-one; |
| 373 | 1-[(5-Chloro-3-pyridyl)methyl]-3-methyl-6-[5-(trifluoromethyl)-2-thienyl]imidazo[4,5-b]pyridin-2-one; |
| 374 | 1-[(5-Chloro-3-pyridyl)methyl]-3-methyl-6-(m-tolyl)imidazo[4,5-b]pyridin-2-one; |
| 375 | 1-[(5-Chloro-3-pyridyl)methyl]-6-(2,3-difluorophenyl)-3-methyl-imidazo[4,5-b]pyridin-2-one; |
| 376 | 6-(3-Chlorophenyl)-3-methyl-1-(pyridazin-3-ylmethyl)imidazo[4,5-b]pyridin-2-one; |
| 377 | 6-[3-(Difluoromethyl)phenyl]-3-methyl-1-(pyridazin-3-ylmethyl)imidazo[4,5-b]pyridin-2-one; |
| 378 | 3-Methyl-1-(pyridazin-3-ylmethyl)-6-[3-(trifluoromethyl)phenyl]imidazo[4,5-b]pyridin-2-one; |
| 379 | 3-Methyl-6-(m-tolyl)-1-(pyridazin-3-ylmethyl)imidazo[4,5-b]pyridin-2-one; |
| 380 | 6-(3-Chloro-4-fluoro-phenyl)-3-methyl-1-(pyridazin-3-ylmethyl)imidazo[4,5-b]pyridin-2-one; |
| 381 | 6-(3-Fluoro-5-methyl-phenyl)-3-methyl-1-(pyridazin-3-ylmethyl)imidazo[4,5-b]pyridin-2-one; |
| 382 | 6-[4-Fluoro-3-(trifluoromethyl)phenyl]-3-methyl-1-(pyridazin-3-ylmethyl)imidazo[4,5-b]pyridin-2-one; |
| 383 | 6-[3-Fluoro-5-(trifluoromethyl)phenyl]-3-methyl-1-(pyridazin-3-ylmethyl)imidazo[4,5-b]pyridin-2-one; |
| 384 | 6-[4-Chloro-3-(trifluoromethyl)phenyl]-3-methyl-1-(pyridazin-3-ylmethyl)imidazo[4,5-b]pyridin-2-one; |
| 387 | 6-[3,4-Difluoro-5-(trifluoromethyl)phenyl]-3-methyl-1-(pyridazin-3-ylmethyl)imidazo[4,5-b]pyridin-2-one; |
| 388 | 3-Methyl-1-(2-oxobutyl)-6-[3-(trifluoromethyl)phenyl]imidazo[4,5-b]pyridin-2-one; |
| 389 | 6-(4-Fluoro-3-methyl-phenyl)-3-methyl-1-(2-oxobutyl)imidazo[4,5-b]pyridin-2-one; |
| 390 | 6-(3,4-Difluorophenyl)-3-methyl-1-(2-oxobutyl)imidazo[4,5-b]pyridin-2-one; |
| 391 | 6-(2,4-Difluoro-3-methyl-phenyl)-3-methyl-1-(2-oxobutyl)imidazo[4,5-b]pyridin-2-one; |
| 392 | 6-(3-Cyclopropylphenyl)-3-methyl-1-(2-oxobutyl)imidazo[4,5-b]pyridin-2-one; |
| 393 | (R/S)-6-(4-Fluoro-3-methyl-phenyl)-1-(2-hydroxy-4-methoxy-butyl)-3-methyl-imidazo[4,5-b]pyridin-2-one; |
| 394 | (R/S)-6-[3-(Difluoromethyl)phenyl]-3-methyl-1-(oxetan-2-ylmethyl)imidazo[4,5-b]pyridin-2-one; |
| 395 | (R/S)-6-(4-Fluoro-3-methyl-phenyl)-3-methyl-1-(oxetan-2-ylmethyl)imidazo[4,5-b]pyridin-2-one; |
| 396 | (R/S)-6-[2-Fluoro-3-(trifluoromethyl)phenyl]-3-methyl-1-(oxetan-2-ylmethyl)imidazo[4,5-b]pyridin-2-one; |
| 397 | (R/S)-6-(3-Chlorophenyl)-3-methyl-1-(oxetan-2-ylmethyl)imidazo[4,5-b]pyridin-2-one; |
| 398 | (R/S)-3-Methyl-6-[2-methyl-3-(trifluoromethyl)phenyl]-1-(oxetan-2-ylmethyl)imidazo[4,5-b]pyridin-2-one; |
| 399 | (R/S)-1-(2,4-Dihydroxybutyl)-3-methyl-6-[2-methyl-3-(trifluoromethyl)phenyl]imidazo[4,5-b]pyridin-2-one; |
| 400 | 6-(2,4-Difluoro-3-methyl-phenyl)-1-[2-(3-fluoroazetidin-1-yl)-2-oxo-ethyl]-3-methyl-imidazo[4,5-b]pyridin-2-one; |
| 401 | 1-[2-(3-Fluoroazetidin-1-yl)-2-oxo-ethyl]-6-(4-fluoro-3-methyl-phenyl)-3-methyl-imidazo[4,5-b]pyridin-2-one; |
| 402 | 1-[2-(3-Fluoroazetidin-1-yl)-2-oxo-ethyl]-3-methyl-6-(3,4,5-trifluorophenyl)imidazo[4,5-b]pyridin-2-one; |
| 403 | 6-(3,4-Difluorophenyl)-1-[2-(3-fluoroazetidin-1-yl)-2-oxo-ethyl]-3-methyl-imidazo[4,5-b]pyridin-2-one; |
| 404 | 1-[2-(3-Fluoroazetidin-1-yl)-2-oxo-ethyl]-3-methyl-6-(m-tolyl)imidazo[4,5-b]pyridin-2-one; |
| 405 | 1-[2-(3-Fluoroazetidin-1-yl)-2-oxo-ethyl]-6-(2-fluoro-3-methyl-phenyl)-3-methyl-imidazo[4,5-b]pyridin-2-one; |
| 406 | 6-(3-Chlorophenyl)-1-[2-(3-fluoroazetidin-1-yl)-2-oxo-ethyl]-3-methyl-imidazo[4,5-b]pyridin-2-one; |
| 407 | 1-[2-(3-Fluoroazetidin-1-yl)-2-oxo-ethyl]-6-[4-fluoro-3-(trifluoromethyl)phenyl]-3-methyl-imidazo[4,5-b]pyridin-2-one; |
| 408 | 1-[2-(Azetidin-1-yl)-2-oxo-ethyl]-3-methyl-6-[3-(trifluoromethyl)phenyl]imidazo[4,5-b]pyridin-2-one; |
| 409 | 1-[2-(Azetidin-1-yl)-2-oxo-ethyl]-6-(2,4-difluoro-3-methyl-phenyl)-3-methyl-imidazo[4,5-b]pyridin-2-one; |
| 410 | 1-[2-(Azetidin-1-yl)-2-oxo-ethyl]-6-(4-fluoro-3-methyl-phenyl)-3-methyl-imidazo[4,5-b]pyridin-2-one; |
| 411 | 1-[2-(Azetidin-1-yl)-2-oxo-ethyl]-3-methyl-6-(3,4,5-trifluorophenyl)imidazo[4,5-b]pyridin-2-one; |

-continued

| Ex # | Compound Name |
|---|---|
| 412 | 1-[2-(Azetidin-1-yl)-2-oxo-ethyl]-6-(3,5-difluorophenyl)-3-methyl-imidazo[4,5-b]pyridin-2-one; |
| 413 | 1-(2-(3,3-Difluoroazetidin-1-yl)-2-oxoethyl)-6-(4-fluoro-3-methylphenyl)-3-methyl-1H-imidazo[4,5-b]pyridin-2(3H)-one; |
| 414 | 1-[2-(3,3-Difluoroazetidin-1-yl)-2-oxo-ethyl]-6-(2,4-difluoro-3-methyl-phenyl)-3-methyl-imidazo[4,5-b]pyridin-2-one; |
| 415 | 1-[2-(3,3-Difluoroazetidin-1-yl)-2-oxo-ethyl]-6-[2-fluoro-3-(trifluoromethyl)phenyl]-3-methyl-imidazo[4,5-b]pyridin-2-one; |
| 416 | 1-[2-(3,3-Difluoroazetidin-1-yl)-2-oxo-ethyl]-6-(3,4-difluorophenyl)-3-methyl-imidazo[4,5-b]pyridin-2-one; |
| 417 | 1-[2-(3,3-Difluoroazetidin-1-yl)-2-oxo-ethyl]-6-(3-fluorophenyl)-3-methyl-imidazo[4,5-b]pyridin-2-one; |
| 418 | 1-[2-(3,3-Difluoroazetidin-1-yl)-2-oxo-ethyl]-6-(2-fluoro-3-methyl-phenyl)-3-methyl-imidazo[4,5-b]pyridin-2-one; |
| 419 | N,N-Dimethyl-2-[3-methyl-2-oxo-6-[3-(trifluoromethyl)phenyl]imidazo[4,5-b]pyridin-1-yl]acetamide; |
| 420 | 2-[6-(4-Fuoro-3-methyl-phenyl)-3-methyl-2-oxo-imidazo[4,5-b]pyridin-1-yl]-N,N-dimethyl-acetamide; |
| 421 | 2-[6-(3,4-Difluorophenyl)-3-methyl-2-oxo-imidazo[4,5-b]pyridin-1-yl]-N,N-dimethyl-acetamide; |
| 422 | 1-[2-(Azetidin-1-yl)-2-oxo-ethyl]-6-(3,4-difluorophenyl)-3-methyl-imidazo[4,5-b]pyridin-2-one; |
| 423 | 2-[6-(2,4-Difluoro-3-methyl-phenyl)-3-methyl-2-oxo-imidazo[4,5-b]pyridin-1-yl]-N,N-dimethyl-acetamide; |
| 424 | 2-[6-[2-Fluoro-3-(trifluoromethyl)phenyl]-3-methyl-2-oxo-imidazo[4,5-b]pyridin-1-yl]-N,N-dimethyl-acetamide; |
| 425 | 2-[6-(2,3-Difluorophenyl)-3-methyl-2-oxo-imidazo[4,5-b]pyridin-1-yl]-N,N-dimethyl-acetamide; |
| 426 | 2-[6-[3-(Difluoromethyl)phenyl]-3-methyl-2-oxo-imidazo[4,5-b]pyridin-1-yl]-N,N-dimethyl-acetamide; |
| 427 | 2-[6-(2-Fluoro-3-methyl-phenyl)-3-methyl-2-oxo-imidazo[4,5-b]pyridin-1-yl]-N,N-dimethyl-acetamide; |
| 428 | 2-[6-(3,5-Difluorophenyl)-3-methyl-2-oxo-imidazo[4,5-b]pyridin-1-yl]-N,N-dimethyl-acetamide; |
| 429 | N,N-Dimethyl-2-[3-methyl-2-oxo-6-(3-pyridyl)imidazo[4,5-b]pyridin-1-yl]acetamide; |
| 430 | 1-[2-(3,3-Difluoroazetidin-1-yl)-2-oxo-ethyl]-3-methyl-6-[5-(trifluoromethyl)-2-thienyl]imidazo[4,5-b]pyridin-2-one; |
| 431 | 2-[6-[3,4-Difluoro-5-(trifluoromethyl)phenyl]-3-methyl-2-oxo-imidazo[4,5-b]pyridin-1-yl]-N,N-dimethyl-acetamide; |
| 432 | 2-[2-Oxo-6-[3-(trifluoromethyl)phenyl]-3H-imidazo[4,5-b]pyridin-1-yl]acetamide; |
| 433 | 2-[6-(4-Fluoro-2-methoxy-phenyl)-2-oxo-3H-imidazo[4,5-b]pyridin-1-yl]acetamide; |
| 434 | 2-[6-(3-Chloro-4-fluoro-phenyl)-2-oxo-3H-imidazo[4,5-b]pyridin-1-yl]acetamide; |
| 435 | N-Methyl-2-[2-oxo-6-[3-(trifluoromethyl)phenyl]-3H-imidazo[4,5-b]pyridin-1-yl]acetamide; |
| 436 | 2-[6-(4-Chlorophenyl)-2-oxo-3H-imidazo[4,5-b]pyridin-1-yl]-N-methyl-acetamide; |
| 437 | 2-[6-(4-Fluoro-2-methyl-phenyl)-2-oxo-3H-imidazo[4,5-b]pyridin-1-yl]-N-methyl-acetamide; |
| 438 | 2-[6-(3,5-Dimethylphenyl)-2-oxo-3H-imidazo[4,5-b]pyridin-1-yl]-N-methyl-acetamide; |
| 439 | 2-[6-(4-Methoxy-3-methyl-phenyl)-2-oxo-3H-imidazo[4,5-b]pyridin-1-yl]-N-methyl-acetamide; |
| 440 | 2-[6-(4-Fluoro-2-methoxy-phenyl)-2-oxo-3H-imidazo[4,5-b]pyridin-1-yl]-N-methyl-acetamide; |
| 441 | 2-[6-(2-Ethoxyphenyl)-2-oxo-3H-imidazo[4,5-b]pyridin-1-yl]-N-methyl-acetamide; |
| 442 | N-(2-Methoxyethyl)-2-[2-oxo-6-[3-(trifluoromethyl)phenyl]-3H-imidazo[4,5-b]pyridin-1-yl]acetamide; |
| 443 | 2-[6-(2-Ethoxy-5-fluoro-phenyl)-2-oxo-3H-imidazo[4,5-b]pyridin-1-yl]-N-(2-methoxyethyl)acetamide; |
| 444 | N-(2-Methoxyethyl)-2-[6-(4-methoxyphenyl)-2-oxo-3H-imidazo[4,5-b]pyridin-1-yl]acetamide; |
| 445 | N-(2-Methoxyethyl)-2-[2-oxo-6-(3-pyridyl)-3H-imidazo[4,5-b]pyridin-1-yl]acetamide; |
| 446 | 2-[6-(4-Fluoro-2-methoxy-phenyl)-2-oxo-3H-imidazo[4,5-b]pyridin-1-yl]-N-(2-methoxyethyl)acetamide; |
| 447 | N-Cyclopropyl-2-[6-(3,5-difluorophenyl)-2-oxo-3H-imidazo[4,5-b]pyridin-1-yl]acetamide; |
| 448 | 2-[6-(3-Chloro-4-fluoro-phenyl)-2-oxo-3H-imidazo[4,5-b]pyridin-1-yl]-N-cyclopropyl-acetamide; |
| 449 | N-Cyclopropyl-2-[6-(3-ethoxyphenyl)-2-oxo-3H-imidazo[4,5-b]pyridin-1-yl]acetamide; |

-continued

| Ex # | Compound Name |
|---|---|
| 450 | N-Cyclopropyl-2-[6-(3-methoxyphenyl)-2-oxo-3H-imidazo[4,5-b]pyridin-1-yl]acetamide; |
| 451 | N-Cyclopropyl-2-[6-(4-methoxy-3-methyl-phenyl)-2-oxo-3H-imidazo[4,5-b]pyridin-1-yl]acetamide; |
| 452 | N-Cyclopropyl-2-[6-(4-fluoro-2-methoxy-phenyl)-2-oxo-3H-imidazo[4,5-b]pyridin-1-yl]acetamide; |
| 453 | 2-[6-(4-Chlorophenyl)-2-oxo-3H-imidazo[4,5-b]pyridin-1-yl]-N-cyclopropyl-acetamide; |
| 454 | N-Cyclopropyl-2-[6-(2,4-dimethoxyphenyl)-2-oxo-3H-imidazo[4,5-b]pyridin-1-yl]acetamide; |
| 455 | N-Cyclopropyl-2-[6-(2-fluoro-6-methoxy-phenyl)-2-oxo-3H-imidazo[4,5-b]pyridin-1-yl]acetamide; |
| 456 | N-Cyclopropyl-2-[6-(2-ethoxyphenyl)-2-oxo-3H-imidazo[4,5-b]pyridin-1-yl]acetamide; |
| 457 | 6-(3-Fluoro-4-methoxy-phenyl)-1-[2-oxo-2-(2-thienyl)ethyl]-3H-imidazo[4,5-b]pyridin-2-one; |
| 458 | 6-(2-Ethoxyphenyl)-1-[2-oxo-2-(2-thienyl)ethyl]-3H-imidazo[4,5-b]pyridin-2-one; |
| 459 | 6-(4-Chlorophenyl)-1-[2-oxo-2-(2-thienyl)ethyl]-3H-imidazo[4,5-b]pyridin-2-one; |
| 460 | 6-(2-Ethoxy-5-fluoro-phenyl)-1-[2-oxo-2-(2-thienyl)ethyl]-3H-imidazo[4,5-b]pyridin-2-one; |
| 461 | 6-(4-Methoxyphenyl)-1-[2-oxo-2-(2-thienyl)ethyl]-3H-imidazo[4,5-b]pyridin-2-one; |
| 462 | 6-(4-Fluoro-2-methoxy-phenyl)-1-[2-oxo-2-(2-thienyl)ethyl]-3H-imidazo[4,5-b]pyridin-2-one; |
| 463 | 6-(3-Ethoxyphenyl)-1-[2-oxo-2-(2-thienyl)ethyl]-3H-imidazo[4,5-b]pyridin-2-one; |
| 464 | 6-(3-Chloro-4-fluoro-phenyl)-1-[2-oxo-2-(2-thienyl)ethyl]-3H-imidazo[4,5-b]pyridin-2-one; |
| 465 | 1-(Cyclopropylmethyl)-6-(2,4-dimethoxyphenyl)-3H-imidazo[4,5-b]pyridin-2-one; |
| 466 | 1-(Cyclopropylmethyl)-6-(2-ethoxy-5-fluoro-phenyl)-3H-imidazo[4,5-b]pyridin-2-one; |
| 467 | 1-(Cyclopropylmethyl)-6-(4-fluoro-2-methoxy-phenyl)-3H-imidazo[4,5-b]pyridin-2-one; |
| 468 | 1-(Cyclopropylmethyl)-6-(4-methoxy-3-methyl-phenyl)-3H-imidazo[4,5-b]pyridin-2-one; |
| 469 | 1-(Cyclopropylmethyl)-6-(3-fluoro-4-methoxy-phenyl)-3H-imidazo[4,5-b]pyridin-2-one; |
| 470 | 1-(Cyclopropylmethyl)-6-(3,5-difluorophenyl)-3H-imidazo[4,5-b]pyridin-2-one; |
| 471 | 1-(Cyclopropylmethyl)-6-(4-methoxyphenyl)-3H-imidazo[4,5-b]pyridin-2-one; |
| 472 | 1-(Cyclopropylmethyl)-6-(2-thienyl)-3H-imidazo[4,5-b]pyridin-2-one; |
| 473 | 1-(Cyclopropylmethyl)-6-[3-(dimethylamino)phenyl]-3H-imidazo[4,5-b]pyridin-2-one; |
| 474 | 1-(Cyclopropylmethyl)-6-(3,5-dimethylphenyl)-3H-imidazo[4,5-b]pyridin-2-one; |
| 475 | 6-(3-Methoxyphenyl)-1-(tetrahydrofuran-2-ylmethyl)-3H-imidazo[4,5-b]pyridin-2-one; |
| 476 | 4-[[6-(4-Methoxyphenyl)-2-oxo-3H-imidazo[4,5-b]pyridin-1-yl]methyl]benzonitrile; |
| 477 | 3-[[6-(4-Methoxyphenyl)-2-oxo-3H-imidazo[4,5-b]pyridin-1-yl]methyl]benzonitrile; |
| 478 | 3-[[6-(4-Fluoro-2-methoxy-phenyl)-2-oxo-3H-imidazo[4,5-b]pyridin-1-yl]methyl]benzonitrile; |
| 479 | 3-[[6-(4-Fluoro-2-methyl-phenyl)-2-oxo-3H-imidazo[4,5-b]pyridin-1-yl]methyl]benzonitrile; |
| 480 | 3-[[6-(3-Chloro-4-fluoro-phenyl)-2-oxo-3H-imidazo[4,5-b]pyridin-1-yl]methyl]benzonitrile; |
| 481 | 2-[[6-(2-Fluoro-6-methoxy-phenyl)-2-oxo-3H-imidazo[4,5-b]pyridin-1-yl]methyl]benzonitrile; |
| 482 | 2-[[6-(4-Chlorophenyl)-2-oxo-3H-imidazo[4,5-b]pyridin-1-yl]methyl]benzonitrile; |
| 483 | 2-[[6-(4-Fluoro-2-methyl-phenyl)-2-oxo-3H-imidazo[4,5-b]pyridin-1-yl]methyl]benzonitrile; |
| 484 | 2-[[6-(2-Ethoxyphenyl)-2-oxo-3H-imidazo[4,5-b]pyridin-1-yl]methyl]benzonitrile; |
| 485 | 2-[[6-(3-Methoxyphenyl)-2-oxo-3H-imidazo[4,5-b]pyridin-1-yl]methyl]benzonitrile; |
| 486 | 2-[[6-(3-Cyanophenyl)-2-oxo-3H-imidazo[4,5-b]pyridin-1-yl]methyl]benzonitrile; |
| 487 | 2-[[6-(2,4-Dimethoxyphenyl)-2-oxo-3H-imidazo[4,5-b]pyridin-1-yl]methyl]benzonitrile; |
| 488 | 2-[[6-(3,5-Dimethylphenyl)-2-oxo-3H-imidazo[4,5-b]pyridin-1-yl]methyl]benzonitrile; |

| Ex # | Compound Name |
| --- | --- |
| 489 | 2-[[6-(2-Ethoxy-5-fluoro-phenyl)-2-oxo-3H-imidazo[4,5-b]pyridin-1-yl]methyl]benzonitrile; |
| 490 | 2-[[6-(4-Fluoro-2-methoxy-phenyl)-2-oxo-3H-imidazo[4,5-b]pyridin-1-yl]methyl]benzonitrile; |
| 491 | 2-[[6-(3-Fluoro-4-methoxy-phenyl)-2-oxo-3H-imidazo[4,5-b]pyridin-1-yl]methyl]benzonitrile; |
| 492 | 6-(4-Fluoro-2-methyl-phenyl)-1-[(4-fluorophenyl)methyl]-3H-imidazo[4,5-b]pyridin-2-one; |
| 493 | 6-(2,3-Dimethoxyphenyl)-1-[(4-fluorophenyl)methyl]-3H-imidazo[4,5-b]pyridin-2-one; |
| 494 | 6-(2-Ethoxy-5-fluoro-phenyl)-1-[(3-fluorophenyl)methyl]-3H-imidazo[4,5-b]pyridin-2-one; |
| 495 | 6-(3,5-Dimethylphenyl)-1-[(3-fluorophenyl)methyl]-3H-imidazo[4,5-b]pyridin-2-one; |
| 496 | 6-(2,4-Dimethoxyphenyl)-1-[(3-fluorophenyl)methyl]-3H-imidazo[4,5-b]pyridin-2-one; |
| 497 | 6-(2-Ethoxyphenyl)-1-[(3-fluorophenyl)methyl]-3H-imidazo[4,5-b]pyridin-2-one; |
| 498 | 1-[(3-Fluorophenyl)methyl]-6-(4-methoxy-3-methyl-phenyl)-3H-imidazo[4,5-b]pyridin-2-one; |
| 499 | 6-(4-Fluoro-2-methoxy-phenyl)-1-[(3-fluorophenyl)methyl]-3H-imidazo[4,5-b]pyridin-2-one; |
| 500 | 6-[3-(Dimethylamino)phenyl]-1-[(3-fluorophenyl)methyl]-3H-imidazo[4,5-b]pyridin-2-one; |
| 501 | 6-(4-Fluoro-2-methoxy-phenyl)-1-[(4-fluorophenyl)methyl]-3H-imidazo[4,5-b]pyridin-2-one; |
| 502 | 6-(3-Chloro-4-fluoro-phenyl)-1-[(4-fluorophenyl)methyl]-3H-imidazo[4,5-b]pyridin-2-one; |
| 503 | 6-(2-Ethoxyphenyl)-1-[(2-fluorophenyl)methyl]-3H-imidazo[4,5-b]pyridin-2-one; |
| 504 | 1-[(3-Chlorophenyl)methyl]-6-(3,5-difluorophenyl)-3H-imidazo[4,5-b]pyridin-2-one; |
| 505 | 6-(4-Fluoro-2-methoxy-phenyl)-1-[(3-methoxyphenyl)methyl]-3H-imidazo[4,5-b]pyridin-2-one; |
| 506 | 1-[(3-Methoxyphenyl)methyl]-6-(3-pyridyl)-3H-imidazo[4,5-b]pyridin-2-one; |
| 507 | 1-[(3-Methoxyphenyl)methyl]-6-(4-methyl-2-thienyl)-3H-imidazo[4,5-b]pyridin-2-one; |
| 508 | 6-(3,5-Difluorophenyl)-1-[(4-methoxyphenyl)methyl]-3H-imidazo[4,5-b]pyridin-2-one; |
| 509 | 1-[(3,5-Dimethoxyphenyl)methyl]-6-(2-fluoro-6-methoxy-phenyl)-3H-imidazo[4,5-b]pyridin-2-one; |
| 510 | 1-[(3,5-Dimethoxyphenyl)methyl]-6-[3-(trifluoromethyl)phenyl]-3H-imidazo[4,5-b]pyridin-2-one; |
| 511 | 6-(4-Chlorophenyl)-1-[(4-isopropylphenyl)methyl]-3H-imidazo[4,5-b]pyridin-2-one; |
| 512 | 6-(4-tert-Butylphenyl)-1-[(3,4-dimethoxy-2-pyridyl)methyl]-3H-imidazo[4,5-b]pyridin-2-one; |
| 513 | 3-[1-[(3,5-Dimethylisoxazol-4-yl)methyl]-2-oxo-3H-imidazo[4,5-b]pyridin-6-yl]benzonitrile; |
| 514 | 1-[(3,5-Dimethylisoxazol-4-yl)methyl]-6-(2-ethoxy-5-fluoro-phenyl)-3H-imidazo[4,5-b]pyridin-2-one; |
| 515 | 6-(4-Methoxy-3-methyl-phenyl)-1-[(5-methylisoxazol-3-yl)methyl]-3H-imidazo[4,5-b]pyridin-2-one; |
| 516 | 6-(3,5-Dimethylphenyl)-1-[(5-methylisoxazol-3-yl)methyl]-3H-imidazo[4,5-b]pyridin-2-one; |
| 517 | 6-(2-Ethoxyphenyl)-1-[(5-methylisoxazol-3-yl)methyl]-3H-imidazo[4,5-b]pyridin-2-one; |
| 518 | 6-(2,4-Dimethoxyphenyl)-1-[(5-methylisoxazol-3-yl)methyl]-3H-imidazo[4,5-b]pyridin-2-one; |
| 519 | 6-(3-Fluoro-4-methoxy-phenyl)-1-[(5-methylisoxazol-3-yl)methyl]-3H-imidazo[4,5-b]pyridin-2-one; |
| 520 | 6-(4-Fluoro-2-methoxy-phenyl)-1-[(5-methylisoxazol-3-yl)methyl]-3H-imidazo[4,5-b]pyridin-2-one; |
| 521 | 6-(2-Ethoxy-5-fluoro-phenyl)-1-[(5-methylisoxazol-3-yl)methyl]-3H-imidazo[4,5-b]pyridin-2-one; |
| 522 | 6-(4-Fluoro-2-methyl-phenyl)-1-[(5-methylisoxazol-3-yl)methyl]-3H-imidazo[4,5-b]pyridin-2-one; |
| 523 | 6-(3,5-Difluorophenyl)-1-[(5-methylisoxazol-3-yl)methyl]-3H-imidazo[4,5-b]pyridin-2-one; |
| 532 | N-(3-Chloropropyl)-2-[3-methyl-2-oxo-6-[5-(trifluoromethyl)-2-thienyl]imidazo[4,5-b]pyridin-1-yl]acetamide; |
| 533 | 2-[6-[3-(Difluoromethyl)-4-fluoro-phenyl]-3-methyl-2-oxo-imidazo[4,5-b]pyridin-1-yl]-N,N-dimethyl-acetamide; |
| 534 | 1-[2-(Azetidin-1-yl)-2-oxo-ethyl]-3-(fluoromethyl)-6-[5-(trifluoromethyl)-2-thienyl]imidazo[4,5-b]pyridin-2-one; |
| 535 | 1-[2-(Azetidin-1-yl)-2-oxo-ethyl]-3-(2-fluoroethyl)-6-[5-(trifluoromethyl)-2-thienyl]imidazo[4,5-b]pyridin-2-one; |

| Ex # | Compound Name |
|---|---|
| 536 | 1-[2-[3-(2-Fluoroethyl)azetidin-1-yl]-2-oxo-ethyl]-6-[3-(trifluoromethyl)phenyl]-3H-imidazo[4,5-b]pyridin-2-one; |
| 537 | 6-(6-Fluoro-2-pyridyl)-1-(2-oxobutyl)-3H-imidazo[4,5-b]pyridin-2-one; |
| 538 | 1-[2-(Azetidin-1-yl)-2-oxo-ethyl]-6-[4-(2-fluoroethoxy)-3-(trifluoromethyl)phenyl]-3H-imidazo[4,5-b]pyridin-2-one; |
| 539 | 1-[2-(Azetidin-1-yl)-2-oxo-ethyl]-6-[3-(2-fluoroethoxy)-5-(trifluoromethyl)phenyl]-3H-imidazo[4,5-b]pyridin-2-one; |
| 540 | 1-[2-(3-$^{18}$F-Fluoranylazetidin-1-yl)-2-oxo-ethyl]-6-(4-fluoro-3-methyl-phenyl)-3-methyl-imidazo[4,5-b]pyridin-2-one; |
| 541 | 6-[3-(Difluoromethyl)-4-fluoro-phenyl]-3-methyl-1-(pyridazin-3-ylmethyl)imidazo[4,5-b]pyridin-2-one; |
| 542 | 6-[3-(Difluoromethoxy)-4-fluoro-phenyl]-3-methyl-1-(pyridazin-3-ylmethyl)imidazo[4,5-b]pyridin-2-one; |
| 543 | 6-[4-Chloro-3-(difluoromethoxy)phenyl]-3-methyl-1-(pyridazin-3-ylmethyl)imidazo[4,5-b]pyridin-2-one; |
| 544 | 6-[4-Chloro-3-(difluoromethoxy)phenyl]-1-[(5-fluoro-3-pyridyl)methyl]-3-methyl-imidazo[4,5-b]pyridin-2-one; |
| 545 | 6-(3,4-Difluorophenyl)-3-methyl-1-(thiadiazol-4-ylmethyl)imidazo[4,5-b]pyridin-2-one; |
| 546 | 6-[3-(Difluoromethyl)-4-fluoro-phenyl]-1-[(5-fluoro-3-pyridyl)methyl]-3-methyl-imidazo[4,5-b]pyridin-2-one; |
| 547 | 6-[3-(Difluoromethoxy)-4-fluoro-phenyl]-1-[(5-fluoro-3-pyridyl)methyl]-3-methyl-imidazo[4,5-b]pyridin-2-one; |
| 548 | 3-Methyl-1-(thiadiazol-4-ylmethyl)-6-[3-(trifluoromethyl)phenyl]imidazo[4,5-b]pyridin-2-one; |
| 549 | 6-(3,4-Difluorophenyl)-3-methyl-1-[(1-methyltriazol-4-yl)methyl]imidazo[4,5-b]pyridin-2-one; |
| 550 | 6-(3,4-Difluorophenyl)-3-methyl-1-[(1-methylpyrazol-4-yl)methyl]imidazo[4,5-b]pyridin-2-one; |
| 551 | 3-Methyl-1-[(1-methylpyrazol-4-yl)methyl]-6-[3-(trifluoromethyl)phenyl]imidazo[4,5-b]pyridin-2-one; |
| 552 | 3-Methyl-1-[(1-methyltriazol-4-yl)methyl]-6-[3-(trifluoromethyl)phenyl]imidazo[4,5-b]pyridin-2-one; |
| 553 | 3-Methyl-6-(5-methyl-2-thienyl)-1-[(1-methyltriazol-4-yl)methyl]imidazo[4,5-b]pyridin-2-one; |
| 554 | 3-Methyl-1-[(5-methyl-1,3,4-oxadiazol-2-yl)methyl]-6-(5-methyl-2-thienyl)imidazo[4,5-b]pyridin-2-one; |
| 555 | 3-Methyl-1-[(1-methylpyrazol-4-yl)methyl]-6-(5-methyl-2-thienyl)imidazo[4,5-b]pyridin-2-one; |
| 556 | 3-Methyl-6-(5-methyl-2-thienyl)-1-(thiadiazol-4-ylmethyl)imidazo[4,5-b]pyridin-2-one; |
| 557 | 3-Methyl-1-[(3-methyl-1,2,4-oxadiazol-5-yl)methyl]-6-(5-methyl-2-thienyl)imidazo[4,5-b]pyridin-2-one; |
| 558 | 3-Methyl-1-[(5-methylisoxazol-3-yl)methyl]-6-(5-methyl-2-thienyl)imidazo[4,5-b]pyridin-2-one; |
| 559 | 6-[5-(Difluoromethyl)-2-thienyl]-3-methyl-1-[(1-methyltriazol-4-yl)methyl]imidazo[4,5-b]pyridin-2-one; |
| 560 | 6-[5-(Difluoromethyl)-2-thienyl]-3-methyl-1-[(5-methyl-1,3,4-oxadiazol-2-yl)methyl]imidazo[4,5-b]pyridin-2-one; |
| 561 | 6-[5-(Difluoromethyl)-2-thienyl]-3-methyl-1-[(1-methylpyrazol-4-yl)methyl]imidazo[4,5-b]pyridin-2-one; |
| 562 | 6-[5-(Difluoromethyl)-2-thienyl]-3-methyl-1-(thiadiazol-4-ylmethyl)imidazo[4,5-b]pyridin-2-one; |
| 563 | 6-[5-(Difluoromethyl)-2-thienyl]-3-methyl-1-[(3-methyl-1,2,4-oxadiazol-5-yl)methyl]imidazo[4,5-b]pyridin-2-one; |
| 564 | 6-[5-(Difluoromethyl)-2-thienyl]-3-methyl-1-[(5-methylisoxazol-3-yl)methyl]imidazo[4,5-b]pyridin-2-one; |
| 565 | 3-Methyl-1-[(1-methylpyrazol-4-yl)methyl]-6-[5-(trifluoromethyl)-2-thienyl]imidazo[4,5-b]pyridin-2-one; |
| 566 | 3-Methyl-1-[(1-methyltriazol-4-yl)methyl]-6-[5-(trifluoromethyl)-2-thienyl]imidazo[4,5-b]pyridin-2-one; |
| 567 | 3-Methyl-1-[(5-methyl-1,3,4-oxadiazol-2-yl)methyl]-6-[5-(trifluoromethyl)-2-thienyl]imidazo[4,5-b]pyridin-2-one; |
| 568 | 3-Methyl-1-(thiadiazol-4-ylmethyl)-6-[5-(trifluoromethyl)-2-thienyl]imidazo[4,5-b]pyridin-2-one; |
| 569 | 3-Methyl-1-[(3-methyl-1,2,4-oxadiazol-5-yl)methyl]-6-[5-(trifluoromethyl)-2-thienyl]imidazo[4,5-b]pyridin-2-one; |
| 570 | 3-Methyl-1-[(5-methylisoxazol-3-yl)methyl]-6-[5-(trifluoromethyl)-2-thienyl]imidazo[4,5-b]pyridin-2-one; |
| 571 | 6-(2,4-Difluoro-3-methyl-phenyl)-3-methyl-1-[(5-methylisoxazol-3-yl)methyl]imidazo[4,5-b]pyridin-2-one; |
| 572 | 6-(2,4-Difluoro-3-methyl-phenyl)-3-methyl-1-[(1-methylpyrazol-4-yl)methyl]imidazo[4,5-b]pyridin-2-one; |
| 573 | 6-(2,4-Difluoro-3-methyl-phenyl)-3-methyl-1-[(3-methyl-1,2,4-oxadiazol-5-yl)methyl]imidazo[4,5-b]pyridin-2-one; |
| 574 | 6-(2,4-Difluoro-3-methyl-phenyl)-3-methyl-1-[(1-methyltriazol-4-yl)methyl]imidazo[4,5-b]pyridin-2-one; |

| Ex # | Compound Name |
|---|---|
| 575 | 6-(2,4-Difluoro-3-methyl-phenyl)-3-methyl-1-[(5-methyl-1,3,4-oxadiazol-2-yl)methyl]imidazo[4,5-b]pyridin-2-one; |
| 576 | 6-(2,4-Difluoro-3-methyl-phenyl)-3-methyl-1-(thiadiazol-4-ylmethyl)imidazo[4,5-b]pyridin-2-one; |
| 577 | N-(2-Fluoroethyl)-N-methyl-2-[3-methyl-2-oxo-6-[5-(trifluoromethyl)-2-thienyl]imidazo[4,5-b]pyridin-1-yl]acetamide; |
| 578 | 1-[2-(3-Fluoroazetidin-1-yl)-2-oxo-ethyl]-6-[5-(trifluoromethyl)-2-thienyl]-3H-imidazo[4,5-b]pyridin-2-one; |
| 579 | 1-[2-(Azetidin-1-yl)-2-oxo-ethyl]-6-(2,4-difluoro-3-methyl-phenyl)-3H-imidazo[4,5-b]pyridin-2-one; |
| 580 | 1-[2-(3,3-Difluoroazetidin-1-yl)-2-oxo-ethyl]-6-(m-tolyl)-3H-imidazo[4,5-b]pyridin-2-one; |
| 581 | 1-[2-(3,3-Difluoroazetidin-1-yl)-2-oxo-ethyl]-3-methyl-6-(m-tolyl)imidazo[4,5-b]pyridin-2-one; |
| 582 | 1-[2-(Azetidin-1-yl)-2-oxo-ethyl]-6-[3-(2-fluoroethoxy)-5-(trifluoromethyl)phenyl]-3-methyl-imidazo[4,5-b]pyridin-2-one; |
| 583 | N,N-Dimethyl-2-[3-methyl-6-(m-tolyl)-2-oxo-imidazo[4,5-b]pyridin-1-yl]acetamide; |
| 584 | 1-[2-(Azetidin-1-yl)-2-oxo-ethyl]-6-[3-(difluoromethyl)-4-fluoro-phenyl]-3-methyl-imidazo[4,5-b]pyridin-2-one; |
| 585 | 6-[3-(Difluoromethyl)-4-fluoro-phenyl]-1-[2-(3-fluoroazetidin-1-yl)-2-oxo-ethyl]-3-methyl-imidazo[4,5-b]pyridin-2-one; |
| 586 | 1-[2-(3,3-Difluoroazetidin-1-yl)-2-oxo-ethyl]-6-[3-(difluoromethyl)-4-fluoro-phenyl]-3-methyl-imidazo[4,5-b]pyridin-2-one; |
| 587 | 2-[6-[3-(Difluoromethoxy)-4-fluoro-phenyl]-3-methyl-2-oxo-imidazo[4,5-b]pyridin-1-yl]-N,N-dimethyl-acetamide; |
| 588 | 1-[2-(Azetidin-1-yl)-2-oxo-ethyl]-6-[3-(difluoromethoxy)-4-fluoro-phenyl]-3-methyl-imidazo[4,5-b]pyridin-2-one; |
| 589 | 6-[3-(Difluoromethoxy)-4-fluoro-phenyl]-1-[2-(3-fluoroazetidin-1-yl)-2-oxo-ethyl]-3-methyl-imidazo[4,5-b]pyridin-2-one; |
| 590 | 1-[2-(3,3-Difluoroazetidin-1-yl)-2-oxo-ethyl]-6-[3-(difluoromethoxy)-4-fluoro-phenyl]-3-methyl-imidazo[4,5-b]pyridin-2-one; |
| 591 | 2-[6-[4-Chloro-3-(difluoromethoxy)phenyl]-3-methyl-2-oxo-imidazo[4,5-b]pyridin-1-yl]-N,N-dimethyl-acetamide; |
| 592 | 1-[2-(Azetidin-1-yl)-2-oxo-ethyl]-6-[4-chloro-3-(difluoromethoxy)phenyl]-3-methyl-imidazo[4,5-b]pyridin-2-one; |
| 593 | 6-[4-Chloro-3-(difluoromethoxy)phenyl]-1-[2-(3-fluoroazetidin-1-yl)-2-oxo-ethyl]-3-methyl-imidazo[4,5-b]pyridin-2-one; |
| 594 | 6-[4-Chloro-3-(difluoromethoxy)phenyl]-1-[2-(3,3-difluoroazetidin-1-yl)-2-oxo-ethyl]-3-methyl-imidazo[4,5-b]pyridin-2-one; |
| 595 | 1-[2-(Azetidin-1-yl)-2-oxo-ethyl]-6-(2,4-difluoro-3-methyl-phenyl)-3-(fluoromethyl)imidazo[4,5-b]pyridin-2-one; |
| 596 | 2-[3-(Fluoromethyl)-2-oxo-6-[5-(trifluoromethyl)-2-thienyl]imidazo[4,5-b]pyridin-1-yl]-N,N-dimethyl-acetamide; |
| 597 | 1-[2-(3-Fluoroazetidin-1-yl)-2-oxo-ethyl]-3-(fluoromethyl)-6-[5-(trifluoromethyl)-2-thienyl]imidazo[4,5-b]pyridin-2-one; |
| 598 | 3-(Fluoromethyl)-1-(2-oxo-2-pyrrolidin-1-yl-ethyl)-6-[5-(trifluoromethyl)-2-thienyl]imidazo[4,5-b]pyridin-2-one; |
| 599 | 2-[6-(2,4-Difluoro-3-methyl-phenyl)-3-(fluoromethyl)-2-oxo-imidazo[4,5-b]pyridin-1-yl]-N,N-dimethyl-acetamide; |
| 600 | 6-(2,4-Difluoro-3-methyl-phenyl)-1-[2-(3-fluoroazetidin-1-yl)-2-oxo-ethyl]-3-(fluoromethyl)imidazo[4,5-b]pyridin-2-one; |
| 601 | 1-(3,3-Dimethyl-2-oxo-butyl)-6-(4-methoxyphenyl)-3H-imidazo[4,5-b]pyridin-2-one; |
| 602 | 6-(3-Methoxyphenyl)-1-[2-oxo-2-(2-thienyl)ethyl]-3H-imidazo[4,5-b]pyridin-2-one; |
| 603 | 1-(3,3-Dimethyl-2-oxo-butyl)-6-(4-methoxy-3-methyl-phenyl)-3H-imidazo[4,5-b]pyridin-2-one; |
| 604 | 1-Isobutyl-6-(4-methoxyphenyl)-3H-imidazo[4,5-b]pyridin-2-one; |
| 605 | 6-(2-Ethoxyphenyl)-1-[(3-methoxyphenyl)methyl]-3H-imidazo[4,5-b]pyridin-2-one; |
| 606 | 6-(2-Ethoxyphenyl)-1-[(4-fluorophenyl)methyl]-3H-imidazo[4,5-b]pyridin-2-one; |
| 607 | N-Cyclopropyl-2-[6-(2-ethoxy-5-fluoro-phenyl)-2-oxo-3H-imidazo[4,5-b]pyridin-1-yl]acetamide; |
| 608 | 2-[[6-(4-Methoxy-3-methyl-phenyl)-2-oxo-3H-imidazo[4,5-b]pyridin-1-yl]methyl]benzonitrile; |
| 609 | 1-(3,3-Dimethyl-2-oxo-butyl)-6-(3-fluoro-4-methoxy-phenyl)-3H-imidazo[4,5-b]pyridin-2-one; |
| 610 | 2-[6-(3,5-Difluorophenyl)-2-oxo-3H-imidazo[4,5-b]pyridin-1-yl]-N-(2-methoxyethyl)acetamide; |
| 611 | 1-(3,3-Dimethyl-2-oxo-butyl)-6-[3-(trifluoromethyl)phenyl]-3H-imidazo[4,5-b]pyridin-2-one; and |
| 612 | 2-[6-(3-Chloro-4-fluoro-phenyl)-2-oxo-3H-imidazo[4,5-b]pyridin-1-yl]-N-(2-methoxyethyl)acetamide; | and pharmaceutically acceptable salts, N-oxides, or solvates thereof.

A further embodiment of the current invention is a compound selected from the group consisting of:
1-[2-(Azetidin-1-yl)-2-oxo-ethyl]-3-methyl-6-[5-(trifluoromethyl)-2-thienyl]imidazo[4,5-b]pyridin-2-one;
N,N-Dimethyl-2-[3-methyl-2-oxo-6-[5-(trifluoromethyl)-2-thienyl]imidazo[4,5-b]pyridin-1-yl]acetamide;
1-[2-(Azetidin-1-yl)-2-oxo-ethyl]-6-[5-(trifluoromethyl)-2-thienyl]-3H-imidazo[4,5-b]pyridin-2-one;
1-[2-(Azetidin-1-yl)-2-oxo-ethyl]-6-(5-chloro-4-methyl-2-thienyl)-3H-imidazo[4,5-b]pyridin-2-one;
1-[2-(3-Fluoroazetidin-1-yl)-2-oxo-ethyl]-6-(4-fluoro-3-methyl-phenyl)-3-methyl-imidazo[4,5-b]pyridin-2-one;
1-[2-(Azetidin-1-yl)-2-oxo-ethyl]-6-(2,4-difluoro-3-methyl-phenyl)-3-methyl-imidazo[4,5-b]pyridin-2-one;
1-[2-(Azetidin-1-yl)-2-oxo-ethyl]-6-(4-fluoro-3-methyl-phenyl)-3-methyl-imidazo[4,5-b]pyridin-2-one;
1-(2-(3,3-Difluoroazetidin-1-yl)-2-oxoethyl)-6-(4-fluoro-3-methylphenyl)-3-methyl-1H-imidazo[4,5-b]pyridin-2(3H)-one;
1-[2-(3,3-Difluoroazetidin-1-yl)-2-oxo-ethyl]-6-(2,4-difluoro-3-methyl-phenyl)-3-methyl-imidazo[4,5-b]pyridin-2-one; and
2-[6-(4-Fluoro-3-methyl-phenyl)-3-methyl-2-oxo-imidazo[4,5-b]pyridin-1-yl]-N, N-dimethyl-acetamide;
and pharmaceutically acceptable salts, solvates, or N-oxides thereof.

A further embodiment of the current invention is a compound selected from the group consisting of:
6-(5-(Difluoromethyl)-2-fluorophenyl)-3-methyl-1-(pyridazin-3-ylmethyl)-1,3-dihydro-2H-imidazo[4,5-b]pyridin-2-one;
6-(5-(Difluoromethyl)-2-fluorophenyl)-3-methyl-1-(pyridin-3-ylmethyl)-1,3-dihydro-2H-imidazo[4,5-b]pyridin-2-one;
N-(3-Chloropropyl)-2-[3-methyl-2-oxo-6-[5-(trifluoromethyl)-2-thienyl]imidazo[4,5-b]pyridin-1-yl]acetamide;
2-[6-[3-(Difluoromethyl)-4-fluoro-phenyl]-3-methyl-2-oxo-imidazo[4,5-b]pyridin-1-yl]-N,N-dimethyl-acetamide;
1-[2-(Azetidin-1-yl)-2-oxo-ethyl]-3-(fluoromethyl)-6-[5-(trifluoromethyl)-2-thienyl]imidazo[4,5-b]pyridin-2-one;
1-[2-(Azetidin-1-yl)-2-oxo-ethyl]-3-(2-fluoroethyl)-6-[5-(trifluoromethyl)-2-thienyl]imidazo[4,5-b]pyridin-2-one;
1-[2-[3-(2-Fluoroethyl)azetidin-1-yl]-2-oxo-ethyl]-6-[3-(trifluoromethyl)phenyl]-3H-imidazo[4,5-b]pyridin-2-one;
6-(6-Fluoro-2-pyridyl)-1-(2-oxobutyl)-3H-imidazo[4,5-b]pyridin-2-one;
1-[2-(Azetidin-1-yl)-2-oxo-ethyl]-6-[4-(2-fluoroethoxy)-3-(trifluoromethyl)phenyl]-3H-imidazo[4,5-b]pyridin-2-one;
1-[2-(Azetidin-1-yl)-2-oxo-ethyl]-6-[3-(2-fluoroethoxy)-5-(trifluoromethyl)phenyl]-3H-imidazo[4,5-b]pyridin-2-one;
1-[2-(3-[18]F-Fluoranylazetidin-1-yl)-2-oxo-ethyl]-6-(4-fluoro-3-methyl-phenyl)-3-methyl-imidazo[4,5-b]pyridin-2-one
6-[3-(Difluoromethyl)-4-fluoro-phenyl]-3-methyl-1-(pyridazin-3-ylmethyl)imidazo[4,5-b]pyridin-2-one;
6-[3-(Difluoromethoxy)-4-fluoro-phenyl]-3-methyl-1-(pyridazin-3-ylmethyl)imidazo[4,5-b]pyridin-2-one;
6-[4-Chloro-3-(difluoromethoxy)phenyl]-3-methyl-1-(pyridazin-3-ylmethyl)imidazo[4,5-b]pyridin-2-one;
6-[4-Chloro-3-(difluoromethoxy)phenyl]-1-[(5-fluoro-3-pyridyl)methyl]-3-methyl-imidazo[4,5-b]pyridin-2-one;
6-(3,4-Difluorophenyl)-3-methyl-1-(thiadiazol-4-ylmethyl)imidazo[4,5-b]pyridin-2-one;
6-[3-(Difluoromethyl)-4-fluoro-phenyl]-1-[(5-fluoro-3-pyridyl)methyl]-3-methyl-imidazo[4,5-b]pyridin-2-one;
6-[3-(Difluoromethoxy)-4-fluoro-phenyl]-1-[(5-fluoro-3-pyridyl)methyl]-3-methyl-imidazo[4,5-b]pyridin-2-one;
3-Methyl-1-(thiadiazol-4-ylmethyl)-6-[3-(trifluoromethyl)phenyl]imidazo[4,5-b]pyridin-2-one;
6-(3,4-Difluorophenyl)-3-methyl-1-[(1-methyltriazol-4-yl)methyl]imidazo[4,5-b]pyridin-2-one;
6-(3,4-Difluorophenyl)-3-methyl-1-[(1-methylpyrazol-4-yl)methyl]imidazo[4,5-b]pyridin-2-one;
3-Methyl-1-[(1-methylpyrazol-4-yl)methyl]-6-[3-(trifluoromethyl)phenyl]imidazo[4,5-b]pyridin-2-one;
3-Methyl-1-[(1-methyltriazol-4-yl)methyl]-6-[3-(trifluoromethyl)phenyl]imidazo[4,5-b]pyridin-2-one;
3-Methyl-6-(5-methyl-2-thienyl)-1-[(1-methyltriazol-4-yl)methyl]imidazo[4,5-b]pyridin-2-one;
3-Methyl-1-[(5-methyl-1,3,4-oxadiazol-2-yl)methyl]-6-(5-methyl-2-thienyl)imidazo[4,5-b]pyridin-2-one;
3-Methyl-1-[(1-methylpyrazol-4-yl)methyl]-6-(5-methyl-2-thienyl)imidazo[4,5-b]pyridin-2-one;
3-Methyl-6-(5-methyl-2-thienyl)-1-(thiadiazol-4-ylmethyl)imidazo[4,5-b]pyridin-2-one;
3-Methyl-1-[(3-methyl-1,2,4-oxadiazol-5-yl)methyl]-6-(5-methyl-2-thienyl)imidazo[4,5-b]pyridin-2-one;
3-Methyl-1-[(5-methylisoxazol-3-yl)methyl]-6-(5-methyl-2-thienyl)imidazo[4,5-b]pyridin-2-one;
6-[5-(Difluoromethyl)-2-thienyl]-3-methyl-1-[(1-methyltriazol-4-yl)methyl]imidazo[4,5-b]pyridin-2-one;
6-[5-(Difluoromethyl)-2-thienyl]-3-methyl-1-[(5-methyl-1,3,4-oxadiazol-2-yl)methyl]imidazo[4,5-b]pyridin-2-one;
6-[5-(Difluoromethyl)-2-thienyl]-3-methyl-1-[(1-methylpyrazol-4-yl)methyl]imidazo[4,5-b]pyridin-2-one;
6-[5-(Difluoromethyl)-2-thienyl]-3-methyl-1-(thiadiazol-4-ylmethyl)imidazo[4,5-b]pyridin-2-one;
6-[5-(Difluoromethyl)-2-thienyl]-3-methyl-1-[(3-methyl-1,2,4-oxadiazol-5-yl)methyl]imidazo[4,5-b]pyridin-2-one;
6-[5-(Difluoromethyl)-2-thienyl]-3-methyl-1-[(5-methylisoxazol-3-yl)methyl]imidazo[4,5-b]pyridin-2-one;
3-Methyl-1-[(1-methylpyrazol-4-yl)methyl]-6-[5-(trifluoromethyl)-2-thienyl]imidazo[4,5-b]pyridin-2-one;
3-Methyl-1-[(1-methyltriazol-4-yl)methyl]-6-[5-(trifluoromethyl)-2-thienyl]imidazo[4,5-b]pyridin-2-one;
3-Methyl-1-[(5-methyl-1,3,4-oxadiazol-2-yl)methyl]-6-[5-(trifluoromethyl)-2-thienyl]imidazo[4,5-b]pyridin-2-one;
3-Methyl-1-(thiadiazol-4-ylmethyl)-6-[5-(trifluoromethyl)-2-thienyl]imidazo[4,5-b]pyridin-2-one;
3-Methyl-1-[(3-methyl-1,2,4-oxadiazol-5-yl)methyl]-6-[5-(trifluoromethyl)-2-thienyl]imidazo[4,5-b]pyridin-2-one;
3-Methyl-1-[(5-methyl isoxazol-3-yl)methyl]-6-[5-(trifluoromethyl)-2-thienyl]imidazo[4,5-b]pyridin-2-one;
6-(2,4-Difluoro-3-methyl-phenyl)-3-methyl-1-[(5-methylisoxazol-3-yl)methyl]imidazo[4,5-b]pyridin-2-one;
6-(2,4-Difluoro-3-methyl-phenyl)-3-methyl-1-[(1-methylpyrazol-4-yl)methyl]imidazo[4,5-b]pyridin-2-one;
6-(2,4-Difluoro-3-methyl-phenyl)-3-methyl-1-[(3-methyl-1,2,4-oxadiazol-5-yl)methyl]imidazo[4,5-b]pyridin-2-one;
6-(2,4-Difluoro-3-methyl-phenyl)-3-methyl-1-[(1-methyl-triazol-4-yl)methyl]imidazo[4,5-b]pyridin-2-one;
6-(2,4-Difluoro-3-methyl-phenyl)-3-methyl-1-[(5-methyl-1,3,4-oxadiazol-2-yl)methyl]imidazo[4,5-b]pyridin-2-one;
6-(2,4-Difluoro-3-methyl-phenyl)-3-methyl-1-(thiadiazol-4-ylmethyl)imidazo[4,5-b]pyridin-2-one;
N-(2-Fluoroethyl)-N-methyl-2-[3-methyl-2-oxo-6-[5-(trifluoromethyl)-2-thienyl]imidazo[4,5-b]pyridin-1-yl]acetamide;
1-[2-(3-Fluoroazetidin-1-yl)-2-oxo-ethyl]-6-[5-(trifluoromethyl)-2-thienyl]-3H-imidazo[4,5-b]pyridin-2-one;

1-[2-(Azetidin-1-yl)-2-oxo-ethyl]-6-(2,4-difluoro-3-methyl-phenyl)-3H-imidazo[4,5-b]pyridin-2-one;
1-[2-(3,3-Difluoroazetidin-1-yl)-2-oxo-ethyl]-6-(m-tolyl)-3H-imidazo[4,5-b]pyridin-2-one;
1-[2-(3,3-Difluoroazetidin-1-yl)-2-oxo-ethyl]-3-methyl-6-(m-tolyl)imidazo[4,5-b]pyridin-2-one;
1-[2-(Azetidin-1-yl)-2-oxo-ethyl]-6-[3-(2-fluoroethoxy)-5-(trifluoromethyl)phenyl]-3-methyl-imidazo[4,5-b]pyridin-2-one;
N,N-Dimethyl-2-[3-methyl-6-(m-tolyl)-2-oxo-imidazo[4,5-b]pyridin-1-yl]acetamide;
1-[2-(Azetidin-1-yl)-2-oxo-ethyl]-6-[3-(difluoromethyl)-4-fluoro-phenyl]-3-methyl-imidazo[4,5-b]pyridin-2-one;
6-[3-(Difluoromethyl)-4-fluoro-phenyl]-1-[2-(3-fluoroazetidin-1-yl)-2-oxo-ethyl]-3-methyl-imidazo[4,5-b]pyridin-2-one;
1-[2-(3,3-Difluoroazetidin-1-yl)-2-oxo-ethyl]-6-[3-(difluoromethyl)-4-fluoro-phenyl]-3-methyl-imidazo[4,5-b]pyridin-2-one;
2-[6-[3-(Difluoromethoxy)-4-fluoro-phenyl]-3-methyl-2-oxo-imidazo[4,5-b]pyridin-1-yl]-N,N-dimethyl-acetamide;
1-[2-(Azetidin-1-yl)-2-oxo-ethyl]-6-[3-(difluoromethoxy)-4-fluoro-phenyl]-3-methyl-imidazo[4,5-b]pyridin-2-one;
6-[3-(Difluoromethoxy)-4-fluoro-phenyl]-1-[2-(3-fluoroazetidin-1-yl)-2-oxo-ethyl]-3-methyl-imidazo[4,5-b]pyridin-2-one;
1-[2-(3,3-Difluoroazetidin-1-yl)-2-oxo-ethyl]-6-[3-(difluoromethoxy)-4-fluoro-phenyl]-3-methyl-imidazo[4,5-b]pyridin-2-one;
2-[6-[4-Chloro-3-(difluoromethoxy)phenyl]-3-methyl-2-oxo-imidazo[4,5-b]pyridin-1-yl]-N,N-dimethyl-acetamide;
1-[2-(Azetidin-1-yl)-2-oxo-ethyl]-6-[4-chloro-3-(difluoromethoxy)phenyl]-3-methyl-imidazo[4,5-b]pyridin-2-one;
6-[4-Chloro-3-(difluoromethoxy)phenyl]-1-[2-(3-fluoroazetidin-1-yl)-2-oxo-ethyl]-3-methyl-imidazo[4,5-b]pyridin-2-one;
6-[4-Chloro-3-(difluoromethoxy)phenyl]-1-[2-(3,3-difluoroazetidin-1-yl)-2-oxo-ethyl]-3-methyl-imidazo[4,5-b]pyridin-2-one;
1-[2-(Azetidin-1-yl)-2-oxo-ethyl]-6-(2,4-difluoro-3-methyl-phenyl)-3-(fluoromethyl)imidazo[4,5-b]pyridin-2-one;
2-[3-(Fluoromethyl)-2-oxo-6-[5-(trifluoromethyl)-2-thienyl]imidazo[4,5-b]pyridin-1-yl]-N,N-dimethyl-acetamide;
1-[2-(3-Fluoroazetidin-1-yl)-2-oxo-ethyl]-3-(fluoromethyl)-6-[5-(trifluoromethyl)-2-thienyl]imidazo[4,5-b]pyridin-2-one;
3-(Fluoromethyl)-1-(2-oxo-2-pyrrolidin-1-yl-ethyl)-6-[5-(trifluoromethyl)-2-thienyl]imidazo[4,5-b]pyridin-2-one;
2-[6-(2,4-Difluoro-3-methyl-phenyl)-3-(fluoromethyl)-2-oxo-imidazo[4,5-b]pyridin-1-yl]-N,N-dimethyl-acetamide;
6-(2,4-Difluoro-3-methyl-phenyl)-1-[2-(3-fluoroazetidin-1-yl)-2-oxo-ethyl]-3-(fluoromethyl)imidazo[4,5-b]pyridin-2-one;
1-(3,3-Dimethyl-2-oxo-butyl)-6-(4-methoxyphenyl)-3H-imidazo[4,5-b]pyridin-2-one;
6-(3-Methoxyphenyl)-1-[2-oxo-2-(2-thienyl)ethyl]-3H-imidazo[4,5-b]pyridin-2-one;
1-(3,3-Dimethyl-2-oxo-butyl)-6-(4-methoxy-3-methyl-phenyl)-3H-imidazo[4,5-b]pyridin-2-one;
1-Isobutyl-6-(4-methoxyphenyl)-3H-imidazo[4,5-b]pyridin-2-one;

6-(2-Ethoxyphenyl)-1-[(3-methoxyphenyl)methyl]-3H-imidazo[4,5-b]pyridin-2-one;
6-(2-Ethoxyphenyl)-1-[(4-fluorophenyl)methyl]-3H-imidazo[4,5-b]pyridin-2-one;
N-Cyclopropyl-2-[6-(2-ethoxy-5-fluoro-phenyl)-2-oxo-3H-imidazo[4,5-b]pyridin-1-yl]acetamide;
2-[[6-(4-Methoxy-3-methyl-phenyl)-2-oxo-3H-imidazo[4,5-b]pyridin-1-yl]methyl]benzonitrile;
1-(3,3-Dimethyl-2-oxo-butyl)-6-(3-fluoro-4-methoxy-phenyl)-3H-imidazo[4,5-b]pyridin-2-one;
2-[6-(3,5-Difluorophenyl)-2-oxo-3H-imidazo[4,5-b]pyridin-1-yl]-N-(2-methoxyethyl)acetamide;
1-(3,3-Dimethyl-2-oxo-butyl)-6-[3-(trifluoromethyl)phenyl]-3H-imidazo[4,5-b]pyridin-2-one; and
2-[6-(3-Chloro-4-fluoro-phenyl)-2-oxo-3H-imidazo[4,5-b]pyridin-1-yl]-N-(2-methoxyethyl)acetamide;
and pharmaceutically acceptable salts, solvates, or N-oxides thereof.

A further embodiment of the current invention is a compound selected from the group consisting of:
and pharmaceutically acceptable salts, solvates, or N-oxides thereof.

1-(2-Oxo-2-(pyrrolidin-1-yl)ethyl)-6-(thiazol-5-yl)-1H-imidazo[4,5-b]pyridin-2(3H)-one;
1-(2-(3-hydroxy-3-methylazetidin-1-yl)-2-oxoethyl)-6-(5-methylpyridin-3-yl)-1H-imidazo[4,5-b]pyridin-2(3H)-one;
1-(2-(Azetidin-1-yl)-2-oxoethyl)-6-(6-fluoropyridin-3-yl)-1H-imidazo[4,5-b]pyridin-2(3H)-one;
1-(2-(2-Oxo-6-(3-(trifluoromethyl)phenyl)-2,3-dihydro-1H-imidazo[4,5-b]pyridin-1-yl)acetyl)azetidine-3-carbonitrile;
1-Benzyl-6-(4-fluoro-3-(trifluoromethyl)phenyl)-1H-imidazo[4,5-b]pyridin-2(3H)-one;
1-(2-(3-Methylazetidin-1-yl)-2-oxoethyl)-6-(3-(trifluoromethyl)phenyl)-1H-imidazo[4,5-b]pyridin-2(3H)-one;
1-(2-(3-(Methoxymethyl)azetidin-1-yl)-2-oxoethyl)-6-(3-(trifluoromethyl)phenyl)-1H-imidazo[4,5-b]pyridin-2(3H)-one; and
6-(2-Fluoro-3-methylphenyl)-1-(2-oxo-2-(3-(trifluoromethyl)azetidin-1-yl)ethyl)-1H-imidazo[4,5-b]pyridin-2(3H)-one; and
pharmaceutically acceptable salts, solvates, or N-oxides thereof.

An additional embodiment of the invention is a pharmaceutical composition comprising:
(A) an effective amount of at least one compound selected from compounds of Formula (I):

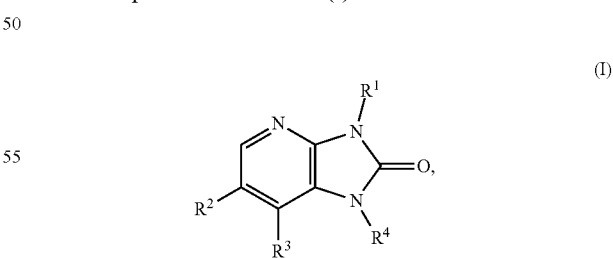

wherein
$R^1$ is H; $CH_2F$; or $CH_3$;
$R^2$ is selected from the group consisting of: phenyl; phenyl substituted with one, two, or three members each independently selected from the group consisting of: halo, $C_{1-6}$alkyl, $C_{1-6}$haloalkyl, CN, $OC_{1-6}$alkyl, $OC_{1-6}$haloalkyl, $N(CH_3)_2$, and cyclopropyl; pyridinyl;

pyridinyl substituted with F, $C_{1-4}$alkyl, or $C_{1-4}$haloalkyl; thiazolyl; thiazolyl substituted with $C_{1-6}$alkyl or $C_{1-6}$haloalkyl; thienyl; and thienyl substituted with one or two members each independently selected from the group consisting of: halo, $C_{1-6}$alkyl, $C_{1-6}$haloalkyl, $CH_2OH$, $CH_2OCH_3$, and cyclopropyl;

$R^3$ is H;

$R^4$ is selected from the group consisting of:

(a)

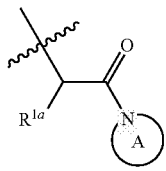

wherein ring A is a 4-6 membered heterocycle optionally containing an additional oxygen heteroatom selected from the group consisting of: azetidinyl; azetidinyl substituted with one or two members independently selected from the group consisting of: F, OH, $C_{1-4}$alkyl, $C_{1-4}$haloalkyl, $CH_2OCH_3$, CN, and $OCH_3$; pyrrolidinyl; pyrrolidinyl substituted two F members; morpholinyl; piperidinyl; piperazinyl substituted with $C_{1-6}$alkyl; and (2,6-diazaspiro[3.3]heptan-6-yl);

(b)

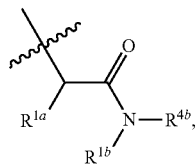

where $R^{4b}$ is selected from the group consisting of: H; $C_{1-6}$alkyl; $CH_2CH_2OCH_3$; $C_{3-6}$cycloalkyl; $C_{3-6}$cycloalkyl substituted with two or three members independently selected from the group consisting of F or $CH_3$; oxetanyl; oxetanyl substituted with $CH_3$; and pyridinyl;

(c)

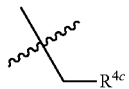

wherein $R^{4c}$ is selected from the group consisting of: cyclopropyl; cyclopropyl substituted with one or two F members; CH(OH)cyclopropyl; azetidinyl; $CH_2$-azetidinyl; $CH_2$-azetidinyl substituted with one or two members independently selected from: F, OH, $OCH_3$, and $CF_3$; oxetanyl; oxetanyl substituted with F or $CH_3$; tetrahydrofuranyl; tetrahydropyranyl; $CH_2$pyrrolidinyl; $CH_2$pyrrolidinyl substituted with $CH_3$, OH, or $OCH_3$; $CH_2$piperidinyl; $CH_2$piperidinyl substituted with OH, or F; morpholinyl; pyrazolyl substituted with one or two $CH_3$ members; triazolyl substituted with $CH_3$; tetrazolyl; isoxazolyl substituted with one or two $CH_3$ members; oxadiazolyl substituted with $CH_3$, or $CH_2OCH_3$; thiadiazolyl; pyridinyl; pyridinyl substituted with one or two members independently selected from the group consisting of: Cl, F, $CH_3$, $OCH_3$, and $CF_3$; (2-oxo-1H-pyridin-3-yl); 6-oxo-1H-pyridin-3-yl; pyrimidinyl; pyrimidinyl substituted with F or $CH_3$; pyrazinyl; pyridazinyl; pyridazinyl substituted with $OCH_3$; phenyl; phenyl substituted with one or two members independently selected from the group consisting of: halo, CN, $OCH_3$, $C_{1-6}$alkyl, and $CF_3$;

(d)

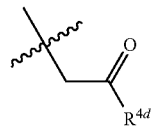

wherein $R^{4d}$ is selected from the group consisting of: OH, $C_{1-6}$alkyl, O—$C_{1-6}$alkyl, $C_{3-6}$cycloalkyl, thienyl, and thiazolyl; and (e) $C_{2-6}$alkyl substituted with one or two members independently selected from OH, $OC_{1-6}$alkyl, or cyclopropyl; $CH_2CH_2NH(C_{1-6}$alkyl); $CH_2CH_2NH(CH_2CH_2OH)$; $CH_2CH_2NH(C_{3-6}$cycloalkyl); and difluoro(3-pyridyl)methyl; and $R^{1a}$ and $R^{1b}$ are each independently H or $CH_3$;

and pharmaceutically acceptable salts, stereoisomers, isotopic variants, N-oxides or solvates of compounds of Formula (I);

and (B) at least one pharmaceutically acceptable excipient.

An additional embodiment of the invention is a pharmaceutical composition comprising and effective amount of at least one compound of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA); and at least one pharmaceutically acceptable excipient.

An additional embodiment of the invention is a pharmaceutical composition comprising and effective amount of at least one compound of Formula (IB), as well as pharmaceutically acceptable salts, N-oxides or solvates of compounds of Formula (IB), pharmaceutically acceptable prodrugs of compounds of Formula (IB), and pharmaceutically active metabolites of Formula (IB); and at least one pharmaceutically acceptable excipient.

An additional embodiment of the invention is a pharmaceutical composition comprising and effective amount of at least one compound of Formula (IC), as well as pharmaceutically acceptable salts, N-oxides or solvates of compounds of Formula (IC), pharmaceutically acceptable prodrugs of compounds of Formula (IC), and pharmaceutically active metabolites of Formula (IC); and at least one pharmaceutically acceptable excipient.

An additional embodiment of the invention is a pharmaceutical composition comprising and effective amount of at least one compound of Formula (ID), as well as pharmaceutically acceptable salts, N-oxides or solvates of compounds of Formula (ID), pharmaceutically acceptable prodrugs of compounds of Formula (ID), and pharmaceutically active metabolites of Formula (ID); and at least one pharmaceutically acceptable excipient.

An additional embodiment of the invention is a pharmaceutical composition comprising and effective amount of at least one compound in Table 1, as well as pharmaceutically acceptable salts, N-oxides or solvates of compounds of Table 1, pharmaceutically acceptable prodrugs of compounds of Table 1, and pharmaceutically active metabolites of Table 1; and at least one pharmaceutically acceptable excipient.

Also within the scope of the invention are enantiomers and diastereomers of the compounds of Formula (I) (as well as Formulas (IA), (IB), (IC), and (ID)). Also within the scope of the invention are the pharmaceutically acceptable salts, N-oxides or solvates of the compounds of Formula (I) (as well as Formulas (IA), (IB), (IC), and (ID)). Also within the scope of the invention are the pharmaceutically acceptable prodrugs of compounds of Formula (I) (as well as Formulas (IA), (IB), (IC), and (ID)), and pharmaceutically active metabolites of the compounds of Formula (I) (as well as Formulas (IA), (IB), (IC), and (ID)).

Also within the scope of the invention are isotopic variations of compounds of Formula (I) (as well as Formulas (IA), (IB), (IC), and (ID)), such as, e.g., deuterated compounds of Formula (I). Also within the scope of the invention are the pharmaceutically acceptable salts, N-oxides or solvates of the isotopic variations of the compounds of Formula (I) (as well as Formulas (IA), (IB), (IC), and (ID)). Also within the scope of the invention are the pharmaceutically acceptable prodrugs of the isotopic variations of the compounds of Formula (I) (as well as Formulas (IA), (IB), (IC), and (ID)), and pharmaceutically active metabolites of the isotopic variations of the compounds of Formula (I) (as well as Formulas (IA), (IB), (IC), and (ID)).

An additional embodiment of the invention is a method of treating a subject suffering from or diagnosed with a disease, disorder, or medical condition mediated by NR2B receptor activity, comprising administering to a subject in need of such treatment an effective amount of at least one compound selected from compounds of Formula (I):

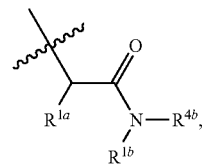

(I)

wherein
$R^1$ is H; $CH_2F$; or $CH_3$;
$R^2$ is selected from the group consisting of: phenyl; phenyl substituted with one, two, or three members each independently selected from the group consisting of: halo, $C_{1-6}$alkyl, $C_{1-6}$haloalkyl, CN, $OC_{1-6}$alkyl, $OC_{1-6}$haloalkyl, $N(CH_3)_2$, and cyclopropyl; pyridinyl; pyridinyl substituted with F, $C_{1-4}$alkyl, or $C_{1-4}$haloalkyl; thiazolyl; thiazolyl substituted with $C_{1-6}$alkyl or $C_{1-6}$haloalkyl; thienyl; and thienyl substituted with one or two members each independently selected from the group consisting of: halo, $C_{1-6}$alkyl, $C_{1-6}$haloalkyl, $CH_2OH$, $CH_2OCH_3$, and cyclopropyl;
$R^3$ is H;
$R^4$ is selected from the group consisting of:
(a)

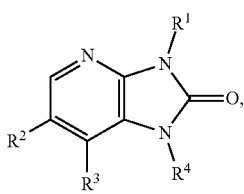

wherein ring A is a 4-6 membered heterocycle optionally containing an additional oxygen heteroatom selected from the group consisting of: azetidinyl; azetidinyl substituted with one or two members independently selected from the group consisting of: F, OH, $C_{1-4}$alkyl, $C_{1-4}$haloalkyl, $CH_2OCH_3$, CN, and $OCH_3$; pyrrolidinyl; pyrrolidinyl substituted two F members; morpholinyl; piperidinyl; piperazinyl substituted with $C_{1-6}$alkyl; and (2,6-diazaspiro[3.3]heptan-6-yl);
(b)

wherein $R^{4b}$ is selected from the group consisting of: H; $C_{1-6}$alkyl; $CH_2CH_2OCH_3$; $C_{3-6}$cycloalkyl; $C_{3-6}$cycloalkyl substituted with two or three members independently selected from the group consisting of F or $CH_3$; oxetanyl; oxetanyl substituted with $CH_3$; and pyridinyl;
(c)

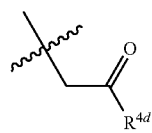

wherein $R^{4c}$ is selected from the group consisting of: cyclopropyl; cyclopropyl substituted with one or two F members; CH(OH)cyclopropyl; azetidinyl; $CH_2$-azetidinyl; $CH_2$-azetidinyl substituted with one or two members independently selected from: F, OH, $OCH_3$, and $CF_3$; oxetanyl; oxetanyl substituted with F or $CH_3$; tetrahydrofuranyl; tetrahydropyranyl; $CH_2$pyrrolidinyl; $CH_2$pyrrolidinyl substituted with $CH_3$, OH, or $OCH_3$; $CH_2$piperidinyl; $CH_2$piperidinyl substituted with OH, or F; morpholinyl; pyrazolyl substituted with one or two $CH_3$ members; triazolyl substituted with $CH_3$; tetrazolyl; isoxazolyl substituted with one or two $CH_3$ members; oxadiazolyl substituted with $CH_3$, or $CH_2OCH_3$; thiadiazolyl; pyridinyl; pyridinyl substituted with one or two members independently selected from the group consisting of: Cl, F, $CH_3$, $OCH_3$, and $CF_3$; (2-oxo-1H-pyridin-3-yl); 6-oxo-1H-pyridin-3-yl; pyrimidinyl; pyrimidinyl substituted with F or $CH_3$; pyrazinyl; pyridazinyl; pyridazinyl substituted with $OCH_3$; phenyl; phenyl substituted with one or two members independently selected from the group consisting of: halo, CN, $OCH_3$, $C_{1-6}$alkyl, and $CF_3$;
(d)

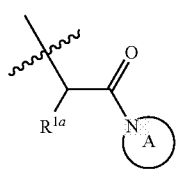

wherein $R^{4d}$ is selected from the group consisting of: OH, $C_{1-6}$alkyl, O—$C_{1-6}$alkyl, $C_{3-6}$cycloalkyl, thienyl, and thiazolyl; and
(e) $C_{2-6}$alkyl substituted with one or two members independently selected from OH, $OC_{1-6}$alkyl, or cyclopropyl; CH$_2$CH$_2$NH(C$_{1-6}$alkyl); CH$_2$CH$_2$NH(CH$_2$CH$_2$OH); CH$_2$CH$_2$NH(C$_{3-6}$cycloalkyl); and difluoro(3-pyridyl)methyl; and R$^{1a}$ and R$^{1b}$ are each independently H or CH$_3$;

and pharmaceutically acceptable salts, stereoisomers, isotopic variants, N-oxides, or solvates thereof, to a subject in need thereof.

An additional embodiment of the invention is a method of treating a subject suffering from or diagnosed with a disease, disorder, or medical condition mediated by NR2B receptor activity, comprising administering to a subject in need of such treatment an effective amount of at least one compound selected from compounds of Formula (I) (as well as Formulas (IA), (IB), (IC), and (ID)), enantiomers and diastereomers of the compounds of Formula (I), isotopic variations of the compounds of Formula (I), and pharmaceutically acceptable salts of all of the foregoing.

In preferred embodiments of the inventive method, the disease, disorder, or medical condition is selected from: neurologic and psychiatric disorders including, but not limited to: (1) mood disorders and mood affective disorders; (2) neurotic, stress-related and somatoform disorders including anxiety disorders; (3) disorders of psychological development; (4) behavioral syndromes associated with physiological disturbances and physical factors; (5) extrapyramidal and movement disorders; (6) episodic and paroxysmal disorders, epilepsy; (7) pain; (8) forms of neurodegeneration; (9) cerebrovascular diseases, acute and chronic; and any sequelae of cerebrovascular diseases.

Examples of mood disorders and mood affective disorders that can be treated according to the present invention include, but are not limited to, bipolar disorder I depressed, hypomanic, manic and mixed form; bipolar disorder II; depressive disorders, such as single depressive episode or recurrent major depressive disorder, minor depressive disorder, treatment-resistant depression, depressive disorder with postpartum onset, depressive disorders with psychotic symptoms; persistent mood disorders, such as cyclothymia, dysthymia, euthymia; and premenstrual dysphoric disorder. In specific embodiments, the mood disorders and mood affective disorders that can be treated according to the present invention are major depressive disorder, treatment-resistant depression and bipolar disorder.

Examples of disorders belonging to the neurotic, stress-related and somatoform disorders that can be treated according to the present invention include, but are not limited to, anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post-traumatic stress disorder (PTSD); other neurotic disorders such as depersonalisation-derealisation syndrome.

Examples of disorders of psychological development that can be treated according to the present invention include, but are not limited to pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills.

Examples of behavioral syndromes associated with physiological disturbances and physical factors according to the present invention include, but are not limited to mental and behavioural disorders associated with childbirth, including but not limited to postnatal (postpartum) and prenatal depression; eating disorders, including but not limited to anorexia nervosa, bulimia nervosa, pica and binge eating disorder.

Examples of extrapyramidal and movement disorders that can be treated according to the present invention include, but are not limited to Parkinson's disease; second Parkinsonism, such as postencephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome.

Further examples of movement disorders with malfunction and/or degeneration of basal ganglia that can be treated according to the present invention include, but are not limited to dystonia including but not limited to focal dystonia, multiple-focal or segmental dystonia, torsion dystonia, hemispheric, generalised and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord);

Examples for episodic and paroxysmal disorders that can be treated according to the present invention include, but are not limited to epilepsy, including localization-related (focal) (partial) idiopathic epilepsy and epileptic syndromes with seizures of localized onset, localization-related (focal)(partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures.

Further examples of epilepsy that can be treated according to the present invention include, but are not limited to epilepsy with myoclonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus.

Examples of pain include, but are not limited to pain disorders related to psychological factors, such as persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy.

Examples of diseases that include forms of neurodegeneration include, but are not limited to, acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis and ALS.

Examples of cerebrovascular diseases include, but are not limited to, subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, non-pyogenic thrombosis of intracranial venous system, cerebral arteritis, cerebral amyloid angiopathy and sequelae of cerebrovascular diseases.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_{1-4}$alkyl as used here refers to a straight- or branched-chain alkyl group having from 1 to 4 carbon atoms in the chain. The term $C_{1-6}$alkyl as used here refers to a straight- or branched-chain alkyl group having from 1 to 6 carbon atoms in the chain.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on.

The term "aryl" refers to a monocyclic, aromatic carbocycle (ring structure having ring atoms that are all carbon) having 6 atoms per ring. (Carbon atoms in the aryl groups are $sp^2$ hybridized.)

The term "phenyl" represents the following moiety:

The term "thienyl" represents the following moiety:

The term "heteroaryl" refers to a monocyclic or fused bicyclic heterocycle (ring structure having ring atoms selected from carbon atoms and up to four heteroatoms selected from nitrogen, oxygen, and sulfur) having from 3 to 9 ring atoms per heterocycle. Illustrative examples of heteroaryl groups include the following entities, in the form of properly bonded moieties:

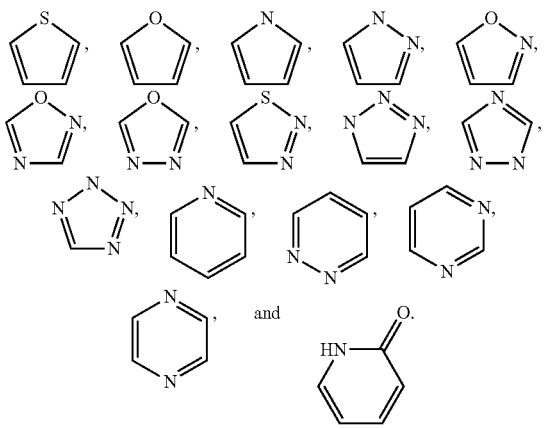

Those skilled in the art will recognize that the species of heteroaryl, cycloalkyl, aryl and heterocycloalkyl groups listed or illustrated above are not exhaustive, and that additional species within the scope of these defined terms may also be selected.

A "heterocycloalkyl" refers to a monocyclic ring structure that is saturated or partially saturated and has from 4 to 7 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

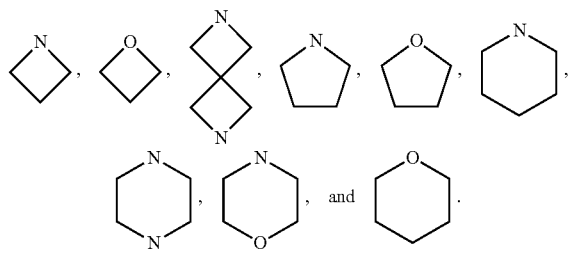

The term "cyano" refers to the group —CN.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

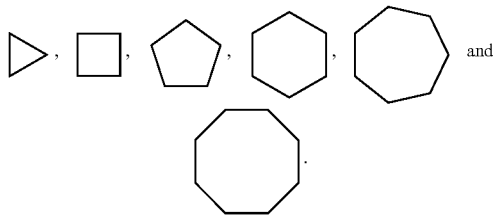

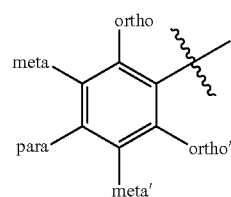

The term "halo" represents chloro, fluoro, bromo or iodo.

The term "perhaloalkyl" or "haloalkyl" refers to a straight- or branched-chain alkyl group having from 1 to 6 carbon atoms in the chain optionally substituting hydrogens with halogens. The term "$C_{1-4}$haloalkyl" as used here refers to a straight- or branched-chain alkyl group having from 1 to 4 carbon atoms in the chain, optionally substituting hydrogens with halogens. The term "$C_{1-6}$haloalkyl" as used here refers to a straight- or branched-chain alkyl group having from 1 to 6 carbon atoms in the chain, optionally substituting hydrogens with halogens. Examples of "perhaloalkyl", "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl ($-CF(CF_3)_2$), and groups that in light of the ordinary skill in the art and the teachings provided herein would be considered equivalent to any one of the foregoing examples.

The term "perhaloalkoxy" or "haloalkoxy" refers to a straight- or branched-chain alkoxy group having from 1 to 6 carbon atoms in the chain optionally substituting hydrogens with halogens. Examples of perhaloalkoxy groups include trifluoromethoxy ($OCF_3$), difluoromethoxy ($OCF_2H$), monofluoromethoxy ($OCH_2F$), monofluoroethoxy ($OCH_2CH_2F$), pentafluoroethoxy ($OCF_2CF_3$), tetrafluoroethoxy ($OCHFCF_3$), trifluoroethoxy ($OCH_2CF_3$), tetrafluorotrifluoromethylethoxy ($-OCF(CF_3)_2$), and groups that in light of the ordinary skill in the art and the teachings provided herein would be considered equivalent to any one of the foregoing examples.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

When referring to substituents on a pyridyl group, the terms "para", "meta", and "ortho" refer to the placement of a substituent relative to the point of attachment of the pyridyl ring. For example the structure below is described as 3-pyridyl with the $X^1$ substituent in the ortho position, the $X^2$ substituent in the meta position, and $X^3$ substituent in the para position:

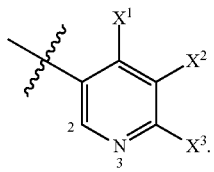

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5$^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enantiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

The symbols  and  are used as meaning the same spatial arrangement in chemical structures shown herein. Analogously, the symbols  and  are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I) (as well as Formulas (IA), (IB), (IC), and (ID)), or pharmaceutically acceptable salts of compounds of Formula (I) (as well as Formulas (IA), (IB), (IC), and (ID)) may be obtained as solvates. Solvates include those formed from the interaction or complexation of compounds of the invention with one or more solvents, either in solution or as a solid or crystalline form. In some embodiments, the solvent is water and the solvates are hydrates. In addition, certain crystalline forms of compounds of Formula (I) (as well as Formulas (IA), (IB), (IC), and (ID)) or pharmaceutically acceptable salts of compounds of Formula (I) (as well as Formulas (IA), (IB), (IC), and (ID)) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example deuterium (i.e., D or $^2H$); or tritium (i.e., T or $^3H$)), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^{1a}$, $R^{1b}$, $R^2$, $R^3$, $R^4$, $R^{4b}$, $R^{4c}$, $R^{4d}$, $R^a$, $R^b$, $R^c$, $Het^1$, $HAL^1$, PG, Y, and ring A, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^{1a}$, $R^{1b}$, $R^2$, $R^3$, $R^4$, $R^{4b}$, $R^{4c}$, $R^{4d}$, $R^a$, $R^b$, $R^c$, $Het^1$, $HAL^1$, PG, Y, and ring A, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-4}$ refers independently to embodiments that have one carbon member ($C_1$), embodiments that have two carbon members ($C_2$), embodiments that have three carbon members ($C_3$), and embodiments that have four carbon members ($C_4$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The invention includes also pharmaceutically acceptable salts of the compounds of Formula (I) (as well as Formulas (IA), (IB), (IC), and (ID)), preferably of those described above and of the specific compounds exemplified herein, and methods of treatment using such salts.

The term "pharmaceutically acceptable" means approved or approvable by a regulatory agency of Federal or a state government or the corresponding agency in countries other than the United States, or that is listed in the U.S. Pharmcopoeia or other generally recognized pharmacopoeia for use in animals, and more particularly, in humans.

A "pharmaceutically acceptable salt" is intended to mean a salt of a free acid or base of compounds represented by Formula (I) (as well as Formulas (IA), (IB), (IC), and (ID)) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", $J.$ $Med.$ $Chem.,$ 2007, 50:6665-72, S. M. Berge, et al., "Pharmaceutical Salts", $J$ $Pharm$ $Sci.,$ 1977, 66:1-19, and Handbook of Pharmaceutical Salts, Properties, Selection, and Use, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) (as well as Formulas (IA), (IB), (IC), and (ID)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) (as well as Formulas (IA), (IB), (IC), and (ID)) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) (as well as Formulas (IA), (IB), (IC), and (ID)) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I) (as well as Formulas (IA), (IB), (IC), and (ID)), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I) (as well as Formulas (IA), (IB), (IC), and (ID)). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) (as well as Formulas (IA), (IB), (IC), and (ID)) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl) amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) (as well as Formulas (IA), (IB), (IC), and (ID)), which may also be used in the methods of the invention. A "pharmaceutically active metabolite" means a pharmacologically active product of metabolism in the body of a compound of Formula (I) (as well as Formulas (IA), (IB), (IC), and (ID) as applicable) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) (as well as Formulas (IA), (IB), (IC), and (ID)) and their pharmaceutically acceptable salts, pharmaceutically acceptable prodrugs, and pharmaceutically active metabolites of the present invention are useful as modulators of the NR2B receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the NR2B receptor expression or activity, and "activators" are compounds that increase, activate, facilitate, sensitize, or up-regulate NR2B receptor expression or activity.

The term "treat", "treatment" or "treating", as used herein, is intended to refer to administration of an active agent or composition of the invention to a subject for the purpose of affecting a therapeutic or prophylactic benefit through modulation of NR2B receptor activity. Treating includes reversing, ameliorating, alleviating, inhibiting the progress of, lessening the severity of, or preventing a disease, disorder, or condition, or one or more symptoms of such disease, disorder or condition mediated through modulation of NR2B receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by NR2B receptor activity, such as: bipolar disorder I depressed, hypomanic, manic and mixed form; bipolar disorder II; depressive disorders, such as single depressive episode or recurrent major depressive disorder, minor depressive disorder, treatment-resistant depression, depressive disorder with postpartum onset, disruptive mood dysregulation disorder, depressive disorders with psychotic symptoms; persistent mood disorders, such as cyclothymia, dysthymia, euthymia; and premenstrual dysphoric disorder; anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post traumatic stress disorder (PTSD); other neurotic disorders such as depersonalisation-derealisation syndrome; pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills; postnatal (postpartum) and prenatal depression; eating disorders, including but not limited to anorexia nervosa, bulimia nervosa, pica and binge eating disorder; Parkinson's disease; second Parkinsonism, such as postencephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome; dystonia including but not limited to focal dystonia, multiple-focal or segmental dystonia, torsion dystonia, hemispheric, generalised and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord); epilepsy, including localization-related (focal)(partial) idiopathic epilepsy and epileptic syndromes with seizures of localized onset, localization-related (focal)(partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures; epilepsy with myoclonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus; persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy; and acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis, and ALS; subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, non-pyogenic thrombosis of intracranial venous system, cerebral arteritis, cerebral amyloid angiopathy and sequelae of cerebrovascular diseases; glaucoma and other neuopathies; dementias, vascular demensia, Lewy body dementia, frontotemporal dementia, and HIV-dementia; vertigo and nystagmus; tinnitus; neuropsychiatric systemic lupus erythematosus; disruptive mood dysregulation disorder; schizophrenia spectrum disorder; and sleep/wake disorders. In specific embodiments, subjects that can be treated according to the present invention are diagnosed with or suffering from major depressive disorder, treatment-resistant depression and bipolar disorder.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be co-administered separately with an active agent of compounds of Table 1 or included with such an agent in a pharmaceutical composition according to the invention. In an exemplary embodiment, additional active ingredients are those that are known or discovered to be effective in the treatment of conditions, disorders, or diseases mediated by NR2B activity, such as another NR2B modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

TABLE 2

| Term | Acronym |
|---|---|
| Acetonitrile | ACN |
| Aqueous | aq |
| Atmosphere | atm |
| Gold(III) chloride | Au(III)Cl$_3$ |
| tert-Butylcarbamoyl | Boc |
| Benzotriazol-1-yloxy-tris(dimethylamino)phosphonium hexafluorophosphate | BOP |
| Broad | br |
| 1,1'-Carbonyldiimidazole | CDI |
| Diatomaceous Earth | Celite ® |
| Diethylaminosulfur trifluoride | DAST |
| 1,8-Diazabicyclo[5.4.0]undec-7-ene | DBU |
| N,N'-Dicyclohexylcarbodiimide | DCC |
| Dichloroethane | DCE |
| Dichloromethane | DCM |
| Bis(2-methoxyethyl)aminosulfur trifluoride | Deoxo-Fluor ® |
| Diisopropylethylamine | DIPEA, DIEA, or Hunig's base |
| 4-Dimethylaminopyridine | DMAP |
| 1,2-Dimethoxyethane | DME |
| N,N-Dimethylformamide | DMF |
| Dimethylsulfoxide | DMSO |
| 1-Ethyl-3-(3-dimethylaminopropyl)carbodiimide | EDCI, EDAC, or EDC |
| Diethyl ether | Ether, Et$_2$O |
| Ethyl Acetate | EtOAc, or EA |
| Ethanol | EtOH |
| Electrospray ionization | ESI |
| Normal-phase silica gel chromatography | FCC |
| Grams | g |
| Hours | h |
| 1-[Bis(dimethylamino)methylene]-1H-1,2,3-triazolo[4,5-b]pyridinium 3-oxid hexafluorophosphate | HATU |
| N,N,N',N'-Tetramethyl-O-(1H-benzotriazol-1-yl)uronium hexafluorophosphate | HBTU |
| Hydroxybenzotriazole | HOBt |
| High-pressure liquid chromatography | HPLC |
| Hertz | Hz |
| Isopropyl alcohol | iPrOH, IPA |
| Liquid chromatography and mass spectrometry | LCMS |
| Lithium bis(trimethylsilyl)amide | LHMDS |
| Molar | M |
| Mass to charge ratio | m/z |
| meta-Chloroperoxybenzoic acid | mCPBA |
| Methyl Iodide | MeI |
| Methanol | MeOH |
| Milligrams | mg |
| Minute | min |
| Milliliter | mL |
| Microliter | μL |
| Millimoles | mmol |
| Mass spectrometry | MS |
| Normal | N |
| N-Bromosuccinimide | NBS |
| N-Chlorosuccinimide | NCS |
| N-Iodosuccinimide | NIS |
| Nuclear magnetic resonance | NMR |
| CF$_3$SO$_3$— or triflate | OTf |
| Palladium(II)bis(triphenylphosphine) dichloride | Pd(PPh$_3$)$_2$Cl$_2$ |
| Tetrakis(triphenylphosphine)palladium(0) | Pd(PPh$_3$)$_4$ |
| [1,1'-Bis(di-tert-butylphosphino)ferrocene]dichloropalladium(II) | PdCl$_2$(dtbpf) or Pd(dtbpf)$_2$Cl$_2$ |

TABLE 2-continued

| Term | Acronym |
| --- | --- |
| [1,1'-Bis(diphenylphosphino)ferrocene]dichloro-palladium(II) | PdCl$_2$(dppf) or Pd(dppf)$_2$Cl$_2$ |
| Parts per million | ppm |
| Precipitate | ppt |
| Polytetrafluoroethylene | PTFE |
| Bromotripyrrolidinophosphonium hexafluorophosphate | PyBroP ® |
| Retention time | R$_t$ |
| Room temperature | rt |
| Saturated | sat |
| 1-Chloromethyl-4-fluoro-1,4-diazoniabicyclo[2.2.2]octane bis(tetrafluoroborate) | Selectfluor ® |
| [2-(Trimethylsilyl)ethoxy]methyl acetal | SEM |
| Supercritical Fluid Chromatography | SFC |
| Temperature | T |
| Triphenylmethyl | Trityl |
| Tetra-n-butylammonium fluoride | TBAF |
| Triethylamine | TEA |
| Trifluoroacetic acid | TFA |
| 2,4,6-Tripropyl-1,3,5,2,4,6-trioxatriphosphorinane-2,4,6-trioxide | T$_3$P |
| Tetrahydrofuran | THF |
| Thin layer chromatography | TLC |
| Volume in milliliters of solvent per gram of substrate | V, or volumes |

PREPARATIVE EXAMPLES

Exemplary compounds useful in methods of the invention will now be described by reference to the illustrative synthetic schemes for their general preparation below and the specific examples to follow.

SCHEME 1

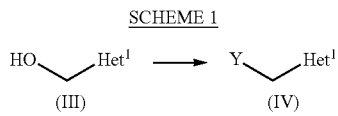

(III)  →  (IV)

According to SCHEME 1, a compound of formula (IV), where Y is a suitable leaving group such as Cl or —OSO$_2$CH$_3$ and Het$^1$ is a suitably substituted heteroaryl such as pyrimidinyl, pyrazinyl, pyridinyl, is prepared from a compound of formula (III), under conditions known to one skilled in the art. For example, a compound of formula (III) is reacted with a base such as TEA, methanesulfonyl chloride, in a solvent such as DCM, a temperatures ranging from 0° C. to rt, to afford a compound of formula (IV), where Y is —OSO$_2$CH$_3$. A compound of formula (III), where Het$^1$ is pyrazinyl, pyridazinyl, pyrimidinyl and the like, is reacted under chlorination conditions, for example, reaction with thionyl chloride, and the like, in a solvent such as DCM, a temperatures ranging from 0° C. to rt, to afford a compound of formula (IV), where Y is Cl.

SCHEME 2

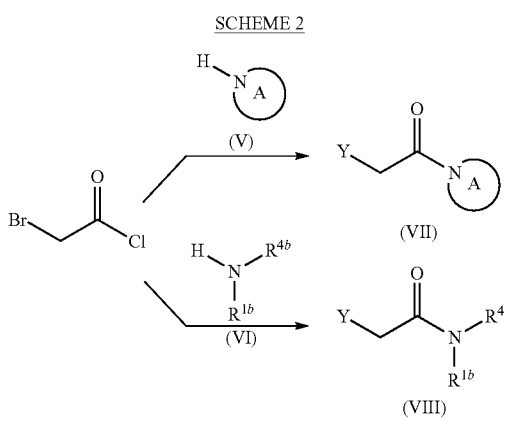

According to SCHEME 2, 2-bromoacetyl chloride is reacted with a commercially available or synthetically accessible suitably substituted heterocycloalkylamine of formula (V), where A is a fully saturated or partially saturated 3-6 membered ring optionally containing additional S, N, or O atoms, or suitably substituted amine of formula (VI), where R$^{4b}$ and R$^{1b}$ are as defined in Formula (I), in the presence of a suitable base such as Et$_3$N (TEA), in a solvent such as acetonitrile (ACN), at temperatures ranging from −78° C. to rt, to provide a compound of formula (VII) or (VIII).

SCHEME 3

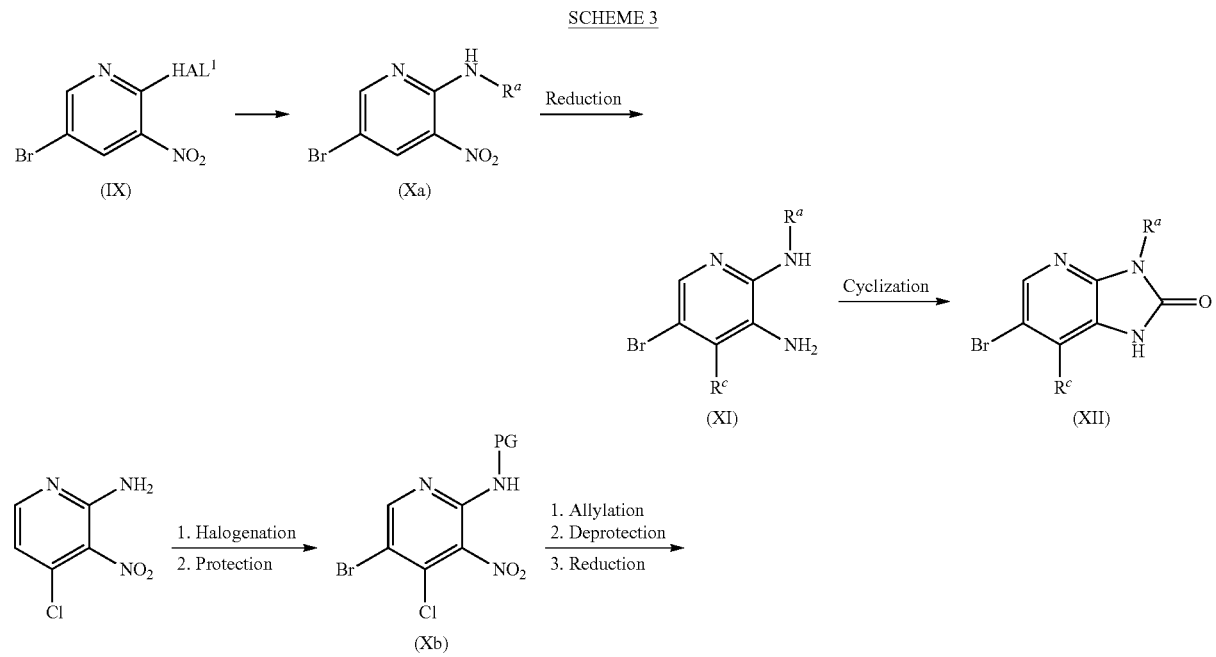

According to SCHEME 3, a compound of formula (Xa) is prepared from a compound of formula (IX), where HAL$^1$ is Cl or Br, by reaction with an amine such as methylamine, benzhydrylamine and the like, with or without a base such as DIPEA, in a solvent such as THF, EtOH, and the like, at temperatures ranging from 0° C. to the reflux temperature of the solvent, for a period of 3 to 24 h to provide a compound of formula (Xa), where R$^a$ is CH$_3$ or benzhydryl. Reduction of the nitro compound of formula (Xa), where R$^a$ is H, CH$_3$, or a suitable nitrogen protecting group such as benzhydryl, employing conditions known to one skilled in the art, provides a diamine compound of formula (XI). For example, reduction with zinc in the presence of NH$_4$Cl, in a solvent such as acetone/water, for a period of 24 to 72 h; or reduction with Pt/C, aq. H$_3$PO$_2$, NH$_4$VO$_3$, under H$_2$, at temperatures ranging from 20 to 45° C., for a period of 1-3 h; or reduction with Na$_2$S$_2$O$_4$, NH$_3$ in H$_2$O, in a solvent such as THF, water, or a mixture thereof, provides a compound of formula (XI), where R$^a$ is H, CH$_3$ or benzhydryl and R$^c$ is H.

A compound of formula (Xb) is prepared from in two steps from 4-chloro-3-nitropyridin-2-amine. In the first step, 4-chloro-3-nitropyridin-2-amine is halogenated with a halogenating agent such as N-bromosuccinimide (NBS), in a solvent such as ACN, at temperatures ranging from rt to 80° C. In the second step, 5-bromo-4-chloro-3-nitropyridin-2-amine is protected with a suitable nitrogen protecting group (PG) such as BOC, and the like, under conditions known to one skilled in the art, to provide a compound of formula (Xb).

A compound of formula (XI), where R$^a$ is CH$_3$ and R$^c$ is Cl, is prepared in three steps from a compound of formula (Xb). In the first step, alkylation with an alkylating agent such as MeI, in a solvent such as DMF, THF and the like, at temperatures ranging from 0° C. to rt, for a period of 3 to 16 h. In the second step, deprotection of the tert-butylcarbamate protecting group (PG), is achieved by reaction with an acid such as TFA, in a solvent such as DCM, and the like, at rt. In the third step, reduction of the nitro group employing reduction conditions previously described, affords a compound of formula (XI), where R$^a$ is CH$_3$ and R$^c$ is Cl.

Cyclization of a commercially available or synthetically accessible compound of formula (XI), where R$^a$ is H; a suitable nitrogen protecting group such as benzhydryl; or CH$_3$; and R$^c$ is H or Cl, in the presence of CDI, in a solvent such as ACN, DMF, THF and the like, at a temperature ranging from 5° C. to 60° C., for a period of 1-16 h, provides a compound of formula (XII), where R$^a$ is H, a suitable nitrogen protecting group such as benzhydryl, or CH$_3$.

According to SCHEME 4, a compound of formula (Xa), where R$^a$ is H, CH$_3$ or a suitable nitrogen protecting group such as BOC, benzhydryl, and the like, is reacted in a metal mediated cross coupling reaction to provide a compound of formula (XIII), where R$^2$ is a suitably substituted phenyl, pyridinyl, or thienyl. For example, a compound of formula (Xa), where R$^a$ is H, CH$_3$, or BOC, is reacted with a suitably substituted commercially available or synthetically accessible aryl or heteroaryl boronic acid, boronate ester, and the like, in the presence of a palladium catalyst such as PdCl$_2$(dtbpf), Pd(PPh$_3$)$_4$, PdCl$_2$(dppf), Pd(PPh$_3$)$_2$Cl$_2$, and the like, a base such as K$_3$PO$_4$, aq. Na$_2$CO$_3$, Na$_2$CO$_3$, Cs$_2$CO$_3$, and the like, in a suitable solvent such as 1,2-dimethoxyethane, 1,4-dioxane, DMF, water, or a mixture thereof, at a temperature ranging from 60 to 180° C., employing microwave or conventional heating, for a period of about 30 min to 16 h, to provide a compound of formula (XIII). Reduction of the nitro group, under hydrogenation conditions, for example, Pd/C, in a solvent such as EtOH, and the like, at a temperature ranging from 25-35° C., under an atmosphere of H$_2$, provides a compound of formula (XIV).

A compound of formula (XIV) is also prepared from a compound of formula (XI), where R$^a$ and R$^c$ are H, employing a metal mediated cross coupling reaction as previously described. Cyclization of a compound of formula (XIV), employing CDI conditions previously described provides a compound of formula (XV).

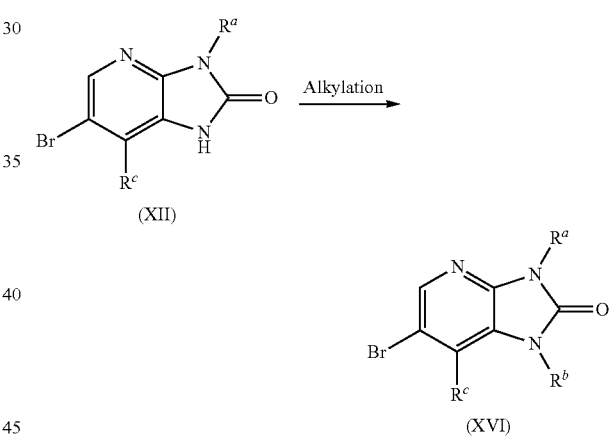

SCHEME 5

(XII)

Alkylation →

(XVI)

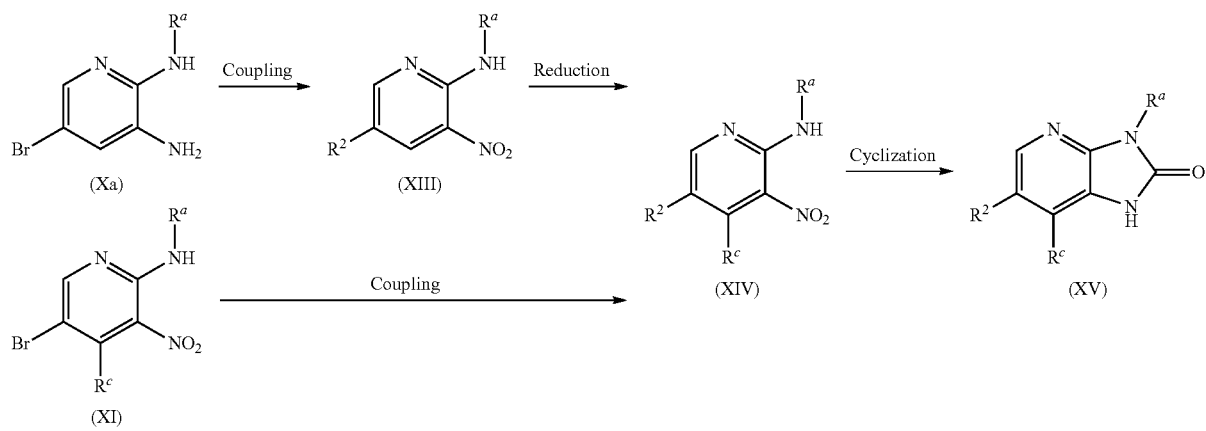

SCHEME 4

(Xa) → Coupling → (XIII) → Reduction → (XIV) → Cyclization → (XV)

(XI) → Coupling →

According to SCHEME 5, a compound of formula (XII), where $R^a$ is H, $CH_3$, or a suitable nitrogen protecting group such as 4-methoxybenzyl, benzhydryl, trityl, and the like, is alkylated with a suitable alkylating agent, employing a base such as NaH, $K_2CO_3$, $Na_2CO_3$, TEA, and the like, in a suitable solvent such as DMF, ACN, DCM, at temperatures ranging from 0° C. to 85° C., to afford a compound of formula (XVI).

Alkylation with a compound of formula (IV); where Y is Cl, Br or $OSO_2CH_3$ and $Het^1$ is an appropriately substituted heteroaryl, or heterocycloalkyl such as pyridazinyl, pyrimidinyl, pyrazinyl, isoxazolyl, oxadiazolyl, oxetanyl, and the like, affords a compound of formula (XVI), where $R^b$ is $-CH_2R^{4c}$.

Alkylation with a compound of formula (VII); where Y is Cl, and ring A is a suitably substituted heterocycloalkylamine such as azetidin-1-yl, 3-fluoroazetidin-1-yl, pyrrolidinyl, and the like, affords a compound of formula (XVI), where $R^b$ is

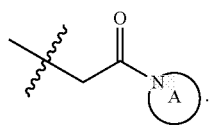

Alkylation with a compound of formula (VIII); where Y is Cl, $R^{1b}$ is H or $CH_3$, and $R^{4b}$ is as defined in Formula (I) affords a compound of formula (XVI), where $R^b$ is

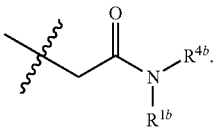

Alkylation with 2-bromo-1-cyclopropylethanone, tert-butyl bromoacetate, ethyl bromoacetate, and the like, affords a compound of formula (XVI), where $R^b$ is

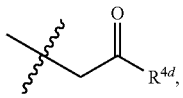

where $R^{4d}$ is $C_{1-6}$alkyl, $OC_{1-6}$alkyl, or $C_{3-6}$cycloalkyl. Further reduction of a compound of formula (XVI), where $R^{4d}$ is $C_{1-6}$alkyl or $C_{3-6}$cycloalkyl, with a reducing agent such as $NaBH_4$, in a suitable solvent such as EtOH, provides a compound of formula (XVI) where $R^b$ is $CH_2CH(OH)C_{1-6}$alkyl or $CH_2CH(OH)C_{3-6}$cycloalkyl. Reduction of a compound of formula (XVI), where $R^{4d}$ is $OC_{1-6}$alkyl, with a reducing agent such as $LiBH_4$, provides a compound of formula (XVI), where $R^b$ is $CH_2CH_2OH$. Subsequent oxidation, employing an oxidizing agent such as Dess-Martin Periodinane, provides a compound of formula (XVI), where $R^b$ is $CH_2(C=O)H$.

A compound of formula (XVI), where $R^b$ is $CH_2(C=O)H$, is reacted under reductive amination conditions, for example, reaction with a suitably substituted amine such as azetidine, pyrrolidine, piperidine, cyclopropylamine, cyclobutyl amine, ethanolamine, and the like, a reducing agent such as $NaBH(OAc)_3$, $NaCNBH_3$, $NaBH_4$, and the like, in a suitable solvent such as DCM, and the like, for a period of 12-24 h.

Alkylation of a compound of formula (XII) with an alkylating agent such as ethyl pyridin-2-yl carbonate provides a compound of formula (XVI), where $R^a$ is H, $R^b$ is $CO_2Et$. Alkylation with 1-bromo-2-methoxyethane provides a compound of formula (XVI), where $R^a$ is trityl, and $R^b$ is $CH_2CH_2OCH_3$.

A compound of formula (XVI), where $R^a$ is H, and $R^b$ is $CO_2Et$, is further alkylated with an alkylating agent such as trityl chloride, under conditions previously described, for a period of 24-28 h, at rt, to provide a compound of formula (XVI), where $R^a$ is the trityl protecting group. Subsequent removal of the carboxylate, with isopropylamine, in THF, affords a compound of formula (XVI), where $R^a$ is trityl and $R^b$ is H. A compound of formula (XVI), where $R^a$ is trityl and $R^b$ is H, is alkylated under conditions described for SCHEME 5.

A compound of formula (XVI), where $R^a$ is trityl and $R^b$ is $CH_2CO_2C_{1-6}$alkyl, is saponified, employing conditions known to one skilled in the art, to provide an acid compound formula (XVI), where $R^a$ is trityl and $R^b$ is $CH_2CO_2H$.

Deprotection of protecting group on a compound of formula (XVI), where $R^a$ is benzhydryl, is achieved in TFA, in the presence of thioanisole, at 80° C., for a period of 1 h, to afford a compound of formula (XVI), where $R^a$ is H.

SCHEME 7

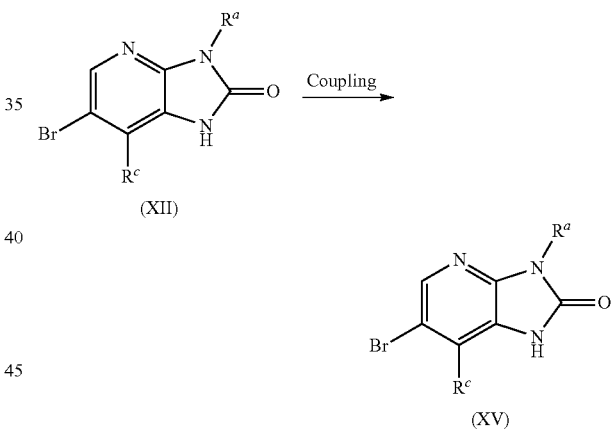

According to Scheme 7, a compound of formula (XII), where $R^a$ is a suitable nitrogen protecting group such as 4-methoxybenzyl, trityl, and the like, is coupled in a metal mediated cross coupling reaction using conditions previously described, to provide a compound of formula (XV), where $R^2$ is a suitably substituted phenyl or pyridyl.

SCHEME 8

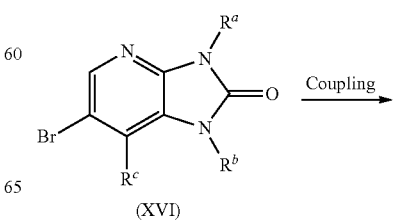

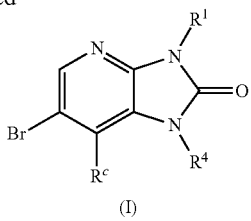

According to SCHEME 8, a compound of formula (XVI), where $R^a$ is H, $CH_3$, or a suitable nitrogen protecting group such as trityl, is reacted in a metal mediated cross coupling reaction with a commercially available or synthetically accessible boronic acid or boronate ester, as previously described to provide a compound of Formula (I), where $R^2$ is suitably substituted phenyl, pyridinyl or thienyl. Boronate esters are also prepared in-situ, under conditions known to one skilled in the art, in a one pot coupling reaction.

When $R^a$ is a protecting group such as trityl, a deprotection step, employing an acid such as TFA, in a solvent such as DCM, provides a compound of Formula (I), where $R^1$ is H.

A compound of Formula (I) is also prepared from a compound of formula (XVI) in two steps. In a first step, a compound of formula (XVI) is converted into the boronate ester, by reaction with bis(pinacolato)diboron, KOAc, and $PdCl_2(dppf)$, in a suitable solvent such as 1,4-dioxane, at a temperature of about 130° C., for period of about 2 h. In a second step, the boronate ester is reacted in a metal mediated cross coupling reaction, as previously described, with suitably substituted phenyl, to provide a compound of Formula (I).

protecting group such as 4-methoxybenzyl, or trityl, a deprotection step is employed to provide a compound of Formula (I), where $R^1$ is H.

A compound of formula (XII) is reacted under Mitsonobu conditions to form a compound of Formula (I), where $R^4$ is $CH_2$—$R^{4c}$, where $R^{4c}$ is pyrimidinyl. For example, a compound of formula (XII), where $R^2$ is a suitably substituted phenyl or thienyl, $R^a$ is $CH_3$, and $R^c$ is H, is reacted with a compound of formula (III), where $Het^1$ is pyrimidinyl, using triphenylphosphine and di-tert-butyl azodicarboxylate, in a solvent such as ACN, and the like, at a temperature ranging from 90 to 110° C., to provide a compound of Formula (I), where $R^4$ is $CH_2$—$R^{4c}$, where $R^{4c}$ is pyrimidinyl, $R^1$ is $CH_3$ and $R^2$ is H.

Saponification of an ester compound of Formula (I) under basic conditions such as LiOH, and the like, in a solvent such as THF and water, at a temperature of about rt, affords a compound of Formula (I), where $R^4$ is $CH_2CO_2H$.

Alkylation of a compound of Formula (I), where $R^1$ is H, with a base such as NaH, an alkylating agent such as MeI, in a suitable solvent such as DMF, affords a compound of Formula (I) where $R^1$ is $CH_3$.

Reduction of a compound of Formula (I), where $R^1$ is H, $R^2$ is a suitably substituted phenyl or thienyl, $R^3$ is H and $R^4$ is $CH_2C(=O)$cyclopropyl, $CH_2C(=O)C_{1-6}$alkyl, and the like, using a reducing agent such as $NaBH_4$, in a suitable solvent such as MeOH, provides a compound of Formula (I), where $R^4$ is $C_{1-6}$alkyl substituted with one or two members independently selected from OH or cyclopropyl.

SCHEME 9

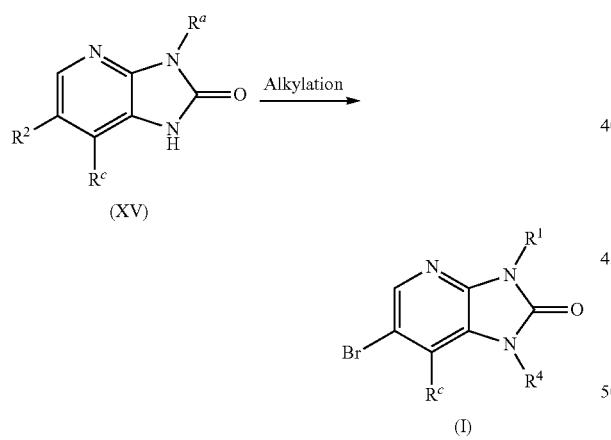

According to SCHEME 9, a compound of Formula (I), is prepared from a compound of formula (XV). A compound of formula (XV) where $R^a$ is H, $CH_3$, or a protecting group such as 4-methoxybenzyl or trityl, $R^c$ is H, and $R^2$ is a suitably substituted phenyl or thienyl, is alkylated according to methods described in SCHEME 5. For example, alkylation with an electrophile such as ethyl 2-bromoacetate, tert-butyl 2-bromoacetate, 2-(chloromethyl)pyridine, 3-(chloromethyl)-5-methylisoxazole, 2-(chloromethyl)-5-methyl-1,3,4-oxadiazole, 1-(bromomethyl)-3-chlorobenzene, pyrimidin-4-ylmethyl methanesulfonate, 2-bromo-1-cyclopropylethanone, and the like, a base such as NaH, $K_2CO_3$, and the like, in a suitable solvent such as ACN, DMF, and the like, at temperatures ranging from 0 to 85° C., provides a compound of Formula (I), where $R^4$ is $CH_2CO_2C_{1-6}$alkyl, $CH_2$pyridine, and the like. Where $R^a$ is a

SCHEME 10

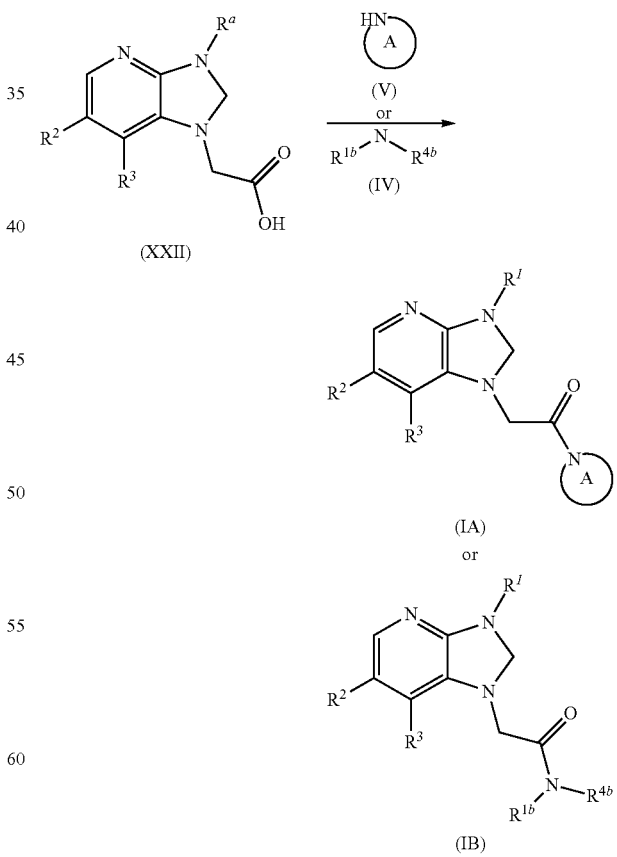

According to SCHEME 10, a compound of Formula (IA) or (IB), where $R^a$ is H, $CH_3$, or a suitable nitrogen protecting group such as trityl, and $R^2$ is a suitably substituted phenyl or thienyl, is prepared by conventional amide bond forming techniques such as coupling reactions which are well known to those skilled in the art. For example, reaction of a suitably substituted heterocycloalkyl amine of formula (V) or amine of formula (IV) where $R^{1b}$ is H or $CH_3$ and $R^{4b}$ is $C_{1-6}$alkyl, $C_{3-6}$cycloalkyl, with an acid compound of formula (XXII), where the acid is activated with an appropriate activating reagent, for example a carbodiimide, such as DCC or EDCl optionally in the presence of HOBt and/or a catalyst such as DMAP; a halotrisaminophosphonium salt such as BOP, or PyBroP; a suitable pyridinium salt such as 2-chloro-1-methyl pyridinium chloride; or another suitable coupling agent such as HBTU, HATU, 2,4,6-tripropyl-1,3,5,2,4,6-trioxatriphosphorinane-2,4,6-trioxide (T3P®) and the like. Coupling reactions are conducted in a suitable solvent such as DCM, THF, DMF and the like, optionally in the presence of a tertiary amine such as N-methylmorpholine, N-ethyl-diisopropylamine (DIEA, DIPEA), or triethylamine (TEA), at a temperature ranging from about 0° C. to rt, to provide compound a of Formula (IA) or Formula (IB). Deprotection, in instances where $R^a$ is a protecting group, employing conditions known to one skilled in the art provides a compound of Formula (IA) or Formula (IB).

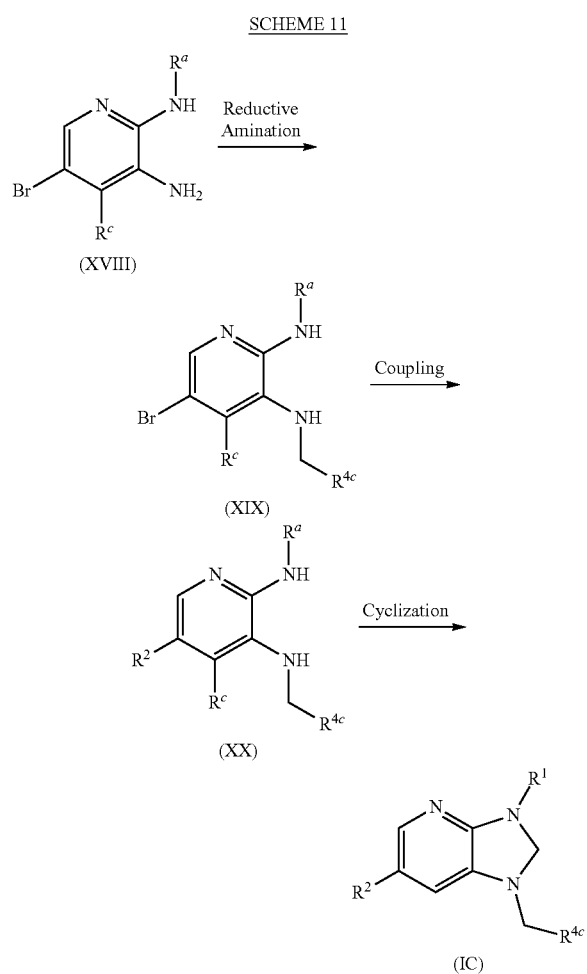

According to SCHEME 11, a compound of formula (XVIII) where $R^a$ and $R^c$ are H, is reacted under a two step reductive amination reaction, with a suitably substituted aldehyde such as 5-methylisoxazole-3-carbaldehyde. In a first step, the imine is formed by reaction of the aldehyde with an amine compound of formula (XVIII), in the presence of molecular sieves, at a temperature of about 70° C., for a period of 16-24 h. In a second step, reduction of the imine, with a reducing agent such as $NaBH_4$, in a suitable solvent such as EtOH, and the like, provides a compound of formula (XIX), where $R^{4c}$ is a suitably substituted heteroaryl such as 5-methylisoxazole. Coupling of a compound of formula (XIX), under conditions previously described provides a compound of formula (XX). Cyclization of a compound of formula (XX), under conditions previously described, such as reaction with CDI, provides a compound of Formula (IC).

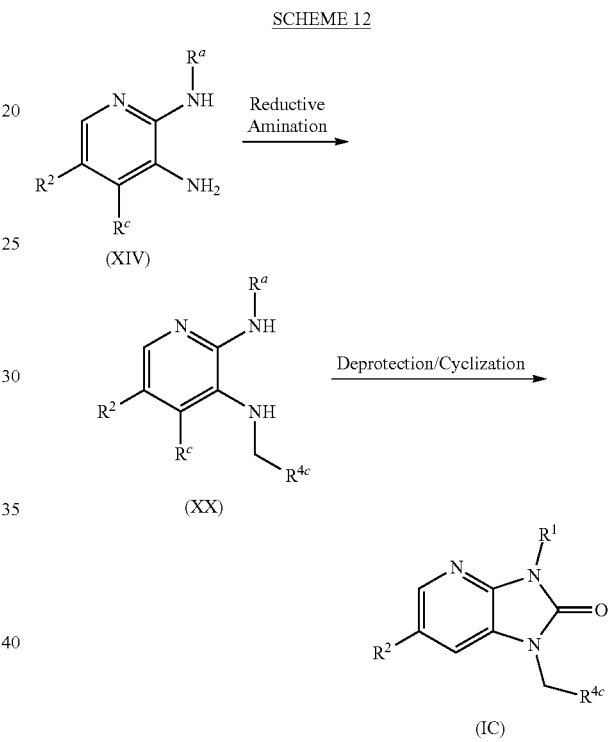

According to SCHEME 12, an amine compound of formula (XIV), where $R^a$ is a protecting group such as BOC, and $R^c$ is H, and $R^2$ is an appropriately substituted phenyl, is reacted under reductive amination conditions with an aldehyde such as 1,5-dimethyl-1 h-pyrazole-3-carbaldehyde, AcOH, in a solvent such as DCE, and a reducing agent such as $NaBH(OAc)_3$, to provide a compound of formula (XX). Deprotection of a compound of formula (XX), where $R^a$ is BOC, and $R^c$ is H, with an acid such as TFA, in a solvent such as DCM, at room temperature, afforded the cyclized compound of Formula (IC).

A compound of formula (XXI), where $R^a$ is H, and $R^{4c}$ is 5-methylisoxazol-3-yl, and the like, is cyclized under CDI conditions previously described, to provide a compound of Formula (IC).

Compounds of Formula (I) may be converted to their corresponding salts using methods known to one of ordinary skill in the art. For example, an amine of Formula (I) is treated with trifluoroacetic acid, HCl, or citric acid in a solvent such as $Et_2O$, $CH_2Cl_2$, THF, MeOH, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In Obtaining the Compounds Described in the Examples Below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via 1/16" PTFE tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

Method A.

An Agilent HPLC with an Xterra Prep RP18 column (5 μM, 30×100 or 50×150 mm) or an XBridge C18 OBD column (5 μM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

Method B.

A Shimadzu LC-8A Series HPLC with an Inertsil ODS-3 column (3 μm, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

Method C.

A Shimadzu LC-8A Series HPLC with an XBridge C18 OBD column (5 μm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

Method D.

A Gilson HPLC with an XBridge C18 column (5 μm, 100×50 mm), mobile phase of 5-99% ACN in 20 mM $NH_4OH$ over 10 min and then hold at 99 ACN for 2 min, at a flow rate of 80 mL/min.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100 to 150 bar with a flow rate ranging from 40 to 60 mL/min. The column was heated to 35 to 40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Compounds designated as R* or S* are enantiopure compounds where the absolute configuration was not determined.

Intermediate 1: 2-(Chloromethyl)pyrazine

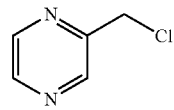

To a solution of 2-pyrazinylmethanol (500 mg, 4.54 mmol) in DCM (15 mL) at 0° C. was added thionyl chloride (0.66 mL, 9.1 mmol). The reaction mixture was stirred at 0° C. for 3 h. The reaction mixture was concentrated in vacuo. The crude reaction mixture was triturated with $Et_2O$ to yield the title compound as a black solid (749 mg, 4.54 mmol, 99.9%), which was used without further purification. $^1H$ NMR (400 MHz, DMSO-$d_6$) δ 4.87 (s, 2H), 8.63-8.69 (m, 2H), 8.82 (d, J=1.39 Hz, 1H).

Intermediate 2: 3-(Chloromethyl)pyridazine Hydrochloride

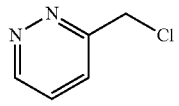

Method A: 3-(Chloromethyl)pyridazine Hydrochloride

The title compound was prepared in a manner analogous to Intermediate 1. MS (ESI): mass calcd. for C$_5$H$_5$ClN$_2$, 128.0; m/z found, 129.0 [M+H]$^+$.

Method B: 3-(Chloromethyl)pyridazine

Trichloroisocyanuric acid (148 mg, 0.6 mmol) was added in portions to a mixture of 3-methylpyridazine (145 µL, 1.6 mmol) in CHCl$_3$ at reflux. The mixture was stirred at reflux overnight. After cooling, the mixture was filtered, and the filtrate was diluted with DCM, washed with an aqueous solution of 1M NaOH followed by brine, dried (MgSO$_4$) and concentrated under reduced pressure to yield title compound (205 mg, 80%). MS (ESI): mass calcd. for C$_5$H$_5$ClN$_2$, 128.0; m/z found, 129 [M+H]$^+$.

Intermediate 3: 5-(Chloromethyl)pyrimidine Hydrochloride

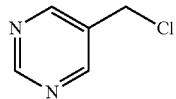

The title compound was prepared in a manner analogous to Intermediate 1. $^1$H NMR (400 MHz, DMSO-d$_6$) δ 4.85 (s, 2H) 8.90 (s, 2H) 9.16 (s, 1H).

Intermediate 4: 2-Bromo-N,N-dimethylacetamide

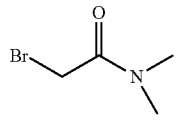

Under an atmosphere of nitrogen, 2-bromoacetyl chloride (1.3 mL, 16 mmol) was added to a mixture of TEA (2.2 mL, 16 mmol) and dimethylamine (8 mL, 16 mmol) in MeCN (20 mL) at −78° C. The stirred reaction mixture was then allowed to slowly warm to room temperature. After stirring for 2 hours, water was added (30 mL) and the mixture was extracted with DCM (3×40 mL). The combined organic layers were dried, and concentrated under vacuum to afford the desired product (2.03 g, 76%) which was carried forward as crude material. MS (ESI): mass calcd. for C$_4$H$_8$BrNO, 166.1. $^1$H NMR (500 MHz, DMSO-d$_6$) δ 4.35 (s, 2H), 2.99 (s, 3H), 2.85 (s, 3H).

Intermediate 5: 1-(Azetidin-1-yl)-2-bromoethan-1-one

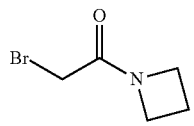

The title compound was prepared in a manner analogous to 2-bromo-N,N-dimethylacetamide (Intermediate 4), using azetidine. MS (ESI): mass calcd. for C$_5$H$_8$BrNO, 178.1. $^1$H NMR (500 MHz, CDCl$_3$) δ 4.35-4.29 (m, 2H), 4.14-4.09 (m, 2H), 3.91-3.88 (s, 2H), 2.38-2.31 (m, 2H).

Intermediate 6: 2-Bromo-1-(3-fluoroazetidin-1-yl)ethan-1-one

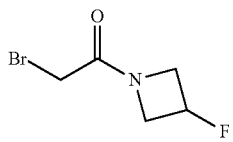

The title compound was prepared in a manner analogous to 2-bromo-N,N-dimethylacetamide (Intermediate 4) using 3-fluoroazetidine.HCl. MS (ESI): mass calcd. for C$_5$H$_7$BrFNO, 196.1. $^1$H NMR (400 MHz, DMSO-d$_6$) δ 5.50-5.29 (m, 1H), 4.57-4.45 (m, 1H), 4.32-4.14 (m, 2H), 4.01-3.86 (m, 3H).

Intermediate 7: Potassium trimethoxy(trifluoromethyl)borate

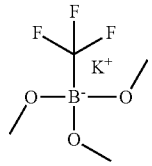

To a three-necked round-bottom flask equipped with a thermometer and nitrogen inlet/outlet adapter were added KF (1000 g, 17.2 mol, 1.0 equiv.) and anhydrous THF (15 L). The mixture was stirred at 23±2° C. under a nitrogen flow. B(OMe)$_3$ (1860 g, 17.9 mol, 1.04 equiv.) was added to the mixture while a slight temperature drop was observed. F$_3$CTMS (2690 g, 18.9 mol, 1.1 equiv.) was added to the mixture while a slight temperature drop was observed. The mixture was stirred at 23±2° C. for 20 hours under a nitrogen flow until the solid was completely dissolved. The resulting mixture was concentrated to 6 L under reduced pressure, then hexane 12 L was added to the mixture and the mixture was stirred for 20 min. The precipitated solid was collected by filtration followed by washing with hexane 2 L×2. The wet solid was dried under vacuum to give the title compound (3840 g, 94.5%). $^1$H NMR (400 MHz, D$_2$O) 3.22 (s, 9H). $^{19}$F NMR (376 MHz, D$_2$O) δ −74.83 (dd, J=59.1, 28.5 Hz).

Intermediate 8: 2-(2,4-difluoro-3-methylphenyl)-4,4,5,5-tetramethyl-1,3,2-dioxaborolane

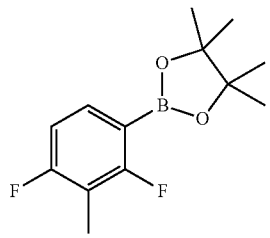 [SMILES: Cc1c(F)ccc(B2OC(C)(C)C(C)(C)O2)c1F]

To a solution a 3-bromo-2,6-difluorotoluene (0.95 mL, 7.2 mmol), 4,4,4',4',5,5,5',5'-octamethyl-2,2'-bi-1,3,2-dioxaborolane (3.68 g, 14.5 mmol) and KOAc (1.07 g, 10.9 mmol) in 1,4-dioxane (38 mL) was added PdCl$_2$(dppf) (265 mg, 0.362 mmol). The reaction mixture was stirred at 120° C. for 16 h. Then, the crude reaction mixture was cooled, filtered through Celite® and concentrated in vacuo. The crude product was purified (FCC, SiO$_2$, 0-20% EtOAc in hexanes) to yield the title compound (1.8 g, 98%).

Intermediate 9: Ethyl 6-bromo-2-oxo-2,3-dihydro-1H-imidazo[4,5-b]pyridine-1-carboxylate

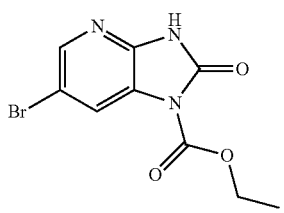 [SMILES: CCOC(=O)n1c(=O)[nH]c2ncc(Br)cc21]

Step A: 6-Bromo-1,3-dihydro-2H-imidazo[4,5-b]pyridin-2-one

To a solution of 2,3-diamino-5-bromopyridine (5 g, 27 mmol) in THF (87 mL) was added CDI (3.02 g, 18.6 mmol), and the reaction mixture was stirred at 80° C. for 16 h. Then, water was added, and the mixture was filtered. The solids were collected by filtration, washed with water and Et$_2$O, and dried under vacuum to afford the title compound (5.3 g, 25 mmol, 93%), which was used in the next step without further purification. MS (ESI): mass calcd. for C$_6$H$_4$BrN$_3$O, 212.95; m/z found, 214 [M+H]$^+$.

Step B: Ethyl 6-bromo-2-oxo-2,3-dihydro-1H-imidazo[4,5-b]pyridine-1-carboxylate A mixture of 6-bromo-1,3-dihydro-2H-imidazo[4,5-b]pyridin-2-one (5.3 g, 25 mmol), ethyl pyridin-2-yl carbonate (5.36 g, 27.2 mmol) and K$_2$CO$_{03}$ (3.77 g, 27.2 mmol) in DMF (245 mL) was heated to 75° C. for 3 h. The crude reaction mixture was concentrated in vacuo and diluted with water and 1 M HCl until the mixture reached pH 1. The solution was filtered and triturated with Et$_2$O to afford the title compound (6.6 g, 23 mmol, 93%), which was used in the next step without further purification. MS (ESI): mass calcd. for C$_9$H$_8$BrN$_3$O$_3$, 284.97; m/z found, 286 [M+H]$^+$.

Intermediate 10: 6-Bromo-3-(4-methoxybenzyl)-1H-imidazo[4,5-b]pyridin-2(3H)-one

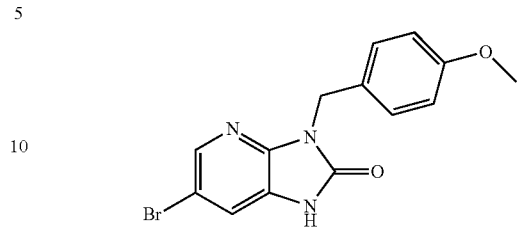

To a solution of ethyl 6-bromo-2-oxo-2,3-dihydro-1H-imidazo[4,5-b]pyridine-1-carboxylate (11.48 g, 40.21 mmol), and K$_2$CO$_3$ (6.65 g, 48.1 mmol), in DMF (120 mL) was added 4-methoxybenzylchloride (6.01 mL, 44.1 mmol) dropwise. The reaction mixture was heated to 50° C. for 6 h. The reaction mixture was cooled to rt, and isopropylamine (3.4 mL, 40.1 mmol) was added, the reaction mixture was stirred at rt for 1 h. Water and EtOAc were added. The organic layer was separated, dried (MgSO$_4$), filtered and concentrated under reduced pressure. Purification (FCC, SiO$_2$, EtOAc in DCM from 0% to 35%) afforded the title compound as a cream solid. Trituration with Et$_2$O to afforded the title compound (6.9 g, 51%). MS (ESI): m/z found [M+H]=334.

Intermediate 11: 6-Bromo-3-methyl-1,3-dihydro-2H-imidazo[4,5-b]pyridin-2-one

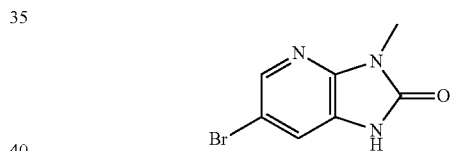

Method A

Step A: 5-Bromo-N-methyl-3-nitropyridin-2-amine

To a solution of 5-bromo-2-chloro-3-nitropyridine (15 g, 63 mmol) in THF (570 mL) at 0° C. was added a solution of methylamine (40% in H$_2$O, 10.9 mL, 126 mmol). The reaction mixture was stirred at room temperature for 16 h. Upon completion, the reaction mixture was extracted with EtOAc (3×500 mL). The combined organic layers were dried (Na$_2$SO$_4$), filtered and concentrated under reduced pressure to yield the title compound as a yellow solid (14.6 g, 62.7 mmol, 99%), which was used in the next step without further purification. MS (ESI): mass calcd. for C$_6$H$_6$BrN$_3$O$_2$, 230.96; m/z found, 232 [M+H]$^+$. $^1$H NMR (500 MHz, DMSO-d$_6$) δ 8.54 (d, J=2.3 Hz, 1H), 8.46 (d, J=2.3 Hz, 1H), 8.17 (br s, 1H), 3.16 (d, J=4.9 Hz, 3H).

Step B: 5-Bromo-N$^2$-methylpyridine-2,3-diamine

To a stirred suspension of 5-bromo-N-methyl-3-nitropyridin-2-amine (14.6 g, 62.7 mmol) and zinc (41 g, 627 mmol) in a mixture of water (29 mL) and acetone (291 mL) was added NH$_4$Cl (33.6 g, 627 mmol). The reaction mixture was stirred at room temperature for 72 h. Upon completion the mixture was filtered through Celite® and rinsed with DCM. The filtrate was washed with water and the aqueous layer was extracted with DCM (3×). The combined organic layers were dried ($Na_2SO_4$), filtered and concentrated under reduced pressure to yield the title compound as an oil (12.7 g, 69.3 mmol), which was used in the next step without further purification. MS (ESI): mass calcd. for $C_6H_8BrN_3$, 200.99; m/z found, 202 $[M+H]^+$.

Step C: 6-Bromo-3-methyl-1,3-dihydro-2H-imidazo[4,5-b]pyridin-2-one

To a solution of 5-bromo-$N^2$-methylpyridine-2,3-diamine (14 g, 69 mmol) in DMF (702 mL) at room temperature was added CDI (29 g, 180 mmol). The reaction mixture was stirred for 16 h. LCMS analysis of the crude reaction mixture showed that the reaction was not complete, and the resultant residue was re-dissolved in THF and CDI (11.2, 69 mmol) was added. The reaction mixture was stirred at 60° C. for 16 h. The reaction mixture was quenched with water and diluted with $Et_2O$. The suspension was filtered and the resulting solid was washed with $Et_2O$ and dried under vacuum to yield the title compound as a black solid (15.8 g, 35.7 mmol), which was used in the next step without further purification. MS (ESI): mass calcd. for $C_7H_6BrN_3O$, 226.97; m/z found, 227.0 $[M+H]^+$.

Method B

Step A: 5-Bromo-N-methyl-3-nitropyridin-2-amine

Into a 20 L four-necked flask were charged with EtOH (10.5 L) and 2,5-dibromo-3-nitropyridine (1500 g, 5.32 mol). The mixture was heated to 50° C. followed by addition of aq. $MeNH_2$ (40% w/w, 1032.5 g, 13.3 mol) during 1 h. After stirring at 55 to 65° C. for 2 h, the reaction mixture was cooled 20° C. and filtered. The cake was washed with $EtOH/H_2O$ (V/V=1/1, 1 L) followed by slurring in water (8 L) at room temperature for 1.5 h. Then the suspension was filtered and the cake was washed with water (1 L). The cake was collected and dried at room temperature overnight to give the title compound (1198 g, 97%). $^1$H NMR (400 MHz, $CDCl_3$) δ 8.55 (d, J=2.3 Hz, 1H), 8.48 (d, J=2.3 Hz, 1H), 8.20 (bs, 1H), 3.18 (d, J=8.0 Hz, 3H).

Step B: 5-Bromo-$N^2$-methylpyridine-2,3-diamine

Into a pressure reactor was charged with Pt/C (5% wt, 78.7 g, 10.6% w/w), aq. $H_3PO_2$ (50% wt, 5.8 g), $NH_4VO_3$ (2.1 g), THF/EtOH (V/V=1/1, 12.1 L) and 5-bromo-N-methyl-3-nitropyridin-2-amine (740 g, 3.19 mol). The reactor was purged with hydrogen and pressurized to 20 atm followed by stirring at 20 to 30° C. for about 0.5 h. Then the mixture was re-pressurized to 20 atm with hydrogen and stirred at 30 to 45° C. for 1 h. The reaction mixture was cooled to room temperature and filtered through a pad of Celite® followed by washing the cake with THF (1 L). The combined filtrate was concentrated at 40 to 45° C. under vacuum. Solvent chasing distillation by n-heptane (1 L×2) and dilution with ACN (3 L) afforded a dark solution of the title compound in ACN which was used in the next step without further purification.

Step C: 6-Bromo-3-methyl-1H-imidazo[4,5-b]pyridin-2(3H)-one

Into a 5 L three-necked flask was charged with a solution of 5-bromo-$N^2$-methylpyridine-2,3-diamine (in ACN (3.05 L). The mixture was cooled to 5° C. followed by addition of CDI (564.55 g, 3.48 mol) in portions. The mixture was stirred at 5 to 25° C. for 3 h followed by concentration until about 2 L of solvent was left. The resulting mixture was filtered and the cake was slurried with $H_2O$ (3.5 L) at 20 to 25° C. for 3 h. The suspension was filtered and the cake was dried at 20 to 25° C. for 48 h to give the title compound (680 g, 87.9%, over two steps). $^1$H NMR (300 MHz, DMSO-$d_6$) δ 11.30 (s, 1H), 8.06 (d, J=3.0 Hz, 1H), 7.49 (d, J=3.0 Hz, 1H), 3.29 (s, 3H).

Intermediate 12: Ethyl 2-(6-bromo-3-methyl-2-oxo-2,3-dihydro-1H-imidazo[4,5-b]pyridin-1-yl)acetate

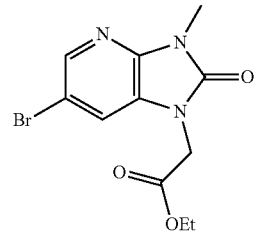

To a mixture of 6-bromo-3-methyl-1H-imidazo[4,5-b]pyridin-2(3H)-one (Intermediate 11, 350.0 g, 1.535 mol) and ACN (4800 mL) was charged with $K_2CO_3$ (318.2 g). The resulting mixture was warmed to 45 to 50° C. followed by dropwise addition of ethyl 2-bromoacetate (281.9 g, 1.688 mol) at 50 to 60° C. Then the reaction mixture was warmed to 80 to 85° C. and kept at this temperature for 7.5 h. Additional ethyl 2-bromoacetate (25.6 g, 0.153 mol) was charged into the reaction mixture. After stirring at 80 to 85° C. for 3 h, the mixture was cooled to room temperature naturally and stirred overnight. The mixture was warmed to 80 to 85° C. followed by addition of ethyl 2-bromoacetate (51.2 g, 0.306 mmol) and $K_2CO_3$ (42.4 g). Another portion of $K_2CO_3$ (106.0 g) was added into the mixture after stirring for 3.5 h. The reaction was cooled to 65 to 70° C. followed by filtration. The cake was washed with ACN (1400 mL) and the combined filtrate was concentrated at 40 to 45° C. until about 2.8 volume of ACN was left. HCl (0.08 N, 2500 mL) was poured into the residue and the resulting suspension was stirred at 20 to 25° C. for 30 min followed by filtration. The cake was collected and dried at 45° C. vacuum oven for 14 h to give the title compound (438 g, 91%). $^1$H NMR (300 MHz, $CDCl_3$) δ 8.12 (d, J=1.9 Hz, 1H), 7.23 (d, J=1.9 Hz, 1H), 4.61 (s, 2H), 4.25 (q, J=7.5 Hz, 2H), 3.49 (s, 3H), 1.30 (t, J=7.5 Hz, 3H).

Intermediate 13: 2-(6-Bromo-3-methyl-2-oxo-2,3-dihydro-1H-imidazo[4,5-b]pyridin-1-yl)acetic Acid. Lithium Salt

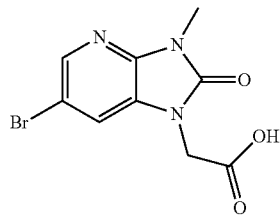 [SMILES: Cn1c(=O)n(CC(=O)O)c2cc(Br)cnc21]

Step A: Ethyl 2-(6-bromo-3-methyl-2-oxo-2,3-dihydro-1H-imidazo[4,5-b]pyridin-1-yl)acetate Under a nitrogen atmosphere was added 6-bromo-3-methyl-1,3-dihydro-2H-imidazo[4,5-b]pyridin-2-one (Intermediate 11, 5 g, 21.9 mmol) to a suspension of sodium hydride (60% dispersion in mineral oil, 1.3 g, 32.9 mmol) in DMF (171 mL) at room temperature. After 10 minutes ethyl bromoacetate (3.2 mL, 28.5 mmol) was added and the reaction was stirred at room temperature. After 4 h, complete conversion was observed. The reaction was cooled to 0° C. and water was added (200 mL). The precipitates were collected by filtration and washed with water to give the title compound (6.1 g, 88%). MS (ESI): mass calcd. for $C_{11}H_{12}BrN_3O_3$, 313.0; m/z found, 313.9 [M+H]$^+$. $^1$H NMR (500 MHz, DMSO-$d_6$) δ 8.14 (d, J=2.0 Hz, 1H), 7.92 (d, J=2.0 Hz, 1H), 4.76 (s, 2H), 4.16 (q, J=7.1 Hz, 2H), 3.35 (s, 3H), 1.22 (t, J=7.1 Hz, 3H).

Step B: 2-(6-bromo-3-methyl-2-oxo-2,3-dihydro-1H-imidazo[4,5-b]pyridin-1-yl)acetic Acid Lithium hydroxide (2M, 1.2 mL, 2.3 mmol) was added to a mixture of ethyl 2-(6-bromo-3-methyl-2-oxo-2,3-dihydro-1H-imidazo[4,5-b]pyridin-1-yl)acetate (612 mg, 1.9 mmol) in THF (23 mL) at room temperature. The precipitates were collected by filtration and washed with THF to give the title compound (465 mg, 83%). MS (ESI): mass calcd. for $C_9H_8BrN_3O_3$, 285.0; m/z found, 286.0 [M+H]$^+$. $^1$H NMR (500 MHz, DMSO-$d_6$) δ 8.02 (d, J=2.0 Hz, 1H), 7.46 (d, J=2.0 Hz, 1H), 4.03 (s, 2H), 3.31 (s, 3H).

Intermediate 14: 2-(6-Bromo-7-chloro-3-methyl-2-oxo-2,3-dihydro-1H-imidazo[4,5-b]pyridin-1-yl) acetic Acid and its Trifluoroacetic Acid Salt

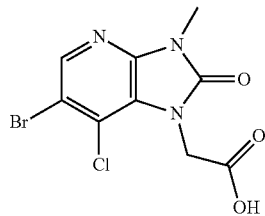 [SMILES: Cn1c(=O)n(CC(=O)O)c2c(Cl)c(Br)cnc21]

Step A. 5-Bromo-4-chloro-3-nitropyridin-2-amine

A solution of 4-chloro-3-nitropyridin-2-amine (2 g, 11.5 mmol) and N-bromosuccinimide (2.5 g, 13.8 mmol) in ACN (125 mL) was heated at 80° C. After 1 h, the reaction mixture was cooled was cooled to room temperature and volatiles were removed under reduced pressure. Purification (FCC, SiO$_2$, 0-5% EtOAc in DCM), afforded the title compound (2.9 g, 99%). MS (ESI): mass calcd. for $C_5H_3BrClN_3O_2$, 250.9; m/z found, 251.8 [M+H]$^+$. $^1$H NMR (400 MHz, DMSO-$d_6$) δ 8.42 (s, 1H), 7.37 (br s, 2H).

Step B: tert-Butyl (5-bromo-4-chloro-3-nitropyridin-2-yl)carbamate

To a mixture of 5-bromo-4-chloro-3-nitropyridin-2-amine (2.9 g, 11.4 mmol) in THF (200 mL) at room temperature, under a nitrogen atmosphere was added sodium hydride (60% dispersion in mineral oil, 1.1 g, 27.4 mmol) in small batches. After 30 minutes, BOC-anhydride (2.4 mL, 11.4 mmol) was added to the reaction mixture. After 16 h, water (5 mL) was added to the reaction mixture and volatiles were removed. The residue was partitioned between water (100 mL) and EtOAc (150 mL). The organic layer was collected. The aqueous layer was washed with EtOAc (3×150 mL). The combined organics were dried (MgSO$_4$), filtered and concentrated under vacuum. Purification (FCC, SiO$_2$, 0-5% EtOAc in DCM), afforded the title compound (3.0 g, 75%). MS (ESI): mass calcd. for $C_{10}H_{11}BrClN_3O_4$, 351.0; m/z found, 295.9 [M-tBu]$^+$. $^1$H NMR (500 MHz, DMSO-$d_6$) δ 10.62 (s, 1H), 8.89 (s, 1H), 1.42 (s, 9H).

Step C: tert-Butyl (5-bromo-4-chloro-3-nitropyridin-2-yl)(methyl)carbamate

To a mixture of tert-butyl (5-bromo-4-chloro-3-nitropyridin-2-yl)carbamate (3.0 g, 8.6 mmol) in DMF (140 mL) at room temperature, under a nitrogen atmosphere was added sodium hydride (60% dispersion in mineral oil, 445 mg, 11.1 mmol) in small batches. After 30 minutes, iodomethane (0.64 mL, 10.3 mmol) was added to the reaction mixture at 0° C. After 16 h, EtOAc (200 mL) was added to the reaction mixture. The mixture was washed with brine (1×350 mL). The organic was dried (MgSO$_4$), filtered and concentrated under vacuum to give the title compound (3.1 g, 99%). MS (ESI): mass calcd. for $C_{11}H_{13}BrClN_3O_4$, 365.0; m/z found, 309.9 [M-tBu]$^+$.

Step D: 5-Bromo-4-chloro-N-methyl-3-nitropyridin-2-amine, TFA Salt

To a solution of tert-butyl (5-bromo-4-chloro-3-nitropyridin-2-yl)(methyl)carbamate (3.1 g, 8.6 mmol) in DCM (100 mL) at room temperature was added TFA (13 mL, 171 mmol). After completion, volatiles were removed. The solid was dissolved in EtOAc (200 mL). The mixture was washed with brine (2×300 mL). The organic was dried over MgSO$_4$, filtered and concentrated under vacuum to give the title compound (2.3 g, 99%). MS (ESI): mass calcd. for $C_6H_5BrClN_3O_2$, 265.0; m/z found, 265.8 [M+H]$^+$. $^1$H NMR (400 MHz, DMSO-$d_6$) δ 8.53 (s, 1H), 7.60-7.52 (m, 1H), 2.86 (d, J=4.5 Hz, 3H).

Step E: 5-Bromo-4-chloro-N$^2$-methylpyridine-2,3-diamine

To a stirred suspension of 5-bromo-4-chloro-N-methyl-3-nitropyridin-2-amine (500 mg, 1.9 mmol) and zinc (1.2 g, 18.8 mmol) in a mixture of water (0.9 mL) and acetone (8.7 mL) was slowly added ammonium chloride (1 g, 18.8 mmol) at 0° C. Upon completion, the mixture was filtered through Celite® and rinsed with MeOH. The volatiles were removed and the material was partitioned between water (40 mL) and EtOAc (40 mL). The organic layer was collected. The aqueous layer was washed with EtOAc (3×60 mL). The combined organics were dried (MgSO$_4$), filtered and concentrated under vacuum. Purification (FCC, SiO$_2$, 0-10% MeOH in DCM), afforded the title compound (280 mg, 63%). MS (ESI): mass calcd. for $C_6H_7BrClN_3$, 235.0; m/z found, 235.8 [M+H]$^+$.

Step F: 6-Bromo-7-chloro-3-methyl-1,3-dihydro-2H-imidazo[4,5-b]pyridin-2-one

To a mixture of 5-bromo-4-chloro-N$^2$-methylpyridine-2,3-diamine (210 mg, 0.9 mmol) in DMF (7 mL), under a nitrogen atmosphere, at room temperature was added CDI (432 mg, 2.7 mmol). After 16 h, additional CDI (432 mg, 2.7 mmol) was added to the reaction mixture. The reaction mixture was heated at 70° C. Upon complete conversion, the reaction mixture was slowly poured into ice. The resulting mixture was extracted using EtOAc (3×). The combined organics were washed with 1N HCl (1×), dried (MgSO$_4$), filtered and concentrated under vacuum to afford title product which was used crude without further purification. MS (ESI): mass calcd. for $C_7H_5BrClN_3O$, 260.9; m/z found, 261.8 [M+H]$^+$. $^1$H NMR (500 MHz, DMSO-d$_6$) δ 11.98 (s, 1H), 8.21 (s, 1H), 3.28 (s, 3H).

Step G: tert-Butyl 2-(6-bromo-7-chloro-3-methyl-2-oxo-2,3-dihydro-1H-imidazo[4,5-b]pyridin-1-yl) acetate To a suspension of sodium hydride (60% dispersion in mineral oil, 38 mg, 1.0 mmol) in DMF (5 mL), under a nitrogen atmosphere, at room temperature was added 6-bromo-7-chloro-3-methyl-1,3-dihydro-2H-imidazo[4,5-b]pyridin-2-one (170 mg, 0.6 mmol). After 10 min, tert-butyl bromoacetate (0.12 mL, 0.84 mmol) was added to the reaction mixture. After 16 h, water (50 mL) was added to the mixture. After 30 minutes, the resulting precipitates were filtered off and washed with water to give title compound, which was used crude without further purification. MS (ESI): mass calcd. for $C_{13}H_{15}BrClN_3O_3$, 375.0; m/z found, 375.8 [M+H]$^+$. $^1$H NMR (500 MHz, DMSO-d$_6$) δ 8.33 (s, 1H), 4.80 (s, 2H), 3.37 (s, 3H), 1.43 (s, 9H).

Step H: 2-(6-Bromo-7-chloro-3-methyl-2-oxo-2,3-dihydro-1H-imidazo[4,5-b]pyridin-1-yl)acetic acid and its trifluoroacetic acid salt To a solution of tert-butyl 2-(6-bromo-7-chloro-3-methyl-2-oxo-2,3-dihydro-1H-imidazo[4,5-b]pyridin-1-yl)acetate (126 mg, 0.3 mmol) in DCM (3.8 mL) at room temperature was added TFA (0.26 mL, 3.3 mmol). After completion, volatiles were removed. The resulting solid was triturated in MeOH. The solids were collected by filtration and washed with MeOH to give the title compound (112 mg, 77%). MS (ESI): mass calcd. for $C_9H_7BrClN_3O_3$, 318.9; m/z found, 319.8 [M+H]$^+$.

Intermediate 15: 2-(6-bromo-3-methyl-2-oxo-2,3-dihydro-1H-imidazo[4,5-b]pyridin-1-yl)-N,N-dimethylacetamide

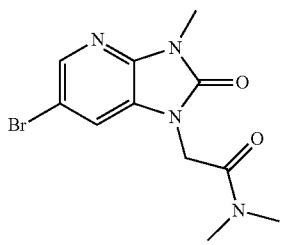 [SMILES: CN(C)C(=O)Cn1c(=O)n(C)c2ncc(Br)cc21]

To a solution of 6-bromo-3-methyl-1,3-dihydro-2H-imidazo[4,5-b]pyridin-2-one (Intermediate 11, 600 mg, 2.6 mmol) in DMF (20 mL) was added NaH (72 mg, 3.2 mmol). Upon addition of NaH vigorous bubbling occurred. After 30 min of stirring at room temperature, bubbling had ceased and 2-bromo-N,N-dimethylacetamide (Intermediate 4, 618 mg, 3.7 mmol) was added. The resulting reaction mixture was stirred at room temperature then diluted with ethyl acetate and quenched with water. The combined organic layers were dried using Mg$_2$SO$_4$ and concentrated under reduced pressure to yield a yellow oil which was purified (FCC, SiO$_2$, 0-7% 2M NH$_3$/MeOH in DCM) to provide the title compound (504 mg, 61%) as a beige solid. MS (ESI): mass calcd. for $C_{11}H_{13}BrN_4O_2$, 313.1; m/z found, 314.1 [M+H]$^+$. $^1$H NMR (400 MHz, DMSO-d$_6$) δ 8.12-8.08 (d, J=2.0 Hz, 1H), 7.81-7.77 (d, J=2.0 Hz, 1H), 4.83-4.75 (s, 2H), 3.35-3.33 (s, 3H), 3.08-3.06 (s, 3H), 2.85-2.83 (s, 3H).

Intermediate 16: 1-(2-(Azetidin-1-yl)-2-oxoethyl)-6-bromo-3-methyl-1,3-dihydro-2H-imidazo[4,5-b] pyridin-2-one

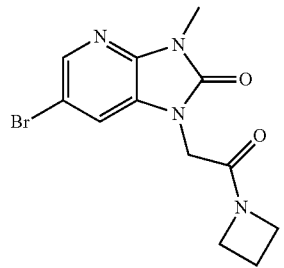 [SMILES: Cn1c(=O)n(CC(=O)N2CCC2)c2cc(Br)cnc21]

The title compound was prepared in a manner analogous to 2-(6-bromo-3-methyl-2-oxo-2,3-dihydro-1H-imidazo[4,5-b]pyridin-1-yl)-N,N-dimethylacetamide (Intermediate 15), using 1-(azetidin-1-yl)-2-bromoethan-1-one (Intermediate 5). MS (ESI): mass calcd. for $C_{11}H_{13}BrN_4O_2$, 325.1; m/z found, 326.1 [M+H]$^+$. $^1$H NMR (500 MHz, DMSO-d$_6$) δ 8.10 (d, J=2.0 Hz, 1H), 7.78 (d, J=2.0 Hz, 1H), 4.55 (s, 2H), 4.27 (t, J=7.6 Hz, 2H), 3.91 (t, J=7.7 Hz, 2H), 3.33 (s, 3H), 2.32-2.24 (m, 2H).

Intermediate 17: 1-(2-(Azetidin-1-yl)-2-oxoethyl)-6-bromo-7-chloro-3-methyl-1,3-dihydro-2H-imidazo[4,5-b]pyridin-2-one and its Trifluoroacetic Acid Salt

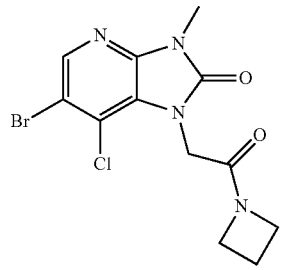 [SMILES: Cn1c(=O)n(CC(=O)N2CCC2)c2c(Cl)c(Br)cnc21]

A mixture of 2-(6-bromo-7-chloro-3-methyl-2-oxo-2,3-dihydro-1H-imidazo[4,5-b]pyridin-1-yl)acetic acid. TFA salt (Intermediate 14, 112 mg, 0.3 mmol), azetidine (0.03 mL, 0.5 mmol), DIPEA (0.15 mL, 0.9 mmol) and 2,4,6-tripropyl-1,3,5,2,4,6-trioxatriphosphorinane-2,4,6-trioxide (50% solution in DCM, 0.7 mL, 1.2 mmol) in DMF (3.4 mL) was stirred at room temperature. After 3 days, azetidine (0.03 mL, 0.5 mmol), DIPEA (0.15 mL, 0.9 mmol) and 2,4,6-tripropyl-1,3,5,2,4,6-trioxatriphosphorinane-2,4,6-trioxide (50% solution in DCM, 0.7 mL, 1.2 mmol) were added again. After 16 h, a saturated aqueous solution NaHCO$_3$(20 mL) was added. The mixture was extracted using DCM (3×30 mL). The combined organics were dried over MgSO$_4$, filtered and concentrated under vacuum to give the title compound (92 mg, 0.3 mmol, 99%) which was used crude without further purification. MS (ESI): mass calcd. for C$_2$H$_{12}$BrClN$_4$O$_2$, 358.0; m/z found, 358.8 [M+H]$^+$. $^1$H NMR (400 MHz, DMSO) δ 8.10 (s, 1H), 4.54 (s, 2H), 4.08 (t, J=7.6 Hz, 2H), 3.71 (t, J=7.7 Hz, 2H), 3.17 (s, 3H), 2.15-2.05 (m, 2H).

Intermediate 18: 6-Bromo-1-(2-(3-fluoroazetidin-1-yl)-2-oxoethyl)-3-methyl-1,3-dihydro-2H-imidazo[4,5-b]pyridin-2-one

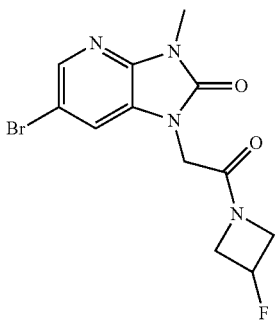 [SMILES: Cn1c(=O)n(CC(=O)N2CC(F)C2)c2cc(Br)cnc21]

The title compound was prepared in a manner analogous to 2-(6-bromo-3-methyl-2-oxo-2,3-dihydro-1H-imidazo[4,5-b]pyridin-1-yl)-N,N-dimethylacetamide (Intermediate 15), using 2-bromo-1-(3-fluoroazetidin-1-yl)ethan-1-one (Intermediate 6). MS (ESI): mass calcd. for C$_2$H$_{12}$BrFN$_4$O$_2$, 343.1; m/z found, 344.1 [M+H]$^+$. $^1$H NMR (500 MHz, DMSO-d$_6$) δ 8.11 (d, J=2.0 Hz, 1H), 7.79 (d, J=2.0 Hz, 1H), 5.55-5.37 (m, 1H), 4.68-4.56 (m, 3H), 4.45-4.34 (m, 1H), 4.30-4.19 (m, 1H), 4.02-3.91 (m, 1H), 3.34 (s, 3H).

Intermediate 19: 6-Bromo-3-methyl-1-(pyridazin-3-ylmethyl)-1,3-dihydro-2H-imidazo[4,5-b]pyridin-2-one

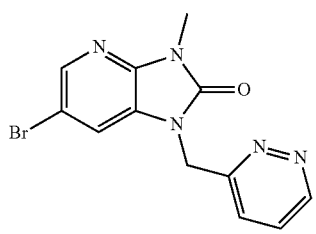 [SMILES: Cn1c(=O)n(Cc2cccnn2)c2cc(Br)cnc21]

The title compound was prepared in a manner analogous to Intermediate 15, using 3-(chloromethyl)pyridazine (Intermediate 2). MS (ESI): mass calcd. for C$_2$H$_{10}$BrN$_5$O, 320.1; m/z found, 321.1 [M+H]$^+$. $^1$H NMR (500 MHz, DMSO-d$_6$) δ 0.9.16 (dd, J=4.6, 2.0 Hz, 1H), 8.13 (d, J=1.9 Hz, 1H), 7.82 (d, J=2.0 Hz, 1H), 7.72-7.65 (m, 2H), 5.41 (s, 2H), 3.36 (s, 3H).

Intermediate 20: 6-Bromo-3-methyl-1-(pyrimidin-4-ylmethyl)-1,3-dihydro-2H-imidazo[4,5-b]pyridin-2-one

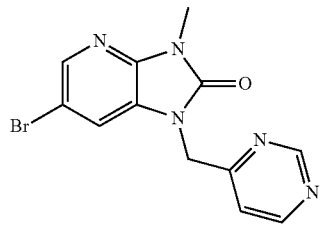 [SMILES: Cn1c(=O)n(Cc2ccncn2)c2cc(Br)cnc21]

To a cooled (0° C.) solution of 6-bromo-3-methyl-1,3-dihydro-2H-imidazo[4,5-b]pyridin-2-one (Intermediate 11, 65 mg, 0.28 mmol), triphenylphosphine (149 mg, 0.57 mmol), and pyrimidin-4-ylmethanol (31 mg, 0.28 mmol) in ACN (1.6 mmL) was added (E)-di-tert-butyl diazene-1,2-dicarboxylate (98 mg, 0.43 mmol). The reaction mixture was heated under microwave irradiation at 110° C. for 15 minutes. The reaction mixture was cooled to rt, and concentrated under reduced pressure. Purification (Reverse phase HPLC; Stationary phase: C18 XBridge 30×100 mm 5 um; gradient 81% 10 mM NH$_4$CO$_3$H pH 9 solution in Water, 19% CH$_3$CN to 64% 10 mM NH$_4$CO$_3$H pH 9 solution in Water, 36% CH$_3$CN) afforded the title compound as a white solid (28 mg, 31%).

Intermediate 21: 6-Bromo-3-methyl-1-(pyrazin-2-ylmethyl)-1H-imidazo[4,5-b]pyridin-2(3H)-one

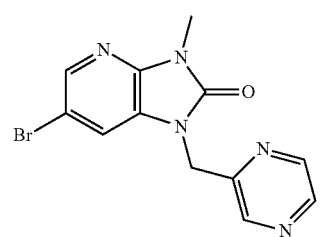 [SMILES: Cn1c(=O)n(Cc2cnccn2)c2cc(Br)cnc21]

The title compound was prepared in a manner analogous to Intermediate 20, using pyrazin-2-ylmethanol.

Intermediate 22: 6-Bromo-3-methyl-1-((5-methyl-isoxazol-3-yl)methyl)-1,3-dihydro-2H-imidazo[4,5-b]pyridin-2-one

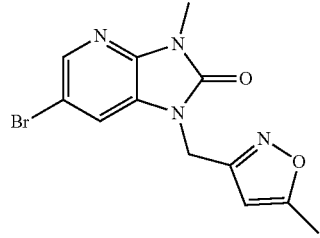 [SMILES: Cc1cc(Cn2c(=O)n(C)c3ncc(Br)cc32)no1]

To a solution of 6-bromo-3-methyl-1,3-dihydro-2H-imidazo[4,5-b]pyridin-2-one (Intermediate 11, 600 mg, 2.63 mmol) in DMF (8 mL) at 0° C. was added NaH (60% dispersion in mineral oil, 137 mg, 3.42 mmol), and the reaction mixture was stirred at room temperature for 10 min. Then, 3-chloromethyl-5-methylisoxazole (288 µL, 2.63 mmol) was added at 0° C., and the mixture was stirred at room temperature overnight.

The crude reaction mixture was quenched with water and extracted with EtOAc. The combined organic layers were dried (MgSO$_4$), filtered and concentrated under reduced pressure. The residue was purified (FCC, SiO$_2$, 0-40% EtOAc in heptanes) to yield the title compound (850 mg, 83%). MS (ESI): mass calcd. for $C_{12}H_{11}BrN_4O_2$, 322.0; m/z found, 323 [M+H]$^+$. $^1$H NMR (300 MHz, DMSO-d$_6$) δ 8.12 (d, J=1.2 Hz, 1H), 7.79 (d, J=1.3 Hz, 1H), 6.18 (s, 1H), 5.14 (s, 2H), 3.34 (s, 3H), 2.35 (s, 3H).

Intermediate 23: 6-Bromo-3-methyl-1-((5-methyl-1,3,4-oxadiazol-2-yl)methyl)-1,3-dihydro-2H-imidazo[4,5-b]pyridin-2-one

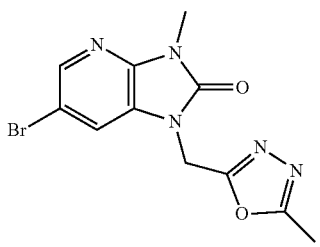 [SMILES: Cc1nnc(Cn2c(=O)n(C)c3ncc(Br)cc32)o1]

The title compound was prepared in a manner analogous to Intermediate 22: 6-bromo-3-methyl-1-((5-methylisoxazol-3-yl)methyl)-1,3-dihydro-2H-imidazo[4,5-b]pyridin-2-one using 2-(chloromethyl)-5-methyl-1,3,4-oxadiazole.

Intermediate 24: 6-Bromo-3-methyl-1-((3-methyl-1,2,4-oxadiazol-5-yl)methyl)-1,3-dihydro-2H-imidazo[4,5-b]pyridin-2-one

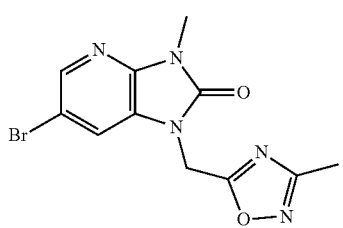 [SMILES: Cc1noc(Cn2c(=O)n(C)c3ncc(Br)cc32)n1]

The title compound was prepared in a manner analogous to Intermediate 22: 6-bromo-3-methyl-1-((5-methylisoxazol-3-yl)methyl)-1,3-dihydro-2H-imidazo[4,5-b]pyridin-2-one using 5-(chloromethyl)-3-methyl-1,2,4-oxadiazole. MS (ESI): m/z found, 325.9 [M+H], $^1$H NMR (300 MHz, DMSO-d$_6$) δ 8.17 (d, J=1.7 Hz, 1H), 7.96 (d, J=1.7 Hz, 1H), 5.48 (s, 2H), 3.36 (s, 3H), 2.29 (s, 3H).

Intermediate 25: 6-Bromo-3-methyl-1-(oxetan-2-ylmethyl)-1,3-dihydro-2H-imidazo[4,5-b]pyridin-2-one

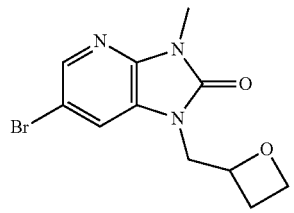 [SMILES: Cn1c(=O)n(CC2CCO2)c2cc(Br)cnc21]

The title compound was prepared in a manner analogous to Intermediate 22, using 6-bromo-3-methyl-1,3-dihydro-2H-imidazo[4,5-b]pyridin-2-one (Intermediate 11) and 2-(bromomethyl)oxetane. MS (ESI): mass calcd. for $C_{11}H_{12}BrN_3O_2$, 297.0; m/z found, 298.1 [M+H]$^+$. $^1$H NMR (500 MHz, DMSO-d$_6$) δ 8.10 (d, J=2.0 Hz, 1H), 7.83 (d, J=2.0 Hz, 1H), 5.02-4.96 (m, 1H), 4.45 (ddd, J=8.6, 7.1, 5.7 Hz, 1H), 4.32 (dt, J=9.0, 6.0 Hz, 1H), 4.19-4.01 (m, 2H), 3.34 (s, 3H), 2.69-2.61 (m, 1H), 2.46-2.38 (m, 1H).

Intermediate 26: 3-Methyl-6-(3-(trifluoromethyl)phenyl)-1,3-dihydro-2H-imidazo[4,5-b]pyridin-2-one

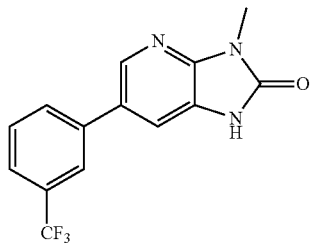 [SMILES: Cn1c(=O)[nH]c2cc(-c3cccc(C(F)(F)F)c3)cnc21]

Step A: N-Methyl-3-nitro-5-(3-(trifluoromethyl)phenyl)pyridin-2-amine

A mixture of 5-bromo-N-methyl-3-nitropyridin-2-amine (Intermediate 11, product from Step A, 2.2 g, 9.5 mmol), 3-(trifluoromethyl)phenylboronic acid (2.7 g, 14.2 mmol), 1,1'-bis(diphenylphosphino)ferrocene palladium(II)dichloride dichloromethane complex (542 mg, 0.66 mmol), Cs$_2$CO$_3$ (6.2 g, 19.0 mmol), dioxane (87 mL) and H$_2$O (17 mL) was heated to 90° C. using an oil bath. After 16 h, the reaction mixture was cooled to room temperature and volatiles were removed. The crude material was purified (FCC, SiO$_2$, 0-100% EtOAc in hexanes), to give the title compound (2.6 g, 91%).

Step B: N$^2$-Methyl-5-(3-(trifluoromethyl)phenyl)pyridine-2,3-diamine

A mixture of N-methyl-3-nitro-5-(3-(trifluoromethyl)phenyl)pyridin-2-amine (2.6 g, 8.6 mmol) and 10% palladium on carbon (0.46 g, 0.43 mmol) in EtOH (80 mL) was allowed to stir at room temperature under a hydrogen atmosphere (1 atm, balloon). After 16 h, the reaction was filtered through a pad of Celite® and the filtrate was concentrated under vacuum. The material was dissolved in a minimum amount of MeOH and filtered through an acrodisc syringe filter and the filtrate was concentrated under vacuum to give the title compound (2.3 g, 99%), which was used in the next step without further purification. MS (ESI): mass calcd. for $C_{13}H_{12}F_3N_3$, 267.1; m/z found, 268.1 [M+H]+. 1H NMR (500 MHz, DMSO-$d_6$) δ 8.04 (d, J=2.1 Hz, 1H), 7.74-7.71 (m, 1H), 7.70-7.66 (m, 1H), 7.56-7.48 (m, 2H), 7.09 (d, J=2.1 Hz, 1H), 4.37-4.26 (m, 1H), 3.29 (s, 2H), 3.08 (d, J=5.1 Hz, 3H).

Step C: 3-Methyl-6-(3-(trifluoromethyl)phenyl)-1,3-dihydro-2H-imidazo[4,5-b]pyridin-2-one To a mixture of $N^2$-methyl-5-(3-(trifluoromethyl)phenyl)pyridine-2,3-diamine (2.3 g, 8.6 mmol) in DMF (87 mL), under a nitrogen atmosphere, at room temperature was added CDI (1.7 g, 10.3 mmol). After 16 h, conversion was not complete and additional CDI (2.1 g, 12.9 mmol) was added to the reaction mixture. After 3 h, complete conversion was observed and water (200 mL) was added. The precipitates were collected by filtration, washed with water and dried under vacuum to give the title compound (2.2 g, 87%). MS (ESI): mass calcd. for $C_{14}H_{10}F_3N_3O$, 293.1; m/z found, 294.1 [M+H]+. 1H NMR (400 MHz, DMSO) δ 11.29 (s, 1H), 8.33 (d, J=2.0 Hz, 1H), 8.05-7.94 (m, 2H), 7.77-7.67 (m, 2H), 7.63 (d, J=2.0 Hz, 1H), 3.34 (s, 3H).

Intermediate 27: 6-(4-Fluoro-3-methylphenyl)-3-methyl-1,3-dihydro-2H-imidazo[4,5-b]pyridin-2-one

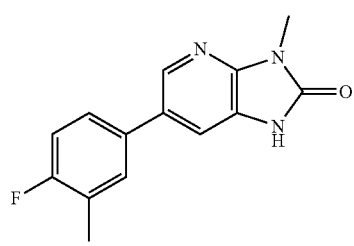 [SMILES: Cc1cc(-c2cnc3c(c2)[nH]c(=O)n3C)ccc1F]

To a solution a 6-bromo-3-methyl-1,3-dihydro-2H-imidazo[4,5-b]pyridin-2-one (Intermediate 11, 75 mg, 0.29 mmol), (4-fluoro-3-methylphenyl)boronic acid (1.01 g, 6.58 mmol) and a saturated aqueous solution of $NaHCO_3$ (10 mL) in 1,4-dioxane (20 mL) was added Pd(Ph$_3$)$_4$ (253 mg, 0.219 mmol). The reaction mixture was stirred at 120° C. for 20 min under microwave irradiation. Then, the crude reaction mixture cooled, diluted with EtOAc and washed with water. The organic layer was separated, dried $Na_2SO_4$, filtered, and concentrated. The crude product was triturated with Et$_2$O and filtered to yield the title compound as a black solid (1.1 g, 4.28 mmol), which was used in the next step without further purification. MS (ESI): mass calcd. for $C_{14}H_{12}FN_3O$, 257.1; m/z found, 258.2 [M+H]+. 1H NMR (500 MHz, DMSO-$d_6$) δ 2.31 (d, J=1.44 Hz, 3H), 7.18-7.25 (m, 1H), 7.49 (d, J=2.02 Hz, 1H), 7.49-7.52 (m, 1H), 7.60 (dd, J=7.37, 1.88 Hz, 1H), 8.22 (d, J=2.02 Hz, 1H), 11.17 (s, 1H).

Intermediate 28: 6-(3-Fluorophenyl)-3-methyl-1,3-dihydro-2H-imidazo[4,5-b]pyridin-2-one

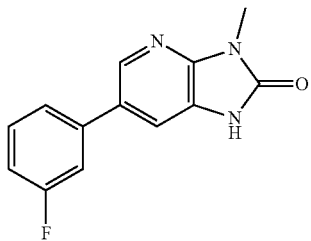 [SMILES: Cn1c(=O)[nH]c2cc(-c3cccc(F)c3)cnc21]

To a solution a 6-bromo-3-methyl-1,3-dihydro-2H-imidazo[4,5-b]pyridin-2-one (Intermediate 11, 1 g, 4.4 mmol), (3-fluorophenyl)boronic acid (920 mg, 6.58 mmol) and $Na_2CO_3$ (10 mL) in 1,4-dioxane (20 mL) was added $PdCl_2$(dppf) (449 mg, 0.614 mmol). The reaction mixture was stirred at 170° C. for 15 min under microwave irradiation. Then, the crude reaction mixture was cooled, diluted with water and extracted with EtOAc. The organic layer was separated, dried $Na_2SO_4$, filtered, and concentrated. The crude product was purified (FCC, $SiO_2$, 0-4% 7 M solution of $NH_3$/MeOH in DCM) to yield the title compound as a brown solid (460 mg, 43%). MS (ESI): mass calcd. for $C_{13}H_{10}FN_3O$, 243.1; m/z found, 244.1 [M+H]+.

Intermediate 29: 6-(3,4-Difluorophenyl)-3-methyl-1,3-dihydro-2H-imidazo[4,5-b]pyridin-2-one

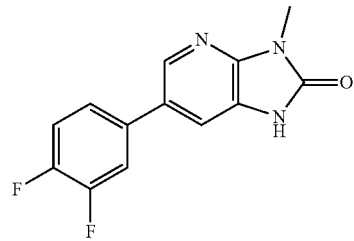 [SMILES: Cn1c(=O)[nH]c2cc(-c3ccc(F)c(F)c3)cnc21]

The title compound was prepared in a manner analogous to Intermediate 28: 6-(3-fluorophenyl)-3-methyl-1,3-dihydro-2H-imidazo[4,5-b]pyridin-2-one using (3,4-difluorophenyl)boronic acid. MS (ESI): mass calcd. for $C_{13}H_9F_2N_3O$, 261.1; m/z found, 262.1 [M+H]+.

Intermediate 30: 6-(2,4-Difluoro-3-methylphenyl)-3-methyl-1,3-dihydro-2H-imidazo[4,5-b]pyridin-2-one

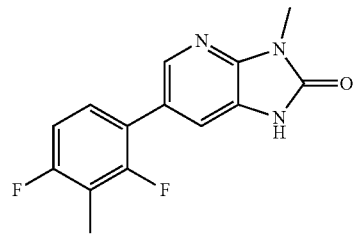 [SMILES: Cc1c(F)ccc(-c2cnc3c(c2)[nH]c(=O)n3C)c1F]

The title compound was prepared in a manner analogous to Intermediate 27: 6-(4-fluoro-3-methylphenyl)-3-methyl-1,3-dihydro-2H-imidazo[4,5-b]pyridin-2-one using Intermediate 8: 2-(2,4-difluoro-3-methylphenyl)-4,4,5,5-tetramethyl-1,3,2-dioxaborolane. MS (ESI): mass calcd. for $C_{14}H_{11}F_2N_3O$, 275.1; m/z found, 276.1 [M+H]$^+$. $^1$H NMR (400 MHz, DMSO-d$_6$) δ 2.22 (s, 3H) 3.33 (s, 3H) 7.17 (t, J=8.67 Hz, 1H) 7.40 (s, 1H) 7.36-7.46 (m, 1H) 8.07 (s, 1H) 11.20 (br s, 1H).

Intermediate 31: N-Benzhydryl-5-bromo-3-nitropyridin-2-amine

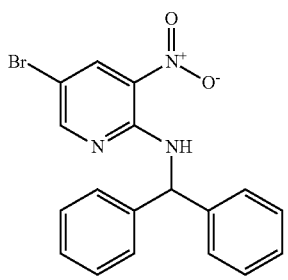 [SMILES: O=[N+]([O-])c1cc(Br)cnc1NC(c1ccccc1)c1ccccc1]

A solution of 5-bromo-2-chloro-3-nitropyridine (71.2 g, 300 mmol), benzhydrylamine (60 g, 330 mmol), and DIPEA (78 g, 600 mmol) in EtOH (600 mL) was heated to reflux overnight. Then solvent was removed in vacuo. Cold EtOH (1000 mL) was added to the crude residue and the mixture was stirred in an ice bath for 30 minutes upon which time a precipitate formed. The precipitate was filtered, collected and washed with cold EtOH to afford the title compound (93 g, 81%).

Intermediate 32: 6-Bromo-1-(2-methoxyethyl)-1,3-dihydro-2H-imidazo[4,5-b]pyridin-2-one

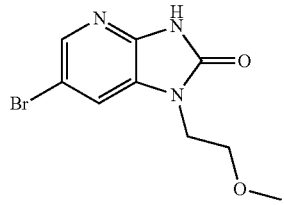

Step A: N$^2$-benzhydryl-5-bromopyridine-2,3-diamine

To a solution of 28% NH$_3$ in H$_2$O (60 mL), THF (300 mL) and water (300 mL) was added N-benzhydryl-5-bromo-3-nitropyridin-2-amine (Intermediate 31, 60 g, 156 mmol). Then, Na$_2$S$_2$O$_4$ (81.5 g, 468 mmol) was added portion-wise to the reaction mixture, and the mixture was stirred at room temperature overnight. The crude reaction mixture was extracted with EtOAc (3×300 mL) and washed with water (300 mL). The combined organic layers were dried over Na$_2$SO$_4$, filtered and concentrated to yield the title compound (40 g, 73%), which was used in the next step without further purification.

Step B: 3-Benzhydryl-6-bromo-1,3-dihydro-2H-imidazo[4,5-b]pyridin-2-one

A solution of N$^2$-benzhydryl-5-bromopyridine-2,3-diamine (50 g, 141 mmol) and CDI (45.7 g, 282 mmol) in 1,4-dioxane (500 mL) was refluxed for 5 h. Then, the solvent was evaporated and the resultant solid was washed with water and dried to yield the title compound (54 g, 99%), which was used in the next step without further purification.

Step C: 3-Benzhydryl-6-bromo-1-(2-methoxyethyl)-1,3-dihydro-2H-imidazo[4,5-b]pyridin-2-one A solution of 3-benzhydryl-6-bromo-1,3-dihydro-2H-imidazo[4,5-b]pyridin-2-one (4 g, 11 mmol), 1-bromo-2-methoxyethane (3 g, 21 mmol and K$_2$CO3 (4.3 g, 32 mmol) in MeCN (50 mL) was refluxed for 3 h. Then, the crude reaction mixture was filtered and the solvent was evaporated to yield the title compound (4.5 g, 97%), which was used in the next step without further purification.

Step D: 6-Bromo-1-(2-methoxyethyl)-1,3-dihydro-2H-imidazo[4,5-b]pyridin-2-one To a solution of 3-benzhydryl-6-bromo-1-(2-methoxyethyl)-1,3-dihydro-2H-imidazo[4,5-b]pyridin-2-one (4.5 g, 10.2 mmol) in TFA (40 mL) was added thioanisole (0.045 g), and the reaction mixture was stirred at 80° C. for 1 h. Then, the solvent was evaporated and the crude residue was purified (FCC, SiO$_2$, 0-10% MeOH in DCM) to yield the title compound (1.4 g, 51%).

Intermediate 33: 2-(6-Bromo-2-oxo-2,3-dihydro-1H-imidazo[4,5-b]pyridin-1-yl)-N-ethylacetamide

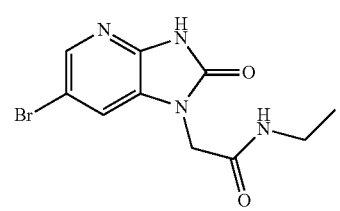 [SMILES: CCNC(=O)Cn1c(=O)[nH]c2ncc(Br)cc21]

The title compound was prepared in a manner analogous to Intermediate 32, using 2-chloro-N-ethylacetamide in Step C.

Intermediate 34: 2-(6-Bromo-2-oxo-2,3-dihydro-1H-imidazo[4,5-b]pyridin-1-yl)-N-cyclopropylacetamide

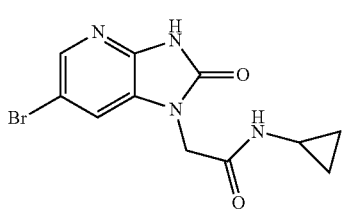 [SMILES: O=C(Cn1c(=O)[nH]c2ncc(Br)cc21)NC1CC1]

The title compound was prepared in a manner analogous to Intermediate 32, using 2-bromo-N-cyclopropylacetamide in Step C.

Intermediate 35: Ethyl 6-bromo-2-oxo-3-trityl-2,3-dihydro-1H-imidazo[4,5-b]pyridine-1-carboxylate

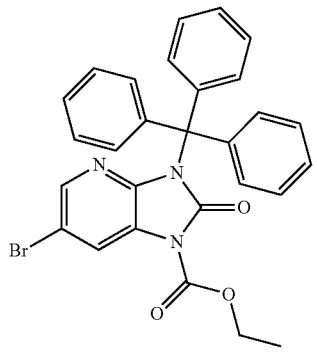 [SMILES: CCOC(=O)n1c(=O)n(C(c2ccccc2)(c2ccccc2)c2ccccc2)c2ncc(Br)cc21]

To a solution of ethyl 6-bromo-2-oxo-2,3-dihydro-1H-imidazo[4,5-b]pyridine-1-carboxylate (Intermediate 9, 703 mg, 2.46 mmol) in DCM (25 mL) was added trityl chloride (788 mg, 2.82 mmol) followed by Et$_3$N (615 µL, 4.42 mmol). The mixture was stirred at room temperature for 48 h then concentrated and the crude oil was purified by SiO$_2$ (0 to 25% EtOAc in hexanes) to yield the title compound as an amorphous solid (1.22 g, 94%). $^1$H NMR (500 MHz, CDCl$_3$): 8.15 (d, J=2.1 Hz, 1H), 7.90 (d, J=2.2 Hz, 1H), 7.54-7.43 (m, 6H), 7.25-7.14 (m, 9H), 4.47 (q, J=7.1 Hz, 2H), 1.42 (t, J=7.1 Hz, 3H).

Intermediate 36: 6-Bromo-3-trityl-1,3-dihydro-2H-imidazo[4,5-b]pyridin-2-one

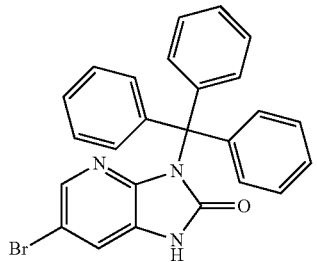 [SMILES: O=c1[nH]c2cc(Br)cnc2n1C(c1ccccc1)(c1ccccc1)c1ccccc1]

A mixture of ethyl 6-bromo-2-oxo-3-trityl-2,3-dihydro-1H-imidazo[4,5-b]pyridine-1-carboxylate (Intermediate 35, 3.7 g, 7.0 mmol) and isopropylamine (0.72 mL, 8.4 mmol) in THF (35 mL) was stirred at room temperature for 2 h. Then, the reaction mixture was concentrated under vacuum to yield the title compound as a yellow oil (3.2 g, 7.0 mmol, 100%), which was used without further purification. MS (ESI): mass calcd. for C$_{25}$H$_{18}$BrN$_3$O, 455.1; m/z found, 454 [M+H]$^+$.

Intermediate 37: Ethyl 2-(6-bromo-2-oxo-3-trityl-2,3-dihydro-1H-imidazo[4,5-b]pyridin-1-yl)acetate

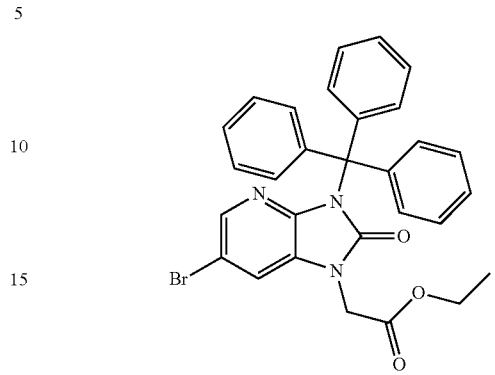

Under a nitrogen atmosphere was added 6-bromo-3-trityl-1,3-dihydro-2H-imidazo[4,5-b]pyridin-2-one (Intermediate 36, 2 g, 4.4 mmol) to a suspension of NaH (60% dispersion in mineral oil, 245 mg, 6.1 mmol) in DMF (20 mL). After 5 minutes, ethyl bromoacetate (0.68 mL, 6.1 mmol) was added to the reaction mixture. After 16 h, the reaction mixture was quenched with water (100 mL). The precipitates were filtered off, washed with water and dried under vacuum to afford the title product. The crude material was moved forward to the next step as is.

Intermediate 38: 1-(2-(Azetidin-1-yl)-2-oxoethyl)-6-bromo-3-trityl-1,3-dihydro-2H-imidazo[4,5-b]pyridin-2-one

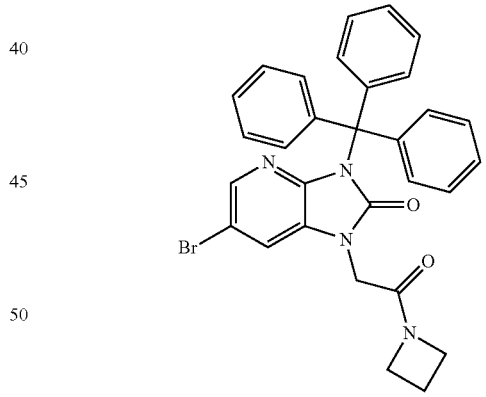

Step A: 2-(6-Bromo-2-oxo-3-trityl-2,3-dihydro-1H-imidazo[4,5-b]pyridin-1-yl)acetic acid To a solution of ethyl 2-(6-bromo-2-oxo-3-trityl-2,3-dihydro-1H-imidazo[4,5-b]pyridin-1-yl)acetate (Intermediate 37, 2.4 g, 4.4 mmol) in THF (60 mL) at room temperature was added LiOH (2 M, 3.1 mL, 6.1 mmol). After 16 h, the precipitates were collected by filtration, washed with water and dried under vacuum to afford the title compound (546 mg, 1.1 mmol, 24.3%). A saturated aqueous solution of NH$_4$Cl was added to the filtrate. The mixture was extracted with EtOAc (3×) to remove organic impurities. The solids in the aqueous layer were collected by filtration, rinsed with water and dried under vacuum to afford the title compound (1.51 g, 67%). ¹H NMR (400 MHz, DMSO-d₆) δ 7.70 (d, J=2.1 Hz, 1H), 7.44-7.38 (m, 6H), 7.36 (d, J=2.1 Hz, 1H), 7.25-7.11 (m, 10H), 3.93 (s, 2H).

Step B: 1-(2-(Azetidin-1-yl)-2-oxoethyl)-6-bromo-3-trityl-1,3-dihydro-2H-imidazo[4,5-b]pyridin-2-one HATU (582 mg, 1.5 mmol) was added to a mixture of 2-(6-bromo-2-oxo-3-trityl-2,3-dihydro-1H-imidazo[4,5-b]pyridin-1-yl)acetic acid (656 mg, 1.3 mmol), azetidine (0.103 mL, 1.5 mmol) and DIPEA (0.44 mL, 2.6 mmol) in DMF (15 mL) at room temperature. After completion, a saturated aqueous solution of NaHCO₃ (20 mL) was added, and the mixture was extracted using EtOAc (3×30 mL). The combined organics were dried over MgSO₄, filtered and concentrated under vacuum. The crude material was purified (FCC, SiO₂, 0-90% EtOAc in hexanes) to afford the title compound (260 mg, 37%). ¹H NMR (500 MHz, DMSO-d₆) δ 7.79 (d, J=2.1 Hz, 1H), 7.70 (d, J=2.1 Hz, 1H), 7.42-7.38 (m, 6H), 7.26-7.12 (m, 9H), 4.47 (s, 2H), 4.09 (t, J=7.6 Hz, 2H), 3.87 (t, J=7.6 Hz, 2H), 2.22 (p, J=7.8 Hz, 2H).

Intermediate 39: 2-(6-Bromo-2-oxo-3-trityl-2,3-dihydro-1H-imidazo[4,5-b]pyridin-1-yl)-N,N-dimethylacetamide

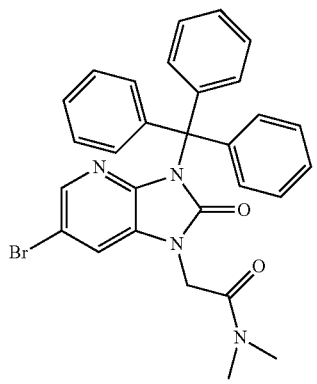 [SMILES: CN(C)C(=O)Cn1c(=O)n(C(c2ccccc2)(c2ccccc2)c2ccccc2)c2ncc(Br)cc21]

2,4,6-Tripropyl-1,3,5,2,4,6-trioxatriphosphorinane-2,4,6-trioxide solution (T3P®) (3.25 mL, 5.4 mmol) was added to a mixture of 2-(6-bromo-2-oxo-3-trityl-2,3-dihydro-1H-imidazo[4,5-b]pyridin-1-yl)acetic acid (Intermediate 38, product from Step A, 941 mg, 1.8 mmol), dimethylamine hydrochloride (177 mg, 2.2 mmol) and DIPEA (0.94 mL, 5.4 mmol) in DCM (10 mL) at room temperature. After completion, a saturated aqueous solution of NaHCO₃ (20 mL) was added, and the mixture was extracted using DCM (3×30 mL). The combined organics were dried over MgSO₄, filtered and concentrated under vacuum. The crude material was purified (FCC, SiO₂, 0-100% EtOAc in hexanes) to afford the title compound (927 mg, 1.7 mmol, 94%). No NMR only LCMS of reaction. TFA used to deprotect trityl in LCMS sample; trityl group swamps out product signal.

Intermediate 40: 1-(2-(3-Fluoroazetidin-1-yl)-2-oxoethyl)-6-bromo-3-trityl-1,3-dihydro-2H-imidazo[4,5-b]pyridin-2-one

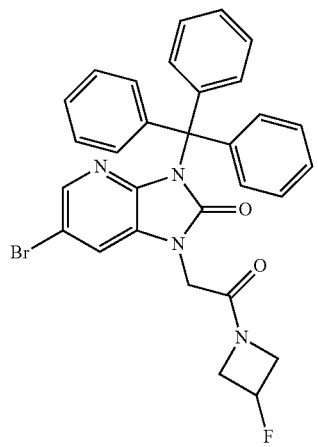 [SMILES: O=C(Cn1c(=O)n(C(c2ccccc2)(c2ccccc2)c2ccccc2)c2ncc(Br)cc21)N1CC(F)C1]

The title compounds was made in an analogous manner to 2-(6-bromo-2-oxo-3-trityl-2,3-dihydro-1H-imidazo[4,5-b]pyridin-1-yl)-N,N-dimethylacetamide (Intermediate 39) using 3-fluoroazetidine hydrochloride in Step B. ¹H NMR (500 MHz, CDCl₃) δ 7.85-7.82 (m, 1H), 7.51-7.46 (m, 6H), 7.29-7.27 (m, 1H), 7.25-7.15 (m, 9H), 5.23-5.06 (m, 1H), 4.44-4.31 (m, 2H), 4.31-4.21 (m, 1H), 4.11-4.05 (m, 1H), 4.02-3.93 (m, 1H), 3.93-3.83 (m, 1H).

Intermediate 41: 1-(2-(Pyrrolidin-1-yl)-2-oxoethyl)-6-bromo-3-trityl-1,3-dihydro-2H-imidazo[4,5-b]pyridin-2-one

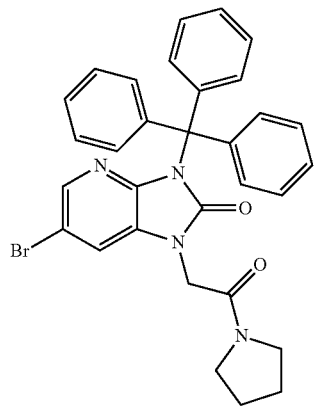 [SMILES: O=C(Cn1c(=O)n(C(c2ccccc2)(c2ccccc2)c2ccccc2)c2ncc(Br)cc21)N1CCCC1]

The title compounds was made in an analogous manner to 2-(6-bromo-2-oxo-3-trityl-2,3-dihydro-1H-imidazo[4,5-b]pyridin-1-yl)-N,N-dimethylacetamide (Intermediate 39) using pyrrolidine in Step B.

Intermediate 42: 2-(6-Bromo-2-oxo-3-trityl-2,3-dihydro-1H-imidazo[4,5-b]pyridin-1-yl)acetaldehyde

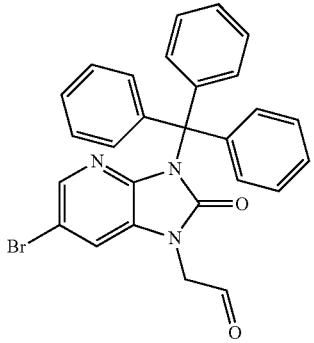 [SMILES: O=CCn1c(=O)n(C(c2ccccc2)(c2ccccc2)c2ccccc2)c2ncc(Br)cc21]

Step A: 6-Bromo-1-(2-hydroxyethyl)-3-trityl-1,3-dihydro-2H-imidazo[4,5-b]pyridin-2-one A solution of ethyl 2-(6-bromo-2-oxo-3-trityl-2,3-dihydro-1H-imidazo[4,5-b]pyridin-1-yl)acetate (Intermediate 37, 8.1 g, 15 mmol) in THF (406 mL) was cooled to 0° C. in an ice and acetone bath. To the reaction was added lithium borohydride (15 mL, 30 mmol) and the reaction was allowed to warm to room temperature for 10 minutes and then heated to 65° C. for an additional hour. Then, the reaction mixture was cooled to room temperature, and the crude mixture was quenched with water (250 mL) and extracted with ethyl acetate (500 mL). The organics were dried over MgSO$_4$, concentrated in vacuo, and purified (FCC, SiO$_2$, 0-100% EtOAc in hexanes) to provide the title compound (6.6 g, 88%). $^1$H NMR (500 MHz, DMSO-d$_6$) δ 7.80-7.75 (m, 1H), 7.75-7.66 (m, 1H), 7.49-7.39 (m, 6H), 7.28-7.18 (m, 6H), 7.18-7.07 (m, 3H), 4.96-4.85 (m, 1H), 3.87-3.74 (m, 2H), 3.65-3.53 (d, J=5.1 Hz, 2H).

Step B: 2-(6-Bromo-2-oxo-3-trityl-2,3-dihydro-1H-imidazo[4,5-b]pyridin-1-yl)acetaldehyde A solution of 6-bromo-1-(2-hydroxyethyl)-3-trityl-1,3-dihydro-2H-imidazo[4,5-b]pyridin-2-one (5.5 g, 11 mmol) and sodium bicarbonate (2.8 g, 33 mmol) in DCM (48 mL) was cooled to 0° C. in an ice and acetone bath, and Dess-Martin Periodinane (5.6 g, 13 mmol) was added. The reaction mixture was warmed to room temperature and stirred for 1 hour. Then, the reaction mixture was concentrated in vacuo and taken up in THF (50 mL). The crude reaction was filtered through a pad of Celite®, concentrated down in vacuo and purified (FCC, SiO$_2$, 25-80% EtOAc in hexanes) to afford the title compound (4.2 g, 90%). $^1$H NMR (400 MHz, DMSO-d$_6$) δ 9.53 (s, 1H), 7.85-7.80 (d, J=2.1 Hz, 1H), 7.75-7.69 (d, J=2.1 Hz, 1H), 7.52-7.39 (m, 6H), 7.31-7.20 (m, 6H), 7.20-7.12 (m, 3H), 4.82 (s, 2H).

Intermediate 43: 6-(3-(trifluoromethyl)phenyl)-3-trityl-1,3-dihydro-2H-imidazo[4,5-b]pyridin-2-one

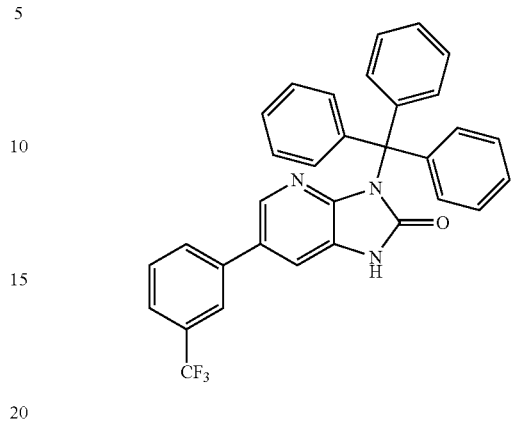

Step A: 5-(3-(Trifluoromethyl)phenyl)pyridine-2,3-diamine

A mixture of 2,3-diamino-5-bromopyridine (2 g, 10.6 mmol), 3-(trifluoromethyl)phenylboronic acid (4.04 g, 21.3 mmol), 1,1'-bis(diphenylphosphino)ferrocene palladium(II) dichloride dichloromethane complex (608 mg, 0.75 mmol), Cs$_2$CO$_3$ (6.93 g, 21.3 mmol), dioxane (98 mL) and H$_2$O (21 mL) was heated to 90° C. using an oil bath. After 16 h, starting material was completely consumed. The reaction mixture was cooled to room temperature and volatiles were removed. A saturated aqueous solution of NaHCO$_3$ (30 mL) followed by solid NaCl was added to the reaction mixture, and the mixture was extracted with EtOAc (3×60 mL). The combined organic layers were dried over MgSO$_4$, filtered and concentrated under vacuum. The crude material was purified (FCC, 0-100% EtOAc in hexanes), to give the title compound (2.6 g, 97%). MS (ESI): mass calcd. for C$_{12}$H$_{10}$F$_3$N$_3$, 253.1; m/z found, 254.1 [M+H]$^+$. $^1$H NMR (400 MHz, DMSO-d$_6$) δ 7.84-7.79 (m, 1H), 7.77-7.74 (m, 1H), 7.69 (d, J=2.2 Hz, 1H), 7.64-7.56 (m, 2H), 7.06 (d, J=2.3 Hz, 1H), 5.68 (s, 2H), 4.84 (s, 2H)

Step B: 6-(3-(Trifluoromethyl)phenyl)-1,3-dihydro-2H-imidazo[4,5-b]pyridin-2-one Under a nitrogen atmosphere, CDI (8.2 g, 50.8 mmol) was added to a mixture of 5-(3-(trifluoromethyl)phenyl)pyridine-2,3-diamine (10.7 g, 42.3 mmol) in DMF (428 mL) at room temperature. After 3 h, conversion was not complete and additional CDI (3.4 g, 21.4 mmol) was added to the reaction mixture. Once complete conversion was observed water was added, and the mixture was allowed to stir for an additional 30 min.

The solids were collected by filtration, washed with water and dried under vacuum to afford the title compound (11.3 g, 40.6 mmol, 96%), which was used in the next step without further purification. MS (ESI): mass calcd. for C$_{13}$H$_8$F$_3$N$_3$O, 279.1; m/z found, 280.1 [M+H]$^+$. $^1$H NMR (400 MHz, DMSO-d$_6$) δ 11.47 (s, 1H), 11.02 (s, 1H), 8.25 (d, J=2.0 Hz, 1H), 8.01-7.95 (m, 2H), 7.75-7.66 (m, 2H), 7.55 (d, J=2.0 Hz, 1H).

Step C: Ethyl 2-oxo-6-(3-(trifluoromethyl)phenyl)-2,3-dihydro-1H-imidazo[4,5-b]pyridine-1-carboxylate Under a nitrogen atmosphere, a mixture of 6-(3-(trifluoromethyl)phenyl)-1,3-dihydro-2H-imidazo[4,5-b]pyridin-2- one (2.86 g, 10.2 mmol), ethyl pyridin-2-yl carbonate (2.57 g, 15.4 mmol) and $K_2CO_3$ (2.12 g, 15.4 mmol) in DMF (80 mL) was heated to 75° C. After 16 h, water was added followed by 10% HCl until the mixture reached pH 1. The precipitates were filtered, washed with water and collected to afford the title compound, which was used in the next step without further purification. MS (ESI): mass calcd. for $C_{16}H_{12}F_3N_3O_3$, 351.1; m/z found, 352.1 [M+H]$^+$. $^1$H NMR (400 MHz, DMSO) δ 12.15 (s, 1H), 8.46 (d, J=2.1 Hz, 1H), 8.15 (d, J=2.1 Hz, 1H), 8.01-7.94 (m, 2H), 7.80-7.70 (m, 2H), 4.44 (q, J=7.1 Hz, 2H), 1.38 (t, J=7.1 Hz, 3H).

Step D: Ethyl 2-oxo-6-(3-(trifluoromethyl)phenyl)-3-trityl-2,3-dihydro-1H-imidazo[4,5-b]pyridine-1-carboxylate A mixture of TEA (1.42 mL, 10.2 mmol), ethyl 2-oxo-6-(3-(trifluoromethyl)phenyl)-2,3-dihydro-1H-imidazo[4,5-b]pyridine-1-carboxylate (2.0 g, 5.7 mmol) and trityl chloride (1.9 g, 6.8 mmol) in DMF was stirred at room temperature. After 16 h, the reaction mixture was quenched with a saturated aqueous solution of $NH_4Cl$ (40 mL). The precipitates were collected by filtration, washed with water and dried under vacuum to afford the title compound, which was contaminated with a small amount of impurities. The crude material was moved forward to the next step as is.

Step E: 6-(3-(Trifluoromethyl)phenyl)-3-trityl-1,3-dihydro-2H-imidazo[4,5-b]pyridin-2-one A mixture of ethyl 2-oxo-6-(3-(trifluoromethyl)phenyl)-3-trityl-2,3-dihydro-1H-imidazo[4,5-b]pyridine-1-carboxylate (3.4 g, 5.7 mmol) and isopropylamine (0.59 mL, 6.8 mmol) in THF (30 mL) was stirred at room temperature. After 16 h, the reaction mixture was concentrated under vacuum and the crude material was purified (FCC, $SiO_2$, 0-90% EtOAc in hexanes) to give the title compound (2.7 g, 92%). $^1$H NMR (500 MHz, DMSO-$d_6$) δ 11.21 (s, 1H), 8.08 (d, J=2.1 Hz, 1H), 7.96-7.91 (m, 2H), 7.70-7.62 (m, 2H), 7.55-7.47 (m, 7H), 7.26-7.21 (m, 6H), 7.18-7.12 (m, 3H).

Intermediate 44: 2-(2-Oxo-6-(3-(trifluoromethyl)phenyl)-3-trityl-2,3-dihydro-1H-imidazo[4,5-b]pyridin-1-yl)acetic acid

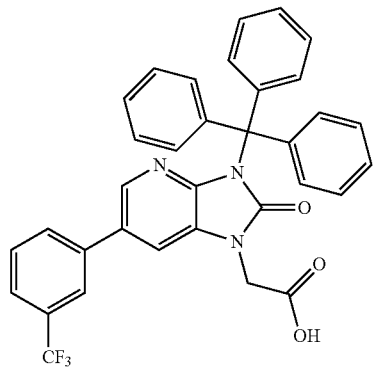 [SMILES: O=C(O)Cn1c(=O)n(C(c2ccccc2)(c2ccccc2)c2ccccc2)c2ncc(-c3cccc(C(F)(F)F)c3)cc21]

Step A: Ethyl 2-(2-oxo-6-(3-(trifluoromethyl)phenyl)-3-trityl-2,3-dihydro-1H-imidazo[4,5-b]pyridin-1-yl)acetate Under a nitrogen atmosphere was added 6-(3-(trifluoromethyl)phenyl)-3-trityl-1,3-dihydro-2H-imidazo[4,5-b]pyridin-2-one (Intermediate 43, 1 g, 1.9 mmol) to a suspension of NaH (60% dispersion in mineral oil, 107 mg, 2.7 mmol) in DMF (20 mL). After 5 minutes, ethyl bromoacetate (0.30 mL, 2.7 mmol) was added to the reaction mixture. After 16 h, the reaction mixture was quenched with water (100 mL). The precipitates were filtered off, washed with water and dried under vacuum.

The crude material was purified (FCC, $SiO_2$, 0-90% EtOAc in hexanes) to give the title compound (904 mg, 78%) as a foam. $^1$H NMR (400 MHz, DMSO-$d_6$) δ 8.19 (d, J=2.0 Hz, 1H), 8.02 (d, J=2.1 Hz, 1H), 8.01-7.93 (m, 2H), 7.72-7.63 (m, 2H), 7.49-7.42 (m, 6H), 7.29-7.11 (m, 9H), 4.76 (s, 2H), 4.10 (q, J=7.1 Hz, 2H), 1.14 (t, J=7.1 Hz, 3H).

Step B: 2-(2-Oxo-6-(3-(trifluoromethyl)phenyl)-3-trityl-2,3-dihydro-1H-imidazo[4,5-b]pyridin-1-yl)acetic acid To a solution of ethyl 2-(2-oxo-6-(3-(trifluoromethyl)phenyl)-3-trityl-2,3-dihydro-1H-imidazo[4,5-b]pyridin-1-yl)acetate (904 mg, 1.5 mmol) in THF at room temperature was added LiOH (2 M, 1.04 mL, 2.1 mmol). After 16 h, complete conversion was observed and a saturated aqueous solution of $NH_4Cl$ (20 mL) was added. The mixture was extracted using EtOAc (3×30 mL). The combined organics were dried over $MgSO_4$, filtered and concentrated under vacuum to afford the title compound. The crude product was used in the next step without further purification.

Intermediate 45: 2-(2-Oxo-6-(3-(trifluoromethyl)phenyl)-3-trityl-2,3-dihydro-1H-imidazo[4,5-b]pyridin-1-yl)propanoic acid

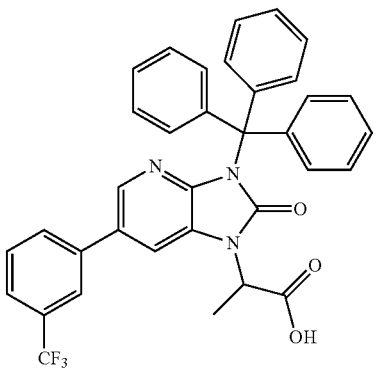 [SMILES: CC(C(=O)O)n1c(=O)n(C(c2ccccc2)(c2ccccc2)c2ccccc2)c2ncc(-c3cccc(C(F)(F)F)c3)cc21]

The title compound was prepared in a manner analogous to Intermediate 44, using ethyl 2-bromopropanoate in Step A. $^1$H NMR (400 MHz, DMSO-$d_6$) δ 8.10 (d, J=2.1 Hz, 1H), 7.98-7.89 (m, 2H), 7.82-7.60 (m, 3H), 7.51-7.40 (m, 6H), 7.29-7.10 (m, 9H), 5.04-4.88 (m, 1H), 1.53 (d, J=7.2 Hz, 3H).

Intermediate 46: 1-((2-Methoxypyridin-3-yl)methyl)-6-(3-(trifluoromethyl)phenyl)-3-trityl-1,3-dihydro-2H-imidazo[4,5-b]pyridin-2-one

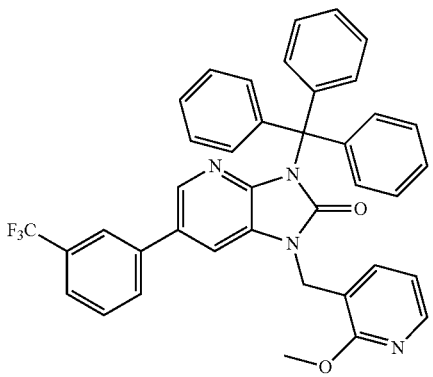 [SMILES: COc1ncccc1Cn1c(=O)n(C(c2ccccc2)(c2ccccc2)c2ccccc2)c2ncc(-c3cccc(C(F)(F)F)c3)cc21]

The title compound was prepared in a manner analogous to Intermediate 37 using 6-(3-(trifluoromethyl)phenyl)-3-trityl-1H-imidazo[4,5-b]pyridin-2(3H)-one (Intermediate 43) and 3-(chloromethyl)-2-methoxypyridine.

Intermediate 47: $N^3$-((5-Methylisoxazol-3-yl)methyl)-5-(3-(trifluoromethyl)phenyl) pyridine-2,3-diamine

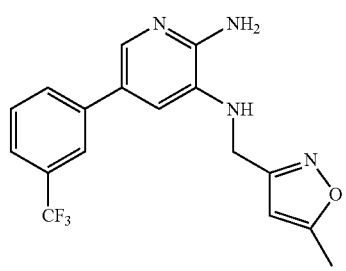 [SMILES: Cc1cc(CNc2cc(-c3cccc(C(F)(F)F)c3)cnc2N)no1]

Step A: 5-Bromo-$N^3$-((5-methylisoxazol-3-yl)methyl)pyridine-2,3-diamine

A 1 L round bottomed flask was charged with 5-bromopyridine-2,3-diamine (16 g), 5-methylisoxazole-3-carbaldehyde (11.3 g), activated 4 Å molecular sieves (24 g) and THF (500 mL). The solution was heated to reflux at 70° C. overnight and then filtered to remove the molecular sieves. All volatiles were removed under vacuum to leave a crude yellow solid which consisted of a mixture of multiple products and excess aldehyde. This material was used directly in the next step without any further purification. The crude was dissolved in EtOH and NaBH$_4$ (1.40 g) was added and the solution was heated to reflux at 85° C. for 18 h. Then the reaction was quenched with water and the product was extracted with DCM, dried over Na$_2$SO$_4$, filtered and concentrated down to a red residue. The product was purified (FCC, SiO$_2$, 0-10% MeOH in DCM) to afford the title compound as solid. $^1$H NMR (300 MHz, CDCl$_3$) δ 7.70 (d, 1H), 6.98 (d, 1H), 5.98 (s, 1H), 4.43 (d, 2H), 4.20 (br s, 2H), 3.81 (br s, 1H), 2.45 (s, 3H).

Step B: $N^3$-((5-Methylisoxazol-3-yl)methyl)-5-(3-(trifluoromethyl)phenyl)pyridine-2,3-diamine To a solution of 5-bromo-$N^3$-((5-methylisoxazol-3-yl)methyl)pyridine-2,3-diamine (2.8 g, 9.8 mmol) in 1,4-dioxane (50 mL) was added 3-(trifluoromethyl)phenylboronic acid (2.8 g, 14.8 mmol). Then, Na$_2$CO$_3$ (2.1 g, 19.7 mmol), deionized water (7 mL), and Pd(PPh$_3$)$_4$ (569.4 mg, 0.49 mmol) was added, and the reaction was heated to 100° C. overnight. The reaction was cooled to room temperature, diluted with ethyl acetate (100 mL) and washed with water (50 mL). The organic layer was collected, dried, filtered and concentrated in vacuo. The crude reaction was purified (FCC, SiO$_2$, 0-20% MeOH in DCM) to provide the title compound (1.0 g, 31%). MS (ESI): mass calcd. for C$_{17}$H$_{15}$F$_3$N$_4$O, 348.3; m/z found, 349.2 [M+H]$^+$.

Intermediate 48: 2-Bromo-5-methylthiophene

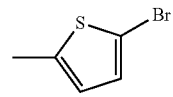

NBS (1.1 eq, 4.0 g, 22.7 mmol) was added to a solution of 2-methylthiophene (1.0 eq., 2 mL, 20.7 mmol) in a mixture of chloroform/AcOH (10:1, 20 mL) at 0° C. in the absence of light. The mixture reaction was stirred at 0° C. for 1 h. Then the mixture was warmed to rt for 12 hours. The reaction was quenched with aqueous sat. NaHCO$_3$ solution. The organic layer was dried (MgSO$_4$), filtered and the solvents were evaporated in vacuo. The crude product was purified (FCC, SiO$_2$, 0-100% EtOAc in heptane) to provide the title compound (2.5 g, 69%). $^1$H NMR (300 MHz, CDCl$_3$) δ 6.83 (d, J=3.6 Hz, 1H), 6.52 (d, J=2.5 Hz, 1H), 2.43 (s, 3H).

Intermediate 49: 2-Bromo-5-(difluoromethyl)thiophene

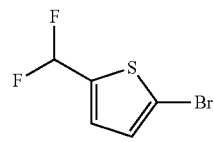

Step A: 5-bromothiophene-2-carbaldehyde

NBS (1.5 eq, 5.8 g, 33 mmol) was added to a solution of thiophene-2-carbaldehyde (1.0 eq., 2 mL, 22 mmol) in a mixture of chloroform/AcOH (10:1, 22 mL) at 0° C. in the absence of light. The reaction mixture was stirred at 0° C. for 1 h. Then the mixture was allowed to warm to rt for 12 hours. The reaction was quenched with an aqueous sat. NaHCO$_3$ solution. The organic layer was washed with brine, dried (MgSO$_4$), filtered, and the solvents were evaporated in vacuo.

The crude product was purified (FCC, SiO$_2$, 0-100% EtOAc in heptane) to provide the title compound (1.4 g, 35%). $^1$H NMR (300 MHz, CDCl$_3$) δ 9.76 (s, 1H), 7.51 (d, J=4.0 Hz, 1H), 7.18 (d, J=4.0 Hz, 1H).

Step B: 2-Bromo-5-(difluoromethyl)thiophene

DAST (2.9 eq., 2.9 mL, 22 mmol) was added to a solution of 5-bromothiophene-2-carbaldehyde (1.0 eq., 1.44 g, 7.5 mmol) in DCM at 0° C. under inert atmosphere. The mixture was stirred at rt for 16 hours. The mixture was quenched with ice-cold water and extracted with DCM. The combined organic extracts were washed with water and brine, the organic layer was separated, dried (MgSO$_4$), filtered and the solvents were evaporated in vacuo. The crude product was purified (FCC, SiO$_2$, 0-100% EtOAc in heptane) to provide the title compound (511 mg, 32%). $^1$H NMR (300 MHz, CDCl$_3$) δ 7.03 (d, J=3.9 Hz, 2H), 6.74 (t, J=55.9 Hz, 1H).

Intermediate 50: 6-Bromo-3-methyl-1-((1-methyl-1H-1,2,3-triazol-4-yl)methyl)-1,3-dihydro-2H-imidazo[4,5-b]pyridin-2-one

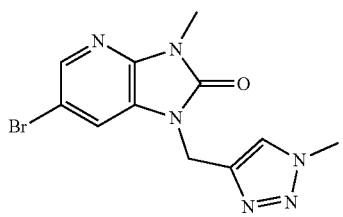 [SMILES: Cn1cc(Cn2c(=O)n(C)c3ncc(Br)cc32)nn1]

The title compound was prepared in a manner analogous to 6-bromo-3-methyl-1-((5-methylisoxazol-3-yl)methyl)-1,3-dihydro-2H-imidazo[4,5-b]pyridin-2-one (Intermediate 22) using 4-(chloromethyl)-1-methyl-1H-1,2,3-triazole hydrochloride. MS (ESI): mass calcd. for C$_{11}$H$_{11}$BrN$_6$O, 322.0; m/z found, 324 [M+H]$^+$. $^1$H NMR (300 MHz, DMSO) δ 8.10 (d, J=1.7 Hz, 1H), 8.05 (s, 1H), 7.83 (d, J=1.6 Hz, 1H), 5.13 (s, 2H), 3.99 (s, 3H), 3.32 (s, 3H).

Intermediate 51: 6-Bromo-3-methyl-1-((5-methyl-1,3,4-oxadiazol-2-yl)methyl)-1,3-dihydro-2H-imidazo[4,5-b]pyridin-2-one

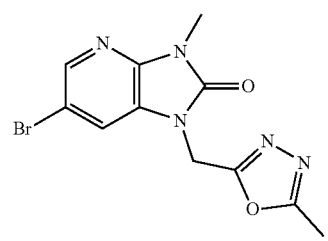 [SMILES: Cc1nnc(Cn2c(=O)n(C)c3ncc(Br)cc32)o1]

The title compound was prepared in a manner analogous to 6-bromo-3-methyl-1-((5-methylisoxazol-3-yl)methyl)-1,3-dihydro-2H-imidazo[4,5-b]pyridin-2-one (Intermediate 22) using 2-(chloromethyl)-5-methyl-1,3,4-oxadiazole. MS (ESI): mass calcd. for C$_{11}$H$_{10}$BrN$_5$O$_2$, 323.0; m/z found, 325 [M+H]$^+$. $^1$H NMR (300 MHz, CDCl$_3$) δ 8.14 (d, J=1.6 Hz, 1H), 7.44 (d, J=1.6 Hz, 1H), 5.25 (s, 2H), 3.50 (s, 3H), 2.52 (s, 3H).

Intermediate 52: 6-Bromo-3-methyl-1-((1-methyl-1H-pyrazol-4-yl)methyl)-1,3-dihydro-2H-imidazo[4,5-b]pyridin-2-one

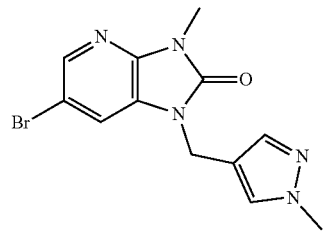 [SMILES: Cn1cc(Cn2c(=O)n(C)c3ncc(Br)cc32)cn1]

The title compound was prepared in a manner analogous to 6-bromo-3-methyl-1-((5-methylisoxazol-3-yl)methyl)-1,3-dihydro-2H-imidazo[4,5-b]pyridin-2-one (Intermediate 22) using 4-(chloromethyl)-1-methyl-1H-pyrazole. The halide was added as a solution of DMF (5 mL) and DIPEA (1 equivalent). MS (ESI): mass calcd. for C$_{12}$H$_{12}$BrN$_5$O, 321.0; m/z found, 322 [M+H]$^+$. $^1$H NMR (300 MHz, DMSO-d$_6$) δ 8.07 (s, 1H), 7.87 (s, 1H), 7.70 (s, 1H), 7.43 (s, 1H), 4.89 (s, 2H), 3.75 (s, 3H), 3.27 (s, 3H).

Intermediate 53: 1-((1,2,3-Thiadiazol-4-yl)methyl)-6-bromo-3-methyl-1,3-dihydro-2H-imidazo[4,5-b]pyridin-2-one

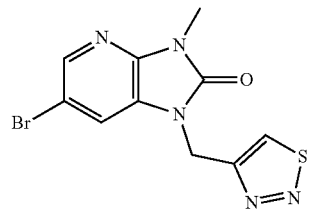 [SMILES: Cn1c(=O)n(Cc2csnn2)c2cc(Br)cnc21]

The title compound was prepared in a manner analogous to 6-bromo-3-methyl-1-((5-methylisoxazol-3-yl)methyl)-1,3-dihydro-2H-imidazo[4,5-b]pyridin-2-one (Intermediate 22) using 4-(chloromethyl)-1,2,3-thiadiazole (Intermediate 61). MS (ESI): mass calcd. for C$_{10}$H$_8$BrN$_5$OS, 325.0. m/z found, 326 [M+H]$^+$.

Intermediate 54: 6-Bromo-3-methyl-1-((5-methylisoxazol-3-yl)methyl)-1,3-dihydro-2H-imidazo[4,5-b]pyridin-2-one

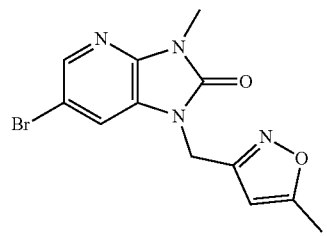 [SMILES: Cc1cc(Cn2c(=O)n(C)c3ncc(Br)cc32)no1]

The title compound was prepared in a manner analogous to 6-bromo-3-methyl-1-((5-methylisoxazol-3-yl)methyl)-1,3-dihydro-2H-imidazo[4,5-b]pyridin-2-one (Intermediate 22) using 3-chloromethyl-5-methylisoxazole. MS (ESI): mass calcd. for $C_{11}H_{11}BrN_6O$, 322.0; m/z found, 324 [M+H]$^+$. $^1$H NMR (300 MHz, DMSO-d$_6$) δ 8.10 (d, J=1.7 Hz, 1H), 8.05 (s, 1H), 7.83 (d, J=1.6 Hz, 1H), 5.13 (s, 2H), 3.99 (s, 3H), 3.32 (s, 3H).

Intermediate 55: 6-Bromo-3-methyl-1-((3-methyl-1,2,4-oxadiazol-5-yl)methyl)-1,3-dihydro-2H-imidazo[4,5-b]pyridin-2-one

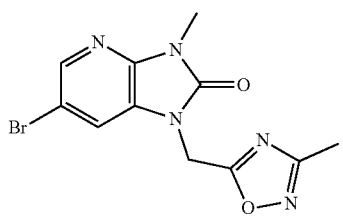 [SMILES: Cc1noc(Cn2c(=O)n(C)c3ncc(Br)cc32)n1]

The title compound was prepared in a manner analogous to 6-bromo-3-methyl-1-((5-methylisoxazol-3-yl)methyl)-1,3-dihydro-2H-imidazo[4,5-b]pyridin-2-one (Intermediate 22) using 5-(chloromethyl)-3-methyl-1,2,4-oxadiazole. $^1$H NMR (300 MHz, DMSO-d$_6$) δ 8.17 (d, J=1.7 Hz, 1H), 7.96 (d, J=1.7 Hz, 1H), 5.48 (s, 2H), 3.36 (s, 3H), 2.29 (s, 3H).

Intermediate 56: 6-(3-(Difluoromethyl)-4-fluorophenyl)-3-methyl-1,3-dihydro-2H-imidazo[4,5-b]pyridin-2-one

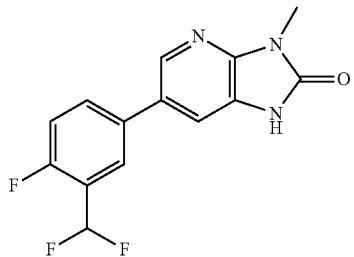 [SMILES: Cn1c(=O)[nH]c2cc(-c3ccc(F)c(C(F)F)c3)cnc21]

The title compound was prepared in a manner analogous to 6-(4-fluoro-3-methylphenyl)-3-methyl-1,3-dihydro-2H-imidazo[4,5-b]pyridin-2-one (Intermediate 27) using PdCl$_2$(dppf)$_2$ and (3-(difluoromethyl)-4-fluorophenyl)boronic acid (Intermediate 62). MS (ESI): mass calcd. for $C_{14}H_{10}F_3N_3O$, 293.1; m/z found, 294 [M+H]$^+$. $^1$H NMR (300 MHz, DMSO-d$_6$) δ 11.28 (s, 1H), 8.25 (s, 1H), 7.89 (d, J=6.1 Hz, 2H), 7.54 (s, 1H), 7.47 (t, J=9.7 Hz, 1H), 7.23 (t, J=54.2 Hz, 1H), 3.33-3.31 (m, 3H).

Intermediate 57: 6-(4-Chloro-3-(difluoromethoxy)phenyl)-3-methyl-1,3-dihydro-2H-imidazo[4,5-b]pyridin-2-one

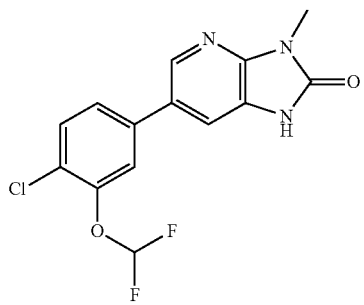 [SMILES: Cn1c(=O)[nH]c2cc(-c3ccc(Cl)c(OC(F)F)c3)cnc21]

The title compound was prepared in a manner analogous to 6-(4-fluoro-3-methylphenyl)-3-methyl-1,3-dihydro-2H-imidazo[4,5-b]pyridin-2-one (Intermediate 27) using PdCl$_2$(dppf)$_2$ and 2-(4-chloro-3-(difluoromethoxy)phenyl)-4,4,5,5-tetramethyl-1,3,2-dioxaborolane (Intermediate 63). MS (ESI): mass calcd. for $C_{14}H_{10}ClF_2N_3O_2$, 325.0. m/z found, 326 [M+H]$^+$.

Intermediate 58: 6-(3-(Difluoromethoxy)-4-fluorophenyl)-3-methyl-1,3-dihydro-2H-imidazo[4,5-b]pyridin-2-one

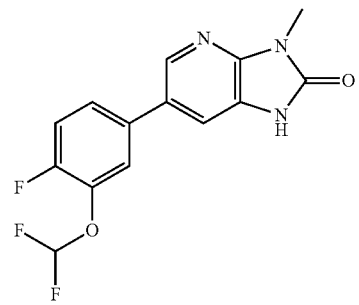 [SMILES: Cn1c(=O)[nH]c2cc(-c3ccc(F)c(OC(F)F)c3)cnc21]

The title compound was prepared in a manner analogous to 6-(4-fluoro-3-methylphenyl)-3-methyl-1,3-dihydro-2H-imidazo[4,5-b]pyridin-2-one (Intermediate 27), using PdCl$_2$(dppf)$_2$ and (3-(difluoromethoxy)-4-fluorophenyl)boronic acid. MS (ESI): mass calcd. for $C_{14}H_{10}F_3N_3O_2$, 309.1; m/z found, 310 [M+H]$^+$. $^1$H NMR (300 MHz, DMSO-d$_6$) δ 11.28 (s, 1H), 8.26 (s, 1H), 7.69-7.10 (m, 5H), 3.34 (s, 3H).

Intermediate 59: 2-(6-(3-(Difluoromethyl)-4-fluorophenyl)-3-methyl-2-oxo-2,3-dihydro-1H-imidazo[4,5-b]pyridin-1-yl)acetic acid

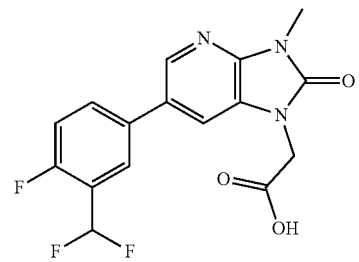 [SMILES: Cn1c(=O)n(CC(=O)O)c2cc(-c3ccc(F)c(C(F)F)c3)cnc21]

The title compound was prepared in a manner analogous to 2-(6-bromo-3-methyl-2-oxo-2,3-dihydro-1H-imidazo[4,5-b]pyridin-1-yl)acetic acid (Intermediate 13) using 6-(3-(difluoromethyl)-4-fluorophenyl)-3-methyl-1,3-dihydro- 2H-imidazo[4,5-b]pyridin-2-one (Intermediate 56) in Step A and 3M sodium hydroxide in Step B. MS (ESI): mass calcd. for $C_{16}H_{12}F_3N_3O_3$, 351.1; m/z found, 352 [M+H]$^+$. $^1$H NMR (300 MHz, DMSO-d$_6$) δ 8.35 (s, 1H), 8.00 (s, 1H), 7.92 (d, J=6.0 Hz, 2H), 7.50 (t, J=9.7 Hz, 1H), 7.26 (t, J=54.2 Hz, 1H), 4.70 (s, 2H), 3.39 (s, 3H).

Intermediate 60: 2-(6-(3-(Difluoromethoxy)-4-fluorophenyl)-3-methyl-2-oxo-2,3-dihydro-1H-imidazo[4,5-b]pyridin-1-yl)acetic Acid

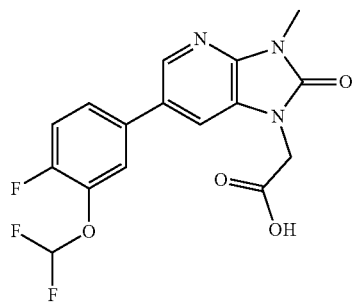 [SMILES: Cn1c(=O)n(CC(=O)O)c2cc(-c3ccc(F)c(OC(F)F)c3)cnc21]

The title compound was prepared in a manner analogous to 2-(6-bromo-3-methyl-2-oxo-2,3-dihydro-1H-imidazo[4,5-b]pyridin-1-yl)acetic acid (Intermediate 13) using 6-(3-(difluoromethoxy)-4-fluorophenyl)-3-methyl-1,3-dihydro-2H-imidazo[4,5-b]pyridin-2-one (Intermediate 58) in Step A and 3M sodium hydroxide in Step B. MS (ESI): mass calcd. for $C_{16}H_{12}F_3N_3O_4$, 367.1; m/z found, 368 [M+H]$^+$.

Intermediate 61: 4-(Chloromethyl)-1,2,3-thiadiazole

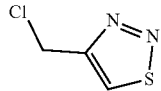

Step A: Methyl 1,2,3-thiadiazole-4-carboxylate 1,2,3-Thiadiazole-4-carboxylic acid (1.0, 1 g, 7.7 mmol) was added to HCl (1.25 M in MeOH, 10 mL) and the reaction mixture was stirred at 65° C. for 16 h. The solvent was removed under reduced pressure and the resulting crude mixture was purified (FCC, SiO$_2$, 0-100% EtOAc in DCM) to provide the title compound (1.1 g, 99.9%). MS (ESI): mass calcd. for $C_4H_4N_2O_2S$, 144.0; m/z found, 145 [M+H]$^+$. $^1$H NMR (300 MHz, CDCl$_3$) δ 9.27 (s, 1H), 4.07 (s, 3H).

Step B: (1,2,3-Thiadiazol-4-yl)methanol

CaCl$_2$ (5 mg, 0.05 mmol) and NaBH$_4$ (945 mg, 25 mmol) were added to a mixture of methyl 1,2,3-thiadiazole-4-carboxylate (1.1 g, 7.8 mmol) in THF (9 mL) and EtOH (18 mL). The mixture was stirred at rt for 2 h. The mixture was diluted with water and extracted with DCM/MeOH (9:1). The organic layer was separated, dried (MgSO$_4$), filtered, and concentrated under reduced pressure. Purification (FCC, SiO$_2$, 0-10% MeOH in DCM) provided the title compound (389 mg, 43%). MS (ESI): mass calcd. for $C_3H_4N_2OS$, 116.0; m/z found, 117 [M+H]$^+$. $^1$H NMR (300 MHz, CDCl$_3$) δ 8.51 (s, 1H), 6.45 (s, 1H), 5.22 (s, 2H).

Step C: 4-(Chloromethyl)-1,2,3-thiadiazole

A flask containing (1,2,3-thiadiazol-4-yl)methanol (380 mg, 3.3 mmol) and DCM (20 mL) was placed under N$_2$ atmosphere at 0° C. To this solution was added SOCl$_2$ (1.5 eq., 357 µL, 4.9 mmol) portionwise and the reaction mixture was stirred at rt for 30 minutes. The solvent was removed under reduced pressure. Purification (FCC, SiO$_2$, 0-100% EtOAc in heptane) afforded the title compound (175 mg, 40%). $^1$H NMR (300 MHz, CDCl$_3$) δ 8.58 (s, 1H), 5.09 (s, 2H).

Intermediate 62: (3-(Difluoromethyl)-4-fluorophenyl)boronic acid

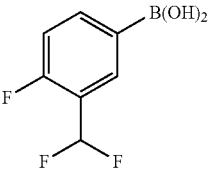 [SMILES: OB(O)c1ccc(F)c(C(F)F)c1]

To a cooled, −78° C., solution of bromo-2-difluoromethyl-1-fluorobenzene (1.5 mL, 11.1 mmol) and triisopropyl borate (3.8 mL, 16.7 mmol) in THF (25 mL), under a nitrogen atmosphere, was added nBuLi (2.5 M in hexanes, 8.9 mL, 22.2 mmol). The reaction mixture was stirred at rt for 30 minutes. The reaction mixture was quenched using 2 N aq. HCl. The resulting mixture was extracted with EtOAc. The organic layers were separated and the aqueous was extracted with DCM. The combined organic layers were dried (MgSO$_4$), filtered, and concentrated under reduced pressure to afford title compound (2.4 g, 99%, 87% pure), which was used crude without further purification.

Intermediate 63: 2-(4-Chloro-3-(difluoromethoxy)phenyl)-4,4,5,5-tetramethyl-1,3,2-dioxaborolane

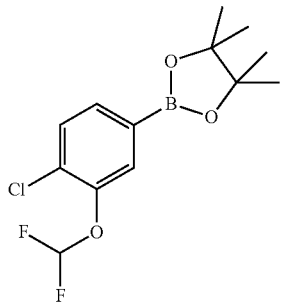 [SMILES: CC1(C)OB(c2ccc(Cl)c(OC(F)F)c2)OC1(C)C]

Step A: 4-Bromo-1-chloro-2-(difluoromethoxy)benzene

To a mixture of 5-bromo-2-chlorophenol (7 g, 34 mmol) and K$_2$CO$_3$ (16 g, 118 mmol) in DMF (200 mL) was added ethyl chlorodifluoroacetate (15 mL, 118 mmol). The reaction mixture was heated to 80° C. overnight. The residue was diluted with ice-water and was extracted with EtOAc. The combined organic layers were dried (MgSO₄), filtered and concentrated under vacuo. Purification (FCC, SiO₂, 0-100% EtOAc in heptane) afforded the title compound (5.8 g, 67%). $^1$H NMR (300 MHz, CDCl₃) δ 7.41 (s, 1H), 7.32 (s, 2H), 6.53 (t, J=72.9 Hz, 1H).

Step B: 2-(4-Chloro-3-(difluoromethoxy)phenyl)-4,4,5,5-tetramethyl-1,3,2-dioxaborolane The title compound was prepared in a manner analogous to Intermediate 8, using 4-bromo-1-chloro-2-(difluoromethoxy)benzene.

Intermediate 64: 3-(Chloromethyl)-5-fluoropyridine

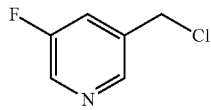

Step A: (5-Fluoropyridin-3-yl)methanol

To a cooled, 0° C., solution of 5-fluoropyridine-3-carboxylic acid (1.0 g, 7.1 mmol) in THF (30 mL) under a nitrogen atmosphere was added LAH (430 mg, 11 mmol). After 1 h, the reaction mixture was quenched with water and extracted with DCM/MeOH (9:1). The organic layer was dried (MgSO₄), filtered and concentrated under reduced pressure to provide title compound (480 mg, 53%) which was used crude without further purification. MS (ESI): mass calcd. for C₆H₆FNO, 127.0; m/z found, 128 [M+H]⁺. $^1$H NMR (300 MHz, CDCl₃) δ 8.40 (s, 2H), 7.48 (d, J=9.2 Hz, 1H), 4.78 (s, 2H).

Step B: 3-(Chloromethyl)-5-fluoropyridine

The title compound was prepared in a manner analogous to Intermediate 61, Step C, using (5-fluoropyridin-3-yl)methanol. MS (ESI): mass calcd. for C₆H₅ClFN, 145.0; m/z found, 146 [M+H]⁺.

Intermediate 65: 2-(6-(4-Chloro-3-(difluoromethoxy)phenyl)-3-methyl-2-oxo-2,3-dihydro-1H-imidazo[4,5-b]pyridin-1-yl)acetic acid

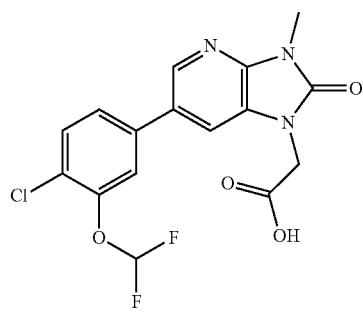 [SMILES: Cn1c(=O)n(CC(=O)O)c2cc(-c3ccc(Cl)c(OC(F)F)c3)cnc21]

The title compound was prepared in a manner analogous to 2-(6-bromo-3-methyl-2-oxo-2,3-dihydro-1H-imidazo[4,5-b]pyridin-1-yl)acetic acid (Intermediate 13) using 6-(4-chloro-3-(difluoromethoxy)phenyl)-3-methyl-1,3-dihydro-2H-imidazo[4,5-b]pyridin-2-one (Intermediate 57). (ESI): mass calcd. for C₁₆H₁₂ClF₂N₃O₄, 383.1; m/z found, 384 [M+H]⁺.

Intermediate 66: 2-(6-Bromo-3-methyl-2-oxo-2,3-dihydro-1H-imidazo[4,5-b]pyridin-1-yl)-N-(2-fluoroethyl)-N-methylacetamide

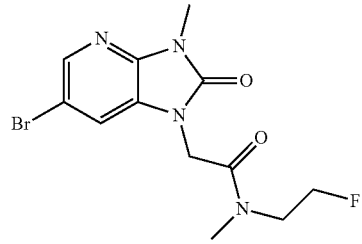 [SMILES: CN(CCF)C(=O)Cn1c(=O)n(C)c2ncc(Br)cc21]

The title compound was prepared in a manner analogous to Intermediate 39, using 2-(6-bromo-3-methyl-2-oxo-2,3-dihydro-1H-imidazo[4,5-b]pyridin-1-yl)acetic acid Lithium salt (Intermediate 13) and 2-fluoro-N-methylethan-1-amine HCl salt. MS (ESI): mass calcd. for C₁₂H₁₄BrFN₄O₂, 344.0. m/z found, 345.1 [M+H]⁺.

Intermediate 67: 2-(3-Methyl-2-oxo-6-(5-(trifluoromethyl)thiophen-2-yl)-2,3-dihydro-1H-imidazo[4,5-b]pyridin-1-yl)acetic acid

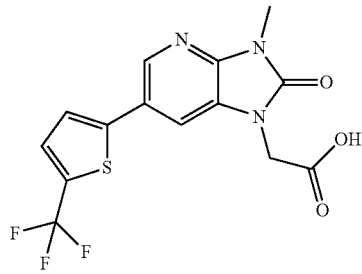 [SMILES: Cn1c(=O)n(CC(=O)O)c2cc(-c3ccc(C(F)(F)F)s3)cnc21]

The title compound was prepared in a manner analogous to Intermediate 26, Step A, using 2-(6-bromo-3-methyl-2-oxo-2,3-dihydro-1H-imidazo[4,5-b]pyridin-1-yl)acetic acid (Intermediate 13) and (5-(trifluoromethyl)thiophen-2-yl)boronic acid. MS (ESI): mass calcd. for C₁₄H₁₀F₃N₃O₃S, 357.3; m/z found, 358.1 [M+H]⁺.

Intermediate 68: 6-Bromo-1-(2-(3-(2-fluoroethyl)azetidin-1-yl)-2-oxoethyl)-3-trityl-1,3-dihydro-2H-imidazo[4,5-b]pyridin-2-one

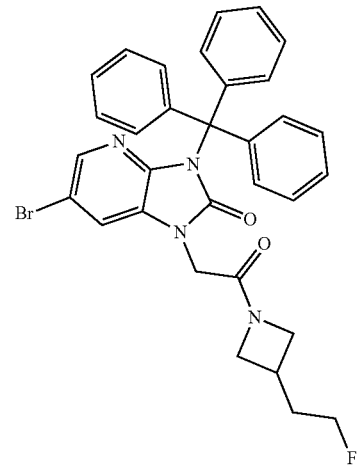 [SMILES: O=C(Cn1c(=O)n(C(c2ccccc2)(c2ccccc2)c2ccccc2)c2ncc(Br)cc21)N1CC(CCF)C1]

Step A: 6-Bromo-1-(2-(3-(2-hydroxyethyl)azetidin-1-yl)-2-oxoethyl)-3-trityl-1,3-dihydro-2H-imidazo[4,5-b]pyridin-2-one The title compound was prepared in a manner analogous to Intermediate 39 using 2-(6-bromo-2-oxo-3-trityl-2,3-dihydro-1H-imidazo[4,5-b]pyridin-1-yl)acetic acid (Intermediate 38, product from Step A) and 2-(azetidin-3-yl)ethan-1-ol. MS (ESI): mass calcd. for $C_{32}H_{29}BrFN_4O_3$, 596.1. m/z found, 619.1 [M+Na]$^+$.

Step B: 2-(1-(2-(6-Bromo-2-oxo-3-trityl-2,3-dihydro-1H-imidazo[4,5-b]pyridin-1-yl)acetyl)azetidin-3-yl)ethyl 4-methanesulfonate To a solution of 6-bromo-1-(2-(3-(2-hydroxyethyl)azetidin-1-yl)-2-oxoethyl)-3-trityl-1,3-dihydro-2H-imidazo[4,5-b]pyridin-2-one (95 mg, 0.16 mmol) and 4-methylbenzenesulfonyl chloride (91 mg, 0.48 mmol) in DCM (0.5 mL), was added TEA (0.11 mL, 0.80 mmol). The reaction mixture was stirred at rt overnight. Purification (50 mg) (FCC, SiO$_2$, Ethyl Acetate in hexanes (20-90%)) afforded the title compound. MS (ESI): mass calcd. for $C_{39}H_{35}BrFN_4O_5S$ 750.2. m/z found, 783.2 [M+Na]$^+$.

Step C: 6-Bromo-1-(2-(3-(2-fluoroethyl)azetidin-1-yl)-2-oxoethyl)-3-trityl-1,3-dihydro-2H-imidazo[4,5-b]pyridin-2-one 2-(1-(2-(6-Bromo-2-oxo-3-trityl-2,3-dihydro-1H-imidazo[4,5-b]pyridin-1-yl)acetyl)azetidin-3-yl)ethyl 4-methanesulfonate (50 mg) was dissolved in THF (0.5 mL), and TBAF (1.0 M in THF, 200 µL, 0.2 mmol) was added. The reaction mixture was heated at 60° C. for an hour. The solvent was removed under vacuum. Purification (FCC, SiO$_2$, Ethyl Acetate in hexanes (10% to 80%)) provided the title compound as a colorless oil (26 mg, 26% over Steps B-C). MS (ESI): mass calcd. for $C_{32}H_{28}BrFN_4O_2$, 598.1. m/z found, 626.1 [M+Na]$^+$.

Example 1: 6-(4-Methoxyphenyl)-1-(2-morpholino-2-oxo-ethyl)-3H-imidazo[4,5-b]pyridin-2-one and its Trifluoroacetic Acid Salt

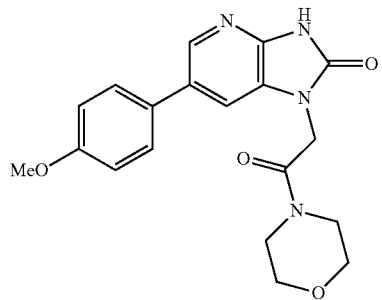 [SMILES: COc1ccc(-c2cnc3[nH]c(=O)n(CC(=O)N4CCOCC4)c3c2)cc1]

Step A: N-Benzhydryl-5-(4-methoxyphenyl)-3-nitropyridin-2-amine

To a solution a N-benzhydryl-5-bromo-3-nitropyridin-2-amine (Intermediate 31, 7.58 g, 19.7 mmol) and 4-methoxyphenylboronic acid (3 g, 19.7 mmol) in EtOH (30 mL) and toluene (40 mL) was added an aqueous solution of 2 M Na$_2$CO$_3$ (20 mL) and Pd(Ph$_3$)$_4$ (2.27 g, 1.97 mmol). The reaction mixture was stirred at 80° C. overnight. Then, the crude reaction mixture cooled, filtered, and the filtrate was evaporated. The crude residue was purified (FCC, SiO$_2$, 20:1 petroleum ether/EtOAc) to yield the title compound (2.8 g, 35%).

Step B: N$^2$-Benzhydryl-5-(4-methoxyphenyl)pyridine-2,3-diamine

To a solution of N-benzhydryl-5-(4-methoxyphenyl)-3-nitropyridin-2-amine (2.7 g, 6.6 mmol) in EtOH (80 mL) was added Pd/C (0.27 g), and the reaction mixture was stirred at room temperature for 5 h under an atmosphere of H$_2$. After uptake of H$_2$ (1 equivalent), the catalyst was filtered off and the filtrate as evaporated to yield the title compound (2.3 g, 92%), which was used in the next step without further purification.

Step C: 3-Benzhydryl-6-(4-methoxyphenyl)-1,3-dihydro-2H-imidazo[4,5-b]pyridin-2-one A solution of N$^2$-benzhydryl-5-(4-methoxyphenyl)pyridine-2,3-diamine (2.2 g, 5.8 mmol) and CDI (1.9 g, 11.5 mmol) in 1,4-dioxane (100 mL) was refluxed for 5 h. Then, the solvent was evaporated and the resultant solid was washed with water and dried to yield the title compound (2.3 g, 100%), which was used in the next step without further purification.

Step D: tert-Butyl 2-(3-benzhydryl-6-(4-methoxyphenyl)-2-oxo-2,3-dihydro-1H-imidazo[4,5-b]pyridin-1-yl)acetate A solution of 3-benzhydryl-6-(4-methoxyphenyl)-1,3-dihydro-2H-imidazo[4,5-b]pyridin-2-one (2.2 g, 5.4 mmol), tert-butyl bromoacetate (1.3 g, 6.5 mmol) and K$_2$CO$_3$ (1.5 g, 10.8 mmol) in MeCN (80 mL) was heated to reflux for 5 h. Then, the reaction mixture was cooled, filtered, and the filtrate was evaporated to yield the title compound (2.8 g, 100%), which was used in the next step without further purification.

Step E: 2-(6-(4-Methoxyphenyl)-2-oxo-2,3-dihydro-1H-imidazo[4,5-b]pyridin-1-yl)acetic Acid To a solution of tert-butyl 2-(3-benzhydryl-6-(4-methoxyphenyl)-2-oxo-2,3-dihydro-1H-imidazo[4,5-b]pyridin-1-yl)acetate (2.8 g, 5.4 mmol) in TFA (50 mL) was added thioanisole (0.28 g), and the reaction mixture was stirred at 80° C. for 1 h. Then, the solvent was evaporated to yield the title compound as the TFA salt (2.2 g, 100%).

Step F: 6-(4-Methoxyphenyl)-1-(2-morpholino-2-oxo-ethyl)-3H-imidazo[4,5-b]pyridin-2-one A solution of 2-(6-(4-methoxyphenyl)-2-oxo-2,3-dihydro-1H-imidazo[4,5-b]pyridin-1-yl)acetic acid TFA salt (0.4 g, 0.97 mmol), morpholine (0.25 g, 2.9 mmol), HBTU (0.38 g, 0.97 mmol), HOBT (0.13 g, 0.97 mmol), and NEt$_3$ (0.29 g, 2.9 mmol) in DMF (10 mL) was stirred at room temperature for 12 h. Then, water (20 mL) was added to the reaction mixture and the reaction was extracted with EtOAc (3×30 mL). The combined organic layers were washed with water, brine, dried over Na$_2$SO$_4$, filtered and concentrated under reduced pressure to afford the free base of the title compound. The residue was purified by preparative HPLC (gradient elution: 0.1% TFA in CH$_3$CN/0.1% TFA in H$_2$O) and the desired fractions were collected and washed with a saturated aqueous solution of NaHCO$_3$. The biphasic mixture was extracted with EtOAc (3×30 mL). The combined organic layers were dried over Na$_2$SO$_4$, filtered and concentrated to yield the title compound as a white solid (0.11 g, 30%). MS (ESI): mass calcd. for C$_{19}$H$_{20}$N$_4$O$_4$, 368.1; m/z found, 369.0 [M+H]$^+$. MP=239.1-244.1° C.

Example 2: 6-(4-Fluoro-2-methyl-phenyl)-1-(2-methoxyethyl)-3H-imidazo[4,5-b]pyridin-2-one

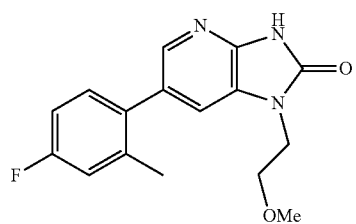 [SMILES: COCCn1c(=O)[nH]c2ncc(-c3ccc(F)cc3C)cc21]

A solution of 6-bromo-1-(2-methoxyethyl)-1,3-dihydro-2H-imidazo[4,5-b]pyridin-2-one (Intermediate 32, 0.3 g, 1.1 mmol), (4-fluoro-2-methylphenyl)boronic acid (0.25 g, 1.7 mmol), Pd(PPh$_3$)$_2$Cl$_2$ (0.03 g, 0.04 mmol), and 2 M Na$_2$CO$_3$ (2 mL) in 1,2-dimethoxyethane (6 mL) was heated to 140° C. via microwave irradiation for 10 min. Then, water (30 mL) was added to the crude reaction mixture and the mixture was extracted with EtOAc (3×30 mL). The combined organic layers were washed with water, brine, dried over Na$_2$SO$_4$, filtered and concentrated under reduced pressure. The crude residue was purified by preparative HPLC (gradient elution: 0.1% TFA in CH$_3$CN/0.1% TFA in H$_2$O) and the desired fractions were collected and washed with a saturated aqueous solution of NaHCO$_3$. The biphasic mixture was extracted with EtOAc (3×30 mL). The combined organic layers were dried over Na$_2$SO$_4$, filtered and concentrated to yield the title compound as a white solid (0.23 g, 69%). MS (ESI): mass calcd. for C$_{16}$H$_{16}$FN$_3$O$_2$, 301.1; m/z found, 302.1 [M+H]$^+$.

Example 3: N-Ethyl-2-[6-(4-fluoro-2-methyl-phenyl)-2-oxo-3H-imidazo[4,5-b]pyridin-1-yl]acetamide

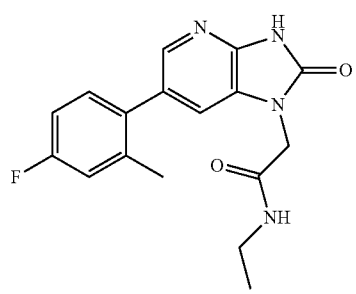 [SMILES: CCNC(=O)Cn1c(=O)[nH]c2ncc(-c3ccc(F)cc3C)cc21]

A solution of 2-(6-bromo-2-oxo-2,3-dihydro-1H-imidazo[4,5-b]pyridin-1-yl)-N-ethylacetamide (Intermediate 33, 0.3 g, 1 mmol), (4-fluoro-2-methylphenyl)boronic acid (0.23 g, 1.5 mmol), Pd(PPh$_3$)$_2$C$_2$ (0.03 g, 0.04 mmol), and 2 M Na$_2$CO$_3$ (2 mL) in EtOH (6 mL) was heated to 180° C. via microwave irradiation for 1 h. Then, water (30 mL) was added to the crude reaction mixture and the mixture was extracted with EtOAc (3×30 mL). The combined organic layers were washed with water, brine, dried over Na$_2$SO$_4$, filtered and concentrated under reduced pressure. The crude residue was purified by preparative HPLC (gradient elution: 0.1% TFA in CH$_3$CN/0.1% TFA in H$_2$O) and the desired fractions were collected and washed with a saturated aqueous solution of NaHCO$_3$. The biphasic mixture was extracted with EtOAc (3×30 mL). The combined organic layers were dried over Na$_2$SO$_4$, filtered and concentrated to yield the title compound as a white solid (0.061 g, 18%). MS (ESI): mass calcd. for C$_{17}$H$_{17}$FN$_4$O$_2$, 328.1; m/z found, 329.0 [M+H]$^+$. MP=225.1-232.3° C.

Example 4: (S*)-1-(2-Hydroxybutyl)-6-(4-methoxyphenyl)-3H-imidazo[4,5-b]pyridin-2-one

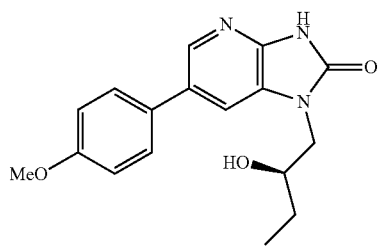 [SMILES: CC[C@@H](O)Cn1c(=O)[nH]c2ncc(-c3ccc(OC)cc3)cc21]

Step A: 3-Benzhydryl-6-bromo-1-(2-oxobutyl)-1,3-dihydro-2H-imidazo[4,5-b]pyridin-2-one 1-Bromobutan-2-one (1.6 g, 11 mmol) was added to a solution of 3-benzhydryl-6-bromo-1,3-dihydro-2H-imidazo[4,5-b]pyridin-2-one (Intermediate 32, Product from Step B, 2 g, 5.3 mmol), and Na$_2$CO$_3$ (1.1 g, 11 mmol) in MeCN (30 mL), and the reaction mixture was refluxed for 2 h. Then, the crude reaction mixture was filtered and washed with MeOH. The solvent was evaporated to yield the title compound (2.3 g, 96%), which was used in the next step without further purification.

Step B: 3-Benzhydryl-6-bromo-1-(2-hydroxybutyl)-1,3-dihydro-2H-imidazo[4,5-b]pyridin-2-one To a solution of 3-benzhydryl-6-bromo-1-(2-oxobutyl)-1,3-dihydro-2H-imidazo[4,5-b]pyridin-2-one (2.3 g, 5.1 mmol) in EtOH (50 mL) at 0° C. was added NaBH$_4$ (0.8 g, 21 mmol), and the mixture was warmed to room temperature and stirred for 2 h. Then water was added and the reaction mixture was filtered. The solids were collected and dried to yield the title compound (2 g, 87%), which was used in the next step without further purification.

Step C: 6-Bromo-1-(2-hydroxybutyl)-1H-imidazo[4,5-b]pyridin-2(3H)-one

A solution of 3-benzhydryl-6-bromo-1-(2-hydroxybutyl)-1,3-dihydro-2H-imidazo[4,5-b]pyridin-2-one (2 g, 4.4 mmol) in TFA (20 mL) and thioanisole (0.05 mL) was heated to reflux for 4 h. The reaction mixture was cooled, and concentrated under reduced pressure. Ammonia/water was added to adjust the pH to 8. The reaction mixture was concentrated under reduced pressure and purified (FCC, SiO$_2$, DCM/MeOH 1:0 to 0:1) to afford the title compound the desired (1.2 g, 96%).

Step D: (S*)-1-(2-Hydroxybutyl)-6-(4-methoxyphenyl)-3H-imidazo[4,5-b]pyridin-2-one The title compound was prepared in a manner analogous to Example 2, using (4-methoxyphenyl)boronic acid in and 6-bromo-1-(2-hydroxybutyl)-1H-imidazo[4,5-b]pyridin-2(3H)-one. Purification (SFC separation, Chiralcel AD-H, 20 μm; Supercritical CO$_2$: MeOH, v/v, 200 mL/min) afforded the title compound and (R*)-1-(2-Hydroxybutyl)-6-(4-methoxyphenyl)-3H-imidazo[4,5-b]pyridin-2-one (Example 5). MS (ESI): mass calcd. for C$_{17}$H$_{19}$N$_3$O$_3$, 313.1; m/z found, 314.0 [M+H]$^+$.

Example 5: (R*)-1-(2-Hydroxybutyl)-6-(4-methoxyphenyl)-3H-imidazo[4,5-b]pyridin-2-one

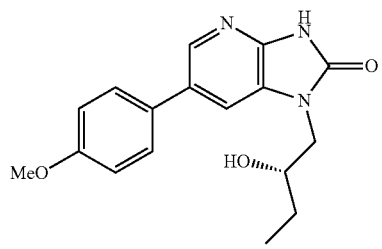 [SMILES: CC[C@H](O)Cn1c(=O)[nH]c2ncc(-c3ccc(OC)cc3)cc21]

The title compound was separated as a product from Example 4. MS (ESI): mass calcd. for C$_{17}$H$_{19}$N$_3$O$_3$, 313.1; m/z found, 314.1 [M+H]$^+$.

Example 6: 6-(4-Fluoro-3-methyl-phenyl)-3-methyl-1-(2-pyridylmethyl)imidazo[4,5-b]pyridin-2-one

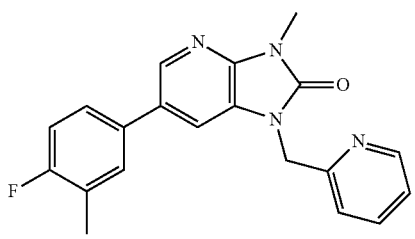 [SMILES: Cc1cc(-c2cnc3c(c2)n(Cc2ccccn2)c(=O)n3C)ccc1F]

To a solution a 6-(4-fluoro-3-methylphenyl)-3-methyl-1,3-dihydro-2H-imidazo[4,5-b]pyridin-2-one (Intermediate 27, 75 mg, 0.29 mmol) and 2-(chloromethyl)pyridine hydrochloride (74 mg, 0.45 mmol) in DMF (7.5 mL) at 0° C. was added portion-wise NaH (60% dispersion in mineral oil, 27 mg, 0.67 mmol), and the reaction mixture was stirred at 0° C. for 20 min. Then, the mixture was heated to 75° C. and stirred for 2 h. Upon completion, water was added followed by EtOAc. The resulting biphasic mixture was separated and the aqueous layer further extracted with DCM. The combined organic layers were dried (MgSO$_4$), filtered and concentrated under reduced pressure. The residue was purified (FCC, SiO$_2$, 0-10% 7 M solution of NH$_3$/MeOH in EtOAc) to yield the title compound as a pink solid (25 g, 25%). MS (ESI): mass calcd. for C$_{20}$H$_{17}$FN$_4$O, 348.1; m/z found, 349.1 [M+H]$^+$. $^1$H NMR (400 MHz, DMSO-d$_6$) δ 2.22 (d, J=1.62 Hz, 3H), 3.34 (s, 3H), 5.19 (s, 2H), 7.15 (t, J=9.13 Hz, 1H), 7.21 (dd, J=7.40, 4.85 Hz, 1H), 7.25 (d, J=7.86 Hz, 1H), 7.36-7.44 (m, 1H), 7.50 (dd, J=7.40, 1.85 Hz, 1H), 7.65-7.74 (m, 2H), 8.21 (d, J=1.85 Hz, 1H), 8.41 (d, J=3.93 Hz, 1H).

Example 7: 6-(3-Fluorophenyl)-3-methyl-1-(pyrimidin-4-ylmethyl)imidazo[4,5-b]pyridin-2-one

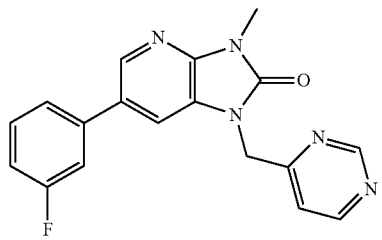 [SMILES: Cn1c(=O)n(Cc2ccncn2)c2cc(-c3cccc(F)c3)cnc21]

To a solution of 6-(3-fluorophenyl)-3-methyl-1,3-dihydro-2H-imidazo[4,5-b]pyridin-2-one (Intermediate 28, 60 mg, 0.25 mmol), pyrimidin-4-ylmethanol (27 mg, 0.25 mmol) and triphenylphosphine (129 mg, 0.493 mmol) in CH$_3$CN (7.5 mL) at 0° C. was added di-tert-butyl azodicarboxylate (85 mg, 0.37 mmol), and the reaction mixture was stirred at 110° C. for 15 min under microwave irradiation. Then, the mixture was concentrated to dryness and the crude product was purified by HPLC purification (Stationary phase: C18 XBridge 30×100 mm 5 um), Mobile phase: Gradient from 74% 10 mM NH$_4$CO$_3$H pH 9 solution in Water, 26% CH$_3$CN to 58% 10 mM NH$_4$CO$_3$H pH 9 solution in Water, 42% CH$_3$CN) to yield the title compound as a white solid (36 mg, 44%). MS (ESI): mass calcd. for C$_{18}$H$_{14}$FN$_5$O, 335.1; m/z found, 336.1 [M+H]$^+$. $^1$H NMR (400 MHz, DMSO-d$_6$) δ 3.42 (s, 3H), 5.31 (s, 2H), 7.09-7.30 (m, 1H), 7.41-7.58 (m, 4H), 7.91 (d, J=2.08 Hz, 1H), 8.41 (d, J=2.08 Hz, 1H), 8.75 (d, J=5.32 Hz, 1H), 9.08 (d, J=1.39 Hz, 1H).

Example 8: 6-(3,4-Difluorophenyl)-3-methyl-1l-[(5-methylisoxazol-3-yl)methyl]imidazo[4,5-b]pyridin-2-one

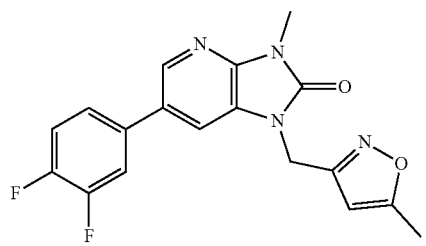 [SMILES: Cc1cc(Cn2c(=O)n(C)c3ncc(-c4ccc(F)c(F)c4)cc32)no1]

Step A: 3-Methyl-1-((5-methylisoxazol-3-yl)methyl)-6-(4,4,5,5-tetramethyl-1,3,2-dioxaborolan-2-yl)-1,3-dihydro-2H-imidazo[4,5-b]pyridin-2-one To a solution a of 6-bromo-3-methyl-1-((5-methylisoxazol-3-yl)methyl)-1,3-dihydro-2H-imidazo[4,5-b]pyridin-2-one (Intermediate 22, 150 mg, 0.46) in 1,4-dioxane (3 mL)

was added bis(pinacolato)diboron (140 mg, 0.551 mmol), KOAc (135 mg, 1.38 mmol) and PdCl$_2$(dppf) (11 mg, 0.014 mmol). The reaction mixture was stirred at 130° C. for 2 h. Then, the crude reaction mixture was cooled and filtered through Celite®. The filtrate was diluted with water and extracted with EtOAc. The combined organic layers were dried (MgSO$_4$), filtered and concentrated under reduced pressure. The residue was purified (FCC, SiO$_2$, 0-40% EtOAc in heptanes) to yield the title compound (130 mg, 76%). MS (ESI): mass calcd. for C$_{18}$H$_{23}$BN$_4$O$_4$, 370.2; m/z found, 371 [M+H]$^+$. $^1$H NMR (300 MHz, CDCl$_3$) δ 8.44 (s, 1H), 7.60 (s, 1H), 5.99 (s, 1H), 5.08 (s, 2H), 3.53 (s, 3H), 2.37 (s, 3H), 1.34 (s, 12H).

Step B: 6-(3,4-Difluorophenyl)-3-methyl-1l-[(5-methylisoxazol-3-yl)methyl]imidazo[4,5-b]pyridin-2-one To a solution of 3-methyl-1-((5-methylisoxazol-3-yl)methyl)-6-(4,4,5,5-tetramethyl-1,3,2-dioxaborolan-2-yl)-1,3-dihydro-2H-imidazo[4,5-b]pyridin-2-one (210 mg, 0.567 mmol), 1-bromo-3,4-difluorobenzene (84 μL, 0.732 mmol) and NaHCO$_3$ (164 mg, 1.95 mmol) in 1,4-dioxane (4 mL) and water (0.9 mL) was added [1,1'-bis(di-tert-butylphosphino)ferrocene]dichloropalladium(II) (32 mg, 0.049 mmol). The reaction mixture was stirred at 70° C. for 3 h. Then, the crude reaction mixture was cooled, diluted with water and extracted with EtOAc. The organic layer was separated, dried Na$_2$SO$_4$, filtered, and concentrated. The crude product was purified (FCC, SiO$_2$, 0-80% EtOAc in heptanes) and the fractions containing desired product were concentrated. The product was then triturated with DIPE to yield the title compound (204 mg, 36%). MS (ESI): mass calcd. for C$_{18}$H$_{14}$F$_2$N$_4$O$_2$, 356.1; m/z found, 357 [M+H]$^+$. $^1$H NMR (300 MHz, CDCl$_3$) δ 8.19 (s, 1H), 7.40 (s, 1H), 7.36-7.26 (m, 2H), 7.25-7.21 (m, 1H), 6.03 (s, 1H), 5.13 (s, 2H), 3.54 (s, 3H), 2.38 (s, 3H).

Example 9: 2-[6-(5-Chloro-2-thienyl)-3-methyl-2-oxo-imidazo[4,5-b]pyridin-1-yl]-N,N-dimethyl-acetamide

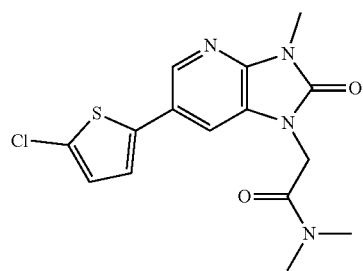 [SMILES: CN(C)C(=O)Cn1c(=O)n(C)c2ncc(-c3ccc(Cl)s3)cc21]

A mixture of 2-(6-bromo-3-methyl-2-oxo-2,3-dihydro-1H-imidazo[4,5-b]pyridin-1-yl)-N,N-dimethylacetamide (Intermediate 15, 180 mg, 0.58 mmol), 5-chlorothiophene-2-boronic acid (140 mg, 0.86 mmol), Cs$_2$CO$_3$ (375 mg, 1.15 mmol), and Pd(dppf)Cl$_2$.DCM (29.4 mg, 0.04 mmol) in dioxane (5 mL) and water (1 mL) was sealed in a microwave vial and heated to 90° C. The reaction mixture was stirred at 90° C. for 3 hours then cooled down to room temperature and quenched with a saturated aqueous solution of NaHCO$_3$. The resulting reaction mixture was extracted with EtOAc (3×60 mL) and the combined organic layers were dried using MgSO$_4$, filtered and concentrated under vacuum. The crude material was purified via basic HPLC (Agilent prep system, Waters XBridge C18 5 μm 50×100 mm column, 5-95% MeCN/20 nM NH$_4$OH over 22 min at 80 mL/min) to provide the title compound (42 mg, 21%). MS (ESI): mass calcd. for C$_{15}$H$_{15}$ClN$_4$O$_2$S, 350.1; m/z found, 351.1 [M+H]$^+$. $^1$H NMR (400 MHz, CDCl$_3$) δ 8.23-8.17 (d, J=1.9 Hz, 1H), 7.26-7.25 (m, 1H), 7.02-6.97 (d, J=3.9 Hz, 1H), 6.92-6.86 (d, J=3.8 Hz, 1H), 4.73-4.69 (s, 2H), 3.54-3.49 (s, 3H), 3.19-3.14 (s, 3H), 3.02-2.97 (s, 3H).

Example 10: 6-[5-(Difluoromethyl)-2-thienyl]-1-[2-(3-fluoroazetidin-1-yl)-2-oxo-ethyl]-3-methyl-imidazo[4,5-b]pyridin-2-one

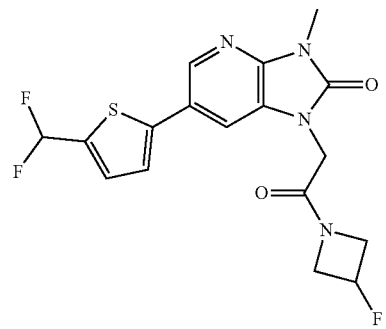 [SMILES: Cn1c(=O)n(CC(=O)N2CC(F)C2)c2cc(-c3ccc(C(F)F)s3)cnc21]

To a solution of 2-bromo-5-(difluoromethyl)thiophene (100 mg, 0.47 mmol) in dioxane (3 mL) was added bis(pinacolato)diboron (143 mg, 0.56 mmol), KOAc (138 mg, 1.4 mmol), and PdCl$_2$(dppf).DCM (34 mg, 0.5 mmol). The resulting reaction mixture was stirred at 90° C. for 2 hours under a nitrogen atmosphere. The reaction mixture was then cooled down to room temperature and 6-bromo-1-(2-(3-fluoroazetidin-1-yl)-2-oxoethyl)-3-methyl-1,3-dihydro-2H-imidazo[4,5-b]pyridin-2-one (Intermediate 18) (32 mg, 0.09 mmol) was subsequently added to the reaction mixture along with Cs$_2$CO$_3$ (114 mg, 0.35 mmol), dioxane (2 mL) and an additional amount of PdCl$_2$(dppf).DCM (34 mg, 0.5 mmol). The resulting reaction mixture was stirred at 90° C. for an additional 2 hours under a nitrogen atmosphere. The reaction was cooled to room temperature and washed with water. The organic layer was dried with MgSO$_4$ and concentrated into a brown residue which was purified (FCC, SiO$_2$, 0-7% 2M NH$_3$/MeOH in DCM). Further purification via basic HPLC (Agilent prep system, Waters XBridge C$_{18\ 5}$ μm 50×100 mm column, 5-95% MeCN/20 nM NH$_4$OH over 22 min at 80 mL/min) to provide the title compound (6 mg, 16%). MS (ESI): mass calcd. for C$_{17}$H$_{15}$F$_3$N$_4$O$_2$S, 396.1; m/z found, 396.9 [M+H]$^+$. $^1$H NMR (400 MHz, CDCl$_3$) δ 8.34-8.30 (d, J=1.9 Hz, 1H), 7.45-7.42 (d, J=1.9 Hz, 1H), 7.28-7.26 (m, 1H), 7.20-7.17 (m, 1H), 6.98-6.68 (m, 1H), 5.48-5.25 (m, 1H), 4.68-4.11 (m, 6H), 3.56-3.50 (s, 3H).

Example 11: 1-[(5-Methylisoxazol-3-yl)methyl]-6-phenyl-3H-imidazo[4,5-b]pyridin-2-one

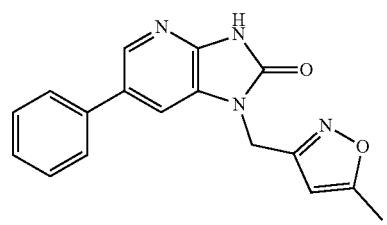 [SMILES: Cc1cc(Cn2c(=O)[nH]c3ncc(-c4ccccc4)cc32)no1]

Step A: 6-Bromo-1-((5-methylisoxazol-3-yl)methyl)-3-trityl-1,3-dihydro-2H-imidazo[4,5-b]pyridin-2-one To a solution of 6-bromo-3-trityl-1,3-dihydro-2H-imidazo[4,5-b]pyridin-2-one (Intermediate 36, 303 mg, 0.66 mmol) in DMF (3 mL) was added NaH (60% dispersion in mineral oil, 35 mg, 0.87 mmol) in one portion at room temperature. The reaction was stirred until gas evolution had ceased, then 3-(chloromethyl)-5-methylisoxazole (87 µL, 0.79 mmol) was added. The mixture was stirred at room temperature overnight then diluted with water. The aqueous layer was extracted with EtOAc. The combined organic layers were washed with water (2×), then dried over Na$_2$SO$_4$, filtered and concentrated under reduced pressure. The crude solid was purified (FCC, SiO$_2$, 0 to 25% EtOAc in hexanes) to yield the title compound as a solid (356 mg, 97%). $^1$H NMR (500 MHz, CDCl$_3$) δ 7.79 (d, J=2.0 Hz, 1H), 7.53-7.45 (m, 6H), 7.29 (d, J=2.0 Hz, 1H), 7.25-7.16 (m, 9H), 5.67 (d, J=0.9 Hz, 1H), 4.94 (s, 2H), 2.34 (d, J=0.9 Hz, 3H).

Step B: 1-((5-Methylisoxazol-3-yl)methyl)-6-phenyl-3-trityl-1,3-dihydro-2H-imidazo[4,5-b]pyridin-2-one To a microwave tube was added solid 6-bromo-1-((5-methylisoxazol-3-yl)methyl)-3-trityl-1,3-dihydro-2H-imidazo[4,5-b]pyridin-2-one (184 mg, 0.33 mmol) followed by phenylboronic acid (60 mg, 0.49 mmol) and Pd(PPh$_3$)$_4$ (25 mg, 0.02 mmol). To these solids were added dioxane (1.6 mL) followed by 2M Na$_2$CO$_3$ (332 µL, 0.67 mmol). The vial was capped and heated at 100° C. for 5 h. Then dioxane was removed via pipette and the remaining solids were triturated with EtOAc (3×). The combined organic layers were concentrated to yield the title compound (287 mg, 81%) as a solid, which was used in the next step without further purification.

Step C: 1-[(5-Methylisoxazol-3-yl)methyl]-6-phenyl-3H-imidazo[4,5-b]pyridin-2-one To a solution of 1-((5-methylisoxazol-3-yl)methyl)-6-phenyl-3-trityl-1,3-dihydro-2H-imidazo[4,5-b]pyridin-2-one (183 mg, 0.33 mmol) in DCM (3 mL) was added TFA (666 µL). The mixture was stirred at room temperature overnight and then concentrated. The residue was dissolved in DCM and washed with a saturated aqueous solution of NaHCO$_3$. The organic layer was dried over Na$_2$SO$_4$, filtered and concentrated under reduced pressure. The crude oil was purified (FCC, SiO$_2$, 0 to 50% EtOAc in hexanes) to yield the title compound as a solid (62 mg, 60%). MS (ESI): mass calcd. for C$_{17}$H$_{14}$N$_4$O$_2$, 306.1; m/z found, 307.1 [M+H]$^+$. $^1$H NMR (500 MHz, CDCl$_3$) δ 10.44 (s, 1H), 8.31 (d, J=1.9 Hz, 1H), 7.57-7.52 (m, 2H), 7.51 (d, J=1.9 Hz, 1H), 7.50-7.43 (m, 2H), 7.41-7.36 (m, 1H), 6.05 (d, J=1.0 Hz, 1H), 5.14 (s, 2H), 2.38 (d, J=0.9 Hz, 3H).

Example 12: 6-(4-Fluorophenyl)-1-[(5-methylisoxazol-3-yl)methyl]-3H-imidazo[4,5-b]pyridin-2-one

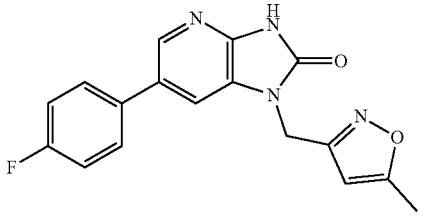 [SMILES: Cc1cc(Cn2c(=O)[nH]c3ncc(-c4ccc(F)cc4)cc32)no1]

Step A: 6-(4-Fluorophenyl)-3-(4-methoxybenzyl)-1,3-dihydro-2H-imidazo[4,5-b]pyridin-2-one To a microwave tube was added 6-bromo-3-(4-methoxybenzyl)-1,3-dihydro-2H-imidazo[4,5-b]pyridin-2-one (Intermediate 10, 287 mg, 0.86 mmol) followed by 4-fluorophenylboronic acid (159 mg, 1.14 mmol) and Pd(PPh$_3$)$_4$ (51 mg, 0.04 mmol). To these solids were added dioxane (4 mL) followed by 2 M Na$_2$CO$_3$ (859 µL, 1.72 mmol). The vial was capped and heated in the microwave at 150° C. for 1 h. Then dioxane was removed via pipette and the remaining solids were triturated with EtOAc (3×). The combined organic layers were concentrated and the crude solid was purified (FCC, SiO$_2$, 0 to 55% 1% IPA in EtOAc in hexanes) to yield the title compound (52 mg, 17%) as a solid. MS (ESI): mass calcd. for C$_{20}$H$_{16}$FN$_3$O$_2$, 349.1; m/z found, 350.1 [M+H]$^+$. $^1$H NMR (500 MHz, CDCl$_3$) δ 9.34 (s, 1H), 8.24 (d, J=2.0 Hz, 1H), 7.52-7.45 (m, 4H), 7.43 (d, J=1.9 Hz, 1H), 7.19-7.11 (m, 2H), 6.88-6.81 (m, 2H), 5.14 (s, 2H), 3.76 (s, 3H).

Step B: 6-(4-Fluorophenyl)-3-(4-methoxybenzyl)-1-((5-methylisoxazol-3-yl)methyl)-1,3-dihydro-2H-imidazo[4,5-b]pyridin-2-one To a solution of 6-(4-fluorophenyl)-3-(4-methoxybenzyl)-1,3-dihydro-2H-imidazo[4,5-b]pyridin-2-one (43 mg, 0.12 mmol) in DMF (2 mL) was added NaH (60% dispersion in mineral oil, 6 mg, 0.16 mmol) in one portion at room temperature. The reaction was stirred until gas evolution ceased, and then 3-(chloromethyl)-5-methylisoxazole (16 µL, 0.15 mmol) was added. The mixture was stirred at room temperature overnight but was incomplete. To the reaction mixture was added additional NaH (60% dispersion in mineral oil, 6 mg, 0.16 mmol) in one portion at room temperature. The reaction was stirred until gas evolution ceased, and then additional 3-(chloromethyl)-5-methylisoxazole (16 µL, 0.15 mmol) was added. The mixture was again stirred at room temperature overnight. Then, the reaction was diluted with water and the aqueous layer was extracted with EtOAc. The combined organic layers were dried over Na$_2$SO$_4$, filtered and concentrated to yield the title compound (66 mg) as a solid, which was used in the next step without further purification. MS (ESI): mass calcd. for C$_{25}$H$_{21}$FN$_4$O$_3$, 444.2; m/z found, 445.2 [M+H]$^+$. $^1$H NMR (500 MHz, CDCl$_3$) δ 8.21 (d, J=1.9 Hz, 1H), 7.51-7.42 (m, 4H), 7.40 (d, J=1.9 Hz, 1H), 7.17-7.10 (m, 2H), 6.88-6.82 (m, 2H), 6.03-5.96 (m, 1H), 5.18-5.07 (m, 4H), 3.77 (s, 3H), 2.37 (d, J=0.9 Hz, 3H).

Step C: 6-(4-Fluorophenyl)-1-[(5-methylisoxazol-3-yl)methyl]-3H-imidazo[4,5-b]pyridin-2-one A solution of 48% aqueous HBr (3 mL) was added to 6-(4-fluorophenyl)-3-(4-methoxybenzyl)-1-((5-methylisoxazol-3-yl)methyl)-1,3-dihydro-2H-imidazo[4,5-b]pyridin-2-one (55 mg, 0.12 mmol) and the mixture was heated at 115° C. for 7 h. The mixture was concentrated and the residue was partitioned between DCM and a saturated aqueous solution of NaHCO$_3$. The layers were separated and the aqueous layer was extracted with DCM. The combined organic layers were dried over Na$_2$SO$_4$, filtered and concentrated under reduced pressure. The crude material was purified (FCC, SiO$_2$, 0 to 50% 1.5% IPA in EtOAc in hexanes) to yield the title compound (33 mg, 82%) as a solid. MS (ESI): mass calcd. for C$_{17}$H$_{13}$FN$_4$O$_2$, 324.1; m/z found, 325.1 [M+H]$^+$. $^1$H NMR (500 MHz, CDCl$_3$) δ 10.08 (s, 1H), 8.24 (d, J=1.9 Hz, 1H), 7.52-7.45 (m, 3H), 7.18-7.11 (m, 2H), 6.06 (d, J=1.0 Hz, 1H), 5.13 (s, 2H), 2.38 (d, J=1.0 Hz, 3H).

Example 13: 6-(4-Fluorophenyl)-1-[(5-methyl-1,3,4-oxadiazol-2-yl)methyl]-3H-imidazo[4,5-b]pyridin-2-one

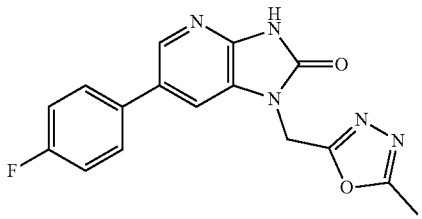 [SMILES: Cc1nnc(Cn2c(=O)[nH]c3ncc(-c4ccc(F)cc4)cc32)o1]

Step A: 6-(4-Fluorophenyl)-3-trityl-1,3-dihydro-2H-imidazo[4,5-b]pyridin-2-one

To a round bottom flask was added 6-bromo-3-trityl-1,3-dihydro-2H-imidazo[4,5-b]pyridin-2-one (Intermediate 36, 706 mg, 1.55 mmol) followed by 4-fluorophenylboronic acid (294 mg, 2.10 mmol) and Pd(PPh$_3$)$_4$ (357 mg, 0.31 mmol). To these solids were added dioxane (8 mL) followed by 2M Na$_2$CO$_3$ (2.3 mL, 4.64 mmol). The mixture was heated at 90° C. for 15 h. Then, the crude reaction mixture was concentrated to remove dioxane, and the resultant residue was partitioned between EtOAc and water. The layers were separated and the aqueous layer was extracted with EtOAc. The combined organic layers were dried over Na$_2$SO$_4$, filtered and concentrated under reduced pressure. The crude material was purified (FCC, SiO$_2$, 0 to 50% 1.5% IPA in EtOAc in hexanes) to yield the title compound (400 mg, 55%) as a solid. $^1$H NMR (500 MHz, CDCl$_3$) δ 8.26-8.18 (m, 1H), 7.95 (d, J=2.0 Hz, 1H), 7.78-7.72 (m, 1H), 7.59-7.52 (m, 6H), 7.44-7.38 (m, 2H), 7.31-7.08 (m, 10H).

Step B: 6-(4-Fluorophenyl)-1-((5-methyl-1,3,4-oxadiazol-2-yl)methyl)-3-trityl-1,3-dihydro-2H-imidazo[4,5-b]pyridin-2-one To a solution of 6-(4-fluorophenyl)-3-trityl-1,3-dihydro-2H-imidazo[4,5-b]pyridin-2-one (205 mg, 0.44 mmol) in DMF (4 mL) was added NaH (60% dispersion in mineral oil, 23 mg, 0.57 mmol) in one portion at room temperature. The reaction was stirred until gas evolution had ceased, then 2-(chloromethyl)-5-methyl-1,3,4-oxadiazole (58 µL, 0.57 mmol) was added. The mixture was stirred at room temperature overnight. Then the reaction mixture was diluted with water and the aqueous layer was extracted with EtOAc. The combined organic layers were washed with water (2×), dried over Na$_2$SO$_4$, filtered, and concentrated. The crude solid was purified (FCC, SiO$_2$, 0 to 60% EtOAc in hexanes) to yield the title compound (129 mg, 52%) as a foam. $^1$H NMR (500 MHz, CDCl$_3$) δ 7.97 (d, J=2.0 Hz, 1H), 7.57-7.50 (m, 6H), 7.44-7.36 (m, 2H), 7.34 (d, J=2.0 Hz, 1H), 7.28-7.26 (m, 1H), 7.26-7.17 (m, 7H), 7.12-7.05 (m, 2H), 5.21 (s, 2H), 2.49 (s, 3H).

Step C: 6-(4-Fluorophenyl)-1-[(5-methyl-1,3,4-oxadiazol-2-yl)methyl]-3H-imidazo[4,5-b]pyridin-2-one To a solution of 6-(4-fluorophenyl)-1-((5-methyl-1,3,4-oxadiazol-2-yl)methyl)-3-trityl-1,3-dihydro-2H-imidazo[4,5-b]pyridin-2-one (129 mg, 0.23 mmol) in DCM (2 mL) was added TFA (455 µL). The mixture was stirred at room temperature overnight and then concentrated. The crude residue was purified (FCC, SiO$_2$, 0 to 10% IPA in EtOAc) to yield the title compound (61 mg, 83%) as a solid. MS (ESI): mass calcd. for C$_{16}$H$_{12}$FN$_5$O$_2$, 325.1; m/z found, 326.1 [M+H]$^+$. $^1$H NMR (500 MHz, DMF-d$_7$) δ 11.86 (br s, 1H), 8.30 (d, J=2.0 Hz, 1H), 7.91 (d, J=2.0 Hz, 1H), 7.79-7.70 (m, 2H), 7.38-7.29 (m, 2H), 5.50 (s, 2H), 2.50 (s, 3H).

Example 14: 3-Methyl-1-[(5-methylisoxazol-3-yl)methyl]-6-(4-methyl-2-thienyl)imidazo[4,5-b]pyridin-2-one

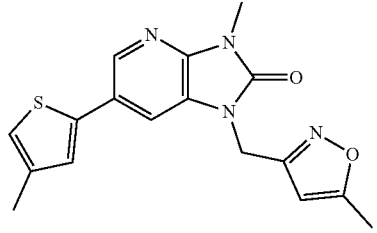 [SMILES: Cc1csc(-c2cnc3c(c2)n(Cc2cc(C)on2)c(=O)n3C)c1]

Step A: 1-((5-Methylisoxazol-3-yl)methyl)-6-(4-methylthiophen-2-yl)-1,3-dihydro-2H-imidazo[4,5-b]pyridin-2-one The title compound was prepared in a manner analogous to Example 11 using (4-methylthiophen-2-yl)boronic acid in Step B. MS (ESI): mass calcd. for C$_{16}$H$_{14}$N$_4$O$_2$S, 326.1; m/z found, 327.1 [M+H]$^+$. $^1$H NMR (500 MHz, DMF-d$_7$) δ 11.79 (s, 1H), 8.25 (d, J=2.0 Hz, 1H), 7.77 (d, J=1.9 Hz, 1H), 7.36-7.31 (m, 1H), 7.16-7.11 (m, 1H), 6.25 (t, J=0.9 Hz, 1H), 5.24 (s, 2H), 2.40 (d, J=0.9 Hz, 3H), 2.26 (d, J=1.0 Hz, 3H).

Step B: 3-Methyl-1-[(5-methylisoxazol-3-yl)methyl]-6-(4-methyl-2-thienyl)imidazo[4,5-b]pyridin-2-one To a solution of 1-((5-methylisoxazol-3-yl)methyl)-6-(4-methylthiophen-2-yl)-1,3-dihydro-2H-imidazo[4,5-b]pyridin-2-one (43 mg, 0.13 mmol) in DMF (2 mL) was added NaH (60% dispersion in mineral oil, 13 mg, 0.87 mmol) in one portion at room temperature. The reaction was stirred until gas evolution had ceased, then iodomethane (11 µL, 0.17 mmol) was added. The mixture was stirred at room temperature overnight then diluted with water. The aqueous layer was extracted with EtOAc. The combined organic layers were dried over Na$_2$SO$_4$, filtered and concentrated under reduced pressure. The crude solid was purified (FCC, SiO$_2$, 0 to 50% 1% IPA in EtOAc in DCM) to yield the title compound as a solid (37 mg, 82%). MS (ESI): mass calcd. for C$_{17}$H$_{16}$N$_4$O$_2$S, 340.1; m/z found, 341.1 [M+H]$^+$. $^1$H NMR (500 MHz, CDCl$_3$) δ 8.28 (d, J=1.9 Hz, 1H), 7.42 (d, J=1.9 Hz, 1H), 7.06 (d, J=1.4 Hz, 1H), 6.87 (p, J=1.2 Hz, 1H), 6.01 (d, J=1.0 Hz, 1H), 5.11 (s, 2H), 3.53 (s, 3H), 2.38 (d, J=0.8 Hz, 3H), 2.29 (d, J=1.0 Hz, 3H).

Example 15: 6-(4-Fluorophenyl)-1-[(1-methylpyrazol-4-yl)methyl]-3H-imidazo[4,5-b]pyridin-2-one

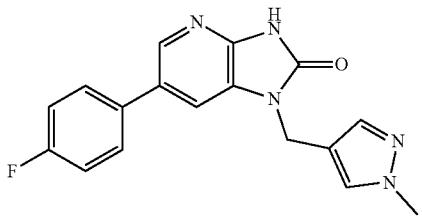 [SMILES: Cn1cc(Cn2c(=O)[nH]c3ncc(-c4ccc(F)cc4)cc32)cn1]

Step A: 5-(4-Fluorophenyl)-3-nitropyridin-2-amine

A solution of 2-amino-5-bromo-3-nitropyridine (623 mg, 2.86 mmol), 4-fluorophenylboronic acid (525 mg, 3.75 mmol), Cs$_2$CO$_3$ (1.87 g, 5.74 mmol), and PdCl$_2$(dppf) (209 mg, 0.29 mmol) in 1,4-dioxane (14 mL) and water (3 mL) was heated to 80° C. for 4 h and then concentrated. The residue was partitioned between DCM and water, upon which time the product crashed out. The heterogeneous mixture was redissolved with a solution of EtOAc containing 1.5% IPA. The aqueous layer was further extracted with EtOAc containing 1.5% IPA. The combined organic layers were dried, filtered and concentrated to yield the title compound (400 mg, 60%) as a solid, which was used in the next step without further purification.

Step B: Bis-tert-Butyl (5-(4-fluorophenyl)-3-nitropyridin-2-yl)carbamate

To a heterogeneous mixture of 5-(4-fluorophenyl)-3-nitropyridin-2-amine (400 mg, 1.72 mmol) in THF (9 mL) was added boc-anhydride (1.14 g, 5.2 mmol) followed by DMAP (316 mg, 2.59 mmol). The mixture became homogeneous and was complete after 30 min. The reaction was concentrated and the crude residue was purified (0 to 25% EtOAc in hexanes) to yield the title compound (663 mg, 89%) as a solid. $^1$H NMR (400 MHz, CDCl$_3$) δ 8.92 (d, J=2.3 Hz, 1H), 8.57 (d, J=2.3 Hz, 1H), 7.68-7.59 (m, 2H), 7.29-7.19 (m, 3H), 1.45 (s, 18H).

Step C: Bis-tert-Butyl (3-amino-5-(4-fluorophenyl) pyridin-2-yl)carbamate

To a round bottom flask containing bis-tert-butyl (5-(4-fluorophenyl)-3-nitropyridin-2-yl)carbamate (649 mg, 1.50 mmol) dissolved in EtOH (15) was added 10% Pd/C (301 mg), and the reaction mixture was stirred under an atmosphere of H$_2$ (balloon). After 3 h the reaction was complete and the Pd/C was removed by filtration and washed with EtOH. The filtrate was concentrated and the crude residue was purified (FCC, SiO$_2$, 0 to 50% EtOAc in hexanes) to yield the title compound (459 mg, 76%) as a solid. MS (ESI): mass calcd. for C$_{21}$H$_{26}$FN$_3$O$_4$, 403.2; m/z found, 404.2 [M+H]$^+$. $^1$H NMR (500 MHz, CDCl$_3$) δ 8.11 (d, J=2.2 Hz, 1H), 7.56-7.50 (m, 2H), 7.20 (d, J=2.1 Hz, 1H), 7.18-7.11 (m, 2H), 3.84 (s, 2H), 1.45 (s, 19H).

Step D: Bis-tert-Butyl (5-(4-fluorophenyl)-3-(((1-methyl-1H-pyrazol-4-yl)methyl)amino)pyridin-2-yl) carbamate To a heterogeneous mixture of bis-tert-butyl (3-amino-5-(4-fluorophenyl)pyridin-2-yl)carbamate (101 mg, 0.25 mmol) in DCE (3.5 mL) was added HOAc (14 μL, 0.25 mmol) followed by 1-methyl-1 h-pyrazole-4-carbaldehyde (43 mg, 0.39 mmol). After 10 min NaBH(OAc)$_3$ (162 mg, 0.76 mmol) was added and the mixture stirred at room temperature overnight. LCMS analysis showed that the reaction was not complete, and additional 1-methyl-1 h-pyrazole-4-carbaldehyde (43 mg, 0.39 mmol) was added. After 5 h the reaction had progressed further and no sign of over alkylated product was seen. Additional 1-methyl-1 h-pyrazole-4-carbaldehyde (43 mg, 0.39 mmol) was added and the mixture was stirred overnight during which time it went to completion. The reaction was quenched by the addition of a saturated aqueous solution of NaHCO$_3$ and the layers separated. The aqueous layer was extracted with DCM and the combined organic extracts were dried over Na$_2$SO$_4$, filtered and concentrated under reduced pressure. The crude residue was purified by (FCC, SiO$_2$, 0 to 55% EtOAc in hexanes) to yield the title compound (107 mg, 85%) as a foam. MS (ESI): mass calcd. for C$_{26}$H$_{32}$FN$_5$O$_4$, 497.2; m/z found, 498.3 [M+H]$^+$. $^1$H NMR (400 MHz, CDCl$_3$) δ 8.04 (d, J=2.1 Hz, 1H), 7.56-7.49 (m, 2H), 7.43 (s, 1H), 7.30 (s, 1H), 7.18-7.10 (m, 3H), 4.29 (d, J=5.4 Hz, 2H), 4.18-4.10 (m, 1H), 3.87 (s, 3H), 1.43 (s, 18H).

Step E: 5-(4-Fluorophenyl)-N3-((1-methyl-1H-pyrazol-4-yl)methyl)pyridine-2,3-diamine To a solution of bis-tert-butyl (5-(4-fluorophenyl)-3-(((1-methyl-1H-pyrazol-4-yl)methyl)amino)pyridin-2-yl)carbamate. (107 mg, 0.22 mmol) in DCM (2 mL) was added TFA (430 μL). After 3 h at room temperature the reaction was concentrated and the crude residue was purified (FCC, SiO$_2$, 0 to 9% 2M NH$_3$ in MeOH in DCM) to yield the title compound (59 mg, 93%) as an oil. MS (ESI): mass calcd. for C$_{16}$H$_{16}$FN$_5$, 297.2; m/z found, 298.2 [M+H]$^+$.

Step F: 6-(4-Fluorophenyl)-1-[(1-methylpyrazol-4-yl)methyl]-3H-imidazo[4,5-b]pyridin-2-one To a solution of 5-(4-fluorophenyl)-N3-((1-methyl-1H-pyrazol-4-yl)methyl)pyridine-2,3-diamine (28 mg, 0.09 mmol) in THF (2 mL) was added CDI (22 mg, 0.14 mmol), and the reaction was stirred at room temperature overnight. The reaction did not go to completion and additional CDI (34 mg, 0.21 mmol) was added, and the reaction was stirred at room temperature for 5 h. Analysis showed that the reaction was still not complete and additional CDI (22 mg, 0.14 mmol) was added and the mixture stirred at room temperature overnight and then concentrated. The residue was purified (FCC, SiO$_2$, 0 to 100% 2% IPA in EtOAc in hexanes), but the material was contaminated with imidazole. The compound was dissolved in DCM and washed with a 2 M citric acid solution. The organic layer was dried over Na$_2$SO$_4$, filtered and concentrated to yield the title compound (29 mg, 94%) as a foam. MS (ESI): mass calcd. for $C_{17}H_{14}FN_5O$, 323.1; m/z found, 324.1 [M+H]$^+$. $^1$H NMR (500 MHz, DMF-d$_7$) δ 11.62 (s, 1H), 8.22 (d, J=2.0 Hz, 1H), 7.91 (d, J=2.0 Hz, 1H), 7.83 (s, 1H), 7.81-7.74 (m, 2H), 7.56 (s, 1H), 7.38-7.28 (m, 2H), 5.03 (s, 2H), 3.83 (s, 3H).

Example 16: 1-[(1,5-Dimethylpyrazol-3-yl)methyl]-6-(4-fluorophenyl)-3H-imidazo[4,5-b]pyridin-2-one

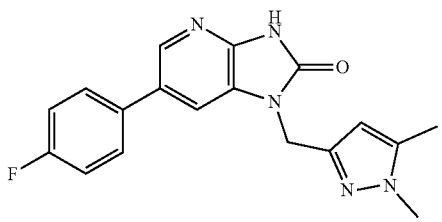 [SMILES: Cc1cc(Cn2c(=O)[nH]c3ncc(-c4ccc(F)cc4)cc32)nn1C]

Step A: Bis-tert-Butyl (5-bromo-3-nitropyridin-2-yl)carbamate

To a heterogeneous mixture of 2-amino-5-bromo-3-nitropyridine (2.28 g, 10.45 mmol) in THF (52 mL) was added boc-anhydride (6.84 g, 31.34 mmol) followed by DMAP (1.91 g, 15.67 mmol). The mixture was stirred at room temperature overnight during which time it became homogeneous. The mixture was concentrated and purified (FCC, SiO$_2$, 0 to 30% EtOAc in hexanes) to yield the title compound (3.09 g, 71%) as a foam. $^1$H NMR (400 MHz, CDCl$_3$) δ 8.80 (d, J=2.3 Hz, 1H), 8.56 (d, J=2.3 Hz, 1H), 1.43 (s, 18H).

Step B: tert-Butyl (5-bromo-3-nitropyridin-2-yl)carbamate

To a solution of bis-tert-butyl (5-bromo-3-nitropyridin-2-yl)carbamate (269 mg, 0.64 mmol) dissolved in EtOAc (3 mL) was added N,N-dimethylethylenediamine (351 μL, 3.22 mmol). The mixture was stirred at room temperature overnight and then concentrated. The residue was purified (FCC, SiO$_2$, 0 to 30% EtOAc in hexanes) to afford the title compound (200 mg, 98%) as a yellow solid. MS (ESI): mass calcd. for $C_{10}H_{12}BrN_3O_4$, 317.0; m/z found, 262.0 [M+H-tBu]$^+$. $^1$H NMR (500 MHz, CDCl$_3$) δ 9.45 (s, 1H), 8.74 (d, J=2.3 Hz, 1H), 8.62 (d, J=2.3 Hz, 1H), 1.54 (s, 9H).

Step C: tert-Butyl (5-(4-fluorophenyl)-3-nitropyridin-2-yl)carbamate

To a microwave vial was added tert-butyl (5-bromo-3-nitropyridin-2-yl)carbamate (198 mg, 0.62 mmol), 4-fluorophenylboronic acid (124 mg, 0.88 mmol) and Pd(PPh$_3$)$_4$ (41 mg, 0.035 mmol). Then, dioxane (4 mL) followed by 2M Na$_2$CO$_3$ (653 μL, 1.31 mmol) was added and the reaction was heated conventionally at 90° C. for 2 h. Then, the reaction mixture was cooled to room temperature, concentrated and the solids were washed with EtOAc (3×). The combined organic layers were concentrated and purified (FCC, SiO$_2$, 0 to 20% 1.5% IPA in EtOAc in hexanes) to afford the title compound (197 mg, 95%) as a solid. MS (ESI): mass calcd. for $C_{16}H_{16}FN_3O_4$, 333.1; m/z found, 278.1 [M+H-tBu]$^+$. $^1$H NMR (500 MHz, CDCl$_3$) δ 9.57 (s, 1H), 8.94-8.89 (m, 1H), 8.67-8.61 (m, 1H), 7.59-7.52 (m, 2H), 7.25-7.18 (m, 2H), 1.58 (s, 9H).

Step D: tert-Butyl (3-amino-5-(4-fluorophenyl)pyridin-2-yl)carbamate

To a heterogeneous mixture of tert-butyl (5-(4-fluorophenyl)-3-nitropyridin-2-yl)carbamate (191 mg, 0.57 mmol) in EtOH (8 mL) was added 10% Pd/C (154 mg) followed by a H$_2$ balloon. The mixture slowly turned homogeneous and after 1 h the reaction was filtered. The filter cake and Pd/C was washed with EtOH. The filtrate was concentrated to afford the title compound (152 mg, 87%) as an oil, which was used in the next step without further purification.

Step E: tert-Butyl (3-(((1,5-dimethyl-1H-pyrazol-3-yl)methyl)amino)-5-(4-fluorophenyl)pyridin-2-yl)carbamate To a heterogeneous mixture of tert-butyl (3-amino-5-(4-fluorophenyl)pyridin-2-yl)carbamate (152 mg, 0.50 mmol) dissolved in DCE (9 mL) was added HOAc (28 μL, 0.50 mmol) followed by 1,5-dimethyl-1 h-pyrazole-3-carbaldehyde (158 mg, 1.28 mmol). After 10 min NaBH(OAc)$_3$ (321 mg, 1.51 mmol) was added and the mixture stirred at room temperature overnight. The reaction was quenched by the addition of a saturated aqueous solution of NaHCO$_3$ and the layers separated. The aqueous layer was extracted with DCM and the combined organic extracts were dried over Na$_2$SO$_4$, filtered and concentrated under reduced pressure. The crude material was taken on to the next step without further purification. MS (ESI): mass calcd. for $C_{22}H_{26}FN_5O_2$, 411.2; m/z found, 412.2 [M+H]$^+$.

Step F: 1-[(1,5-Dimethylpyrazol-3-yl)methyl]-6-(4-fluorophenyl)-3H-imidazo[4,5-b]pyridin-2-one To a solution of tert-butyl (3-(((1,5-dimethyl-1H-pyrazol-3-yl)methyl)amino)-5-(4-fluorophenyl)pyridin-2-yl)carbamate (206 mg, 0.50 mmol) in DCM (9 mL) was added TFA (2 mL). The mixture was stirred at room temperature for 3 h, concentrated and purified (FCC, SiO$_2$, 0 to 9% 2M NH$_3$ in MeOH in DCM) to afford impure material. This material was then stirred in Et$_2$O overnight and then filtered to afford the title compound (46 mg, 27%) as a foam. MS (ESI): mass calcd. for $C_{18}H_{16}FN_5O$, 337.1; m/z found, 338.2 [M+H]$^+$. $^1$H NMR (500 MHz, DMF-d$_7$) δ 11.64 (s, 1H), 8.22 (d, J=2.1 Hz, 1H), 7.78-7.68 (m, 3H), 7.38-7.27 (m, 2H), 5.99 (s, 1H), 5.03 (s, 2H), 3.69 (s, 3H), 2.20 (s, 3H).

Example 17: 1-[2-(Azetidin-1-yl)ethyl]-6-[3-(trifluoromethyl)phenyl]-3H-imidazo[4,5-b]pyridin-2-one and its Trifluoroacetic Acid Salt

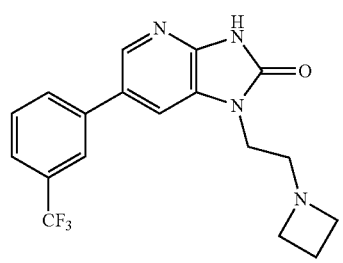 [SMILES: O=c1[nH]c2ncc(-c3cccc(C(F)(F)F)c3)cc2n1CCN1CCC1]

Step A: 1-(2-(Azetidin-1-yl)ethyl)-6-bromo-3-trityl-1,3-dihydro-2H-imidazo[4,5-b]pyridin-2-one To a solution of 2-(6-bromo-2-oxo-3-trityl-2,3-dihydro-1H-imidazo[4,5-b]pyridin-1-yl)acetaldehyde (Intermediate 42, 400 mg, 0.80 mmol) in DCM (1 mL) was added azetidine (0.11 mL, 1.61 mmol) followed by sodium triacetoxyborohydride (336 mg, 1.6 mmol). The reaction was stirred at room temperature overnight and then diluted with a saturated aqueous solution of $NaHCO_3$(25 mL) and stirred for 30 minutes. The organics were then extracted with DCM, combined, dried, and purified (FCC, $SiO_2$, 0-20% MeOH in DCM) to provide the title compound (195 mg, 45%). $^1$H NMR (500 MHz, DMSO-$d_6$) δ 7.84-7.70 (m, 2H), 7.55-7.38 (m, 6H), 7.32-7.19 (m, 6H), 7.19-7.10 (m, 3H), 3.81-3.55 (m, 2H), 3.02-2.77 (m, 4H), 1.88-1.79 (m, 2H).

Step B: 1-(2-(Azetidin-1-yl)ethyl)-6-(3-(trifluoromethyl)phenyl)-3-trityl-1H-imidazo[4,5-b]pyridin-2(3H)-one To a solution of 1-(2-(azetidin-1-yl)ethyl)-6-bromo-3-trityl-1,3-dihydro-2H-imidazo[4,5-b]pyridin-2-one (22.7 mg, 0.042 mmol) and 3-trifluoromethyl phenyl boronic acid (12 mg, 0.063 mmol) in 1,4-dioxane (0.5 mL) was added sodium bicarbonate (8.9 mg, 0.084 mmol), distilled water (0.03 mL, 1.7 mmol), and tetrakis(triphenylphosphine)palladium (2.4 mg, 0.002 mmol). The reaction was heated to 100° C. overnight. The reaction was then cooled to room temperature and diluted with ethyl acetate (10 mL) and water (10 mL). The organic layer was extracted, dried over $Na_2SO_4$, filtered, and concentrated in vacuo. The title compound was used crude in the next step without further purification.

Step C: 1-[2-(Azetidin-1-yl)ethyl]-6-[3-(trifluoromethyl)phenyl]-3H-imidazo[4,5-b]pyridin-2-one and its Trifluoroacetic Acid Salt Crude 1-(2-(azetidin-1-yl)ethyl)-6-(3-(trifluoromethyl)phenyl)-3-trityl-1H-imidazo[4,5-b]pyridin-2(3H)-one was taken up in DCM (2 mL) and TFA (2 mL) and stirred at room temperature for 30 minutes. The reaction was concentrated down, taken up in 2 mL of methanol and loaded onto the acidic HPLC (Method C) to provide the title compound. MS (ESI): mass calcd. for $C_{18}H_{17}F_3N_4O$, 362.1; m/z found, 363.2 [M+H]$^+$. $^1$H NMR (400 MHz, DMSO-$d_6$) δ 11.85 (s, 1H), 9.77-9.64 (s, 1H), 8.43-8.31 (m, 1H), 8.10-8.01 (m, 2H), 8.00-7.93 (d, J=2.0 Hz, 1H), 7.79-7.66 (m, 2H), 4.17-4.04 (d, J=11.4 Hz, 6H), 3.63-3.56 (d, J=5.3 Hz, 2H), 2.46-2.35 (m, 1H), 2.26 (s, 1H).

Example 18: 1-[2-(Azetidin-1-yl)ethyl]-3-methyl-6-[3-(trifluoromethyl)phenyl]imidazo[4,5-b]pyridin-2-one

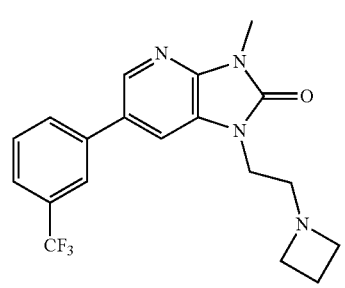 [SMILES: Cn1c(=O)n(CCN2CCC2)c2cc(-c3cccc(C(F)(F)F)c3)cnc21]

To a solution of 1-[2-(azetidin-1-yl)ethyl]-6-[3-(trifluoromethyl)phenyl]-3H-imidazo[4,5-b]pyridin-2-one (Example 17, 49.6 mg, 0.10 mmol) in DMF (2 mL) was added sodium hydride (60% dispersion in oil, 8.3 mg, 0.21 mmol), and the reaction mixture was stirred at room temperature for 10 minutes. Then, iodomethane (0.0078 mL, 0.13 mmol) was added, and the reaction mixture was stirred at room temperature for an additional 3 hours. The crude reaction mixture was quenched with distilled water (1 mL) and concentrated in vacuo. The reaction was taken up in MeOH, filtered, and loaded onto the basic HPLC for purification (Method A) to provide the title compound (11.8 mg, 30%). MS (ESI): mass calcd. for $C_{19}H_{19}F_3N_4O$, 376.2; m/z found, 377.2 [M+H]$^+$. $^1$H NMR (500 MHz, DMSO-$d_6$) δ 8.43-8.29 (d, J=1.9 Hz, 1H), 8.10-8.01 (d, J=2.8 Hz, 2H), 8.01-7.91 (m, 1H), 7.78-7.59 (m, 2H), 3.91-3.79 (t, J=6.1 Hz, 2H), 3.38 (s, 3H), 3.15-3.06 (t, J=7.0 Hz, 4H), 2.71-2.64 (m, 2H), 1.97-1.83 (m, 2H).

Example 19: 1-[(5-Methylisoxazol-3-yl)methyl]-6-[3-(trifluoromethyl)phenyl]-3H-imidazo[4,5-b]pyridin-2-one

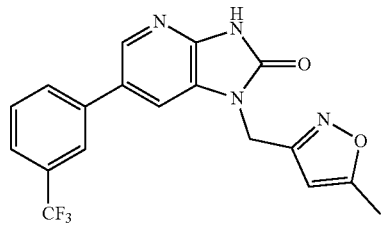 [SMILES: Cc1cc(Cn2c(=O)[nH]c3ncc(-c4cccc(C(F)(F)F)c4)cc32)no1]

To a solution of $N^3$-((5-methylisoxazol-3-yl)methyl)-5-(3-(trifluoromethyl)phenyl)pyridine-2,3-diamine (Intermediate 47, 1.0 g, 3.0 mmol) in DMF (19.5 mL) was added 1,1'-carbonyldiimidazole (1.5 g, 9.0 mmol). The reaction was heated to 85° C. for one hour. The crude mixture was cooled to room temperature and a saturated aqueous solution of $NH_4Cl$ (10 mL) was added. The resulting solid was collected via filtration, triturated with $Et_2O$ and filtered to provide the title compound (761 mg, 68%). MS (ESI): mass calcd. for $C_{18}H_{13}F_3N_4O_2$, 374.1; m/z found, 375.1 [M+H]$^+$. $^1$H NMR (400 MHz, DMSO-$d_6$) δ 11.97-11.79 (s, 1H), 8.42-8.25 (d, J=2.0 Hz, 1H), 8.06-7.96 (m, 2H), 7.93-7.87 (d, J=2.0 Hz, 1H), 7.78-7.64 (m, 2H), 6.25-6.13 (s, 1H), 5.24-4.92 (s, 2H), 2.39-2.26 (s, 3H).

Example 20: N-Cyclopropyl-2-[2-oxo-6-[3-(trifluoromethyl)phenyl]-3H-imidazo[4,5-b]pyridin-1-yl]acetamide and its Trifluoroacetic Acid Salt

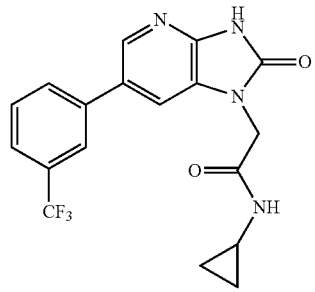 [SMILES: O=C(Cn1c(=O)[nH]c2ncc(-c3cccc(C(F)(F)F)c3)cc21)NC1CC1]

Step A: N-cyclopropyl-2-(2-oxo-6-(3-(trifluoromethyl)phenyl)-3-trityl-2,3-dihydro-1H-imidazo[4,5-b]pyridin-1-yl)acetamide HATU (59 mg, 0.16 mmol) was added to a mixture of 2-(2-oxo-6-(3-(trifluoromethyl)phenyl)-3-trityl-2,3-dihydro-1H-imidazo[4,5-b]pyridin-1-yl)acetic acid (Intermediate 44, 75 mg, 0.13 mmol), cyclopropylamine (0.011 mL, 0.16 mmol) and DIPEA (0.045 mL, 0.26 mmol) in DMF at room temperature. After completion, a saturated aqueous solution of NaHCO$_3$ (10 mL) was added and the mixture was extracted using EtOAc (3×15 mL). The combined organics were dried over MgSO$_4$, filtered and concentrated under vacuum. The crude material was purified (FCC, SiO$_2$, 0-90% EtOAc in hexanes) to afford the title compound (61 mg, 76%). $^1$H NMR (400 MHz, DMSO-d$_6$) δ 8.28 (d, J=4.2 Hz, 1H), 8.19-8.13 (m, 1H), 8.00-7.94 (m, 2H), 7.87 (d, J=2.1 Hz, 1H), 7.72-7.63 (m, 2H), 7.51-7.44 (m, 6H), 7.29-7.13 (m, 9H), 4.44 (s, 2H), 2.71-2.61 (m, 1H), 0.64 (td, J=7.0, 4.8 Hz, 2H), 0.47-0.41 (m, 2H).

Step B: N-cyclopropyl-2-[2-oxo-6-[3-(trifluoromethyl)phenyl]-3H-imidazo[4,5-b]pyridin-1-yl]acetamide and its Trifluoroacetic Acid Salt To a solution of N-cyclopropyl-2-(2-oxo-6-(3-(trifluoromethyl)phenyl)-3-trityl-2,3-dihydro-1H-imidazo[4,5-b]pyridin-1-yl)acetamide (90 mg, 0.15 mmol) in DCM at room temperature was added TFA (0.34 mL, 4.4 mmol). After completion the reaction mixture was concentrated under vacuum. MeOH was added and a precipitate appeared. The solids were filtered off and rinsed with MeOH to afford the title compound (11 mg, 15%). MS (ESI): mass calcd. for C$_{18}$H$_{15}$F$_3$N$_4$O$_2$, 376.1; m/z found, 377.1 [M+H]$^+$. $^1$H NMR (500 MHz, DMSO-d$_6$) δ 11.73 (s, 1H), 8.33 (d, J=2.0 Hz, 1H), 8.29 (d, J=4.2 Hz, 1H), 8.04-7.97 (m, 2H), 7.84 (d, J=1.9 Hz, 1H), 7.76-7.68 (m, 2H), 4.48 (s, 2H), 2.65 (tq, J=7.7, 4.0 Hz, 1H), 0.62 (td, J=7.0, 4.8 Hz, 2H), 0.43 (dt, J=7.1, 4.6 Hz, 2H).

Example 21: 1-[(3-Chlorophenyl)methyl]-6-[3-(trifluoromethyl)phenyl]-3H-imidazo[4,5-b]pyridin-2-one and its Trifluoroacetic Acid Salt

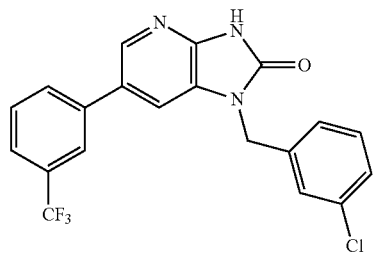 [SMILES: O=c1[nH]c2ncc(-c3cccc(C(F)(F)F)c3)cc2n1Cc1cccc(Cl)c1]

Step A: 1-(3-Chlorobenzyl)-6-(3-(trifluoromethyl)phenyl)-3-trityl-1,3-dihydro-2H-imidazo[4,5-b]pyridin-2-one Under a nitrogen atmosphere was added 6-(3-(trifluoromethyl)phenyl)-3-trityl-1,3-dihydro-2H-imidazo[4,5-b]pyridin-2-one (Intermediate 43, 100 mg, 0.19 mmol) to a suspension of NaH (60% dispersion in mineral oil, 10.7 mg, 0.3 mmol) in THF (2.1 mL). After 10 minutes 1-(bromomethyl)-3-chlorobenzene (0.035 mL, 0.3 mmol) was added to the reaction mixture, and the reaction mixture was heated to 75° C. After 6 h, complete conversion was observed. The reaction mixture was cooled down to room temperature and quenched with water (10 mL). The mixture was extracted using EtOAc (3×20 mL). The combined organics were dried over MgSO$_4$, filtered and concentrated under vacuum to give the title compound. The crude material was moved forward to the next step as is.

Step B: 1-[(3-chlorophenyl)methyl]-6-[3-(trifluoromethyl)phenyl]-3H-imidazo[4,5-b]pyridin-2-one and its Trifluoroacetic Acid Salt To a solution of 1-(3-chlorobenzyl)-6-(3-(trifluoromethyl)phenyl)-3-trityl-1,3-dihydro-2H-imidazo[4,5-b]pyridin-2-one (153 mg, 0.24 mmol) in DCM at room temperature was added TFA (0.55 mL, 7.1 mmol). After completion, the reaction mixture was concentrated under vacuum. The crude material was purified using reversed phase HPLC (Method C) to afford the title compound (29 mg, 23%). MS (ESI): mass calcd. for C$_{20}$H$_{13}$ClF$_3$N$_3$O, 403.1; m/z found, 404.1 [M+H]$^+$. $^1$H NMR (500 MHz, DMSO-d$_6$) δ 11.87 (s, 1H), 8.34 (d, J=2.0 Hz, 1H), 8.01-7.96 (m, 2H), 7.94 (d, J=2.0 Hz, 1H), 7.75-7.68 (m, 2H), 7.49-7.45 (m, 1H), 7.40-7.29 (m, 3H), 5.13 (s, 2H).

Example 22: 1-[(2-Methoxy-3-pyridyl)methyl]-6-[3-(trifluoromethyl)phenyl]-3H-imidazo[4,5-b]pyridin-2-one and its Trifluoroacetic Acid Salt

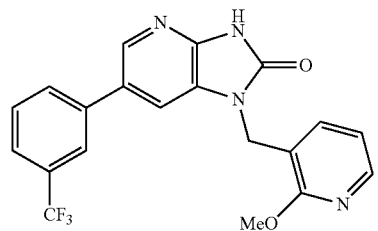 [SMILES: COc1ncccc1Cn1c(=O)[nH]c2ncc(-c3cccc(C(F)(F)F)c3)cc21]

The title compound was prepared in a manner analogous to Example 21 using 3-(chloromethyl)-2-methoxypyridine. MS (ESI): mass calcd. for C$_{20}$H$_{15}$F$_3$N$_4$O$_2$, 400.1; m/z found, [M+H]$^+$. $^1$H NMR (500 MHz, DMSO) δ 11.84 (s, 1H), 8.34 (d, J=2.0 Hz, 1H), 8.09 (dd, J=5.0, 1.8 Hz, 1H), 8.01-7.96 (m, 2H), 7.85 (d, J=2.0 Hz, 1H), 7.74-7.66 (m, 2H), 7.33 (dd, J=7.3, 1.8 Hz, 1H), 6.93 (dd, J=7.3, 5.0 Hz, 1H), 5.04 (s, 2H), 3.93 (s, 3H).

Example 23: 1-(Pyrimidin-4-ylmethyl)-6-[3-(trifluoromethyl)phenyl]-3H-imidazo[4,5-b]pyridin-2-one and its Trifluoroacetic Acid Salt

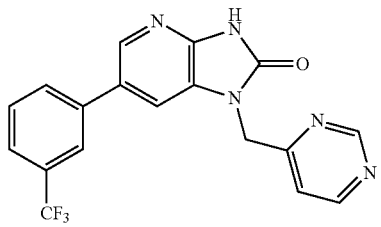

Step A: Pyrimidin-4-ylmethyl methanesulfonate

To a mixture of pyrimidin-4-ylmethanol (100 mg, 0.9 mmol) and triethylamine (0.2 mL, 1.4 mmol) in DCM (3.5 mL) at 0° C. was added methanesulfonyl chloride (0.9 mL, 1.2 mmol). After 30 minutes, water (10 mL) and a saturated aqueous solution of $NaHCO_3$ (10 mL) were added to the reaction mixture, respectively. The mixture was extracted with DCM (2×30 mL). The combined organics were dried ($MgSO_4$), filtered and concentrated under vacuum to give the title compound (170 mg, 99%). $^1$H NMR (400 MHz, DMSO-$d_6$) δ 9.20 (d, J=1.4 Hz, 1H), 8.89 (d, J=5.1 Hz, 1H), 7.63-7.60 (m, 1H), 5.35 (s, 2H), 3.34 (s, 3H).

Step B: 1-(Pyrimidin-4-ylmethyl)-6-[3-(trifluoromethyl)phenyl]-3H-imidazo[4,5-b]pyridin-2-one and its Trifluoroacetic Acid Salt The title compound was prepared in a manner analogous to Example 21 using pyrimidin-4-ylmethyl methanesulfonate and 6-(3-(trifluoromethyl)phenyl)-3-trityl-1,3-dihydro-2H-imidazo[4,5-b]pyridin-2-one (Intermediate 43) in Step A. MS (ESI): mass calcd. for $C_{18}H_{12}F_3N_5O$, 371.1; m/z found, 372.1 [M+H]$^+$. $^1$H NMR (400 MHz, DMSO-$d_6$) δ 11.87 (s, 1H), 9.09 (d, J=1.4 Hz, 1H), 8.75 (d, J=5.2 Hz, 1H), 8.36 (d, J=2.0 Hz, 1H), 8.01-7.96 (m, 2H), 7.91 (d, J=2.0 Hz, 1H), 7.73-7.65 (m, 2H), 7.44 (dd, J=5.2, 1.4 Hz, 1H), 5.27 (s, 2H).

Example 24: (R/S)-1-(Tetrahydrofuran-2-ylmethyl)-6-[3-(trifluoromethyl)phenyl]-3H-imidazo[4,5-b]pyridin-2-one and its Trifluoroacetic Acid Salt

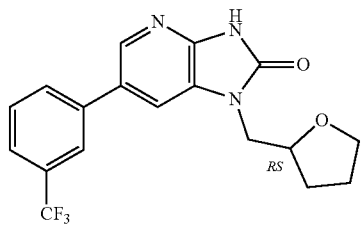 [SMILES: O=c1[nH]c2ncc(-c3cccc(C(F)(F)F)c3)cc2n1CC1CCCO1]

Step A: 6-Bromo-1-((tetrahydrofuran-2-yl)methyl)-3-trityl-1,3-dihydro-2H-imidazo[4,5-b]pyridin-2-one To a solution of 6-bromo-3-trityl-1,3-dihydro-2H-imidazo[4,5-b]pyridin-2-one (Intermediate 36, 500 mg, 1.10 mmol) and NaH (60% dispersion in mineral oil, 61 mg, 1.5 mmol) in DMF (11 mL), was added tetrahydrofurfuryl bromide (0.18 mL, 1.5 mmol). After 16 h, low conversion to the desired product was observed and additional NaH (60% dispersion in mineral oil, 131 mg, 3.29 mmol) and tetrahydrofurfuryl bromide (0.37 mL, 3.29 mmol) was added and the reaction mixture was heated to 80° C. After completion, the reaction mixture was quenched with a saturated aqueous solution of $NH_4Cl$ (50 mL). The precipitates were filtered off, washed with water and dried under vacuum to afford the title product, contaminated with some impurities. The crude material was moved forward to the next step as is.

Step B: 1-((tetrahydrofuran-2-yl)methyl)-6-(3-(trifluoromethyl)phenyl)-3-trityl-1,3-dihydro-2H-imidazo[4,5-b]pyridin-2-one A mixture of 6-bromo-1-((tetrahydrofuran-2-yl)methyl)-3-trityl-1,3-dihydro-2H-imidazo[4,5-b]pyridin-2-one (150 mg, 0.3 mmol), 3-(trifluoromethyl)phenylboronic acid (105 mg, 0.6 mmol), 1,1'-bis(diphenylphosphino) ferrocene palladium(II)dichloride dichloromethane complex (Pd(dppf)Cl$_2$—CH$_2$Cl$_2$) (16 mg, 0.02 mmol), Cs$_2$CO$_3$ (181 mg, 0.6 mmol), dioxane (2.6 mL) and H$_2$O (0.5 mL) was heated to 90° C. using an oil bath. After 16 h, the reaction mixture was concentrated under vacuum. The crude material was purified (FCC, SiO$_2$, 0-100% EtOAc in hexanes), to give the title compound (51 mg, 30%).

Step C: (R/S)-1-(tetrahydrofuran-2-ylmethyl)-6-[3-(trifluoromethyl)phenyl]-3H-imidazo[4,5-b]pyridin-2-one and its Trifluoroacetic Acid Salt To a solution of 1-((tetrahydrofuran-2-yl)methyl)-6-(3-(trifluoromethyl)phenyl)-3-trityl-1,3-dihydro-2H-imidazo[4,5-b]pyridin-2-one (51 mg, 0.08 mmol) in DCM at room temperature was added TFA (0.59 mL, 9.2 mmol). After completion, the reaction mixture was concentrated under vacuum. The crude material was purified using reversed phase HPLC (Method C) to give the title compound (32 mg, 23%). MS (ESI): mass calcd. for $C_{18}H_{16}F_3N_3O_2$, 363.1; m/z found, 364.1 M+H]$^+$. $^1$H NMR (400 MHz, DMSO-$d_6$) δ 11.71 (s, 1H), 8.30 (d, J=2.0 Hz, 1H), 8.04-7.98 (m, 2H), 7.89 (d, J=2.0 Hz, 1H), 7.76-7.69 (m, 2H), 4.27-4.18 (m, 1H), 3.99-3.87 (m, 2H), 3.77-3.69 (m, 1H), 3.65-3.56 (m, 1H), 2.00-1.73 (m, 3H), 1.70-1.60 (m, 1H).

Example 25: 1-[2-(Azetidin-1-yl)-2-oxo-ethyl]-6-[3-(trifluoromethyl)phenyl]-3H-imidazo[4,5-b]pyridin-2-one and its Trifluoroacetic Acid Salt

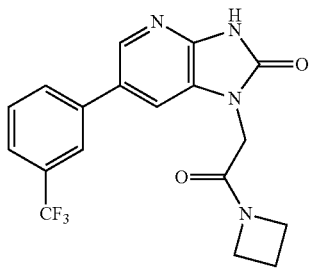 [SMILES: O=C(Cn1c(=O)[nH]c2ncc(-c3cccc(C(F)(F)F)c3)cc21)N1CCC1]

Step A: 1-(2-(Azetidin-1-yl)-2-oxoethyl)-6-(3-(trifluoromethyl)phenyl)-3-trityl-1,3-dihydro-2H-imidazo[4,5-b]pyridin-2-one A mixture of 1-(2-(azetidin-1-yl)-2-oxoethyl)-6-bromo-3-trityl-1,3-dihydro-2H-imidazo[4,5-b]pyridin-2-one (Intermediate 38, 260 mg, 0.47 mmol), 1,1'-bis(diphenylphosphino) ferrocene palladium(II)dichloride dichloromethane complex (24 mg, 0.033 mmol), Cs$_2$CO$_3$ (306 mg, 0.94 mmol), (3-(trifluoromethyl)phenyl)boronic acid (178 mg, 0.94 mmol), dioxane (5 mL) and H$_2$O (0.9 mL) was heated to 90° C. using an oil bath. After 16 h, the reaction mixture was cooled to room temperature and volatiles were removed. The crude material was purified (FCC SiO$_2$, 0-100% EtOAc in hexanes), to give the title compound (90 mg, 31%).

Step B: 1-[2-(Azetidin-1-yl)-2-oxo-ethyl]-6-[3-(trifluoromethyl)phenyl]-3H-imidazo[4,5-b]pyridin-2-one and its Trifluoroacetic Acid Salt To a solution of 1-(2-(azetidin-1-yl)-2-oxoethyl)-6-(3-(trifluoromethyl)phenyl)-3-trityl-1,3-dihydro-2H-imidazo

[4,5-b]pyridin-2-one (80 mg, 0.13 mmol) in DCM at room temperature was added TFA (0.30 mL, 3.9 mmol). After completion the reaction mixture was concentrated under vacuum. The was crude material was purified (Method C) to afford the title compound (13 mg, 21%). MS (ESI): mass calcd. for $C_{18}H_{15}F_3N_4O_2$, 376.1; m/z found, 377.1[M+H]$^+$. $^1$H NMR (500 MHz, DMSO-d$_6$) δ 11.76 (s, 1H), 8.32 (d, J=2.0 Hz, 1H), 8.03-7.97 (m, 2H), 7.82 (d, J=2.0 Hz, 1H), 7.76-7.70 (m, 2H), 4.86 (s, 2H), 4.28 (t, J=7.6 Hz, 2H), 3.91 (t, J=7.7 Hz, 2H), 2.33-2.23 (m, 2H).

Example 26: N,N-Dimethyl-2-[2-oxo-6-[5-(trifluoromethyl)-2-thienyl]-3H-imidazo[4,5-b]pyridin-1-yl]acetamide

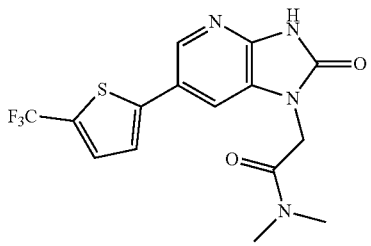 [SMILES: CN(C)C(=O)Cn1c(=O)[nH]c2ncc(-c3ccc(C(F)(F)F)s3)cc21]

Method A

Step A: Ethyl 2-(2-oxo-6-(5-(trifluoromethyl)thiophen-2-yl)-3-trityl-2,3-dihydro-1H-imidazo[4,5-b]pyridin-1-yl)acetate A mixture of ethyl 2-(6-bromo-2-oxo-3-trityl-2,3-dihydro-1H-imidazo[4,5-b]pyridin-1-yl)acetate (Intermediate 37, 230 mg, 0.4 mmol), 4,4,5,5-tetramethyl-2-(5-(trifluoromethyl)thiophen-2-yl)-1,3,2-dioxaborolane (153 mg, 0.6 mmol), Cs$_2$CO$_3$ (240 mg, 0.7 mmol) and PdCl$_2$(dppf).DCM (21 mg, 0.06 mmol) in dioxane (3.5 mL) was combined in a microwave vial and heated to 75° C. The reaction mixture was stirred at 75° C. for 16 hours then cooled down to room temperature and quenched with a saturated aqueous solution of NaHCO$_3$. The resulting reaction mixture was extracted with EtOAc (3×60 mL) and the combined organic layers were dried using MgSO$_4$, filtered and concentrated under vacuum. The crude material was purified (FCC, SiO$_2$, 0-40% EtOAc in hexanes) to afford the title compound (215 mg, 0.4 mmol, 82%). $^1$H NMR (500 MHz, CDCl$_3$) δ 7.97-7.95 (d, J=2.1 Hz, 1H), 7.45-7.40 (m, 6H), 7.30-7.27 (m, 1H), 7.19-7.14 (m, 6H), 7.14-7.09 (m, 3H), 7.04-7.03 (d, J=2.0 Hz, 1H), 7.03-7.00 (m, 1H), 4.49-4.45 (s, 2H), 4.17-4.10 (m, 2H), 1.19-1.15 (m, 3H).

Step B: 2-(2-Oxo-6-(5-(trifluoromethyl)thiophen-2-yl)-3-trityl-2,3-dihydro-1H-imidazo[4,5-b]pyridin-1-yl)acetic acid To a solution ethyl 2-(2-oxo-6-(5-(trifluoromethyl)thiophen-2-yl)-3-trityl-2,3-dihydro-1H-imidazo[4,5-b]pyridin-1-yl)acetate (210 mg, 0.34 mmol) in THF (4.5 mL) at room temperature was added LiOH (2 M, 0.24 mL, 0.47 mmol). After stirring over the weekend, 2 M HCl was added (~0.1 mL). The mixture was rotovaped, then placed on high vac overnight. The solids were used as is in the next step (450 mg, contains water).

Step C: N,N-Dimethyl-2-(2-oxo-6-(5-(trifluoromethyl)thiophen-2-yl)-3-trityl-2,3-dihydro-1H-imidazo[4,5-b]pyridin-1-yl)acetamide T3P (w/w 50% in DCM)) (0.365 mL, 0.61 mmol) was added to a mixture of 2-(2-oxo-6-(5-(trifluoromethyl)thiophen-2-yl)-3-trityl-2,3-dihydro-1H-imidazo[4,5-b]pyridin-1-yl)acetic acid (246 mg, 0.20 mmol), dimethylamine hydrochloride (20 mg, 0.24 mmol) and DIPEA (0.11 mL, 0.61 mmol) in DCM (1 mL) at room temperature for 16 hours. After completion, the reaction mixture was concentrated under reduced pressure and the crude material was purified (FCC, SiO$_2$, 0-100% EtOAc in hexanes). To the EA/hexanes solution containing the product was added 1 mL TFA. The resulting reaction mixture was allowed to stir at room temperature for 16 hours. The excess TFA was evaporated under reduced pressure and the crude material was purified (FCC, SiO$_2$, 0-15% 2M NH$_3$/MeOH in DCM) to afford the title compound (25 mg, 33%). MS (ESI): mass calcd. for $C_{15}H_{13}F_3N_4O_2S$, 370.1; m/z found, 371.0 [M+H]$^+$. $^1$H NMR (500 MHz, DMSO-d$_6$) δ 11.8-11.7 (s, 1H), 8.34-8.32 (d, J=2.0 Hz, 1H), 7.79-7.76 (s, 1H), 7.76-7.74 (d, J=3.7 Hz, 1H), 7.57-7.55 (s, 1H), 4.80-4.75 (s, 2H), 3.12-3.07 (s, 3H), 2.87-2.83 (s, 3H).

Method B

The title compound was prepared in a manner analogous to Example 25, Steps A-B, using 2-(6-bromo-2-oxo-3-trityl-2,3-dihydro-1H-imidazo[4,5-b]pyridin-1-yl)-N,N-dimethylacetamide (Intermediate 39) and (5-(trifluoromethyl)thiophen-2-yl)boronic acid in step A.

Example 27: 1-[2-(Azetidin-1-yl)-2-oxo-ethyl]-3-methyl-6-[5-(trifluoromethyl)-2-thienyl]imidazo[4,5-b]pyridin-2-one

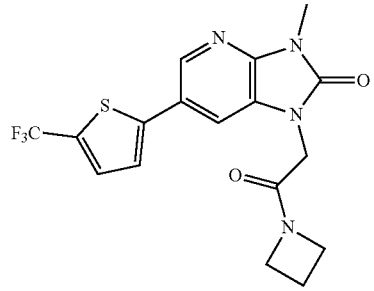 [SMILES: Cn1c(=O)n(CC(=O)N2CCC2)c2cc(-c3ccc(C(F)(F)F)s3)cnc21]

Method A

The title compound was prepared in a manner analagous to Example 15, Step B, using 1-[2-(azetidin-1-yl)-2-oxo-ethyl]-6-[5-(trifluoromethyl)-2-thienyl]-3H-imidazo[4,5-b]pyridin-2-one (Example 323).

Method B

Step A: Ethyl 2-(3-methyl-2-oxo-6-(5-(trifluoromethyl)thiophen-2-yl)-2,3-dihydroimidazo[4,5-b]pyridin-1-yl)acetate Into a 10 L four-necked flask was charged with ethyl 2-(6-bromo-3-methyl-2-oxo-2,3-dihydro-1H-imidazo[4,5- b]pyridin-1-yl)acetate (Intermediate 12, 410.0 g, 1.31 mol), K$_2$CO$_3$ (360.8 g, 2.62 mol), PdCl$_2$(dppf).CH$_2$Cl$_2$ (32.0 g, 0.04 mol), a solution of 4,4,5,5-tetramethyl-2-(5-(trifluoromethyl)thiophen-2-yl)-1,3,2-dioxaborolane in toluene (5100 g, 10% w/w, assay by Q-NMR, 1.83 mol), toluene (291 mL) and H$_2$O (559 mL) successively under N2 atmosphere. The resulting mixture was stirred at 80 to 85° C. for 2.5 h and then cooled to 60 to 65° C. followed by filtration through a pad of Celite®. The cake was washed with toluene (500 mL) and the filtrate was concentrated at 40 to 45° C. under vacuum until the total volume was less than 2 V. n-heptane (1500 mL) was added into the residue and the resulting mixture was stirred at 25 to 30° C. for 3 min followed by filtration. The cake was washed with n-heptane (500 mL) and dried in vacuum oven at 50° C. for 8 h to give the title compound (530 g). The title compound (530 g) and THF (11 L, 20 V) was charged into a 50 L reactor followed by stirring at 25 to 30° C. for 5 min. Then Darco®-G60 (60 g, 11% w/w) was charged into the THF solution and the resulting mixture was stirred at 25 to 30° C. for 2 h followed by filtration through a pad of Celite®. After washing the cake with THF (500 mL), the combined filtrate and Darco®-G60 (60 g, 11% w/w) was charged into the reactor again. The mixture was stirred at 25 to 30° C. for another 2 h followed by filtration through a pad of Celite®. The cake was washed with THF (500 mL) then the combined filtrate and SiliaMetS (50 g, 10% w/w) was charged into the reactor. After stirring at 25 to 30° C. overnight, the mixture was filtered through a pad of Celite® and the cake was washed with THF (500 mL). The filtrate was concentrated at 40 to 45° C. under vacuum until 3~4 volume of THF was left. n-Heptane (3500 mL) was added into the residue and the resulting mixture was stirred at 25 to 30° C. for 5 min followed by filtration. The cake was washed with n-heptane (500 mL) and dried at 50° C. vacuum oven to give the title compound (402 g, 80%). $^1$H NMR (300 MHz, CDCl$_3$) δ 8.33 (d, J=1.9 Hz, 1H), 7.42 (dq, J=4.0, 1.3 Hz, 1H), 7.23 (d, J=3.0 Hz, 1H), 7.18 (dq, J=4.0, 1.3 Hz, 1H), 4.68 (s, 2H), 4.27 (q, J=7.1 Hz, 2H), 3.55 (s, 3H), 1.32 (t, J=7.1 Hz, 3H).

Step B: 2-(3-Methyl-2-oxo-6-(5-(trifluoromethyl)thiophen-2-yl)-2,3-dihydroimidazo[4,5-b]pyridin-1-yl)acetic acid The title compound was prepared in a manner analogous to Intermediate 38, Step A, using ethyl 2-(3-methyl-2-oxo-6-(5-(trifluoromethyl)thiophen-2-yl)-2,3-dihydroimidazo[4,5-b]pyridin-1-yl)acetate. $^1$H NMR (400 MHz, DMSO-d$_6$) δ 8.42 (d, J=1.9 Hz, 1H), 8.03 (d, J=2.0 Hz, 1H), 7.76 (dq, J=3.9, 1.3 Hz, 1H), 7.60 (dq, J=3.9, 1.3 Hz, 1H), 4.69 (s, 2H).

Step C: 1-(2-(Azetidin-1-yl)-2-oxoethyl)-3-methyl-6-(5-(trifluoromethyl)thiophen-2-yl)-1H-imidazo[4,5-b]pyridin-2(3H)-one Into a suspension of 2-(3-methyl-2-oxo-6-(5-(trifluoromethyl)thiophen-2-yl)-2,3-dihydroimidazo[4,5-b]pyridin-1-yl)acetic acid (357.4 g, 1.0 mol, 1.0 eq.) and ACN (7.2 L) was added DIEA (530.02 g, 4.1 mol, 4.1 eq.). Then T3P (w/w 50% in EA, 1368.52 g, 2.15 mol, 2.15 eq.) was added dropwise into the mixture at 10 to 20° C. followed by the addition of azetidine (74.24 g, 1.3 mol, 1.3 eq.) at the same temperature. After stirring at 10 to 15° C. for 2 h, the mixture was poured into water (14.4 L) and stirred for 10 min followed by filtration. The cake was washed with water (500 mL) and dried at 50° C. vacuum oven for 24 h to give 340 g of crude solid as a light purple solid of the title compound. Purification (FCC, SiO$_2$, eluent: EA/n-heptane=50/1 to 100/1 then DCM/MeOH=10/1) afforded the title compound (260 g). $^1$H NMR (400 MHz, CDCl$_3$) δ 8.32 (d, J=1.9 Hz, 1H), 7.46 (d, J=1.9 Hz, 1H), 7.43 (dq, J=3.7, 1.1 Hz, 1H), 7.21 (dq, J=3.7, 1.1 Hz, 1H), 4.51 (s, 2H), 4.36 (t, J=7.8 Hz, 2H), 4.11 (t, J=7.8 Hz, 2H), 3.55 (s, 3H), 2.43-2.35 (m, 2H). $^{19}$F NMR (376 MHz, CDCl$_3$) δ −55.34. $^{13}$C NMR (101 MHz, CDCl$_3$) δ 165.56, 153.75, 145.16, 143.99, 138.72, 129.46, 129.42, 124.42, 123.64, 123.19, 112.78, 77.35, 77.23, 77.03, 76.71, 50.47, 48.62, 40.70, 26.39, 15.73. LC/MS (ES$^+$) m/z 397.1 (M+H).

Example 28: N,N-Dimethyl-2-[3-methyl-2-oxo-6-[5-(trifluoromethyl)-2-thienyl]imidazo[4,5-b]pyridin-1-yl]acetamide

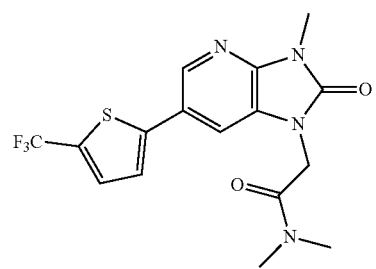 [SMILES: CN(C)C(=O)Cn1c(=O)n(C)c2ncc(-c3ccc(C(F)(F)F)s3)cc21]

The title compound was prepared in a manner analogous to Example 14, Step B, using N,N-dimethyl-2-(2-oxo-6-(5-(trifluoromethyl)thiophen-2-yl)-2,3-dihydro-1H-imidazo[4,5-b]pyridin-1-yl)acetamide (Example 26). MS (ESI): mass calcd. for C$_{16}$H$_{15}$F$_3$N$_4$O$_2$S, 384.1; m/z found, 385.2 [M+H]$^+$. $^1$H NMR (400 MHz, CDCl$_3$) δ 8.31-8.29 (d, J=1.9 Hz, 1H), 7.42-7.39 (m, 1H), 7.34-7.32 (d, J=1.9 Hz, 1H), 7.19-7.16 (m, 1H), 4.75-4.70 (s, 2H), 3.56-3.50 (s, 3H), 3.20-3.17 (s, 3H), 3.02-2.97 (s, 3H).

Example 29: 1-[2-(Azetidin-1-yl)-2-oxo-ethyl]-6-[2-methyl-5-(trifluoromethyl)phenyl]-3H-imidazo[4,5-b]pyridin-2-one

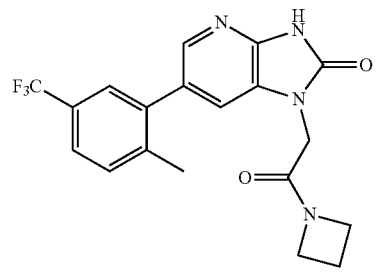 [SMILES: Cc1ccc(C(F)(F)F)cc1-c1cnc2[nH]c(=O)n(CC(=O)N3CCC3)c2c1]

Step A: 2-(6-(2-Methyl-5-(trifluoromethyl)phenyl)-2-oxo-3-trityl-2,3-dihydro-1H-imidazo[4,5-b]pyridin-1-yl)acetic acid A solution of 2-(6-bromo-2-oxo-3-trityl-2,3-dihydro-1H-imidazo[4,5-b]pyridin-1-yl)acetic acid (Intermediate 38, product from Step A, 200 mg, 0.39 mmol), 1,1'-bis(diphenylphosphino) ferrocene palladium(II)dichloride dichloromethane complex (22 mg, 0.027 mmol), Cs$_2$CO$_3$ (253 mg, 0.78 mmol), (2-methyl-5-(trifluoromethyl)phenyl)boronic acid (135 mg, 0.66 mmol), dioxane (3.6 mL) and H$_2$O (0.8 mL) was heated to 90° C. using an oil bath. After 16 h, the reaction mixture was cooled to room temperature and quenched with a saturated aqueous solution of NH$_4$Cl (15 mL). The mixture was extracted with EtOAc (3×20 mL). The combined organics were dried over MgSO$_4$, filtered and concentrated under vacuum to afford the title compound, contaminated with some impurities. The crude material was moved forward to the next step as is.

Step B: 1-(2-(Azetidin-1-yl)-2-oxoethyl)-6-(2-methyl-5-(trifluoromethyl)phenyl)-3-trityl-1,3-dihydro-2H-imidazo[4,5-b]pyridin-2-one HATU (177 mg, 0.5 mmol) was added to a mixture of 2-(6-(2-methyl-5-(trifluoromethyl)phenyl)-2-oxo-3-trityl-2,3-dihydro-1H-imidazo[4,5-b]pyridin-1-yl)acetic acid (230 mg, 0.4 mmol), azetidine (0.031 mL, 0.47 mmol) and DIPEA (0.13 mL, 0.78 mmol) in DMF (3 mL) at room temperature. After completion, a saturated aqueous solution of NaHCO$_3$(10 mL) was added, and the mixture was extracted using EtOAc (3×15 mL). The combined organics were dried over MgSO$_4$, filtered and concentrated under vacuum to afford the title compound. The crude material was moved forward to the next step as is.

Step C: 1-[2-(azetidin-1-yl)-2-oxo-ethyl]-6-[2-methyl-5-(trifluoromethyl)phenyl]-3H-imidazo[4,5-b]pyridin-2-one TFA (0.89 mL, 12 mmol) was added to a mixture of 1-(2-(azetidin-1-yl)-2-oxoethyl)-6-(2-methyl-5-(trifluoromethyl)phenyl)-3-trityl-1,3-dihydro-2H-imidazo[4,5-b]pyridin-2-one (245 mg, 0.39 mmol) in DCM at room temperature. After 1 h, complete conversion was observed and the mixture was purified using reversed phase HPLC (Method C) to afford the title compound contaminated with impurities. The material was triturated between EtOAc (10 mL) and a saturated aqueous solution of NaHCO$_3$(10 mL). The organic layer was collected and the aqueous layer was washed with EtOAc (3×15 mL). The combined organics were dried over MgSO$_4$, filtered and concentrated under vacuum. The material was further purified (FCC, SiO$_2$, 0-90% EtOAc in hexanes) to afford the title compound (17 mg, 11% over 3 steps). MS (ESI): mass calcd. for C$_{19}$H$_{17}$F$_3$N$_4$O$_2$, 390.1; m/z found, 391.1 [M+H]$^+$. $^1$H NMR (400 MHz, DMSO-d$_6$) δ 11.73 (br s, 1H), 7.92 (d, J=1.9 Hz, 1H), 7.68-7.64 (m, 1H), 7.60-7.55 (m, 1H), 7.54-7.50 (m, 1H), 7.46 (d, J=1.9 Hz, 1H), 4.51 (s, 2H), 4.24 (t, J=7.6 Hz, 2H), 3.88 (t, J=7.7 Hz, 2H), 2.33 (s, 3H), 2.34-2.20 (m, 2H).

Example 30: 6-(2,4-Difluoro-3-methyl-phenyl)-1-(2-oxobutyl)-3H-imidazo[4,5-b]pyridin-2-one

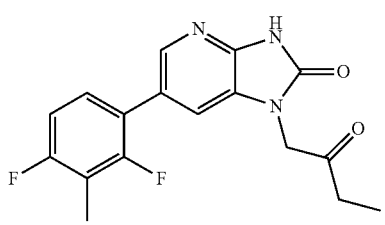 [SMILES: CCC(=O)Cn1c(=O)[nH]c2ncc(-c3ccc(F)c(C)c3F)cc21]

Step A: 6-Bromo-3-(4-methoxybenzyl)-1-(2-oxobutyl)-1,3-dihydro-2H-imidazo[4,5-b]pyridin-2-one Under a nitrogen atmosphere was added 6-bromo-3-(4-methoxybenzyl)-1,3-dihydro-2H-imidazo[4,5-b]pyridin-2-one (Intermediate 10, 2 g, 6.0 mmol) to a suspension of NaH (527 mg, 13 mmol) in DMF (30 mL). After 10 minutes, 1-bromo-2-butanone (1.3 mL, 13.2 mmol) was added to the reaction mixture, and the reaction was heated to 65° C. After 3 h, the reaction mixture was cooled to room temperature and quenched with water (150 mL) and a solid precipitate appeared. The precipitates were collected by filtration, washed with water and dried under vacuum to give the title compound (1.7 g, 68%). MS (ESI): mass calcd. for C$_{18}$H$_{18}$BrN$_3$O$_3$, 403.1; m/z found, 404.0 [M+H]$^+$. $^1$H NMR (500 MHz, DMSO-d$_6$) δ 8.10 (d, J=2.0 Hz, 1H), 7.80 (d, J=2.0 Hz, 1H), 7.28-7.24 (m, 2H), 6.91-6.84 (m, 2H), 4.98 (s, 2H), 4.88 (s, 2H), 3.71 (s, 3H), 2.61 (q, J=7.3 Hz, 2H), 0.98 (t, J=7.3 Hz, 3H).

Step B: 6-(2,4-difluoro-3-methylphenyl)-3-(4-methoxybenzyl)-1-(2-oxobutyl)-1,3-dihydro-2H-imidazo[4,5-b]pyridin-2-one A mixture of 6-bromo-3-(4-methoxybenzyl)-1-(2-oxobutyl)-1,3-dihydro-2H-imidazo[4,5-b]pyridin-2-one (200 mg, 0.5 mmol), (2,4-difluoro-3-methylphenyl)boronic acid (128 mg, 0.7 mmol), 1,1'-bis(diphenylphosphino)ferrocene palladium(II)dichloride dichloromethane complex (25 mg, 0.03 mmol), Cs$_2$CO$_3$ (322 mg, 1.0 mmol), dioxane (4.6 mL) and H$_2$O (0.4 mL) was heated to 110° C. using an oil bath. After 16 h, the reaction mixture was cooled to room temperature and volatiles were removed. The crude material was purified (FCC, SiO$_2$, 0-100% EtOAc in hexanes) to give the title compound (148 mg, 66%). MS (ESI): mass calcd. for C$_{25}$H$_{23}$F$_2$N$_3$O$_3$, 451.2; m/z found, 452.1 [M+H]$^+$. $^1$H NMR (500 MHz, DMSO-d$_6$) δ 8.11 (t, J=1.6 Hz, 1H), 7.65 (t, J=1.6 Hz, 1H), 7.42-7.35 (m, 1H), 7.34-7.28 (m, 2H), 7.21-7.14 (m, 1H), 6.92-6.87 (m, 2H), 5.04 (s, 2H), 4.92 (s, 2H), 3.71 (s, 3H), 2.61 (q, J=7.4 Hz, 2H), 2.22 (t, J=1.9 Hz, 3H), 0.98 (t, J=7.3 Hz, 3H).

Step C: 6-(2,4-difluoro-3-methyl-phenyl)-1-(2-oxobutyl)-3H-imidazo[4,5-b]pyridin-2-one A mixture of 6-(2,4-difluoro-3-methylphenyl)-3-(4-methoxybenzyl)-1-(2-oxobutyl)-1,3-dihydro-2H-imidazo[4,5-b]pyridin-2-one (140 mg, 0.31 mmol) and hydrobromic acid (48% in H$_2$O, 6 mL) was heated to 115° C. After completion, the reaction was cooled to 0° C. and sodium hydroxide pellets were added until basic pH was reached. The mixture was extracted with EtOAc (3×). The combined organics were dried over MgSO$_4$, filtered and concentrated under vacuum. The crude material was triturated in MeOH and the solids were filtered off and rinsed with MeOH to afford the title compound (16 mg, 16%). MS (ESI): mass calcd. for C$_{17}$H$_{15}$F$_2$N$_3$O$_2$, 331.1; m/z found, 332.1 [M+H]$^+$. $^1$H NMR (500 MHz, DMSO-d$_6$) δ 11.76 (s, 1H), 8.04 (t, J=1.6 Hz, 1H), 7.55 (t, J=1.6 Hz, 1H), 7.42-7.35 (m, 1H), 7.21-7.14 (m, 1H), 4.82 (s, 2H), 2.59 (q, J=7.2 Hz, 2H), 2.22 (t, J=1.8 Hz, 3H), 0.97 (t, J=7.3 Hz, 3H).

Example 31: (R/S)-1-(2-Cyclopropyl-2-hydroxy-ethyl)-6-[3-(trifluoromethyl)phenyl]-3H-imidazo[4,5-b]pyridin-2-one and its Trifluoroacetic Acid Salt

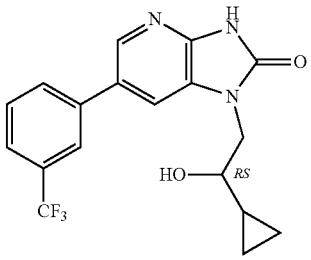

Step A: 1-(2-Cyclopropyl-2-oxoethyl)-6-(3-(trifluoromethyl)phenyl)-3-trityl-1,3-dihydro-2H-imidazo[4,5-b]pyridin-2-one Under a nitrogen atmosphere was added 6-(3-(trifluoromethyl)phenyl)-3-trityl-1,3-dihydro-2H-imidazo[4,5-b]pyridin-2-one (Intermediate 43, 200 mg, 0.38 mmol) to a suspension of NaH (60% dispersion in mineral oil, 30.7 mg, 0.8 mmol) in DMF (4 mL). After 10 minutes 2-bromo-1-cyclopropylethanone (93.8 mg, 0.6 mmol) was added to the reaction mixture, and the reaction mixture was heated to 75° C. After completion, the reaction mixture was cooled down to room temperature and quenched with water (20 mL). The mixture was extracted using EtOAc (3×20 mL). The precipitates were collected by filtration, washed with water and dried under vacuum to give the title compound which was used crude without further purification.

Step B: 1-(2-Cyclopropyl-2-hydroxyethyl)-6-(3-(trifluoromethyl)phenyl)-3-trityl-1,3-dihydro-2H-imidazo[4,5-b]pyridin-2-one Under a nitrogen atmosphere was added sodium borohydride (18 mg, 0.5 mmol) to a mixture of 1-(2-cyclopropyl-2-oxoethyl)-6-(3-(trifluoromethyl)phenyl)-3-trityl-1,3-dihydro-2H-imidazo[4,5-b]pyridin-2-one (140 mg, 0.2 mmol) in MeOH at 0° C., and then the reaction mixture was allowed to warm to room temperature. After completion, the reaction mixture was concentrated under vacuum. The crude material was partitioned between EtOAc (20 mL) and water (20 mL). The organic layer was isolated and the aqueous layer was washed with EtOAc (2×30 mL). The combined organics were dried over MgSO$_4$, filtered and concentrated under vacuum to afford the title compound, which was used in the next step without further purification.

Step C: (R/S)-1-(2-Cyclopropyl-2-hydroxy-ethyl)-6-[3-(trifluoromethyl)phenyl]-3H-imidazo[4,5-b]pyridin-2-one and its Trifluoroacetic Acid Salt To a solution of 1-(2-cyclopropyl-2-hydroxyethyl)-6-(3-(trifluoromethyl)phenyl)-3-trityl-1,3-dihydro-2H-imidazo[4,5-b]pyridin-2-one (140 mg, 0.2 mmol) in DCM at room temperature was added TFA (0.26 mL, 3.5 mmol). After completion the reaction mixture was concentrated under vacuum and the crude material was purified using reversed phase HPLC (Method C) to afford the title compound (30 mg, 27%). MS (ESI): mass calcd. for C$_{18}$H$_{16}$F$_3$N$_3$O$_2$, 363.1; m/z found, 364.1 [M+H]$^+$. $^1$H NMR (500 MHz, DMSO-d$_6$) δ 11.65 (s, 1H), 8.28 (d, J=2.0 Hz, 1H), 8.03-7.97 (m, 2H), 7.86 (d, J=2.0 Hz, 1H), 7.75-7.69 (m, 2H), 3.31-3.24 (m, 1H), 0.94-0.84 (m, 1H), 0.41-0.23 (m, 3H), 0.15-0.07 (m, 1H).

Example 32: 1-[(2-Oxo-1H-pyridin-3-yl)methyl]-6-[3-(trifluoromethyl)phenyl]-3H-imidazo[4,5-b]pyridin-2-one and its Trifluoroacetic Acid Salt

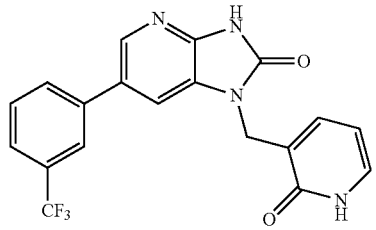 [SMILES: O=c1[nH]cccc1Cn1c(=O)[nH]c2ncc(-c3cccc(C(F)(F)F)c3)cc21]

Under a nitrogen atmosphere was added chlorotrimethylsilane (0.06 mL, 0.5 mmol) to a mixture of 1-[(2-methoxy-3-pyridyl)methyl]-6-[3-(trifluoromethyl)phenyl]-3H-imidazo[4,5-b]pyridin-2-one (Example 22, 100 mg, 0.2 mmol) and sodium iodide (73 mg, 0.5 mmol) in MeCN (0.7 mL) at room temperature. After 16 hours, almost complete conversion was observed, and the reaction mixture was concentrated under vacuum to afford the title compound as a free base. The crude material was purified using reversed phase HPLC (Method C) to afford title compound (36 mg, 37%). MS (ESI): mass calcd. for C$_{19}$H$_{13}$F$_3$N$_4$O$_2$, 386.1; m/z found, 387.0 [M+H]$^+$. $^1$H NMR (500 MHz, DMSO-d$_6$) δ 11.82-11.72 (m, 2H), 8.32 (d, J=2.0 Hz, 1H), 8.01-7.96 (m, 2H), 7.93 (d, J=2.0 Hz, 1H), 7.73-7.67 (m, 2H), 7.32 (dd, J=6.5, 2.0 Hz, 1H), 7.15-7.11 (m, 1H), 6.13 (t, J=6.6 Hz, 1H), 4.85 (s, 2H).

Example 33: (R/S)-6-(4-Fluoro-2-methyl-phenyl)-3-methyl-1-(oxetan-2-ylmethyl)imidazo[4,5-b]pyridin-2-one

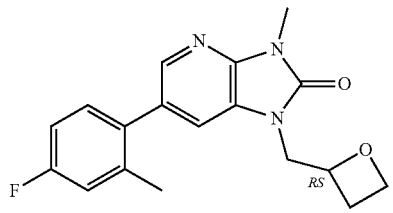 [SMILES: Cc1cc(F)ccc1-c1cnc2c(c1)n(CC1CCO1)c(=O)n2C]

Step A: 6-Bromo-3-methyl-1-(oxetan-2-ylmethyl)-1,3-dihydro-2H-imidazo[4,5-b]pyridin-2-one The title compound was prepared in a manner analogous to Intermediate 22, using 6-bromo-3-methyl-1,3-dihydro-2H-imidazo[4,5-b]pyridin-2-one (Intermediate 11) and 2-(bromomethyl)oxetane.

Step B: (R/S)-6-(4-Fluoro-2-methyl-phenyl)-3-methyl-1-(oxetan-2-ylmethyl)imidazo[4,5-b]pyridin-2-one A mixture of 6-bromo-3-methyl-1-(oxetan-2-ylmethyl)-1,3-dihydro-2H-imidazo[4,5-b]pyridin-2-one (Intermediate 25, 85 mg, 0.3 mmol), (4-fluoro-2-methylphenyl)boronic acid (57 mg, 0.4 mmol), 1,1'-bis(diphenylphosphino)ferrocene palladium(II)dichloride dichloromethane complex (15 mg, 0.02 mmol), Cs$_2$CO$_3$ (186 mg, 0.6 mmol) and dioxane (2.6 mL) was heated to 110° C. After completion, the reaction mixture was filtered and was (Method C). The collected fractions were combined and diluted with a saturated aqueous solution of NaHCO$_3$. The mixture was extracted using DCM (3×). The combined organics were dried over MgSO$_4$, filtered and concentrated under vacuum to give title compound (9.9 mg, 11%). MS (ESI): mass calcd. for C$_{18}$H$_{18}$FN$_3$O$_2$, 327.1; m/z found, 328.2 [M+H]$^+$. $^1$H NMR (400 MHz, DMSO-d$_6$) δ 7.93 (d, J=1.8 Hz, 1H), 7.60 (d, J=1.9 Hz, 1H), 7.29-7.24 (m, 1H), 7.22-7.17 (m, 1H), 7.15-7.09 (m, 1H), 5.05-4.95 (m, 1H), 4.48-4.40 (m, 1H), 4.35-4.27 (m, 1H), 4.23-4.03 (m, 2H), 3.40 (s, 3H), 2.71-2.57 (m, 1H), 2.51-2.37 (m, 1H), 2.24 (s, 3H).

Example 34: 1-[2-(3-Fluoroazetidin-1-yl)-2-oxo-ethyl]-3-methyl-6-[3-(trifluoromethyl)phenyl]imidazo[4,5-b]pyridin-2-one and its Trifluoroacetic Acid Salt

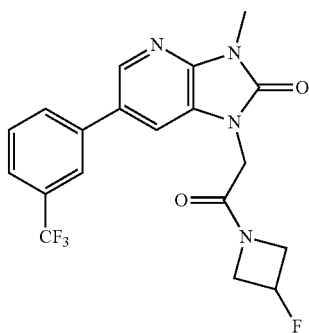 [SMILES: Cn1c(=O)n(CC(=O)N2CC(F)C2)c2cc(-c3cccc(C(F)(F)F)c3)cnc21]

Step A: 6-Bromo-1-(2-(3-fluoroazetidin-1-yl)-2-oxoethyl)-3-methyl-1,3-dihydro-2H-imidazo[4,5-b]pyridin-2-one A mixture of 2-(6-bromo-3-methyl-2-oxo-2,3-dihydro-1H-imidazo[4,5-b]pyridin-1-yl)acetic acid (Intermediate 13, 500 mg, 1.7 mmol), 3-fluoroazetidine hydrochloride (234 mg, 2.1 mmol), DIPEA (0.7 mL, 3.9 mmol), 2,4,6-tripropyl-1,3,5,2,4,6-trioxatriphosphorinane-2,4,6-trioxide (T3P®, 50% solution in DMF, 3.1 mL, 5.2 mmol) in DMF (13 mL) was heated to 50° C. After completion, the reaction mixture was cooled to room temperature and a saturated aqueous solution of NaHCO$_3$ (20 mL) was added. The mixture was extracted using DCM (3×30 mL). The combined organics were dried over MgSO$_4$, filtered and concentrated under vacuum to give the title compound (435 mg, 73%). MS (ESI): mass calcd. for C$_{12}$H$_{12}$BrFN$_4$O$_2$, 342.0; m/z found, 342.8 [M+H]$^+$. $^1$H NMR (500 MHz, DMSO-d$_6$) δ 8.11 (d, J=2.0 Hz, 1H), 7.79 (d, J=2.0 Hz, 1H), 5.55-5.38 (m, 1H), 4.67-4.57 (m, 3H), 4.45-4.33 (m, 1H), 4.30-4.18 (m, 1H), 4.03-3.91 (m, 1H), 3.34 (s, 3H).

Step B: 1-[2-(3-Fluoroazetidin-1-yl)-2-oxo-ethyl]-3-methyl-6-[3-(trifluoromethyl)phenyl]imidazo[4,5-b]pyridin-2-one and its Trifluoroacetic Acid Salt A mixture of 6-bromo-1-(2-(3-fluoroazetidin-1-yl)-2-oxoethyl)-3-methyl-1,3-dihydro-2H-imidazo[4,5-b]pyridin-2-one (40 mg, 0.1 mmol), 3-(trifluoromethyl)phenylboronic acid (43 mg, 0.2 mmol), 1,1'-bis(diphenylphosphino)ferrocene palladium(II)dichloride dichloromethane complex (6 mg, 0.01 mmol), Cs$_2$CO$_3$ (76 mg, 0.2 mmol) and dioxane (1.1 mL) was heated to 100° C. using an oil bath. After 16 h, the reaction mixture cooled to rt to afford the crude title compound as a free base. Purification (Method C), afforded the title compound (19 mg, 31%). MS (ESI): mass calcd. for C$_{19}$H$_{16}$F$_4$N$_4$O$_2$, 408.1; m/z found, 409.2 [M+H]$^+$. $^1$H NMR (400 MHz, DMSO-d$_6$) δ 8.40 (d, J=1.9 Hz, 1H), 8.02-7.97 (m, 2H), 7.89 (d, J=2.0 Hz, 1H), 7.78-7.70 (m, 2H), 5.58-5.37 (m, 1H), 4.76-4.57 (m, 3H), 4.47-4.34 (m, 1H), 4.31-4.18 (m, 1H), 4.04-3.90 (m, 1H), 3.40 (s, 3H).

Example 35: 6-(4-Methoxyphenyl)-1-(2-oxo-2-pyrrolidin-1-yl-ethyl)-3H-imidazo[4,5-b]pyridin-2-one

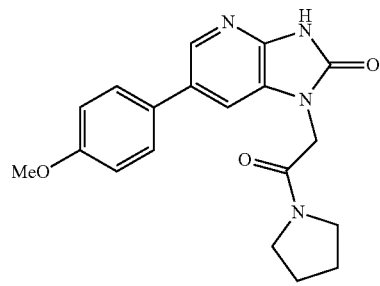 [SMILES: COc1ccc(-c2cnc3[nH]c(=O)n(CC(=O)N4CCCC4)c3c2)cc1]

The title compound was prepared in a manner analogous to Example 1, using morpholine in Step F. MS (ESI): mass calcd. for C$_{19}$H$_{20}$N$_4$O$_3$, 352.2; m/z found, 353.1 [M+H]$^+$.

Example 36: N-Cyclopropyl-2-[6-(4-fluoro-2-methyl-phenyl)-2-oxo-3H-imidazo[4,5-b]pyridin-1-yl]acetamide

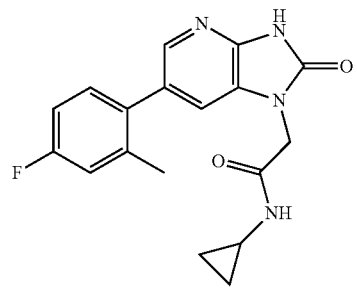 [SMILES: Cc1cc(F)ccc1-c1cnc2[nH]c(=O)n(CC(=O)NC3CC3)c2c1]

The title compound was prepared in a manner analogous to Example 3, using 2-(6-bromo-2-oxo-2,3-dihydro-1H-imidazo[4,5-b]pyridin-1-yl)-N-cyclopropylacetamide (Intermediate 34). MS (ESI): mass calcd. for C$_{18}$H$_{17}$FN$_4$O$_2$, 340.1; m/z found, 341.3 [M+H]$^+$.

Example 37: 2-[6-(2-Chloro-4-methoxy-phenyl)-2-oxo-3H-imidazo[4,5-b]pyridin-1-yl]-N-cyclopropylacetamide

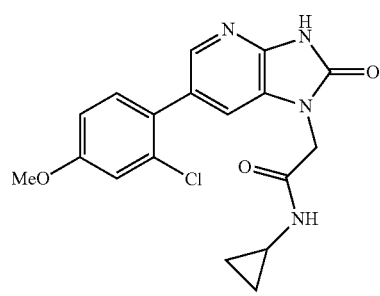 [SMILES: COc1ccc(-c2cnc3[nH]c(=O)n(CC(=O)NC4CC4)c3c2)c(Cl)c1]

The title compound was prepared in a manner analogous to Example 3, using 2-(6-bromo-2-oxo-2,3-dihydro-1H-imidazo[4,5-b]pyridin-1-yl)-N-cyclopropylacetamide (Intermediate 34) and (2-chloro-4-methoxyphenyl)boronic acid. MS (ESI): mass calcd. for $C_{18}H_{17}ClN_4O_3$, 372.1; m/z found, 373.1 $[M+H]^+$.

Example 38: N-Cyclopropyl-2-[6-(4-methoxyphenyl)-2-oxo-3H-imidazo[4,5-b]pyridin-1-yl]acetamide

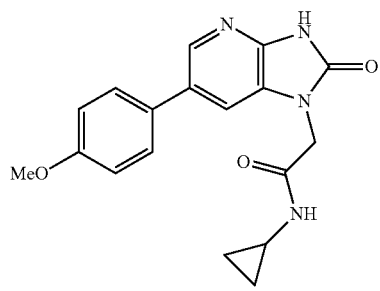 [SMILES: COc1ccc(-c2cnc3[nH]c(=O)n(CC(=O)NC4CC4)c3c2)cc1]

The title compound was prepared in a manner analogous to Example 3, using 2-(6-bromo-2-oxo-2,3-dihydro-1H-imidazo[4,5-b]pyridin-1-yl)-N-cyclopropylacetamide (Intermediate 34) and 4-methoxyphenylboronic acid. MS (ESI): mass calcd. for $C_{18}H_{18}N_4O_3$, 338.1; m/z found, 339.2 $[M+H]^+$.

Example 39: N-Cyclopropyl-2-[6-(3,5-dimethylphenyl)-2-oxo-3H-imidazo[4,5-b]pyridin-1-yl]acetamide

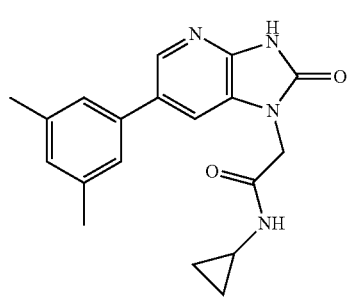 [SMILES: Cc1cc(C)cc(-c2cnc3[nH]c(=O)n(CC(=O)NC4CC4)c3c2)c1]

The title compound was prepared in a manner analogous to Example 3, using 2-(6-bromo-2-oxo-2,3-dihydro-1H-imidazo[4,5-b]pyridin-1-yl)-N-cyclopropylacetamide (Intermediate 34) and (3,5-dimethyl)boronic acid. MS (ESI): mass calcd. for $C_{19}H_{20}N_4O_2$, 336.2; m/z found, 337.2 $[M+H]^+$.

Example 40: N-Cyclopropyl-2-[6-(4-fluoro-2-methyl-phenyl)-2-oxo-3H-imidazo[4,5-b]pyridin-1-yl]-N-methyl-acetamide

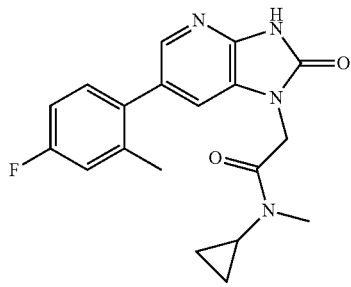 [SMILES: Cc1cc(F)ccc1-c1cnc2[nH]c(=O)n(CC(=O)N(C)C3CC3)c2c1]

The title compound was prepared in a manner analogous to Example 3, using 2-(6-bromo-2-oxo-1H-imidazo[4,5-b]pyridin-3(2H)-yl)-N-cyclopropyl-N-methylacetamide. MS (ESI): mass calcd. for $C_{19}H_{19}FN_4O_2$, 354.1; m/z found, 355.0 $[M+H]^+$.

Example 41: N-Cyclopropyl-2-[6-(4-methoxyphenyl)-2-oxo-3H-imidazo[4,5-b]pyridin-1-yl]-N-methyl-acetamide

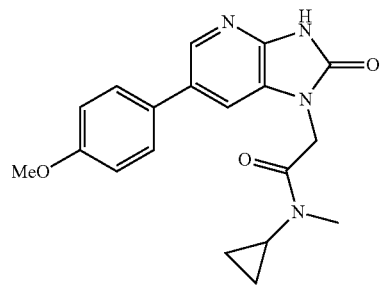 [SMILES: COc1ccc(-c2cnc3[nH]c(=O)n(CC(=O)N(C)C4CC4)c3c2)cc1]

The title compound was prepared in a manner analogous to Example 3, using 2-(6-bromo-2-oxo-1H-imidazo[4,5-b]pyridin-3(2H)-yl)-N-cyclopropyl-N-methylacetamide and 4-methoxyphenylboronic acid. MS (ESI): mass calcd. for $C_{19}H_{20}N_4O_3$, 352.2; m/z found, 353.0 $[M+H]^+$.

Example 42: N-Cyclopropyl-2-[6-(4-fluoro-2-methyl-phenyl)-3-methyl-2-oxo-imidazo[4,5-b]pyridin-1-yl]acetamide

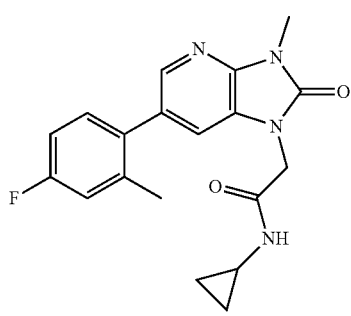 [SMILES: Cc1cc(F)ccc1-c1cnc2c(c1)n(CC(=O)NC1CC1)c(=O)n2C]

The title compound was prepared in a manner analogous to Example 3, using 2-(6-bromo-1-methyl-2-oxo-1H-imidazo[4,5-b]pyridin-3(2H)-yl)-N-cyclopropylacetamide. MS (ESI): mass calcd. for $C_{19}H_{19}FN_4O_2$, 354.1; m/z found, 354.96 [M+H]$^+$.

Example 43: (R*)-6-(4-Fluoro-2-methyl-phenyl)-1-(2-hydroxybutyl)-3H-imidazo[4,5-b]pyridin-2-one

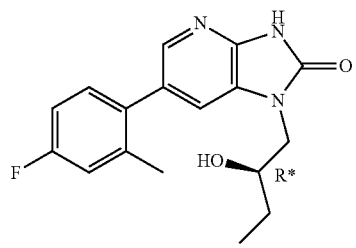 [SMILES: CC[C@@H](O)Cn1c(=O)[nH]c2ncc(-c3ccc(F)cc3C)cc21]

The title compound was prepared in a manner analogous to Example 4, using (4-fluoro-2-methylphenyl)boronic acid in Step D. Purification (SFC separation, Chiralcel AD-H, 20 μm; Supercritical $CO_{O2}$: MeOH, v/v, 200 mL/min) afforded the title compound and (S*)-6-(4-Fluoro-2-methyl-phenyl)-1-(2-hydroxybutyl)-3H-imidazo[4,5-b]pyridin-2-one (Example 44). MS (ESI): mass calcd. for $C_{17}H_{18}FN_3O_2$, 315.1; m/z found, 316.0 [M+H]$^+$.

Example 44: (S*)-6-(4-Fluoro-2-methyl-phenyl)-1-(2-hydroxybutyl)-3H-imidazo[4,5-b]pyridin-2-one

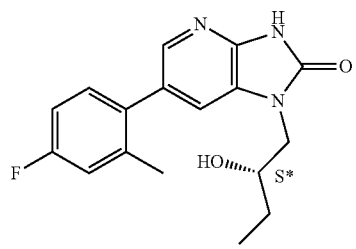 [SMILES: CC[C@H](O)Cn1c(=O)[nH]c2ncc(-c3ccc(F)cc3C)cc21]

Isolated during purification of Example 43. MS (ESI): mass calcd. for $C_{17}H_{18}FN_3O_2$, 315.1; m/z found, 315.93 [M+H]$^+$.

Example 45: 6-(4-Fluoro-3-methyl-phenyl)-3-methyl-1-(3-pyridylmethyl)imidazo[4,5-b]pyridin-2-one

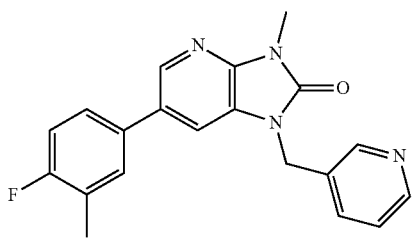 [SMILES: Cc1cc(-c2cnc3c(c2)n(Cc2cccnc2)c(=O)n3C)ccc1F]

The title compound was prepared in a manner analogous to Example 6 using 3-(chloromethyl)pyridine hydrochloride. MS (ESI): mass calcd. for $C_{20}H_{17}FN_4O$, 348.1; m/z found, 349.1 [M+H]$^+$. $^1$H NMR (400 MHz, CDCl$_3$) δ 2.30 (d, J=1.16 Hz, 3H), 3.39 (s, 3H), 5.19 (s, 2H), 7.24 (t, J=9.13 Hz, 1H), 7.36 (dd, J=7.86, 4.85 Hz, 1H), 7.50 (ddd, J=8.03, 5.03, 2.43 Hz, 1H), 7.60 (dd, J=7.28, 1.73 Hz, 1H), 7.76 (d, J=7.86 Hz, 1H), 7.90 (d, J=1.85 Hz, 1H), 8.28 (d, J=1.85 Hz, 1H), 8.48 (dd, J=4.74, 1.50 Hz, 1H), 8.67 (d, J=1.62 Hz, 1H).

Example 46: 6-(4-Fluoro-3-methyl-phenyl)-3-methyl-1-(4-pyridylmethyl)imidazo[4,5-b]pyridin-2-one

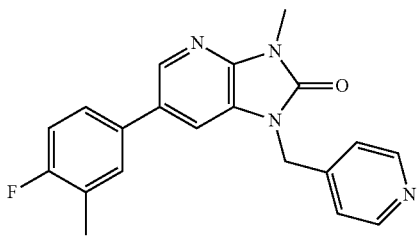 [SMILES: Cc1cc(-c2cnc3c(c2)n(Cc2ccncc2)c(=O)n3C)ccc1F]

The title compound was prepared in a manner analogous to Example 6 using 4-(chloromethyl)pyridine hydrochloride. MS (ESI): mass calcd. for $C_{20}H_{17}FN_4O$, 348.1; m/z found, 349.1 [M+H]$^+$. $^1$H NMR (400 MHz, DMSO-d$_6$) δ 2.29 (d, J=1.39 Hz, 3H), 3.42 (s, 3H), 5.20 (s, 2H), 7.16-7.27 (m, 1H), 7.30 (d, J=6.01 Hz, 2H), 7.49 (ddd, J=8.15, 5.14, 2.43 Hz, 1H), 7.59 (dd, J=7.28, 1.96 Hz, 1H), 7.81 (d, J=1.85 Hz, 1H), 8.30 (d, J=1.85 Hz, 1H), 8.45-8.59 (m, 2H).

Example 47: 6-(4-Fluoro-3-methyl-phenyl)-3-methyl-1-(pyrazin-2-ylmethyl)imidazo[4,5-b]pyridin-2-one

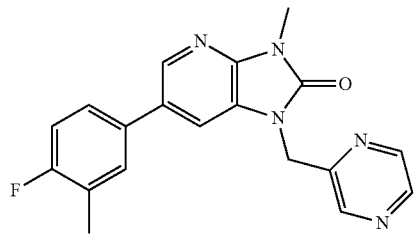 [SMILES: Cc1cc(-c2cnc3c(c2)n(Cc2cnccn2)c(=O)n3C)ccc1F]

The title compound was prepared in a manner analogous to Example 6 using Intermediate 27: 6-(4-fluoro-3-methylphenyl)-3-methyl-1,3-dihydro-2H-imidazo[4,5-b]pyridin-2-one and Intermediate 1: 2-(chloromethyl)pyrazine. MS (ESI): mass calcd. for $C_{19}H_{16}FN_5O$, 349.1; m/z found, 350.1 [M+H]$^+$. $^1$H NMR (400 MHz, CDCl$_3$) δ 2.34 (d, J=1.85 Hz, 3H), 3.57 (s, 3H), 5.27 (s, 2H), 7.08 (t, J=8.79 Hz, 1H), 7.20-7.33 (m, 4H), 7.37 (d, J=1.85 Hz, 1H), 8.21 (d, J=1.85 Hz, 1H), 8.29 (s, 1H), 8.47-8.59 (m, 2H), 8.69 (d, J=0.92 Hz, 1H).

Example 48: 6-(4-Fluoro-3-methyl-phenyl)-3-methyl-1-(pyrimidin-5-ylmethyl)imidazo[4,5-b]pyridin-2-one

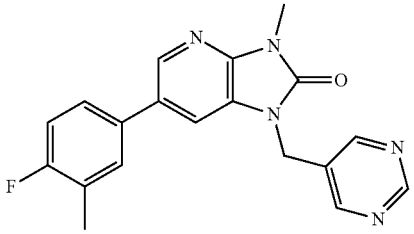 [SMILES: Cc1cc(-c2cnc3c(c2)n(Cc2cncnc2)c(=O)n3C)ccc1F]

The title compound was prepared in a manner analogous to Example 6 using Intermediate 27: 6-(4-fluoro-3-methylphenyl)-3-methyl-1,3-dihydro-2H-imidazo[4,5-b]pyridin-2-one and Intermediate 3: 5-(chloromethyl)pyrimidine hydrochloride. MS (ESI): mass calcd. for $C_{19}H_{16}FN_5O$, 349.1; m/z found, 350.2 [M+H]$^+$. $^1$H NMR (400 MHz, CDCl$_3$) δ 2.35 (d, J=1.62 Hz, 3H), 3.58 (s, 3H), 5.14 (s, 2H), 7.09 (t, J=8.79 Hz, 1H), 7.19 (d, J=1.85 Hz, 1H), 7.22-7.33 (m, 2H), 8.23 (d, J=1.85 Hz, 1H), 8.80 (s, 2H), 9.19 (s, 1H).

Example 49: 6-(4-Fluoro-3-methyl-phenyl)-3-methyl-1-(pyrimidin-2-ylmethyl)imidazo[4,5-b]pyridin-2-one

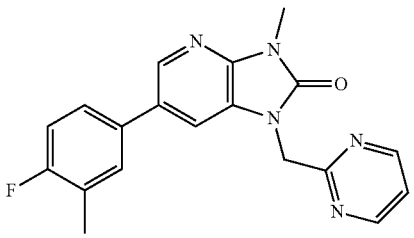 [SMILES: Cc1cc(-c2cnc3c(c2)n(Cc2ncccn2)c(=O)n3C)ccc1F]

The title compound was prepared in a manner analogous to Example 6 using Intermediate 27: 6-(4-fluoro-3-methylphenyl)-3-methyl-1,3-dihydro-2H-imidazo[4,5-b]pyridin-2-one and 2-(chloromethyl)pyrimidine hydrochloride. MS (ESI): mass calcd. for $C_{19}H_{16}FN_5O$, 349.1; m/z found, 350.1 [M+H]$^+$. $^1$H NMR (400 MHz, CDCl$_3$) δ 2.32 (d, J=1.85 Hz, 3H), 3.59 (s, 3H), 5.37 (s, 2H), 7.05 (t, J=8.90 Hz, 1H), 7.17-7.35 (m, 4H), 8.20 (d, J=1.85 Hz, 1H), 8.69 (d, J=5.09 Hz, 2H).

Example 50: 6-(4-Fluoro-3-methyl-phenyl)-3-methyl-1-(pyridazin-3-ylmethyl)imidazo[4,5-b]pyridin-2-one

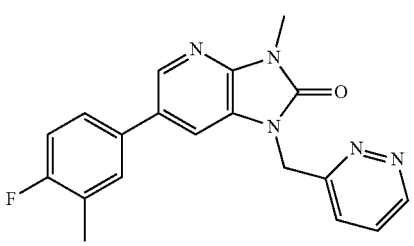 [SMILES: Cc1cc(-c2cnc3c(c2)n(Cc2cccnn2)c(=O)n3C)ccc1F]

The title compound was prepared in a manner analogous to Example 6 using Intermediate 27: 6-(4-fluoro-3-methylphenyl)-3-methyl-1,3-dihydro-2H-imidazo[4,5-b]pyridin-2-one and 3-(chloromethyl)pyridazine (Intermediate 2). MS (ESI): mass calcd. for $C_{19}H_{16}FN_5O$, 349.1; m/z found, 350.1 [M+H]$^+$. $^1$H NMR (400 MHz, DMSO-d$_6$) δ 2.29 (d, J=1.62 Hz, 3H), 3.41 (s, 3H), 5.47 (s, 2H), 7.11-7.33 (m, 1H), 7.37-7.53 (m, 1H), 7.58 (dd, J=7.40, 2.08 Hz, 1H), 7.62-7.74 (m, 2H), 7.83 (d, J=1.85 Hz, 1H), 8.30 (d, J=2.08 Hz, 1H), 9.15 (dd, J=4.62, 2.08 Hz, 1H).

Example 51: 6-(3-Fluorophenyl)-3-methyl-1-(3-pyridylmethyl)imidazo[4,5-b]pyridin-2-one

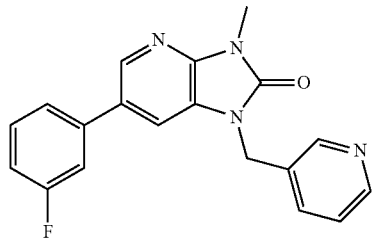 [SMILES: Cn1c(=O)n(Cc2cccnc2)c2cc(-c3cccc(F)c3)cnc21]

The title compound was prepared in a manner analogous to Example 6 using Intermediate 28: 6-(3-fluorophenyl)-3-methyl-1,3-dihydro-2H-imidazo[4,5-b]pyridin-2-one and 3-(chloromethyl)pyridine hydrochloride. MS (ESI): mass calcd. for $C_{19}H_{15}FN_4O$, 334.1; m/z found, 335.1 [M+H]$^+$. $^1$H NMR (400 MHz, CDCl$_3$) δ 3.59 (s, 3H), 5.15 (s, 2H), 7.02-7.12 (m, 1H), 7.17 (dt, J=9.94, 2.08 Hz, 1H), 7.20 (d, J=2.08 Hz, 1H), 7.22-7.26 (m, 1H), 7.30 (dd, J=7.86, 4.86 Hz, 1H), 7.42 (td, J=7.98, 6.01 Hz, 1H), 7.70 (dt, J=7.86, 1.97 Hz, 1H), 8.25 (d, J=1.85 Hz, 1H), 8.58 (dd, J=4.86, 1.62 Hz, 1H), 8.68 (d, J=2.08 Hz, 1H).

Example 52: 6-(3-Fluorophenyl)-3-methyl-1-(4-pyridylmethyl)imidazo[4,5-b]pyridin-2-one

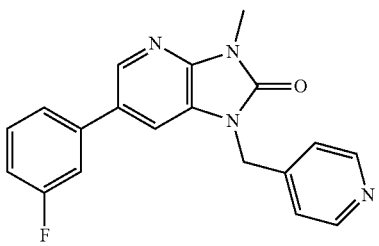 [SMILES: Cn1c(=O)n(Cc2ccncc2)c2cc(-c3cccc(F)c3)cnc21]

The title compound was prepared in a manner analogous to Example 6 using Intermediate 28: 6-(3-fluorophenyl)-3-methyl-1,3-dihydro-2H-imidazo[4,5-b]pyridin-2-one and 4-(chloromethyl)pyridine hydrochloride. MS (ESI): mass calcd. for $C_{19}H_{15}FN_4O$, 334.1; m/z found, 335.1 [M+H]$^+$. $^1$H NMR (400 MHz, CDCl$_3$) δ 3.60 (s, 3H), 5.14 (s, 2H), 7.07 (tdd, J=8.41, 2.49, 0.81 Hz, 1H), 7.12 (d, J=1.85 Hz, 1H), 7.16 (dt, J=9.83, 2.14 Hz, 1H), 7.20-7.26 (m, 3H), 7.41 (td, J=7.98, 6.01 Hz, 1H), 8.28 (d, J=1.85 Hz, 1H), 8.36-8.84 (m, 2H).

Example 53: 6-(3-Fluorophenyl)-3-methyl-1-(2-pyridylmethyl)imidazo[4,5-b]pyridin-2-one

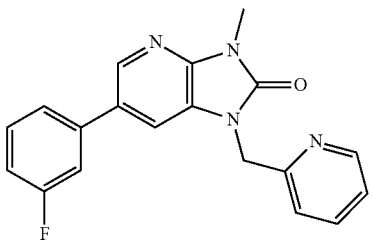 [SMILES: Cn1c(=O)n(Cc2ccccn2)c2cc(-c3cccc(F)c3)cnc21]

The title compound was prepared in a manner analogous to Example 6 using Intermediate 28: 6-(3-fluorophenyl)-3-methyl-1,3-dihydro-2H-imidazo[4,5-b]pyridin-2-one and 2-(chloromethyl)pyridine hydrochloride. MS (ESI): mass calcd. for $C_{19}H_{15}FN_4O$, 334.1; m/z found, 335.1 [M+H]$^+$. $^1$H NMR (400 MHz, CDCl$_3$) δ 3.58 (s, 3H), 5.25 (s, 2H), 7.06 (tdd, J=8.32, 2.54, 0.92 Hz, 1H), 7.16-7.26 (m, 2H), 7.27 (s, 2H), 7.33 (d, J=7.63 Hz, 1H), 7.36-7.48 (m, 2H), 7.67 (td, J=7.74, 1.85 Hz, 1H), 8.25 (d, J=1.85 Hz, 1H), 8.51-8.70 (m, 1H).

Example 54: 6-(3-Fluorophenyl)-3-methyl-1-(pyrimidin-5-ylmethyl)imidazo[4,5-b]pyridin-2-one

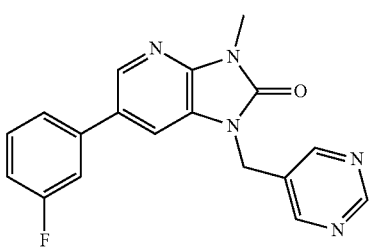 [SMILES: Cn1c(=O)n(Cc2cncnc2)c2cc(-c3cccc(F)c3)cnc21]

The title compound was prepared in a manner analogous to Example 6 using Intermediate 28: 6-(3-fluorophenyl)-3-methyl-1,3-dihydro-2H-imidazo[4,5-b]pyridin-2-one and 5-(chloromethyl)pyrimidine hydrochloride (Intermediate 3). MS (ESI): mass calcd. for $C_{18}H_{14}FN_5O$, 335.1; m/z found, 336.1 [M+H]$^+$. $^1$H NMR (400 MHz, CDCl$_3$) δ 3.58 (s, 2H), 3.52 (s, 1H), 5.15 (s, 2H), 6.95-7.14 (m, 1H), 7.15-7.32 (m, 4H), 7.43 (td, J=7.98, 6.01 Hz, 1H), 8.28 (d, J=1.85 Hz, 1H), 8.80 (s, 2H), 9.20 (s, 1H).

Example 55: 6-(3-Fluorophenyl)-3-methyl-1-(pyrazin-2-ylmethyl)imidazo[4,5-b]pyridin-2-one

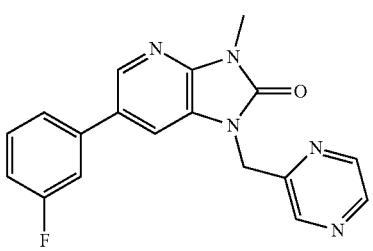 [SMILES: Cn1c(=O)n(Cc2cnccn2)c2cc(-c3cccc(F)c3)cnc21]

The title compound was prepared in a manner analogous to Example 6 using Intermediate 28: 6-(3-fluorophenyl)-3-methyl-1,3-dihydro-2H-imidazo[4,5-b]pyridin-2-one and Intermediate 1: 2-(chloromethyl)pyrazine. MS (ESI): mass calcd. for $C_{18}H_{14}FN_5O$, 335.1; m/z found, 336.1 [M+H]$^+$. $^1$H NMR (400 MHz, CDCl$_3$) δ 3.58 (s, 3H), 5.29 (s, 2H), 7.02-7.13 (m, 1H), 7.22 (dt, J=9.94, 2.08 Hz, 1H), 7.30 (dt, J=7.86, 1.16 Hz, 1H), 7.35-7.50 (m, 2H), 8.27 (d, J=1.85 Hz, 1H), 8.47-8.61 (m, 2H), 8.71 (s, 1H).

Example 56: 6-(3-Fluorophenyl)-3-methyl-1-(pyrimidin-2-ylmethyl)imidazo[4,5-b]pyridin-2-one

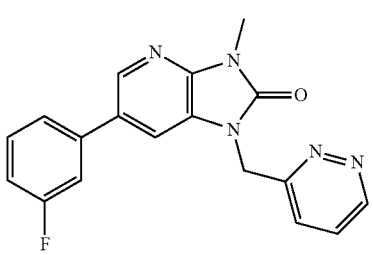

The title compound was prepared in a manner analogous to Example 6 using Intermediate 28: 6-(3-fluorophenyl)-3-methyl-1,3-dihydro-2H-imidazo[4,5-b]pyridin-2-one and 2-(chloromethyl)pyrimidine hydrochloride. MS (ESI): mass calcd. for $C_{18}H_{14}FN_5O$, 335.1; m/z found, 336.1 [M+H]$^+$. $^1$H NMR (500 MHz, DMSO-d$_6$) δ 3.37-3.56 (m, 3H), 5.39 (s, 2H), 7.05-7.28 (m, 1H), 7.41 (t, J=4.91 Hz, 1H), 7.45-7.72 (m, 3H), 7.91 (d, J=2.02 Hz, 1H), 8.39 (d, J=2.02 Hz, 1H), 8.75 (d, J=4.91 Hz, 2H).

Example 57: 6-(3-Fluorophenyl)-3-methyl-1-(pyridazin-3-ylmethyl)imidazo[4,5-b]pyridin-2-one The title compound was prepared in a manner analogous to Example 6 using Intermediate 28: 6-(3-fluorophenyl)-3-methyl-1,3-dihydro-2H-imidazo[4,5-b]pyridin-2-one and Intermediate 2: 3-(chloromethyl)pyridazine. MS (ESI): mass calcd. for $C_{18}H_{14}FN_5O$, 335.1; m/z found, 336.1 [M+H]$^+$. $^1$H NMR (400 MHz, DMSO-d$_6$) δ 3.42 (s, 3H), 5.48 (s, 2H), 7.11-7.28 (m, 1H), 7.40-7.60 (m, 3H), 7.60-7.79 (m, 2H), 7.92 (d, J=2.08 Hz, 1H), 8.40 (d, J=1.85 Hz, 1H), 9.15 (dd, J=4.28, 2.20 Hz, 1H).

Example 58: 6-(3,4-Difluorophenyl)-3-methyl-1-(4-pyridylmethyl)imidazo[4,5-b]pyridin-2-one

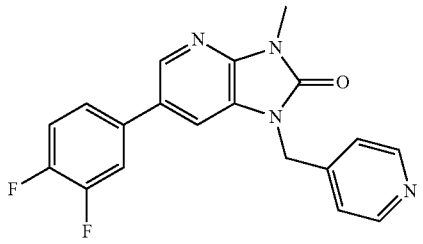 [SMILES: Cn1c(=O)n(Cc2ccncc2)c2cc(-c3ccc(F)c(F)c3)cnc21]

The title compound was prepared in a manner analogous to Example 6 using Intermediate 29: 6-(3,4-difluorophenyl)-3-methyl-1,3-dihydro-2H-imidazo[4,5-b]pyridin-2-one and 4-(chloromethyl)pyridine hydrochloride. MS (ESI): mass calcd. for $C_{19}H_{14}F_2N_4O$, 352.1; m/z found, 353.1 [M+H]$^+$. $^1$H NMR (400 MHz, CDCl$_3$) δ 3.60 (s, 3H), 5.14 (s, 2H), 7.06 (d, J=1.85 Hz, 1H), 7.12-7.19 (m, 1H), 7.19-7.23 (m, 2H), 7.23-7.32 (m, 3H), 8.22 (d, J=1.85 Hz, 1H), 8.38-8.86 (m, 2H).

Example 59: 6-(3,4-Difluorophenyl)-3-methyl-1-(3-pyridylmethyl)imidazo[4,5-b]pyridin-2-one

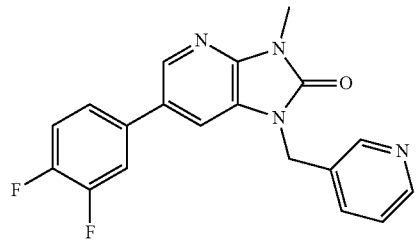 [SMILES: Cn1c(=O)n(Cc2cccnc2)c2cc(-c3ccc(F)c(F)c3)cnc21]

The title compound was prepared in a manner analogous to Example 6 using Intermediate 29: 6-(3,4-difluorophenyl)-3-methyl-1,3-dihydro-2H-imidazo[4,5-b]pyridin-2-one and 3-(chloromethyl)pyridine hydrochloride. MS (ESI): mass calcd. for $C_{19}H_{14}F_2N_4O$, 352.1; m/z found, 353.1 [M+H]$^+$. $^1$H NMR (400 MHz, DMSO-d$_6$) δ 3.39 (s, 9H), 5.18 (s, 2H), 7.36 (dd, J=7.86, 4.86 Hz, 1H), 7.46-7.63 (m, 2H), 7.68-7.90 (m, 2H), 7.97 (d, J=1.85 Hz, 1H), 8.35 (d, J=1.85 Hz, 1H), 8.48 (dd, J=4.74, 1.50 Hz, 1H), 8.67 (d, J=1.85 Hz, 1H).

Example 60: 6-(3,4-Difluorophenyl)-3-methyl-1-(pyrimidin-5-ylmethyl)imidazo[4,5-b]pyridin-2-one

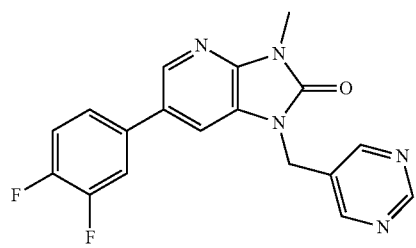 [SMILES: Cn1c(=O)n(Cc2cncnc2)c2cc(-c3ccc(F)c(F)c3)cnc21]

The title compound was prepared in a manner analogous to Example 6 using Intermediate 29: 6-(3,4-difluorophenyl)-3-methyl-1,3-dihydro-2H-imidazo[4,5-b]pyridin-2-one and 5-(chloromethyl)pyrimidine hydrochloride (Intermediate 3). MS (ESI): mass calcd. for $C_{18}H_{13}F_2N_5O$, 353.1; m/z found, 352.1 [M+H]$^+$. $^1$H NMR (400 MHz, CDCl$_3$) δ 3.58 (s, 3H), 5.15 (s, 2H), 7.15-7.22 (m, 2H), 7.27 (s, 3H), 8.23 (d, J=1.85 Hz, 1H), 8.80 (s, 2H), 9.20 (s, 1H). MP=184.9° C.

Example 61: 6-(3,4-Difluorophenyl)-3-methyl-1-(pyridazin-3-ylmethyl)imidazo[4,5-b]pyridin-2-one

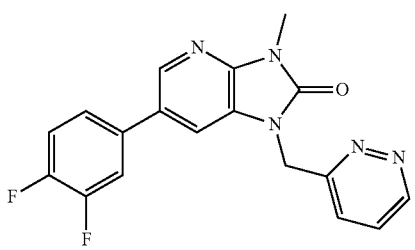

The title compound was prepared in a manner analogous to Example 6 using Intermediate 29: 6-(3,4-difluorophenyl)-3-methyl-1,3-dihydro-2H-imidazo[4,5-b]pyridin-2-one and Intermediate 2: 3-(chloromethyl)pyridazine. MS (ESI): mass calcd. for $C_{18}H_{13}F_2N_5O$, 353.1; m/z found, 354.1 [M+H]$^+$. $^1$H NMR (400 MHz, DMSO-d$_6$) δ 3.41 (s, 3H), 5.47 (s, 2H), 7.42-7.59 (m, 2H), 7.58-7.74 (m, 2H), 7.74-7.85 (m, 1H), 7.91 (d, J=1.85 Hz, 1H), 8.38 (d, J=1.85 Hz, 1H), 9.15 (dd, J=4.39, 2.08 Hz, 1H).

Example 62: 6-(3,4-difluorophenyl)-3-methyl-1-(2-pyridylmethyl)imidazo[4,5-b]pyridin-2-one

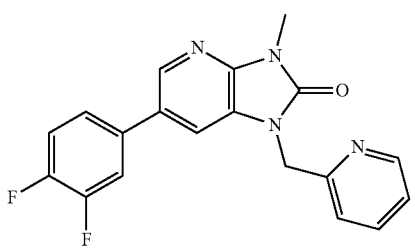

The title compound was prepared in a manner analogous to Example 6 using 6-(3,4-difluorophenyl)-3-methyl-1,3-dihydro-2H-imidazo[4,5-b]pyridin-2-one (Intermediate 29) and 2-(chloromethyl)pyridine hydrochloride. MS (ESI): mass calcd. for $C_{19}H_{14}F_2N_4O$, 352.1; m/z found, [M+H]$^+$. $^1$H NMR (400 MHz, CDCl$_3$) δ 3.58 (s, 3H), 5.24 (s, 2H), 7.19-7.26 (m, 3H), 7.28-7.40 (m, 3H), 7.68 (td, J=7.69, 1.73 Hz, 1H), 8.19 (d, J=1.85 Hz, 1H), 8.47-8.70 (m, 1H).

Example 63: 6-(3,4-Difluorophenyl)-3-methyl-1-(pyrazin-2-ylmethyl)imidazo[4,5-b]pyridin-2-one

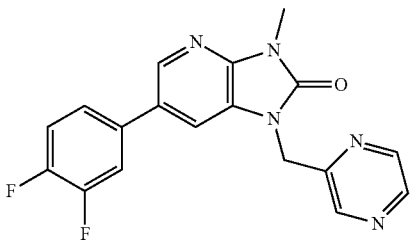 [SMILES: Cn1c(=O)n(Cc2cnccn2)c2cc(-c3ccc(F)c(F)c3)cnc21]

The title compound was prepared in a manner analogous to Example 6 using 6-(3,4-difluorophenyl)-3-methyl-1,3-dihydro-2H-imidazo[4,5-b]pyridin-2-one (Intermediate 29) and 2-(chloromethyl)pyrazine (Intermediate 1). MS (ESI): mass calcd. for $C_{18}H_{13}F_2N_5O$, 353.1; m/z found, 354.1 [M+H]$^+$. $^1$H NMR (400 MHz, DMSO-d$_6$) δ 3.40 (s, 3H), 5.35 (s, 2H), 7.46-7.61 (m, 2H), 7.72-7.84 (m, 1H), 7.90 (d, J=1.85 Hz, 1H), 8.36 (d, J=1.85 Hz, 1H), 8.47-8.64 (m, 2H), 8.74 (s, 1H).

Example 64: 6-(3,4-Difluorophenyl)-3-methyl-1-(pyrimidin-2-ylmethyl)imidazo[4,5-b]pyridin-2-one

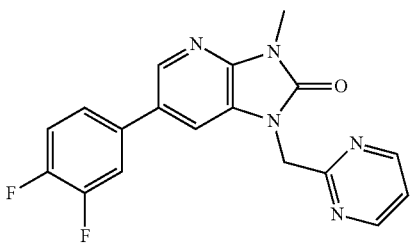 [SMILES: Cn1c(=O)n(Cc2ncccn2)c2cc(-c3ccc(F)c(F)c3)cnc21]

The title compound was prepared in a manner analogous to Example 6 using 6-(3,4-difluorophenyl)-3-methyl-1,3-dihydro-2H-imidazo[4,5-b]pyridin-2-one (Intermediate 29) and 2-(chloromethyl)pyrimidine hydrochloride. MS (ESI): mass calcd. for $C_{18}H_{13}F_2N_5O$, 353.1; m/z found, 354.1 [M+H]$^+$. $^1$H NMR (400 MHz, DMSO-d$_6$) δ 3.42 (s, 3H), 5.37 (s, 2H), 7.41 (t, J=4.97 Hz, 1H), 7.45-7.64 (m, 2H), 7.69-7.84 (m, 1H), 7.89 (d, J=1.85 Hz, 1H), 8.37 (d, J=1.85 Hz, 1H), 8.75 (d, J=4.86 Hz, 2H).

Example 65: 6-(2,4-Difluoro-3-methyl-phenyl)-3-methyl-1-(pyrimidin-2-ylmethyl)imidazo[4,5-b]pyridin-2-one

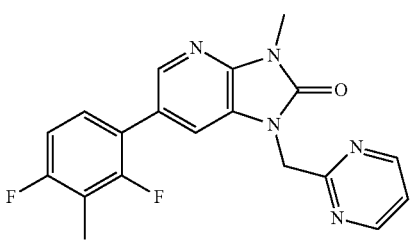 [SMILES: Cc1c(F)ccc(-c2cnc3c(c2)n(Cc2ncccn2)c(=O)n3C)c1F]

The title compound was prepared in a manner analogous to Example 6 using 6-(2,4-difluoro-3-methylphenyl)-3-methyl-1,3-dihydro-2H-imidazo[4,5-b]pyridin-2-one (Intermediate 30) and 2-(chloromethyl)pyrimidine. MS (ESI): mass calcd. for $C_{19}H_{15}F_2N_5O$, 367.1; m/z found, 368.1 [M+H]$^+$. $^1$H NMR (500 MHz, DMSO-d$_6$) δ 2.19 (s, 3H), 3.37-3.59 (m, 3H), 5.36 (s, 2H), 7.15 (t, J=8.67 Hz, 1H), 7.28-7.51 (m, 2H), 7.64 (t, J=1.44 Hz, 1H), 8.14 (t, J=1.59 Hz, 1H), 8.75 (d, J=4.91 Hz, 2H).

Example 66: 6-(2,4-Difluoro-3-methyl-phenyl)-3-methyl-1-(4-pyridylmethyl)imidazo[4,5-b]pyridin-2-one

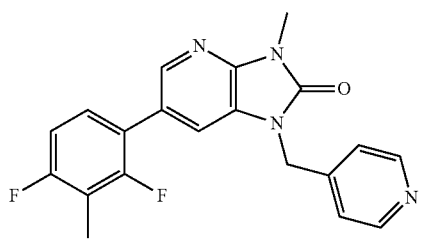 [SMILES: Cc1c(F)ccc(-c2cnc3c(c2)n(Cc2ccncc2)c(=O)n3C)c1F]

The title compound was prepared in a manner analogous to Example 6 using: 6-(2,4-difluoro-3-methylphenyl)-3-methyl-1,3-dihydro-2H-imidazo[4,5-b]pyridin-2-one (Intermediate 30) and 4-(chloromethyl)pyridine hydrochloride. MS (ESI): mass calcd. for $C_{20}H_{16}F_2N_4O$, 366.1; m/z found, 367.1 [M+H]$^+$. $^1$H NMR (400 MHz, CDCl$_3$) δ 2.20-2.28 (m, 3H), 3.59 (s, 3H), 5.12 (s, 2H), 6.92 (td, J=8.55, 1.39 Hz, 1H), 7.08-7.16 (m, 2H), 7.18-7.23 (m, 2H), 8.10-8.20 (m, 1H), 8.54-8.63 (m, 2H).

Example 67: 6-(2,4-Difluoro-3-methyl-phenyl)-3-methyl-1-(pyridazin-3-ylmethyl)imidazo[4,5-b]pyridin-2-one

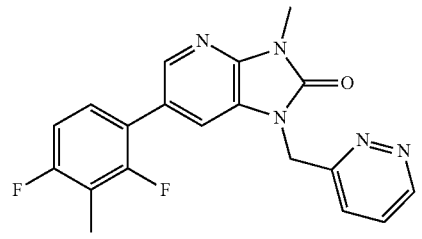 [SMILES: Cc1c(F)ccc(-c2cnc3c(c2)n(Cc2cccnn2)c(=O)n3C)c1F]

The title compound was prepared in a manner analogous to Example 6 using: 6-(2,4-difluoro-3-methylphenyl)-3-methyl-1,3-dihydro-2H-imidazo[4,5-b]pyridin-2-one (Intermediate 30) and 3-(chloromethyl)pyridazine (Intermediate 2). MS (ESI): mass calcd. for $C_{19}H_{15}F_2N_5O$, 367.1; m/z found, 368.1 [M+H]$^+$. $^1$H NMR (500 MHz, DMSO-d$_6$) δ 9.16 (dd, J=4.5, 2.1 Hz, 1H), 8.15 (t, J=1.6 Hz, 1H), 7.72-7.63 (m, 3H), 7.38 (td, J=8.7, 6.4 Hz, 1H), 7.17 (td, J=8.7, 1.3 Hz, 1H), 5.45 (s, 2H), 3.42 (s, 3H), 2.20 (t, J=1.8 Hz, 3H).

Example 68: 6-(2,4-Difluoro-3-methyl-phenyl)-3-methyl-1-(2-pyridylmethyl)imidazo[4,5-b]pyridin-2-one

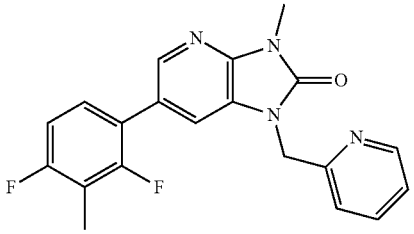 [SMILES: Cc1c(F)ccc(-c2cnc3c(c2)n(Cc2ccccn2)c(=O)n3C)c1F]

The title compound was prepared in a manner analogous to Example 6 using 6-(2,4-difluoro-3-methylphenyl)-3-methyl-1,3-dihydro-2H-imidazo[4,5-b]pyridin-2-one (Intermediate 30) and 2-(chloromethyl)pyridine hydrochloride. MS (ESI): mass calcd. for $C_{20}H_{16}F_2N_4O$, 366.1; m/z found, 367.1 [M+H]$^+$. $^1$H NMR (400 MHz, DMSO-d$_6$) δ 2.20 (s, 3H), 3.42 (s, 3H), 5.23 (s, 2H), 7.16 (t, J=8.44 Hz, 1H), 7.28 (dd, J=7.40, 4.86 Hz, 1H), 7.31-7.48 (m, 2H), 7.57 (t, J=1.50 Hz, 1H), 7.77 (td, J=7.69, 1.73 Hz, 1H), 8.13 (t, J=1.62 Hz, 1H), 8.47 (d, J=3.93 Hz, 1H).

Example 69: 6-(2,4-Difluoro-3-methyl-phenyl)-3-methyl-1-(pyrimidin-5-ylmethyl)imidazo[4,5-b]pyridin-2-one

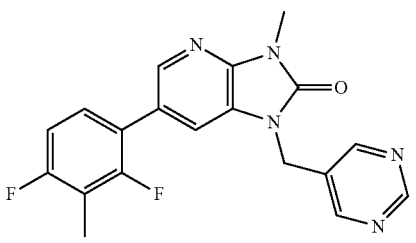 [SMILES: Cc1c(F)ccc(-c2cnc3c(c2)n(Cc2cncnc2)c(=O)n3C)c1F]

The title compound was prepared in a manner analogous to Example 6 using: 6-(2,4-difluoro-3-methylphenyl)-3-methyl-1,3-dihydro-2H-imidazo[4,5-b]pyridin-2-one (Intermediate 30) and 5-(chloromethyl)pyrimidine hydrochloride (Intermediate 3). MS (ESI): mass calcd. for $C_{19}H_{15}F_2N_5O$, 367.1; m/z found, 368.0 [M+H]$^+$. $^1$H NMR (500 MHz, CDCl$_3$) δ 2.27 (t, J=1.73 Hz, 3H), 3.58 (s, 3H), 5.13 (s, 2H), 6.95 (td, J=8.60, 1.30 Hz, 1H), 7.16 (td, J=8.53, 6.36 Hz, 1H), 7.24 (t, J=1.88 Hz, 1H), 8.06-8.28 (m, 1H), 8.80 (s, 2H), 9.19 (s, 1H).

Example 70: 6-(3,4-Difluorophenyl)-3-methyl-1-(pyrimidin-4-ylmethyl)imidazo[4,5-b]pyridin-2-one

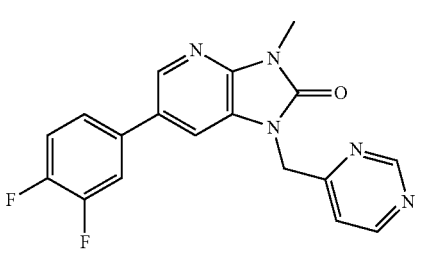 [SMILES: Cn1c(=O)n(Cc2ccncn2)c2cc(-c3ccc(F)c(F)c3)cnc21]

The title compound was prepared in a manner analogous to Example 7 using: 6-(3,4-difluorophenyl)-3-methyl-1,3-dihydro-2H-imidazo[4,5-b]pyridin-2-one (Intermediate 29). MS (ESI): mass calcd. for $C_{18}H_{13}F_2N_5O$, 353.1; m/z found, [M+H]$^+$. $^1$H NMR (500 MHz, DMSO-d$_6$) δ 3.42 (s, 3H), 5.30 (s, 2H), 7.47 (dd, J=5.36, 0.95 Hz, 1H), 7.49-7.58 (m, 2H), 7.75-7.83 (m, 1H), 7.90 (d, J=2.21 Hz, 1H), 8.39 (d, J=1.89 Hz, 1H), 8.75 (d, J=5.36 Hz, 1H), 9.09 (d, J=1.26 Hz, 1H).

Example 71: 6-(4-Fluoro-3-methyl-phenyl)-3-methyl-1-(pyrimidin-4-ylmethyl)imidazo[4,5-b]pyridin-2-one

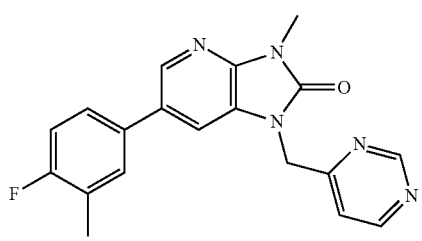 [SMILES: Cc1cc(-c2cnc3c(c2)n(Cc2ccncn2)c(=O)n3C)ccc1F]

The title compound was prepared in a manner analogous to Example 7 using: 6-(4-fluoro-3-methylphenyl)-3-methyl-1,3-dihydro-2H-imidazo[4,5-b]pyridin-2-one (Intermediate 27). MS (ESI): mass calcd. for $C_{19}H_{16}FN_5O$, 349.1; m/z found, 349.9 [M+H]$^+$. $^1$H NMR (500 MHz, DMSO-d$_6$) δ 2.29 (d, J=1.26 Hz, 3H), 3.42 (s, 3H), 5.30 (s, 2H), 7.13-7.29 (m, 1H), 7.41-7.53 (m, 2H), 7.59 (dd, J=7.41, 2.05 Hz, 1H), 7.83 (d, J=1.89 Hz, 1H), 8.31 (d, J=1.89 Hz, 1H), 8.75 (d, J=5.36 Hz, 1H), 9.09 (d, J=1.58 Hz, 1H).

Example 72: 6-(2,4-Difluoro-3-methyl-phenyl)-3-methyl-1-(pyrimidin-4-ylmethyl)imidazo[4,5-b]pyridin-2-one

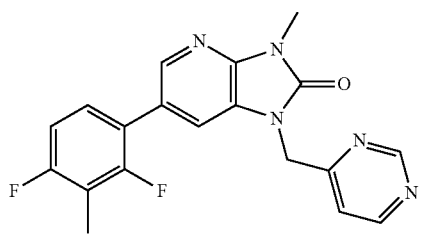 [SMILES: Cc1c(F)ccc(-c2cnc3c(c2)n(Cc2ccncn2)c(=O)n3C)c1F]

The title compound was prepared in a manner analogous to Intermediate 27 using 6-bromo-3-methyl-1-(pyrimidin-4-ylmethyl)-1,3-dihydro-2H-imidazo[4,5-b]pyridin-2-one (Intermediate 20) and 2-(2,4-difluoro-3-methylphenyl)-4,4,5,5-tetramethyl-1,3,2-dioxaborolane (Intermediate 8). MS (ESI): mass calcd. for $C_{19}H_{15}F_2N_5O$, 367.1; m/z found, 368.2 [M+H]$^+$. $^1$H NMR (400 MHz, DMSO-d$_6$) δ 2.20 (s, 3H), 3.37-3.61 (m, 3H), 5.28 (s, 2H), 7.16 (t, J=8.79 Hz, 1H), 7.38 (td, J=8.67, 6.70 Hz, 1H), 7.47 (dd, J=5.32, 1.39 Hz, 1H), 7.65 (t, J=1.62 Hz, 1H), 8.15 (t, J=1.62 Hz, 1H), 8.75 (d, J=5.32 Hz, 1H), 9.08 (d, J=1.39 Hz, 1H).

Example 73: 6-(3,4-Difluorophenyl)-3-methyl-1-[(5-methyl-1,3,4-oxadiazol-2-yl)methyl]imidazo[4,5-b]pyridin-2-one

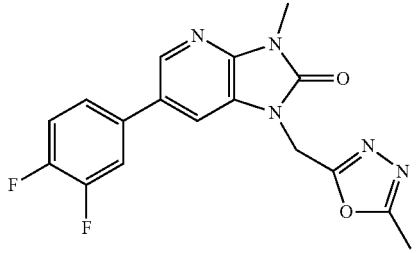 [SMILES: Cc1nnc(Cn2c(=O)n(C)c3ncc(-c4ccc(F)c(F)c4)cc32)o1]

The title compound was prepared in a manner analogous to Example 8 using 6-bromo-3-methyl-1-((5-methyl-1,3,4-oxadiazol-2-yl)methyl)-1,3-dihydro-2H-imidazo[4,5-b]pyridin-2-one (Intermediate 23) in Step A and 4-bromo-1,2-difluorobenzene in Step B. MS (ESI): mass calcd. for $C_{17}H_{13}F_2N_5O_2$, 357.1; m/z found, 358 [M+H]$^+$. $^1$H NMR (300 MHz, CDCl$_3$) δ 8.23 (d, J=0.9 Hz, 1H), 7.43 (s, 1H), 7.37-7.29 (m, 1H), 7.25-7.20 (m, 2H), 5.33 (s, 2H), 3.56 (s, 3H), 2.52 (s, 3H).

Example 74: 3-Methyl-1-[(5-methylisoxazol-3-yl)methyl]-6-[3-(trifluoromethyl)phenyl]imidazo[4,5-b]pyridin-2-one

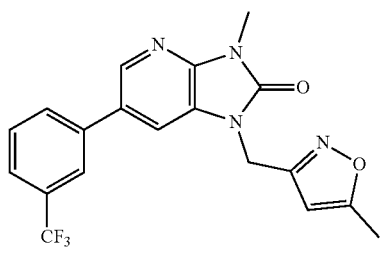 [SMILES: Cc1cc(Cn2c(=O)n(C)c3ncc(-c4cccc(C(F)(F)F)c4)cc32)no1]

The title compound was prepared in a manner analogous to Example 8, Step B using 6-bromo-3-methyl-1-((5-methylisoxazol-3-yl)methyl)-1,3-dihydro-2H-imidazo[4,5-b]pyridin-2-one (Intermediate 22) and (3-(trifluoromethyl)phenyl)boronic acid. MS (ESI): mass calcd. for $C_{19}H_{15}F_3N_4O_2$, 388.1; m/z found, 389 [M+H]$^+$. $^1$H NMR (300 MHz, CDCl$_3$) δ 8.26 (d, J=1.5 Hz, 1H), 7.74 (s, 1H), 7.72-7.52 (m, 3H), 7.46 (d, J=1.6 Hz, 1H), 6.04 (s, 1H), 5.15 (s, 2H), 3.56 (s, 3H), 2.38 (s, 3H).

Example 75: 3-Methyl-1-[(5-methyl-1,3,4-oxadiazol-2-yl)methyl]-6-[3-(trifluoromethyl)phenyl]imidazo[4,5-b]pyridin-2-one

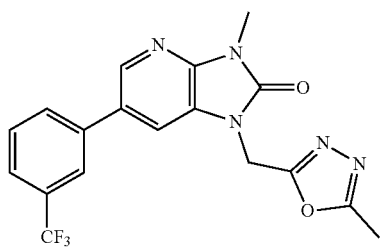 [SMILES: Cc1nnc(Cn2c(=O)n(C)c3ncc(-c4cccc(C(F)(F)F)c4)cc32)o1]

The title compound was prepared in a manner analogous to Example 8, Step B, using 6-bromo-3-methyl-1-((5-methyl-1,3,4-oxadiazol-2-yl)methyl)-1,3-dihydro-2H-imidazo[4,5-b]pyridin-2-one (Intermediate 23) and (3-(trifluoromethyl)phenyl)boronic acid. MS (ESI): mass calcd. for $C_{18}H_{14}F_3N_5O_2$, 389.1; m/z found, 390 [M+H]$^+$. $^1$H NMR (300 MHz, CDCl$_3$) δ 8.29 (d, J=1.3 Hz, 1H), 7.75 (s, 1H), 7.73-7.54 (m, 3H), 7.49 (d, J=1.3 Hz, 1H), 5.35 (s, 2H), 3.57 (s, 3H), 2.52 (s, 3H).

Example 76: 3-Methyl-1-[(3-methyl-1,2,4-oxadiazol-5-yl)methyl]-6-[3-(trifluoromethyl)phenyl]imidazo[4,5-b]pyridin-2-one

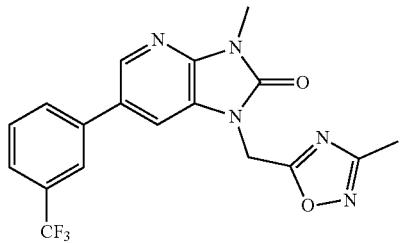 [SMILES: Cc1noc(Cn2c(=O)n(C)c3ncc(-c4cccc(C(F)(F)F)c4)cc32)n1]

The title compound was prepared in a manner analogous to Example 8, Step B using: 6-bromo-3-methyl-1-((3-methyl-1,2,4-oxadiazol-5-yl)methyl)-1,3-dihydro-2H-imidazo[4,5-b]pyridin-2-one (Intermediate 24) and (3-(trifluoromethyl)phenyl)boronic acid. MS (ESI): mass calcd. for $C_{18}H_{14}F_3N_5O_2$, 389.1; m/z found, 390 [M+H]$^+$. $^1$H NMR (300 MHz, CDCl$_3$) δ 8.31 (d, J=1.3 Hz, 1H), 7.75 (s, 1H), 7.71 (d, J=7.5 Hz, 1H), 7.68-7.55 (m, 2H), 7.37 (d, J=1.3 Hz, 1H), 5.35 (s, 2H), 3.58 (s, 3H), 2.38 (s, 3H).

Example 77: 6-(3,4-Difluorophenyl)-3-methyl-1-[(3-methyl-1,2,4-oxadiazol-5-yl)methyl]imidazo[4,5-b]pyridin-2-one

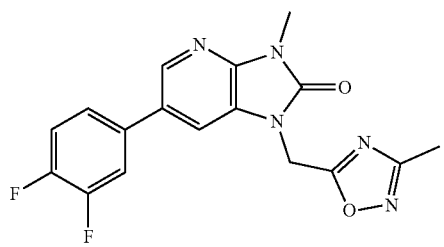 [SMILES: Cc1noc(Cn2c(=O)n(C)c3ncc(-c4ccc(F)c(F)c4)cc32)n1]

The title compound was prepared in a manner analogous to Example 8, using Intermediate 24: 6-bromo-3-methyl-1-((3-methyl-1,2,4-oxadiazol-5-yl)methyl)-1,3-dihydro-2H-imidazo[4,5-b]pyridin-2-one in Step A, and 4-bromo-1,2-difluorobenzene in Step B. MS (ESI): mass calcd. for $C_{17}H_{13}F_2N_5O_2$, 357.1; m/z found, 358.0 [M+H]$^+$. $^1$H NMR (300 MHz, CDCl$_3$) δ 8.28 (d, J=1.4 Hz, 1H), 7.40-7.34 (m, 1H), 7.33 (d, J=1.2 Hz, 1H), 7.29 (s, 1H), 7.28 (d, J=1.9 Hz, 1H), 5.37 (s, 2H), 3.60 (s, 3H), 2.41 (s, 3H).

Example 78: N,N-Dimethyl-2-[3-methyl-6-(5-methyl-2-thienyl)-2-oxo-imidazo[4,5-b]pyridin-1-yl]acetamide

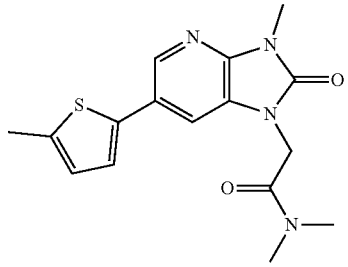 [SMILES: Cc1ccc(-c2cnc3c(c2)n(CC(=O)N(C)C)c(=O)n3C)s1]

The title compound was prepared in a manner analogous to Example 9, using 5-methylthiophene-2-boronic acid. MS (ESI): mass calcd. for $C_{16}H_{18}N_4O_2S$, 330.1; m/z found, 331.1 [M+H]$^+$. $^1$H NMR (400 MHz, CDCl$_3$) δ 8.31-8.25 (d, J=1.9 Hz, 1H), 7.34-7.32 (d, J=1.8 Hz, 1H), 7.09-7.04 (d, J=1.5 Hz, 1H), 6.88-6.84 (m, 1H), 4.75-4.66 (s, 2H), 3.55-3.49 (s, 3H), 3.20-3.13 (s, 3H), 3.03-2.96 (s, 3H), 2.32-2.24 (d, J=1.1 Hz, 3H).

Example 79: 2-[6-(5-Ethyl-2-thienyl)-3-methyl-2-oxo-imidazo[4,5-b]pyridin-1-yl]-N,N-dimethyl-acetamide

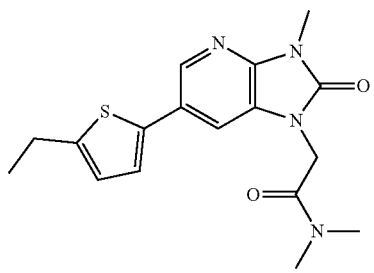 [SMILES: CCc1ccc(-c2cnc3c(c2)n(CC(=O)N(C)C)c(=O)n3C)s1]

The title compound was prepared in a manner analogous to Example 9, using 5-ethylthiophene-2-boronic acid. MS (ESI): mass calcd. for $C_{17}H_{20}N_4O_2S$, 344.1; m/z found, 345.2 [M+H]$^+$. $^1$H NMR (400 MHz, CDCl$_3$) δ 8.27-8.24 (d, J=1.8 Hz, 1H), 7.32-7.29 (d, J=1.9 Hz, 1H), 7.07-7.03 (d, J=3.5 Hz, 1H), 6.77-6.73 (m, 1H), 4.71-4.68 (s, 2H), 3.55-3.48 (s, 3H), 3.19-3.13 (s, 3H), 3.01-2.96 (s, 3H), 2.90-2.81 (m, 2H), 1.37-1.30 (m, 3H).

Example 80: N,N-Dimethyl-2-[3-methyl-6-(4-methyl-2-thienyl)-2-oxo-imidazo[4,5-b]pyridin-1-yl]acetamide

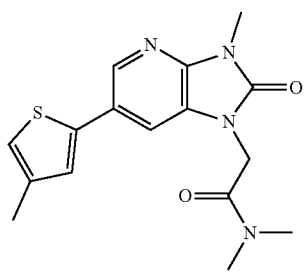 [SMILES: Cc1csc(-c2cnc3c(c2)n(CC(=O)N(C)C)c(=O)n3C)c1]

The title compound was prepared in a manner analogous to Example 9, using 4,4,5,5-tetramethyl-2-(4-methylthiophen-2-yl)-1,3,2-dioxaborolane and 2-(6-bromo-3-methyl-2-oxo-2,3-dihydro-1H-imidazo[4,5-b]pyridin-1-yl)-N,N-dimethylacetamide (Intermediate 15). MS (ESI): mass calcd. for $C_{16}H_{18}N_4O_2S$, 330.1; m/z found, 331.2 [M+H]$^+$. $^1$H NMR (400 MHz, CDCl$_3$) δ 8.30-8.27 (d, J=1.9 Hz, 1H), 7.35-7.31 (d, J=1.9 Hz, 1H), 7.08-7.04 (d, J=1.4 Hz, 1H), 6.88-6.84 (m, 1H), 4.76-4.66 (s, 2H), 3.55-3.49 (s, 3H), 3.20-3.14 (s, 3H), 3.04-2.96 (s, 3H), 2.33-2.25 (d, J=1.1 Hz, 3H).

Example 81: 1-[2-(Azetidin-1-yl)-2-oxo-ethyl]-6-(5-fluoro-2-thienyl)-3-methyl-imidazo[4,5-b]pyridin-2-one

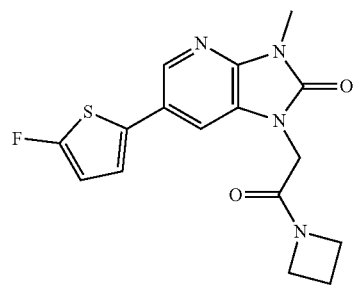 [SMILES: Cn1c(=O)n(CC(=O)N2CCC2)c2cc(-c3ccc(F)s3)cnc21]

The title compound was prepared in a manner analogous to Example 9, using 1-(2-(azetidin-1-yl)-2-oxoethyl)-6-bromo-3-methyl-1,3-dihydro-2H-imidazo[4,5-b]pyridin-2-one (Intermediate 16) and 2-(5-fluoro-2-thienyl)-4,4,5,5-tetramethyl-1,3,2-dioxaborolane. MS (ESI): mass calcd. for $C_{16}H_{15}FN_4O_2S$, 346.1; m/z found, 346.9 [M+H]$^+$. $^1$H NMR (500 MHz, CDCl$_3$) δ 8.19-8.17 (d, J=1.9 Hz, 1H), 7.36-7.33 (d, J=1.9 Hz, 1H), 6.85-6.82 (m, 1H), 6.48-6.45 (m, 1H), 4.50-4.45 (s, 2H), 4.35-4.28 (m, 2H), 4.12-4.06 (m, 2H), 3.53-3.50 (s, 3H), 2.41-2.31 (m, 2H).

Example 82: 2-[6-(5-Fluoro-2-thienyl)-3-methyl-2-oxo-imidazo[4,5-b]pyridin-1-yl]-N,N-dimethyl-acetamide

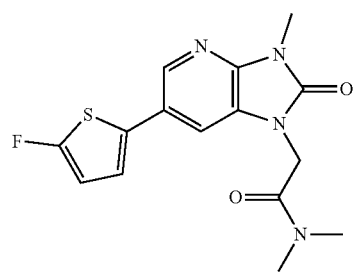

The title compound was prepared in a manner analogous to Example 9, using 2-(5-fluoro-2-thienyl)-4,4,5,5-tetramethyl-1,3,2-dioxaborolane and 2-(6-bromo-3-methyl-2-oxo-2,3-dihydro-1H-imidazo[4,5-b]pyridin-1-yl)-N,N-dimethyl-acetamide (Intermediate 15). MS (ESI): mass calcd. for $C_{15}H_{15}FN_4O_2S$, 334.1; m/z found, 334.9 [M+H]$^+$. $^1$H NMR (500 MHz, CDCl$_3$) δ 8.19-8.17 (d, J=1.9 Hz, 1H), 7.25-7.24 (d, J=1.9 Hz, 1H), 6.84-6.81 (m, 1H), 6.47-6.44 (dd, J=4.1, 1.9 Hz, 1H), 4.72-4.69 (s, 2H), 3.53-3.50 (s, 3H), 3.19-3.15 (s, 3H), 3.02-2.97 (s, 3H).

Example 83: 1-[2-(3-Fluoroazetidin-1-yl)-2-oxo-ethyl]-6-(5-fluoro-2-thienyl)-3-methyl-imidazo[4,5-b]pyridin-2-one

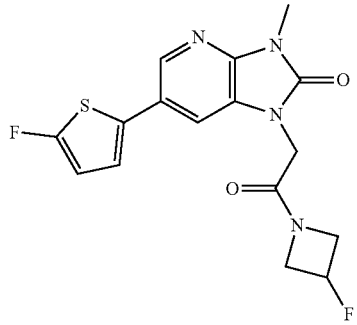 [SMILES: Cn1c(=O)n(CC(=O)N2CC(F)C2)c2cc(-c3ccc(F)s3)cnc21]

The title compound was prepared in a manner analogous to Example 9, using 6-bromo-1-(2-(3-fluoroazetidin-1-yl)-2-oxoethyl)-3-methyl-1,3-dihydro-2H-imidazo[4,5-b]pyridin-2-one (Intermediate 18) and 2-(5-fluoro-2-thienyl)-4,4,5,5-tetramethyl-1,3,2-dioxaborolane. MS (ESI): mass calcd. for $C_{16}H_{14}F_2N_4O_2S$, 364.1; m/z found, 364.9 [M+H]$^+$. $^1$H NMR (500 MHz, CDCl$_3$) δ 8.21-8.19 (d, J=1.9 Hz, 1H), 7.35-7.32 (d, J=1.9 Hz, 1H), 6.86-6.83 (m, 1H), 6.48-6.45 (m, 1H), 5.45-5.27 (m, 1H), 4.66-4.11 (m, 6H), 3.52-3.51 (s, 3H).

Example 84: 3-Methyl-1-(pyridazin-3-ylmethyl)-6-[5-(trifluoromethyl)-2-thienyl]imidazo[4,5-b]pyridin-2-one

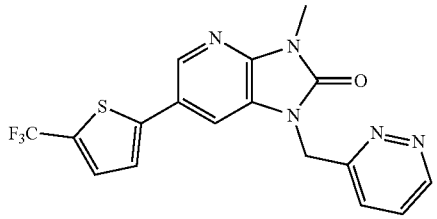 [SMILES: Cn1c(=O)n(Cc2cccnn2)c2cc(-c3ccc(C(F)(F)F)s3)cnc21]

The title compound was prepared in a manner analogous to Example 9, using 6-bromo-3-methyl-1-(pyridazin-3-ylmethyl)-1,3-dihydro-2H-imidazo[4,5-b]pyridin-2-one (Intermediate 19) and (5-(trifluoromethyl)thiophen-2-yl)boronic acid. MS (ESI): mass calcd. for $C_{17}H_{12}F_3N_5OS$, 391.1; m/z found, 391.9 [M+H]$^+$. $^1$H NMR (400 MHz, CDCl$_3$) δ 9.20-9.12 (d, J=4.6 Hz, 1H), 8.32-8.27 (d, J=1.4 Hz, 1H), 7.67-7.62 (d, J=8.3 Hz, 1H), 7.57-7.53 (d, J=1.9 Hz, 1H), 7.53-7.46 (m, 1H), 7.43-7.39 (s, 1H), 7.21-7.13 (s, 1H), 5.46-5.41 (s, 2H), 3.58-3.51 (s, 3H).

Example 85: 6-(5-Fluoro-2-thienyl)-3-methyl-1-(pyridazin-3-ylmethyl)imidazo[4,5-b]pyridin-2-one

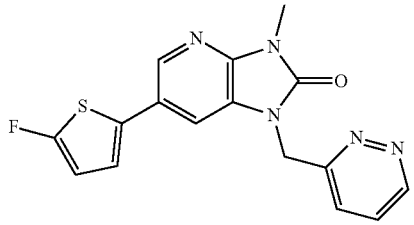 [SMILES: Cn1c(=O)n(Cc2cccnn2)c2cc(-c3ccc(F)s3)cnc21]

The title compound was prepared in a manner analogous to Example 9, using 6-bromo-3-methyl-1-(pyridazin-3-ylmethyl)-1,3-dihydro-2H-imidazo[4,5-b]pyridin-2-one (Intermediate 19) and 2-(5-fluoro-2-thienyl)-4,4,5,5-tetramethyl-1,3,2-dioxaborolane. MS (ESI): mass calcd. for $C_{16}H_{12}FN_5OS$, 341.1; m/z found, 341.9 [M+H]$^+$. $^1$H NMR (400 MHz, CDCl$_3$) δ 9.18-9.12 (m, 1H), 8.19-8.12 (d, J=1.9 Hz, 1H), 7.66-7.58 (dd, J=8.5, 1.7 Hz, 1H), 7.51-7.46 (dd, J=8.5, 4.9 Hz, 1H), 7.46-7.42 (d, J=1.9 Hz, 1H), 6.83-6.79 (m, 1H), 6.48-6.42 (m, 1H), 5.47-5.39 (s, 2H), 3.56-3.51 (s, 3H).

Example 86: 1-[2-(3-Fluoroazetidin-1-yl)-2-oxo-ethyl]-3-methyl-6-(4-methylthiazol-2-yl)imidazo[4,5-b]pyridin-2-one

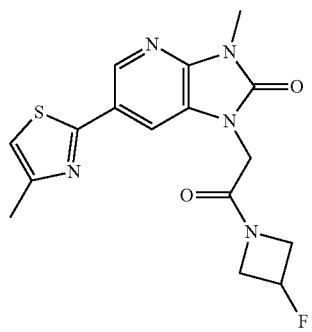 [SMILES: Cc1csc(-c2cnc3c(c2)n(CC(=O)N2CC(F)C2)c(=O)n3C)n1]

The title compound was prepared in a manner analogous to Example 9, using 6-bromo-1-(2-(3-fluoroazetidin-1-yl)-2-oxoethyl)-3-methyl-1,3-dihydro-2H-imidazo[4,5-b]pyridin-2-one (Intermediate 18) and 4-methylthiazol-2yl boronic acid pinacol ester. MS (ESI): mass calcd. for $C_{16}H_{16}FN_5O_2S$, 361.1; m/z found, 361.9 [M+H]$^+$. $^1$H NMR (500 MHz, CDCl$_3$) δ 8.59-8.56 (d, J=1.8 Hz, 1H), 7.86-7.80 (d, J=1.8 Hz, 1H), 6.91-6.84 (m, 1H), 5.46-5.26 (m, 1H), 4.65-4.11 (m, 6H), 3.56-3.51 (s, 3H), 2.54-2.46 (d, J=1.0 Hz, 3H).

Example 87: 1-[2-(Azetidin-1-yl)-2-oxo-ethyl]-6-(5-ethyl-2-thienyl)-3-methyl-imidazo[4,5-b]pyridin-2-one

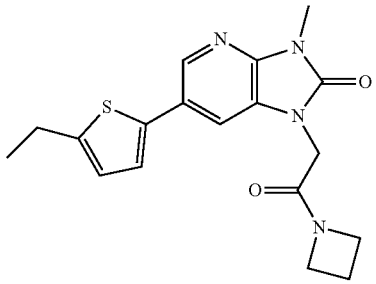 [SMILES: CCc1ccc(-c2cnc3c(c2)n(CC(=O)N2CCC2)c(=O)n3C)s1]

The title compound was prepared in a manner analogous to Example 9, using 1-(2-(azetidin-1-yl)-2-oxoethyl)-6-bromo-3-methyl-1,3-dihydro-2H-imidazo[4,5-b]pyridin-2-one (Intermediate 16) and 5-ethylthiophene-2-boronic acid. MS (ESI): mass calcd. for $C_{18}H_{20}N_4O_2S$, 356.1; m/z found, 356.9 [M+H]$^+$. $^1$H NMR (500 MHz, CDCl$_3$) δ 8.28-8.25 (d, J=1.9 Hz, 1H), 7.42-7.38 (d, J=1.9 Hz, 1H), 7.09-7.05 (d, J=3.5 Hz, 1H), 6.78-6.74 (m, 1H), 4.51-4.44 (s, 2H), 4.32-4.25 (m, 2H), 4.13-4.04 (m, 2H), 3.53-3.49 (s, 3H), 2.90-2.82 (m, 2H), 2.39-2.29 (m, 2H), 1.36-1.30 (m, 3H).

Example 88: 6-(5-Ethyl-2-thienyl)-1-[2-(3-fluoro-azetidin-1-yl)-2-oxo-ethyl]-3-methyl-imidazo[4,5-b]pyridin-2-one

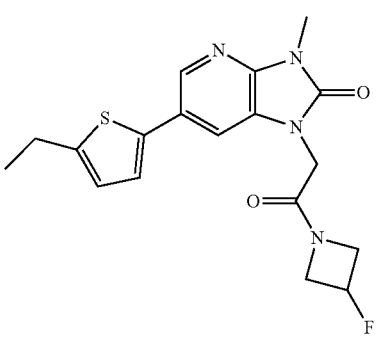 [SMILES: CCc1ccc(-c2cnc3c(c2)n(CC(=O)N2CC(F)C2)c(=O)n3C)s1]

The title compound was prepared in a manner analogous to Example 9, using 6-bromo-1-(2-(3-fluoroazetidin-1-yl)-2-oxoethyl)-3-methyl-1,3-dihydro-2H-imidazo[4,5-b]pyridin-2-one (Intermediate 18) and 5-ethylthiophene-2-boronic acid. MS (ESI): mass calcd. for $C_{18}H_{19}FN_4O_2S$, 374.1; m/z found, 374.9 [M+H]$^+$. $^1$H NMR (500 MHz, CDCl$_3$) δ 8.31-8.26 (d, J=1.9 Hz, 1H), 7.41-7.36 (d, J=1.9 Hz, 1H), 7.10-7.05 (d, J=3.5 Hz, 1H), 6.79-6.72 (m, 1H), 5.43-5.22 (m, 1H), 4.64-4.09 (m, 6H), 3.52-3.50 (s, 3H), 2.90-2.81 (m, 2H), 1.36-1.29 (t, J=7.5 Hz, 3H).

Example 89: 1-[2-(Azetidin-1-yl)-2-oxo-ethyl]-6-[5-(hydroxymethyl)-2-thienyl]-3-methyl-imidazo[4,5-b]pyridin-2-one

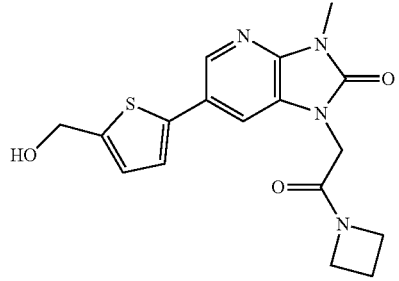 [SMILES: Cn1c(=O)n(CC(=O)N2CCC2)c2cc(-c3ccc(CO)s3)cnc21]

The title compound was prepared in a manner analogous to Example 9, using 1-(2-(azetidin-1-yl)-2-oxoethyl)-6-bromo-3-methyl-1,3-dihydro-2H-imidazo[4,5-b]pyridin-2-one (Intermediate 16) and (5-(4,4,5,5-tetramethyl-1,3,2-dioxaborolan-2-yl)thiophen-2-yl)methanol. MS (ESI): mass calcd. for $C_{17}H_{18}N_4O_3S$, 358.1; m/z found, 358.9 [M+H]$^+$. $^1$H NMR (400 MHz, DMSO-d$_6$) δ 8.28-8.25 (d, J=1.9 Hz, 1H), 7.74-7.71 (d, J=2.0 Hz, 1H), 7.33-7.30 (d, J=3.6 Hz, 1H), 6.99-6.96 (m, 1H), 5.55-5.49 (m, 1H), 4.66-4.62 (m, 2H), 4.62-4.56 (s, 2H), 4.33-4.26 (m, 2H), 3.95-3.88 (m, 2H), 3.38-3.35 (s, 3H), 2.36-2.23 (m, 2H).

Example 90: 1-[2-(3-Fluoroazetidin-1-yl)-2-oxo-ethyl]-6-[5-(hydroxymethyl)-2-thienyl]-3-methyl-imidazo[4,5-b]pyridin-2-one

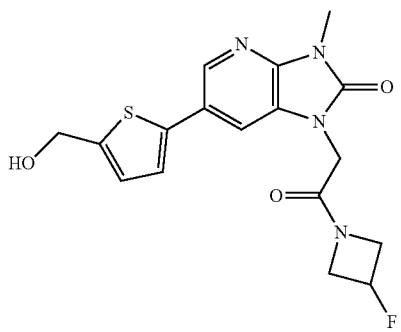 [SMILES: Cn1c(=O)n(CC(=O)N2CC(F)C2)c2cc(-c3ccc(CO)s3)cnc21]

The title compound was prepared in a manner analogous to Example 9, using 6-bromo-1-(2-(3-fluoroazetidin-1-yl)-2-oxoethyl)-3-methyl-1,3-dihydro-2H-imidazo[4,5-b]pyridin-2-one (Intermediate 18) and (5-(4,4,5,5-tetramethyl-1,3,2-dioxaborolan-2-yl)thiophen-2-yl)methanol. MS (ESI): mass calcd. for $C_{17}H_{17}FN_4O_3S$, 376.1; m/z found, 376.9 [M+H]$^+$. $^1$H NMR (400 MHz, DMSO-d$_6$) δ 8.28-8.26 (d, J=1.9 Hz, 1H), 7.73-7.70 (d, J=2.0 Hz, 1H), 7.33-7.29 (d, J=3.6 Hz, 1H), 6.98-6.96 (m, 1H), 5.58-5.37 (m, 2H), 4.70-4.58 (m, 5H), 4.48-4.34 (m, 1H), 4.32-4.20 (m, 1H), 4.04-3.90 (m, 1H), 3.39-3.35 (s, 3H).

Example 91: 2-[6-[5-(Hydroxymethyl)-2-thienyl]-3-methyl-2-oxo-imidazo[4,5-b]pyridin-1-yl]-N,N-dimethyl-acetamide

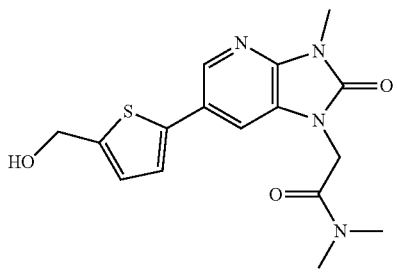 [SMILES: CN(C)C(=O)Cn1c(=O)n(C)c2ncc(-c3ccc(CO)s3)cc21]

The title compound was prepared in a manner analogous to Example 9, using (5-(4,4,5,5-tetramethyl-1,3,2-dioxaborolan-2-yl)thiophen-2-yl)methanol and 2-(6-bromo-3-methyl-2-oxo-2,3-dihydro-1H-imidazo[4,5-b]pyridin-1-yl)-N,N-dimethylacetamide (Intermediate 15). MS (ESI): mass calcd. for $C_{16}H_{18}N_4O_3S$, 346.1; m/z found, 347.0 [M+H]$^+$. $^1$H NMR (400 MHz, DMSO-d$_6$) δ 8.28-8.24 (d, J=1.9 Hz, 1H), 7.75-7.71 (d, J=2.0 Hz, 1H), 7.32-7.27 (d, J=3.6 Hz, 1H), 6.99-6.94 (d, J=3.6 Hz, 1H), 5.54-5.48 (t, J=5.7 Hz, 1H), 4.87-4.80 (s, 2H), 4.68-4.59 (m, 2H), 3.40-3.34 (s, 3H), 3.15-3.06 (s, 3H), 2.89-2.81 (s, 3H).

Example 92: 1-[2-(3-Fluoroazetidin-1-yl)-2-oxo-ethyl]-3-methyl-6-[2-(trifluoromethyl)-3-thienyl]imidazo[4,5-b]pyridin-2-one

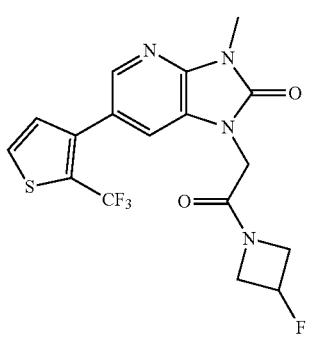 [SMILES: Cn1c(=O)n(CC(=O)N2CC(F)C2)c2cc(-c3ccsc3C(F)(F)F)cnc21]

The title compound was prepared in a manner analogous to Example 10, using 3-bromo-2-(trifluoromethyl) thiophene and 6-bromo-1-(2-(3-fluoroazetidin-1-yl)-2-oxoethyl)-3-methyl-1,3-dihydro-2H-imidazo[4,5-b]pyridin-2-one (Intermediate 18). MS (ESI): mass calcd. for $C_{17}H_{14}F_4N_4O_2S$, 414.1; m/z found, 414.9 [M+H]$^+$. $^1$H NMR (500 MHz, CDCl$_3$) δ 8.17-8.11 (d, J=1.9 Hz, 1H), 7.53-7.50 (d, J=5.1 Hz, 1H), 7.36-7.32 (d, J=1.9 Hz, 1H), 7.12-7.08 (dd, J=4.5, 1.7 Hz, 1H), 5.44-5.26 (m, 1H), 4.64-4.11 (m, 6H), 3.58-3.51 (s, 3H).

Example 93: 1-[2-(Azetidin-1-yl)-2-oxo-ethyl]-6-[5-(difluoromethyl)-2-thienyl]-3-methyl-imidazo[4,5-b]pyridin-2-one

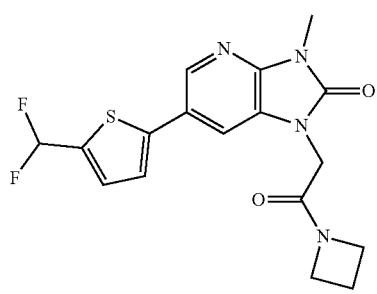 [SMILES: Cn1c(=O)n(CC(=O)N2CCC2)c2cc(-c3ccc(C(F)F)s3)cnc21]

The title compound was prepared in a manner analogous to Example 10 using 1-(2-(azetidin-1-yl)-2-oxoethyl)-6-bromo-3-methyl-1,3-dihydro-2H-imidazo[4,5-b]pyridin-2-one (Intermediate 16). MS (ESI): mass calcd. for $C_{17}H_{16}F_2N_4O_2S$, 378.1; m/z found, 378.9 [M+H]$^+$. $^1$H NMR (500 MHz, CDCl$_3$) δ 8.33-8.27 (d, J=2.0 Hz, 1H), 7.47-7.40 (d, J=2.1 Hz, 1H), 7.26-7.24 (m, 1H), 7.21-7.15 (m, 1H), 6.96-6.68 (t, J=56.1 Hz, 1H), 4.53-4.43 (s, 2H), 4.38-4.25 (m, 2H), 4.12-4.05 (m, 2H), 3.55-3.50 (s, 3H), 2.43-2.26 (m, 2H).

Example 94: 2-[6-[5-(Difluoromethyl)-2-thienyl]-3-methyl-2-oxo-imidazo[4,5-b]pyridin-1-yl]-N,N-dimethyl-acetamide

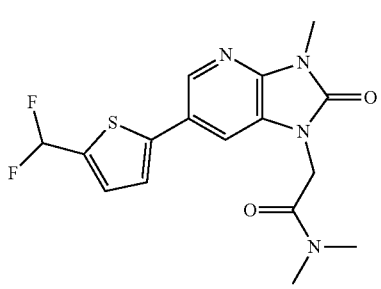 [SMILES: CN(C)C(=O)Cn1c(=O)n(C)c2ncc(-c3ccc(C(F)F)s3)cc21]

The title compound was prepared in a manner analogous to Example 10 using 2-(6-bromo-3-methyl-2-oxo-2,3-dihydro-1H-imidazo[4,5-b]pyridin-1-yl)-N,N-dimethylacetamide (Intermediate 15). MS (ESI): mass calcd. for $C_{16}H_{16}F_2N_4O_2S$, 366.1; m/z found, 366.9 [M+H]$^+$. $^1$H NMR (500 MHz, CDCl$_3$) δ 8.33-8.28 (d, J=1.9 Hz, 1H), 7.35-7.31 (d, J=1.9 Hz, 1H), 7.26-7.24 (m, 1H), 7.18-7.15 (m, 1H), 6.95-6.70 (m, 1H), 4.75-4.68 (s, 2H), 3.56-3.50 (s, 3H), 3.20-3.14 (s, 3H), 3.02-2.96 (s, 3H).

Example 95: 1-[2-(Azetidin-1-yl)-2-oxo-ethyl]-3-methyl-6-[2-(trifluoromethyl)-3-thienyl]imidazo[4,5-b]pyridin-2-one

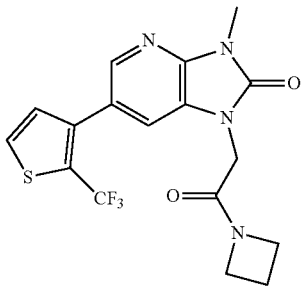 [SMILES: Cn1c(=O)n(CC(=O)N2CCC2)c2cc(-c3ccsc3C(F)(F)F)cnc21]

The title compound was prepared in a manner analogous to Example 10 using 3-bromo-2-(trifluoromethyl) thiophene and 1-(2-(azetidin-1-yl)-2-oxoethyl)-6-bromo-3-methyl-1,3-dihydro-2H-imidazo[4,5-b]pyridin-2-one (Intermediate 16). MS (ESI): mass calcd. for $C_{17}H_{15}F_3N_4O_2S$, 396.1; m/z found, 396.9 [M+H]$^+$. $^1$H NMR (500 MHz, CDCl$_3$) δ 8.15-8.10 (d, J=1.8 Hz, 1H), 7.52-7.49 (d, J=5.1 Hz, 1H), 7.36-7.32 (d, J=1.8 Hz, 1H), 7.12-7.08 (m, 1H), 4.50-4.43 (s, 2H), 4.33-4.27 (m, 2H), 4.11-4.04 (m, 2H), 3.56-3.51 (s, 3H), 2.39-2.29 (m, 2H).

Example 96: N,N-Dimethyl-2-[3-methyl-2-oxo-6-[2-(trifluoromethyl)-3-thienyl]imidazo[4,5-b]pyridin-1-yl]acetamide

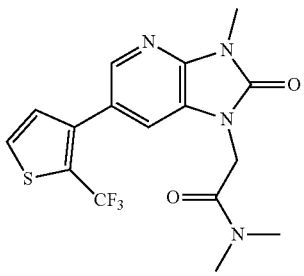 [SMILES: CN(C)C(=O)Cn1c(=O)n(C)c2ncc(-c3ccsc3C(F)(F)F)cc21]

The title compound was prepared in a manner analogous to Example 10, using 3-Bromo-2-(trifluoromethyl) thiophene and 2-(6-bromo-3-methyl-2-oxo-2,3-dihydro-1H-imidazo[4,5-b]pyridin-1-yl)-N,N-dimethylacetamide (Intermediate 15). MS (ESI): mass calcd. for $C_{16}H_{15}F_3N_4O_2S$, 384.1; m/z found, 384.9 [M+H]$^+$. $^1$H NMR (500 MHz, CDCl$_3$) δ 8.14-8.09 (d, J=1.8 Hz, 1H), 7.52-7.48 (d, J=5.1 Hz, 1H), 7.26-7.25 (d, J=2.2 Hz, 1H), 7.12-7.07 (m, 1H), 4.73-4.68 (s, 2H), 3.57-3.51 (s, 3H), 3.18-3.13 (s, 3H), 3.00-2.94 (s, 3H).

Example 97: 2-[6-[5-(Difluoromethyl)-3-thienyl]-3-methyl-2-oxo-imidazo[4,5-b]pyridin-1-yl]-N,N-dimethyl-acetamide

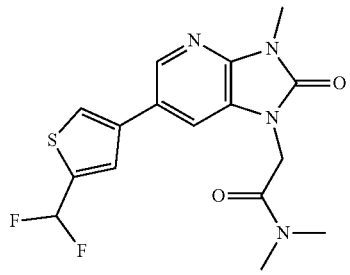

The title compound was prepared in a manner analogous to Example 10, using 4-bromo-2-(difluoromethyl)-thiophene and 2-(6-bromo-3-methyl-2-oxo-2,3-dihydro-1H-imidazo[4,5-b]pyridin-1-yl)-N,N-dimethylacetamide (Intermediate 15). MS (ESI): mass calcd. for $C_{16}H_{16}F_2N_4O_2S$, 366.1; m/z found, 366.9 [M+H]$^+$. $^1$H NMR (500 MHz, CDCl$_3$) δ 8.27-8.26 (d, J=1.8 Hz, 1H), 7.52-7.50 (m, 2H), 7.35-7.34 (d, J=1.9 Hz, 1H), 6.99-6.75 (t, J=56.1 Hz, 1H), 4.74-4.71 (s, 2H), 3.55-3.52 (s, 3H), 3.19-3.16 (s, 3H), 3.01-2.98 (s, 3H).

Example 98: 1-[2-(Azetidin-1-yl)-2-oxo-ethyl]-6-[5-(difluoromethyl)-3-thienyl]-3-methyl-imidazo[4,5-b]pyridin-2-one

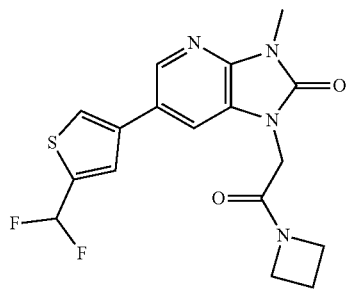

The title compound was prepared in a manner analogous to Example 10, using 4-bromo-2-(difluoromethyl)-thiophene and 1-(2-(azetidin-1-yl)-2-oxoethyl)-6-bromo-3-methyl-1,3-dihydro-2H-imidazo[4,5-b]pyridin-2-one (Intermediate 16). MS (ESI): mass calcd. for $C_{17}H_{16}F_2N_4O_2S$, 378.1; m/z found, 378.9 [M+H]$^+$. $^1$H NMR (400 MHz, CDCl$_3$) δ 8.28-8.27 (d, J=1.8 Hz, 1H), 7.55-7.51 (m, 2H), 7.45-7.43 (d, J=1.8 Hz, 1H), 7.02-6.72 (m, 1H), 4.52-4.47 (s, 2H), 4.36-4.29 (m, 2H), 4.12-4.05 (m, 2H), 3.54-3.51 (s, 3H), 2.41-2.30 (m, 2H).

Example 99: 6-[5-(Difluoromethyl)-3-thienyl]-1-[2-(3-fluoroazetidin-1-yl)-2-oxo-ethyl]-3-methyl-imidazo[4,5-b]pyridin-2-one

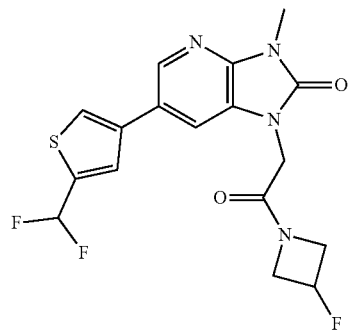 [SMILES: Cn1c(=O)n(CC(=O)N2CC(F)C2)c2cc(-c3csc(C(F)F)c3)cnc21]

The title compound was prepared in a manner analogous to Example 10, using 4-bromo-2-(difluoromethyl)-thiophene and 6-bromo-1-(2-(3-fluoroazetidin-1-yl)-2-oxo-ethyl)-3-methyl-1,3-dihydro-2H-imidazo[4,5-b]pyridin-2-one (Intermediate 18). MS (ESI): mass calcd. for $C_{17}H_{15}F_3N_4O_2S$, 396.1; m/z found, 369.9 [M+H]$^+$. $^1$H NMR (400 MHz, CDCl$_3$) δ 8.30-8.28 (d, J=1.7 Hz, 1H), 7.54-7.51 (m, 2H), 7.44-7.42 (d, J=1.8 Hz, 1H), 7.03-6.71 (m, 1H), 5.46-5.25 (d, J=56.3 Hz, 1H), 4.70-4.10 (m, 6H), 3.56-3.51 (s, 3H).

Example 100: 6-[5-(Difluoromethyl)-2-thienyl]-3-methyl-1-(pyridazin-3-ylmethyl)imidazo[4,5-b]pyridin-2-one

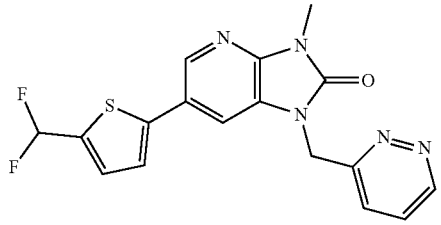 [SMILES: Cn1c(=O)n(Cc2cccnn2)c2cc(-c3ccc(C(F)F)s3)cnc21]

The title compound was prepared in a manner analogous to Example 10, using 6-bromo-3-methyl-1-(pyridazin-3-ylmethyl)-1,3-dihydro-2H-imidazo[4,5-b]pyridin-2-one (Intermediate 19). MS (ESI): mass calcd. for $C_{17}H_{13}F_2N_5OS$, 373.1; m/z found, 373.9 [M+H]$^+$. $^1$H NMR (400 MHz, CDCl$_3$) δ 9.18-9.13 (m, 1H), 8.31-8.28 (d, J=1.9 Hz, 1H), 7.66-7.62 (m, 1H), 7.55-7.53 (d, J=1.9 Hz, 1H), 7.51-7.47 (m, 1H), 7.26-7.23 (m, 1H), 7.18-7.15 (m, 1H), 6.98-6.67 (m, 1H), 5.45-5.42 (s, 2H), 3.56-3.53 (s, 3H).

Example 101: N,N-Dimethyl-2-[3-methyl-2-oxo-6-[5-(trifluoromethyl)-3-thienyl]imidazo[4,5-b]pyridin-1-yl]acetamide

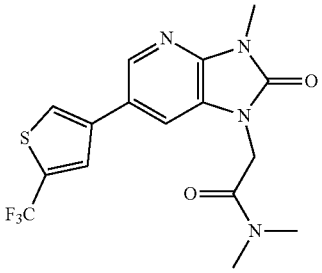 [SMILES: CN(C)C(=O)Cn1c(=O)n(C)c2ncc(-c3csc(C(F)(F)F)c3)cc21]

The title compound was prepared in a manner analogous to Example 10, using 4-bromo-2-(trifluoromethyl)thiophene and 2-(6-bromo-3-methyl-2-oxo-2,3-dihydro-1H-imidazo[4,5-b]pyridin-1-yl)-N,N-dimethylacetamide (Intermediate 15). MS (ESI): mass calcd. for $C_{16}H_{15}F_3N_4O_2S$, 384.1; m/z found, 384.9 [M+H]$^+$. $^1$H NMR (500 MHz, CDCl$_3$) δ 8.27-8.25 (d, J=1.8 Hz, 1H), 7.67-7.64 (m, 1H), 7.56-7.53 (d, J=1.6 Hz, 1H), 7.35-7.32 (d, J=1.9 Hz, 1H), 4.75-4.72 (s, 2H), 3.55-3.53 (s, 3H), 3.19-3.17 (s, 3H), 3.01-2.98 (s, 3H).

Example 102: 1-[2-(3-Fluoroazetidin-1-yl)-2-oxo-ethyl]-3-methyl-6-[5-(trifluoromethyl)-3-thienyl]imidazo[4,5-b]pyridin-2-one

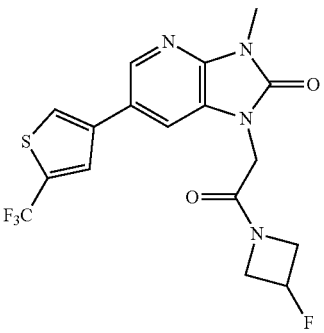 [SMILES: Cn1c(=O)n(CC(=O)N2CC(F)C2)c2cc(-c3csc(C(F)(F)F)c3)cnc21]

The title compound was prepared in a manner analogous to Example 10, using 4-bromo-2-(trifluoromethyl)thiophene and 6-bromo-1-(2-(3-fluoroazetidin-1-yl)-2-oxoethyl)-3-methyl-1,3-dihydro-2H-imidazo[4,5-b]pyridin-2-one (Intermediate 18). MS (ESI): mass calcd. for $C_{17}H_{14}F_4N_4O_2S$, 414.1; m/z found, 441.9 [M+H]$^+$. $^1$H NMR (500 MHz, CDCl$_3$) δ 8.29-8.27 (d, J=1.8 Hz, 1H), 7.68-7.66 (m, 1H), 7.57-7.55 (d, J=1.6 Hz, 1H), 7.44-7.41 (d, J=1.9 Hz, 1H), 5.45-5.26 (m, 1H), 4.68-4.10 (m, 6H), 3.54-3.53 (s, 3H).

Example 103: 3-Methyl-1-(pyridazin-3-ylmethyl)-6-[5-(trifluoromethyl)-3-thienyl]imidazo[4,5-b]pyridin-2-one

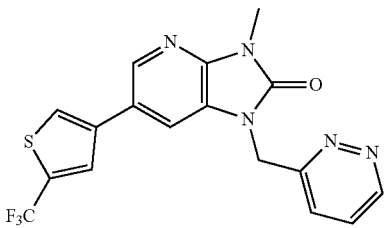 [SMILES: Cn1c(=O)n(Cc2cccnn2)c2cc(-c3csc(C(F)(F)F)c3)cnc21]

The title compound was prepared in a manner analogous to Example 10, using 4-bromo-2-(trifluoromethyl)thiophene and 6-bromo-3-methyl-1-(pyridazin-3-ylmethyl)-1,3-dihydro-2H-imidazo[4,5-b]pyridin-2-one (Intermediate 19). MS (ESI): mass calcd. for $C_{17}H_{12}F_3N_5OS$, 391.1; m/z found, 391.9 [M+H]$^+$. $^1$H NMR (500 MHz, CDCl$_3$) δ 9.17-9.13 (m, 1H), 8.28-8.23 (d, J=1.9 Hz, 1H), 7.68-7.65 (m, 1H), 7.65-7.63 (m, 1H), 7.55-7.53 (m, 2H), 7.51-7.48 (m, 1H), 5.48-5.41 (s, 2H), 3.61-3.53 (s, 3H).

Example 104: 1-[2-(Azetidin-1-yl)-2-oxo-ethyl]-3-methyl-6-[5-(trifluoromethyl)-3-thienyl]imidazo[4,5-b]pyridin-2-one

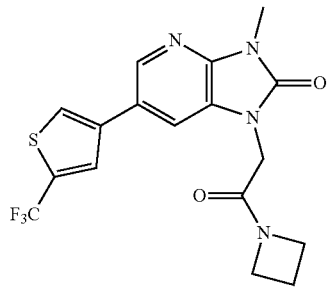 [SMILES: Cn1c(=O)n(CC(=O)N2CCC2)c2cc(-c3csc(C(F)(F)F)c3)cnc21]

The title compound was prepared in a manner analogous to Example 10, using 4-bromo-2-(trifluoromethyl)thiophene and 1-(2-(azetidin-1-yl)-2-oxoethyl)-6-bromo-3-methyl-1,3-dihydro-2H-imidazo[4,5-b]pyridin-2-one (Intermediate 16). MS (ESI): mass calcd. for $C_{17}H_{15}F_3N_4O_2S$, 396.1; m/z found, 397.1 [M+H]$^+$. $^1$H NMR (500 MHz, CDCl$_3$) δ 8.31-8.20 (s, 1H), 7.71-7.63 (s, 1H), 7.59-7.52 (s, 1H), 7.49-7.41 (s, 1H), 4.58-4.42 (s, 2H), 4.40-4.26 (m, 2H), 4.18-4.01 (m, 2H), 3.73-3.38 (s, 3H), 2.45-2.27 (m, 2H).

Example 105: 1-[2-(Azetidin-1-yl)-2-oxo-ethyl]-6-(5-cyclopropyl-2-thienyl)-3-methyl-imidazo[4,5-b]pyridin-2-one

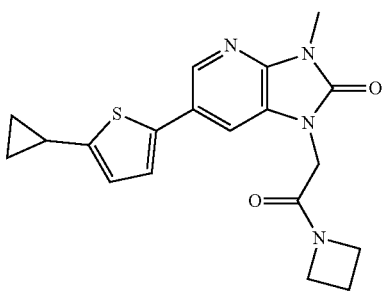 [SMILES: Cn1c(=O)n(CC(=O)N2CCC2)c2cc(-c3ccc(C4CC4)s3)cnc21]

The title compound was prepared in a manner analogous to Example 10, using 2-bromo-5-(cyclopropyl)thiophene and 1-(2-(azetidin-1-yl)-2-oxoethyl)-6-bromo-3-methyl-1,3-dihydro-2H-imidazo[4,5-b]pyridin-2-one (Intermediate 16). MS (ESI): mass calcd. for $C_{19}H_{20}N_4O_2S$, 368.1; m/z found, 369.1 [M+H]$^+$. $^1$H NMR (500 MHz, CDCl$_3$) δ 8.26-8.23 (d, J=1.8 Hz, 1H), 7.39-7.37 (d, J=1.9 Hz, 1H), 7.05-7.01 (d, J=3.6 Hz, 1H), 6.75-6.71 (m, 1H), 4.50-4.44 (s, 2H), 4.32-4.24 (m, 2H), 4.12-4.05 (m, 2H), 3.52-3.49 (s, 3H), 2.38-2.28 (m, 2H), 2.12-2.04 (m, 1H), 1.05-0.97 (m, 2H), 0.80-0.72 (m, 2H).

Example 106: 6-(5-Cyclopropyl-2-thienyl)-1-[2-(3-fluoroazetidin-1-yl)-2-oxo-ethyl]-3-methyl-imidazo[4,5-b]pyridin-2-one

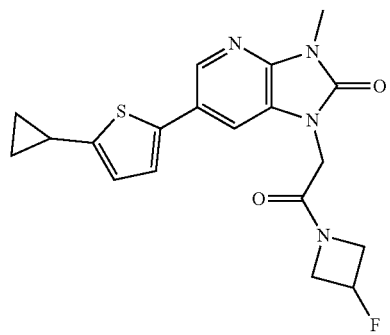 [SMILES: Cn1c(=O)n(CC(=O)N2CC(F)C2)c2cc(-c3ccc(C4CC4)s3)cnc21]

The title compound was prepared in a manner analogous to Example 10, using 2-bromo-5-(cyclopropyl)thiophene and 6-bromo-1-(2-(3-fluoroazetidin-1-yl)-2-oxoethyl)-3-methyl-1,3-dihydro-2H-imidazo[4,5-b]pyridin-2-one (Intermediate 18). MS (ESI): mass calcd. for $C_{19}H_{19}FN_4O_2S$, 386.1; m/z found, 387.1 [M+H]$^+$. $^1$H NMR (500 MHz, CDCl$_3$) δ 8.28-8.24 (d, J=1.9 Hz, 1H), 7.39-7.34 (d, J=1.9 Hz, 1H), 7.06-7.00 (d, J=3.6 Hz, 1H), 6.76-6.71 (m, 1H), 5.43-5.26 (m, 1H), 4.62-4.11 (m, 6H), 3.55-3.47 (s, 3H), 2.14-2.03 (m, 1H), 1.04-0.98 (m, 2H), 0.79-0.74 (m, 2H).

Example 107: 1-[2-(Azetidin-1-yl)-2-oxo-ethyl]-3-methyl-6-[2-(trifluoromethyl)thiazol-4-yl]imidazo[4,5-b]pyridin-2-one

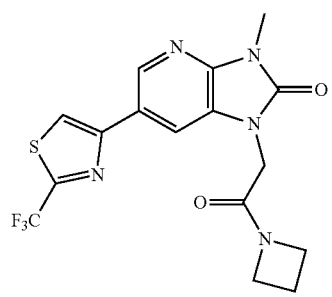 [SMILES: Cn1c(=O)n(CC(=O)N2CCC2)c2cc(-c3csc(C(F)(F)F)n3)cnc21]

The title compound was prepared in a manner analogous to Example 10, using 4-bromo-2-(trifluoromethyl)-1,3-thiazole and 1-(2-(azetidin-1-yl)-2-oxoethyl)-6-bromo-3-methyl-1,3-dihydro-2H-imidazo[4,5-b]pyridin-2-one (Intermediate 16). MS (ESI): mass calcd. for $C_{16}H_{14}F_3N_5O_2S$, 397.1; m/z found, 397.9 [M+H]$^+$. $^1$H NMR (500 MHz, CDCl$_3$) δ 8.58-8.55 (d, J=1.8 Hz, 1H), 7.83-7.79 (d, J=1.9

Hz, 1H), 7.71-7.67 (s, 1H), 4.54-4.49 (s, 2H), 4.38-4.29 (m, 2H), 4.11-4.05 (m, 2H), 3.55-3.52 (s, 3H), 2.43-2.31 (m, 2H).

Example 108: N,N-Dimethyl-2-[3-methyl-2-oxo-6-[2-(trifluoromethyl)thiazol-4-yl]imidazo[4,5-b]pyridin-1-yl]acetamide

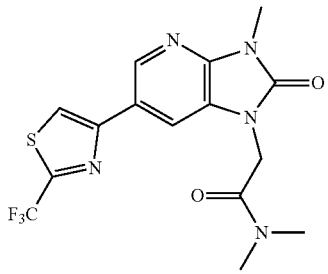 [SMILES: CN(C)C(=O)Cn1c(=O)n(C)c2ncc(-c3csc(C(F)(F)F)n3)cc21]

The title compound was prepared in a manner analogous to Example 10, using 4-bromo-2-(trifluoromethyl)-1,3-thiazole and 2-(6-bromo-3-methyl-2-oxo-2,3-dihydro-1H-imidazo[4,5-b]pyridin-1-yl)-N,N-dimethylacetamide (Intermediate 15). MS (ESI): mass calcd. for $C_{15}H_{14}F_3N_5O_2S$, 385.1; m/z found, 385.9 [M+H]$^+$. $^1$H NMR (500 MHz, CDCl$_3$) δ 8.56-8.51 (d, J=1.8 Hz, 1H), 7.76-7.70 (d, J=1.8 Hz, 1H), 7.70-7.66 (s, 1H), 4.78-4.72 (s, 2H), 3.56-3.51 (s, 3H), 3.19-3.15 (s, 3H), 3.01-2.96 (s, 3H).

Example 109: 1-[2-(3-Fluoroazetidin-1-yl)-2-oxoethyl]-3-methyl-6-[2-(trifluoromethyl)thiazol-4-yl]imidazo[4,5-b]pyridin-2-one

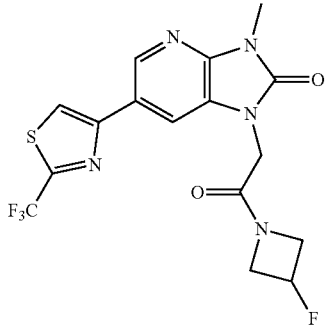 [SMILES: Cn1c(=O)n(CC(=O)N2CC(F)C2)c2cc(-c3csc(C(F)(F)F)n3)cnc21]

The title compound was prepared in a manner analogous to Example 10, using 4-bromo-2-(trifluoromethyl)-1,3-thiazole and 6-bromo-1-(2-(3-fluoroazetidin-1-yl)-2-oxoethyl)-3-methyl-1,3-dihydro-2H-imidazo[4,5-b]pyridin-2-one (Intermediate 18). MS (ESI): mass calcd. for $C_{16}H_{13}F_4N_5O_2S$, 415.1; m/z found, 415.9 [M+H]$^+$. $^1$H NMR (500 MHz, CDCl$_3$) δ 8.59-8.55 (d, J=1.8 Hz, 1H), 7.84-7.79 (d, J=1.8 Hz, 1H), 7.73-7.68 (s, 1H), 5.46-5.29 (m, 1H), 4.67-4.11 (m, 6H), 3.56-3.51 (s, 3H).

Example 110: 2-[6-(5-Cyclopropyl-2-thienyl)-3-methyl-2-oxo-imidazo[4,5-b]pyridin-1-yl]-N,N-dimethyl-acetamide

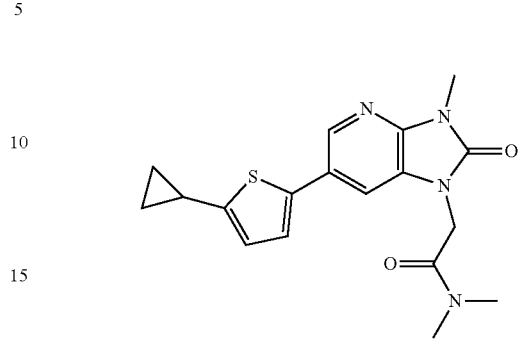

The title compound was prepared in a manner analogous to Example 10, using 2-bromo-5-(cyclopropyl)thiophene and 2-(6-bromo-3-methyl-2-oxo-2,3-dihydro-1H-imidazo[4,5-b]pyridin-1-yl)-N,N-dimethylacetamide (Intermediate 15). MS (ESI): mass calcd. for $C_{18}H_{20}N_4O_2S$, 356.1; m/z found, 356.9 [M+H]$^+$. $^1$H NMR (500 MHz, CDCl$_3$) δ 8.26-8.22 (d, J=1.8 Hz, 1H), 7.31-7.28 (d, J=1.9 Hz, 1H), 7.03-6.99 (d, J=3.6 Hz, 1H), 6.75-6.70 (m, 1H), 4.72-4.67 (s, 2H), 3.53-3.50 (s, 3H), 3.18-3.14 (s, 3H), 3.00-2.96 (s, 3H), 2.12-2.03 (m, 1H), 1.03-0.97 (m, 2H), 0.78-0.73 (m, 2H).

Example 111: 1-[2-(Azetidin-1-yl)-2-oxo-ethyl]-3-methyl-6-[5-(1,1,2,2,2-pentafluoroethyl)-2-thienyl]imidazo[4,5-b]pyridin-2-one

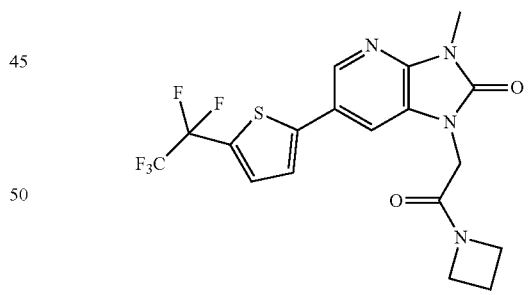

The title compound was prepared in a manner analogous to Example 10, using 2-bromo-5-pentafluoroethyl-thiophene and 1-(2-(azetidin-1-yl)-2-oxoethyl)-6-bromo-3-methyl-1,3-dihydro-2H-imidazo[4,5-b]pyridin-2-one (Intermediate 16). MS (ESI): mass calcd. for $C_{18}H_{15}F_5N_4O_2S$, 446.1; m/z found, 446.9 [M+H]$^+$. $^1$H NMR (500 MHz, CDCl$_3$) δ 8.32-8.29 (d, J=1.9 Hz, 1H), 7.46-7.43 (d, J=1.9 Hz, 1H), 7.42-7.39 (m, 1H), 7.26-7.22 (m, 1H), 4.52-4.46 (s, 2H), 4.37-4.31 (m, 2H), 4.12-4.06 (m, 2H), 3.56-3.50 (s, 3H), 2.43-2.31 (m, 2H).

Example 112: 1-[2-(Azetidin-1-yl)-2-oxo-ethyl]-3-methyl-6-(2-methylthiazol-5-yl)imidazo[4,5-b]pyridin-2-one

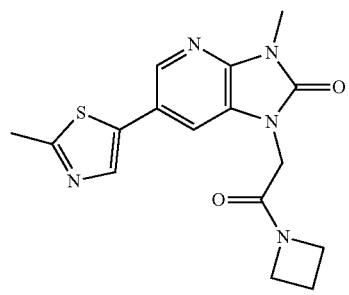 [SMILES: Cc1ncc(-c2cnc3c(c2)n(CC(=O)N2CCC2)c(=O)n3C)s1]

The title compound was prepared in a manner analogous to Example 10, using 5-bromo-2-methylthiazole and 1-(2-(azetidin-1-yl)-2-oxoethyl)-6-bromo-3-methyl-1,3-dihydro-2H-imidazo[4,5-b]pyridin-2-one (Intermediate 16). MS (ESI): mass calcd. for $C_{16}H_{17}N_5O_2S$, 343.1; m/z found, 343.9 [M+H]$^+$. $^1$H NMR (400 MHz, CDCl$_3$) δ 8.23-8.17 (d, J=2.0 Hz, 1H), 7.77-7.71 (s, 1H), 7.41-7.35 (d, J=2.0 Hz, 1H), 4.52-4.41 (s, 2H), 4.39-4.28 (m, 2H), 4.15-4.03 (m, 2H), 3.58-3.47 (s, 3H), 2.81-2.64 (s, 3H), 2.44-2.30 (m, 2H).

Example 113: 1-[2-(3-Fluoroazetidin-1-yl)-2-oxo-ethyl]-3-methyl-6-(2-methylthiazol-5-yl)imidazo[4,5-b]pyridin-2-one

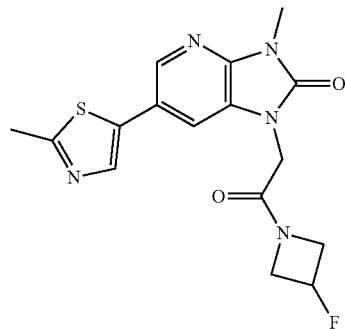 [SMILES: Cc1ncc(-c2cnc3c(c2)n(CC(=O)N2CC(F)C2)c(=O)n3C)s1]

The title compound was prepared in a manner analogous to Example 10, using 5-bromo-2-methylthiazole and 6-bromo-1-(2-(3-fluoroazetidin-1-yl)-2-oxoethyl)-3-methyl-1,3-dihydro-2H-imidazo[4,5-b]pyridin-2-one (Intermediate 18). MS (ESI): mass calcd. for $C_{16}H_{16}FN_5O_2S$, 361.1; m/z found, [M+H]$^+$. $^1$H NMR (400 MHz, CDCl$_3$) δ 8.24-8.17 (d, J=1.9 Hz, 1H), 7.76-7.72 (s, 1H), 7.39-7.36 (d, J=1.9 Hz, 1H), 5.48-5.23 (m, 1H), 4.68-4.08 (m, 6H), 3.56-3.48 (s, 3H), 2.80-2.71 (s, 3H).

Example 114: N,N-Dimethyl-2-[3-methyl-6-(2-methylthiazol-5-yl)-2-oxo-imidazo[4,5-b]pyridin-1-yl]acetamide

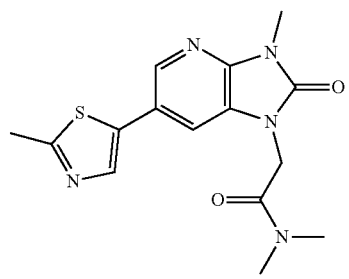 [SMILES: Cc1ncc(-c2cnc3c(c2)n(CC(=O)N(C)C)c(=O)n3C)s1]

The title compound was prepared in a manner analogous to Example 10, using 5-bromo-2-methylthiazole and 2-(6-bromo-3-methyl-2-oxo-2,3-dihydro-1H-imidazo[4,5-b]pyridin-1-yl)-N,N-dimethylacetamide (Intermediate 15). MS (ESI): mass calcd. for $C_{15}H_{17}N_5O_2S$, 331.1; m/z found, 332.0 [M+H]$^+$. $^1$H NMR (400 MHz, CDCl$_3$) δ 8.23-8.18 (d, J=1.9 Hz, 1H), 7.75-7.69 (s, 1H), 7.30-7.27 (d, J=1.9 Hz, 1H), 4.76-4.67 (s, 2H), 3.56-3.47 (s, 3H), 3.20-3.12 (s, 3H), 3.04-2.96 (s, 3H), 2.78-2.69 (s, 3H).

Example 115: 1-[2-(Azetidin-1-yl)-2-oxo-ethyl]-3-methyl-6-[2-(trifluoromethyl)thiazol-5-yl]imidazo[4,5-b]pyridin-2-one

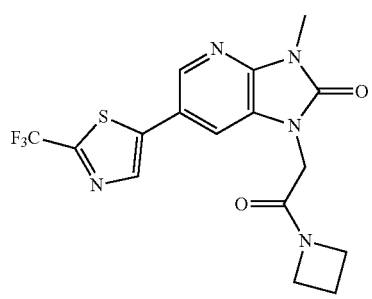 [SMILES: Cn1c(=O)n(CC(=O)N2CCC2)c2cc(-c3cnc(C(F)(F)F)s3)cnc21]

The title compound was prepared in a manner analogous to Example 10, using 5-bromo-2-(trifluoromethyl)thiazole and 1-(2-(azetidin-1-yl)-2-oxoethyl)-6-bromo-3-methyl-1,3-dihydro-2H-imidazo[4,5-b]pyridin-2-one (Intermediate 16). MS (ESI): mass calcd. for $C_{16}H_{14}F_3N_5O_2S$, 397.1; m/z found, 397.9 [M+H]$^+$. $^1$H NMR (400 MHz, CDCl$_3$) δ 8.29-8.25 (d, J=1.9 Hz, 1H), 8.04-8.01 (m, 1H), 7.46-7.43 (d, J=2.0 Hz, 1H), 4.52-4.45 (s, 2H), 4.40-4.31 (m, 2H), 4.14-4.04 (m, 2H), 3.58-3.46 (s, 3H), 2.45-2.30 (m, 2H).

Example 116: 1-[2-(3-Fluoroazetidin-1-yl)-2-oxo-ethyl]-3-methyl-6-[2-(trifluoromethyl)thiazol-5-yl]imidazo[4,5-b]pyridin-2-one

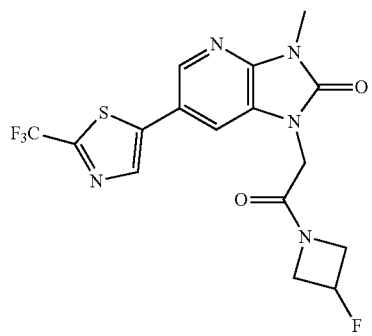 [SMILES: Cn1c(=O)n(CC(=O)N2CC(F)C2)c2cc(-c3cnc(C(F)(F)F)s3)cnc21]

The title compound was prepared in a manner analogous to Example 10, using 5-bromo-2-(trifluoromethyl)thiazole and 6-bromo-1-(2-(3-fluoroazetidin-1-yl)-2-oxoethyl)-3-methyl-1,3-dihydro-2H-imidazo[4,5-b]pyridin-2-one (Intermediate 18). MS (ESI): mass calcd. for $C_{16}H_{13}F_4N_5O_2S$, 415.1; m/z found, 415.9 [M+H]$^+$. $^1$H NMR (400 MHz, CDCl$_3$) δ 8.31-8.28 (d, J=1.9 Hz, 1H), 8.05-8.01 (m, 1H), 7.46-7.41 (d, J=1.9 Hz, 1H), 5.48-5.26 (m, 1H), 4.71-4.08 (m, 6H), 3.57-3.50 (s, 3H).

Example 117: 1-[2-(Azetidin-1-yl)-2-oxo-ethyl]-6-[4-(difluoromethyl)-2-thienyl]-3-methyl-imidazo[4,5-b]pyridin-2-one

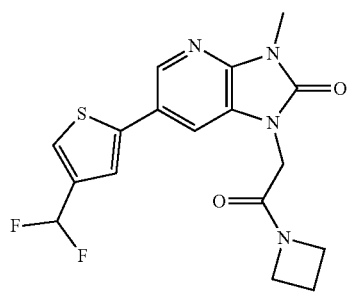 [SMILES: Cn1c(=O)n(CC(=O)N2CCC2)c2cc(-c3cc(C(F)F)cs3)cnc21]

The title compound was prepared in a manner analogous to Example 10, using 4-bromo-2-(difluoromethyl)-thiophene and 1-(2-(azetidin-1-yl)-2-oxoethyl)-6-bromo-3-methyl-1,3-dihydro-2H-imidazo[4,5-b]pyridin-2-one (Intermediate 16). MS (ESI): mass calcd. for $C_{17}H_{16}F_2N_4O_2S$, 378.1; m/z found, 378.9 [M+H]$^+$. $^1$H NMR (500 MHz, CDCl$_3$) δ 8.30-8.28 (d, J=1.9 Hz, 1H), 7.51-7.47 (m, 1H), 7.45-7.41 (d, J=1.9 Hz, 1H), 7.35-7.32 (d, J=1.3 Hz, 1H), 6.81-6.54 (m, 1H), 4.51-4.45 (s, 2H), 4.37-4.29 (m, 2H), 4.13-4.06 (m, 2H), 3.55-3.48 (s, 3H), 2.41-2.30 (m, 2H).

Example 118: 6-[4-(Difluoromethyl)-2-thienyl]-1-[2-(3-fluoroazetidin-1-yl)-2-oxo-ethyl]-3-methyl-imidazo[4,5-b]pyridin-2-one

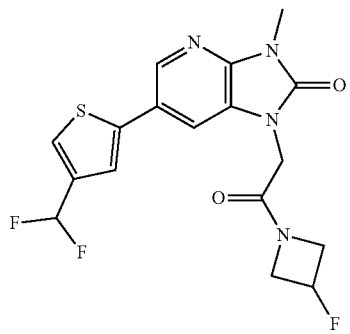

The title compound was prepared in a manner analogous to Example 10, using 4-bromo-2-(difluoromethyl)-thiophene and 6-bromo-1-(2-(3-fluoroazetidin-1-yl)-2-oxoethyl)-3-methyl-1,3-dihydro-2H-imidazo[4,5-b]pyridin-2-one (Intermediate 18). MS (ESI): mass calcd. for $C_{17}H_{15}F_3N_4O_2S$, 396.1; m/z found, 396.9 [M+H]$^+$. $^1$H NMR (500 MHz, CDCl$_3$) δ 8.33-8.29 (d, J=1.9 Hz, 1H), 7.52-7.48 (m, 1H), 7.45-7.41 (d, J=1.9 Hz, 1H), 7.36-7.32 (s, 1H), 6.81-6.54 (m, 1H), 5.46-5.26 (m, 1H), 4.68-4.13 (m, 6H), 3.55-3.48 (s, 3H).

Example 119: N,N-Dimethyl-2-[3-methyl-2-oxo-6-[2-(trifluoromethyl)thiazol-5-yl]imidazo[4,5-b]pyridin-1-yl]acetamide

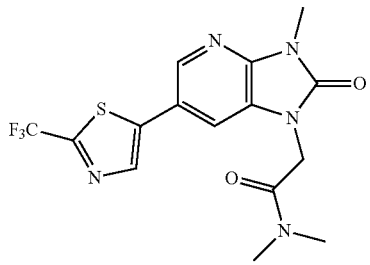 [SMILES: CN(C)C(=O)Cn1c(=O)n(C)c2ncc(-c3cnc(C(F)(F)F)s3)cc21]

The title compound was prepared in a manner analogous to Example 10, using 5-bromo-2-(trifluoromethyl)thiazole and 2-(6-bromo-3-methyl-2-oxo-2,3-dihydro-1H-imidazo[4,5-b]pyridin-1-yl)-N,N-dimethylacetamide (Intermediate 15). MS (ESI): mass calcd. for $C_{15}H_{14}F_3N_5O_2S$, 385.1; m/z found, 385.9 [M+H]$^+$. $^1$H NMR (400 MHz, CDCl$_3$) δ 8.29-8.26 (d, J=1.9 Hz, 1H), 8.03-8.00 (m, 1H), 7.33-7.31 (d, J=1.9 Hz, 1H), 4.76-4.71 (s, 2H), 3.56-3.51 (s, 3H), 3.20-3.16 (s, 3H), 3.02-2.97 (s, 3H).

Example 120: 1-(2-(Azetidin-1-yl)-2-oxoethyl)-3-methyl-6-(5-(trifluoromethyl)thiophen-2-yl)-1,3-dihydro-2H-imidazo[4,5-b]pyridin-2-one-7-D and its Trifluoroacetic Acid Salt

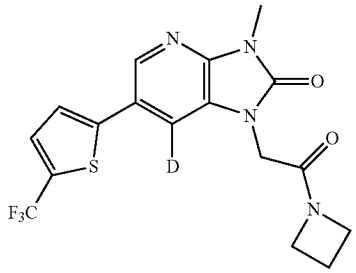 [SMILES: [2H]c1c(-c2ccc(C(F)(F)F)s2)cnc2c1n(CC(=O)N1CCC1)c(=O)n2C]

Step A: 1-[2-(Azetidin-1-yl)-2-oxoethyl)-7-chloro-3-methyl-6-(5-(trifluoromethyl)thiophen-2-yl)-1,3-dihydro-2H-imidazo[4,5-b]pyridin-2-one The title compound was prepared in a manner analogous to Intermediate 26, Step A, using 1-(2-(azetidin-1-yl)-2-oxoethyl)-6-bromo-7-chloro-3-methyl-1,3-dihydro-2H-imidazo[4,5-b]pyridin-2-one (Intermediate 17) and (5-(trifluoromethyl)thiophen-2-yl)boronic acid, no H$_2$O.

Step B: 1-(2-(Azetidin-1-yl)-2-oxoethyl)-3-methyl-6-(5-(trifluoromethyl)thiophen-2-yl)-1,3-dihydro-2H-imidazo[4,5-b]pyridin-2-one-7-D and its Trifluoroacetic Acid Salt To a solution of 1-(2-(azetidin-1-yl)-2-oxoethyl)-7-chloro-3-methyl-6-(5-(trifluoromethyl)thiophen-2-yl)-1,3-dihydro-2H-imidazo[4,5-b]pyridin-2-one (7 mg, 0.02 mmol) in a mixture of CD$_3$OD (1 mL) and EtOAc (1 mL) was added Pd/C (10% on carbon, dry, 1 mg, 0.0008 mmol) and the reaction mixture was stirred at room temperature under an atmosphere of D$_2$ (99.8 atom % D, 1 atm, balloon). After 1 day, the reaction mixture was filtered through Celite® and rinsed with EtOAc followed by MeOH. The volatiles were removed to afford the title compound as the free base. The crude material was purified (Method C, using a Sunfire C18 OBD column), to give the title compound (4.8 mg, 0.009 mmol, 57%). MS (ESI): mass calcd. for C$_{17}$H$_{15}$F$_3$N$_4$O$_2$S, 397.1; m/z found, 397.9 [M+H]$^+$. $^1$H NMR (400 MHz, DMSO-d$_6$) δ 8.42 (s, 1H), 7.79-7.76 (m, 1H), 7.61-7.58 (m, 1H), 4.60 (s, 2H), 4.30 (t, J=7.6 Hz, 2H), 3.91 (t, J=7.7 Hz, 2H), 3.38 (s, 3H), 2.34-2.25 (m, 2H).

Example 121: N,N-Dimethyl-2-[3-methyl-2-oxo-6-[5-(trideuteriomethoxymethyl)-2-thienyl]imidazo[4,5-b]pyridin-1-yl]acetamide

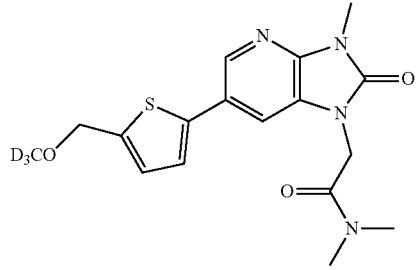

Under a nitrogen atmosphere was added 2-[6-[5-(hydroxymethyl)-2-thienyl]-3-methyl-2-oxo-imidazo[4,5-b]pyridin-1-yl]-N,N-dimethyl-acetamide (Example 91, 38 mg, 0.11 mmol) to a suspension of NaH (6.5 mg, 0.17 mmol) in DMF (1 mL). After 10 minutes, iodomethane-D$_3$ (21 mg, 0.14 mmol) was added to the reaction mixture at room temperature and the reaction was stirred at room temperature for 16 hours. Then, the reaction mixture was quenched with water and extracted with EtOAc (3×20 mL). The combined organic layers were dried using MgSO$_4$, filtered and concentrated under vacuum. The crude material was purified via basic HPLC (Method A) to provide the title compound (19 mg, 47%). MS (ESI): mass calcd. for C$_{17}$H$_{17}$D$_3$N$_4$O$_3$S, 363.1; m/z found, 364.0 [M+H]$^+$. $^1$H NMR (400 MHz, CDCl$_3$) δ 8.32-8.25 (d, J=2.0 Hz, 1H), 7.35-7.30 (d, J=2.0 Hz, 1H), 7.13-7.06 (d, J=3.6 Hz, 1H), 6.98-6.93 (d, J=3.6 Hz, 1H), 4.75-4.65 (s, 2H), 4.63-4.58 (s, 2H), 3.57-3.49 (s, 3H), 3.20-3.14 (s, 3H), 3.02-2.97 (s, 3H).

Example 122: 1-[2-(Azetidin-1-yl)-2-oxo-ethyl]-3-methyl-6-[5-(trideuteriomethoxymethyl)-2-thienyl]imidazo[4,5-b]pyridin-2-one

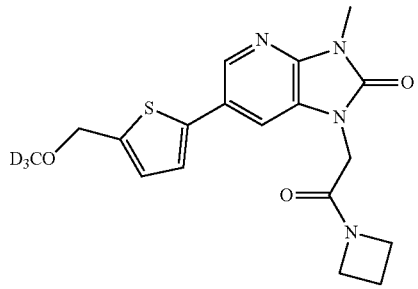

The title compound was prepared in a manner analogous to Example 121 using 1-(2-(azetidin-1-yl)-2-oxoethyl)-6-(5-(hydroxymethyl)thiophen-2-yl)-3-methyl-1,3-dihydro-2H-imidazo[4,5-b]pyridin-2-one (Example 89). MS (ESI): mass calcd. for C$_{18}$H$_{17}$D$_3$N$_4$O$_3$S, 375.1; m/z found, 376.0 [M+H]$^+$. $^1$H NMR (400 MHz, CDCl$_3$) δ 8.32-8.28 (d, J=1.9 Hz, 1H), 7.44-7.39 (d, J=1.9 Hz, 1H), 7.14-7.09 (d, J=3.6 Hz, 1H), 7.00-6.94 (m, 1H), 4.64-4.57 (d, J=0.8 Hz, 2H), 4.50-4.46 (s, 2H), 4.36-4.26 (m, 2H), 4.14-4.04 (m, 2H), 3.56-3.47 (s, 3H), 2.43-2.27 (m, 2H).

Example 123: 1-[2-(3-Fluoroazetidin-1-yl)-2-oxo-ethyl]-3-methyl-6-[5-(trideuteriomethoxymethyl)-2-thienyl]imidazo[4,5-b]pyridin-2-one

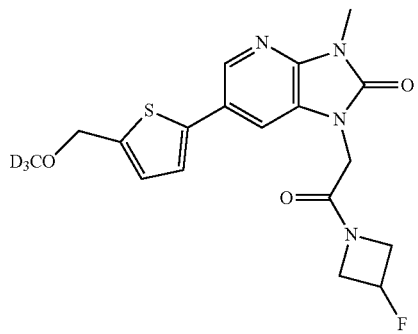

The title compound was prepared in a manner analogous to Example 121 using 1-(2-(3-fluoroazetidin-1-yl)-2-oxoethyl)-6-(5-(hydroxymethyl)thiophen-2-yl)-3-methyl-1,3-dihydro-2H-imidazo[4,5-b]pyridin-2-one (Example 90). MS (ESI): mass calcd. for $C_{18}H_{16}D_3FN_4O_3S$, 393.1; m/z found, 393.9 [M+H]$^+$. $^1$H NMR (500 MHz, CDCl$_3$) δ 8.32-8.29 (d, J=1.9 Hz, 1H), 7.44-7.39 (d, J=1.9 Hz, 1H), 7.15-7.09 (d, J=3.6 Hz, 1H), 7.01-6.95 (m, 1H), 5.44-5.24 (m, 1H), 4.65-4.13 (m, 8H), 3.56-3.48 (s, 3H).

Example 124: 1-(2-(Azetidin-1-yl)-2-oxoethyl)-3-methyl-6-(5-(trifluoromethyl)thiophen-2-yl)-1,3-dihydro-2H-imidazo[4,5-b]pyridin-2-one-7-T and its Trifluoroacetic Acid Salt

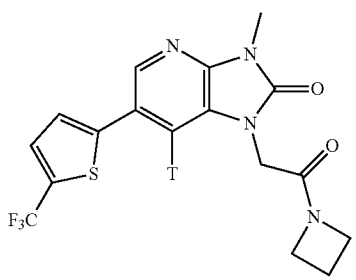

A solution of 1-(2-(azetidin-1-yl)-2-oxoethyl)-7-chloro-3-methyl-6-(5-(trifluoromethyl)thiophen-2-yl)-1,3-dihydro-2H-imidazo[4,5-b]pyridin-2-one (Example 120, product from Step A, 4.3 mg), in DMF (0.3 mL), was added 10% Pd/C (3 mg), DIPEA (0.02 mL). The mixture was stirred under 760 mmHg tritium gas for 90 min. The crude product was dissolved in ethanol and filtered. The labile tritium was removed by under reduced pressure. The process was repeated 2× to afford the free base of the title compound. Purification (HPLC-C18 column, mobile phase: Gradient A: 0.1% TFA, B: 100% ACN: A to 100% B in 60 min, flow 6 mL/min, U.V.=241 nm) afforded the title compound.

Example 125: 1-[(5-Methylisoxazol-3-yl)methyl]-6-(4-methyl-2-thienyl)-3H-imidazo[4,5-b]pyridin-2-one

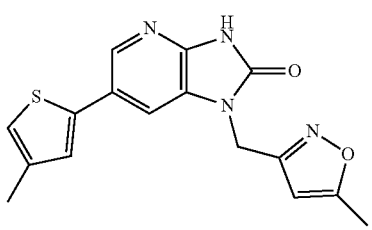 [SMILES: Cc1csc(-c2cnc3[nH]c(=O)n(Cc4cc(C)on4)c3c2)c1]

The title compound was made analogous to Example 11, using 4,4,5,5-tetramethyl-2-(4-methylthiophen-2-yl)-1,3,2-dioxaborolane in Step B. MS (ESI): mass calcd. for $C_{16}H_{14}N_4O_2S$, 326.1; m/z found, 327.1 [M+H]$^+$. $^1$H NMR (500 MHz, DMF-d$_7$) δ 11.79 (s, 1H), 8.25 (d, J=1.9 Hz, 1H), 7.78 (d, J=1.9 Hz, 1H), 7.34 (d, J=1.4 Hz, 1H), 7.14 (p, J=1.1 Hz, 1H), 6.25 (d, J=1.0 Hz, 1H), 5.24 (s, 2H), 2.40 (d, J=1.0 Hz, 3H), 2.26 (d, J=1.1 Hz, 3H).

Example 126: 1-[(5-Methylisoxazol-3-yl)methyl]-6-(o-tolyl)-3H-imidazo[4,5-b]pyridin-2-one

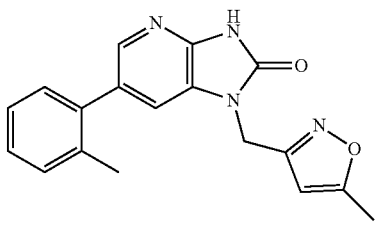 [SMILES: Cc1cc(Cn2c(=O)[nH]c3ncc(-c4ccccc4C)cc32)no1]

The title compound was prepared in a manner analogous to Example 11, using o-tolylboronic acid in Step B. MS (ESI): mass calcd. for $C_{18}H_{16}N_4O_2$, 320.1; m/z found, 321.2 [M+H]$^+$. $^1$H NMR (500 MHz, CDCl$_3$) δ 9.97 (s, 1H), 8.03 (d, J=1.8 Hz, 1H), 7.32-7.26 (m, 3H), 7.26-7.17 (m, 2H), 6.04 (t, J=0.9 Hz, 1H), 5.10 (s, 2H), 2.38 (d, J=0.9 Hz, 3H), 2.24 (s, 3H).

Example 127: 1-[(3-Methyl-1,2,4-oxadiazol-5-yl)methyl]-6-(4-methyl-2-thienyl)-3H-imidazo[4,5-b]pyridin-2-one

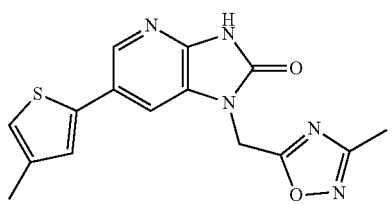 [SMILES: Cc1csc(-c2cnc3[nH]c(=O)n(Cc4nc(C)no4)c3c2)c1]

The title compound was prepared in a manner analogous to Example 11, using 5-(chloromethyl)-3-methyl-1,2,4-oxadiazole in Step A and (4-methylthiophen-2-yl)boronic acid in Step B. MS (ESI): mass calcd. for $C_{15}H_{13}N_5O_2S$, 327.1; m/z found, 328.1 [M+H]$^+$. $^1$H NMR (500 MHz, CDCl$_3$) δ 9.47 (s, 1H), 8.44-8.24 (m, 1H), 7.43-7.29 (m, 1H), 7.14-7.04 (m, 1H), 6.96-6.84 (m, 1H), 5.31 (s, 2H), 2.39 (s, 3H), 2.30 (s, 3H).

Example 128: 6-(4-Fluorophenyl)-1-[(1-methylpyrazol-3-yl)methyl]-3H-imidazo[4,5-b]pyridin-2-one

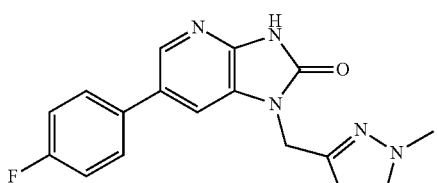

The title compound was prepared in a manner analogous to Example 11, using 3-(chloromethyl)-1-methyl-1H-pyrazole in Step A and 4-fluorophenylboronic acid in Step B. MS (ESI): mass calcd. for $C_{17}H_{14}FN_5O$, 323.1; m/z found, 324.1 [M+H]$^+$. $^1$H NMR (500 MHz, CDCl$_3$) δ 8.04 (d, J=1.8 Hz, 1H), 7.70 (d, J=1.8 Hz, 1H), 7.52-7.42 (m, 2H), 7.31 (d, J=2.3 Hz, 1H), 7.22-7.14 (m, 2H), 6.27 (d, J=2.3 Hz, 1H), 5.12 (s, 2H), 3.87 (s, 3H).

Example 129: 6-(4-Fluoro-3-methyl-phenyl)-1-[(1-methylpyrazol-3-yl)methyl]-3H-imidazo[4,5-b]pyridin-2-one

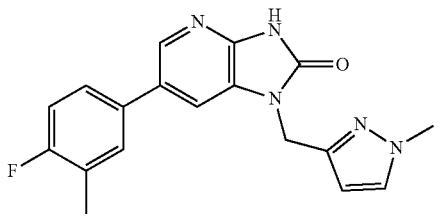 [SMILES: Cc1cc(-c2cnc3[nH]c(=O)n(Cc4ccn(C)n4)c3c2)ccc1F]

The title compound was prepared in a manner analogous to Example 11, using 3-(chloromethyl)-1-methyl-1H-pyrazole in Step A and (4-fluoro-3-methylphenyl)boronic acid in Step B. MS (ESI): mass calcd. for $C_{18}H_{16}FN_5O$, 337.1; m/z found, 338.2 [M+H]$^+$. $^1$H NMR (500 MHz, DMF-d$_7$) δ 11.62 (s, 1H), 8.21 (d, J=2.0 Hz, 1H), 7.73 (d, J=2.0 Hz, 1H), 7.67-7.59 (m, 2H), 7.57-7.49 (m, 1H), 7.29-7.19 (m, 1H), 6.23 (d, J=2.2 Hz, 1H), 5.11 (s, 2H), 3.83 (s, 3H), 3.48 (s, 3H).

Example 130: 6-(3-Chloro-4-fluoro-phenyl)-1-[(1-methylpyrazol-3-yl)methyl]-3H-imidazo[4,5-b]pyridin-2-one

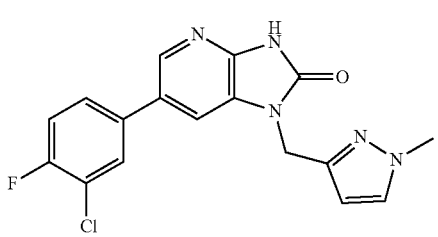 [SMILES: Cn1ccc(Cn2c(=O)[nH]c3ncc(-c4ccc(F)c(Cl)c4)cc32)n1]

The title compound was prepared in a manner analogous to Example 11, using 3-(chloromethyl)-1-methyl-1H-pyrazole in Step A and (3-chloro-4-fluorophenyl)boronic acid in Step B. MS (ESI): mass calcd. for $C_{17}H_{13}ClFN_5O$, 357.1; m/z found, 358.1 [M+H]$^+$. $^1$H NMR (500 MHz, DMF-d$_7$) δ 11.70 (s, 1H), 8.28 (d, J=2.0 Hz, 1H), 7.92 (dd, J=7.1, 2.3 Hz, 1H), 7.83 (d, J=2.0 Hz, 1H), 7.77-7.69 (m, 1H), 7.63 (d, J=2.2 Hz, 1H), 7.53 (t, J=9.0 Hz, 1H), 6.24 (d, J=2.2 Hz, 1H), 5.12 (s, 2H), 3.83 (s, 3H).

Example 131: 6-(3,4-Difluorophenyl)-1-[(1-methylpyrazol-3-yl)methyl]-3H-imidazo[4,5-b]pyridin-2-one

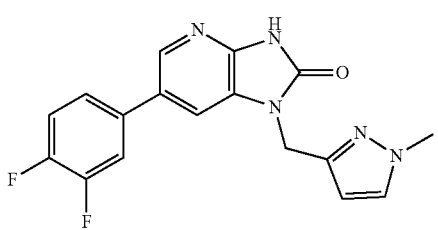 [SMILES: Cn1ccc(Cn2c(=O)[nH]c3ncc(-c4ccc(F)c(F)c4)cc32)n1]

The title compound was prepared in a manner analogous to Example 11, using 3-(chloromethyl)-1-methyl-1H-pyrazole in Step A and 3,4-difluorophenylboronic acid in Step B. MS (ESI): mass calcd. for $C_{17}H_{13}F_2N_5O$, 341.1; m/z found, 342.1 [M+H]$^+$. $^1$H NMR (500 MHz, DMF-d$_7$) δ 11.69 (s, 1H), 8.28 (d, J=2.0 Hz, 1H), 7.84-7.75 (m, 2H), 7.63 (d, J=2.2 Hz, 1H), 7.60-7.50 (m, 2H), 6.24 (d, J=2.2 Hz, 1H), 5.11 (s, 2H), 3.83 (s, 3H).

Example 132: 6-(2,4-Difluorophenyl)-1-[(1-methylpyrazol-3-yl)methyl]-3H-imidazo[4,5-b]pyridin-2-one

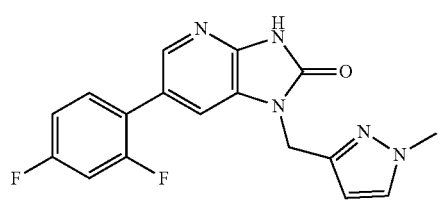 [SMILES: Cn1ccc(Cn2c(=O)[nH]c3ncc(-c4ccc(F)cc4F)cc32)n1]

The title compound was prepared in a manner analogous to Example 11, using 3-(chloromethyl)-1-methyl-1H-pyrazole in Step A and 2,4-difluorophenylboronic acid in Step B. MS (ESI): mass calcd. for $C_{17}H_{13}F_2N_5O$, 341.1; m/z found, 342.1 [M+H]$^+$. $^1$H NMR (500 MHz, DMF)-d$_7$) δ 11.73 (s, 1H), 8.14-8.06 (m, 1H), 7.70-7.59 (m, 3H), 7.42-7.31 (m, 1H), 7.28-7.19 (m, 1H), 6.23 (d, J=2.2 Hz, 1H), 5.09 (s, 2H), 3.83 (s, 3H).

Example 133: (R/S)-3-methyl-1-(oxetan-2-ylmethyl)-6-[3-(trifluoromethyl)phenyl]imidazo[4,5-b]pyridin-2-one

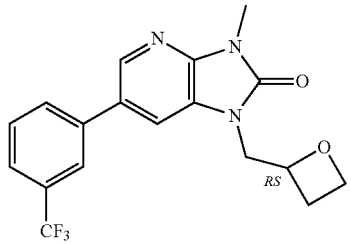

The title compound was prepared in a manner analogous to Example 11, Step A using 3-methyl-6-(3-(trifluoromethyl)phenyl)-1,3-dihydro-2H-imidazo[4,5-b]pyridin-2-one (Intermediate 26) and 2-(bromomethyl)oxetane. MS (ESI): mass calcd. for $C_{18}H_{16}F_3N_3O_2$, 363.1; m/z found, 364.1[M+H]$^+$. $^1$H NMR (500 MHz, DMSO-d$_6$) δ 8.40-8.38 (m, 1H), 8.04-7.99 (m, 3H), 7.77-7.70 (m, 2H), 5.10-5.03 (m, 1H), 4.49-4.42 (m, 1H), 4.37-4.31 (m, 1H), 4.27-4.12 (m, 2H), 3.42-3.40 (m, 3H), 2.72-2.61 (m, 1H), 2.51-2.42 (m, 1H overlaps with DMSO).

Example 134: Ethyl 2-[2-oxo-6-[3-(trifluoromethyl)phenyl]-3H-imidazo[4,5-b]pyridin-1-yl]acetate and its Trifluoroacetic Acid Salt

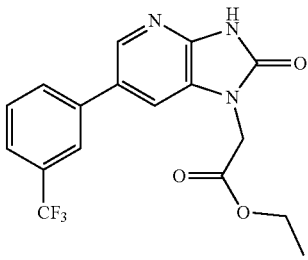 [SMILES: CCOC(=O)Cn1c(=O)[nH]c2ncc(-c3cccc(C(F)(F)F)c3)cc21]

The title compound was prepared in a manner analogous to Example 11, Step C using ethyl 2-(2-oxo-6-(3-(trifluoromethyl)phenyl)-3-trityl-2,3-dihydro-1H-imidazo[4,5-b]pyridin-1-yl)acetate (Intermediate 44, product from Step A). MS (ESI): mass calcd. for $C_{17}H_{14}F_3N_3O_3$, 365.1; m/z found, 366.1 [M+H]$^+$. $^1$H NMR (500 MHz, DMSO-d$_6$) δ 11.84 (s, 1H), 8.36 (d, J=2.0 Hz, 1H), 8.04-7.99 (m, 3H), 7.75-7.69 (m, 2H), 4.77 (s, 2H), 4.17 (q, J=7.1 Hz, 2H), 1.22 (t, J=7.1 Hz, 3H).

Example 135: 2-[2-Oxo-6-[3-(trifluoromethyl)phenyl]-3H-imidazo[4,5-b]pyridin-1-yl]acetic Acid and its Trifluoroacetic Acid Salt

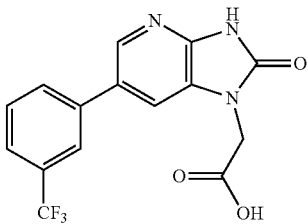 [SMILES: O=C(O)Cn1c(=O)[nH]c2ncc(-c3cccc(C(F)(F)F)c3)cc21]

The title compound was prepared in a manner analogous to Example 11, Step C using 2-(2-oxo-6-(3-(trifluoromethyl)phenyl)-3-trityl-2,3-dihydro-1H-imidazo[4,5-b]pyridin-1-yl)acetic acid (Intermediate 44). MS (ESI): mass calcd. for $C_{15}H_{10}F_3N_3O_3$, 337.1; m/z found, 338.1 [M+H]$^+$. $^1$H NMR (500 MHz, DMSO-d$_6$) δ 13.14 (s, 1H), 11.80 (s, 1H), 8.36 (d, J=2.0 Hz, 1H), 8.05-7.99 (m, 3H), 7.76-7.68 (m, 2H), 4.67 (s, 2H).

Example 136: Ethyl 2-[3-methyl-2-oxo-6-[3-(trifluoromethyl)phenyl]imidazo[4,5-b]pyridin-1-yl]acetate

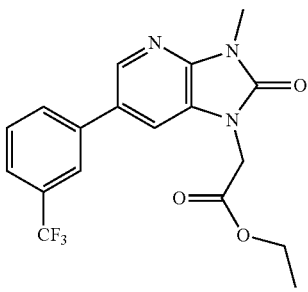 [SMILES: CCOC(=O)Cn1c(=O)n(C)c2ncc(-c3cccc(C(F)(F)F)c3)cc21]

The title compound was prepared in a manner analogous to Example 11, Step A using 3-methyl-6-(3-(trifluoromethyl)phenyl)-1,3-dihydro-2H-imidazo[4,5-b]pyridin-2-one (Intermediate 26) and ethyl 2-bromoacetate. MS (ESI): mass calcd. for $C_{18}H_{16}F_3N_3O_3$, 379.1; m/z found, 380.2 [M+H]$^+$. $^1$H NMR (400 MHz, DMSO-d$_6$) δ 8.45 (d, J=1.9 Hz, 1H), 8.08 (d, J=2.0 Hz, 1H), 8.06-8.00 (m, 2H), 7.78-7.69 (m, 2H), 4.84 (s, 2H), 4.17 (q, J=7.1 Hz, 2H), 3.41 (s, 3H), 1.22 (t, J=7.1 Hz, 3H).

Example 137: 2-[3-Methyl-2-oxo-6-[3-(trifluoromethyl)phenyl]imidazo[4,5-b]pyridin-1-yl]acetic acid and its Trifluoroacetic Acid Salt

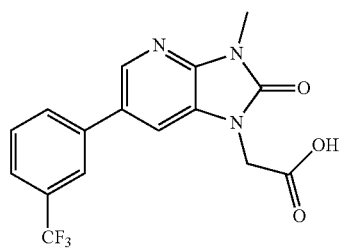 [SMILES: Cn1c(=O)n(CC(=O)O)c2cc(-c3cccc(C(F)(F)F)c3)cnc21]

The title compound was prepared in a manner analogous to Intermediate 38, Step A, using ethyl 2-[3-methyl-2-oxo-6-[3-(trifluoromethyl)phenyl]imidazo[4,5-b]pyridin-1-yl]acetate (Example 136). MS (ESI): mass calcd. for $C_{16}H_{12}F_3N_3O_3$, 351.1; m/z found, 352.1 [M+H]$^+$. $^1$H NMR (500 MHz, DMSO-d$_6$) δ 13.19 (s, 1H), 8.44 (d, J=1.8 Hz, 1H), 8.09 (d, J=2.0 Hz, 1H), 8.06-8.01 (m, 2H), 7.76-7.69 (m, 2H), 4.73 (s, 2H), 3.42-3.40 (m, 3H).

Example 138: 1-[2-(3,3-difluoroazetidin-1-yl)-2-oxoethyl]-3-methyl-6-[3-(trifluoromethyl)phenyl]imidazo[4,5-b]pyridin-2-one

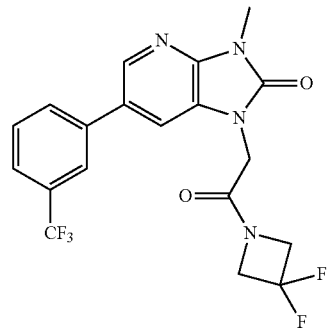 [SMILES: Cn1c(=O)n(CC(=O)N2CC(F)(F)C2)c2cc(-c3cccc(C(F)(F)F)c3)cnc21]

The title compound was prepared in a manner analogous to Intermediate 38, Step B, using 2-[3-methyl-2-oxo-6-[3-(trifluoromethyl)phenyl]imidazo[4,5-b]pyridin-1-yl]acetic acid (Example 137). MS (ESI): mass calcd. for $C_{19}H_{15}F_5N_4O_2$, 426.1; m/z found, 427.1 [M+H]$^+$. $^1$H NMR (400 MHz, DMSO-d$_6$) δ 8.40 (d, J=1.9 Hz, 1H), 8.03-7.95 (m, 2H), 7.88 (d, J=2.0 Hz, 1H), 7.79-7.70 (m, 2H), 4.90-4.73 (m, 4H), 4.38 (t, J=12.5 Hz, 2H), 3.41 (s, 3H).

Example 139: 6-(2,4-Difluoro-3-methyl-phenyl)-3-methyl-1-(pyrazin-2-ylmethyl)imidazo[4,5-b]pyridin-2-one

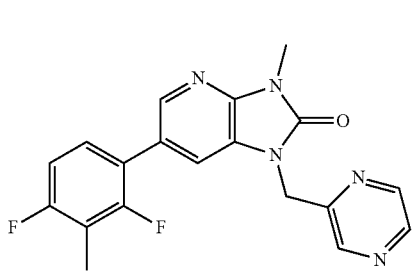 [SMILES: Cc1c(F)ccc(-c2cnc3c(c2)n(Cc2cnccn2)c(=O)n3C)c1F]

The title compound was prepared in a manner analogous to Example 12, Step A, using 6-bromo-3-methyl-1-(pyrazin-2-ylmethyl)-1H-imidazo[4,5-b]pyridin-2(3H)-one (Intermediate 21) and 2-(2,4-difluoro-3-methylphenyl)-4,4,5,5-tetramethyl-1,3,2-dioxaborolane. MS (ESI): mass calcd. for $C_{19}H_{15}F_2N_5O$, 367.1; m/z found, 368.0 [M+H]$^+$.

Example 140: 6-(4-Fluorophenyl)-1-[(3-methyl-1,2,4-oxadiazol-5-yl)methyl]-3H-imidazo[4,5-b]pyridin-2-one

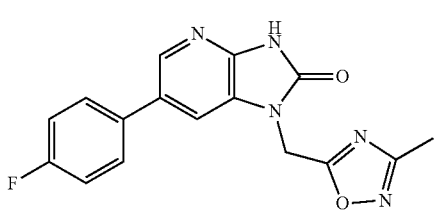 [SMILES: Cc1noc(Cn2c(=O)[nH]c3ncc(-c4ccc(F)cc4)cc32)n1]

The title compound was prepared in a manner analogous to Example 13, using 5-(chloromethyl)-3-methyl-1,2,4-oxadiazole in Step B. MS (ESI): mass calcd. for $C_{16}H_{12}FN_5O_2$, 325.1; m/z found, 326.1 [M+H]$^+$. $^1$H NMR (500 MHz, DMF-d$_7$) δ 11.91 (br s, 1H), 8.32 (d, J=1.9 Hz, 1H), 8.01 (d, J=2.0 Hz, 1H), 7.83-7.72 (m, 2H), 7.38-7.28 (m, 2H), 5.60 (s, 2H), 2.31 (s, 3H).

Example 141: 6-(4-Fluorophenyl)-1-[(1-methyl-1,2,4-triazol-3-yl)methyl]-3H-imidazo[4,5-b]pyridin-2-one

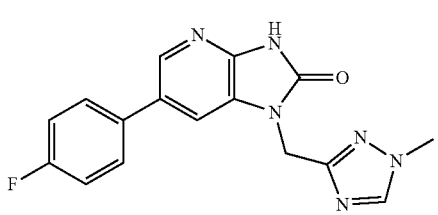 [SMILES: Cn1cnc(Cn2c(=O)[nH]c3ncc(-c4ccc(F)cc4)cc32)n1]

The title compound was prepared in a manner analogous to Example 13, using 3-(chloromethyl)-1-methyl-1H-1,2,4-triazole in Step B. MS (ESI): mass calcd. for $C_{16}H_{13}FN_6O$, 324.1; m/z found, 325.1 [M+H]$^+$. $^1$H NMR (500 MHz, DMF-d$_7$) δ 11.68 (s, 1H), 8.42 (s, 1H), 8.24 (d, J=2.0 Hz, 1H), 7.79 (d, J=2.0 Hz, 1H), 7.77-7.70 (m, 2H), 7.39-7.27 (m, 2H), 5.22 (s, 2H), 3.88 (s, 3H).

Example 142: 6-(4-Fluorophenyl)-1-[(1-methyltriazol-4-yl)methyl]-3H-imidazo[4,5-b]pyridin-2-one

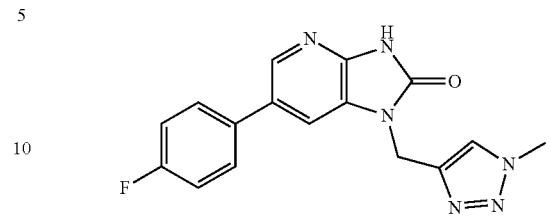

The title compound was prepared in a manner analogous to Example 13, using 4-(chloromethyl)-1-methyl-1H-1,2,3-triazole in Step B. MS (ESI): mass calcd. for $C_{16}H_{13}FN_6O$, 324.1; m/z found, 325.1 [M+H]$^+$. $^1$H NMR (500 MHz, DMF-d$_7$) δ 11.67 (s, 1H), 8.24 (d, J=2.0 Hz, 1H), 8.14 (s, 1H), 7.87 (d, J=2.0 Hz, 1H), 7.79-7.71 (m, 2H), 7.37-7.29 (m, 2H), 5.25 (s, 2H), 4.08 (s, 3H).

Example 143: 6-(3,4-Difluorophenyl)-1-[(3-methyl-1,2,4-oxadiazol-5-yl)methyl]-3H-imidazo[4,5-b]pyridin-2-one

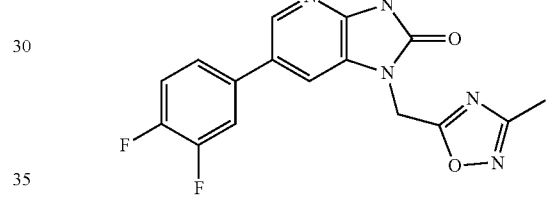

The title compound was prepared in a manner analogous to Example 13, using 3,4-difluorophenylboronic acid in Step A and 5-(chloromethyl)-3-methyl-1,2,4-oxadiazole in Step B. MS (ESI): mass calcd. for $C_{16}H_{11}F_2N_5O_2$, 343.1; m/z found, 344.1 [M+H]$^+$. $^1$H NMR (500 MHz, DMF-d$_7$) δ 11.96 (s, 1H), 8.42-8.36 (m, 1H), 8.08-8.05 (m, 1H), 7.86-7.77 (m, 1H), 7.64-7.50 (m, 2H), 5.59 (s, 2H), 2.31 (s, 3H).

Example 144: 6-(3,4-Difluorophenyl)-1-[(5-methyl-1,2,4-oxadiazol-3-yl)methyl]-3H-imidazo[4,5-b]pyridin-2-one

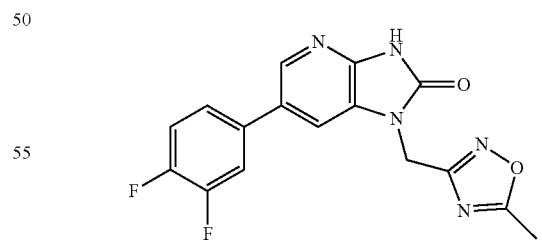

The title compound was prepared in a manner analogous to Example 13, using 3,4-difluorophenylboronic acid in Step A and 3-(chloromethyl)-5-methyl-1,2,4-oxadiazole in Step B. MS (ESI): mass calcd. for $C_{16}H_{11}F_2N_5O_2$, 343.1; m/z found, 344.1 [M+H]$^+$. $^1$H NMR (500 MHz, DMF-d$_7$) δ 11.86 (s, 1H), 8.35 (d, J=2.0 Hz, 1H), 7.96 (d, J=2.0 Hz, 1H), 7.84-7.77 (m, 1H), 7.63-7.51 (m, 2H), 5.36 (s, 2H), 2.59 (s, 3H).

Example 145: 6-(3,4-Difluorophenyl)-1-[[3-(methoxymethyl)-1,2,4-oxadiazol-5-yl]methyl]-3H-imidazo[4,5-b]pyridin-2-one

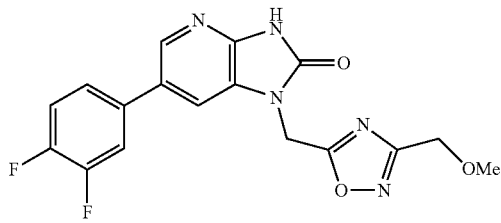 [SMILES: COCc1noc(Cn2c(=O)[nH]c3ncc(-c4ccc(F)c(F)c4)cc32)n1]

The title compound was prepared in a manner analogous to Example 13, using 3,4-difluorophenylboronic acid in Step A and 5-(chloromethyl)-3-(methoxymethyl)-1,2,4-oxadiazole in Step B. MS (ESI): mass calcd. for $C_{17}H_{13}F_2N_5O_3$, 373.1; m/z found, [M+H]$^+$. $^1$H NMR (500 MHz, DMF): 11.97 (s, 1H), 8.39 (d, J=2.0 Hz, 1H), 8.07 (d, J=2.0 Hz, 1H), 7.85-7.76 (m, 1H), 7.64-7.51 (m, 2H), 5.65 (s, 2H), 4.53 (s, 2H), 3.35 (s, 3H).

Example 146: 1-(2-Pyrrolidin-1-ylethyl)-6-[3-(trifluoromethyl)phenyl]-3H-imidazo[4,5-b]pyridin-2-one and its Trifluoroacetic Acid Salt

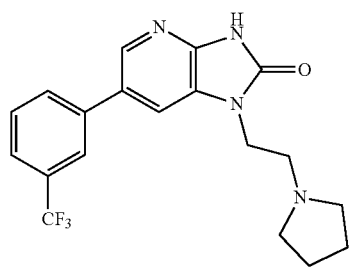 [SMILES: O=c1[nH]c2ncc(-c3cccc(C(F)(F)F)c3)cc2n1CCN1CCCC1]

The title compound was prepared in a manner analogous to Example 17, using pyrrolidine. MS (ESI): mass calcd. for $C_{19}H_{19}F_3N_4O$, 376.2; m/z found 377.2, [M+H]$^+$. $^1$H NMR (400 MHz, DMSO-d$_6$) δ 11.87 (s, 1H), 9.42 (s, 1H), 8.42-8.31 (d, J=1.9 Hz, 1H), 8.10-8.02 (m, 2H), 8.02-7.96 (d, J=2.0 Hz, 1H), 7.78-7.71 (m, 2H), 4.31-4.18 (m, 2H), 3.66 (s, 2H), 3.20-3.01 (m, 2H), 2.01 (s, 2H), 1.91-1.78 (d, J=4.6 Hz, 2H).

Example 147: 1-[2-(3-Hydroxyazetidin-1-yl)ethyl]-6-[3-(trifluoromethyl)phenyl]-3H-imidazo[4,5-b]pyridin-2-one and its Trifluoroacetic Acid Salt

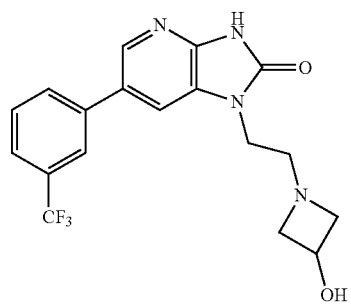 [SMILES: O=c1[nH]c2ncc(-c3cccc(C(F)(F)F)c3)cc2n1CCN1CC(O)C1]

The title compound was prepared in a manner analogous to Example 17, using 3-hydroxyazetidine. MS (ESI): mass calcd. for $C_{18}H_{17}F_3N_4O_2$, 378.1; m/z found 379.2, [M+H]$^+$. $^1$H NMR (400 MHz, CD$_3$OD) δ 8.33-8.29 (d, J=1.9 Hz, 1H), 7.98-7.91 (m, 2H), 7.89-7.86 (d, J=2.0 Hz, 1H), 7.73-7.66 (m, 2H), 4.65 (s, 1H), 4.54 (s, 1H), 4.37 (s, 1H), 4.31-4.22 (m, 2H), 4.14 (s, 1H), 4.00 (s, 1H), 3.76-3.60 (d, J=18.1 Hz, 2H).

Example 148: 1-[2-(Cyclopropylamino)ethyl]-6-[3-(trifluoromethyl)phenyl]-3H-imidazo[4,5-b]pyridin-2-one and its Trifluoroacetic Acid Salt

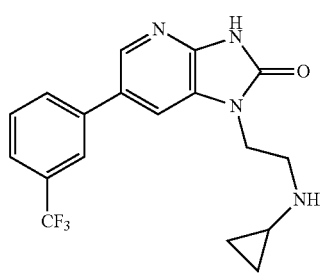 [SMILES: O=c1[nH]c2ncc(-c3cccc(C(F)(F)F)c3)cc2n1CCNC1CC1]

The title compound was prepared in a manner analogous to Example 17, using cyclopropylamine. MS (ESI): mass calcd. for $C_{18}H_{17}F_3N_4O$, 362.1; m/z found 363.2, [M+H]$^+$. $^1$H NMR (400 MHz, DMSO-d$_6$) δ 11.85 (s, 1H), 8.80 (s, 2H), 8.40-8.28 (m, 1H), 8.13-8.02 (m, 2H), 7.96-7.91 (d, J=2.0 Hz, 1H), 7.80-7.72 (m, 2H), 4.24-4.12 (m, 2H), 3.45 (s, 2H), 2.81 (s, 1H), 0.88-0.71 (m, 4H).

Example 149: 1-[2-(3-Methoxyazetidin-1-yl)ethyl]-6-[3-(trifluoromethyl)phenyl]-3H-imidazo[4,5-b]pyridin-2-one and its Trifluoroacetic Acid Salt

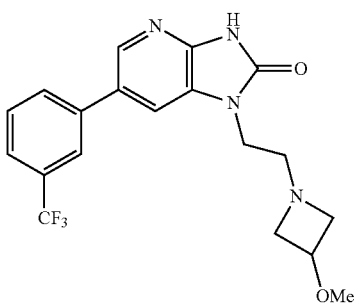 [SMILES: COC1CN(CCn2c(=O)[nH]c3ncc(-c4cccc(C(F)(F)F)c4)cc32)C1]

The title compound was prepared in a manner analogous to Example 17, using 3-hydroxymethylazetidine. MS (ESI): mass calcd. for $C_{19}H_{19}F_3N_4O_2$, 392.1; m/z found 393.2 [M+H]$^+$. $^1$H NMR (400 MHz, DMSO-d$_6$) δ 11.85 (s, 1H), 10.22 (s, 0.5H), 9.61 (s, 0.5H), 8.43-8.25 (m, 1H), 8.12-8.02 (m, 2H), 8.00-7.92 (m, 1H), 7.78-7.69 (m, 2H), 4.45-4.29 (m, 2H), 4.27-4.10 (m, 6H), 3.62 (s, 1H), 3.31-3.22 (d, J=5.6 Hz, 3H).

Example 150: 1-[2-(Cyclobutylamino)ethyl]-6-[3-(trifluoromethyl)phenyl]-3H-imidazo[4,5-b]pyridin-2-one and its Trifluoroacetic Acid Salt

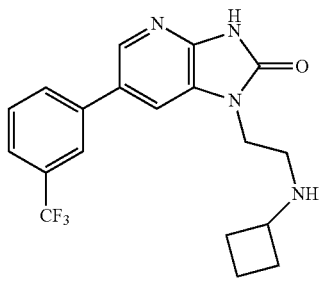 [SMILES: O=c1[nH]c2ncc(-c3cccc(C(F)(F)F)c3)cc2n1CCNC1CCC1]

The title compound was prepared in a manner analogous to Example 17, using cyclobutylamine. MS (ESI): mass calcd. for $C_{19}H_{19}F_3N_4O$, 376.2; m/z found 377.2 [M+H]$^+$. $^1$H NMR (400 MHz, DMSO-d$_6$) δ 11.84 (s, 1H), 8.73 (s, 2H), 8.47-8.27 (d, J=2.0 Hz, 1H), 8.15-8.02 (m, 2H), 7.96-7.85 (d, J=1.9 Hz, 1H), 7.80-7.68 (m, 2H), 4.23-4.12 (m, 2H), 3.81-3.68 (m, 1H), 3.20 (s, 2H), 2.22-2.02 (m, 4H), 1.85-1.68 (m, 2H).

Example 151: 1-[2-(Azetidin-1-yl)ethyl]-6-(4-fluoro-2-methyl-phenyl)-3H-imidazo[4,5-b]pyridin-2-one and its Trifluoroacetic Acid Salt

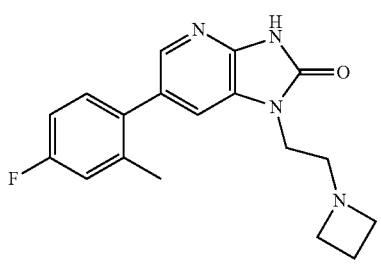 [SMILES: Cc1cc(F)ccc1-c1cnc2[nH]c(=O)n(CCN3CCC3)c2c1]

The title compound was prepared in a manner analogous to Example 17, using 4-fluoro-2-methylphenylboronic acid. MS (ESI): mass calcd. for $C_{18}H_{19}FN_4O$, 326.2; m/z found 327.2 [M+H]$^+$. $^1$H NMR (500 MHz, DMSO-d$_6$) δ 11.69 (s, 1H), 9.58 (s, 1H), 7.97-7.76 (m, 1H), 7.60-7.49 (d, J=1.9 Hz, 1H), 7.31-7.25 (m, 1H), 7.25-7.17 (m, 1H), 7.15-7.07 (m, 1H), 4.16-4.03 (m, 6H), 3.76-3.34 (m, 2H), 2.45-2.33 (m, 1H), 2.26 (s, 3H).

Example 152: 1-[2-(Azetidin-1-yl)ethyl]-6-(o-tolyl)-3H-imidazo[4,5-b]pyridin-2-one and its Trifluoroacetic Acid Salt

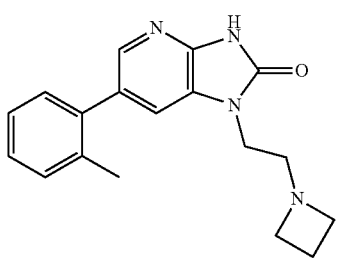 [SMILES: Cc1ccccc1-c1cnc2[nH]c(=O)n(CCN3CCC3)c2c1]

The title compound was prepared in a manner analogous to Example 17, using 2-methylphenylboronic acid. MS (ESI): mass calcd. for $C_{18}H_{20}N_4O$, 308.2; m/z found 309.2 [M+H]$^+$. $^1$H NMR (500 MHz, DMSO-d$_6$) δ 11.75 (s, 1H), 9.59 (s, 1H), 7.98-7.80 (m, 1H), 7.65-7.54 (d, J=1.9 Hz, 1H), 7.41-7.20 (m, 4H), 4.23-3.97 (m, 6H), 2.47-2.35 (d, J=10.1 Hz, 2H), 2.46-2.21 (m, 5H).

Example 153: 1-[2-(Azetidin-1-yl)ethyl]-6-phenyl-3H-imidazo[4,5-b]pyridin-2-one and its Trifluoroacetic Acid Salt

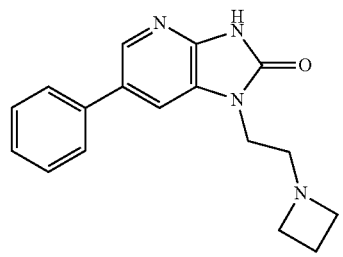 [SMILES: O=c1[nH]c2ncc(-c3ccccc3)cc2n1CCN1CCC1]

The title compound was prepared in a manner analogous to Example 17, using phenylboronic acid. MS (ESI): mass calcd. for $C_{17}H_{18}N_4O$, 294.1; m/z found 395.2 [M+H]$^+$. $^1$H NMR (500 MHz, DMSO-d$_6$) δ 11.71 (s, 1H), 9.58 (s, 1H), 8.35-8.14 (m, 1H), 7.92-7.82 (d, J=1.8 Hz, 1H), 7.78-7.62 (m, 2H), 7.58-7.44 (m, 2H), 7.42-7.32 (m, 1H), 4.22-3.97 (m, 6H), 3.61-3.52 (m, 2H), 2.44-2.33 (m, 1H), 2.26 (s, 1H).

Example 154: 1-[2-(Azetidin-1-yl)ethyl]-6-(m-tolyl)-3H-imidazo[4,5-b]pyridin-2-one and its Trifluoroacetic Acid Salt

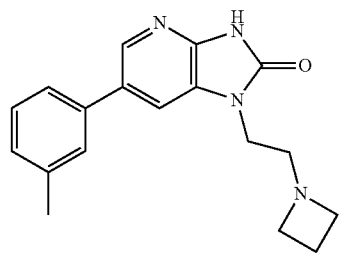 [SMILES: Cc1cccc(-c2cnc3[nH]c(=O)n(CCN4CCC4)c3c2)c1]

The title compound was prepared in a manner analogous to Example 17, using 3-methylphenylboronic acid. MS (ESI): mass calcd. for $C_{18}H_{20}N_4O$, 308.2; m/z found, 309.2 [M+H]$^+$. $^1$H NMR (500 MHz, DMSO-d$_6$) δ 11.75 (s, 1H), 9.68-9.44 (d, J=11.1 Hz, 1H), 8.33-8.17 (m, 1H), 7.90-7.77 (m, 1H), 7.58-7.44 (m, 2H), 7.41-7.32 (m, 1H), 7.25-7.11 (d, J=7.4 Hz, 1H), 4.15-4.01 (m, 6H), 3.62-3.50 (d, J=6.9 Hz, 2H), 2.38 (s, 4H), 2.26 (s, 1H).

Example 155: 1-[2-(Azetidin-1-yl)ethyl]-6-[2-(trifluoromethyl)-4-pyridyl]-3H-imidazo[4,5-b]pyridin-2-one and its Trifluoroacetic Acid Salt

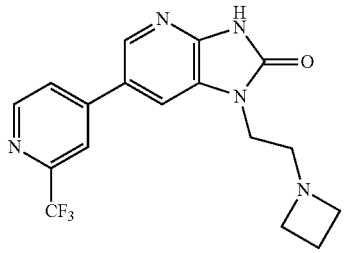 [SMILES: O=c1[nH]c2ncc(-c3ccnc(C(F)(F)F)c3)cc2n1CCN1CCC1]

The title compound was prepared in a manner analogous to Example 17, using (2-(trifluoromethyl)pyridin-4-yl)boronic acid. MS (ESI): mass calcd. for $C_{17}H_{16}F_3N_5O$, 363.1; m/z found, 364.2 [M+H]$^+$. $^1$H NMR (500 MHz, DMSO-d$_6$) δ 11.96 (s, 1H), 9.67 (s, 1H), 8.92-8.76 (m, 1H), 8.64-8.53 (d, J=2.7 Hz, 1H), 8.29 (s, 1H), 8.20-8.06 (d, J=2.1 Hz, 2H), 4.30-3.95 (m, 6H), 3.55 (s, 2H), 2.51-2.34 (m, 1H), 2.28 (s, 1H).

Example 156: 1-[2-(Azetidin-1-yl)ethyl]-6-(4-fluoro-3-methyl-phenyl)-3H-imidazo[4,5-b]pyridin-2-one and its Trifluoroacetic Acid Salt

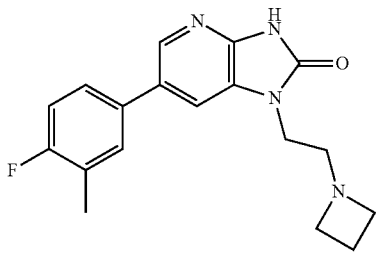 [SMILES: Cc1cc(-c2cnc3[nH]c(=O)n(CCN4CCC4)c3c2)ccc1F]

The title compound was prepared in a manner analogous to Example 17, using 3-methyl-4-fluoroboronic acid. MS (ESI): mass calcd. for $C_{18}H_{19}FN_4O$, 326.2; m/z found 327.2 [M+H]$^+$. $^1$H NMR (500 MHz, DMSO-d$_6$) δ 11.73 (s, 1H), 9.61 (s, 1H), 8.33-8.10 (m, 1H), 7.87-7.78 (d, J=2.1 Hz, 1H), 7.68-7.59 (m, 1H), 7.60-7.49 (m, 1H), 7.34-7.14 (m, 1H), 4.28-3.93 (m, 6H), 3.57 (s, 2H), 2.54-2.46 (m, 1H), 2.45-2.33 (m, 3H), 2.25 (s, 1H).

Example 157: 1-[2-(Azetidin-1-yl)ethyl]-6-(2,6-dimethylphenyl)-3H-imidazo[4,5-b]pyridin-2-one and its Trifluoroacetic Acid Salt

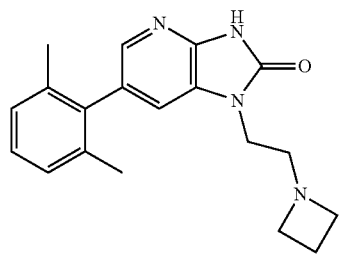 [SMILES: Cc1cccc(C)c1-c1cnc2[nH]c(=O)n(CCN3CCC3)c2c1]

The title compound was prepared in a manner analogous to Example 17, using 2,6-dimethylphenylboronic acid. MS (ESI): mass calcd. for $C_{19}H_{22}N_4O$, 322.2; m/z found 323.2 [M+H]$^+$. $^1$H NMR (500 MHz, DMSO-d$_6$) δ 11.77 (s, 1H), 9.54 (s, 1H), 7.83-7.59 (m, 1H), 7.51-7.39 (d, J=2.3 Hz, 1H), 7.30-7.07 (m, 3H), 4.27-3.95 (m, 6H), 3.75-3.05 (m, 2H), 2.44-2.34 (m, 1H), 2.28 (s, 1H), 2.16-1.79 (m, 6H).

Example 158: 1-[2-(Azetidin-1-yl)ethyl]-6-(3-chlorophenyl)-3H-imidazo[4,5-b]pyridin-2-one and its Trifluoroacetic Acid Salt

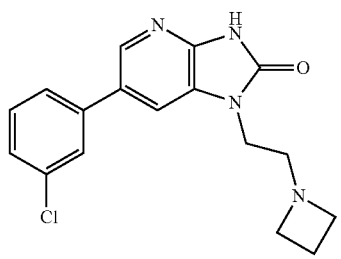

The title compound was prepared in a manner analogous to Example 17, using 3-chlorophenylboronic acid. MS (ESI): mass calcd. for $C_{17}H_{17}ClN_4O$, 328.1; m/z found 329.1 [M+H]$^+$. $^1$H NMR (500 MHz, DMSO-d$_6$) δ 11.78 (s, 1H), 9.62 (s, 1H), 8.50-8.11 (m, 1H), 8.00-7.89 (m, 1H), 7.88-7.77 (m, 1H), 7.77-7.67 (m, 1H), 7.60-7.48 (m, 1H), 7.48-7.39 (m, 1H), 4.24-4.01 (d, J=5.9 Hz, 6H), 3.59 (s, 2H), 2.46-2.35 (d, J=9.6 Hz, 1H), 2.26 (s, 1H).

Example 159: 1-[2-(Azetidin-1-yl)ethyl]-6-(3,5-difluorophenyl)-3H-imidazo[4,5-b]pyridin-2-one and its Trifluoroacetic Acid Salt

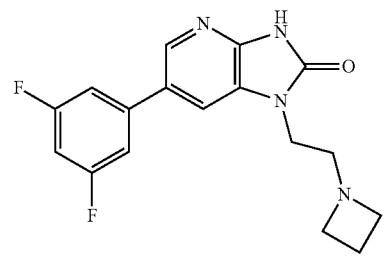 [SMILES: O=c1[nH]c2ncc(-c3cc(F)cc(F)c3)cc2n1CCN1CCC1]

The free base of the title compound was prepared in a manner analogous to Example 17, using 3,5-difluorophenylboronic acid. MS (ESI): mass calcd. for $C_{17}H_{16}F_2N_4O$, 330.1; m/z found 331.2 [M+H]$^+$. $^1$H NMR (500 MHz, DMSO-d$_6$) δ 11.88 (s, 1H), 9.64 (s, 1H), 8.58-8.34 (d, J=2.1 Hz, 1H), 8.08-7.85 (m, 1H), 7.68-7.41 (d, J=9.2 Hz, 2H), 7.26 (s, 1H), 4.66 (s, 6H), 3.59 (s, 2H), 2.41 (s, 1H), 2.27 (s, 1H).

Example 160: 1-[2-(Azetidin-1-yl)ethyl]-6-[3-(trifluoromethoxy)phenyl]-3H-imidazo[4,5-b]pyridin-2-one and its Trifluoroacetic Acid Salt

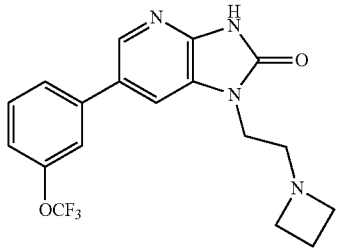 [SMILES: O=c1[nH]c2ncc(-c3cccc(OC(F)(F)F)c3)cc2n1CCN1CCC1]

The title compound was prepared in a manner analogous to Example 17, using 3-(trifluoromethoxy)phenylboronic acid. MS (ESI): mass calcd. for $C_{18}H_{17}F_3N_4O_2$, 378.1; m/z found 379.2 [M+H]$^+$. $^1$H NMR (500 MHz, DMSO-d$_6$) δ 11.83 (s, 1H), 9.61 (s, 1H), 8.49-8.26 (m, 1H), 8.01-7.89 (d, J=1.8 Hz, 1H), 7.84-7.76 (d, J=8.2 Hz, 1H), 7.72 (s, 1H), 7.69-7.59 (m, 1H), 7.46-7.31 (m, 1H), 4.09 (s, 6H), 3.60 (s, 2H), 2.47-2.35 (d, J=8.9 Hz, 1H), 2.27 (s, 1H).

Example 161: 1-[2-(1-Piperidyl)ethyl]-6-[3-(trifluoromethyl)phenyl]-3H-imidazo[4,5-b]pyridin-2-one and its Trifluoroacetic Acid Salt

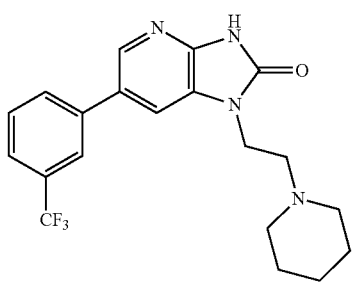 [SMILES: O=c1[nH]c2ncc(-c3cccc(C(F)(F)F)c3)cc2n1CCN1CCCCC1]

The title compound was prepared in a manner analogous to Example 17, using piperidine. MS (ESI): mass calcd. for $C_{20}H_{21}F_3N_4O$, 390.2; m/z found 391.2 [M+H]$^+$. $^1$H NMR (500 MHz, DMSO-d$_6$) δ 11.87 (s, 1H), 8.90 (s, 1H), 8.43-8.32 (d, J=1.9 Hz, 1H), 8.05 (s, 2H), 8.00-7.90 (d, J=2.1 Hz, 1H), 7.80-7.69 (d, J=7.2 Hz, 2H), 4.37-4.22 (m, 2H), 3.74-3.64 (d, J=11.6 Hz, 2H), 3.41 (s, 2H), 3.08-2.89 (m, 2H), 1.91-1.81 (d, J=14.3 Hz, 2H), 1.77-1.68 (d, J=12.3 Hz, 1H), 1.65-1.53 (d, J=13.4 Hz, 2H), 1.44-1.32 (d, J=13.0 Hz, 1H).

Example 162: 1-[2-(4-Fluoro-1-piperidyl)ethyl]-6-[3-(trifluoromethyl)phenyl]-3H-imidazo[4,5-b]pyridin-2-one and its Trifluoroacetic Acid Salt

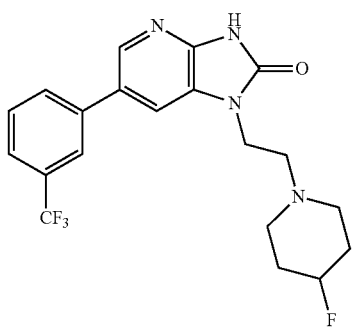 [SMILES: O=c1[nH]c2ncc(-c3cccc(C(F)(F)F)c3)cc2n1CCN1CCC(F)CC1]

The title compound was prepared in a manner analogous to Example 17, using 4-fluoropiperidine. MS (ESI): mass calcd. for $C_{20}H_{20}F_4N_4O$, 408.2; m/z found 409.2 [M+H]$^+$. $^1$H NMR (500 MHz, DMSO-d$_6$) δ 11.87 (s, 1H), 8.90 (s, 1H), 8.43-8.32 (d, J=1.9 Hz, 1H), 8.05 (s, 2H), 8.00-7.90 (d, J=2.1 Hz, 1H), 7.80-7.69 (d, J=7.2 Hz, 2H), 4.37-4.22 (m, 2H), 3.74-3.64 (d, J=11.6 Hz, 2H), 3.41 (s, 2H), 3.08-2.89 (m, 2H), 1.91-1.81 (d, J=14.3 Hz, 2H), 1.77-1.68 (d, J=12.3 Hz, 1H), 1.65-1.53 (d, J=13.4 Hz, 2H).

Example 163: 1-[2-(3-Fluoroazetidin-1-yl)ethyl]-6-[3-(trifluoromethyl)phenyl]-3H-imidazo[4,5-b]pyridin-2-one and its Trifluoroacetic Acid Salt

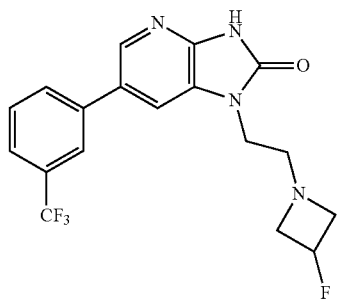 [SMILES: O=c1[nH]c2ncc(-c3cccc(C(F)(F)F)c3)cc2n1CCN1CC(F)C1]

The title compound was prepared in a manner analogous to Example 17, using 3-fluoroazetidine. MS (ESI): mass calcd. for $C_{18}H_{16}F_4N_4O$, 380.1; m/z found 381.2 [M+H]$^+$. $^1$H NMR (500 MHz, DMSO-d$_6$) δ 11.82 (s, 1H), 8.52-8.23 (d, J=1.9 Hz, 1H), 8.09-8.02 (m, 2H), 7.99 (s, 1H), 7.79-7.63 (m, 2H), 5.44 (s, 1H), 5.30 (s, 1H), 4.51 (s, 3H), 4.19 (s, 2H), 3.65 (s, 2H).

Example 164: 1-[2-(3-Methylpyrrolidin-1-yl)ethyl]-6-[3-(trifluoromethyl)phenyl]-3H-imidazo[4,5-b]pyridin-2-one and its Trifluoroacetic Acid Salt

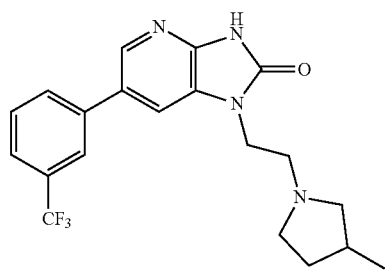 [SMILES: CC1CCN(CCn2c(=O)[nH]c3ncc(-c4cccc(C(F)(F)F)c4)cc32)C1]

The title compound was prepared in a manner analogous to Example 17, using 3-methylpyrrolidine. MS (ESI): mass calcd. for $C_{20}H_{21}F_3N_4O$, 390.2; m/z found 391.2 [M+H]$^+$. $^1$H NMR (500 MHz, DMSO-d$_6$) δ 9.51 (s, 1H), 8.39 (s, 1H), 8.12-8.02 (d, J=6.3 Hz, 2H), 8.95 (s, 1H), 7.85-7.65 (m, 2H), 4.54-4.22 (d, J=4.5 Hz, 2H), 3.77 (s, 1H), 3.62 (s, 1H), 3.22 (s, 2H), 2.81-2.66 (d, J=10.2 Hz, 1H), 2.26 (s, 1H), 2.08 (s, 1H), 1.67 (s, 1H), 1.41 (s, 1H), 1.18-0.90 (m, 3H).

Example 165: 1-[2-(4-Hydroxy-1-piperidyl)ethyl]-6-[3-(trifluoromethyl)phenyl]-3H-imidazo[4,5-b]pyridin-2-one and its Trifluoroacetic Acid Salt

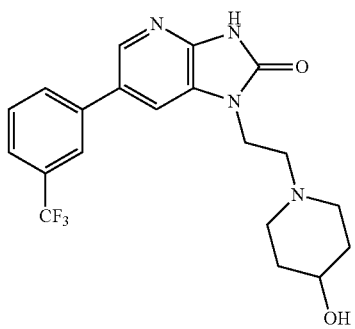 [SMILES: O=c1[nH]c2ncc(-c3cccc(C(F)(F)F)c3)cc2n1CCN1CCC(O)CC1]

The title compound was prepared in a manner analogous to Example 17, using 4-hydroxypiperidine. MS (ESI): mass calcd. for $C_{20}H_{21}F_3N_4O_2$, 406.2; m/z found 407.2 [M+H]$^+$. $^1$H NMR (500 MHz, MeOD) δ 6.89-6.70 (d, J=1.8 Hz, 1H), 6.46 (s, 1H), 6.45-6.42 (d, J=7.2 Hz, 1H), 6.38 (s, 1H), 6.21-6.17 (m, 2H), 2.88 (s, 2H), 2.35 (s, 2H), 2.26 (s, 1H), 2.07 (s, 2H), 1.88 (s, 2H), 1.69-1.57 (m, 1H), 0.66 (s, 1H), 0.45 (s, 2H), 0.21 (s, 1H).

Example 166: 1-[2-[3-(Trifluoromethyl)azetidin-1-yl]ethyl]-6-[3-(trifluoromethyl)phenyl]-3H-imidazo[4,5-b]pyridin-2-one and its Trifluoroacetic Acid Salt

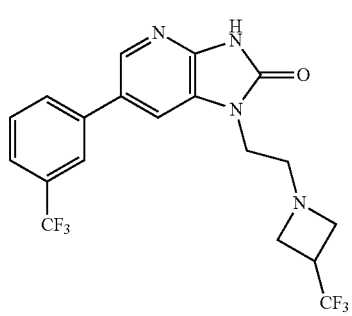 [SMILES: O=c1[nH]c2ncc(-c3cccc(C(F)(F)F)c3)cc2n1CCN1CC(C(F)(F)F)C1]

The title compound was prepared in a manner analogous to Example 17, using 3-(trifluoromethyl)azetidine. MS (ESI): mass calcd. for $C_{19}H_{16}F_6N_4O$, 430.1; m/z found 431.1 [M+H]$^+$. $^1$H NMR (500 MHz, DMSO-d$_6$) δ 11.74 (s, 1H), 8.50-8.17 (m, 1H), 8.17-7.85 (m, 3H), 7.85-7.53 (m, 2H), 4.35 (s, 6H), 3.91-3.21 (m, 3H).

Example 167: 1-[2-(3,3-Difluoroazetidin-1-yl)ethyl]-6-[3-(trifluoromethyl)phenyl]-3H-imidazo[4,5-b]pyridin-2-one and its Trifluoroacetic Acid Salt

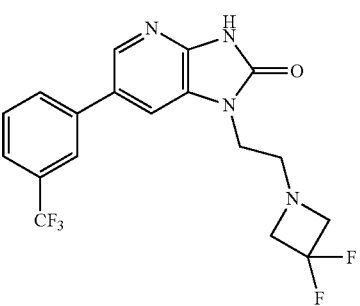 [SMILES: O=c1[nH]c2ncc(-c3cccc(C(F)(F)F)c3)cc2n1CCN1CC(F)(F)C1]

The title compound was prepared in a manner analogous to Example 17, using 3,3-difluoroazetidine. MS (ESI): mass calcd. for $C_{18}H_{15}F_5N_4O$, 398.1; m/z found 399.1 [M+H]$^+$. $^1$H NMR (500 MHz, DMSO-d$_6$) δ 11.79 (s, 1H), 8.49-8.21 (m, 1H), 8.09-7.92 (m, 4H), 7.80-7.61 (m, 3H), 4.39 (s, 4H), 4.06 (s, 2H).

Example 168: 1-[2-(Azetidin-1-yl)ethyl]-6-[2-methyl-3-(trifluoromethyl)phenyl]-3H-imidazo[4,5-b]pyridin-2-one and its Trifluoroacetic Acid Salt

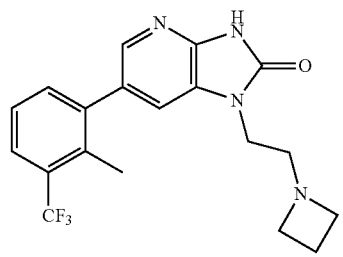 [SMILES: Cc1c(-c2cnc3[nH]c(=O)n(CCN4CCC4)c3c2)cccc1C(F)(F)F]

The title compound was prepared in a manner analogous to Example 17, using 2-methyl-3-(trifluoromethyl)phenylboronic acid. MS (ESI): mass calcd. for $C_{19}H_{19}F_3N_4O$, 376.2; m/z found 377.2 [M+H]$^+$. $^1$H NMR (400 MHz, DMSO-d$_6$) δ 11.78 (s, 1H), 9.65 (s, 1H), 7.94-7.91 (d, J=1.8 Hz, 1H), 7.79-7.73 (m, 1H), 7.64-7.60 (d, J=1.9 Hz, 1H), 7.59-7.45 (m, 2H), 4.17-3.98 (m, 6H), 3.54 (s, 2H), 2.45-2.38 (m, 1H), 2.37-2.32 (d, J=1.9 Hz, 3H), 2.25 (s, 1H).

Example 169: 1-[2-(Azetidin-1-yl)ethyl]-6-(2,3-dimethylphenyl)-3H-imidazo[4,5-b]pyridin-2-one and its Trifluoroacetic Acid Salt

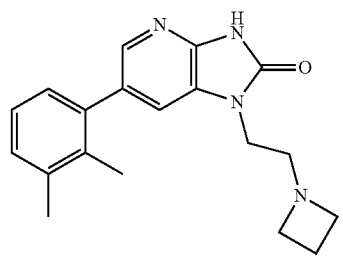 [SMILES: Cc1cccc(-c2cnc3[nH]c(=O)n(CCN4CCC4)c3c2)c1C]

The title compound was prepared in a manner analogous to Example 17, using 2,3-dimethylphenylboronic acid. MS (ESI): mass calcd. for $C_{19}H_{22}N_4O$, 322.2; m/z found 323.2 [M+H]$^+$. $^1$H NMR (400 MHz, DMSO-d$_6$) δ 11.75 (s, 1H), 9.64 (s, 1H), 7.97-7.78 (m, 1H), 7.59-7.48 (d, J=1.8 Hz, 1H), 7.25-7.12 (m, 2H), 7.13-7.03 (m, 1H), 4.20-3.92 (m, 6H), 3.45 (s, 2H), 2.44-2.35 (m, 1H), 2.32 (s, 3H), 2.28-2.18 (m, 1H), 2.14 (s, 3H).

Example 170: 1-[2-(Azetidin-1-yl)ethyl]-6-(3,5-dimethylphenyl)-3H-imidazo[4,5-b]pyridin-2-one and its Trifluoroacetic Acid Salt

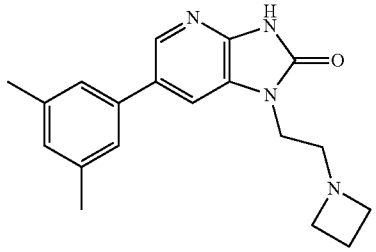 [SMILES: Cc1cc(C)cc(-c2cnc3[nH]c(=O)n(CCN4CCC4)c3c2)c1]

The title compound was prepared in a manner analogous to Example 17, using 3,5-dimethylphenylboronic acid. MS (ESI): mass calcd. for $C_{19}H_{22}N_4O$, 322.2; m/z found 323.2 [M+H]$^+$. $^1$H NMR (400 MHz, DMSO-d$_6$) δ 11.76 (s, 1H), 9.64 (s, 1H), 8.40-8.19 (d, J=1.9 Hz, 1H), 7.92-7.78 (d, J=2.0 Hz, 1H), 7.39-7.24 (m, 2H), 7.00 (s, 1H), 4.20-3.95 (m, 6H), 3.66-3.51 (d, J=5.4 Hz, 2H), 2.45-2.20 (m, 8H).

Example 171: 1-[2-(Azetidin-1-yl)ethyl]-6-(4-fluoro-2,3-dimethyl-phenyl)-3H-imidazo[4,5-b]pyridin-2-one and its Trifluoroacetic Acid Salt

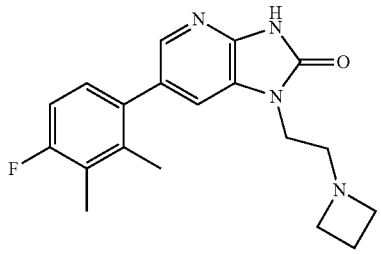

The title compound was prepared in a manner analogous to Example 17, using 4-fluoro-2,3-dimethylphenylboronic. MS (ESI): mass calcd. for $C_{19}H_{21}FN_4O$, 340.2; m/z found, 341.2 [M+H]$^+$. $^1$H NMR (400 MHz, DMSO-d$_6$) δ 11.73 (s, 1H), 9.69 (s, 1H), 7.95-7.66 (d, J=1.8 Hz, 1H), 7.60-7.47 (d, J=1.9 Hz, 1H), 7.21-7.03 (m, 2H), 4.20-3.93 (m, 6H), 3.51 (s, 2H), 2.45-2.32 (m, 2H), 2.25-2.21 (d, J=2.1 Hz, 3H), 2.18 (s, 3H).

Example 172: 1-[2-(Azetidin-1-yl)ethyl]-6-[2-methyl-5-(trifluoromethyl)phenyl]-3H-imidazo[4,5-b]pyridin-2-one and its Trifluoroacetic Acid Salt

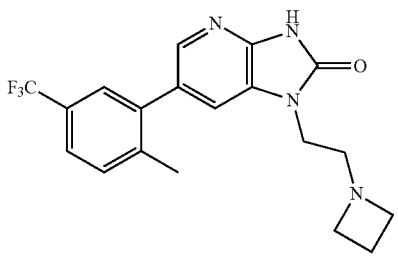 [SMILES: Cc1ccc(C(F)(F)F)cc1-c1cnc2[nH]c(=O)n(CCN3CCC3)c2c1]

The title compound was prepared in a manner analogous to Example 17, using (2-methyl-5-(trifluoromethyl)phenyl) boronic acid. MS (ESI): mass calcd. for $C_{19}H_{19}F_3N_4O$, 376.2; m/z found, 377.2 [M+H]$^+$. $^1$H NMR (400 MHz, DMSO-d$_6$) δ 11.92 (s, 1H), 9.68 (s, 1H), 8.01-7.96 (d, J=1.8 Hz, 1H), 7.71-7.63 (m, 2H), 7.62-7.54 (m, 2H), 4.20-3.97 (m, 6H), 3.68-3.36 (m, 2H), 2.46-2.38 (d, J=9.2 Hz, 1H), 2.36 (s, 3H), 2.32-2.21 (d, J=2.3 Hz, 1H).

Example 173: 6-(3,5-Difluorophenyl)-1-[2-(2-hydroxyethylamino)ethyl]-3H-imidazo[4,5-b]pyridin-2-one and its Trifluoroacetic Acid Salt

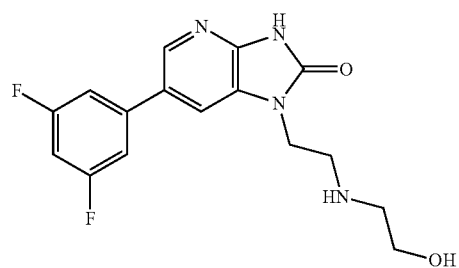 [SMILES: O=c1[nH]c2ncc(-c3cc(F)cc(F)c3)cc2n1CCNCCO]

The title compound was prepared in a manner analogous to Example 17, using ethanolamine in Step A and 3,5-difluorophenylboronic acid in Step B. MS (ESI): mass calcd. for $C_{16}H_{16}F_2N_4O_2$, 334.1; m/z found, 335.2 [M+H]$^+$. $^1$H NMR (500 MHz, CD$_3$OD) δ 8.31 (d, J=2.0 Hz, 1H), 7.84 (d, J=2.0 Hz, 1H), 7.37-7.27 (m, 2H), 6.98 (tt, J=9.1, 2.3 Hz, 1H), 4.33 (t, J=5.8 Hz, 2H), 3.86-3.77 (m, 2H), 3.51 (t, J=5.8 Hz, 2H), 3.28-3.21 (m, 2H).

Example 174: 6-(3,5-Difluorophenyl)-1-(2-pyrrolidin-1-ylethyl)-3H-imidazo[4,5-b]pyridin-2-one and its Trifluoroacetic Acid Salt

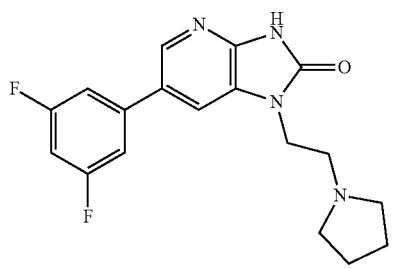 [SMILES: O=c1[nH]c2ncc(-c3cc(F)cc(F)c3)cc2n1CCN1CCCC1]

The title compound was prepared in a manner analogous to Example 17, using pyrrolidine in Step A and 3,5-difluorophenylboronic acid in Step B. MS (ESI): mass calcd. for $C_{18}H_{18}F_2N_4O$, 344.1; m/z found, 345.2 [M+H]$^+$. $^1$H NMR (400 MHz, DMSO-d$_6$) δ 11.91 (s, 1H), 9.54 (s, 1H), 8.41 (d, J=1.9 Hz, 1H), 7.98 (d, J=2.0 Hz, 1H), 7.69-7.51 (m, 2H), 7.26 (tt, J=9.2, 2.3 Hz, 1H), 4.24 (t, J=5.7 Hz, 2H), 3.61 (d, J=6.0 Hz, 2H), 3.17 (s, 2H), 3.13 (dd, J=11.3, 7.3 Hz, 2H), 2.04 (dd, J=9.0, 5.3 Hz, 2H), 1.94-1.62 (m, 2H).

Example 175: 6-(3,5-Difluorophenyl)-1-[2-(3-hydroxypyrrolidin-1-yl)ethyl]-3H-imidazo[4,5-b]pyridin-2-one and its Trifluoroacetic Acid Salt

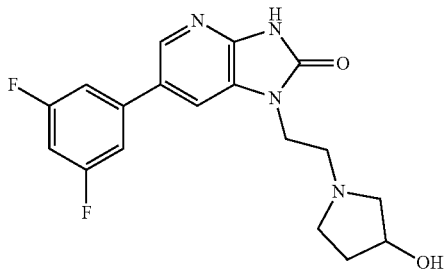 [SMILES: O=c1[nH]c2ncc(-c3cc(F)cc(F)c3)cc2n1CCN1CCC(O)C1]

The title compound was prepared in a manner analogous to Example 17, using 3-hydroxypyrrolidine in Step A and 3,5-difluorophenylboronic acid in Step B. MS (ESI): mass calcd. for $C_{18}H_{18}F_2N_4O_2$, 360.1; m/z found, 361.2 [M+H]$^+$. $^1$H NMR (400 MHz, DMSO-d$_6$) δ 11.64 (s, 1H), 8.25 (d, J=2.0 Hz, 1H), 7.82 (d, J=2.0 Hz, 1H), 7.55-7.39 (m, 2H), 7.15 (tt, J=9.2, 2.3 Hz, 1H), 4.60 (d, J=4.4 Hz, 1H), 4.07 (t, J=8.8 Hz, 1H), 3.88 (t, J=6.5 Hz, 2H), 2.76-2.50 (m, 4H), 2.34-2.24 (m, 1H), 1.84 (dd, J=13.0, 7.1 Hz, 1H), 1.51-1.35 (m, 1H).

Example 176: 6-(3,5-Difluorophenyl)-1-[2-(3-methoxypyrrolidin-1-yl)ethyl]-3H-imidazo[4,5-b]pyridin-2-one and its Trifluoroacetic Acid Salt

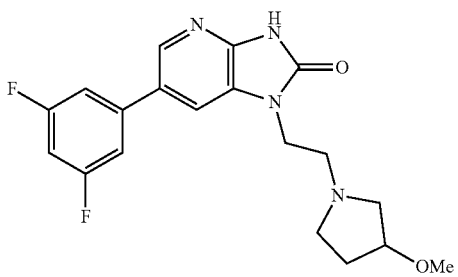 [SMILES: COC1CCN(CCn2c(=O)[nH]c3ncc(-c4cc(F)cc(F)c4)cc32)C1]

The title compound was prepared in a manner analogous to Example 17, using 3-methoxypyrrolidine in Step A and 3,5-difluorophenylboronic acid in Step B. MS (ESI): mass calcd. for $C_{19}H_{20}F_2N_4O_2$, 374.2; m/z found, 375.2 [M+H]$^+$. $^1$H NMR (400 MHz, DMSO-d$_6$) δ 11.73 (s, 1H), 8.33 (d, J=2.0 Hz, 1H), 7.89 (d, J=2.0 Hz, 1H), 7.55 (dt, J=7.8, 2.1 Hz, 2H), 7.24 (tt, J=9.4, 2.3 Hz, 1H), 3.97 (t, J=6.4 Hz, 2H), 3.84 (ddt, J=8.9, 6.3, 3.2 Hz, 1H), 3.14 (s, 3H), 2.84-2.61 (m, 5H), 2.44 (q, J=7.7 Hz, 1H), 2.00-1.86 (m, 1H), 1.67-1.54 (m, 1H).

Example 177: 6-(4-Fluoro-2-methyl-phenyl)-1-(2-pyrrolidin-1-ylethyl)-3H-imidazo[4,5-b]pyridin-2-one and its Trifluoroacetic Acid Salt

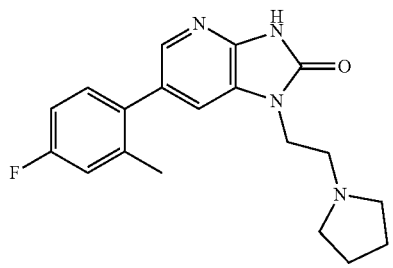 [SMILES: Cc1cc(F)ccc1-c1cnc2[nH]c(=O)n(CCN3CCCC3)c2c1]

The title compound was prepared in a manner analogous to Example 17, using pyrrolidine in Step A and 2-methyl-4-fluorophenylboronic acid. MS (ESI): mass calcd. for $C_{19}H_{21}FN_4O$, 340.2; m/z found, 341.2 [M+H]$^+$. $^1$H NMR (400 MHz, DMSO-d$_6$) δ 11.80 (s, 1H), 9.54 (s, 1H), 8.04-7.76 (d, J=1.8 Hz, 1H), 7.75-7.46 (d, J=1.8 Hz, 1H), 7.34-7.27 (m, 1H), 7.25-7.19 (m, 1H), 7.17-7.09 (m, 1H), 4.25-4.14 (m, 2H), 3.71-3.58 (m, 2H), 3.58-3.48 (m, 2H), 3.20-3.02 (m, 2H), 2.28 (s, 3H), 2.05-1.97 (m, 2H), 1.89-1.76 (m, 2H).

Example 178: 6-(2,6-Dimethylphenyl)-1-(2-pyrrolidin-1-ylethyl)-3H-imidazo[4,5-b]pyridin-2-one and its Trifluoroacetic Acid Salt

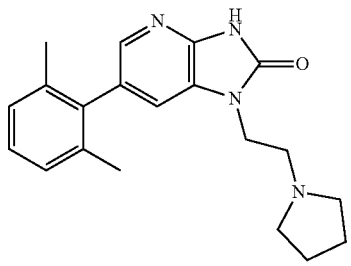 [SMILES: Cc1cccc(C)c1-c1cnc2[nH]c(=O)n(CCN3CCCC3)c2c1]

The title compound was prepared in a manner analogous to Example 17, using pyrrolidine in Step A and 2,6-dimethylphenylboronic acid in Step B. MS (ESI): mass calcd. for $C_{20}H_{24}N_4O$, 336.2; m/z found, 377.2 [M+H]$^+$. 1H NMR (400 MHz, DMSO-d$_6$) δ 11.78 (s, 1H), 9.46 (s, 1H), 7.77-7.68 (d, J=1.7 Hz, 1H), 7.53-7.44 (d, J=1.8 Hz, 1H), 7.25-7.11 (m, 3H), 4.22-4.13 (t, J=5.9 Hz, 2H), 3.79 (s, 2H), 3.55-3.45 (d, J=5.9 Hz, 2H), 3.17-3.01 (m, 2H), 2.01 (s, 8H), 1.88-1.77 (m, 2H).

Example 179: 6-(o-Tolyl)-1-(2-pyrrolidin-1-yl-ethyl)-3H-imidazo[4,5-b]pyridin-2-one and its Trifluoroacetic Acid Salt

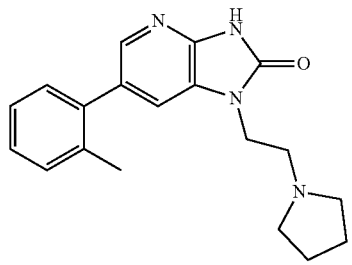 [SMILES: Cc1ccccc1-c1cnc2[nH]c(=O)n(CCN3CCCC3)c2c1]

The title compound was prepared in a manner analogous to Example 17, using pyrrolidine in Step A and 2-methylphenylboronic acid in Step B. MS (ESI): mass calcd. for $C_{19}H_{22}N_4O$, 322.2; m/z found, 323.2 [M+H]$^+$. $^1$H NMR (400 MHz, DMSO-d$_6$) δ 11.77 (s, 1H), 9.45 (s, 1H), 8.01-7.90 (d, J=1.8 Hz, 1H), 7.68-7.54 (d, J=1.8 Hz, 1H), 7.40-7.19 (m, 4H), 4.28-4.10 (m, 2H), 3.74 (s, 2H), 3.58-3.48 (d, J=5.9 Hz, 2H), 3.20-2.99 (m, 2H), 2.29 (s, 3H), 2.06-1.91 (d, J=7.4 Hz, 2H), 1.90-1.77 (m, 2H).

Example 180: 6-Phenyl-1-(2-pyrrolidin-1-ylethyl)-3H-imidazo[4,5-b]pyridin-2-one and its Trifluoroacetic Acid Salt

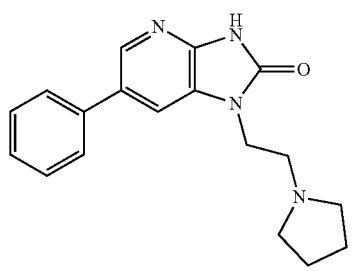 [SMILES: O=c1[nH]c2ncc(-c3ccccc3)cc2n1CCN1CCCC1]

The title compound was prepared in a manner analogous to Example 17, using pyrrolidine in Step A and phenylboronic acid in Step B. MS (ESI): mass calcd. for $C_{18}H_{20}N_4O$, 308.2; m/z found, 309.2 [M+H]$^+$. $^1$H NMR (400 MHz, DMSO-d$_6$) δ 11.80 (s, 1H), 9.48 (s, 1H), 8.35-8.23 (d, J=1.9 Hz, 1H), 7.95-7.85 (d, J=1.9 Hz, 1H), 7.77-7.70 (m, 2H), 7.54-7.45 (m, 2H), 7.43-7.35 (m, 1H), 4.31-4.21 (m, 2H), 3.73-3.50 (m, 4H), 3.20-2.95 (m, 2H), 2.12-1.97 (d, J=7.2 Hz, 2H), 1.92-1.75 (m, 1H).

Example 181: 1-[2-(3-Fluoroazetidin-1-yl)ethyl]-6-[2-methyl-3-(trifluoromethyl)phenyl]-3H-imidazo[4,5-b]pyridin-2-one and its Trifluoroacetic Acid Salt

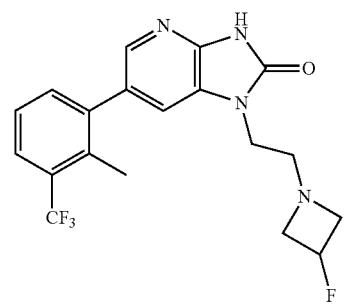 [SMILES: Cc1c(-c2cnc3[nH]c(=O)n(CCN4CC(F)C4)c3c2)cccc1C(F)(F)F]

The title compound was prepared in a manner analogous to Example 17, using 3-fluoroazetidine in Step A and 2-methyl-3(trifluoromethyl)phenylboronic acid in Step B. MS (ESI): mass calcd. for $C_{19}H_{18}F_4N_4O$, 394.1; m/z found, 295.2 [M+H]$^+$. $^1$H NMR (400 MHz, DMSO) δ 11.90-11.73 (s, 1H), 10.66-10.27 (s, 1H), 7.98-7.88 (d, J=1.8 Hz, 1H), 7.85-7.69 (m, 1H), 7.70-7.59 (d, J=1.9 Hz, 1H), 7.60-7.34 (m, 2H), 5.56-5.39 (s, 0.5H), 5.39-5.21 (s, 0.5H), 4.68-3.96 (m, 8H), 2.40-2.27 (m, 3H).

Example 182: 6-(2,3-Dimethylphenyl)-1-[2-(3-fluoroazetidin-1-yl)ethyl]-3H-imidazo[4,5-b]pyridin-2-one and its Trifluoroacetic Acid Salt

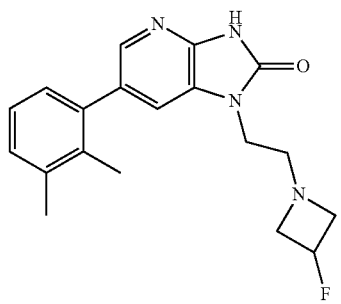 [SMILES: Cc1cccc(-c2cnc3[nH]c(=O)n(CCN4CC(F)C4)c3c2)c1C]

The title compound was prepared in a manner analogous to Example 17, using 3-fluoroazetidine in Step A and 2,3-dimethylphenylboronic acid in Step B. MS (ESI): mass calcd. for $C_{19}H_{21}FN_4O$, 340.2; m/z found, 341.2 [M+H]$^+$. $^1$H NMR (400 MHz, DMSO-d$_6$) δ 11.72 (s, 1H), 10.52 (s, 0.6H), 9.52 (s, 0.4H), 7.96-7.71 (d, J=1.8 Hz, 1H), 7.64-7.45 (d, J=1.8 Hz, 1H), 7.29-7.13 (m, 2H), 7.13-7.00 (m, 1H), 5.46 (s, 0.5H), 5.28 (s, 0.5H), 4.64-3.99 (m, 6H), 3.6-3.2 (m, 2H), 2.32 (s, 3H), 2.11 (s, 3H).

Example 183: 6-(3,5-Dimethylphenyl)-1-[2-(3-fluoroazetidin-1-yl)ethyl]-3H-imidazo[4,5-b]pyridin-2-one and its Trifluoroacetic Acid Salt

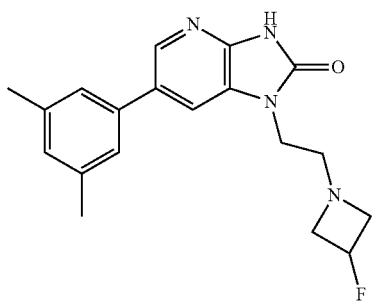 [SMILES: Cc1cc(C)cc(-c2cnc3[nH]c(=O)n(CCN4CC(F)C4)c3c2)c1]

The title compound was prepared in a manner analogous to Example 17, using 3-fluoroazetidine in Step A and 3,5-dimethylphenylboronic acid in Step B. MS (ESI): mass calcd. for $C_{19}H_{21}FN_4O$, 340.2; m/z found, 341.2 [M+H]$^+$.

¹H NMR (400 MHz, DMSO-d₆) δ 11.78 (s, 1H), 10.4 (s, 0.6H), 9.7 (s, 0.4H), 8.37-8.17 (d, J=1.9 Hz, 1H), 7.87-7.76 (d, J=2.0 Hz, 1H), 7.37-7.20 (d, J=1.7 Hz, 2H), 7.01 (s, 1H), 5.44 (s, 0.5H), 5.30 (s, 0.5H), 4.64-4.03 (m, 6H), 3.45 (s, 2H), 2.33 (s, 6H).

Example 184: 1-[2-(3-Fluoroazetidin-1-yl)ethyl]-6-(4-fluoro-2,3-dimethyl-phenyl)-3H-imidazo[4,5-b]pyridin-2-one and its Trifluoroacetic Acid Salt

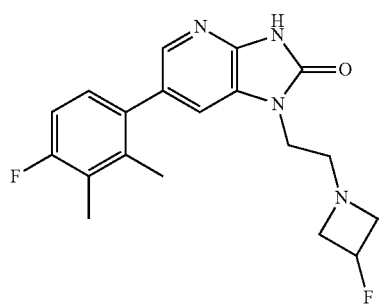 [SMILES: Cc1c(F)ccc(-c2cnc3[nH]c(=O)n(CCN4CC(F)C4)c3c2)c1C]

The title compound was prepared in a manner analogous to Example 17, using 3-fluoroazetidine in Step A and 2,3-dimethyl-4-fluorophenylboronic acid in Step B. MS (ESI): mass calcd. for $C_{19}H_{20}F_2N_4O$, 358.2; m/z found, 359.2 [M+H]⁺. ¹H NMR (400 MHz, DMSO-d₆) δ 11.84 (s, 1H), 10.7 (s, 0.6H), 9.6 (s, 0.4H), 8.01-7.75 (d, J=1.8 Hz, 1H), 7.62-7.43 (d, J=1.8 Hz, 1H), 7.23-6.95 (m, 2H), 5.51-5.39 (m, 0.5H), 5.39-5.23 (m, 0.5H), 4.67-3.92 (m, 6H), 3.48 (s, 2H), 2.25-2.19 (d, J=2.1 Hz, 3H), 2.17 (s, 3H).

Example 185: 1-[2-(3-Fluoroazetidin-1-yl)ethyl]-6-[2-methyl-5-(trifluoromethyl)phenyl]-3H-imidazo[4,5-b]pyridin-2-one and its Trifluoroacetic Acid Salt

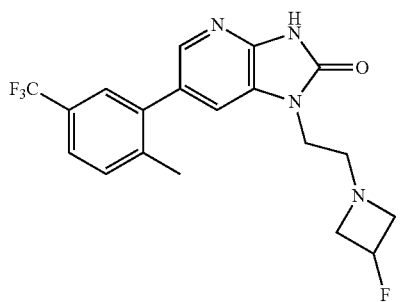 [SMILES: Cc1ccc(C(F)(F)F)cc1-c1cnc2[nH]c(=O)n(CCN3CC(F)C3)c2c1]

The title compound was prepared in a manner analogous to Example 17, using 3-fluoroazetidine in Step A and 2-methyl-5-(trifluoromethyl)phenylboronic acid in Step B. MS (ESI): mass calcd. for $C_{19}H_{18}F_4N_4O$, 394.1; m/z found, 395.2 [M+H]⁺. ¹H NMR (400 MHz, DMSO-d₆) δ 11.88 (s, 1H), 10.55 (s, 0.6H), 9.7 (s, 0.4H), 8.06-7.92 (d, J=1.8 Hz, 1H), 7.77-7.42 (m, 4H), 5.46 (s, 0.5H), 5.39-5.20 (d, J=6.0 Hz, 0.5H), 4.63-4.43 (m, 2H), 4.31 (s, 2H), 4.20-4.02 (m, 2H), 3.44 (s, 2H), 2.34 (s, 3H).

Example 186: 1-[2-(3-Fluoroazetidin-1-yl)ethyl]-6-(o-tolyl)-3H-imidazo[4,5-b]pyridin-2-one and its Trifluoroacetic Acid Salt

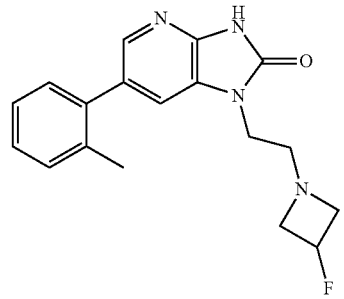 [SMILES: Cc1ccccc1-c1cnc2[nH]c(=O)n(CCN3CC(F)C3)c2c1]

The title compound was prepared in a manner analogous to Example 17, using 3-fluoroazetidine in Step A and 2-methylphenylboronic acid in Step B. MS (ESI): mass calcd. for $C_{18}H_{19}FN_4O$, 326.2; m/z found, 327.2 [M+H]⁺.

Example 187: 1-[2-(3-Fluoroazetidin-1-yl)ethyl]-6-(4-fluoro-2-methyl-phenyl)-3H-imidazo[4,5-b]pyridin-2-one and its Trifluoroacetic Acid Salt

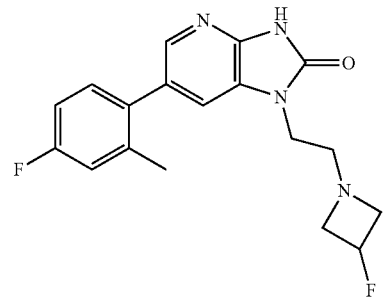 [SMILES: Cc1cc(F)ccc1-c1cnc2[nH]c(=O)n(CCN3CC(F)C3)c2c1]

The title compound was prepared in a manner analogous to Example 17, using 3-fluoroazetidine in Step A and 2-methyl-4-fluorophenylboronic acid in Step B. MS (ESI): mass calcd. for $C_{18}H_{18}F_2N_4O$, 344.1; m/z found, 345.2 [M+H]⁺.

Example 188: 1-[2-(3-Fluoroazetidin-1-yl)ethyl]-6-phenyl-3H-imidazo[4,5-b]pyridin-2-one and its Trifluoroacetic Acid Salt

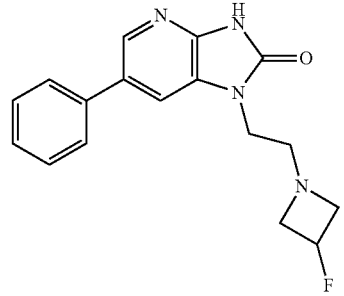 [SMILES: O=c1[nH]c2ncc(-c3ccccc3)cc2n1CCN1CC(F)C1]

The title compound was prepared in a manner analogous to Example 17, using 3-fluoroazetidine in Step A and phenylboronic acid in Step B. MS (ESI): mass calcd. for $C_{17}H_{17}FN_4O$, 312.1; m/z found, 313.1 [M+H]$^+$.

Example 189: 6-(3,5-Difluorophenyl)-1-[2-(propylamino)ethyl]-3H-imidazo[4,5-b]pyridin-2-one and its Trifluoroacetic Acid Salt

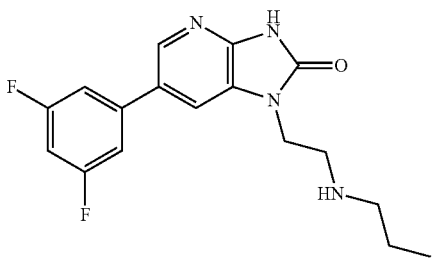 [SMILES: CCCNCCn1c(=O)[nH]c2ncc(-c3cc(F)cc(F)c3)cc21]

The title compound was prepared in a manner analogous to Example 17, using propylamine in Step A and 3,5-difluorophenylboronic acid in Step B. MS (ESI): mass calcd. for $C_{17}H_{18}F_2N_4O$, 332.1; m/z found, 333.2 [M+H]$^+$. $^1$H NMR (500 MHz, DMSO-d$_6$) δ 11.87 (s, 1H), 8.48 (s, 2H), 8.39 (d, J=2.0 Hz, 1H), 7.93 (d, J=2.0 Hz, 1H), 7.67-7.36 (m, 2H), 7.26 (tt, J=9.3, 2.3 Hz, 1H), 4.18 (t, J=5.7 Hz, 2H), 3.35 (t, J=6.1 Hz, 2H), 2.95 (d, J=6.9 Hz, 2H), 1.58 (dt, J=15.1, 7.5 Hz, 2H), 0.90 (t, J=7.4 Hz, 3H).

Example 190: N-Cyclobutyl-2-[2-oxo-6-[3-(trifluoromethyl)phenyl]-3H-imidazo[4,5-b]pyridin-1-yl]acetamide and its Trifluoroacetic Acid Salt

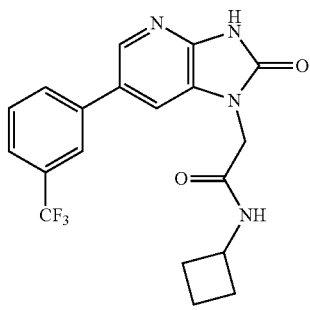 [SMILES: O=C(Cn1c(=O)[nH]c2ncc(-c3cccc(C(F)(F)F)c3)cc21)NC1CCC1]

The title compound was prepared in a manner analogous to Example 20, using cyclobutylamine in Step A. MS (ESI): mass calcd. for $C_{19}H_{17}F_3N_4O_2$, 390.1; m/z found, 391.3 [M+H]$^+$.

Example 191: 1-[2-(3-Methoxyazetidin-1-yl)-2-oxo-ethyl]-6-[3-(trifluoromethyl)phenyl]-3H-imidazo[4,5-b]pyridin-2-one and its Trifluoroacetic Acid Salt

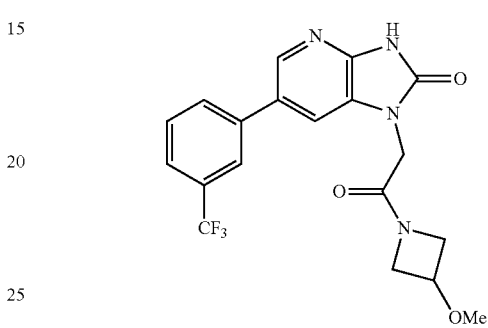

The title compound was prepared in a manner analogous to Example 20 using 3-methoxyazetidine hydrochloride in Step A. $^1$H NMR (500 MHz, DMSO-d$_6$) δ 11.75 (s, 1H), 8.32 (d, J=2.0 Hz, 1H), 8.01-7.96 (m, 2H), 7.82 (d, J=2.0 Hz, 1H), 7.75-7.69 (m, 2H), 4.60 (s, 2H), 4.49-4.42 (m, 1H), 4.3-4.25 (m, 1H), 4.15-4.05 (m, 2H), 3.74-3.68 (m, 1H), 3.24 (s, 3H).

Example 192: N-(Oxetan-3-yl)-2-[2-oxo-6-[3-(trifluoromethyl)phenyl]-3H-imidazo[4,5-b]pyridin-1-yl]acetamide and its Trifluoroacetic Acid Salt

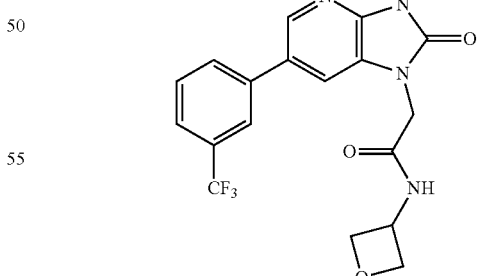

The title compound was prepared in a manner analogous to Example 20, using oxetan-3-amine in Step A. MS (ESI): mass calcd. for $C_{18}H_{15}F_3N_4O_3$, 392.1; m/z found, 393.1 [M+H]$^+$. $^1$H NMR (500 MHz, DMSO-d$_6$) δ 11.75 (s, 1H), 8.98 (d, J=6.9 Hz, 1H), 8.33 (d, J=2.0 Hz, 1H), 8.05-7.96 (m, 2H), 7.88 (d, J=2.0 Hz, 1H), 7.79-7.66 (m, 2H), 4.83 (h, J=6.9 Hz, 1H), 4.70 (t, J=6.8 Hz, 2H), 4.56 (s, 2H), 4.44 (t, J=6.3 Hz, 2H).

Example 193: 1-[2-(4-Methylpiperazin-1-yl)-2-oxo-ethyl]-6-[3-(trifluoromethyl)phenyl]-3H-imidazo[4,5-b]pyridin-2-one and its Trifluoroacetic Acid Salt

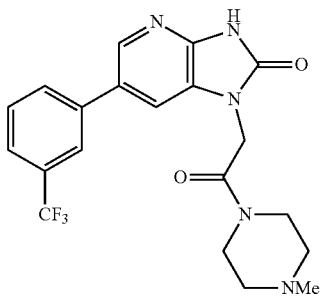 [SMILES: CN1CCN(C(=O)Cn2c(=O)[nH]c3ncc(-c4cccc(C(F)(F)F)c4)cc32)CC1]

The title compound was prepared in a manner analogous to Example 20, using 1-methylpiperazine in Step A. MS (ESI): mass calcd. for $C_{20}H_{20}F_3N_5O_2$, 419.2; m/z found, 420.2 [M+H]$^+$. $^1$H NMR (400 MHz, DMSO) δ 11.78 (s, 1H), 9.96 (s, 1H), 8.32 (d, J=2.0 Hz, 1H), 8.00-7.93 (m, 2H), 7.78-7.68 (m, 3H), 5.10-4.73 (m, 2H), 4.45-4.10 (m, 2H), 3.24-2.91 (m, 4H), 2.85 (s, 3H).

Example 194: 1-[2-(3,3-Difluoroazetidin-1-yl)-2-oxo-ethyl]-6-[3-(trifluoromethyl)phenyl]-3H-imidazo[4,5-b]pyridin-2-one and its Trifluoroacetic Acid Salt

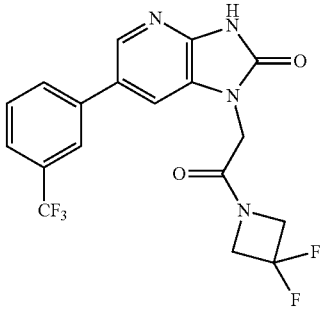 [SMILES: O=C(Cn1c(=O)[nH]c2ncc(-c3cccc(C(F)(F)F)c3)cc21)N1CC(F)(F)C1]

The title compound was prepared in a manner analogous to Example 20, using 3,3-difluoroazetidine hydrochloride in Step A. MS (ESI): mass calcd. for $C_{18}H_{13}F_5N_4O_2$, 412.1; m/z found, 413.1 [M+H]$^+$. $^1$H NMR (400 MHz, DMSO DMSO-d$_6$) δ 11.79 (s, 1H), 8.32 (d, J=2.0 Hz, 1H), 8.01-7.95 (m, 2H), 7.81 (d, J=2.0 Hz, 1H), 7.78-7.69 (m, 2H), 4.81 (t, J=12.3 Hz, 2H), 4.71 (s, 2H), 4.38 (t, J=12.3 Hz, 2H).

Example 195: N-(3,3-Difluorocyclobutyl)-2-[2-oxo-6-[3-(trifluoromethyl)phenyl]-3H-imidazo[4,5-b]pyridin-1-yl]acetamide and its Trifluoroacetic Acid Salt

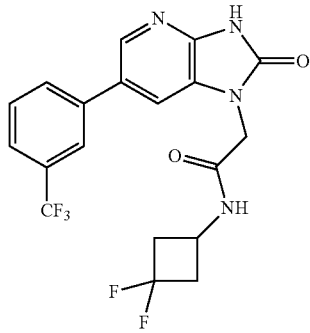 [SMILES: O=C(Cn1c(=O)[nH]c2ncc(-c3cccc(C(F)(F)F)c3)cc21)NC1CC(F)(F)C1]

The title compound was prepared in a manner analogous to Example 20, using 3,3-difluorocyclobutane-1-amine hydrochloride in Step A. MS (ESI): mass calcd. for $C_{19}H_{15}F_5N_4O_2$, 426.1; m/z found, 427.1 [M+H]$^+$. $^1$H NMR (400 MHz, DMSO-d$_6$) δ 11.76 (s, 1H), 8.67 (d, J=6.8 Hz, 1H), 8.34 (d, J=2.0 Hz, 1H), 8.05-7.96 (m, 2H), 7.87 (d, J=2.0 Hz, 1H), 7.77-7.67 (m, 2H), 4.54 (s, 2H), 4.15-4.02 (m, 1H), 2.99-2.84 (m, 2H).

Example 196: 1-[2-(3,3-Difluoropyrrolidin-1-yl)-2-oxo-ethyl]-3-methyl-6-[3-(trifluoromethyl)phenyl]imidazo[4,5-b]pyridin-2-one and its Trifluoroacetic Acid Salt

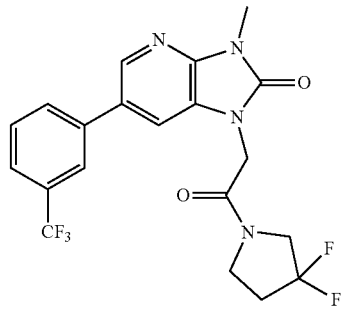 [SMILES: Cn1c(=O)n(CC(=O)N2CCC(F)(F)C2)c2cc(-c3cccc(C(F)(F)F)c3)cnc21]

The title compound was prepared in a manner analogous to Example 20, using 3,3-difluoropyrrolidine hydrochloride and 2-[3-methyl-2-oxo-6-[3-(trifluoromethyl)phenyl]imidazo[4,5-b]pyridin-1-yl]acetic acid (Example 137). MS (ESI): mass calcd. for $C_{20}H_{17}F_5N_4O_2$, 440.1; m/z found, 441.2 [M+H]$^+$. $^1$H NMR (400 MHz, DMSO-d$_6$) δ 8.40 (d, J=1.9 Hz, 1H), 8.03-7.95 (m, 2H), 7.89 (dd, J=10.3, 2.0 Hz, 1H), 7.79-7.71 (m, 2H), 4.91-4.81 (m, 2H), 4.17 (t, J=13.1 Hz, 1H), 3.92 (t, J=7.4 Hz, 1H), 3.74 (t, J=13.1 Hz, 1H), 3.56 (t, J=7.5 Hz, 1H), 3.41 (s, 3H), 2.64-2.53 (m, 1H), 2.49-2.37 (m, 1H).

Example 197: 3-Methyl-1-(2-oxo-2-pyrrolidin-1-yl-ethyl)-6-[3-(trifluoromethyl)phenyl]imidazo[4,5-b]pyridin-2-one and its Trifluoroacetic Acid Salt

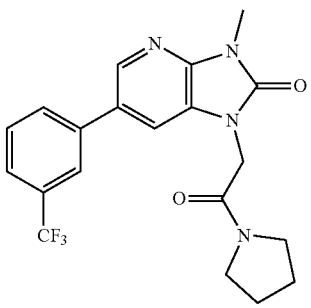 [SMILES: Cn1c(=O)n(CC(=O)N2CCCC2)c2cc(-c3cccc(C(F)(F)F)c3)cnc21]

The title compound was prepared in a manner analogous to Example 20, using pyrrolidine and 2-[3-methyl-2-oxo-6-[3-(trifluoromethyl)phenyl]imidazo[4,5-b]pyridin-1-yl]acetic acid (Example 137). MS (ESI): mass calcd. for $C_{20}H_{19}F_3N_4O_2$, 404.1; m/z found, 405.2 [M+H]$^+$. $^1$H NMR (400 MHz, DMSO-$d_6$) δ 8.40 (d, J=1.9 Hz, 1H), 8.04-7.96 (m, 2H), 7.90 (d, J=2.0 Hz, 1H), 7.77-7.70 (m, 2H), 4.78 (s, 2H), 3.59 (t, J=6.8 Hz, 2H), 3.30 (t, J=6.9 Hz, 2H), 2.00-1.90 (m, 2H), 1.85-1.75 (m, 2H).

Example 198: N-(3,3-Difluoro-1-methyl-cyclobutyl)-2-[3-methyl-2-oxo-6-[3-(trifluoromethyl)phenyl]imidazo[4,5-b]pyridin-1-yl]acetamide and its Trifluoroacetic Acid Salt

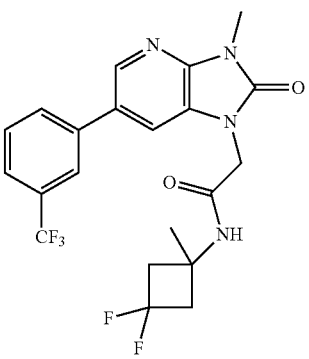 [SMILES: Cn1c(=O)n(CC(=O)NC2(C)CC(F)(F)C2)c2cc(-c3cccc(C(F)(F)F)c3)cnc21]

The title compound was prepared in a manner analogous to Example 20, using 3,3-difluoro-1-methylcyclobutane-1-amine hydrochloride and 2-[3-methyl-2-oxo-6-[3-(trifluoromethyl)phenyl]imidazo[4,5-b]pyridin-1-yl]acetic acid (Example 137). MS (ESI): mass calcd. for $C_{21}H_{19}F_5N_4O_2$, 454.1; m/z found, 455.2 [M+H]$^+$. $^1$H NMR (400 MHz, DMSO-$d_6$) δ 8.65 (s, 1H), 8.41 (d, J=2.0 Hz, 1H), 8.04-7.97 (m, 2H), 7.93 (d, J=2.0 Hz, 1H), 7.78-7.69 (m, 2H), 4.58 (s, 2H), 3.40 (s, 3H), 2.95-2.81 (m, 2H), 2.66-2.53 (m, 2H), 1.46-1.39 (s, 3H).

Example 199: N-(3-Methyloxetan-3-yl)-2-[3-methyl-2-oxo-6-[3-(trifluoromethyl)phenyl]imidazo[4,5-b]pyridin-1-yl]acetamide and its Trifluoroacetic Acid Salt

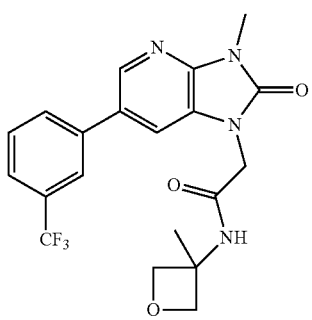 [SMILES: Cn1c(=O)n(CC(=O)NC2(C)COC2)c2cc(-c3cccc(C(F)(F)F)c3)cnc21]

The title compound was prepared in a manner analogous to Example 20, using 3-methyloxetan-3-amine and 2-[3-methyl-2-oxo-6-[3-(trifluoromethyl)phenyl]imidazo[4,5-b]pyridin-1-yl]acetic acid (Example 137). MS (ESI): mass calcd. for $C_{20}H_{19}F_3N_4O_3$, 420.1; m/z found, 421.20 [M+H]$^+$. $^1$H NMR (500 MHz, DMSO-$d_6$) δ 8.71 (s, 1H), 8.41 (d, J=2.0 Hz, 1H), 8.08-7.98 (m, 2H), 7.96 (d, J=2.0 Hz, 1H), 7.78-7.69 (m, 2H), 4.63-4.55 (m, 4H), 4.28 (d, J=6.1 Hz, 2H), 1.50 (s, 3H).

Example 200: N-(3,3-Difluorocyclobutyl)-2-[3-methyl-2-oxo-6-[3-(trifluoromethyl)phenyl]imidazo[4,5-b]pyridin-1-yl]acetamide and its Trifluoroacetic Acid Salt

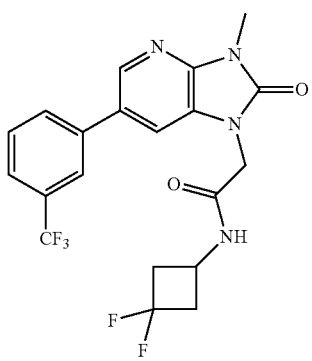 [SMILES: Cn1c(=O)n(CC(=O)NC2CC(F)(F)C2)c2cc(-c3cccc(C(F)(F)F)c3)cnc21]

The title compound was prepared in a manner analogous to Example 20, using 3,3-difluorocyclobutane-1-amine hydrochloride and 2-[3-methyl-2-oxo-6-[3-(trifluoromethyl)phenyl]imidazo[4,5-b]pyridin-1-yl]acetic acid (Example 137). MS (ESI): mass calcd. for $C_{20}H_{17}F_5N_4O_2$, 440.1; m/z found, 441.2 [M+H]$^+$. $^1$H NMR (400 MHz, DMSO-$d_6$) δ 8.68 (d, J=6.7 Hz, 1H), 8.42 (d, J=1.9 Hz, 1H), 8.05-7.99 (m, 2H), 7.96 (d, J=2.0 Hz, 1H), 7.77-7.68 (m, 2H), 4.60 (s, 2H), 4.14-4.01 (m, 1H), 3.40 (s, 3H), 2.98-2.83 (m, 2H), 2.67-2.47 (m, 2H).

Example 201: 1-(2-Oxo-2-pyrrolidin-1-yl-ethyl)-6-[3-(trifluoromethyl)phenyl]-3H-imidazo[4,5-b]pyridin-2-one and its Trifluoroacetic Acid Salt

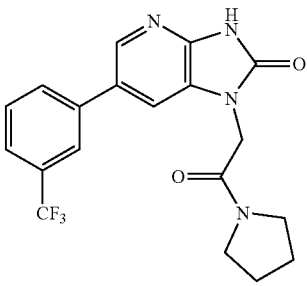 [SMILES: O=C(Cn1c(=O)[nH]c2ncc(-c3cccc(C(F)(F)F)c3)cc21)N1CCCC1]

The title compound was prepared in a manner analogous to Example 20, using pyrrolidine in Step A. MS (ESI): mass calcd. for $C_{19}H_{17}F_3N_4O_2$, 390.1; m/z found, 391.1 [M+H]$^+$. $^1$H NMR (500 MHz, DMSO-d$_6$) δ 11.74 (s, 1H), 8.38-8.29 (m, 1H), 8.06-7.95 (m, 2H), 7.88-7.81 (m, 1H), 7.80-7.68 (m, 2H), 4.72 (s, 2H), 3.58 (t, J=6.7 Hz, 2H), 2.08-1.92 (m, 2H), 1.91-1.76 (m, 2H).

Example 202: (R/S)—N-Cyclopropyl-2-[2-oxo-6-[3-(trifluoromethyl)phenyl]-3H-imidazo[4,5-b]pyridin-1-yl]propanamide and its Trifluoroacetic Acid Salt

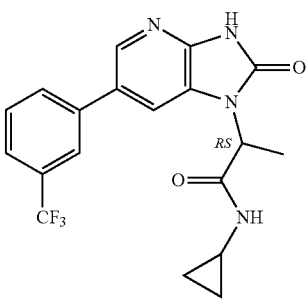 [SMILES: CC(C(=O)NC1CC1)n1c(=O)[nH]c2ncc(-c3cccc(C(F)(F)F)c3)cc21]

The title compound was prepared in a manner analogous to Example 20 using 2-(2-oxo-6-(3-(trifluoromethyl)phenyl)-3-trityl-2,3-dihydro-1H-imidazo[4,5-b]pyridin-1-yl)propanoic acid (Intermediate 44) and cyclopropanamine in Step A. MS (ESI): mass calcd. for $C_{19}H_{17}F_3N_4O_2$, 390.1; m/z found, 391.1 [M+H]$^+$. $^1$H NMR (500 MHz, DMSO-d$_6$) δ 11.73 (s, 1H), 8.30 (d, J=1.9 Hz, 1H), 8.18 (d, J=4.1 Hz, 1H), 8.00-7.94 (m, 2H), 7.76-7.69 (m, 3H), 5.01 (q, J=7.2 Hz, 1H), 2.69-2.60 (m, 1H), 1.57 (d, J=7.2 Hz, 3H), 0.63-0.54 (m, 2H), 0.44-0.34 (m, 2H).

Example 203: (R/S)-1-[2-(Azetidin-1-yl)-1-methyl-2-oxo-ethyl]-6-[3-(trifluoromethyl)phenyl]-3H-imidazo[4,5-b]pyridin-2-one and its Trifluoroacetic Acid Salt

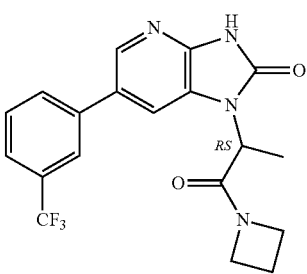 [SMILES: CC(C(=O)N1CCC1)n1c(=O)[nH]c2ncc(-c3cccc(C(F)(F)F)c3)cc21]

The title compound was prepared in a manner analogous to Example 20 using 2-(2-oxo-6-(3-(trifluoromethyl)phenyl)-3-trityl-2,3-dihydro-1H-imidazo[4,5-b]pyridin-1-yl)propanoic acid (Intermediate 44) and azetidine in Step A. MS (ESI): mass calcd. for $C_{19}H_{17}F_3N_4O_2$, 390.1; m/z found, 391.2 [M+H]$^+$. $^1$H NMR (500 MHz, DMSO-d$_6$) δ 11.84 (s, 1H), 8.31 (d, J=2.0 Hz, 1H), 7.98-7.93 (m, 2H), 7.77-7.70 (m, 3H), 5.16 (q, J=7.1 Hz, 1H), 4.26-4.18 (m, 1H), 3.93-3.79 (m, 3H), 2.22-2.09 (m, 2H), 1.52 (d, J=7.1 Hz, 3H).

Example 204: 1-(2-Morpholino-2-oxo-ethyl)-6-[3-(trifluoromethyl)phenyl]-3H-imidazo[4,5-b]pyridin-2-one and its Trifluoroacetic Acid Salt

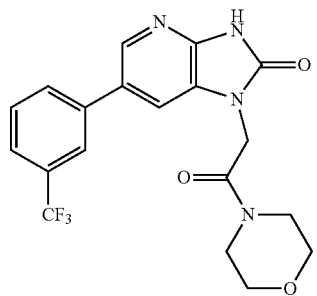 [SMILES: O=C(Cn1c(=O)[nH]c2ncc(-c3cccc(C(F)(F)F)c3)cc21)N1CCOCC1]

The title compound was prepared in a manner analogous to Example 20, using morpholine in Step A. MS (ESI): mass calcd. for $C_{19}H_{17}F_3N_4O_3$, 406.1; m/z found, 407.1 [M+H]$^+$. $^1$H NMR (400 MHz, DMSO-d$_6$) δ 11.75 (s, 1H), 8.31 (d, J=2.0 Hz, 1H), 8.01-7.95 (m, 2H), 7.81 (d, J=2.0 Hz, 1H), 7.76-7.68 (m, 2H), 4.85 (s, 2H), 3.69 (t, J=4.5 Hz, 2H), 3.59 (t, J=4.9 Hz, 4H).

Example 205: N-Cyclopentyl-2-[2-oxo-6-[3-(trifluoromethyl)phenyl]-3H-imidazo[4,5-b]pyridin-1-yl]acetamide and its Trifluoroacetic Acid Salt

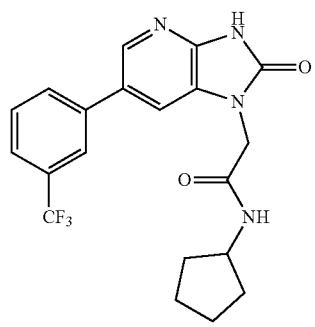 [SMILES: O=C(Cn1c(=O)[nH]c2ncc(-c3cccc(C(F)(F)F)c3)cc21)NC1CCCC1]

The title compound was prepared in a manner analogous to Example 20, using cyclopentanamine in Step A. MS (ESI): mass calcd. for $C_{20}H_{19}F_3N_4O_2$, 404.1; m/z found, 405.2 [M+H]$^+$. $^1$H NMR (500 MHz, DMSO-d$_6$) δ 11.71 (s, 1H), 8.32 (d, J=2.0 Hz, 1H), 8.19 (d, J=7.2 Hz, 1H), 8.03-7.95 (m, 2H), 7.81 (d, J=2.0 Hz, 1H), 7.75-7.68 (m, 2H), 4.49 (s, 2H), 4.05-3.96 (m, 1H), 1.85-1.75 (m, 2H), 1.64 (dd, J=9.8, 5.7 Hz, 2H), 1.56-1.45 (m, 2H), 1.45-1.35 (m, 2H).

Example 206: 1-[2-Oxo-2-(1-piperidyl)ethyl]-6-[3-(trifluoromethyl)phenyl]-3H-imidazo[4,5-b]pyridin-2-one and its Trifluoroacetic Acid Salt

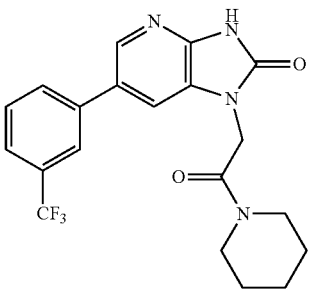 [SMILES: O=C(Cn1c(=O)[nH]c2ncc(-c3cccc(C(F)(F)F)c3)cc21)N1CCCCC1]

The title compound was prepared in a manner analogous to Example 20, using piperidine in Step A. MS (ESI): mass calcd. for $C_{20}H_{19}F_3N_4O_2$, 404.1; m/z found, 405.2 [M+H]$^+$. $^1$H NMR (400 MHz, DMSO-d$_6$) δ 11.72 (s, 1H), 8.31 (d, J=2.0 Hz, 1H), 8.01-7.94 (m, 2H), 7.80 (d, J=2.0 Hz, 1H), 7.76-7.68 (m, 2H), 4.81 (s, 2H), 3.54-3.48 (m, 2H), 3.41 (t, J=5.5 Hz, 2H), 1.65-1.57 (m, 4H), 1.49-1.40 (m, 2H).

Example 207: 1-[2-(2,6-Diazaspiro[3.3]heptan-6-yl)-2-oxo-ethyl]-6-[3-(trifluoromethyl)phenyl]-3H-imidazo[4,5-b]pyridin-2-one

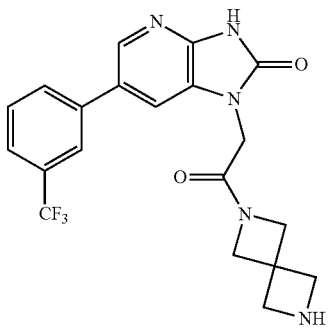 [SMILES: O=C(Cn1c(=O)[nH]c2ncc(-c3cccc(C(F)(F)F)c3)cc21)N1CC2(CNC2)C1]

The title compound was prepared in a manner analogous to Example 20, using tert-butyl 2,6-diazaspiro[3.3]heptane-2-carboxylate oxalate in Step A. MS (ESI): mass calcd. for $C_{20}H_{18}F_3N_5O_2$, 417.1; m/z found, 418.2 [M+H]$^+$.

Example 208: 2-[2-Oxo-6-[3-(trifluoromethyl)phenyl]-3H-imidazo[4,5-b]pyridin-1-yl]-N-(2-pyridyl)acetamide and its Trifluoroacetic Acid Salt

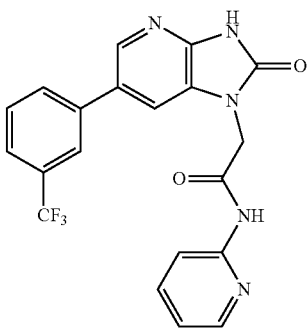 [SMILES: O=C(Cn1c(=O)[nH]c2ncc(-c3cccc(C(F)(F)F)c3)cc21)Nc1ccccn1]

The title compound was prepared in a manner analogous to Example 20, using pyridin-2-amine in Step A. MS (ESI): mass calcd. for $C_{20}H_{14}F_3N_5O_2$, 413.1; m/z found, 414.1 [M+H]$^+$. $^1$H NMR (400 MHz, DMSO-d$_6$) δ 11.80 (s, 1H), 10.92 (s, 1H), 8.39-8.32 (m, 2H), 8.06-7.92 (m, 4H), 7.81-7.66 (m, 3H), 7.12 (ddd, J=7.4, 4.9, 1.1 Hz, 1H), 4.86 (s, 2H).

Example 209: N-(3,3-Difluoro-1-methyl-cyclobutyl)-2-[2-oxo-6-[3-(trifluoromethyl)phenyl]-3H-imidazo[4,5-b]pyridin-1-yl]acetamide and its Trifluoroacetic Acid Salt

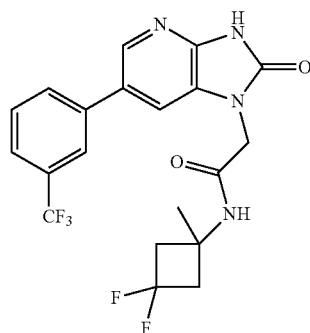 [SMILES: CC1(NC(=O)Cn2c(=O)[nH]c3ncc(-c4cccc(C(F)(F)F)c4)cc32)CC(F)(F)C1]

The title compound was prepared in a manner analogous to Example 20, using 3,3-difluoro-1-methylcyclobutane-1-amine in Step A. MS (ESI): mass calcd. for $C_{20}H_{17}F_5N_4O_2$, 440.1; m/z found, 441.2 [M+H]$^+$. $^1$H NMR (500 MHz, DMSO-d$_6$) δ 11.73 (s, 1H), 8.63 (s, 1H), 8.33 (d, J=2.0 Hz, 1H), 8.02-7.96 (m, 2H), 7.82 (d, J=2.1 Hz, 1H), 7.75-7.68 (m, 2H), 4.51 (s, 2H), 2.95-2.82 (m, 2H), 1.43 (s, 3H).

Example 210: 1-[(6-Methoxy-3-pyridyl)methyl]-6-[3-(trifluoromethyl)phenyl]-3H-imidazo[4,5-b]pyridin-2-one and its Trifluoroacetic Acid Salt

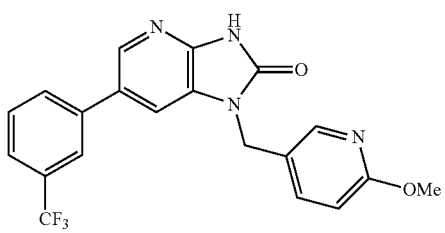 [SMILES: COc1ccc(Cn2c(=O)[nH]c3ncc(-c4cccc(C(F)(F)F)c4)cc32)cn1]

The title compound was prepared in a manner analogous to Example 21, using 5-(chloromethyl)-2-methoxypyridine. MS (ESI): mass calcd. for $C_{20}H_{15}F_3N_4O_2$, 400.1; m/z found, [M+H]$^+$. $^1$H NMR (400 MHz, DMSO) δ 11.82 (s, 1H), 8.31 (dd, J=7.3, 2.2 Hz, 2H), 8.03-7.96 (m, 3H), 7.77-7.68 (m, 3H), 6.79 (d, J=8.6 Hz, 1H), 5.06 (s, 2H), 3.80 (s, 3H).

Example 211: 1-(Cyclopropylmethyl)-6-[3-(trifluoromethyl)phenyl]-3H-imidazo[4,5-b]pyridin-2-one and its Trifluoroacetic Acid Salt

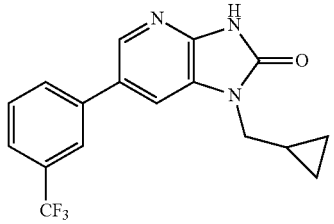 [SMILES: O=c1[nH]c2ncc(-c3cccc(C(F)(F)F)c3)cc2n1CC1CC1]

The title compound was prepared in a manner analogous to Example 21, using (bromomethyl)cyclopropane in Step A (ESI): mass calcd. for $C_{17}H_{14}F_3N_3O$, 333.1; m/z found, 334.1 [M+H]$^+$. $^1$H NMR (400 MHz, DMSO-$d_6$) δ 11.70 (s, 1H), 8.30 (d, J=2.0 Hz, 1H), 8.07-8.00 (m, 2H), 7.97 (d, J=2.0 Hz, 1H), 7.75-7.67 (m, 2H), 3.77 (d, J=7.1 Hz, 2H), 1.36-1.21 (m, 1H), 0.50-0.43 (m, 2H), 0.43-0.34 (m, 2H).

Example 212: 3-[[2-Oxo-6-[3-(trifluoromethyl)phenyl]-3H-imidazo[4,5-b]pyridin-1-yl]methyl]benzonitrile and its Trifluoroacetic Acid Salt

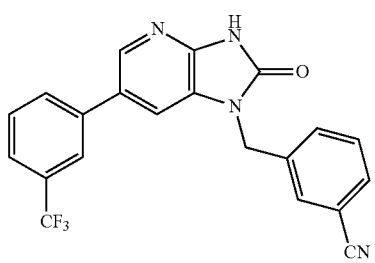 [SMILES: N#Cc1cccc(Cn2c(=O)[nH]c3ncc(-c4cccc(C(F)(F)F)c4)cc32)c1]

The title compound was prepared in a manner analogous to Example 21, using 3-(bromomethyl)benzonitrile in Step A. MS (ESI): mass calcd. for $C_{21}H_{13}F_3N_4O$, 394.1; m/z found, 395.1 [M+H]$^+$. $^1$H NMR (400 MHz, DMSO-$d_6$) δ 11.87 (s, 1H), 8.34 (d, J=2.0 Hz, 1H), 8.02-7.97 (m, 2H), 7.94 (d, J=1.9 Hz, 1H), 7.89-7.86 (m, 1H), 7.79-7.66 (m, 4H), 7.59-7.53 (m, 1H), 5.17 (s, 2H).

Example 213: 2-[[2-Oxo-6-[3-(trifluoromethyl)phenyl]-3H-imidazo[4,5-b]pyridin-1-yl]methyl]benzonitrile and its Trifluoroacetic Acid Salt

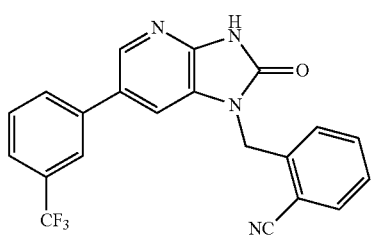 [SMILES: N#Cc1ccccc1Cn1c(=O)[nH]c2ncc(-c3cccc(C(F)(F)F)c3)cc21]

The title compound was prepared in a manner analogous to Example 21, using 2-(bromomethyl)benzonitrile in Step A. MS (ESI): mass calcd. for $C_{21}H_{13}F_3N_4O$, 394.1; m/z found, 395.1 [M+H]$^+$. $^1$H NMR (500 MHz, DMSO-$d_6$) δ 11.92 (s, 1H), 8.37 (d, J=1.9 Hz, 1H), 8.00-7.96 (m, 2H), 7.93-7.89 (m, 2H), 7.74-7.63 (m, 3H), 7.52-7.48 (m, 1H), 7.26 (d, J=7.9 Hz, 1H), 5.33 (s, 2H).

Example 214: 1-[2-Oxo-2-(2-thienyl)ethyl]-6-[3-(trifluoromethyl)phenyl]-3H-imidazo[4,5-b]pyridin-2-one and its Trifluoroacetic Acid Salt

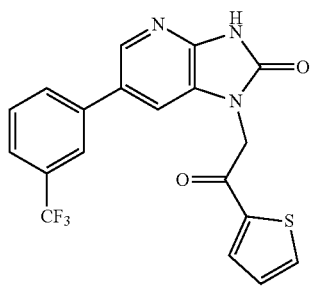 [SMILES: O=C(Cn1c(=O)[nH]c2ncc(-c3cccc(C(F)(F)F)c3)cc21)c1cccs1]

The title compound was prepared in a manner analogous to Example 21, using 2-bromo-1-(thiophen-2-yl)ethanone in Step A MS (ESI): mass calcd. for $C_{19}H_{12}F_3N_3O_2S$, 403.1; m/z found, 404.1 [M+H]$^+$.

Example 215: 1-(2-Oxo-2-thiazol-2-yl-ethyl)-6-[3-(trifluoromethyl)phenyl]-3H-imidazo[4,5-b]pyridin-2-one and its Trifluoroacetic Acid Salt

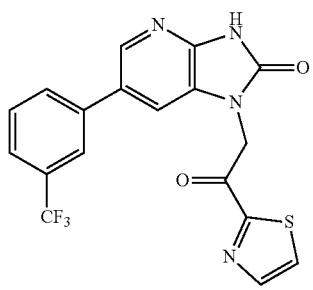 [SMILES: O=C(Cn1c(=O)[nH]c2ncc(-c3cccc(C(F)(F)F)c3)cc21)c1nccs1]

The title compound was prepared in a manner analogous to Example 21, using 2-bromo-1-(thiazol-2-yl)ethan-1-one in Step A. MS (ESI): mass calcd. for $C_{18}H_{11}F_3N_4O_2S$, 404.1; m/z found, 405.1 [M+H]$^+$. $^1$H NMR (500 MHz, DMSO-$d_6$) δ 11.90 (s, 1H), 8.41-8.35 (m, 2H), 8.32-8.28 (m, 1H), 8.09-7.96 (m, 3H), 7.77-7.66 (m, 2H), 5.60 (s, 2H).

Example 216: (R/S)-1-(Oxetan-2-ylmethyl)-6-[3-(trifluoromethyl)phenyl]-3H-imidazo[4,5-b]pyridin-2-one and its Trifluoroacetic Acid Salt

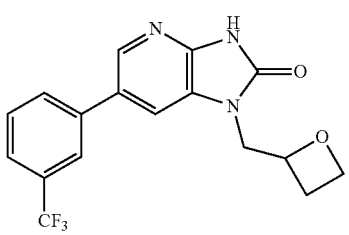 [SMILES: O=c1[nH]c2ncc(-c3cccc(C(F)(F)F)c3)cc2n1CC1CCO1]

The title compound was prepared in a manner analogous to Example 21, using 2-(bromomethyl)oxetane in Step A. MS (ESI): mass calcd. for $C_{17}H_{14}F_3N_3O_2$, 349.1; m/z found, 350.1 [M+H]$^+$. $^1$H NMR (400 MHz, DMSO-d$_6$) δ 11.77 (s, 1H), 8.31 (d, J=2.0 Hz, 1H), 8.05-7.97 (m, 2H), 7.93 (d, J=2.0 Hz, 1H), 7.76-7.68 (m, 2H), 5.10-5.02 (m, 1H), 4.49-4.42 (m, 1H), 4.33 (dt, J=9.0, 6.0 Hz, 1H), 4.22-4.05 (m, 2H), 2.72-2.60 (m, 1H).

Example 217: (R/S)-1-(Morpholin-2-ylmethyl)-6-[3-(trifluoromethyl)phenyl]-3H-imidazo[4,5-b]pyridin-2-one and its Trifluoroacetic Acid Salt

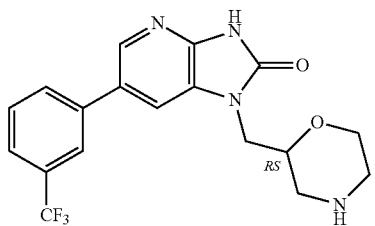 [SMILES: O=c1[nH]c2ncc(-c3cccc(C(F)(F)F)c3)cc2n1CC1CNCCO1]

The title compound was prepared in a manner analogous to Example 21, using tert-butyl 2-(bromomethyl)morpholine-4-carboxylate in Step A. MS (ESI): mass calcd. for $C_{18}H_{17}F_3N_4O_2$, 378.1; m/z found, 379.1 [M+H]$^+$. $^1$H NMR (500 MHz, DMSO-d$_6$) δ 11.81 (s, 1H), 8.94-8.85 (m, 1H), 8.84-8.72 (m, 1H), 8.33 (d, J=2.0 Hz, 1H), 8.03-7.99 (m, 2H), 7.87 (d, J=1.9 Hz, 1H), 7.77-7.70 (m, 2H), 4.11-3.99 (m, 3H), 3.98-3.92 (m, 1H), 3.65 (td, J=12.5, 2.4 Hz, 1H), 3.37-3.30 (m, 1H), 3.18-3.11 (m, 1H), 3.04-2.86 (m, 2H).

Example 218: (R/S)-1-(Tetrahydropyran-2-ylmethyl)-6-[3-(trifluoromethyl)phenyl]-3H-imidazo[4,5-b]pyridin-2-one and its Trifluoroacetic Acid Salt

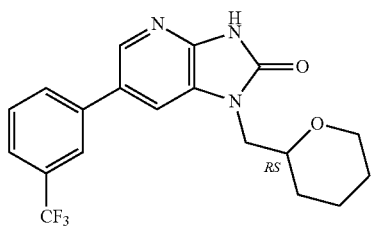 [SMILES: O=c1[nH]c2ncc(-c3cccc(C(F)(F)F)c3)cc2n1CC1CCCCO1]

The title compound was prepared in a manner analogous to Example 21, using 2-(bromomethyl)tetrahydro-2H-pyran in Step A. MS (ESI): mass calcd. for $C_{19}H_{18}F_3N_3O_2$, 377.1; m/z found, 378.1 [M+H]$^+$. $^1$H NMR (500 MHz, DMSO-d$_6$) δ 11.69 (s, 1H), 8.29 (d, J=2.0 Hz, 1H), 8.03-7.98 (m, 2H), 7.85 (d, J=2.0 Hz, 1H), 7.76-7.69 (m, 2H), 3.97-3.90 (m, 1H), 3.87-3.78 (m, 2H), 3.70-3.63 (m, 1H), 1.81-1.73 (m, 1H), 1.64-1.56 (m, 1H), 1.51-1.38 (m, 3H), 1.33-1.22 (m, 1H).

Example 219: 6-[3-(Trifluoromethyl)phenyl]-1-[[4-(trifluoromethyl)phenyl]methyl]-3H-imidazo[4,5-b]pyridin-2-one

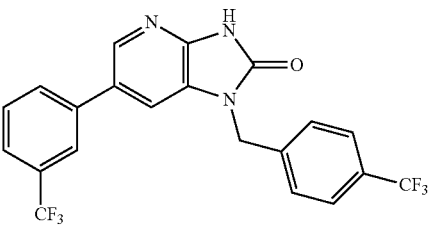

The title compound was prepared in a manner analogous to Example 21, using 1-(bromomethyl)-4-(trifluoromethyl)benzene in Step A. MS (ESI): mass calcd. for $C_{21}H_{13}F_6N_3O$, 437.1; m/z found, 438.1 [M+H]$^+$. $^1$H NMR (500 MHz, DMSO-d$_6$) δ 11.89 (s, 1H), 8.34 (d, J=1.9 Hz, 1H), 8.01-7.96 (m, 2H), 7.93 (d, J=2.0 Hz, 1H), 7.75-7.67 (m, 4H), 7.57 (d, J=8.0 Hz, 2H), 5.23 (s, 2H).

Example 220: 1-[(3-Fluoro-4-methoxy-phenyl)methyl]-6-[3-(trifluoromethyl)phenyl]-3H-imidazo[4,5-b]pyridin-2-one and its Trifluoroacetic Acid Salt

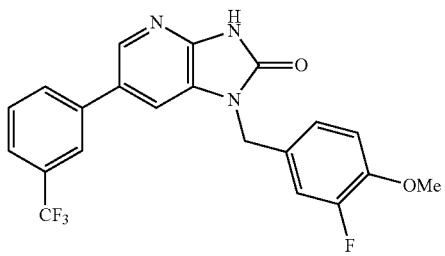 [SMILES: COc1ccc(Cn2c(=O)[nH]c3ncc(-c4cccc(C(F)(F)F)c4)cc32)cc1F]

The title compound was prepared in a manner analogous to Example 21, using 4-(bromomethyl)-2-fluoro-1-methoxybenzene in Step A. MS (ESI): mass calcd. for $C_{21}H_{15}F_4N_3O_2$, 417.1; m/z found, 418.1 [M+H]$^+$. $^1$H NMR (500 MHz, DMSO-d$_6$) δ 11.83 (s, 1H), 8.32 (d, J=2.0 Hz, 1H), 8.02-7.96 (m, 2H), 7.91 (d, J=2.1 Hz, 1H), 7.76-7.68 (m, 2H), 7.32-7.25 (m, 1H), 7.21-7.09 (m, 2H), 5.04 (s, 2H), 3.78 (s, 3H).

Example 221: 1-[(4-Fluoro-3-methyl-phenyl)methyl]-6-[3-(trifluoromethyl)phenyl]-3H-imidazo[4,5-b]pyridin-2-one

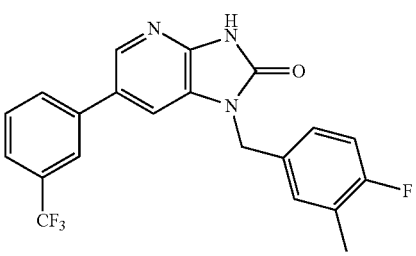 [SMILES: Cc1cc(Cn2c(=O)[nH]c3ncc(-c4cccc(C(F)(F)F)c4)cc32)ccc1F]

The title compound was prepared in a manner analogous to Example 21, using 4-(bromomethyl)-1-fluoro-2-methylbenzene in Step A. MS (ESI): mass calcd. for $C_{21}H_{15}F_4N_3O$, 401.1; m/z found, 402.1 [M+H]$^+$. $^1$H NMR (500 MHz, DMSO-d$_6$) δ 11.82 (s, 1H), 8.31 (d, J=2.0 Hz, 1H), 8.00-7.95 (m, 2H), 7.88 (d, J=2.0 Hz, 1H), 7.75-7.68 (m, 2H), 7.34-7.29 (m, 1H), 7.25-7.20 (m, 1H), 7.12-7.06 (m, 1H), 5.05 (s, 2H), 2.19 (d, J=1.9 Hz, 3H).

Example 222: 1-[(3-Fluorophenyl)methyl]-6-[3-(trifluoromethyl)phenyl]-3H-imidazo[4,5-b]pyridin-2-one

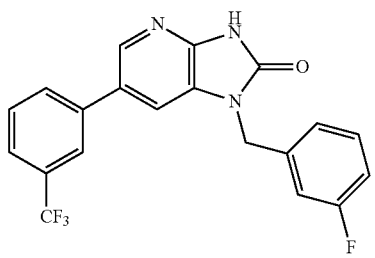 [SMILES: O=c1[nH]c2ncc(-c3cccc(C(F)(F)F)c3)cc2n1Cc1cccc(F)c1]

The title compound was prepared in a manner analogous to Example 21, using 1-(bromomethyl)-3-fluorobenzene in Step A. MS (ESI): mass calcd. for $C_{20}H_{13}F_4N_3O$, 387.1; m/z found, 388.1 [M+H]$^+$. $^1$H NMR (500 MHz, DMSO-d$_6$) δ 11.87 (s, 1H), 8.33 (t, J=1.7 Hz, 1H), 8.01-7.96 (m, 2H), 7.92 (t, J=1.7 Hz, 1H), 7.75-7.68 (m, 2H), 7.42-7.36 (m, 1H), 7.25-7.17 (m, 2H), 7.14-7.08 (m, 1H), 5.14 (s, 2H).

Example 223: (R*)-1-(Oxetan-2-ylmethyl)-6-[3-(trifluoromethyl)phenyl]-3H-imidazo[4,5-b]pyridin-2-one

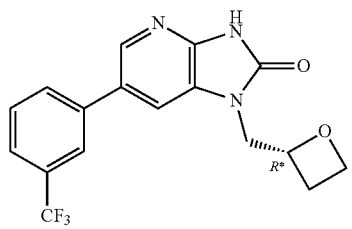

The title compound was prepared in a manner analogous to Example 21, using 2-(bromomethyl)oxetane in Step A. Purification (SFC separation, Chiralpak IA, 5 mm; Supercritical CO$_2$: MeOH, 75/25, 200 mL/min) afforded the title compound and (S*)-1-(Oxetan-2-ylmethyl)-6-[3-(trifluoromethyl)phenyl]-3H-imidazo[4,5-b]pyridin-2-one (Example 224). MS (ESI): mass calcd. for $C_{17}H_{14}F_3N_3O_2$, 349.1; m/z found, 350.2 [M+H]$^-$. $^1$H NMR (400 MHz, DMSO-d$_6$) δ 11.77 (s, 1H), 8.31 (d, J=2.0 Hz, 1H), 8.05-7.97 (m, 2H), 7.93 (d, J=2.0 Hz, 1H), 7.76-7.68 (m, 2H), 5.10-5.02 (m, 1H), 4.49-4.42 (m, 1H), 4.33 (dt, J=9.0, 6.0 Hz, 1H), 4.22-4.05 (m, 2H), 2.72-2.60 (m, 1H).

Example 224: (S*)-1-(Oxetan-2-ylmethyl)-6-[3-(trifluoromethyl)phenyl]-3H-imidazo[4,5-b]pyridin-2-one

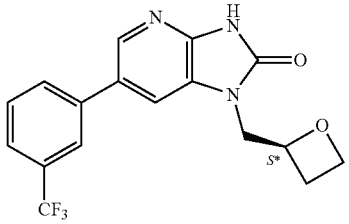 [SMILES: O=c1[nH]c2ncc(-c3cccc(C(F)(F)F)c3)cc2n1C[C@@H]1CCO1]

Isolated from SFC Chiral Separation, Example 223. MS (ESI): mass calcd. for $C_{17}H_{14}F_3N_3O_2$, 349.1; m/z found, 350.2 [M+H]$^+$. $^1$H NMR (400 MHz, DMSO-d$_6$) δ 11.77 (s, 1H), 8.31 (d, J=2.0 Hz, 1H), 8.05-7.97 (m, 2H), 7.93 (d, J=2.0 Hz, 1H), 7.76-7.68 (m, 2H), 5.10-5.02 (m, 1H), 4.49-4.42 (m, 1H), 4.33 (dt, J=9.0, 6.0 Hz, 1H), 4.22-4.05 (m, 2H), 2.72-2.60 (m, 1H).

Example 225: (R/S)-1-[(2,2-Difluorocyclopropyl)methyl]-6-[3-(trifluoromethyl)phenyl]-3H-imidazo[4,5-b]pyridin-2-one and its Trifluoroacetic Acid Salt

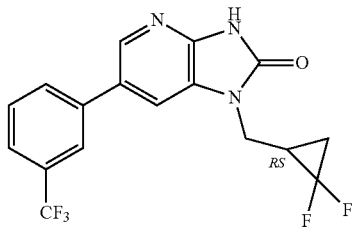 [SMILES: O=c1[nH]c2ncc(-c3cccc(C(F)(F)F)c3)cc2n1CC1CC1(F)F]

The title compound was prepared in a manner analogous to Example 21, using 2-(bromomethyl)-1,1-difluorocyclopropane in Step A. MS (ESI): mass calcd. for $C_{17}H_{12}F_5N_3O$, 369.1; m/z found, 370.2 [M+H]$^+$. $^1$H NMR (500 MHz, DMSO-d$_6$) δ 11.78 (s, 1H), 8.34 (d, J=2.0 Hz, 1H), 8.07-8.01 (m, 2H), 7.98 (d, J=2.0 Hz, 1H), 7.76-7.69 (m, 2H), 4.14-4.07 (m, 1H), 4.02-3.94 (m, 1H), 2.41-2.29 (m, 1H), 1.70-1.60 (m, 1H), 1.52-1.42 (m, 1H).

Example 226: 1-[(3-Fluorooxetan-3-yl)methyl]-6-[3-(trifluoromethyl)phenyl]-3H-imidazo[4,5-b]pyridin-2-one and its Trifluoroacetic Acid Salt

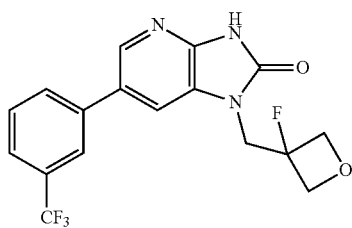 [SMILES: O=c1[nH]c2ncc(-c3cccc(C(F)(F)F)c3)cc2n1CC1(F)COC1]

The title compound was prepared in a manner analogous to Example 21, using 3-(bromomethyl)-3-fluorooxetane in Step A. MS (ESI): mass calcd. for $C_{17}H_{13}F_4N_3O_2$, 367.1; m/z found, 368.1 [M+H]$^+$. $^1$H NMR (400 MHz, DMSO-d$_6$) δ 11.89 (s, 1H), 8.34 (d, J=2.0 Hz, 1H), 8.03-7.96 (m, 2H), 7.89 (t, J=1.7 Hz, 1H), 7.77-7.69 (m, 2H), 4.85-4.62 (m, 4H), 4.55-4.45 (m, 2H).

Example 227: 1-(Pyrimidin-2-ylmethyl)-6-[3-(trifluoromethyl)phenyl]-3H-imidazo[4,5-b]pyridin-2-one and its Trifluoroacetic Acid Salt

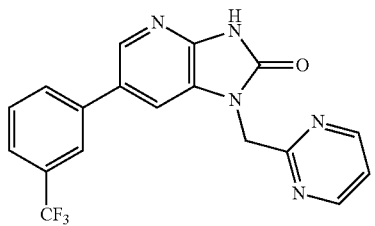

The title compound was prepared in a manner analogous to Example 21, using 2-(chloromethyl)pyrimidine hydrochloride in Step A. MS (ESI): mass calcd. for $C_{18}H_{12}F_3N_5O$, 371.1; m/z found, 372.2 [M+H]$^+$. 1H NMR (400 MHz, DMSO-d$_6$) δ 11.79 (s, 1H), 8.75 (d, J=4.9 Hz, 2H), 8.34 (d, J=2.0 Hz, 1H), 8.01-7.96 (m, 2H), 7.90 (d, J=2.0 Hz, 1H), 7.72-7.65 (m, 2H), 7.41 (t, J=4.9 Hz, 1H), 5.35 (s, 2H).

Example 228: 1-(2-Pyridylmethyl)-6-[3-(trifluoromethyl)phenyl]-3H-imidazo[4,5-b]pyridin-2-one and its Trifluoroacetic Acid Salt

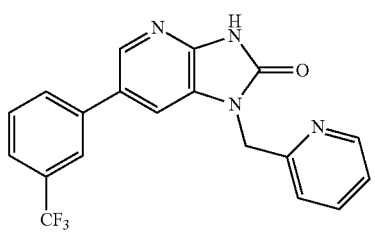 [SMILES: O=c1[nH]c2ncc(-c3cccc(C(F)(F)F)c3)cc2n1Cc1ccccn1]

The title compound was prepared in a manner analogous to Example 21, using 2-(chloromethyl)pyridine hydrochloride in Step A. MS (ESI): mass calcd. for $C_{19}H_{13}F_3N_4O$, 370.1; m/z found, 371.1 [M+H]$^+$. $^1$H NMR (400 MHz, DMSO-d$_6$) δ 11.82 (s, 1H), 8.53-8.47 (m, 1H), 8.33 (d, J=2.0 Hz, 1H), 8.00-7.93 (m, 2H), 7.84 (d, J=2.0 Hz, 1H), 7.80 (td, J=7.7, 1.8 Hz, 1H), 7.73-7.66 (m, 2H), 7.36-7.27 (m, 2H), 5.24 (s, 2H).

Example 229: 1-(4-Pyridylmethyl)-6-[3-(trifluoromethyl)phenyl]-3H-imidazo[4,5-b]pyridin-2-one and its Trifluoroacetic Acid Salt

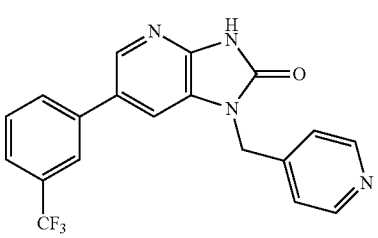 [SMILES: O=c1[nH]c2ncc(-c3cccc(C(F)(F)F)c3)cc2n1Cc1ccncc1]

The title compound was prepared in a manner analogous to Example 21, using 4-(chloromethyl)pyridine hydrochloride in Step A. MS (ESI): mass calcd. for $C_{19}H_{13}F_3N_4O$, 370.1; m/z found, 371.2 [M+H]$^+$. $^1$H NMR (500 MHz, DMSO-d$_6$) δ 11.95 (s, 1H), 8.71-8.67 (m, 2H), 8.37 (d, J=2.0 Hz, 1H), 8.00-7.96 (m, 2H), 7.92 (d, J=2.0 Hz, 1H), 7.74-7.67 (m, 2H), 7.63-7.60 (m, 2H), 5.31 (s, 2H).

Example 230: 1-(3-Pyridylmethyl)-6-[3-(trifluoromethyl)phenyl]-3H-imidazo[4,5-b]pyridin-2-one and its Trifluoroacetic Acid Salt

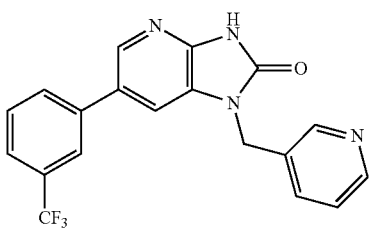 [SMILES: O=c1[nH]c2ncc(-c3cccc(C(F)(F)F)c3)cc2n1Cc1cccnc1]

The title compound was prepared in a manner analogous to Example 21, using 3-(chloromethyl)pyridine hydrochloride in Step A. MS (ESI): mass calcd. for $C_{19}H_{13}F_3N_4O$, 370.1; m/z found, 371.1 [M+H]$^+$. $^1$H NMR (400 MHz, DMSO-d$_6$) δ 11.89 (s, 1H), 8.78 (d, J=2.2 Hz, 1H), 8.62 (dd, J=5.1, 1.6 Hz, 1H), 8.35 (d, J=2.0 Hz, 1H), 8.07-7.96 (m, 4H), 7.76-7.67 (m, 2H), 7.60 (dd, J=7.9, 5.1 Hz, 1H), 5.22 (s, 2H).

Example 231: 1-[(2-Methylpyrimidin-5-yl)methyl]-6-[3-(trifluoromethyl)phenyl]-3H-imidazo[4,5-b]pyridin-2-one

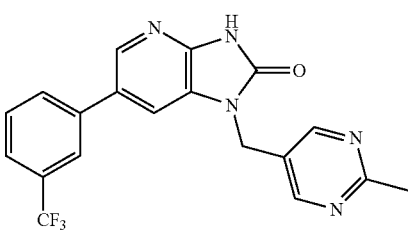 [SMILES: Cc1ncc(Cn2c(=O)[nH]c3ncc(-c4cccc(C(F)(F)F)c4)cc32)cn1]

The title compound was prepared in a manner analogous to Example 21, using 5-(chloromethyl)-2-methylpyrimidine hydrochloride in Step A. MS (ESI): mass calcd. for $C_{19}H_{14}F_3N_5O$, 385.1; m/z found, 386.2 [M+H]$^+$. $^1$H NMR (400 MHz, DMSO-d$_6$) δ 11.86 (s, 1H), 8.75 (s, 2H), 8.33 (d, J=2.0 Hz, 1H), 8.05-7.98 (m, 3H), 7.78-7.67 (m, 2H), 5.12 (s, 2H), 2.58 (s, 3H).

Example 232: 1-(Pyridazin-3-ylmethyl)-6-[3-(trifluoromethyl)phenyl]-3H-imidazo[4,5-b]pyridin-2-one and its Trifluoroacetic Acid Salt

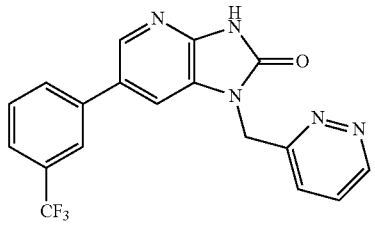

The title compound was prepared in a manner analogous to Example 21, using 3-(chloromethyl)pyridazine hydrochloride (Intermediate 2) in Step A. MS (ESI): mass calcd. for $C_{18}H_{12}F_3N_5O$, 371.1; m/z found, 372.2 [M+H]$^+$. $^1$H NMR (400 MHz, DMSO-d$_6$) δ 11.87 (s, 1H), 9.15 (dd, J=4.8, 1.8 Hz, 1H), 8.36 (d, J=2.0 Hz, 1H), 8.01-7.95 (m, 2H), 7.92 (d, J=2.0 Hz, 1H), 7.74-7.61 (m, 4H), 5.44 (s, 2H).

Example 233: 1-[(3-Methoxy-2-pyridyl)methyl]-6-[3-(trifluoromethyl)phenyl]-3H-imidazo[4,5-b]pyridin-2-one and its Trifluoroacetic Acid Salt

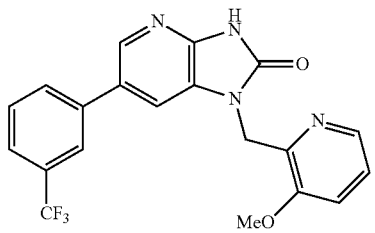 [SMILES: COc1cccnc1Cn1c(=O)[nH]c2ncc(-c3cccc(C(F)(F)F)c3)cc21]

The title compound was prepared in a manner analogous to Example 21, using 2-(chloromethyl)-3-methoxypyridine in Step A. MS (ESI): mass calcd. for $C_{20}H_{15}F_3N_4O_2$, 400.1; m/z found, 401.2 [M+H]$^+$. $^1$H NMR (500 MHz, DMSO-d$_6$) δ 11.72 (s, 1H), 8.31 (d, J=2.0 Hz, 1H), 7.98-7.91 (m, 3H), 7.77 (d, J=2.1 Hz, 1H), 7.72-7.64 (m, 2H), 7.46 (dd, J=8.3, 1.3 Hz, 1H), 7.27 (dd, J=8.3, 4.7 Hz, 1H), 5.21 (s, 2H), 3.91 (s, 3H).

Example 234: 1-[(3-Fluoro-5-methyl-2-pyridyl)methyl]-6-[3-(trifluoromethyl)phenyl]-3H-imidazo[4,5-b]pyridin-2-one and its Trifluoroacetic Acid Salt

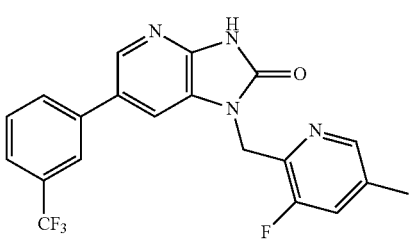 [SMILES: Cc1cnc(Cn2c(=O)[nH]c3ncc(-c4cccc(C(F)(F)F)c4)cc32)c(F)c1]

The title compound was prepared in a manner analogous to Example 21, using 2-(chloromethyl)-3-fluoro-5-methylpyridine in Step A. MS (ESI): mass calcd. for $C_{20}H_{14}F_4N_4O$, 402.1; m/z found, 403.2 [M+H]$^+$. $^1$H NMR (500 MHz, DMSO-d$_6$) δ 11.77 (s, 1H), 8.32 (d, J=2.0 Hz, 1H), 8.13-8.10 (m, 1H), 7.99-7.92 (m, 2H), 7.83 (d, J=2.0 Hz, 1H), 7.73-7.66 (m, 2H), 7.62-7.57 (m, 1H), 5.28 (s, 2H), 2.27 (s, 3H).

Example 235: 1-[(6-Methyl-3-pyridyl)methyl]-6-[3-(trifluoromethyl)phenyl]-3H-imidazo[4,5-b]pyridin-2-one and its Trifluoroacetic Acid Salt

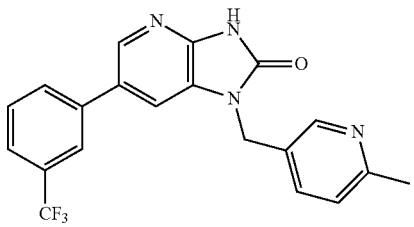 [SMILES: Cc1ccc(Cn2c(=O)[nH]c3ncc(-c4cccc(C(F)(F)F)c4)cc32)cn1]

The title compound was prepared in a manner analogous to Example 21, using 5-(chloromethyl)-2-methylpyridine hydrochloride in Step A. MS (ESI): mass calcd. for $C_{20}H_{15}F_3N_4O$, 384.1; m/z found, 385.2 [M+H]$^+$. $^1$H NMR (600 MHz, DMSO-d$_6$) δ 11.86 (s, 1H), 8.71-8.67 (m, 1H), 8.34 (d, J=1.9 Hz, 1H), 8.04-7.96 (m, 4H), 7.76-7.68 (m, 2H), 7.55-7.48 (m, 1H), 5.18 (s, 2H), 2.54 (s, 3H).

Example 236: 1-(2H-Tetrazol-5-ylmethyl)-6-[3-(trifluoromethyl)phenyl]-3H-imidazo[4,5-b]pyridin-2-one and its Trifluoroacetic Acid Salt

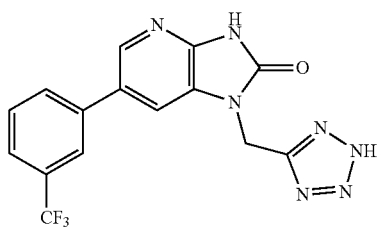 [SMILES: O=c1[nH]c2ncc(-c3cccc(C(F)(F)F)c3)cc2n1Cc1nn[nH]n1]

The title compound was prepared in a manner analogous to Example 21, using 5-(chloromethyl)-2H-tetrazole in Step A. MS (ESI): mass calcd. for $C_{15}H_{10}F_3N_7O$, 361.1; m/z found, 362.0 [M+H]$^+$. $^1$H NMR (500 MHz, DMSO-d$_6$) δ 11.91 (s, 1H), 8.38 (d, J=2.0 Hz, 1H), 8.01-7.98 (m, 2H), 7.95 (d, J=2.0 Hz, 1H), 7.75-7.69 (m, 2H), 5.50-5.46 (s, 2H).

Example 237: 1-[Difluoro(3-pyridyl)methyl]-6-[3-(trifluoromethyl)phenyl]-3H-imidazo[4,5-b]pyridin-2-one and its Trifluoroacetic Acid Salt

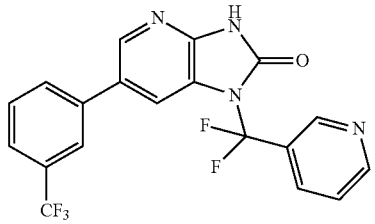 [SMILES: O=c1[nH]c2ncc(-c3cccc(C(F)(F)F)c3)cc2n1C(F)(F)c1cccnc1]

The title compound was prepared in a manner analogous to Example 21, using 3-(chlorodifluoromethyl)pyridine in Step A. MS (ESI): mass calcd. for $C_{19}H_{11}F_5N_4O$, 406.1; m/z found, 407.0 [M+H]$^+$. $^1$H NMR (500 MHz, DMSO-d$_6$) δ 12.25 (s, 1H), 9.02-8.95 (m, 1H), 8.81 (d, J=4.3 Hz, 1H), 8.48 (d, J=1.9 Hz, 1H), 8.23-8.17 (m, 1H), 8.06-8.00 (m, 2H), 7.95-7.92 (m, 1H), 7.80-7.70 (m, 2H), 7.62 (dd, J=8.0, 4.9 Hz, 1H).

Example 238: 1-[(6-Fluoro-3-pyridyl)methyl]-6-[3-(trifluoromethyl)phenyl]-3H-imidazo[4,5-b]pyridin-2-one and its Trifluoroacetic Acid Salt

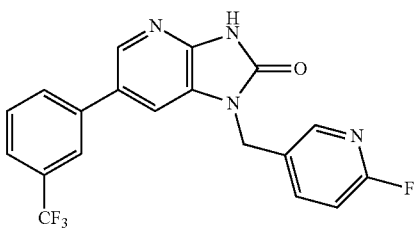 [SMILES: O=c1[nH]c2ncc(-c3cccc(C(F)(F)F)c3)cc2n1Cc1ccc(F)nc1]

The title compound was prepared in a manner analogous to Example 21, using 5-(chloromethyl)-2-fluoropyridine in Step A. MS (ESI): mass calcd. for $C_{19}H_{12}F_4N_4O$, 388.1; m/z found, 389.0 [M+H]$^+$. $^1$H NMR (500 MHz, DMSO-d$_6$) δ 11.86 (s, 1H), 8.38-8.34 (m, 1H), 8.33 (d, J=2.0 Hz, 1H), 8.04-7.95 (m, 4H), 7.76-7.68 (m, 2H), 7.16 (dd, J=8.5, 2.7 Hz, 1H), 5.15 (s, 2H).

Example 239: 1-(2-Cyclopropyl-2-oxo-ethyl)-6-[3-(trifluoromethyl)phenyl]-3H-imidazo[4,5-b]pyridin-2-one and its Trifluoroacetic Acid Salt

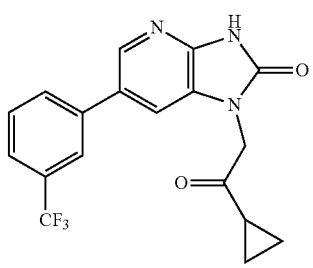 [SMILES: O=C(Cn1c(=O)[nH]c2ncc(-c3cccc(C(F)(F)F)c3)cc21)C1CC1]

The title compound was prepared in a manner analogous to Example 21, using 2-bromo-1-cyclopropylethan-1-one in Step A. MS (ESI): mass calcd. for $C_{18}H_{14}F_3N_3O_2$, 361.1; m/z found, 362.0 [M+H]$^+$. $^1$H NMR (400 MHz, DMSO-d$_6$) δ 11.78 (s, 1H), 8.32 (d, J=1.9 Hz, 1H), 8.01-7.96 (m, 2H), 7.85 (d, J=2.0 Hz, 1H), 7.76-7.67 (m, 2H), 5.03 (s, 2H), 2.26-2.16 (m, 1H), 1.05-0.90 (m, 4H).

Example 240: 1-(2-Oxobutyl)-6-[3-(trifluoromethyl)phenyl]-3H-imidazo[4,5-b]pyridin-2-one and its Trifluoroacetic Acid Salt

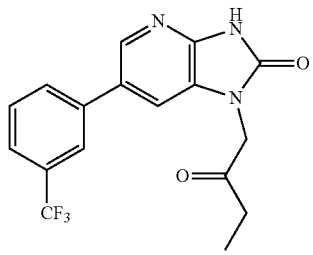 [SMILES: CCC(=O)Cn1c(=O)[nH]c2ncc(-c3cccc(C(F)(F)F)c3)cc21]

The title compound was prepared in a manner analogous to Example 21, using 1-bromobutan-2-one in Step A. MS (ESI): mass calcd. for $C_{17}H_{14}F_3N_3O_2$, 349.1; m/z found, 350.1 [M+H]$^+$. $^1$H NMR (400 MHz, DMSO-d$_6$) δ 11.79 (s, 1H), 8.33 (d, J=2.0 Hz, 1H), 8.01-7.94 (m, 2H), 7.81 (d, J=2.1 Hz, 1H), 7.75-7.67 (m, 2H), 4.86 (s, 2H), 2.62 (q, J=7.2 Hz, 2H), 0.99 (t, J=7.2 Hz, 3H).

Example 241: 1-(3-Methyl-2-oxo-butyl)-6-[3-(trifluoromethyl)phenyl]-3H-imidazo[4,5-b]pyridin-2-one and its Trifluoroacetic Acid Salt

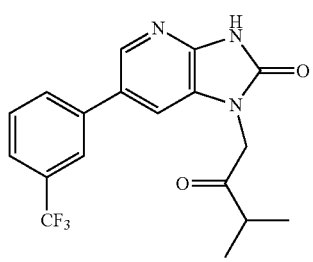 [SMILES: CC(C)C(=O)Cn1c(=O)[nH]c2ncc(-c3cccc(C(F)(F)F)c3)cc21]

The title compound was prepared in a manner analogous to Example 21, using 1-bromo-3-methylbutan-2-one in Step A. MS (ESI): mass calcd. for $C_{18}H_{16}F_3N_3O_2$, 363.1; m/z found, 364.1 [M+H]$^+$. $^1$H NMR (500 MHz, DMSO-d$_6$) δ 11.79 (s, 1H), 8.32 (d, J=2.0 Hz, 1H), 8.00-7.94 (m, 2H), 7.77 (d, J=2.0 Hz, 1H), 7.75-7.69 (m, 2H), 4.95 (s, 2H), 2.90-2.80 (m, 1H), 1.12 (d, J=6.9 Hz, 6H).

Example 242: 1-[(5-Methyl-3-pyridyl)methyl]-6-[3-(trifluoromethyl)phenyl]-3H-imidazo[4,5-b]pyridin-2-one and its Trifluoroacetic Acid Salt

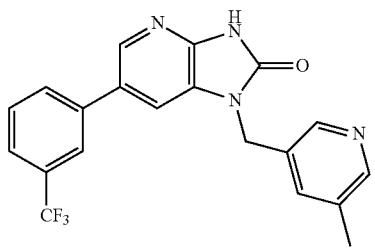 [SMILES: Cc1cncc(Cn2c(=O)[nH]c3ncc(-c4cccc(C(F)(F)F)c4)cc32)c1]

The title compound was prepared in a manner analogous to Example 21, using 3-(chloromethyl)-5-methylpyridine hydrochloride in Step A. MS (ESI): mass calcd. for $C_{20}H_{15}F_3N_4O$, 384.1; m/z found, 385.1 [M+H]$^+$. $^1$H NMR (400 MHz, DMSO-d$_6$) δ 11.88 (s, 1H), 8.61-8.58 (m, 1H), 8.49-8.46 (m, 1H), 8.34 (d, J=2.0 Hz, 1H), 8.03-7.95 (m, 3H), 7.90-7.85 (m, 1H), 7.76-7.67 (m, 2H), 5.18 (s, 2H), 2.33 (s, 3H).

Example 243: 1-(Thiadiazol-4-ylmethyl)-6-[3-(trifluoromethyl)phenyl]-3H-imidazo[4,5-b]pyridin-2-one and its Trifluoroacetic Acid Salt

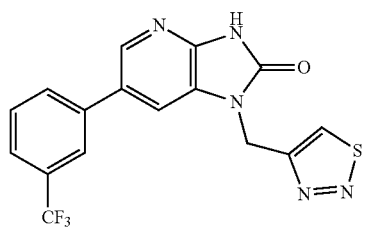 [SMILES: O=c1[nH]c2ncc(-c3cccc(C(F)(F)F)c3)cc2n1Cc1csnn1]

The title compound was prepared in a manner analogous to Example 21, using 4-(chloromethyl)-1,2,3-thiadiazole in Step A. MS (ESI): mass calcd. for $C_{16}H_{10}F_3N_5OS$, 377.1; m/z found, 378.0 [M+H]$^+$. $^1$H NMR (500 MHz, DMSO-d$_6$) δ 11.86 (s, 1H), 9.17 (s, 1H), 8.35 (d, J=2.0 Hz, 1H), 8.02-7.98 (m, 3H), 7.76-7.67 (m, 2H), 5.62 (s, 2H).

Example 244: 1-[(6-Oxo-1H-pyridin-3-yl)methyl]-6-[3-(trifluoromethyl)phenyl]-3H-imidazo[4,5-b]pyridin-2-one and its Trifluoroacetic Acid Salt

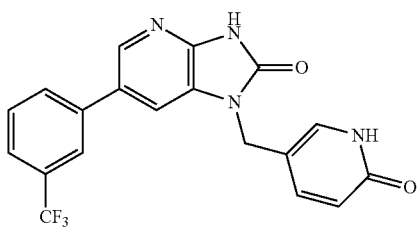 [SMILES: O=c1ccc(Cn2c(=O)[nH]c3ncc(-c4cccc(C(F)(F)F)c4)cc32)c[nH]1]

The title compound was prepared in a manner analogous to Example 21, using 5-(chloromethyl)pyridin-2(1H)-one in Step A. MS (ESI): mass calcd. for $C_{19}H_{13}F_3N_4O_2$, 386.1; m/z found, 387.0 [M+H]$^+$. $^1$H NMR (500 MHz, DMSO-d$_6$) δ 11.80 (s, 1H), 11.51 (br s, 1H), 8.32 (d, J=2.0 Hz, 1H), 8.04-7.98 (m, 3H), 7.76-7.69 (m, 2H), 7.58 (d, J=2.6 Hz, 1H), 7.48 (dd, J=9.5, 2.6 Hz, 1H), 6.30 (d, J=9.5 Hz, 1H), 4.83 (s, 2H).

Example 245: (R/S)-1-(Azetidin-2-ylmethyl)-3-methyl-6-[3-(trifluoromethyl)phenyl]imidazo[4,5-b]pyridin-2-one and its Trifluoroacetic Acid Salt

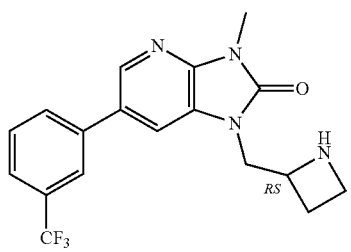 [SMILES: Cn1c(=O)n(CC2CCN2)c2cc(-c3cccc(C(F)(F)F)c3)cnc21]

The title compound was prepared in a manner analogous to Example 21, using 3-methyl-6-(3-(trifluoromethyl)phenyl)-1,3-dihydro-2H-imidazo[4,5-b]pyridin-2-one (Intermediate 26) and tert-butyl 2-(bromomethyl)azetidine-1-carboxylate in Step A. MS (ESI): mass calcd. for $C_{18}H_{17}F_3N_4O$, 362.1; m/z found, 363.2 [M+H]$^+$. $^1$H NMR (400 MHz, CDCl$_3$) δ 10.21-9.98 (m, 1H), 8.88-8.67 (m, 1H), 8.40 (d, J=1.7 Hz, 1H), 7.79-7.76 (m, 1H), 7.76-7.72 (m, 1H), 7.70-7.65 (m, 1H), 7.64-7.58 (m, 1H), 7.52 (d, J=1.8 Hz, 1H), 5.26-5.11 (m, 1H), 4.55-4.21 (m, 3H), 4.11-3.99 (m, 1H), 3.58 (s, 3H), 2.86-2.71 (m, 1H), 2.57-2.42 (m, 1H).

Example 246: 3-Methyl-1-(pyrimidin-4-ylmethyl)-6-[3-(trifluoromethyl)phenyl]imidazo[4,5-b]pyridin-2-one and its Trifluoroacetic Acid Salt

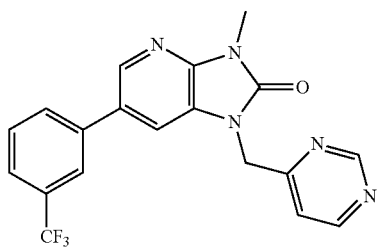 [SMILES: Cn1c(=O)n(Cc2ccncn2)c2cc(-c3cccc(C(F)(F)F)c3)cnc21]

The title compound was prepared in a manner analogous to Example 21, Step A, using 3-methyl-6-(3-(trifluoromethyl)phenyl)-1,3-dihydro-2H-imidazo[4,5-b]pyridin-2-one (Intermediate 26) and pyrimidin-4-ylmethyl methanesulfonate (prepared in a manner analogous to Example 23, Step A) MS (ESI): mass calcd. for $C_{19}H_{14}F_3N_5O$, 385.1; m/z found, 386.1 [M+H]$^+$. $^1$H NMR (400 MHz, DMSO-d$_6$) δ 9.09 (d, J=1.4 Hz, 1H), 8.75 (d, J=5.2 Hz, 1H), 8.44 (d, J=1.9 Hz, 1H), 8.02-7.96 (m, 3H), 7.75-7.66 (m, 2H), 7.47 (dd, J=5.2, 1.4 Hz, 1H), 5.33 (s, 2H), 3.43 (s, 3H).

Example 247: 3-Methyl-1-(pyrimidin-5-ylmethyl)-6-[3-(trifluoromethyl)phenyl]imidazo[4,5-b]pyridin-2-one and its Trifluoroacetic Acid Salt

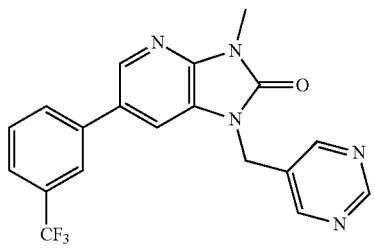 [SMILES: Cn1c(=O)n(Cc2cncnc2)c2cc(-c3cccc(C(F)(F)F)c3)cnc21]

The title compound was prepared in a manner analogous to Example 21, Step A using pyrimidin-5-ylmethyl methanesulfonate (prepared in a manner analogous to Example 23, Step A) and 3-methyl-6-(3-(trifluoromethyl)phenyl)-1,3-dihydro-2H-imidazo[4,5-b]pyridin-2-one (Intermediate 26). MS (ESI): mass calcd. for $C_{19}H_{14}F_3N_5O$, 385.1; m/z found, [M+H]$^+$. $^1$H NMR (500 MHz, DMSO-d$_6$) δ 9.12 (s, 1H), 8.87 (s, 2H), 8.42 (d, J=1.9 Hz, 1H), 8.11 (d, J=1.9 Hz, 1H), 8.04-7.99 (m, 2H), 7.76-7.69 (m, 2H), 5.24 (s, 2H), 3.40 (s, 3H).

Example 248: 3-Methyl-1-[(2-methylpyrimidin-4-yl)methyl]-6-[3-(trifluoromethyl)phenyl]imidazo[4,5-b]pyridin-2-one

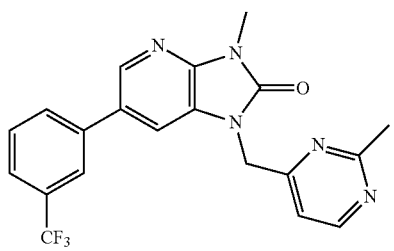 [SMILES: Cc1nccc(Cn2c(=O)n(C)c3ncc(-c4cccc(C(F)(F)F)c4)cc32)n1]

The title compound was prepared in a manner analogous to Example 21, Step A, using 3-methyl-6-(3-(trifluoromethyl)phenyl)-1,3-dihydro-2H-imidazo[4,5-b]pyridin-2-one (Intermediate 26) and (2-methylpyrimidin-4-yl)methyl methanesulfonate (prepared analogous to Example 23, Step A). MS (ESI): mass calcd. for $C_{20}H_{16}F_3N_5O$, 399.1; m/z found, 400.2 [M+H]$^+$. $^1$H NMR (400 MHz, DMSO-d$_6$) δ 8.61 (d, J=5.2 Hz, 1H), 8.45 (d, J=1.9 Hz, 1H), 8.04-7.97 (m, 3H), 7.75-7.65 (m, 2H), 7.12 (d, J=5.2 Hz, 1H), 5.25 (s, 2H), 3.18 (s, 3H), 2.57 (s, 3H).

Example 249: 3-Methyl-1-(pyrazin-2-ylmethyl)-6-[3-(trifluoromethyl)phenyl]imidazo[4,5-b]pyridin-2-one

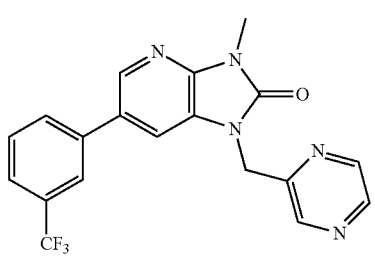 [SMILES: Cn1c(=O)n(Cc2cnccn2)c2cc(-c3cccc(C(F)(F)F)c3)cnc21]

The title compound was prepared in a manner analogous to Example 21, Step A, using 3-methyl-6-(3-(trifluoromethyl)phenyl)-1,3-dihydro-2H-imidazo[4,5-b]pyridin-2-one (Intermediate 26) and pyrazin-2-ylmethyl methanesulfonate (prepared analogous to Example 23, Step A). MS (ESI): mass calcd. for $C_{19}H_{14}F_3N_5O$, 385.1; m/z found, 386.2 [M+H]$^+$. $^1$H NMR (400 MHz, DMSO-d$_6$) δ 8.74 (d, J=1.4 Hz, 1H), 8.57-8.53 (m, 2H), 8.42 (d, J=1.9 Hz, 1H), 8.02-7.96 (m, 3H), 7.76-7.67 (m, 2H), 5.39 (s, 2H), 3.42 (s, 3H).

Example 250: 3-Methyl-1-(4-pyridylmethyl)-6-[3-(trifluoromethyl)phenyl]imidazo[4,5-b]pyridin-2-one and its Trifluoroacetic Acid Salt

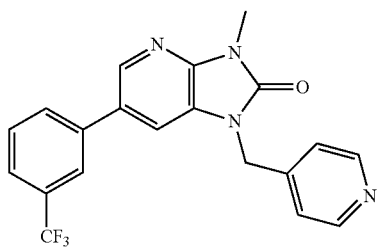 [SMILES: Cn1c(=O)n(Cc2ccncc2)c2cc(-c3cccc(C(F)(F)F)c3)cnc21]

The title compound was prepared in a manner analogous to Example 21, Step A, using 3-methyl-6-(3-(trifluoromethyl)phenyl)-1,3-dihydro-2H-imidazo[4,5-b]pyridin-2-one (Intermediate 26) and 4-(chloromethyl)pyridine hydrochloride. MS (ESI): mass calcd. for $C_{20}H_{15}F_3N_4O$, 384.1; m/z found, 385.2 [M+H]$^+$. $^1$H NMR (400 MHz, DMSO-d$_6$) δ 8.77-8.73 (m, 2H), 8.46 (d, J=1.9 Hz, 1H), 8.02-7.97 (m, 3H), 7.78-7.67 (m, 4H), 5.42 (s, 2H), 3.44 (s, 3H).

Example 251: 3-Methyl-1-(2-pyridylmethyl)-6-[3-(trifluoromethyl)phenyl]imidazo[4,5-b]pyridin-2-one

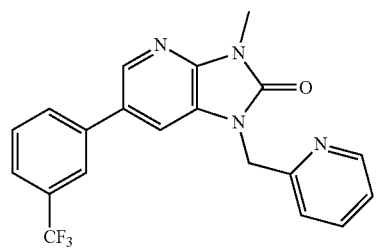 [SMILES: Cn1c(=O)n(Cc2ccccn2)c2cc(-c3cccc(C(F)(F)F)c3)cnc21]

The title compound was prepared in a manner analogous to Example 21, Step A, using 3-methyl-6-(3-(trifluoromethyl)phenyl)-1,3-dihydro-2H-imidazo[4,5-b]pyridin-2-one (Intermediate 26) and 2-(chloromethyl)pyridine hydrochloride. MS (ESI): mass calcd. for $C_{20}H_{15}F_3N_4O$, 384.1; m/z found, 385.2 [M+H]$^+$. $^1$H NMR (400 MHz, DMSO-d$_6$) δ 8.48 (ddd, J=4.8, 1.9, 1.0 Hz, 1H), 8.41 (d, J=1.9 Hz, 1H), 8.01-7.96 (m, 2H), 7.92 (d, J=2.0 Hz, 1H), 7.77 (td, J=7.7, 1.8 Hz, 1H), 7.74-7.67 (m, 2H), 7.35-7.31 (m, 1H), 7.28 (ddd, J=7.6, 4.8, 1.1 Hz, 1H), 5.29 (s, 2H), 3.42 (s, 3H).

Example 252: 1-[(6-Methoxypyridazin-3-yl)methyl]-6-[3-(trifluoromethyl)phenyl]-3H-imidazo[4,5-b]pyridin-2-one and its Trifluoroacetic Acid Salt

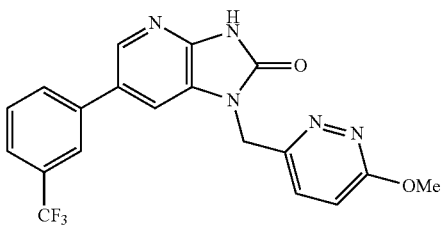 [SMILES: COc1ccc(Cn2c(=O)[nH]c3ncc(-c4cccc(C(F)(F)F)c4)cc32)nn1]

The title compound was prepared in a manner analogous to Example 23, using (6-methoxypyridazin-3-yl)methanol in Step A. MS (ESI): mass calcd. for $C_{19}H_{14}F_3N_5O_2$, 401.1; m/z found, 402.2 [M+H]$^+$. $^1$H NMR (500 MHz, DMSO-d$_6$) δ 11.84 (s, 1H), 8.34 (d, J=2.0 Hz, 1H), 8.00-7.96 (m, 2H), 7.88 (d, J=2.0 Hz, 1H), 7.74-7.67 (m, 2H), 7.61 (d, J=9.2 Hz, 1H), 7.21 (d, J=9.1 Hz, 1H), 5.34 (s, 2H), 3.96 (s, 3H).

Example 253: 1-(Pyrazin-2-ylmethyl)-6-[3-(trifluoromethyl)phenyl]-3H-imidazo[4,5-b]pyridin-2-one and its Trifluoroacetic Acid Salt

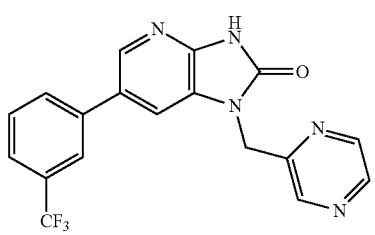 [SMILES: O=c1[nH]c2ncc(-c3cccc(C(F)(F)F)c3)cc2n1Cc1cnccn1]

The title compound was prepared in a manner analogous to Example 23, using pyrazin-2-ylmethanol in Step A. MS (ESI): mass calcd. for $C_{18}H_{12}F_3N_5O$, 371.1; m/z found, 372.2 [M+H]$^+$. $^1$H NMR (400 MHz, DMSO-d$_6$) δ 11.83 (s, 1H), 8.72 (d, J=1.3 Hz, 1H), 8.57-8.53 (m, 2H), 8.34 (d, J=2.0 Hz, 1H), 8.00-7.95 (m, 2H), 7.93-7.90 (d, J=2.0 Hz, 1H), 7.74-7.66 (m, 2H), 5.33 (s, 2H).

Example 254: 1-[(2-Methylpyrimidin-4-yl)methyl]-6-[3-(trifluoromethyl)phenyl]-3H-imidazo[4,5-b]pyridin-2-one and its Trifluoroacetic Acid Salt

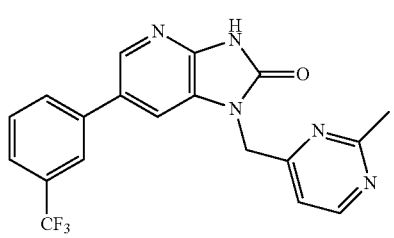 [SMILES: Cc1nccc(Cn2c(=O)[nH]c3ncc(-c4cccc(C(F)(F)F)c4)cc32)n1]

The title compound was prepared in a manner analogous to Example 23, using (2-methylpyrimidin-4-yl)methanol in Step A. MS (ESI): mass calcd. for $C_{19}H_{14}F_3N_5O$, 385.1; m/z found, 386.1 [M+H]$^+$. $^1$H NMR (400 MHz, DMSO-d$_6$) δ 11.89 (s, 1H), 8.62 (d, J=5.2 Hz, 1H), 8.37 (d, J=2.0 Hz, 1H), 8.03-7.96 (m, 2H), 7.92 (d, J=2.0 Hz, 1H), 7.74-7.65 (m, 2H), 7.10 (d, J=5.2 Hz, 1H), 5.20 (s, 2H), 2.57 (s, 3H).

Example 255: 1-(Pyrimidin-5-ylmethyl)-6-[3-(trifluoromethyl)phenyl]-3H-imidazo[4,5-b]pyridin-2-one

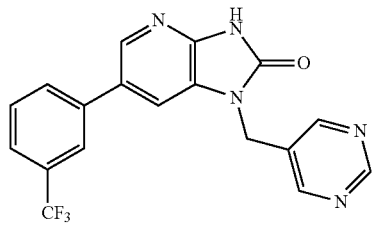 [SMILES: O=c1[nH]c2ncc(-c3cccc(C(F)(F)F)c3)cc2n1Cc1cncnc1]

The title compound was prepared in a manner analogous to Example 23, using pyrimidin-5-ylmethanol in Step A. MS (ESI): mass calcd. for $C_{18}H_{12}F_3N_5O$, 371.1; m/z found, 372.2 [M+H]$^+$. $^1$H NMR (500 MHz, DMSO-d$_6$) δ 11.88 (s, 1H), 9.12 (s, 1H), 8.86 (s, 2H), 8.34 (d, J=1.9 Hz, 1H), 8.05 (d, J=2.0 Hz, 1H), 8.04-7.97 (m, 2H), 7.77-7.68 (m, 2H), 5.18 (s, 2H).

Example 256: 1-[(5-Fluoropyrimidin-2-yl)methyl]-6-[3-(trifluoromethyl)phenyl]-3H-imidazo[4,5-b]pyridin-2-one and its Trifluoroacetic Acid Salt

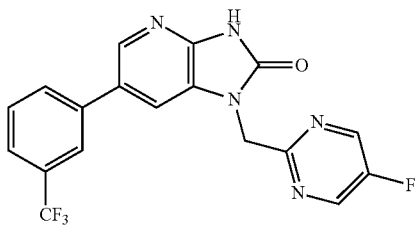 [SMILES: O=c1[nH]c2ncc(-c3cccc(C(F)(F)F)c3)cc2n1Cc1ncc(F)cn1]

The title compound was prepared in a manner analogous to Example 23, using (5-fluoropyrimidin-2-yl)methanol in Step A. MS (ESI): mass calcd. for $C_{18}H_{11}F_4N_5O$, 389.1; m/z found, 390.2 [M+H]$^+$. $^1$H NMR (500 MHz, DMSO-d$_6$) δ 11.82 (s, 1H), 8.86-8.85 (m, 2H), 8.34 (d, J=2.0 Hz, 1H), 8.00-7.96 (m, 2H), 7.90 (d, J=2.0 Hz, 1H), 7.73-7.66 (m, 2H), 5.37 (s, 2H).

Example 257: 6-[3-(Trifluoromethyl)phenyl]-1-[[6-(trifluoromethyl)-3-pyridyl]methyl]-3H-imidazo[4,5-b]pyridin-2-one and its Trifluoroacetic Acid Salt

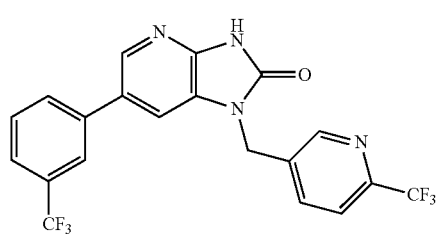 [SMILES: O=c1[nH]c2ncc(-c3cccc(C(F)(F)F)c3)cc2n1Cc1ccc(C(F)(F)F)nc1]

The title compound was prepared in a manner analogous to Example 23, using (6-(trifluoromethyl)pyridin-3-yl)methanol in Step A. MS (ESI): mass calcd. for $C_{20}H_{12}F_6N_4O$, 438.1; m/z found, 439.2 [M+H]$^+$. $^1$H NMR (500 MHz, DMSO-d$_6$) δ 11.90 (s, 1H), 8.85 (d, J=2.3 Hz, 1H), 8.35 (d, J=1.9 Hz, 1H), 8.05-7.96 (m, 4H), 7.90-7.86 (m, 1H), 7.76-7.68 (m, 2H), 5.28 (s, 2H).

Example 258: 1-[(5-Fluoro-3-pyridyl)methyl]-6-[3-(trifluoromethyl)phenyl]-3H-imidazo[4,5-b]pyridin-2-one and its Trifluoroacetic Acid Salt

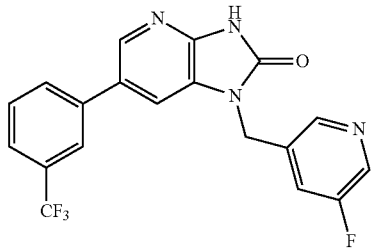 [SMILES: O=c1[nH]c2ncc(-c3cccc(C(F)(F)F)c3)cc2n1Cc1cncc(F)c1]

The title compound was prepared in a manner analogous to Example 23, using (5-fluoropyridin-3-yl)methanol in Step A. MS (ESI): mass calcd. for $C_{19}H_{12}F_4N_4O$, 388.1; m/z found, 389.2 [M+H]$^+$. $^1$H NMR (500 MHz, DMSO-d$_6$) δ 11.88 (s, 1H), 8.54-8.50 (m, 2H), 8.35-8.33 (d, J=2.0 Hz, 1H), 8.02-7.98 (m, 3H), 7.76-7.67 (m, 3H), 5.20 (s, 2H).

Example 259: 6-[3-(Trifluoromethyl)phenyl]-1-[[5-(trifluoromethyl)-3-pyridyl]methyl]-3H-imidazo[4,5-b]pyridin-2-one and its Trifluoroacetic Acid Salt

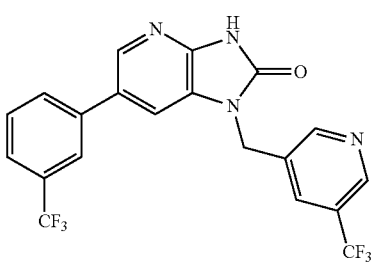 [SMILES: O=c1[nH]c2ncc(-c3cccc(C(F)(F)F)c3)cc2n1Cc1cncc(C(F)(F)F)c1]

The title compound was prepared in a manner analogous to Example 23, using (5-(trifluoromethyl)pyridin-3-yl)methanol in Step A. MS (ESI): mass calcd. for $C_{20}H_{12}F_6N_4O$, 438.1; m/z found, 439.1 [M+H]$^+$. $^1$H NMR (400 MHz, DMSO-d$_6$) δ 11.89 (s, 1H), 8.96-8.89 (m, 2H), 8.35 (d, J=2.0 Hz, 1H), 8.28-8.25 (m, 1H), 8.05 (d, J=2.0 Hz, 1H), 8.03-7.95 (m, 2H), 7.77-7.67 (m, 2H), 5.27 (s, 2H).

Example 260: 6-[3-(Trifluoromethyl)phenyl]-1-[[4-(trifluoromethyl)-3-pyridyl]methyl]-3H-imidazo[4,5-b]pyridin-2-one and its Trifluoroacetic Acid Salt

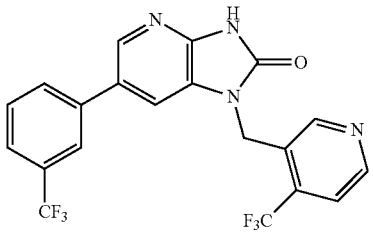 [SMILES: O=c1[nH]c2ncc(-c3cccc(C(F)(F)F)c3)cc2n1Cc1cnccc1C(F)(F)F]

The title compound was prepared in a manner analogous to Example 23, using (4-(trifluoromethyl)pyridin-3-yl)methanol in Step A. MS (ESI): mass calcd. for $C_{20}H_{12}F_6N_4O$, 438.1; m/z found, 439.0 [M+H]$^+$. $^1$H NMR (500 MHz, DMSO-d$_6$) δ 11.96 (s, 1H), 8.80 (d, J=5.1 Hz, 1H), 8.43 (s, 1H), 8.39 (d, J=2.0 Hz, 1H), 8.01-7.96 (m, 2H), 7.91 (d, J=2.0 Hz, 1H), 7.82 (d, J=5.1 Hz, 1H), 7.74-7.67 (m, 2H), 5.36 (s, 2H).

Example 261: 3-Methyl-1-(pyrimidin-2-ylmethyl)-6-[3-(trifluoromethyl)phenyl]imidazo[4,5-b]pyridin-2-one

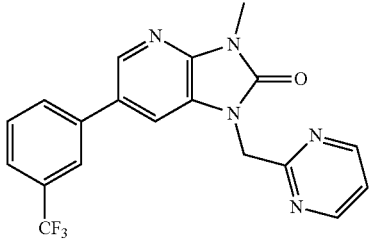

The title compound was prepared in a manner analogous to Example 23, using pyrimidin-2-ylmethanol in Step A and 3-methyl-6-(3-(trifluoromethyl)phenyl)-1,3-dihydro-2H-imidazo[4,5-b]pyridin-2-one (Intermediate 26) in Step B. MS (ESI): mass calcd. for $C_{19}H_{14}F_3N_5O$, 385.1; m/z found, 386.1 [M+H]$^+$. $^1$H NMR (400 MHz, DMSO-d$_6$) δ 8.75 (d, J=4.9 Hz, 2H), 8.43 (d, J=1.9 Hz, 1H), 8.03-7.96 (m, 3H), 7.74-7.65 (m, 2H), 7.42 (t, J=4.9 Hz, 1H), 5.41 (s, 2H), 3.43 (s, 3H).

Example 262: 1-(2-cyclobutyl-2-oxo-ethyl)-6-[3-(trifluoromethyl)phenyl]-3H-imidazo[4,5-b]pyridin-2-one and its Trifluoroacetic Acid Salt

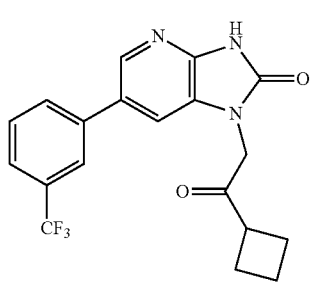 [SMILES: O=C(Cn1c(=O)[nH]c2ncc(-c3cccc(C(F)(F)F)c3)cc21)C1CCC1]

The title compound was prepared in a manner analogous to Example 24, using 2-bromo-1-cyclobutylethan-1-one in Step A. MS (ESI): mass calcd. for $C_{19}H_{16}F_3N_3O_2$, 375.1; m/z found, 376.1 [M+H]⁺. ¹H NMR (400 MHz, DMSO-$d_6$) δ 11.80 (s, 1H), 8.33 (d, J=2.0 Hz, 1H), 8.06-7.94 (m, 2H), 7.82 (d, J=2.0 Hz, 1H), 7.79-7.65 (m, 2H), 4.81 (s, 2H), 2.29-2.09 (m, 4H), 2.05-1.88 (m, 1H), 1.85-1.69 (m, 1H).

Example 263: (R/S)-1-(Azetidin-2-ylmethyl)-6-[3-(trifluoromethyl)phenyl]-3H-imidazo[4,5-b]pyridin-2-one and its Trifluoroacetic Acid Salt

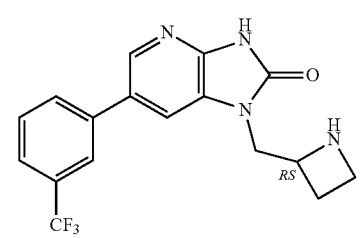 [SMILES: O=c1[nH]c2ncc(-c3cccc(C(F)(F)F)c3)cc2n1CC1CCN1]

The title compound was prepared in a manner analogous to Example 24, using tert-butyl 2-(bromomethyl)azetidine-1-carboxylate in Step A. MS (ESI): mass calcd. for $C_{17}H_{15}F_3N_4O$, 348.1; m/z found, 349.2 [M+H]⁺. ¹H NMR (500 MHz, DMSO-$d_6$) δ 11.92 (s, 1H), 8.72-8.57 (m, 2H), 8.40-8.35 (m, 1H), 8.06-7.98 (m, 3H), 7.78-7.71 (m, 2H), 4.82-4.70 (m, 1H), 4.43-4.25 (m, 2H).

Example 264: (R/S)-1-(Azetidin-2-ylmethyl)-6-[2-fluoro-3-(trifluoromethyl)phenyl]-3H-imidazo[4,5-b]pyridin-2-one and its Trifluoroacetic Acid Salt

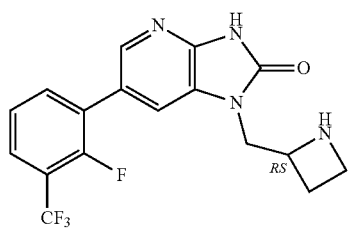 [SMILES: O=c1[nH]c2ncc(-c3cccc(C(F)(F)F)c3F)cc2n1CC1CCN1]

The title compound was prepared in a manner analogous to Example 24, using tert-butyl 2-(bromomethyl)azetidine-1-carboxylate in Step A and (2-fluoro-3-(trifluoromethyl)phenyl)boronic acid in Step B. MS (ESI): mass calcd. for $C_{17}H_{14}F_4N_4O$, 366.1; m/z found, 367.2 [M+H]⁺. ¹H NMR (500 MHz, DMSO-$d_6$) δ 11.98 (s, 1H), 8.67-8.55 (m, 2H), 8.18-8.14 (m, 1H), 7.94-7.89 (m, 1H), 7.88-7.82 (m, 2H), 7.56 (t, J=7.8 Hz, 1H), 4.74-4.67 (m, 1H) 4.39-4.19 (m, 2H), 3.97-3.86 (m, 1H), 3.81-3.72 (m, 1H), 2.45-2.33 (m, 2H).

Example 265: (R/S)-1-(Azetidin-2-ylmethyl)-6-phenyl-3H-imidazo[4,5-b]pyridin-2-one and its Trifluoroacetic Acid Salt

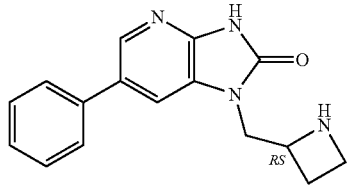 [SMILES: O=c1[nH]c2ncc(-c3ccccc3)cc2n1CC1CCN1]

The title compound was prepared in a manner analogous to Example 24, using tert-butyl 2-(bromomethyl)azetidine-1-carboxylate in Step A and phenylboronic acid in Step B. MS (ESI): mass calcd. for $C_{16}H_{16}N_4O$, 280.1; m/z found, 281.2 [M+H]⁺. ¹H NMR (400 MHz, DMSO-$d_6$) δ 11.83 (s, 1H), 8.73-8.56 (m, 2H), 8.27 (d, J=1.9 Hz, 1H), 7.93 (d, J=2.0 Hz, 1H), 7.74-7.67 (m, 2H), 7.53-7.47 (m, 2H), 7.43-7.36 (m, 1H), 4.81-4.68 (m, 1H), 4.40-4.23 (m, 2H).

Example 266: (R/S)-1-(Azetidin-2-ylmethyl)-6-(4-fluorophenyl)-3H-imidazo[4,5-b]pyridin-2-one and its Trifluoroacetic Acid Salt

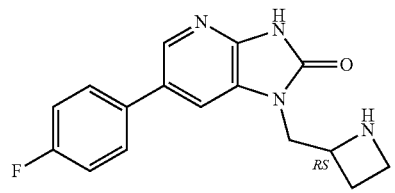 [SMILES: O=c1[nH]c2ncc(-c3ccc(F)cc3)cc2n1CC1CCN1]

The title compound was prepared in a manner analogous to Example 24, using tert-butyl 2-(bromomethyl)azetidine-1-carboxylate in Step A and (4-fluorophenyl)boronic acid in Step B. MS (ESI): mass calcd. for $C_{16}H_{15}FN_4O$, 298.1; m/z found, 299.2 [M+H]⁺. ¹H NMR (500 MHz, DMSO-$d_6$) δ 11.84 (s, 1H), 8.82-8.62 (m, 2H), 8.29-8.23 (m, 1H), 7.92 (d, J=2.0 Hz, 1H), 7.77-7.72 (m, 2H), 7.37-7.31 (m, 2H), 4.80-4.68 (m, 1H), 4.41-4.22 (m, 2H), 3.99-3.86 (m, 1H), 3.84-3.73 (m, 1H), 2.48-2.34 (m, 2H).

Example 267: (R/S)-1-(Azetidin-2-ylmethyl)-6-[4-fluoro-3-(trifluoromethyl)phenyl]-3H-imidazo[4,5-b]pyridin-2-one and its Trifluoroacetic Acid Salt

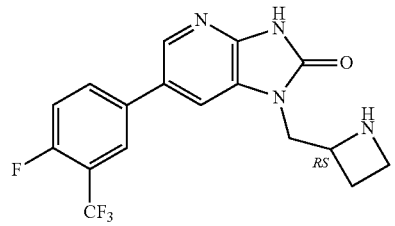 [SMILES: O=c1[nH]c2ncc(-c3ccc(F)c(C(F)(F)F)c3)cc2n1CC1CCN1]

The title compound was prepared in a manner analogous to Example 24, using tert-butyl 2-(bromomethyl)azetidine-1-carboxylate in Step A and (4-fluoro-3-(trifluoromethyl)

phenyl)boronic acid in Step B. MS (ESI): mass calcd. for $C_{17}H_{14}F_4N_4O$, 366.1; m/z found, 367.2 [M+H]$^+$. $^1$H NMR (500 MHz, DMSO-d$_6$) δ 11.91 (s, 1H), 8.74-8.57 (m, 2H), 8.34 (d, J=1.9 Hz, 1H), 8.10-8.05 (m, 1H), 8.03 (dd, J=6.8, 2.4 Hz, 1H), 7.98 (d, J=2.0 Hz, 1H), 4.80-4.70 (m, 1H), 4.40-4.23 (m, 2H), 2.47-2.38 (m, 2H).

Example 268: (R/S)-1-(Azetidin-2-ylmethyl)-6-(2,3-dichlorophenyl)-3H-imidazo[4,5-b]pyridin-2-one and its Trifluoroacetic Acid Salt

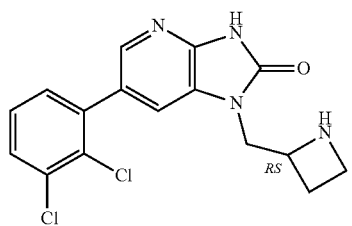 [SMILES: O=c1[nH]c2ncc(-c3cccc(Cl)c3Cl)cc2n1CC1CCN1]

The title compound was prepared in a manner analogous to Example 24, using tert-butyl 2-(bromomethyl)azetidine-1-carboxylate in Step A and (2,3-dichlorophenyl)boronic acid in Step B. MS (ESI): mass calcd. for $C_{16}H_{14}Cl_2N_4O$, 348.1; m/z found, 349.1 [M+H]$^+$. $^1$H NMR (500 MHz, DMSO-d$_6$) δ 11.94 (s, 1H), 8.71-8.55 (m, 2H), 8.02 (d, J=1.8 Hz, 1H), 7.77 (d, J=1.9 Hz, 1H), 7.72 (dd, J=7.9, 1.7 Hz, 1H), 7.51-7.47 (m, 1H), 7.46-7.43 (m, 1H), 4.72-4.62 (m, 1H), 4.35-4.19 (m, 2H), 3.96-3.85 (m, 1H), 3.81-3.71 (m, 1H), 2.45-2.34 (m, 2H).

Example 269: 6-(4-Fluoro-3-methyl-phenyl)-1-[(5-methyl-3-pyridyl)methyl]-3H-imidazo[4,5-b]pyridin-2-one and its Trifluoroacetic Acid Salt

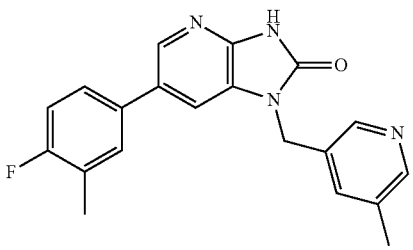 [SMILES: Cc1cncc(Cn2c(=O)[nH]c3ncc(-c4ccc(F)c(C)c4)cc32)c1]

The title compound was prepared in a manner analogous to Example 24, using 3-(chloromethyl)-5-methylpyridine hydrochloride in Step A and (4-fluoro-3-methylphenyl)boronic acid in Step B. MS (ESI): mass calcd. for $C_{20}H_{17}FN_4O$, 348.1; m/z found, 349.1 [M+H]$^+$. $^1$H NMR (500 MHz, DMSO-d$_6$) δ 11.84-11.79 (m, 1H), 8.70-8.68 (m, 1H), 8.60-8.58 (m, 1H), 8.23 (d, J=1.9 Hz, 1H), 8.10-8.06 (m, 1H), 7.83 (d, J=2.0 Hz, 1H), 7.61-7.57 (m, 1H), 7.52-7.47 (m, 1H), 7.26-7.20 (m, 1H), 5.20 (s, 2H), 2.39 (s, 3H), 2.30 (d, J=1.9 Hz, 3H).

Example 270: 6-(2,4-Difluoro-3-methyl-phenyl)-1-[(5-methyl-3-pyridyl)methyl]-3H-imidazo[4,5-b]pyridin-2-one and its Trifluoroacetic Acid Salt

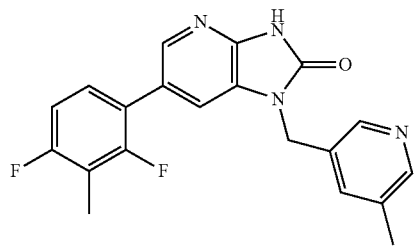 [SMILES: Cc1cncc(Cn2c(=O)[nH]c3ncc(-c4ccc(F)c(C)c4F)cc32)c1]

The title compound was prepared in a manner analogous to Example 24, using 3-(chloromethyl)-5-methylpyridine hydrochloride in Step A and (2,4-difluoro-3-methylphenyl)boronic acid in Step B. MS (ESI): mass calcd. for $C_{20}H_{16}F_2N_4O$, 366.1; m/z found, 367.0 [M+H]$^+$. $^1$H NMR (500 MHz, DMSO-d$_6$) δ 11.86 (s, 1H), 8.60-8.57 (m, 1H), 8.51-8.48 (m, 1H), 8.05 (t, J=1.6 Hz, 1H), 7.91-7.88 (m, 1H), 7.68 (t, J=1.6 Hz, 1H), 7.42-7.36 (m, 1H), 7.20-7.15 (m, 1H), 5.14 (s, 2H), 2.34 (s, 3H), 2.21 (t, J=1.8 Hz, 3H).

Example 271: (R/S)-6-[4-Fluoro-3-(trifluoromethyl)phenyl]-1-(oxetan-2-ylmethyl)-3H-imidazo[4,5-b]pyridin-2-one and its Trifluoroacetic Acid Salt

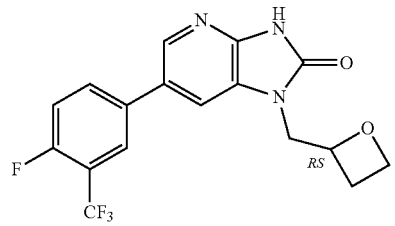 [SMILES: O=c1[nH]c2ncc(-c3ccc(F)c(C(F)(F)F)c3)cc2n1CC1CCO1]

The title compound was prepared in a manner analogous to Example 24, using 2-(bromomethyl)oxetane in Step A and (4-fluoro-3-(trifluoromethyl)phenyl)boronic acid in Step B. MS (ESI): mass calcd. for $C_{17}H_{13}F_4N_3O_2$, 367.1; m/z found, 368.1 [M+H]$^+$. $^1$H NMR (500 MHz, DMSO-d$_6$) δ 11.77 (s, 1H), 8.29 (d, J=2.0 Hz, 1H), 8.09-7.98 (m, 2H), 7.91 (d, J=2.0 Hz, 1H), 7.67-7.60 (m, 1H), 5.10-5.01 (m, 1H), 4.49-4.42 (m, 1H), 4.37-4.30 (m, 1H), 4.21-4.05 (m, 2H), 2.71-2.62 (m, 1H).

Example 272: 6-(3,4-Difluorophenyl)-1-[(5-methyl-3-pyridyl)methyl]-3H-imidazo[4,5-b]pyridin-2-one and its Trifluoroacetic Acid Salt

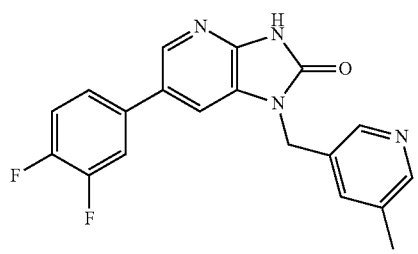 [SMILES: Cc1cncc(Cn2c(=O)[nH]c3ncc(-c4ccc(F)c(F)c4)cc32)c1]

The title compound was prepared in a manner analogous to Example 24, using 3-(chloromethyl)-5-methylpyridine hydrochloride in Step A and (3,4-difluorophenyl)boronic acid in Step B. MS (ESI): mass calcd. for $C_{19}H_{14}F_2N_4O$, 352.1; m/z found, 353.0 [M+H]$^+$. $^1$H NMR (500 MHz, DMSO-d$_6$) δ 11.86 (s, 1H), 8.65 (d, J=2.0 Hz, 1H), 8.53 (d, J=2.1 Hz, 1H), 8.29 (d, J=2.0 Hz, 1H), 7.99-7.95 (m, 1H), 7.89 (d, J=2.0 Hz, 1H), 7.83-7.77 (m, 1H), 7.57-7.50 (m, 2H), 5.17 (s, 2H), 2.38-2.33 (m, 3H).

Example 273: 6-(3-Chlorophenyl)-1-[(5-methyl-3-pyridyl)methyl]-3H-imidazo[4,5-b]pyridin-2-one and its Trifluoroacetic Acid Salt

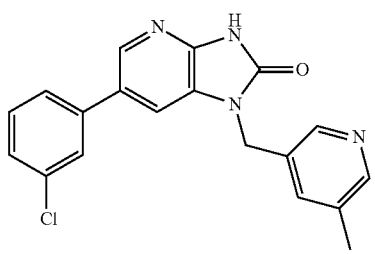 [SMILES: Cc1cncc(Cn2c(=O)[nH]c3ncc(-c4cccc(Cl)c4)cc32)c1]

The title compound was prepared in a manner analogous to Example 24, using 3-(chloromethyl)-5-methylpyridine hydrochloride in Step A and (3-chlorophenyl)boronic acid in Step B. MS (ESI): mass calcd. for $C_{19}H_{15}ClN_4O$, 350.1; m/z found, 351.0 [M+H]$^+$. $^1$H NMR (500 MHz, DMSO-d$_6$) δ 11.86 (s, 1H), 8.64-8.61 (m, 1H), 8.53-8.50 (m, 1H), 8.30 (d, J=1.9 Hz, 1H), 7.96-7.90 (m, 2H), 7.76 (t, J=1.9 Hz, 1H), 7.66 (ddd, J=7.8, 1.8, 1.1 Hz, 1H), 7.50 (t, J=7.9 Hz, 1H), 7.44-7.41 (m, 1H), 5.18 (s, 2H), 2.35 (s, 3H).

Example 274: 6-(3-Fluorophenyl)-1-[(5-methyl-3-pyridyl)methyl]-3H-imidazo[4,5-b]pyridin-2-one and its Trifluoroacetic Acid Salt

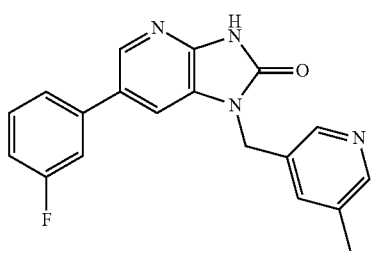 [SMILES: Cc1cncc(Cn2c(=O)[nH]c3ncc(-c4cccc(F)c4)cc32)c1]

The title compound was prepared in a manner analogous to Example 24, using 3-(chloromethyl)-5-methylpyridine hydrochloride in Step A and (3-fluorophenyl)boronic acid in Step B. MS (ESI): mass calcd. for $C_{19}H_{15}FN_4O$, 334.1; m/z found, 335.1 [M+H]$^+$. $^1$H NMR (500 MHz, DMSO-d$_6$) δ 11.86 (s, 1H), 8.65-8.63 (m, 1H), 8.53-8.51 (m, 1H), 8.31 (d, J=2.0 Hz, 1H), 7.96-7.94 (m, 1H), 7.91 (d, J=2.0 Hz, 1H), 7.57-7.48 (m, 3H), 7.23-7.17 (m, 1H), 5.18 (s, 2H), 2.35 (s, 3H).

Example 275: 6-(3,4-Difluorophenyl)-1-[(4-methyl-3-pyridyl)methyl]-3H-imidazo[4,5-b]pyridin-2-one and its Trifluoroacetic Acid Salt

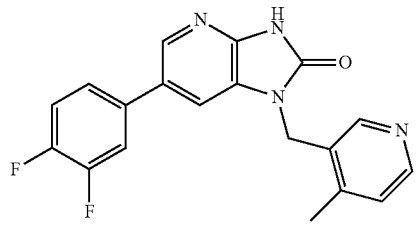

The title compound was prepared in a manner analogous to Example 24, using 3-(chloromethyl)-4-methylpyridine hydrochloride in Step A and (3,4-difluorophenyl)boronic acid in Step B. MS (ESI): mass calcd. for $C_{19}H_{14}F_2N_4O$, 352.1; m/z found, 353.0 [M+H]$^+$. $^1$H NMR (400 MHz, DMSO-d$_6$) δ 11.90 (s, 1H), 8.57 (d, J=5.4 Hz, 1H), 8.43 (s, 1H), 8.31 (d, J=2.0 Hz, 1H), 7.80-7.73 (m, 2H), 7.66 (d, J=5.4 Hz, 1H), 7.58-7.48 (m, 2H), 5.21 (s, 2H), 2.55 (s, 3H).

Example 276: 6-(3-Fluorophenyl)-1-[(4-methyl-3-pyridyl)methyl]-3H-imidazo[4,5-b]pyridin-2-one and its Trifluoroacetic Acid Salt

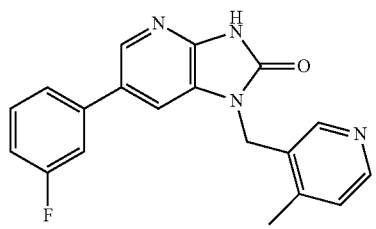 [SMILES: Cc1ccncc1Cn1c(=O)[nH]c2ncc(-c3cccc(F)c3)cc21]

The title compound was prepared in a manner analogous to Example 24, using 3-(chloromethyl)-4-methylpyridine hydrochloride in Step A and (3-fluorophenyl)boronic acid in Step B. MS (ESI): mass calcd. for $C_{19}H_{15}FN_4O$, 334.1; m/z found, 335.1 [M+H]$^+$. 11.90 (s, 1H), 8.62-8.53 (m, 1H), 8.48-8.40 (m, 1H), 8.33 (d, J=1.9 Hz, 1H), 7.79 (d, J=2.0 Hz, 1H), 7.70-7.63 (m, 1H), 7.55-7.43 (m, 3H), 7.23-7.14 (m, 1H), 5.23 (s, 2H), 2.55 (s, 3H).

Example 277: 6-(4-Fluoro-3-methyl-phenyl)-1-[(4-methyl-3-pyridyl)methyl]-3H-imidazo[4,5-b]pyridin-2-one and its Trifluoroacetic Acid Salt

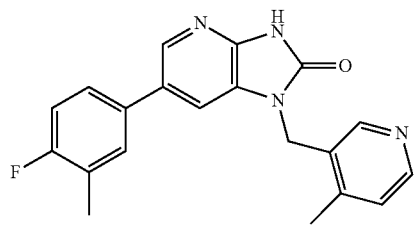 [SMILES: Cc1cc(-c2cnc3[nH]c(=O)n(Cc4cnccc4C)c3c2)ccc1F]

The title compound was prepared in a manner analogous to Example 24, using 3-(chloromethyl)-4-methylpyridine hydrochloride in Step A and (4-fluoro-3-methylphenyl)boronic acid in Step B. MS (ESI): mass calcd. for $C_{20}H_{17}FN_4O$, 348.1; m/z found, 349.1 $[M+H]^+$. $^1H$ NMR (500 MHz, DMSO-$d_6$) δ 11.83 (s, 1H), 8.56 (d, J=5.4 Hz, 1H), 8.41 (s, 1H), 8.24 (d, J=1.9 Hz, 1H), 7.71 (d, J=2.0 Hz, 1H), 7.64 (d, J=5.4 Hz, 1H), 7.58-7.53 (m, 1H), 7.49-7.44 (m, 1H), 7.22 (dd, J=9.7, 8.5 Hz, 1H), 5.22 (s, 2H), 2.54 (s, 3H), 2.29 (d, J=1.9 Hz, 3H).

Example 278: 6-(2,4-Difluoro-3-methyl-phenyl)-1-[(4-methyl-3-pyridyl)methyl]-3H-imidazo[4,5-b]pyridin-2-one and its Trifluoroacetic Acid Salt

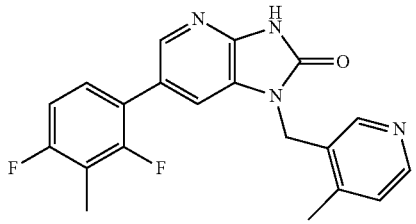 [SMILES: Cc1ccncc1Cn1c(=O)[nH]c2ncc(-c3ccc(F)c(C)c3F)cc21]

The title compound was prepared in a manner analogous to Example 24, using 3-(chloromethyl)-4-methylpyridine hydrochloride in Step A and (2,4-difluoro-3-methylphenyl)boronic acid in Step B. MS (ESI): mass calcd. for $C_{20}H_{16}F_2N_4O$, 366.1; m/z found, 367.1 $[M+H]^+$. $^1H$ NMR (400 MHz, DMSO-$d_6$) δ 11.92 (s, 1H), 8.63 (d, J=5.6 Hz, 1H), 8.49 (s, 1H), 8.09 (t, J=1.7 Hz, 1H), 7.76 (d, J=5.5 Hz, 1H), 7.61 (t, J=1.6 Hz, 1H), 7.42-7.32 (m, 1H), 7.21-7.12 (m, 1H), 5.23 (s, 2H), 2.58 (s, 3H), 2.20 (t, J=1.9 Hz, 3H).

Example 279: 6-(3,4-Difluorophenyl)-1-(2-pyridylmethyl)-3H-imidazo[4,5-b]pyridin-2-one and its Trifluoroacetic Acid Salt

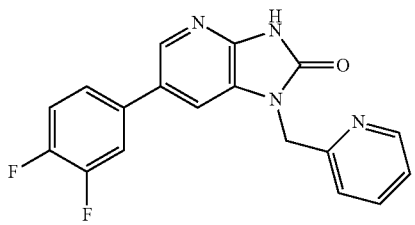 [SMILES: O=c1[nH]c2ncc(-c3ccc(F)c(F)c3)cc2n1Cc1ccccn1]

The title compound was prepared in a manner analogous to Example 24, using 2-(chloromethyl)pyridine hydrochloride in Step A and (3,4-difluorophenyl)boronic acid in Step B. MS (ESI): mass calcd. for $C_{18}H_{12}F_2N_4O$, 338.1; m/z found, 339.1 $[M+H]^+$. $^1H$ NMR (400 MHz, DMSO-$d_6$) δ 11.80 (s, 1H), 8.51 (ddd, J=4.8, 1.8, 1.1 Hz, 1H), 8.28 (d, J=2.0 Hz, 1H), 7.86-7.72 (m, 3H), 7.56-7.46 (m, 2H), 7.37-7.30 (m, 2H), 5.22 (s, 2H).

Example 280: 6-(2,4-Difluoro-3-methyl-phenyl)-1-(2-pyridylmethyl)-3H-imidazo[4,5-b]pyridin-2-one and its Trifluoroacetic Acid Salt

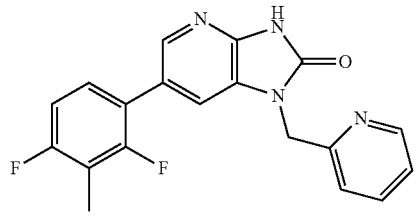 [SMILES: Cc1c(F)ccc(-c2cnc3[nH]c(=O)n(Cc4ccccn4)c3c2)c1F]

The title compound was prepared in a manner analogous to Example 24, using 2-(chloromethyl)pyridine hydrochloride in Step A and (2,4-difluoro-3-methylphenyl)boronic acid in Step B. MS (ESI): mass calcd. for $C_{19}H_{14}F_2N_4O$, 352.1; m/z found, 353.0 $[M+H]^+$. $^1H$ NMR (400 MHz, DMSO-$d_6$) δ 11.81 (s, 1H), 8.51 (ddd, J=4.9, 1.6, 0.9 Hz, 1H), 8.05 (t, J=1.7 Hz, 1H), 7.82 (td, J=7.7, 1.8 Hz, 1H), 7.51 (t, J=1.7 Hz, 1H), 7.41-7.30 (m, 3H), 7.18-7.11 (m, 1H), 5.19 (s, 2H), 2.20 (t, J=1.9 Hz, 3H).

Example 281: 6-(3-Fluorophenyl)-1-(2-pyridylmethyl)-3H-imidazo[4,5-b]pyridin-2-one and its Trifluoroacetic Acid Salt

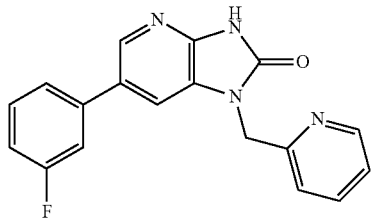 [SMILES: O=c1[nH]c2ncc(-c3cccc(F)c3)cc2n1Cc1ccccn1]

The title compound was prepared in a manner analogous to Example 24, using 2-(chloromethyl)pyridine hydrochloride in Step A and (3-fluorophenyl)boronic acid in Step B. MS (ESI): mass calcd. for $C_{18}H_{13}FN_4O$, 320.1; m/z found, 321.1 $[M+H]^+$. $^1H$ NMR (400 MHz, DMSO-$d_6$) δ 11.80 (s, 1H), 8.51 (ddd, J=4.9, 1.9, 1.1 Hz, 1H), 8.30 (d, J=2.0 Hz, 1H), 7.82 (td, J=7.7, 1.8 Hz, 1H), 7.77 (d, J=2.0 Hz, 1H), 7.54-7.44 (m, 3H), 7.37-7.30 (m, 2H), 7.22-7.14 (m, 1H), 5.23 (s, 2H).

Example 282: 6-(3-Chlorophenyl)-1-(2-pyridylmethyl)-3H-imidazo[4,5-b]pyridin-2-one and its Trifluoroacetic Acid Salt

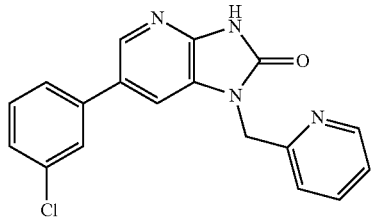 [SMILES: O=c1[nH]c2ncc(-c3cccc(Cl)c3)cc2n1Cc1ccccn1]

The title compound was prepared in a manner analogous to Example 24, using 2-(chloromethyl)pyridine hydrochloride in Step A and (3-chlorophenyl)boronic acid in Step B. MS (ESI): mass calcd. for $C_{18}H_{13}ClN_4O$, 336.1; m/z found, 337.0 [M+H]+. 1H NMR (400 MHz, DMSO-d6) δ 11.80 (s, 1H), 8.54-8.48 (m, 1H), 8.29 (d, J=2.0 Hz, 1H), 7.83 (td, J=7.7, 1.8 Hz, 1H), 7.79 (d, J=2.0 Hz, 1H), 7.72 (t, J=1.9 Hz, 1H), 7.62 (dt, J=7.7, 1.4 Hz, 1H), 7.47 (t, J=7.8 Hz, 1H), 7.43-7.38 (m, 1H), 7.37-7.31 (m, 2H), 5.24 (s, 2H).

Example 283: 6-(4-Fluoro-3-methyl-phenyl)-1-(2-pyridylmethyl)-3H-imidazo[4,5-b]pyridin-2-one and its Trifluoroacetic Acid Salt

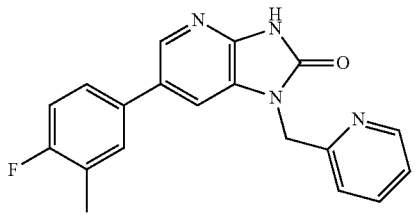 [SMILES: Cc1cc(-c2cnc3[nH]c(=O)n(Cc4ccccn4)c3c2)ccc1F]

The title compound was prepared in a manner analogous to Example 24, using 2-(chloromethyl)pyridine hydrochloride in Step A and (4-fluoro-3-methylphenyl)boronic acid in Step B. MS (ESI): mass calcd. for $C_{19}H_{15}FN_4O$, 334.1; m/z found, 335.1 [M+H]+. 1H NMR (500 MHz, DMSO-d6) δ 11.74 (s, 1H), 8.53-8.51 (m, 1H), 8.21 (d, J=1.9 Hz, 1H), 7.84 (td, J=7.7, 1.8 Hz, 1H), 7.67 (d, J=2.0 Hz, 1H), 7.58-7.54 (m, 1H), 7.48-7.44 (m, 1H), 7.37-7.32 (m, 2H), 7.23-7.17 (m, 1H), 5.22 (s, 2H), 2.28 (d, J=1.8 Hz, 3H).

Example 284: 6-(3,4-Difluorophenyl)-1-[(3-methyl-2-pyridyl)methyl]-3H-imidazo[4,5-b]pyridin-2-one and its Trifluoroacetic Acid Salt

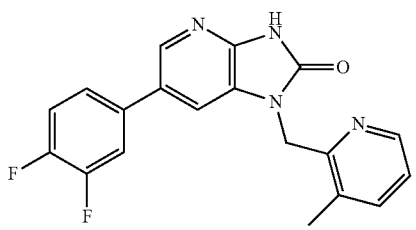

The title compound was prepared in a manner analogous to Example 24, using (3-methylpyridin-2-yl)methyl methanesulfonate (prepared analogous to Example 23, Step A) in Step A and (3,4-difluorophenyl)boronic acid in Step B. MS (ESI): mass calcd. for $C_{19}H_{14}F_2N_4O$, 352.1; m/z found, 323.1 [M+H]+. 1H NMR (500 MHz, DMSO-d6) δ 11.72 (s, 1H), 8.25 (d, J=2.0 Hz, 1H), 8.22-8.19 (m, 1H), 7.72 (ddd, J=12.0, 7.7, 2.1 Hz, 1H), 7.69-7.62 (m, 2H), 7.54-7.44 (m, 2H), 7.24-7.18 (m, 1H), 5.21 (s, 2H), 2.43 (s, 3H).

Example 285: 6-(3-Fluorophenyl)-1-[(3-methyl-2-pyridyl)methyl]-3H-imidazo[4,5-b]pyridin-2-one and its Trifluoroacetic Acid Salt

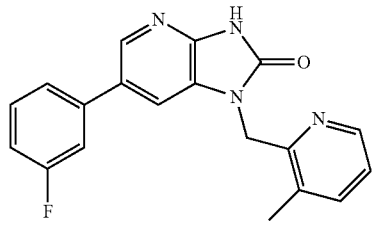 [SMILES: Cc1cccnc1Cn1c(=O)[nH]c2ncc(-c3cccc(F)c3)cc21]

The title compound was prepared in a manner analogous to Example 24, using (3-methylpyridin-2-yl)methyl methanesulfonate (prepared analogous to Example 23, Step A) in Step A and (3-fluorophenyl)boronic acid in Step B. MS (ESI): mass calcd. for $C_{19}H_{15}FN_4O$, 334.1; m/z found, 335.1 [M+H]+. 1H NMR (500 MHz, DMSO-d6) δ 11.75 (s, 1H), 8.30-8.23 (m, 2H), 7.78-7.69 (m, 2H), 7.52-7.44 (m, 3H), 7.34-7.27 (m, 1H), 7.21-7.12 (m, 1H), 5.25 (s, 2H), 2.45 (s, 3H).

Example 286: 6-(4-Fluorophenyl)-1-(2-pyridylmethyl)-3H-imidazo[4,5-b]pyridin-2-one and its Trifluoroacetic Acid Salt

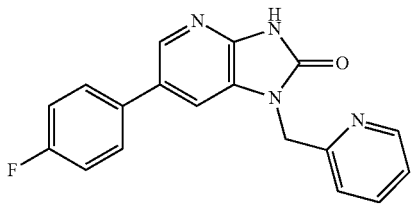 [SMILES: O=c1[nH]c2ncc(-c3ccc(F)cc3)cc2n1Cc1ccccn1]

The title compound was prepared in a manner analogous to Example 24, using 2-(chloromethyl)pyridine hydrochloride in Step A and (4-fluorophenyl)boronic acid in Step B. MS (ESI): mass calcd. for $C_{18}H_{13}FN_4O$, 320.1; m/z found, 321.0 [M+H]+. 1H NMR (500 MHz, DMSO-d6) δ 11.75 (s, 1H), 8.51 (ddd, J=5.0, 1.8, 1.0 Hz, 1H), 8.22 (d, J=2.0 Hz, 1H), 7.82 (td, J=7.7, 1.8 Hz, 1H), 7.70-7.63 (m, 3H), 7.36-7.24 (m, 4H), 5.22 (s, 2H).

Example 287: 6-[3-(Difluoromethyl)phenyl]-1-(2-pyridylmethyl)-3H-imidazo[4,5-b]pyridin-2-one and its Trifluoroacetic Acid Salt

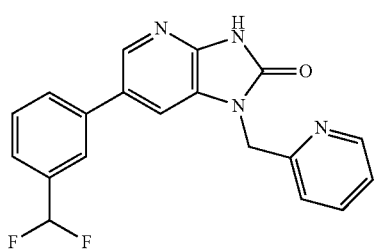 [SMILES: O=c1[nH]c2ncc(-c3cccc(C(F)F)c3)cc2n1Cc1ccccn1]

The title compound was prepared in a manner analogous to Example 24, using 2-(chloromethyl)pyridine hydrochloride in Step A and (3-(difluoromethyl)phenyl)boronic acid in Step B. MS (ESI): mass calcd. for $C_{19}H_{14}F_2N_4O$, 352.1; m/z found, 353.0 [M+H]$^+$. $^1$H NMR (500 MHz, DMSO-d$_6$) δ 11.80 (s, 1H), 8.52-8.49 (m, 1H), 8.28 (d, J=1.9 Hz, 1H), 7.84-7.78 (m, 3H), 7.77 (d, J=2.0 Hz, 1H), 7.64-7.52 (m, 2H), 7.35-7.28 (m, 2H), 7.07 (t, J=55.9 Hz, 1H), 5.24 (s, 2H).

Example 288: 6-(3-Methoxyphenyl)-1-(2-pyridylmethyl)-3H-imidazo[4,5-b]pyridin-2-one and its Trifluoroacetic Acid Salt

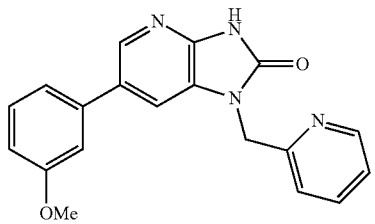 [SMILES: COc1cccc(-c2cnc3[nH]c(=O)n(Cc4ccccn4)c3c2)c1]

The title compound was prepared in a manner analogous to Example 24, using 2-(chloromethyl)pyridine hydrochloride in Step A and (3-methoxyphenyl)boronic acid in Step B. MS (ESI): mass calcd. for $C_{19}H_{16}N_4O_2$, 332.1; m/z found, 333.1 [M+H]$^+$. $^1$H NMR (500 MHz, DMSO-d$_6$) δ 11.75 (s, 1H), 8.51 (ddd, J=4.9, 1.9, 1.0 Hz, 1H), 8.25 (d, J=1.9 Hz, 1H), 7.83 (td, J=7.7, 1.8 Hz, 1H), 7.68 (d, J=2.0 Hz, 1H), 7.42-7.29 (m, 3H), 7.21-7.13 (m, 2H), 6.92 (ddd, J=8.2, 2.6, 0.9 Hz, 1H), 5.23 (s, 2H), 3.81 (s, 3H).

Example 289: 6-(p-Tolyl)-1-(2-pyridylmethyl)-3H-imidazo[4,5-b]pyridin-2-one and its Trifluoroacetic Acid Salt

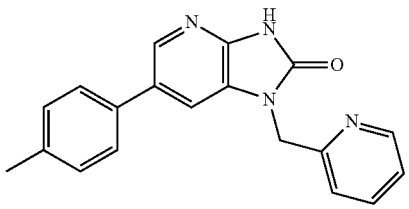 [SMILES: Cc1ccc(-c2cnc3[nH]c(=O)n(Cc4ccccn4)c3c2)cc1]

The title compound was prepared in a manner analogous to Example 24, using 2-(chloromethyl)pyridine hydrochloride in Step A and p-tolylboronic acid in Step B. MS (ESI): mass calcd. for $C_{19}H_{16}N_4O$, 316.1; m/z found, 317.1 [M+H]$^+$. $^1$H NMR (500 MHz, DMSO-d$_6$) δ 11.73 (s, 1H), 8.55-8.52 (m, 1H), 8.21 (d, J=1.9 Hz, 1H), 7.87 (td, J=7.7, 1.7 Hz, 1H), 7.66 (d, J=2.0 Hz, 1H), 7.54-7.48 (m, 2H), 7.42-7.34 (m, 2H), 7.28-7.23 (m, 2H), 5.24 (s, 2H), 2.33 (s, 3H).

Example 290: 6-(3-fluorophenyl)-1-(3-pyridylmethyl)-3H-imidazo[4,5-b]pyridin-2-one and its trifluoroacetic acid salt

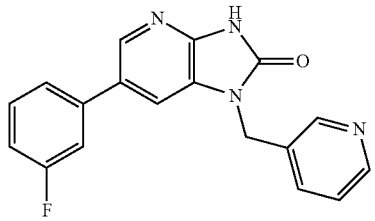

The title compound was prepared in a manner analogous to Example 24, using 3-(chloromethyl)pyridine hydrochloride in Step A and (3-fluorophenyl)boronic acid in Step B. MS (ESI): mass calcd. for $C_{18}H_{13}FN_4O$, 320.1; m/z found, 321.0 [M+H]$^+$. $^1$H NMR (500 MHz, DMSO-d$_6$) δ 11.86 (s, 1H), 8.82-8.73 (m, 1H), 8.65-8.57 (m, 1H), 8.31 (d, J=2.0 Hz, 1H), 8.04-7.99 (m, 1H), 7.93 (d, J=2.0 Hz, 1H), 7.61-7.47 (m, 4H), 7.22-7.16 (m, 1H), 5.20 (s, 2H).

Example 291: 6-[3-(Difluoromethyl)phenyl]-1-(3-pyridylmethyl)-3H-imidazo[4,5-b]pyridin-2-one and its Trifluoroacetic Acid Salt

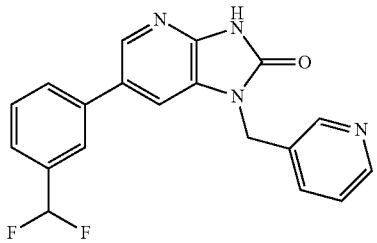 [SMILES: O=c1[nH]c2ncc(-c3cccc(C(F)F)c3)cc2n1Cc1cccnc1]

The title compound was prepared in a manner analogous to Example 24, using 3-(chloromethyl)pyridine hydrochloride in Step A and (3-(difluoromethyl)phenyl)boronic acid in Step B. MS (ESI): mass calcd. for $C_{19}H_{14}F_2N_4O$, 352.1; m/z found, 353.0 [M+H]$^+$. $^1$H NMR (500 MHz, DMSO-d$_6$) δ 11.86 (s, 1H), 8.77-8.73 (m, 1H), 8.61-8.58 (m, 1H), 8.29 (d, J=1.9 Hz, 1H), 8.01-7.96 (m, 1H), 7.93 (d, J=2.0 Hz, 1H), 7.87-7.82 (m, 2H), 7.65-7.53 (m, 3H), 7.08 (t, J=55.8 Hz, 1H), 5.21 (s, 2H).

Example 292: 6-(3,4-Difluorophenyl)-1-(3-pyridylmethyl)-3H-imidazo[4,5-b]pyridin-2-one and its Trifluoroacetic Acid Salt

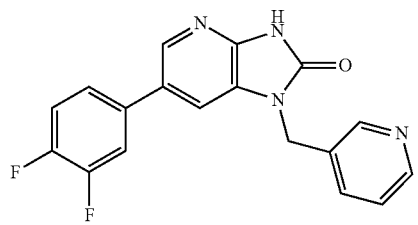 [SMILES: O=c1[nH]c2ncc(-c3ccc(F)c(F)c3)cc2n1Cc1cccnc1]

The title compound was prepared in a manner analogous to Example 24, using 3-(chloromethyl)pyridine hydrochloride in Step A and (3,4-difluorophenyl)boronic acid in Step B. MS (ESI): mass calcd. for $C_{18}H_{12}F_2N_4O$, 338.1; m/z found, 339.0 [M+H]$^+$. $^1$H NMR (500 MHz, DMSO-d$_6$) δ 11.86 (s, 1H), 8.78 (d, J=2.2 Hz, 1H), 8.62 (dd, J=5.2, 1.5 Hz, 1H), 8.29 (d, J=2.0 Hz, 1H), 8.06-8.00 (m, 1H), 7.92 (d, J=2.0 Hz, 1H), 7.84-7.76 (m, 1H), 7.60 (dd, J=8.0, 5.1 Hz, 1H), 7.57-7.49 (m, 2H), 5.19 (s, 2H).

Example 293: 6-(2,4-Difluoro-3-methyl-phenyl)-1-(3-pyridylmethyl)-3H-imidazo[4,5-b]pyridin-2-one and its Trifluoroacetic Acid Salt

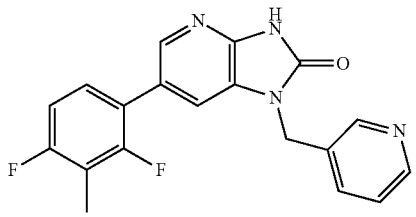 [SMILES: Cc1c(F)ccc(-c2cnc3[nH]c(=O)n(Cc4cccnc4)c3c2)c1F]

The title compound was prepared in a manner analogous to Example 24, using 3-(chloromethyl)pyridine hydrochloride in Step A and (2,4-difluoro-3-methylphenyl)boronic acid in Step B. MS (ESI): mass calcd. for $C_{19}H_{14}F_2N_4O$, 352.1; m/z found, 353.0 [M+H]$^+$. $^1$H NMR (500 MHz, DMSO-d$_6$) δ 11.88 (s, 1H), 8.75 (d, J=2.2 Hz, 1H), 8.61 (dd, J=5.2, 1.5 Hz, 1H), 8.06 (t, J=1.6 Hz, 1H), 8.03-7.98 (m, 1H), 7.70 (t, J=1.6 Hz, 1H), 7.59 (dd, J=7.9, 5.1 Hz, 1H), 7.42-7.35 (m, 1H), 7.21-7.14 (m, 1H), 5.18 (s, 2H), 2.21 (t, J=1.8 Hz, 3H).

Example 294: 6-(4-Fluoro-3-methyl-phenyl)-1-(3-pyridylmethyl)-3H-imidazo[4,5-b]pyridin-2-one and its Trifluoroacetic Acid Salt

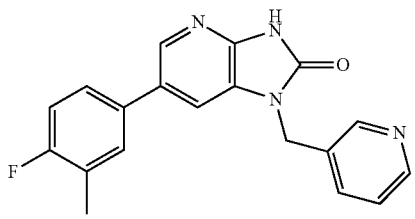 [SMILES: Cc1cc(-c2cnc3[nH]c(=O)n(Cc4cccnc4)c3c2)ccc1F]

The title compound was prepared in a manner analogous to Example 24, using 3-(chloromethyl)pyridine hydrochloride in Step A and (4-fluoro-3-methylphenyl)boronic acid in Step B. MS (ESI): mass calcd. for $C_{19}H_{15}FN_4O$, 334.1; m/z found, 335.0 [M+H]$^+$. $^1$H NMR (500 MHz, DMSO-d$_6$) δ 11.80 (s, 1H), 8.75 (d, J=2.2 Hz, 1H), 8.59 (dd, J=4.8, 1.6 Hz, 1H), 8.22 (d, J=1.9 Hz, 1H), 7.99-7.93 (m, 1H), 7.84 (d, J=2.0 Hz, 1H), 7.61-7.57 (m, 1H), 7.57-7.53 (m, 1H), 7.52-7.47 (m, 1H), 7.26-7.20 (m, 1H), 5.18 (s, 2H), 2.30 (d, J=1.9 Hz, 3H).

Example 295: 6-(4-Fluorophenyl)-1-(3-pyridylmethyl)-3H-imidazo[4,5-b]pyridin-2-one and its Trifluoroacetic Acid Salt

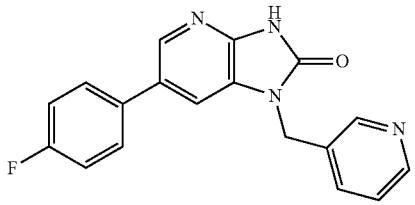 [SMILES: O=c1[nH]c2ncc(-c3ccc(F)cc3)cc2n1Cc1cccnc1]

The title compound was prepared in a manner analogous to Example 24, using 3-(chloromethyl)pyridine hydrochloride in Step A and (4-fluorophenyl)boronic acid in Step B. MS (ESI): mass calcd. for $C_{18}H_{13}FN_4O$, 320.1; m/z found, 321.0 [M+H]$^+$. $^1$H NMR (500 MHz, DMSO-d$_6$) δ 11.82 (s, 1H), 8.78 (d, J=2.2 Hz, 1H), 8.62 (dd, J=5.3, 1.6 Hz, 1H), 8.23 (d, J=2.0 Hz, 1H), 8.06-8.00 (m, 1H), 7.86 (d, J=2.0 Hz, 1H), 7.73-7.67 (m, 2H), 7.60 (dd, J=8.0, 5.1 Hz, 1H), 7.34-7.28 (m, 2H), 5.20 (s, 2H).

Example 296: 6-(3-Chlorophenyl)-1-(3-pyridylmethyl)-3H-imidazo[4,5-b]pyridin-2-one and its Trifluoroacetic Acid Salt

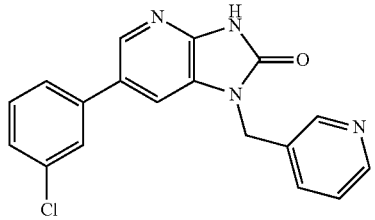 [SMILES: O=c1[nH]c2ncc(-c3cccc(Cl)c3)cc2n1Cc1cccnc1]

The title compound was prepared in a manner analogous to Example 24, using 3-(chloromethyl)pyridine hydrochloride in Step A and (3-chlorophenyl)boronic acid in Step B. MS (ESI): mass calcd. for $C_{18}H_{13}ClN_4O$, 336.1; m/z found, [M+H]$^+$. $^1$H NMR (500 MHz, DMSO-d$_6$) δ 11.87 (s, 1H), 8.77 (d, J=2.2 Hz, 1H), 8.61 (dd, J=5.0, 1.5 Hz, 1H), 8.30 (d, J=2.0 Hz, 1H), 8.04-7.99 (m, 1H), 7.94 (d, J=2.0 Hz, 1H), 7.76 (t, J=2.0 Hz, 1H), 7.68-7.64 (m, 1H), 7.59 (dd, J=8.0, 5.0 Hz, 1H), 7.49 (t, J=7.9 Hz, 1H), 7.45-7.41 (m, 1H), 5.20 (s, 2H).

Example 297: 6-(m-Tolyl)-1-(3-pyridylmethyl)-3H-imidazo[4,5-b]pyridin-2-one and its Trifluoroacetic Acid Salt

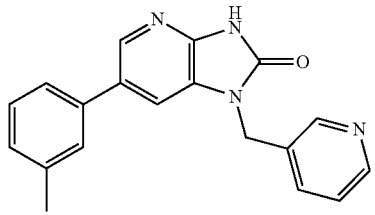 [SMILES: Cc1cccc(-c2cnc3[nH]c(=O)n(Cc4cccnc4)c3c2)c1]

The title compound was prepared in a manner analogous to Example 24, using 3-(chloromethyl)pyridine hydrochloride in Step A and m-tolylboronic acid in Step B. MS (ESI): mass calcd. for $C_{19}H_{16}N_4O$, 316.1; m/z found, 317.0 [M+H]$^+$. $^1$H NMR (500 MHz, DMSO-d$_6$) δ 11.79 (s, 1H), 8.77-8.75 (m, 1H), 8.60 (dd, J=5.1, 1.5 Hz, 1H), 8.23 (d, J=1.9 Hz, 1H), 8.03-7.98 (m, 1H), 7.84 (d, J=1.9 Hz, 1H), 7.58 (dd, J=8.0, 5.1 Hz, 1H), 7.50-7.47 (m, 1H), 7.46-7.42 (m, 1H), 7.35 (t, J=7.6 Hz, 1H), 7.20-7.16 (m, 1H), 5.20 (s, 2H), 2.37 (s, 3H).

Example 298: 6-(3,4-Difluorophenyl)-1-[(5-fluoro-3-pyridyl)methyl]-3H-imidazo[4,5-b]pyridin-2-one and its Trifluoroacetic Acid Salt

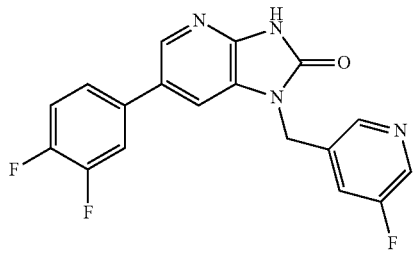 [SMILES: O=c1[nH]c2ncc(-c3ccc(F)c(F)c3)cc2n1Cc1cncc(F)c1]

The title compound was prepared in a manner analogous to Example 24, using 3-(chloromethyl)-5-fluoropyridine hydrochloride in Step A and (3,4-difluorophenyl)boronic acid in Step B. MS (ESI): mass calcd. for $C_{18}H_{11}F_3N_4O$, 356.1; m/z found, 357.1 [M+H]$^+$. $^1$H NMR (500 MHz, DMSO-d$_6$) δ 11.85 (s, 1H), 8.54 (t, J=1.7 Hz, 1H), 8.51 (d, J=2.8 Hz, 1H), 8.29 (d, J=2.0 Hz, 1H), 7.92 (d, J=2.0 Hz, 1H), 7.84-7.78 (m, 1H), 7.76-7.71 (m, 1H), 7.58-7.50 (m, 2H), 5.16 (s, 2H).

Example 299: 6-(4-Fluoro-3-methyl-phenyl)-1-[(5-fluoro-3-pyridyl)methyl]-3H-imidazo[4,5-b]pyridin-2-one and its Trifluoroacetic Acid Salt

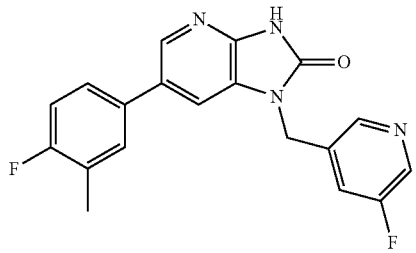 [SMILES: Cc1cc(-c2cnc3[nH]c(=O)n(Cc4cncc(F)c4)c3c2)ccc1F]

The title compound was prepared in a manner analogous to Example 24, using 3-(chloromethyl)-5-fluoropyridine hydrochloride in Step A (4-fluoro-3-methylphenyl)boronic acid in Step B. MS (ESI): mass calcd. for $C_{19}H_{14}F_2N_4O$, 352.1; m/z found, 353.1 [M+H]$^+$. $^1$H NMR (500 MHz, DMSO-d$_6$) δ 11.79 (s, 1H), 8.53 (t, J=1.7 Hz, 1H), 8.51 (d, J=2.8 Hz, 1H), 8.22 (d, J=1.9 Hz, 1H), 7.85 (d, J=2.0 Hz, 1H), 7.72 (ddd, J=9.7, 2.8, 1.7 Hz, 1H), 7.61-7.58 (m, 1H), 7.52-7.48 (m, 1H), 7.23 (dd, J=9.7, 8.5 Hz, 1H), 5.17 (s, 2H), 2.30 (d, J=1.9 Hz, 3H).

Example 300: 6-[3-(Difluoromethoxy)phenyl]-1-(3-pyridylmethyl)-3H-imidazo[4,5-b]pyridin-2-one and its Trifluoroacetic Acid Salt

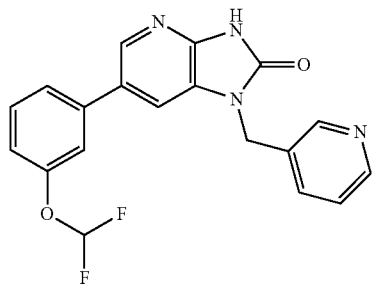 [SMILES: O=c1[nH]c2ncc(-c3cccc(OC(F)F)c3)cc2n1Cc1cccnc1]

The title compound was prepared in a manner analogous to Example 24, using 3-(chloromethyl)pyridine hydrochloride in Step A and (3-(difluoromethoxy)phenyl)boronic acid in Step B. MS (ESI): mass calcd. for $C_{19}H_{14}F_2N_4O_2$, 368.1; m/z found, 369.1 [M+H]$^+$. $^1$H NMR (500 MHz, DMSO-d$_6$) δ 11.86 (s, 1H), 8.76 (d, J=2.3 Hz, 1H), 8.60 (dd, J=5.1, 1.6 Hz, 1H), 8.30 (d, J=1.9 Hz, 1H), 8.02-7.98 (m, 1H), 7.91 (d, J=2.0 Hz, 1H), 7.60-7.15 (m, 6H), 5.20 (s, 2H).

Example 301: 6-(2,4-Difluoro-3-methyl-phenyl)-1-[(5-fluoro-3-pyridyl)methyl]-3H-imidazo[4,5-b]pyridin-2-one and its Trifluoroacetic Acid Salt

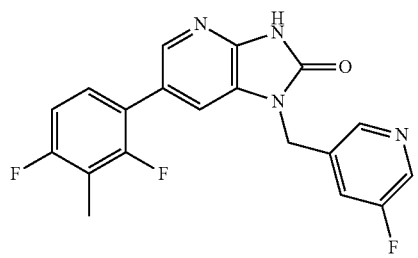 [SMILES: Cc1c(F)ccc(-c2cnc3[nH]c(=O)n(Cc4cncc(F)c4)c3c2)c1F]

The title compound was prepared in a manner analogous to Example 24, using 3-(chloromethyl)-5-fluoropyridine hydrochloride in Step A and (2,4-difluoro-3-methylphenyl)boronic acid in Step B. MS (ESI): mass calcd. for $C_{19}H_{13}F_3N_4O$, 370.1; m/z found, 371.1 [M+H]$^+$. $^1$H NMR (500 MHz, DMSO-d$_6$) δ 11.86 (s, 1H), 8.53-8.50 (m, 2H), 8.05 (t, J=1.6 Hz, 1H), 7.74-7.70 (m, 2H), 7.42-7.36 (m, 1H), 7.20-7.15 (m, 1H), 5.15 (s, 2H), 2.21 (t, J=1.9 Hz, 3H).

Example 302: 6-[3-(Difluoromethyl)phenyl]-1-[(5-fluoro-3-pyridyl)methyl]-3H-imidazo[4,5-b]pyridin-2-one and its Trifluoroacetic Acid Salt

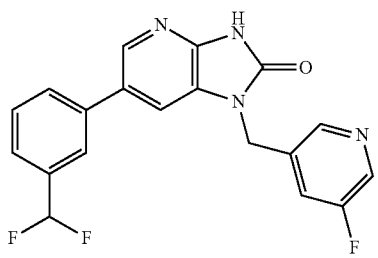 [SMILES: O=c1[nH]c2ncc(-c3cccc(C(F)F)c3)cc2n1Cc1cncc(F)c1]

The title compound was prepared in a manner analogous to Example 24 using 3-(chloromethyl)-5-fluoropyridine hydrochloride in Step A and (3-(difluoromethyl)phenyl)boronic acid in Step B. MS (ESI): mass calcd. for $C_{19}H_{13}F_3N_4O$, 370.1; m/z found, 371.1 [M+H]$^+$. $^1$H NMR (500 MHz, DMSO-$d_6$) δ 11.85 (s, 1H), 8.53 (t, J=1.7 Hz, 1H), 8.51 (d, J=2.7 Hz, 1H), 8.29 (d, J=1.9 Hz, 1H), 7.94 (d, J=2.0 Hz, 1H), 7.87-7.83 (m, 2H), 7.73 (ddd, J=9.7, 2.8, 1.7 Hz, 1H), 7.65-7.55 (m, 2H), 7.08 (t, J=55.8 Hz, 1H), 5.20 (s, 2H).

Example 303: 6-(2,3-Difluorophenyl)-1-[(5-fluoro-3-pyridyl)methyl]-3H-imidazo[4,5-b]pyridin-2-one and its Trifluoroacetic Acid Salt

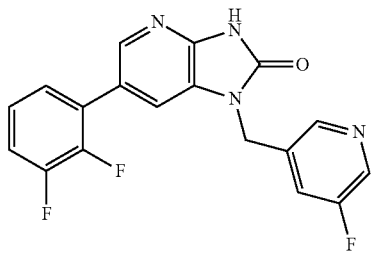 [SMILES: O=c1[nH]c2ncc(-c3cccc(F)c3F)cc2n1Cc1cncc(F)c1]

The title compound was prepared in a manner analogous to Example 24, using 3-(chloromethyl)-5-fluoropyridine hydrochloride in Step A and (2,3-difluorophenyl)boronic acid in Step B. MS (ESI): mass calcd. for $C_{18}H_{11}F_3N_4O$, 356.1; m/z found, 357.1 [M+H]$^+$. $^1$H NMR (500 MHz, DMSO-$d_6$) δ 11.92 (s, 1H), 8.54-8.49 (m, 2H), 8.13 (t, J=1.6 Hz, 1H), 7.79 (t, J=1.6 Hz, 1H), 7.75-7.71 (m, 1H), 7.49-7.42 (m, 1H), 7.39-7.28 (m, 2H), 5.16 (s, 2H).

Example 304: 6-[3-(Difluoromethoxy)phenyl]-1-[(5-fluoro-3-pyridyl)methyl]-3H-imidazo[4,5-b]pyridin-2-one and its Trifluoroacetic Acid Salt

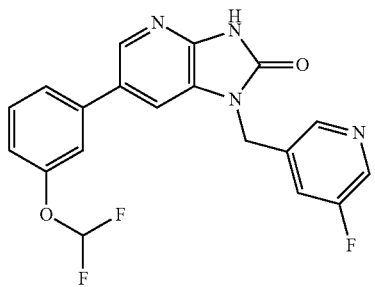 [SMILES: O=c1[nH]c2ncc(-c3cccc(OC(F)F)c3)cc2n1Cc1cncc(F)c1]

The title compound was prepared in a manner analogous to Example 24, using 3-(chloromethyl)-5-fluoropyridine hydrochloride in Step A and (3-(difluoromethoxy)phenyl) boronic acid in Step B. MS (ESI): mass calcd. for $C_{19}H_{13}F_3N_4O_2$, 386.1; m/z found, 387.1 [M+H]$^+$. $^1$H NMR (500 MHz, DMSO-$d_6$) δ 11.85 (s, 1H), 8.53 (t, J=1.8 Hz, 1H), 8.51 (d, J=2.8 Hz, 1H), 8.30 (d, J=1.9 Hz, 1H), 7.92 (d, J=2.0 Hz, 1H), 7.73 (ddd, J=9.7, 2.8, 1.7 Hz, 1H), 7.58-7.15 (m, 5H), 5.18 (s, 2H).

Example 305: 6-(3-Chlorophenyl)-1-[(5-fluoro-3-pyridyl)methyl]-3H-imidazo[4,5-b]pyridin-2-one and its Trifluoroacetic Acid Salt

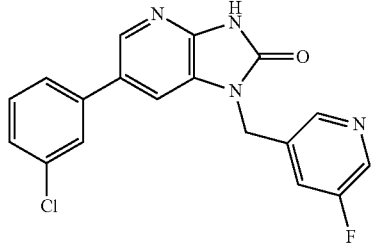 [SMILES: O=c1[nH]c2ncc(-c3cccc(Cl)c3)cc2n1Cc1cncc(F)c1]

The title compound was prepared in a manner analogous to Example 24, using 3-(chloromethyl)-5-fluoropyridine hydrochloride in Step A and (3-chlorophenyl)boronic acid in Step B. MS (ESI): mass calcd. for $C_{18}H_{12}ClFN_4O$, 354.1; m/z found, 355.1 [M+H]$^+$. $^1$H NMR (500 MHz, DMSO-$d_6$) δ 11.86 (s, 1H), 8.54 (t, J=1.7 Hz, 1H), 8.52 (d, J=2.7 Hz, 1H), 8.30 (d, J=2.0 Hz, 1H), 7.95 (d, J=2.0 Hz, 1H), 7.77-7.71 (m, 2H), 7.68-7.64 (m, 1H), 7.50 (t, J=7.9 Hz, 1H), 7.45-7.41 (m, 1H), 5.18 (s, 2H).

Example 306: 6-(4-Chloro-3-methyl-phenyl)-1-[(5-fluoro-3-pyridyl)methyl]-3H-imidazo[4,5-b]pyridin-2-one and its Trifluoroacetic Acid Salt

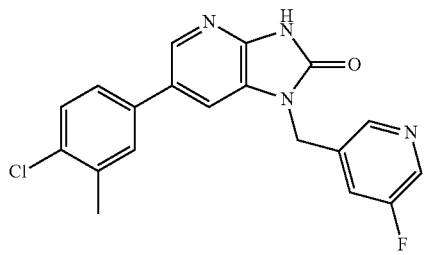 [SMILES: Cc1cc(-c2cnc3[nH]c(=O)n(Cc4cncc(F)c4)c3c2)ccc1Cl]

The title compound was prepared in a manner analogous to Example 24, using 3-(chloromethyl)-5-fluoropyridine hydrochloride in Step A and (4-chloro-3-methylphenyl)boronic acid in Step B. MS (ESI): mass calcd. for $C_{19}H_{14}ClFN_4O$, 368.1; m/z found, 369.1 [M+H]$^+$. $^1$H NMR (500 MHz, DMSO-$d_6$) δ 11.82 (s, 1H), 8.53 (t, J=1.8 Hz, 1H), 8.51 (d, J=2.8 Hz, 1H), 8.26 (d, J=1.9 Hz, 1H), 7.89 (d, J=2.0 Hz, 1H), 7.73 (ddd, J=9.6, 2.7, 1.7 Hz, 1H), 7.70-7.68 (m, 1H), 7.54-7.48 (m, 2H), 5.18 (s, 2H), 2.40 (s, 3H).

Example 307: 1-[(5-Fluoro-3-pyridyl)methyl]-6-[3-(trifluoromethoxy)phenyl]-3H-imidazo[4,5-b]pyridin-2-one and its Trifluoroacetic Acid Salt

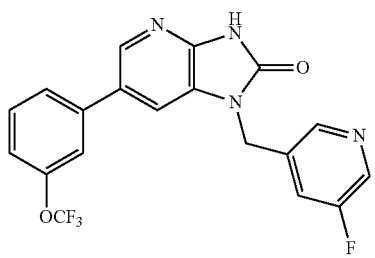 [SMILES: O=c1[nH]c2ncc(-c3cccc(OC(F)(F)F)c3)cc2n1Cc1cncc(F)c1]

The title compound was prepared in a manner analogous to Example 24, using 3-(chloromethyl)-5-fluoropyridine hydrochloride in Step A and (3-(trifluoromethoxy)phenyl)boronic acid in Step B. MS (ESI): mass calcd. for C₁₉H₁₂F₄N₄O₂, 404.1; m/z found, 405.1 [M+H]⁺. ¹H NMR (500 MHz, DMSO-d₆) δ 11.88 (s, 1H), 8.54 (t, J=1.7 Hz, 1H), 8.52 (d, J=2.8 Hz, 1H), 8.32 (d, J=2.0 Hz, 1H), 7.96 (d, J=2.0 Hz, 1H), 7.76-7.72 (m, 2H), 7.70-7.67 (m, 1H), 7.61 (t, J=8.0 Hz, 1H), 7.39-7.35 (m, 1H), 5.19 (s, 2H).

Example 308: 1-[(5-Methyl-3-pyridyl)methyl]-6-(3,4,5-trifluorophenyl)-3H-imidazo[4,5-b]pyridin-2-one and its Trifluoroacetic Acid Salt

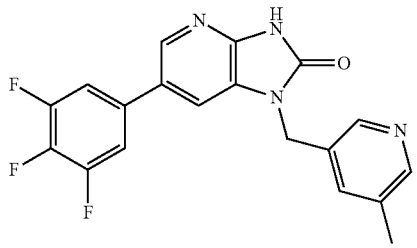 [SMILES: Cc1cncc(Cn2c(=O)[nH]c3ncc(-c4cc(F)c(F)c(F)c4)cc32)c1]

The title compound was prepared in a manner analogous to Example 24, using 3-(chloromethyl)-5-methylpyridine hydrochloride in Step A and (3,4,5-trifluorophenyl)boronic acid in Step B. MS (ESI): mass calcd. for C₁₉H₁₃F₃N₄O, 370.1; m/z found, 371.1 [M+H]⁺. ¹H NMR (500 MHz, DMSO-d₆) δ 11.90 (s, 1H), 8.64-8.62 (m, 1H), 8.53-8.50 (m, 1H), 8.35 (d, J=2.0 Hz, 1H), 7.95-7.91 (m, 2H), 7.77-7.69 (m, 2H), 5.15 (s, 2H), 2.35 (s, 3H).

Example 309: 6-[4-Fluoro-3-(trifluoromethyl)phenyl]-1-[(5-methyl-3-pyridyl)methyl]-3H-imidazo[4,5-b]pyridin-2-one and its Trifluoroacetic Acid Salt

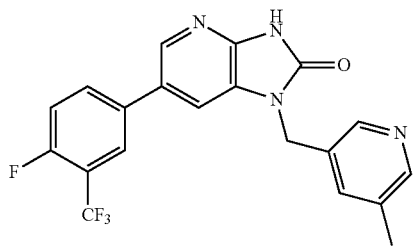 [SMILES: Cc1cncc(Cn2c(=O)[nH]c3ncc(-c4ccc(F)c(C(F)(F)F)c4)cc32)c1]

The title compound was prepared in a manner analogous to Example 24, using 3-(chloromethyl)-5-methylpyridine hydrochloride in Step A and (4-fluoro-3-(trifluoromethyl)phenyl)boronic acid in Step B. MS (ESI): mass calcd. for C₂₀H₁₄F₄N₄O, 402.1; m/z found, 403.1 [M+H]⁺. ¹H NMR (500 MHz, DMSO-d₆) δ 11.88 (s, 1H), 8.61-8.59 (m, 1H), 8.50-8.48 (m, 1H), 8.32 (d, J=2.0 Hz, 1H), 8.08-8.02 (m, 1H), 8.02-7.98 (m, 1H), 7.95 (d, J=2.0 Hz, 1H), 7.90-7.88 (m, 1H), 7.64 (dd, J=10.4, 8.9 Hz, 1H), 5.17 (s, 2H), 2.34 (s, 3H).

Example 310: 6-(2,3-Difluorophenyl)-1-[(5-methyl-3-pyridyl)methyl]-3H-imidazo[4,5-b]pyridin-2-one and its Trifluoroacetic Acid Salt

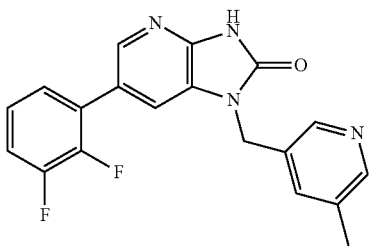 [SMILES: Cc1cncc(Cn2c(=O)[nH]c3ncc(-c4cccc(F)c4F)cc32)c1]

The title compound was prepared in a manner analogous to Example 24, using 3-(chloromethyl)-5-methylpyridine hydrochloride in Step A and (2,3-difluorophenyl)boronic acid in Step B. MS (ESI): mass calcd. for C₁₉H₁₄F₂N₄O, 352.1; m/z found, 353.1 [M+H]⁺. ¹H NMR (500 MHz, DMSO-d₆) δ 11.94 (s, 1H), 8.71-8.68 (m, 1H), 8.62-8.59 (m, 1H), 8.14 (t, J=1.7 Hz, 1H), 8.13-8.10 (m, 1H), 7.77 (t, J=1.6 Hz, 1H), 7.50-7.42 (m, 1H), 7.39-7.28 (m, 2H), 5.20 (s, 2H), 2.39 (s, 3H).

Example 311: 6-(3,5-Difluorophenyl)-1-[(5-methyl-3-pyridyl)methyl]-3H-imidazo[4,5-b]pyridin-2-one and its Trifluoroacetic Acid Salt

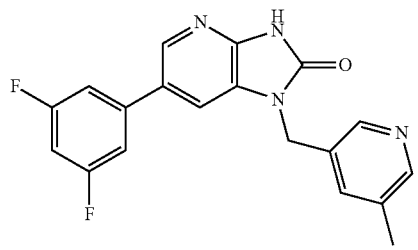 [SMILES: Cc1cncc(Cn2c(=O)[nH]c3ncc(-c4cc(F)cc(F)c4)cc32)c1]

The title compound was prepared in a manner analogous to Example 24, using 3-(chloromethyl)-5-methylpyridine hydrochloride in Step A and (3,5-difluorophenyl)boronic acid in Step B. MS (ESI): mass calcd. for C₁₉H₁₄F₂N₄O, 352.1; m/z found, 353.2 [M+H]⁺. ¹H NMR (500 MHz, DMSO-d₆) δ 11.91 (s, 1H), 8.64 (s, 1H), 8.52 (s, 1H), 8.38 (d, J=2.0 Hz, 1H), 7.98-7.91 (m, 2H), 7.54-7.45 (m, 2H), 7.23 (tt, J=9.3, 2.4 Hz, 1H), 5.17 (s, 2H), 2.35 (s, 3H).

Example 312: 1-[(4-Methyl-3-pyridyl)methyl]-6-(3,4,5-trifluorophenyl)-3H-imidazo[4,5-b]pyridin-2-one and its Trifluoroacetic Acid Salt

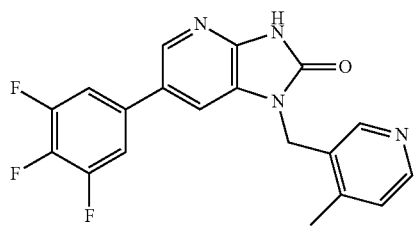 [SMILES: Cc1ccncc1Cn1c(=O)[nH]c2ncc(-c3cc(F)c(F)c(F)c3)cc21]

The title compound was prepared in a manner analogous to Example 24, using 3-(chloromethyl)-4-methylpyridine hydrochloride in Step A and (3,4,5-trifluorophenyl)boronic acid in Step B. MS (ESI): mass calcd. for $C_{19}H_{13}F_3N_4O$, 370.1; m/z found, 371.1 [M+H]$^+$. $^1$H NMR (500 MHz, DMSO-d$_6$) δ 11.95 (s, 1H), 8.59-8.55 (m, 1H), 8.44-8.40 (m, 1H), 8.37 (d, J=2.0 Hz, 1H), 7.82 (d, J=2.1 Hz, 1H), 7.74-7.64 (m, 3H), 5.20 (s, 2H), 2.56 (s, 3H).

Example 313: 1-[(4-Methyl-3-pyridyl)methyl]-6-[3-(trifluoromethyl)phenyl]-3H-imidazo[4,5-b]pyridin-2-one and its Trifluoroacetic Acid Salt

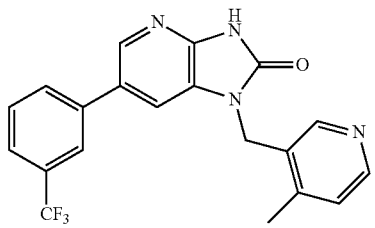

The title compound was prepared in a manner analogous to Example 24, using 3-(chloromethyl)-4-methylpyridine hydrochloride in Step A. MS (ESI): mass calcd. for $C_{20}H_{15}F_3N_4O$, 384.1; m/z found, 385.2 [M+H]$^+$. $^1$H NMR (500 MHz, DMSO-d$_6$) δ 11.95 (s, 1H), 8.65 (d, J=5.6 Hz, 1H), 8.51 (s, 1H), 8.37 (d, J=2.0 Hz, 1H), 7.99-7.95 (m, 2H), 7.88 (d, J=2.0 Hz, 1H), 7.81 (d, J=5.6 Hz, 1H), 7.76-7.67 (m, 2H), 5.28 (s, 2H), 2.62 (s, 3H).

Example 314: 6-[4-Fluoro-3-(trifluoromethyl)phenyl]-1-[(4-methyl-3-pyridyl)methyl]-3H-imidazo[4,5-b]pyridin-2-one and its Trifluoroacetic Acid Salt

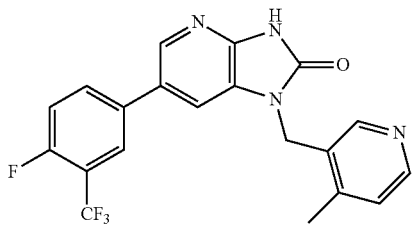

The title compound was prepared in a manner analogous to Example 24, using 3-(chloromethyl)-4-methylpyridine hydrochloride in Step A and (4-fluoro-3-(trifluoromethyl)phenyl)boronic acid in Step B. MS (ESI): mass calcd. for $C_{20}H_{14}F_4N_4O$, 402.1; m/z found, 403.1 [M+H]$^+$. $^1$H NMR (500 MHz, DMSO-d$_6$) δ 11.93 (s, 1H), 8.56 (d, J=5.3 Hz, 1H), 8.41 (s, 1H), 8.34 (d, J=1.9 Hz, 1H), 8.04-7.99 (m, 1H), 7.99-7.95 (m, 1H), 7.84 (d, J=2.0 Hz, 1H), 7.66-7.59 (m, 2H), 5.23 (s, 2H), 2.55 (s, 3H).

Example 315: 1-[(3-Methyl-2-pyridyl)methyl]-6-[3-(trifluoromethyl)phenyl]-3H-imidazo[4,5-b]pyridin-2-one and its Trifluoroacetic Acid Salt

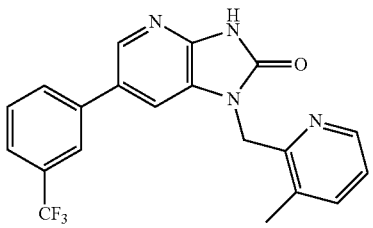

The title compound was prepared in a manner analogous to Example 24, using (3-methylpyridin-2-yl)methyl methanesulfonate (prepared analogous to Example 23, Step A) in Step A. MS (ESI): mass calcd. for $C_{20}H_{15}F_3N_4O$, 384.1; m/z found, 385.1 [M+H]$^+$. $^1$H NMR (500 MHz, DMSO-d$_6$) δ 11.76 (s, 1H), 8.31 (d, J=2.0 Hz, 1H), 8.25-8.21 (m, 1H), 7.96-7.90 (m, 2H), 7.76 (d, J=2.0 Hz, 1H), 7.73-7.65 (m, 3H), 7.27-7.22 (m, 1H), 5.25 (s, 2H), 2.44 (s, 3H).

Example 316: 6-(4-Fluoro-3-methyl-phenyl)-1-[(3-methyl-2-pyridyl)methyl]-3H-imidazo[4,5-b]pyridin-2-one and its Trifluoroacetic Acid Salt

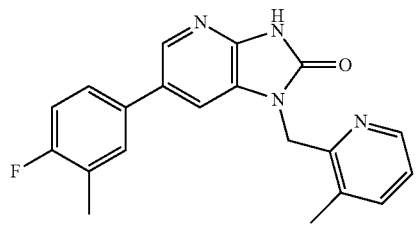

The title compound was prepared in a manner analogous to Example 24, using (3-methylpyridin-2-yl)methyl methanesulfonate (prepared analogous to Example 23, Step A) in Step A and (4-fluoro-3-methylphenyl)boronic acid in Step B. MS (ESI): mass calcd. for $C_{20}H_{17}FN_4O$, 348.1; m/z found, 349.1 [M+H]$^+$. $^1$H NMR (500 MHz, DMSO-d$_6$) δ 11.70 (s, 1H), 8.29-8.26 (m, 1H), 8.19 (d, J=2.0 Hz, 1H), 7.79-7.73 (m, 1H), 7.63 (d, J=2.0 Hz, 1H), 7.56-7.50 (m, 1H), 7.46-7.41 (m, 1H), 7.34-7.29 (m, 1H), 7.23-7.18 (m, 1H), 5.25 (s, 2H), 2.44 (s, 3H), 2.28 (d, J=1.9 Hz, 3H).

Example 317: 6-(2,4-Difluoro-3-methyl-phenyl)-1-[(3-methyl-2-pyridyl)methyl]-3H-imidazo[4,5-b]pyridin-2-one and its Trifluoroacetic Acid Salt

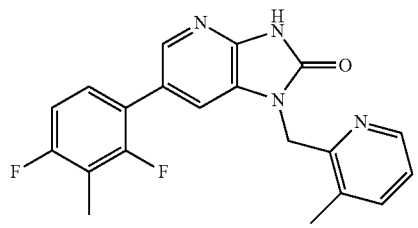

The title compound was prepared in a manner analogous to Example 24, using (3-methylpyridin-2-yl)methyl methanesulfonate (prepared analogous to Example 23, Step A) in Step A and (2,4-difluoro-3-methylphenyl)boronic acid in Step B. MS (ESI): mass calcd. for $C_{20}H_{16}F_2N_4O$, 366.1; m/z found, 367.1 [M+H]$^+$. $^1$H NMR (500 MHz, DMSO-d$_6$) δ 11.74 (s, 1H), 8.28-8.23 (m, 1H), 8.03 (t, J=1.7 Hz, 1H), 7.72-7.67 (m, 1H), 7.48 (t, J=1.7 Hz, 1H), 7.38-7.31 (m, 1H), 7.29-7.24 (m, 1H), 7.17-7.11 (m, 1H), 5.21 (s, 2H), 2.41 (s, 3H), 2.19 (t, J=1.9 Hz, 3H).

Example 318: 6-(3,5-Difluorophenyl)-1-[(3-methyl-2-pyridyl)methyl]-3H-imidazo[4,5-b]pyridin-2-one and its Trifluoroacetic Acid Salt

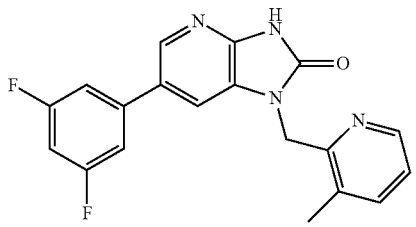 [SMILES: Cc1cccnc1Cn1c(=O)[nH]c2ncc(-c3cc(F)cc(F)c3)cc21]

The title compound was prepared in a manner analogous to Example 24, using (3-methylpyridin-2-yl)methyl methanesulfonate (prepared analogous to Example 23, Step A) in Step A and (3,5-difluorophenyl)boronic acid in Step B. MS (ESI): mass calcd. for $C_{19}H_{14}F_2N_4O$, 352.1; m/z found, 353.2 [M+H]$^+$. $^1$H NMR (500 MHz, DMSO-d$_6$) δ 11.78 (s, 1H), 8.34 (d, J=2.0 Hz, 1H), 8.23-8.20 (m, 1H), 7.76 (d, J=2.0 Hz, 1H), 7.71-7.66 (m, 1H), 7.45-7.38 (m, 2H), 7.27-7.16 (m, 2H), 5.22 (s, 2H), 2.44 (s, 3H).

Example 319: 6-(2,3-Difluorophenyl)-1-[(3-methyl-2-pyridyl)methyl]-3H-imidazo[4,5-b]pyridin-2-one and its Trifluoroacetic Acid Salt

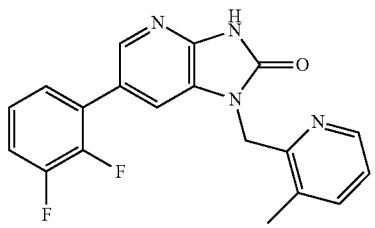 [SMILES: Cc1cccnc1Cn1c(=O)[nH]c2ncc(-c3cccc(F)c3F)cc21]

The title compound was prepared in a manner analogous to Example 24, using (3-methylpyridin-2-yl)methyl methanesulfonate (prepared analogous to Example 23, Step A) in Step A and (2,3-difluorophenyl)boronic acid in Step B. MS (ESI): mass calcd. for $C_{19}H_{14}F_2N_4O$, 352.1; m/z found, 353.1 [M+H]$^+$. $^1$H NMR (500 MHz, DMSO-d$_6$) δ 11.84 (s, 1H), 8.30-8.28 (m, 1H), 8.12 (t, J=1.7 Hz, 1H), 7.79-7.74 (m, 1H), 7.58 (t, J=1.6 Hz, 1H), 7.47-7.39 (m, 1H), 7.36-7.25 (m, 3H), 5.24 (s, 2H), 2.43 (s, 3H).

Example 320: 1-[2-(Azetidin-1-yl)-2-oxo-ethyl]-6-(4-fluoro-2-methyl-phenyl)-3H-imidazo[4,5-b]pyridin-2-one and its Trifluoroacetic Acid Salt

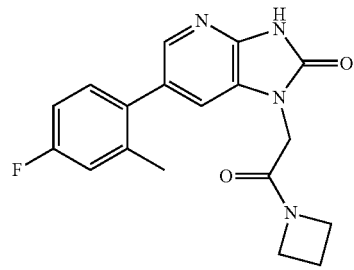 [SMILES: Cc1cc(F)ccc1-c1cnc2[nH]c(=O)n(CC(=O)N3CCC3)c2c1]

The title compound was prepared in a manner analogous to Example 25, using 1-(2-(azetidin-1-yl)-2-oxoethyl)-6-bromo-3-trityl-1,3-dihydro-2H-imidazo[4,5-b]pyridin-2-one (Intermediate 38) and (4-fluoro-2-methylphenyl)boronic acid in Step A. MS (ESI): mass calcd. for $C_{18}H_{17}FN_4O_2$, 340.1; m/z found, 341.1 [M+H]$^+$. $^1$H NMR (400 MHz, DMSO-d$_6$) δ 11.68 (s, 1H), 7.85 (d, J=1.9 Hz, 1H), 7.40 (d, J=1.9 Hz, 1H), 7.26-7.16 (m, 2H), 7.14-7.07 (m, 1H), 4.50 (s, 2H), 4.25 (t, J=7.6 Hz, 2H), 3.88 (t, J=7.7 Hz, 2H), 2.31-2.19 (m, 5H).

Example 321: 2-[6-(5-Chloro-4-methyl-2-thienyl)-2-oxo-3H-imidazo[4,5-b]pyridin-1-yl]-N,N-dimethylacetamide

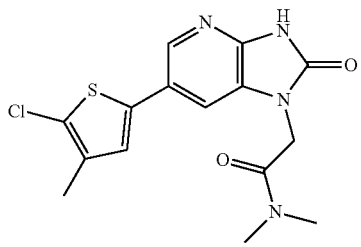 [SMILES: Cc1cc(-c2cnc3[nH]c(=O)n(CC(=O)N(C)C)c3c2)sc1Cl]

The title compound was made in a manner analogous to Example 26, using 2-(5-chloro-4-methylthiophen-2-yl)-4,4,5,5-tetramethyl-1,3,2-dioxaborolane in Step A. MS (ESI): mass calcd. for $C_{15}H_{15}ClN_4O_2S$, 350.1; m/z found, 351.0 [M+H]$^+$. $^1$H NMR (500 MHz, DMSO) δ 11.74-11.71 (s, 1H), 8.15-8.13 (d, J=2.0 Hz, 1H), 7.65-7.63 (d, J=2.0 Hz, 1H), 7.29-7.28 (s, 1H), 4.77-4.74 (s, 2H), 3.11-3.08 (s, 3H), 2.87-2.83 (s, 3H), 2.19-2.16 (s, 3H).

Example 322: 2-[6-(5-Chloro-4-methyl-2-thienyl)-3-methyl-2-oxo-imidazo[4,5-b]pyridin-1-yl]-N,N-dimethyl-acetamide

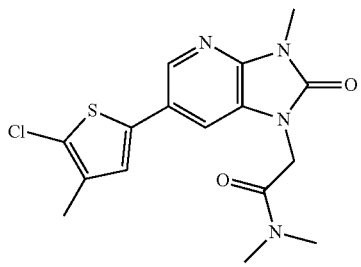 [SMILES: Cc1cc(-c2cnc3c(c2)n(CC(=O)N(C)C)c(=O)n3C)sc1Cl]

The title compound was prepared in a manner analogous to Example 14, Step B, using 2-[6-(5-chloro-4-methyl-2-thienyl)-2-oxo-3H-imidazo[4,5-b]pyridin-1-yl]-N,N-dimethyl-acetamide (Example 321). MS (ESI): mass calcd. for $C_{16}H_{17}ClN_4O_2S$, 364.1; m/z found, 365.0 [M+H]+. 1H NMR (500 MHz, CDCl3) δ 8.13-8.12 (d, J=1.9 Hz, 1H), 7.19-7.18 (d, J=1.9 Hz, 1H), 6.86-6.85 (s, 1H), 4.64-4.63 (s, 2H), 3.45-3.44 (s, 3H), 3.11-3.09 (s, 3H), 2.93-2.92 (s, 3H), 2.14-2.13 (s, 3H).

Example 323: 1-[2-(Azetidin-1-yl)-2-oxo-ethyl]-6-[5-(trifluoromethyl)-2-thienyl]-3H-imidazo[4,5-b]pyridin-2-one

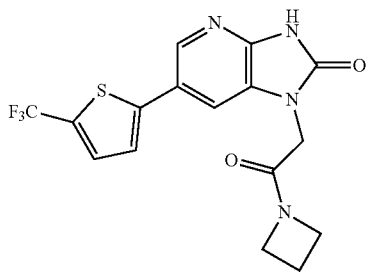 [SMILES: O=C(Cn1c(=O)[nH]c2ncc(-c3ccc(C(F)(F)F)s3)cc21)N1CCC1]

The title compound was made in a manner analogous to Example 26, using azetidine in Step B. MS (ESI): mass calcd. for $C_{16}H_{13}F_3N_4O_2S$, 382.1; m/z found, 383.0 [M+H]+. 1H NMR (500 MHz, DMSO) δ 11.88-11.82 (s, 1H), 8.35-8.33 (d, J=2.0 Hz, 1H), 7.79-7.78 (d, J=2.0 Hz, 1H), 7.77-7.75 (m, 1H), 7.59-7.56 (m, 1H), 4.57-4.49 (s, 2H), 4.31-4.24 (t, J=7.7 Hz, 2H), 3.95-3.86 (m, 2H), 2.32-2.25 (m, 2H).

Example 324: 1-[2-(Azetidin-1-yl)-2-oxo-ethyl]-6-(5-chloro-4-methyl-2-thienyl)-3H-imidazo[4,5-b]pyridin-2-one

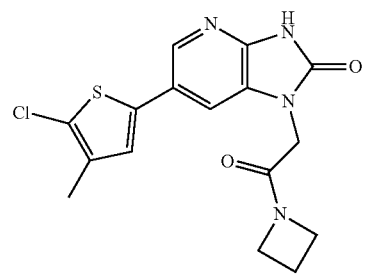 [SMILES: Cc1cc(-c2cnc3[nH]c(=O)n(CC(=O)N4CCC4)c3c2)sc1Cl]

The title compound was made in a manner analogous to Example 26, using 2-(5-chloro-4-methylthiophen-2-yl)-4,4,5,5-tetramethyl-1,3,2-dioxaborolane in Step A and azetidine in Step B. MS (ESI): mass calcd. for $C_{16}H_{15}ClN_4O_2S$, 362.1; m/z found, 363.0 [M+H]+. 1H NMR (400 MHz, DMSO) δ 11.74-11.71 (s, 1H), 8.18-8.12 (m, 1H), 7.65-7.62 (m, 1H), 7.33-7.28 (s, 1H), 4.53-4.49 (s, 2H), 4.32-4.22 (m, 2H), 3.97-3.86 (m, 2H), 2.34-2.25 (m, 2H), 2.22-2.15 (d, J=1.7 Hz, 3H).

Example 325: 1-[2-(Azetidin-1-yl)-2-oxo-ethyl]-6-(5-chloro-4-methyl-2-thienyl)-3-methyl-imidazo[4,5-b]pyridin-2-one

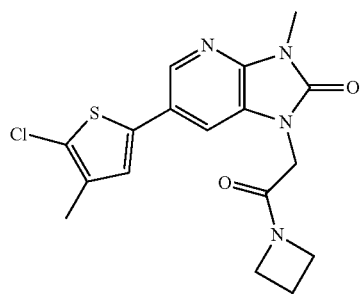 [SMILES: Cc1cc(-c2cnc3c(c2)n(CC(=O)N2CCC2)c(=O)n3C)sc1Cl]

The title compound was prepared in a manner analogous to Example 14, Step B, using 1-[2-(azetidin-1-yl)-2-oxo-ethyl]-6-(5-chloro-4-methyl-2-thienyl)-3H-imidazo[4,5-b]pyridin-2-one (Example 324). MS (ESI): mass calcd. for $C_{17}H_{17}ClN_4O_2S$, 376.1; m/z found, 377.0 [M+H]+. 1H NMR (600 MHz, DMSO) δ 9.70-9.68 (m, 1H), 9.19-9.16 (m, 1H), 8.79-8.76 (s, 1H), 6.05-6.02 (s, 2H), 5.77-5.72 (t, J=7.8 Hz, 2H), 5.39-5.34 (t, J=7.9 Hz, 2H), 4.82-4.81 (s, 3H), 3.79-3.71 (m, 2H), 3.66-3.63 (s, 3H).

Example 326: 1-[2-(Azetidin-1-yl)-2-oxo-ethyl]-3-methyl-6-(5-methyl-2-thienyl)imidazo[4,5-b]pyridin-2-one

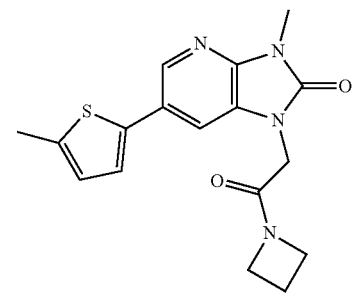 [SMILES: Cc1ccc(-c2cnc3c(c2)n(CC(=O)N2CCC2)c(=O)n3C)s1]

The title compound was made in a manner analogous to Example 28, using 1-(2-(azetidin-1-yl)-2-oxoethyl)-6-bromo-3-trityl-1,3-dihydro-2H-imidazo[4,5-b]pyridin-2-one (Intermediate 38) and 4,4,5,5-tetramethyl-2-(5-methylthiophen-2-yl)-1,3,2-dioxaborolane in Step A. MS (ESI): mass calcd. for $C_{17}H_{18}N_4O_2S$, 342.1; m/z found, 343.2 [M+H]+. 1H NMR (500 MHz, CDCl3) δ 8.27-8.25 (d, J=1.9 Hz, 1H), 7.40-7.38 (d, J=1.9 Hz, 1H), 7.06-7.04 (d, J=3.5 Hz, 1H), 6.75-6.72 (m, 1H), 4.50-4.46 (s, 2H), 4.32-4.27 (m, 2H), 4.12-4.06 (m, 2H), 3.53-3.49 (s, 3H), 2.53-2.49 (d, J=1.1 Hz, 3H), 2.39-2.31 (m, 2H).

Example 327: 1-[2-(3-Fluoroazetidin-1-yl)-2-oxo-ethyl]-3-methyl-6-[5-(trifluoromethyl)-2-thienyl]imidazo[4,5-b]pyridin-2-one

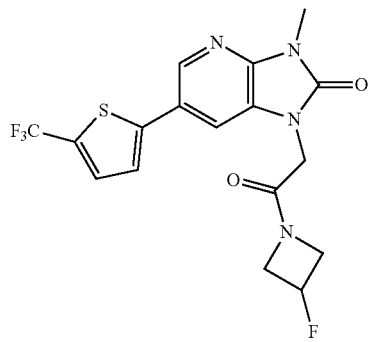 [SMILES: Cn1c(=O)n(CC(=O)N2CC(F)C2)c2cc(-c3ccc(C(F)(F)F)s3)cnc21]

The title compound was made in a manner analogous to Example 28, using 1-(2-(3-fluoroazetidin-1-yl)-2-oxoethyl)-6-bromo-3-trityl-1,3-dihydro-2H-imidazo[4,5-b]pyridin-2-one (Intermediate 40) in Step A. MS (ESI): mass calcd. for $C_{17}H_{14}F_4N_4O_2S$, 414.1; m/z found, 415.1 [M+H]$^+$. $^1$H NMR (500 MHz, CDCl$_3$) δ 8.33-8.30 (d, J=1.9 Hz, 1H), 7.44-7.43 (d, J=1.9 Hz, 1H), 7.43-7.40 (m, 1H), 7.21-7.18 (m, 1H), 5.45-5.28 (m, 1H), 4.68-4.12 (m, 7H), 3.55-3.50 (s, 3H).

Example 328: 3-Methyl-1-(2-oxo-2-pyrrolidin-1-yl-ethyl)-6-[5-(trifluoromethyl)-2-thienyl]imidazo[4,5-b]pyridin-2-one

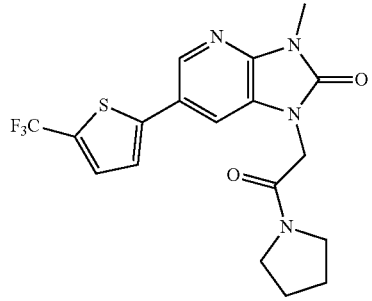 [SMILES: Cn1c(=O)n(CC(=O)N2CCCC2)c2cc(-c3ccc(C(F)(F)F)s3)cnc21]

The title compound was made in a manner analogous to Example 28, using 1-(2-(pyrrolidin-1-yl)-2-oxoethyl)-6-bromo-3-trityl-1,3-dihydro-2H-imidazo[4,5-b]pyridin-2-one (Intermediate 41) in Step A. MS (ESI): mass calcd. for $C_{18}H_{17}F_3N_4O_2S$, 410.1; m/z found, 411.1 [M+H]$^+$. $^1$H NMR (500 MHz, CDCl$_3$) δ 8.31-8.29 (d, J=1.9 Hz, 1H), 7.42-7.39 (m, 1H), 7.39-7.38 (d, J=1.9 Hz, 1H), 7.19-7.17 (m, 1H), 4.67-4.63 (s, 2H), 3.64-3.60 (m, 2H), 3.54-3.53 (s, 3H), 3.53-3.49 (m, 2H), 2.10-2.02 (m, 2H), 1.95-1.87 (m, 2H).

Example 329: 1-[2-(Azetidin-1-yl)-2-oxo-ethyl]-6-[2-methyl-3-(trifluoromethyl)phenyl]-3H-imidazo[4,5-b]pyridin-2-one and its Trifluoroacetic Acid Salt

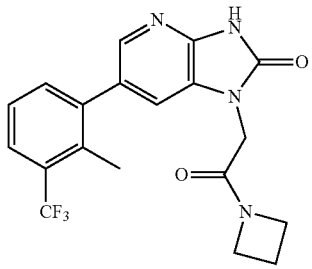 [SMILES: Cc1c(-c2cnc3[nH]c(=O)n(CC(=O)N4CCC4)c3c2)cccc1C(F)(F)F]

The title compound was prepared in a manner analogous to Example 29, using (2-methyl-3-(trifluoromethyl)phenyl)boronic acid in Step A. MS (ESI): mass calcd. for $C_{19}H_{17}F_3N_4O_2$, 390.1; m/z found, 391.1 [M+H]$^+$. $^1$H NMR (500 MHz, DMSO-d$_6$) δ 11.72 (s, 1H), 7.89-7.86 (m, 1H), 7.78-7.71 (m, 1H), 7.55-7.42 (m, 3H), 4.50 (s, 2H), 4.24 (t, J=7.5 Hz, 2H), 3.88 (t, J=7.6 Hz, 2H), 2.34-2.20 (m, 5H).

Example 330: 6-(3,4-Difluorophenyl)-1-(2-oxobutyl)-3H-imidazo[4,5-b]pyridin-2-one and its trifluoroacetic acid salt

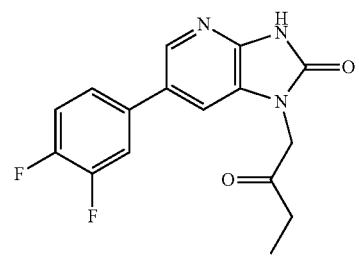 [SMILES: CCC(=O)Cn1c(=O)[nH]c2ncc(-c3ccc(F)c(F)c3)cc21]

Step A: 6-Bromo-3-(4-methoxybenzyl)-1-(2-oxobutyl)-1,3-dihydro-2H-imidazo[4,5-b]pyridin-2-one Under a nitrogen atmosphere was added 6-bromo-3-(4-methoxybenzyl)-1H-imidazo[4,5-b]pyridin-2(3H)-one (Intermediate 10, 2.0 g, 6.0 mmol) to a suspension of NaH (60% dispersion in mineral oil, 527 mg, 13 mmol) in DMF (30 mL) at room temperature. After 10 minutes, 1-bromo-2-butanone (1.3 mL, 13 mmol) was added and the reaction mixture was allowed to heat to 65° C. After 3 hours, water (150 mL) was added. The precipitates were filtered off, washed with water and dried under vacuum to yield the title product (1.7 g, 68%). MS (ESI): mass calcd. for $C_{18}H_{18}BrN_3O_3$, 403.1; m/z found, 404.0 [M+H]$^+$. $^1$H NMR (500 MHz, DMSO-d$_6$) δ 8.10 (d, J=2.0 Hz, 1H), 7.80 (d, J=2.0 Hz, 1H), 7.28-7.24 (m, 2H), 6.91-6.84 (m, 2H), 4.98 (s, 2H), 4.88 (s, 2H), 3.71 (s, 3H), 2.61 (q, J=7.3 Hz, 2H), 0.98 (t, J=7.3 Hz, 3H).

Step B: 6-(3,4-Difluorophenyl)-3-(4-methoxybenzyl)-1-(2-oxobutyl)-1,3-dihydro-2H-imidazo[4,5-b]pyridin-2-one A mixture of 6-bromo-3-(4-methoxybenzyl)-1-(2-oxobutyl)-1,3-dihydro-2H-imidazo[4,5-b]pyridin-2-one (200 mg, 0.5 mmol), (3,4-difluorophenyl)boronic acid (117 mg, 0.7 mmol), $Cs_2CO_3$ (322 mg, 1.0 mmol), dichloro(diphenylphosphinoferrocene)palladium (25 mg, 0.03 mmol) in dioxane (4.5 mL) was heated to 110° C. After 16 hours, the reaction mixture was concentrated under vacuum. The crude material was purified (FCC, $SiO_2$, 0-90% EtOAc in hexanes) to provide the title compound (115 mg, 53%). MS (ESI): mass calcd. for $C_{24}H_{21}F_2N_3O_3$, 437.2; m/z found, 438.1 [M+H]$^+$. $^1$H NMR (500 MHz, DMSO-$d_6$) δ 8.34 (d, J=1.9 Hz, 1H), 7.83 (d, J=1.9 Hz, 1H), 7.81-7.74 (m, 1H), 7.60-7.50 (m, 2H), 7.32-7.27 (m, 2H), 6.92-6.86 (m, 2H), 5.03 (s, 2H), 4.92 (s, 2H), 3.71 (s, 3H), 2.63 (q, J=7.3 Hz, 2H), 0.99 (t, J=7.3 Hz, 3H).

Step C. 6-(3,4-Difluorophenyl)-1-(2-oxobutyl)-3H-imidazo[4,5-b]pyridin-2-one and its Trifluoroacetic Acid Salt A mixture of 6-(3,4-difluorophenyl)-3-(4-methoxybenzyl)-1-(2-oxobutyl)-1,3-dihydro-2H-imidazo[4,5-b]pyridin-2-one (115 mg, 0.2 mmol) in HBr (48% in $H_2O$, 5.1 mL, 45.0 mmol) was heated to 115° C. Upon completion, the reaction mixture was cooled to 0° C. and NaOH pellets were added until the reaction mixture reach basic pH. The mixture was extracted with EtOAc (3×). The combined organics were dried ($MgSO_4$), filtered and concentrated under vacuum. The crude material was purified (METHOD B) to yield title product (9.1 mg, 8.0%). MS (ESI): mass calcd. for $C_{16}H_{13}F_2N_3O_2$, 317.1; m/z found, 318.1 [M+H]$^+$. $^1$H NMR (500 MHz, DMSO-$d_6$) w 11.75 (s, 1H), 8.27 (d, J=2.0 Hz, 1H), 7.80-7.73 (m, 2H), 7.58-7.49 (m, 2H), 4.83 (s, 2H), 2.61 (q, J=7.3 Hz, 2H), 0.99 (t, J=7.3 Hz, 3H).

Example 331: 6-(4-Fluoro-3-methyl-phenyl)-1-(2-oxobutyl)-3H-imidazo[4,5-b]pyridin-2-one

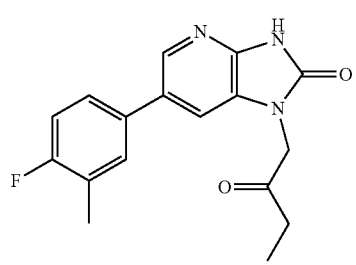 [SMILES: CCC(=O)Cn1c(=O)[nH]c2ncc(-c3ccc(F)c(C)c3)cc21]

The title compound was prepared in a manner analogous to Example 330, using (4-fluoro-3-methylphenyl)boronic acid in Step B. MS (ESI): mass calcd. for $C_{17}H_{16}FN_3O_2$, 313.1; m/z found, 314.1 [M+H]$^+$. $^1$H NMR (500 MHz, DMSO-$d_6$) δ 11.69 (s, 1H), 8.20 (d, J=1.9 Hz, 1H), 7.68 (d, J=2.0 Hz, 1H), 7.59-7.56 (m, 1H), 7.51-7.46 (m, 1H), 7.25-7.20 (m, 1H), 4.83 (s, 2H), 2.61 (q, J=7.4 Hz, 2H), 2.30 (d, J=2.0 Hz, 3H), 0.99 (t, J=7.3 Hz, 3H).

Example 332: 6-(m-Tolyl)-1-(2-oxobutyl)-3H-imidazo[4,5-b]pyridin-2-one

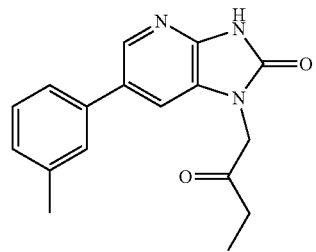 [SMILES: CCC(=O)Cn1c(=O)[nH]c2ncc(-c3cccc(C)c3)cc21]

The title compound was prepared in a manner analogous to Example 330, using m-tolylboronic acid in Step B. MS (ESI): mass calcd. for $C_{17}H_{17}N_3O_2$, 295.1; m/z found, 296.1 [M+H]$^+$. $^1$H NMR (500 MHz, DMSO-$d_6$) δ 11.68 (s, 1H), 8.21 (d, J=2.0 Hz, 1H), 7.69 (d, J=2.0 Hz, 1H), 7.48-7.46 (m, 1H), 7.45-7.42 (m, 1H), 7.35 (t, J=7.6 Hz, 1H), 7.21-7.16 (m, 1H), 4.84 (s, 2H), 2.61 (q, J=7.3 Hz, 2H), 2.38 (s, 3H), 0.99 (t, J=7.3 Hz, 3H).

Example 333: (R/S)-6-(3,4-Difluorophenyl)-1-(2-hydroxybutyl)-3-methyl-imidazo[4,5-b]pyridin-2-one and its Trifluoroacetic Acid Salt

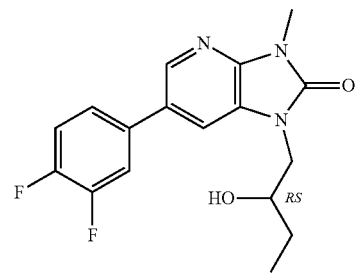 [SMILES: CCC(O)Cn1c(=O)n(C)c2ncc(-c3ccc(F)c(F)c3)cc21]

The title compound was prepared in a manner analogous to Example 31, Step B, using 6-(3,4-difluorophenyl)-3-methyl-1-(2-oxobutyl)imidazo[4,5-b]pyridin-2-one (Example 390, 65 mg, 0.2 mmol) in THF (4.2 mL) and MeOH (4 mL) at 0° C. After completion, the reaction mixture was concentrated under vacuum. The crude material was purified (Method C) to give the title compound (11 mg, 0.03 mmol, 13%). MS (ESI): mass calcd. for $C_{17}H_{17}F_2N_3O_2$, 333.1; m/z found, 334.1 [M+H]$^+$. $^1$H NMR (400 MHz, DMSO-$d_6$) δ

8.31 (d, J=1.9 Hz, 1H), 7.88-7.78 (m, 2H), 7.60-7.50 (m, 2H), 3.91-3.69 (m, 4H), 3.37 (s, 3H), 1.58-1.30 (m, 2H), 0.93 (t, J=7.4 Hz, 3H).

Example 334: (R/S)-6-(4-Fluoro-3-methyl-phenyl)-1-(2-hydroxybutyl)-3H-imidazo[4,5-b]pyridin-2-one and its Trifluoroacetic Acid Salt

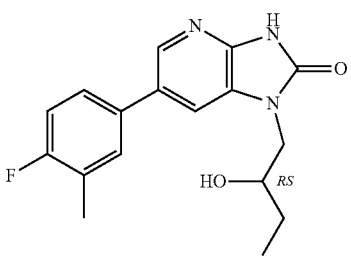 [SMILES: CCC(O)Cn1c(=O)[nH]c2ncc(-c3ccc(F)c(C)c3)cc21]

The title compound was prepared in a manner analogous to Example 31, Step B, using 6-(4-fluoro-3-methylphenyl)-1-(2-oxobutyl)-1,3-dihydro-2H-imidazo[4,5-b]pyridin-2-one (Example 331). MS (ESI): mass calcd. for $C_{17}H_{18}FN_3O_2$, 315.1; m/z found, 316.1 [M+H]$^+$. $^1$H NMR (500 MHz, DMSO-$d_6$) δ 11.55 (s, 1H), 8.16 (d, J=2.0 Hz, 1H), 7.71 (d, J=2.0 Hz, 1H), 7.61-7.58 (m, 1H), 7.53-7.48 (m, 1H), 7.27-7.20 (m, 1H), 2.31 (d, J=1.9 Hz, 3H), 1.53-1.43 (m, 1H), 1.42-1.31 (m, 1H), 0.92 (t, J=7.4 Hz, 3H).

Example 335: (R/S)-1-(2-Hydroxybutyl)-6-(m-tolyl)-3H-imidazo[4,5-b]pyridin-2-one and its trifluoroacetic acid salt

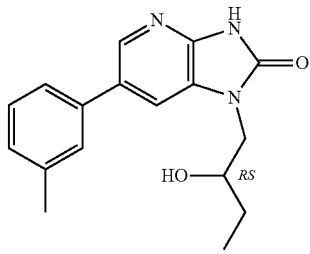 [SMILES: CCC(O)Cn1c(=O)[nH]c2ncc(-c3cccc(C)c3)cc21]

The title compound was prepared in a manner analogous to Example 31, Step B, using. 6-(m-tolyl)-1-(2-oxobutyl)-3H-imidazo[4,5-b]pyridin-2-one (Example 332). MS (ESI): mass calcd. for $C_{17}H_{19}N_3O_2$, 297.1; m/z found, 298.1 [M+H]$^+$. $^1$H NMR (400 MHz, DMSO-$d_6$) δ 11.56 (s, 1H), 8.17 (d, J=1.9 Hz, 1H), 7.73 (d, J=2.0 Hz, 1H), 7.51-7.43 (m, 2H), 7.36 (t, J=7.6 Hz, 1H), 7.21-7.15 (m, 1H), 2.39 (s, 3H), 1.56-1.29 (m, 2H), 0.92 (t, J=7.4 Hz, 3H).

Example 336: (R/S)-6-(2,4-Difluoro-3-methyl-phenyl)-1-(2-hydroxybutyl)-3H-imidazo[4,5-b]pyridin-2-one and its Trifluoroacetic Acid Salt

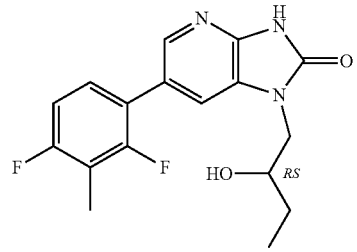 [SMILES: CCC(O)Cn1c(=O)[nH]c2ncc(-c3ccc(F)c(C)c3F)cc21]

The title compound was prepared in a manner analogous to Example 31, Step B, using 6-(2,4-difluoro-3-methyl-phenyl)-1-(2-oxobutyl)-3H-imidazo[4,5-b]pyridin-2-one (Example 30). MS (ESI): mass calcd. for $C_{17}H_{17}F_2N_3O_2$, 333.1; m/z found, 334.1 [M+H]$^+$. $^1$H NMR (400 MHz, DMSO-$d_6$) δ 11.64 (s, 1H), 8.01 (t, J=1.7 Hz, 1H), 7.60 (t, J=1.7 Hz, 1H), 7.45-7.37 (m, 1H), 7.21-7.15 (m, 1H), 2.23 (t, J=1.9 Hz, 3H), 1.53-1.28 (m, 2H), 0.91 (t, J=7.4 Hz, 3H).

Example 337: (R/S)-1-(2-Hydroxybutyl)-6-[3-(trifluoromethyl)phenyl]-3H-imidazo[4,5-b]pyridin-2-one and its Trifluoroacetic Acid Salt

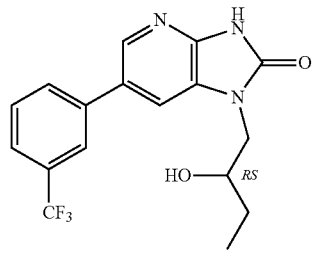 [SMILES: CCC(O)Cn1c(=O)[nH]c2ncc(-c3cccc(C(F)(F)F)c3)cc21]

The title compound was prepared in a manner analogous to Example 31, using 1-bromobutan-2-one in Step A. MS (ESI): mass calcd. for $C_{17}H_{16}F_3N_3O_2$, 351.1; m/z found, 352.1 [M+H]$^+$. $^1$H NMR (500 MHz, DMSO-$d_6$) δ 11.66 (s, 1H), 8.28 (d, J=2.0 Hz, 1H), 8.03-7.97 (m, 2H), 7.85 (d, J=2.0 Hz, 1H), 7.76-7.69 (m, 2H), 4.93-4.75 (m, 1H), 3.87-3.68 (m, 3H), 1.55-1.31 (m, 2H), 0.93 (t, J=7.4 Hz, 3H).

Example 338: (R/S)-1-(2-Hydroxy-3-methyl-butyl)-6-[3-(trifluoromethyl)phenyl]-3H-imidazo[4,5-b] pyridin-2-one and its Trifluoroacetic Acid Salt

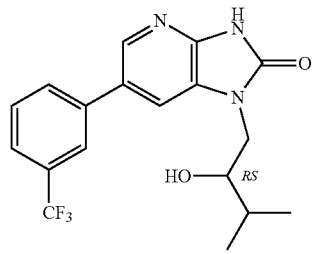 [SMILES: CC(C)C(O)Cn1c(=O)[nH]c2ncc(-c3cccc(C(F)(F)F)c3)cc21]

The title compound was prepared in a manner analogous to Example 31, using 1-bromo-3-methylbutan-2-one in Step A. MS (ESI): mass calcd. for $C_{18}H_{18}F_3N_3O_2$, 365.1; m/z found, 366.1 [M+H]$^+$. $^1$H NMR (500 MHz, DMSO-d$_6$) δ 11.66 (s, 1H), 8.27 (d, J=2.0 Hz, 1H), 8.02-7.96 (m, 2H), 7.81 (d, J=2.0 Hz, 1H), 7.76-7.69 (m, 2H), 3.93-3.87 (m, 1H), 3.78 (dd, J=14.2, 8.5 Hz, 1H), 3.61-3.52 (m, 1H), 1.72-1.61 (m, 1H), 0.95 (t, J=6.7 Hz, 6H).

Example 339: 6-(2,4-Difluoro-3-methyl-phenyl)-3-methyl-1-(3-pyridylmethyl)imidazo[4,5-b]pyridin-2-one

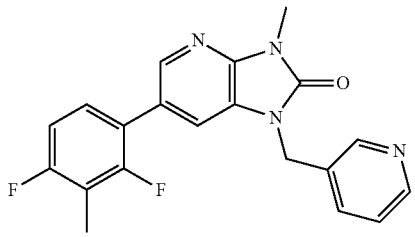 [SMILES: Cc1c(F)ccc(-c2cnc3c(c2)n(Cc2cccnc2)c(=O)n3C)c1F]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (2,4-difluoro-3-methylphenyl)boronic acid in Step B. MS (ESI): mass calcd. for $C_{20}H_{16}F_2N_4O$, 366.1; m/z found, 366.9 [M+H]$^+$. $^1$H NMR (500 MHz, DMSO-d$_6$) δ 8.65-8.64 (m, 1H), 8.49 (dd, J=4.8, 1.6 Hz, 1H), 8.12 (t, J=1.6 Hz, 1H), 7.78-7.72 (m, 2H), 7.43-7.33 (m, 2H), 7.21-7.15 (m, 1H), 5.17 (s, 2H), 3.40 (s, 3H), 2.22 (t, J=1.9 Hz, 3H).

Example 340: 6-(4-Fluoro-3-methyl-phenyl)-1-[(5-fluoro-3-pyridyl)methyl]-3-methyl-imidazo[4,5-b]pyridin-2-one

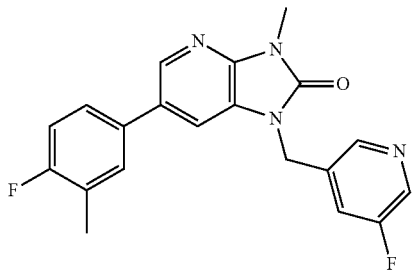

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)-5-fluoropyridine hydrochloride in Step A and (4-fluoro-3-methylphenyl)boronic acid in Step B. MS (ESI): mass calcd. for $C_{20}H_{16}F_2N_4O$, 366.1; m/z found, 367.2 [M+H]$^+$. $^1$H NMR (500 MHz, DMSO-d$_6$) δ 8.54 (t, J=1.9 Hz, 1H), 8.51 (d, J=2.8 Hz, 1H), 8.30 (d, J=1.9 Hz, 1H), 7.91 (d, J=1.9 Hz, 1H), 7.73 (ddd, J=9.7, 2.8, 1.7 Hz, 1H), 7.62-7.59 (m, 1H), 7.54-7.49 (m, 1H), 7.24 (dd, J=9.7, 8.5 Hz, 1H), 5.23 (s, 2H), 3.40 (s, 3H), 2.31 (d, J=1.9 Hz, 3H).

Example 341: 6-(2,4-Difluoro-3-methyl-phenyl)-1-[(5-fluoro-3-pyridyl)methyl]-3-methyl-imidazo[4,5-b]pyridin-2-one

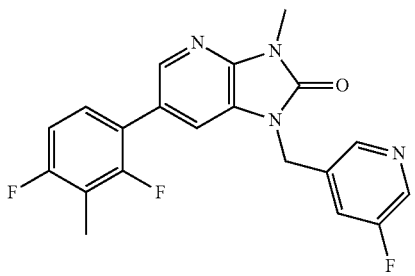 [SMILES: Cc1c(F)ccc(-c2cnc3c(c2)n(Cc2cncc(F)c2)c(=O)n3C)c1F]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)-5-fluoropyridine hydrochloride in Step A and (2,4-difluoro-3-methylphenyl)boronic acid in Step B. MS (ESI): mass calcd. for $C_{20}H_{15}F_3N_4O$, 384.1; m/z found, 385.2 [M+H]$^+$. $^1$H NMR (500 MHz, DMSO-d$_6$) δ 8.52 (t, J=1.8 Hz, 1H), 8.51 (d, J=2.8 Hz, 1H), 8.13 (t, J=1.6 Hz, 1H), 7.77 (t, J=1.6 Hz, 1H), 7.73 (ddd, J=9.7, 2.8, 1.8 Hz, 1H), 7.40 (td, J=8.8, 6.5 Hz, 1H), 7.21-7.16 (m, 1H), 5.21 (s, 2H), 3.40 (s, 3H), 2.22 (t, J=1.8 Hz, 3H).

Example 342: 6-[3-(Difluoromethoxy)phenyl]-1-[(5-fluoro-3-pyridyl)methyl]-3-methyl-imidazo[4,5-b]pyridin-2-one

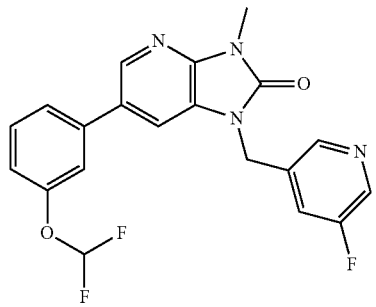 [SMILES: Cn1c(=O)n(Cc2cncc(F)c2)c2cc(-c3cccc(OC(F)F)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)-5-fluoropyridine hydrochloride in A and (3-(difluoromethoxy)phenyl)boronic acid in Step B. MS (ESI): mass calcd. for $C_{20}H_{15}F_3N_4O_2$, 400.1; m/z found, 401.2 [M+H]$^+$. $^1$H NMR (500 MHz, DMSO-d$_6$) δ 8.55 (t, J=1.8 Hz, 1H), 8.51 (d, J=2.8 Hz, 1H), 8.38 (d, J=1.9 Hz, 1H), 7.98 (d, J=1.9 Hz, 1H), 7.74 (ddd, J=9.8, 2.8, 1.8 Hz, 1H), 7.59-7.17 (m, 5H), 5.24 (s, 2H), 3.40 (s, 3H).

Example 343: 6-(3,4-Difluorophenyl)-1-[(5-fluoro-3-pyridyl)methyl]-3-methyl-imidazo[4,5-b]pyridin-2-one

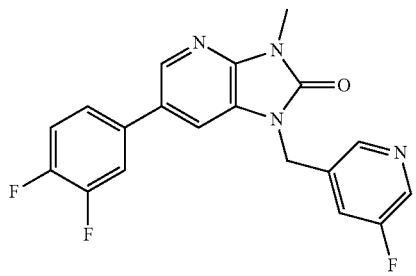 [SMILES: Cn1c(=O)n(Cc2cncc(F)c2)c2cc(-c3ccc(F)c(F)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)-5-fluoropyridine hydrochloride in Step A and (3,4-difluorophenyl)boronic acid in Step B. MS (ESI): mass calcd. for $C_{19}H_{13}F_3N_4O$, 370.1; m/z found, 371.1 [M+H]$^+$. $^1$H NMR (500 MHz, DMSO-d$_6$) δ 8.55 (t, J=1.8 Hz, 1H), 8.51 (d, J=2.8 Hz, 1H), 8.37 (d, J=1.9 Hz, 1H), 7.98 (d, J=2.0 Hz, 1H), 7.86-7.80 (m, 1H), 7.76-7.72 (m, 1H), 7.59-7.50 (m, 2H), 5.22 (s, 2H), 3.40 (s, 3H).

Example 344: 1-[(5-Fluoro-3-pyridyl)methyl]-3-methyl-6-(3,4,5-trifluorophenyl)imidazo[4,5-b]pyridin-2-one

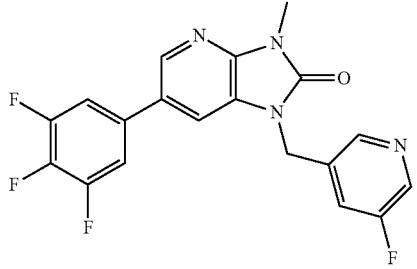 [SMILES: Cn1c(=O)n(Cc2cncc(F)c2)c2cc(-c3cc(F)c(F)c(F)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)-5-fluoropyridine hydrochloride in Step A and (3,4,5-trifluorophenyl)boronic acid in Step B. MS (ESI): mass calcd. for $C_{19}H_{12}F_4N_4O$, 388.1; m/z found, 389.1 [M+H]$^+$. $^1$H NMR (500 MHz, DMSO-d$_6$) δ 8.55 (t, J=1.8 Hz, 1H), 8.51 (d, J=2.8 Hz, 1H), 8.43 (d, J=2.0 Hz, 1H), 8.03 (d, J=2.0 Hz, 1H), 7.80-7.72 (m, 3H), 5.21 (s, 2H), 3.39 (s, 3H).

Example 345: 1-[(5-Fluoro-3-pyridyl)methyl]-3-methyl-6-[3-(trifluoromethoxy)phenyl]imidazo[4,5-b]pyridin-2-one

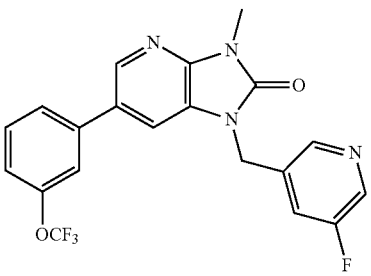 [SMILES: Cn1c(=O)n(Cc2cncc(F)c2)c2cc(-c3cccc(OC(F)(F)F)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)-5-fluoropyridine hydrochloride in Step A and (3-(trifluoromethoxy)phenyl)boronic acid in Step B. MS (ESI): mass calcd. for $C_{20}H_{14}F_4N_4O_2$, 418.1; m/z found, 419.1[M+H]$^+$. $^1$H NMR (500 MHz, DMSO-d$_6$) δ 8.55 (t, J=1.8 Hz, 1H), 8.51 (d, J=2.7 Hz, 1H), 8.40 (d, J=1.9 Hz, 1H), 8.01 (d, J=1.9 Hz, 1H), 7.77-7.72 (m, 2H), 7.70-7.68 (m, 1H), 7.62 (t, J=8.0 Hz, 1H), 7.40-7.36 (m, 1H), 5.24 (s, 2H), 3.40 (s, 3H).

Example 346: 6-(2,3-Difluorophenyl)-1-[(5-fluoro-3-pyridyl)methyl]-3-methyl-imidazo[4,5-b]pyridin-2-one

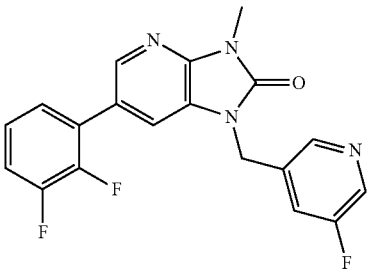

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)-5-fluoropyridine hydrochloride in Step A and (2,3-difluorophenyl)boronic acid in Step B. MS (ESI): mass calcd. for $C_{19}H_{13}F_3N_4O$, 370.1; m/z found, 371.1 [M+H]$^+$. $^1$H NMR (500 MHz, DMSO-d$_6$) δ 8.53 (t, J=1.8 Hz, 1H), 8.51 (d, J=2.7 Hz, 1H), 8.21 (t, J=1.7 Hz, 1H), 7.84 (t, J=1.6 Hz, 1H), 7.74 (ddd, J=9.7, 2.7, 1.7 Hz, 1H), 7.50-7.44 (m, 1H), 7.39-7.30 (m, 2H), 5.22 (s, 2H), 3.41 (s, 3H).

Example 347: 1-[(5-Fluoro-3-pyridyl)methyl]-3-methyl-6-(2,3,4-trifluorophenyl)imidazo[4,5-b]pyridin-2-one

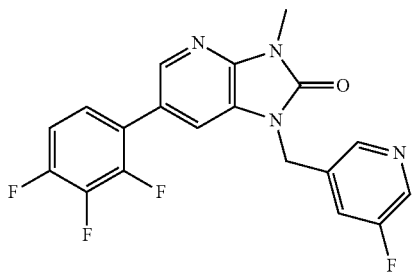 [SMILES: Cn1c(=O)n(Cc2cncc(F)c2)c2cc(-c3ccc(F)c(F)c3F)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)-5-fluoropyridine hydrochloride in Step A and (2,3,4-trifluorophenyl)boronic acid in Step B. MS (ESI): mass calcd. for $C_{19}H_{12}F_4N_4O$, 388.1; m/z found, 389.1 [M+H]$^+$. $^1$H NMR (500 MHz, DMSO-d$_6$) δ 8.53 (t, J=1.7 Hz, 1H), 8.51 (d, J=2.8 Hz, 1H), 8.19 (t, J=1.6 Hz, 1H), 7.82 (t, J=1.6 Hz, 1H), 7.75-7.71 (m, 1H), 7.51-7.38 (m, 2H), 5.21 (s, 2H), 3.41 (s, 3H).

Example 348: 6-(3-Chlorophenyl)-1-[(5-fluoro-3-pyridyl)methyl]-3-methyl-imidazo[4,5-b]pyridin-2-one

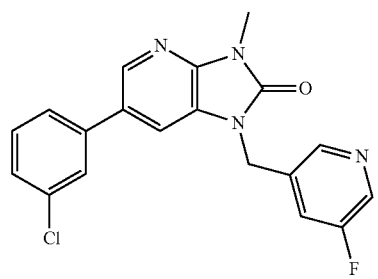 [SMILES: Cn1c(=O)n(Cc2cncc(F)c2)c2cc(-c3cccc(Cl)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)-5-fluoropyridine hydrochloride in Step A and (3-chlorophenyl)boronic acid in Step B. MS (ESI): mass calcd. for $C_{19}H_{14}ClFN_4O$, 368.1; m/z found, 369.1 [M+H]$^+$. $^1$H NMR (500 MHz, DMSO-d$_6$) δ 8.55 (t, J=1.8 Hz, 1H), 8.51 (d, J=2.7 Hz, 1H), 8.38 (d, J=1.9 Hz, 1H), 8.01 (d, J=1.9 Hz, 1H), 7.78 (t, J=1.9 Hz, 1H), 7.74 (ddd, J=9.7, 2.7, 1.7 Hz, 1H), 7.67 (ddd, J=7.8, 1.8, 1.1 Hz, 1H), 7.51 (t, J=7.9 Hz, 1H), 7.45-7.42 (m, 1H), 5.24 (s, 2H), 3.40 (s, 3H).

Example 349: 6-(3-Chloro-2-fluoro-phenyl)-1-[(5-fluoro-3-pyridyl)methyl]-3-methyl-imidazo[4,5-b]pyridin-2-one

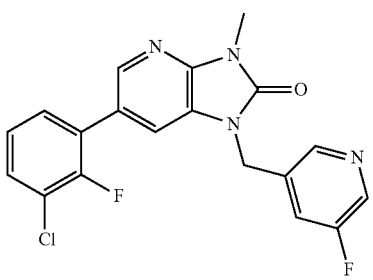

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)-5-fluoropyridine hydrochloride in Step A and (3-chloro-2-fluorophenyl)boronic acid in Step B. MS (ESI): mass calcd. for $C_{19}H_{13}ClF_2N_4O$, 386.1; m/z found, 387.1 [M+H]$^+$. $^1$H NMR (500 MHz, DMSO-d$_6$) δ 8.53 (t, J=1.8 Hz, 1H), 8.51 (d, J=2.8 Hz, 1H), 8.19 (t, J=1.6 Hz, 1H), 7.84 (t, J=1.7 Hz, 1H), 7.73 (ddd, J=9.8, 2.8, 1.8 Hz, 1H), 7.64-7.60 (m, 1H), 7.54-7.50 (m, 1H), 7.34 (td, J=7.9, 1.0 Hz, 1H), 5.22 (s, 2H), 3.41 (s, 3H).

Example 350: 1-[(5-Fluoro-3-pyridyl)methyl]-3-methyl-6-(m-tolyl)imidazo[4,5-b]pyridin-2-one

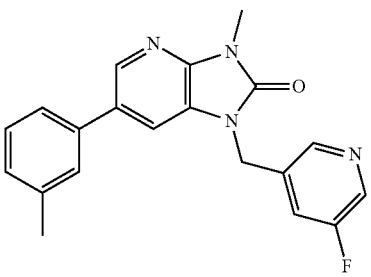 [SMILES: Cc1cccc(-c2cnc3c(c2)n(Cc2cncc(F)c2)c(=O)n3C)c1]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)-5-fluoropyridine hydrochloride in Step A and m-tolylboronic acid in Step B. MS (ESI): mass calcd. for $C_{20}H_{17}FN_4O$, 348.1; m/z found, 349.2 [M+H]$^+$. $^1$H NMR (500 MHz, DMSO-d$_6$) δ 8.54 (t, J=1.8 Hz, 1H), 8.51 (d, J=2.8 Hz, 1H), 8.31 (d, J=1.9 Hz, 1H), 7.91 (d, J=1.9 Hz, 1H), 7.73 (ddd, J=9.7, 2.8, 1.7 Hz, 1H), 7.50-7.48 (m, 1H), 7.47-7.44 (m, 1H), 7.36 (t, J=7.6 Hz, 1H), 7.21-7.17 (m, 1H), 5.24 (s, 2H), 3.40 (s, 3H), 2.38 (s, 3H).

Example 351: 6-(3,4-Dichlorophenyl)-1-[(5-fluoro-3-pyridyl)methyl]-3-methyl-imidazo[4,5-b]pyridin-2-one

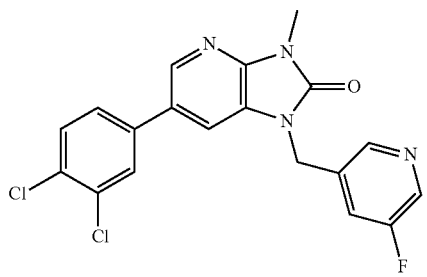 [SMILES: Cn1c(=O)n(Cc2cncc(F)c2)c2cc(-c3ccc(Cl)c(Cl)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)-5-fluoropyridine hydrochloride in Step A and (3,4-dichlorophenyl)boronic acid in Step B. MS (ESI): mass calcd. for $C_{19}H_{13}Cl_2FN_4O$, 402.0; m/z found, 403.1[M+H]$^+$. $^1$H NMR (500 MHz, DMSO-d$_6$) δ 8.55 (t, J=1.8 Hz, 1H), 8.51 (d, J=2.7 Hz, 1H), 8.40 (d, J=1.9 Hz, 1H), 8.03 (d, J=2.0 Hz, 1H), 7.99 (d, J=2.0 Hz, 1H), 7.76-7.69 (m, 3H), 5.23 (s, 2H), 3.40 (s, 3H).

Example 352: 6-(2-Fluoro-3-methyl-phenyl)-1-[(5-fluoro-3-pyridyl)methyl]-3-methyl-imidazo[4,5-b]pyridin-2-one and its Trifluoroacetic Acid Salt

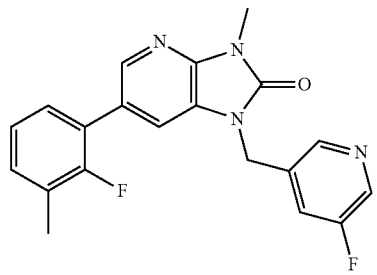 [SMILES: Cc1cccc(-c2cnc3c(c2)n(Cc2cncc(F)c2)c(=O)n3C)c1F]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)-5-fluoropyridine hydrochloride in Step A and (2-fluoro-3-methylphenyl)boronic acid in Step B. MS (ESI): mass calcd. for $C_{20}H_{16}F_2N_4O$, 366.1; m/z found, 367.2 [M+H]$^+$. $^1$H NMR (500 MHz, DMSO-d$_6$) δ 8.52 (t, J=1.7 Hz, 1H), 8.51 (d, J=2.8 Hz, 1H), 8.15 (t, J=1.7 Hz, 1H), 7.77 (t, J=1.6 Hz, 1H), 7.75-7.71 (m, 1H), 7.35-7.29 (m, 2H), 7.20 (t, J=7.6 Hz, 1H), 5.22 (s, 2H), 3.41 (s, 3H), 2.30 (d, J=2.1 Hz, 3H).

Example 353: 3-Methyl-1-(3-pyridylmethyl)-6-(3,4,5-trifluorophenyl)imidazo[4,5-b]pyridin-2-one and its Trifluoroacetic Acid Salt

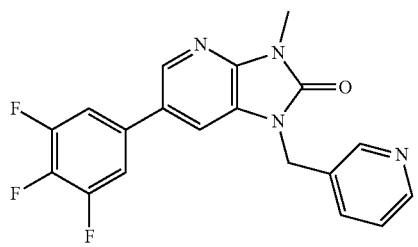 [SMILES: Cn1c(=O)n(Cc2cccnc2)c2cc(-c3cc(F)c(F)c(F)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (3,4,5-trifluorophenyl)boronic acid in Step B. MS (ESI): mass calcd. for $C_{19}H_{13}F_3N_4O$, 370.1; m/z found, 371.1[M+H]$^+$. $^1$H NMR (500 MHz, DMSO-d$_6$) δ 8.78-8.75 (m, 1H), 8.61-8.57 (m, 1H), 8.43 (d, J=1.9 Hz, 1H), 8.03 (d, J=2.0 Hz, 1H), 8.00-7.97 (m, 1H), 7.79-7.71 (m, 2H), 7.57-7.52 (m, 1H), 5.22 (s, 2H), 3.40 (s, 3H).

Example 354: 6-(3,5-Difluorophenyl)-3-methyl-1-(3-pyridylmethyl)imidazo[4,5-b]pyridin-2-one and its Trifluoroacetic Acid Salt

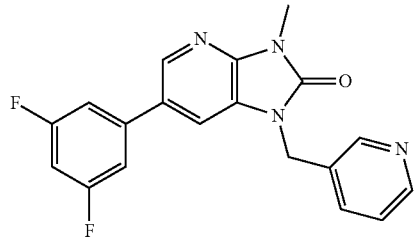 [SMILES: Cn1c(=O)n(Cc2cccnc2)c2cc(-c3cc(F)cc(F)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (3,5-difluorophenyl)boronic acid in Step B. MS (ESI): mass calcd. for $C_{19}H_{14}F_2N_4O$, 352.1; m/z found, 353.2 [M+H]$^+$. $^1$H NMR (500 MHz, DMSO-d$_6$) δ 8.78 (d, J=2.3 Hz, 1H), 8.63-8.60 (m, 1H), 8.45 (d, J=1.9 Hz, 1H), 8.07-8.01 (m, 2H), 7.59 (dd, J=8.0, 5.0 Hz, 1H), 7.54-7.48 (m, 2H), 7.24 (tt, J=9.3, 2.2 Hz, 1H), 5.25 (s, 2H), 3.40 (s, 3H).

Example 355: 6-(3-Chloro-4-fluoro-phenyl)-3-methyl-1-(3-pyridylmethyl)imidazo[4,5-b]pyridin-2-one and its Trifluoroacetic Acid Salt

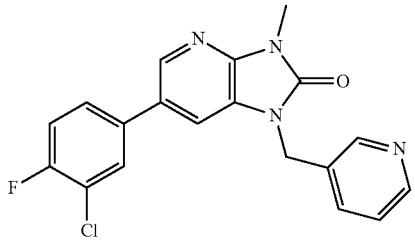 [SMILES: Cn1c(=O)n(Cc2cccnc2)c2cc(-c3ccc(F)c(Cl)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (3-chloro-4-fluorophenyl)boronic acid in Step B. MS (ESI): mass calcd. for $C_{19}H_{14}ClFN_4O$, 368.1; m/z found, 369.1 [M+H]$^+$. $^1$H NMR (500 MHz, DMSO-d$_6$) δ 8.78-8.74 (m, 1H), 8.61-8.57 (m, 1H), 8.37 (d, J=1.9 Hz, 1H), 8.02-7.97 (m, 2H), 7.93 (dd, J=7.1, 2.3 Hz, 1H), 7.71 (ddd, J=8.5, 4.6, 2.4 Hz, 1H), 7.58-7.50 (m, 2H), 5.24 (s, 2H), 3.40 (s, 3H).

Example 356: 3-Methyl-6-(m-tolyl)-1-(3-pyridylmethyl)imidazo[4,5-b]pyridin-2-one and its Trifluoroacetic Acid Salt

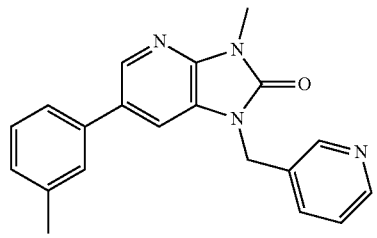 [SMILES: Cc1cccc(-c2cnc3c(c2)n(Cc2cccnc2)c(=O)n3C)c1]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and m-tolylboronic acid in Step B. MS (ESI): mass calcd. for $C_{20}H_{18}N_4O$, 330.1; m/z found, 331.2 [M+H]$^+$. $^1$H NMR (500 MHz, DMSO-d$_6$) δ 8.79-8.78 (m, 1H), 8.62 (dd, J=5.1, 1.5 Hz, 1H), 8.31 (d, J=1.9 Hz, 1H), 8.08-8.03 (m, 1H), 7.91 (d, J=1.9 Hz, 1H), 7.61 (dd, J=7.9, 5.1 Hz, 1H), 7.50-7.48 (m, 1H), 7.47-7.43 (m, 1H), 7.36 (t, J=7.6 Hz, 1H), 7.21-7.17 (m, 1H), 5.27 (s, 2H), 3.40 (s, 3H), 2.38 (s, 3H).

Example 357: 6-(2-Fluoro-3-methyl-phenyl)-3-methyl-1-(3-pyridylmethyl)imidazo[4,5-b]pyridin-2-one and its Trifluoroacetic Acid Salt

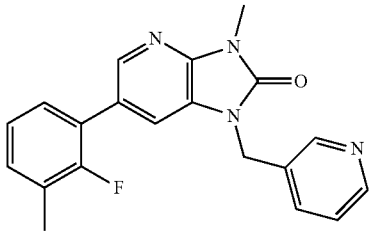 [SMILES: Cc1cccc(-c2cnc3c(c2)n(Cc2cccnc2)c(=O)n3C)c1F]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (2-fluoro-3-methylphenyl)boronic acid in Step B. MS (ESI): mass calcd. for $C_{20}H_{17}FN_4O$, 348.1; m/z found, 349.2 [M+H]$^+$. $^1$H NMR (500 MHz, DMSO-d$_6$) δ 8.78-8.76 (m, 1H), 8.64-8.61 (m, 1H), 8.16 (t, J=1.7 Hz, 1H), 8.07-8.03 (m, 1H), 7.78 (t, J=1.6 Hz, 1H), 7.62 (dd, J=7.9, 5.1 Hz, 1H), 7.35-7.29 (m, 2H), 7.20 (t, J=7.6 Hz, 1H), 5.25 (s, 2H), 3.41 (s, 3H), 2.30 (d, J=2.1 Hz, 3H).

Example 358: 6-[2-Fluoro-3-(trifluoromethyl)phenyl]-3-methyl-1-(3-pyridylmethyl)imidazo[4,5-b]pyridin-2-one and its Trifluoroacetic Acid Salt

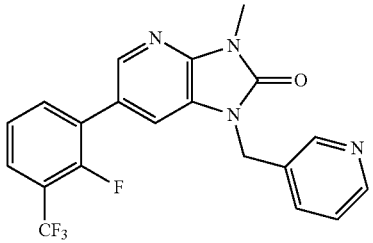

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (2-fluoro-3-(trifluoromethyl)phenyl)boronic acid in Step B. MS (ESI): mass calcd. for $C_{20}H_{14}F_4N_4O$, 402.1; m/z found, 403.2 [M+H]$^+$. $^1$H NMR (500 MHz, DMSO-d$_6$) δ 8.82 (d, J=1.9 Hz, 1H), 8.68 (dd, J=5.3, 1.5 Hz, 1H), 8.22 (t, J=1.6 Hz, 1H), 8.15 (dt, J=8.0, 1.8 Hz, 1H), 7.91-7.86 (m, 2H), 7.85-7.80 (m, 1H), 7.70 (dd, J=7.9, 5.3 Hz, 1H), 7.54 (t, J=7.8 Hz, 1H), 5.29 (s, 2H), 3.42 (s, 3H).

Example 359: 6-(3-Chloro-2-fluoro-phenyl)-3-methyl-1-(3-pyridylmethyl)imidazo[4,5-b]pyridin-2-one and its Trifluoroacetic Acid Salt

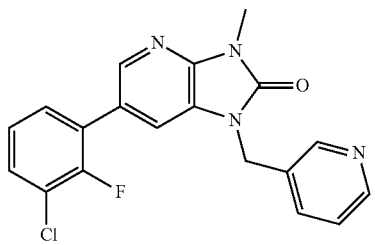 [SMILES: Cn1c(=O)n(Cc2cccnc2)c2cc(-c3cccc(Cl)c3F)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (3-chloro-2-fluorophenyl)boronic acid in Step B. MS (ESI): mass calcd. for $C_{19}H_{14}ClFN_4O$, 368.1; m/z found, 369.1 [M+H]$^+$. $^1$H NMR (400 MHz, DMSO-d$_6$) δ 8.78-8.75 (m, 1H), 8.62 (dd, J=5.4, 1.6 Hz, 1H), 8.20 (t, J=1.7 Hz, 1H), 8.05-8.01 (m, 1H), 7.85 (t, J=1.7 Hz, 1H), 7.66-7.57 (m, 2H), 7.55-7.48 (m, 1H), 7.34 (td, J=7.9, 1.0 Hz, 1H), 5.24 (s, 2H), 3.41 (s, 3H).

Example 360: 6-[4-Fluoro-3-(trifluoromethyl)phenyl]-3-methyl-1-(3-pyridylmethyl)imidazo[4,5-b]pyridin-2-one and its Trifluoroacetic Acid Salt

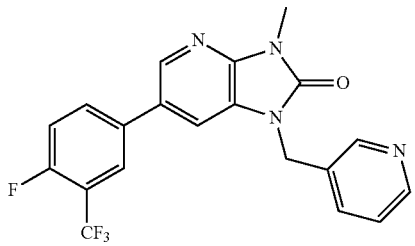

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (4-fluoro-3-(trifluoromethyl)phenyl)boronic acid in Step B. MS (ESI): mass calcd. for $C_{20}H_{14}F_4N_4O$, 402.1; m/z found, 403.2 [M+H]$^+$. $^1$H NMR (400 MHz, DMSO-d$_6$) δ 8.80-8.77 (m, 1H), 8.64-8.61 (m, 1H), 8.40 (d, J=1.9 Hz, 1H), 8.09-7.99 (m, 4H), 7.69-7.57 (m, 2H), 5.27 (s, 2H), 3.41 (s, 3H).

Example 361: 3-Methyl-1-(3-pyridylmethyl)-6-(2,3,4-trifluorophenyl)imidazo[4,5-b]pyridin-2-one and its Trifluoroacetic Acid Salt

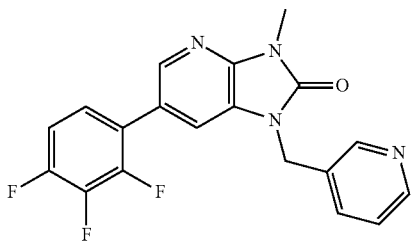 [SMILES: Cn1c(=O)n(Cc2cccnc2)c2cc(-c3ccc(F)c(F)c3F)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (2,3,4-trifluorophenyl)boronic acid in Step B. MS (ESI): mass calcd. for $C_{19}H_{13}F_3N_4O$, 370.1; m/z found, 371.2 [M+H]$^+$. $^1$H NMR (400 MHz, DMSO-d$_6$) δ 8.76-8.74 (m, 1H), 8.63-8.59 (m, 1H), 8.19 (t, J=1.7 Hz, 1H), 8.03-7.97 (m, 1H), 7.82 (t, J=1.6 Hz, 1H), 7.60-7.54 (m, 1H), 7.51-7.37 (m, 2H), 5.23 (s, 2H), 3.41 (s, 3H).

Example 362: 3-Methyl-1-(3-pyridylmethyl)-6-[3-(trifluoromethyl)phenyl]imidazo[4,5-b]pyridin-2-one and its Trifluoroacetic Acid Salt

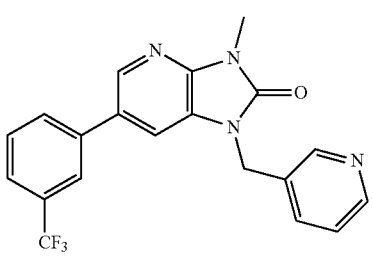

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (3-(trifluoromethyl)phenyl)boronic acid in Step B. MS (ESI): mass calcd. for $C_{20}H_{15}F_3N_4O$, 384.1; m/z found, 385.1 [M+H]$^+$. $^1$H NMR (400 MHz, DMSO-d$_6$) δ 8.79 (d, J=2.1 Hz, 1H), 8.63 (dd, J=5.2, 1.5 Hz, 1H), 8.43 (d, J=1.9 Hz, 1H), 8.09-8.04 (m, 2H), 8.03-7.99 (m, 2H), 7.77-7.69 (m, 2H), 7.65-7.59 (m, 1H), 5.29 (s, 2H), 3.41 (s, 3H).

Example 363: 6-[3-(Difluoromethyl)phenyl]-3-methyl-1-(3-pyridylmethyl)imidazo[4,5-b]pyridin-2-one and its Trifluoroacetic Acid Salt

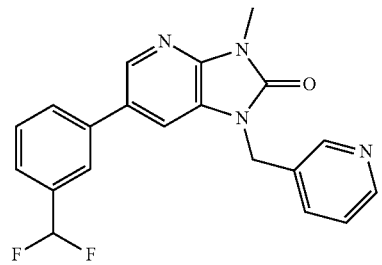 [SMILES: Cn1c(=O)n(Cc2cccnc2)c2cc(-c3cccc(C(F)F)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (3-(difluoromethyl)phenyl)boronic acid in Step B. MS (ESI): mass calcd. for $C_{20}H_{16}F_2N_4O$, 366.1; m/z found, 367.2 [M+H]$^+$. $^1$H NMR (400 MHz, DMSO-d$_6$) δ 8.80-8.77 (m, 1H), 8.64-8.61 (m, 1H), 8.37 (d, J=1.9 Hz, 1H), 8.10-8.04 (m, 1H), 8.01 (d, J=1.9 Hz, 1H), 7.89-7.83 (m, 2H), 7.67-7.55 (m, 3H), 7.09 (t, J=55.8 Hz, 1H), 5.29 (s, 2H), 3.41 (s, 3H).

Example 364: 3-Methyl-1-(3-pyridylmethyl)-6-[5-(trifluoromethyl)-2-thienyl]imidazo[4,5-b]pyridin-2-one and its Trifluoroacetic Acid Salt

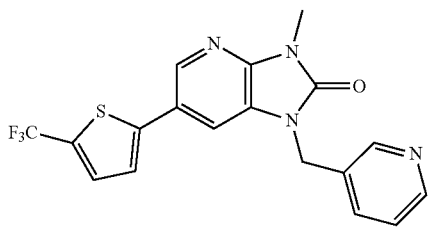 [SMILES: Cn1c(=O)n(Cc2cccnc2)c2cc(-c3ccc(C(F)(F)F)s3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (5-(trifluoromethyl)thiophen-2-yl)boronic acid in Step B. MS (ESI): mass calcd. for $C_{18}H_{13}F_3N_4OS$, 390.1; m/z found, 391.1 [M+H]$^+$. $^1$H NMR (400 MHz, DMSO-d$_6$) δ 8.77 (d, J=2.2 Hz, 1H), 8.61 (dd, J=5.1, 1.6 Hz, 1H), 8.43 (d, J=1.9 Hz, 1H), 8.03-7.98 (m, 2H), 7.78-7.75 (m, 1H), 7.63-7.54 (m, 2H), 5.24 (s, 2H), 3.39 (s, 3H).

Example 365: 6-(5-Chloro-4-methyl-2-thienyl)-3-methyl-1-(3-pyridylmethyl)imidazo[4,5-b]pyridin-2-one and its Trifluoroacetic Acid Salt

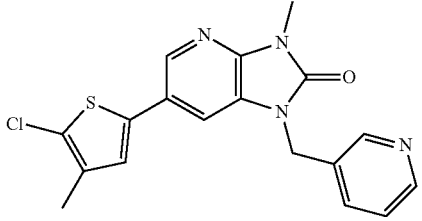 [SMILES: Cc1cc(-c2cnc3c(c2)n(Cc2cccnc2)c(=O)n3C)sc1Cl]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (5-chloro-4-methylthiophen-2-yl)boronic acid in Step B. MS (ESI): mass calcd. for $C_{18}H_{15}ClN_4OS$, 370.1; m/z found, 371.1[M+H]$^+$. $^1$H NMR (400 MHz, DMSO-d$_6$) δ 8.75-8.72 (m, 1H), 8.59 (dd, J=4.9, 1.4 Hz, 1H), 8.23 (d, J=1.9 Hz, 1H), 7.98-7.92 (m, 1H), 7.85 (d, J=2.0 Hz, 1H), 7.56-7.51 (m, 1H), 7.33 (s, 1H), 5.21 (s, 2H), 3.37 (s, 3H), 2.18 (s, 3H).

Example 366: 1-[(5-Chloro-3-pyridyl)methyl]-3-methyl-6-[3-(trifluoromethyl)phenyl]imidazo[4,5-b]pyridin-2-one and its Trifluoroacetic Acid Salt

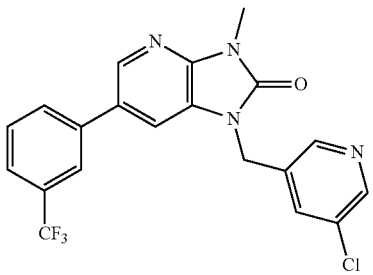 [SMILES: Cn1c(=O)n(Cc2cncc(Cl)c2)c2cc(-c3cccc(C(F)(F)F)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-chloro-5-(chloromethyl)pyridine hydrochloride in Step A and (3-(trifluoromethyl)phenyl)boronic acid in Step B. MS (ESI): mass calcd. for $C_{20}H_{14}ClF_3N_4O$, 418.1; m/z found, 419.1 [M+H]$^+$. $^1$H NMR (500 MHz, DMSO-d$_6$) δ 8.62 (d, J=1.9 Hz, 1H), 8.56 (d, J=2.3 Hz, 1H), 8.42 (d, J=1.9 Hz, 1H), 8.07 (d, J=1.9 Hz, 1H), 8.03-7.99 (m, 2H), 7.96-7.94 (m, 1H), 7.76-7.69 (m, 2H), 5.23 (s, 2H), 3.41 (s, 3H).

Example 367: 1-[(5-Chloro-3-pyridyl)methyl]-6-(4-fluoro-3-methyl-phenyl)-3-methyl-imidazo[4,5-b]pyridin-2-one and its Trifluoroacetic Acid Salt

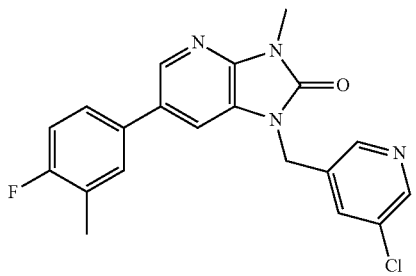

The title compound was prepared in a manner analogous to Example 33, Steps A-B, using 6-bromo-3-methyl-1,3-dihydro-2H-imidazo[4,5-b]pyridin-2-one (Intermediate 11) and 3-chloro-5-(chloromethyl)pyridine hydrochloride in Step A and (4-fluoro-3-methylphenyl)boronic acid in Step B. MS (ESI): mass calcd. for $C_{20}H_{16}ClFN_4O$, 382.1; m/z found, 383.1[M+H]$^+$. $^1$H NMR (500 MHz, DMSO-d$_6$) δ 8.61 (d, J=1.9 Hz, 1H), 8.56 (d, J=2.4 Hz, 1H), 8.29 (d, J=1.9 Hz, 1H), 7.95-7.94 (m, 1H), 7.92 (d, J=1.9 Hz, 1H), 7.62-7.59 (m, 1H), 7.54-7.49 (m, 1H), 7.24 (dd, J=9.7, 8.5 Hz, 1H), 5.21 (s, 2H), 3.39 (s, 3H), 2.31 (d, J=1.9 Hz, 3H).

Example 368: 1-[(5-Chloro-3-pyridyl)methyl]-6-(2,4-difluoro-3-methyl-phenyl)-3-methyl-imidazo[4,5-b]pyridin-2-one and its Trifluoroacetic Acid Salt

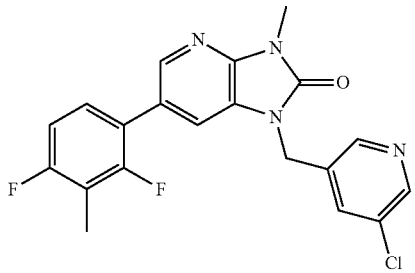 [SMILES: Cc1c(F)ccc(-c2cnc3c(c2)n(Cc2cncc(Cl)c2)c(=O)n3C)c1F]

The title compound was prepared in a manner analogous to Example 33, Steps A-B, using 6-bromo-3-methyl-1,3-dihydro-2H-imidazo[4,5-b]pyridin-2-one (Intermediate 11) and 3-chloro-5-(chloromethyl)pyridine hydrochloride in Step A and (2,4-difluoro-3-methylphenyl)boronic acid in Step B. MS (ESI): mass calcd. for $C_{20}H_{15}ClF_2N_4O$, 400.1; m/z found, 401.2 [M+H]$^+$. $^1$H NMR (500 MHz, DMSO-d$_6$) δ 8.60 (d, J=1.8 Hz, 1H), 8.56 (d, J=2.4 Hz, 1H), 8.13 (t, J=1.6 Hz, 1H), 7.94 (t, J=2.2 Hz, 1H), 7.79 (t, J=1.6 Hz, 1H), 7.43-7.37 (m, 1H), 7.22-7.15 (m, 1H), 5.19 (s, 2H), 3.40 (s, 3H), 2.22 (t, J=1.9 Hz, 3H).

Example 369: 1-[(5-Chloro-3-pyridyl)methyl]-6-(3,4-difluorophenyl)-3-methyl-imidazo[4,5-b]pyridin-2-one and its Trifluoroacetic Acid Salt The title compound was prepared in a manner analogous to Example 33, Steps A-B, using 6-bromo-3-methyl-1,3-dihydro-2H-imidazo[4,5-b]pyridin-2-one (Intermediate 11) and 3-chloro-5-(chloromethyl)pyridine hydrochloride in Step A and (3,4-difluorophenyl)boronic acid in Step B. MS (ESI): mass calcd. for $C_{19}H_{13}ClF_2N_4O$, 386.1; m/z found, 387.1 [M+H]$^+$. $^1$H NMR (400 MHz, DMSO-d$_6$) δ 8.62 (d, J=1.9 Hz, 1H), 8.56 (d, J=2.3 Hz, 1H), 8.37 (d, J=1.9 Hz, 1H), 8.00 (d, J=2.0 Hz, 1H), 7.95 (t, J=2.2 Hz, 1H), 7.86-7.78 (m, 1H), 7.60-7.50 (m, 2H), 5.20 (s, 2H), 3.40 (s, 3H).

Example 370: 1-[(5-Chloro-3-pyridyl)methyl]-3-methyl-6-(3,4,5-trifluorophenyl)imidazo[4,5-b]pyridin-2-one and its Trifluoroacetic Acid Salt

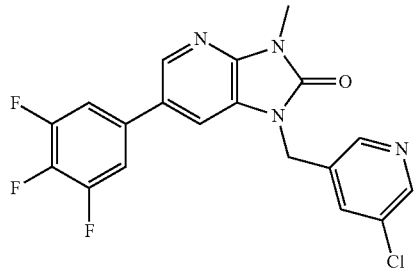 [SMILES: Cn1c(=O)n(Cc2cncc(Cl)c2)c2cc(-c3cc(F)c(F)c(F)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-chloro-5-(chloromethyl)pyridine hydrochloride in Step A and (3,4,5-trifluorophenyl)boronic acid in Step B. MS (ESI): mass calcd. for $C_{19}H_{12}ClF_3N_4O$, 404.1; m/z found, 405.1[M+H]$^+$. $^1$H NMR (400 MHz, DMSO-d$_6$) δ 8.62 (d, J=1.9 Hz, 1H), 8.56 (d, J=2.4 Hz, 1H), 8.43 (d, J=1.9 Hz, 1H), 8.04 (d, J=2.0 Hz, 1H), 7.95 (t, J=2.1 Hz, 1H), 7.80-7.71 (m, 2H), 5.19 (s, 2H), 3.39 (s, 3H).

Example 371: 1-[(5-Chloro-3-pyridyl)methyl]-6-(2-fluoro-3-methyl-phenyl)-3-methyl-imidazo[4,5-b]pyridin-2-one and its Trifluoroacetic Acid Salt

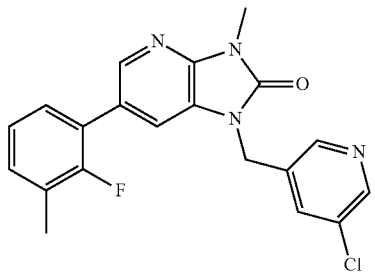 [SMILES: Cc1cccc(-c2cnc3c(c2)n(Cc2cncc(Cl)c2)c(=O)n3C)c1F]

The title compound was prepared in a manner analogous to Example 33, Steps A-B, using 6-bromo-3-methyl-1,3-dihydro-2H-imidazo[4,5-b]pyridin-2-one (Intermediate 11) and 3-chloro-5-(chloromethyl)pyridine hydrochloride in Step A and (2-fluoro-3-methylphenyl)boronic acid in Step B. MS (ESI): mass calcd. for $C_{20}H_{16}ClFN_4O$, 382.1; m/z found, 383.1 [M+H]$^+$. $^1$H NMR (400 MHz, DMSO-d$_6$) δ 8.60 (d, J=1.9 Hz, 1H), 8.56 (d, J=2.4 Hz, 1H), 8.15 (t, J=1.7 Hz, 1H), 7.94 (t, J=2.1 Hz, 1H), 7.80 (t, J=1.7 Hz, 1H), 7.36-7.28 (m, 2H), 7.23-7.16 (m, 1H), 5.19 (s, 2H), 3.40 (s, 3H), 2.30 (d, J=2.2 Hz, 3H).

Example 372: 6-(5-Chloro-4-methyl-2-thienyl)-1-[(5-chloro-3-pyridyl)methyl]-3-methyl-imidazo[4,5-b]pyridin-2-one and its Trifluoroacetic Acid Salt

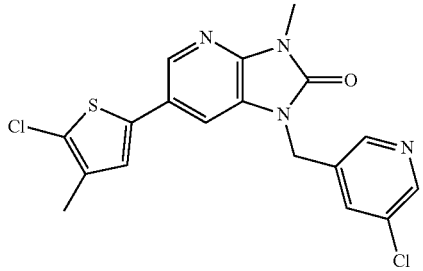 [SMILES: Cc1cc(-c2cnc3c(c2)n(Cc2cncc(Cl)c2)c(=O)n3C)sc1Cl]

The title compound was prepared in a manner analogous to Example 33, Steps A-B, using 6-bromo-3-methyl-1,3-dihydro-2H-imidazo[4,5-b]pyridin-2-one (Intermediate 11) and 3-chloro-5-(chloromethyl)pyridine hydrochloride in Step A and (5-chloro-4-methylthiophen-2-yl)boronic acid in Step B. MS (ESI): mass calcd. for $C_{18}H_{14}Cl_2N_4OS$, 404.0; m/z found, 405.1[M+H]$^+$. $^1$H NMR (500 MHz, DMSO-d$_6$) δ 8.61 (d, J=1.9 Hz, 1H), 8.57 (d, J=2.4 Hz, 1H), 8.23 (d, J=1.9 Hz, 1H), 7.93 (t, J=2.1 Hz, 1H), 7.87 (d, J=1.9 Hz, 1H), 7.34 (s, 1H), 5.18 (s, 2H), 3.37 (s, 3H), 2.18 (s, 3H).

Example 373: 1-[(5-Chloro-3-pyridyl)methyl]-3-methyl-6-[5-(trifluoromethyl)-2-thienyl]imidazo[4,5-b]pyridin-2-one and its Trifluoroacetic Acid Salt The title compound was prepared in a manner analogous to Example 33, Steps A-B, using 6-bromo-3-methyl-1,3-dihydro-2H-imidazo[4,5-b]pyridin-2-one (Intermediate 11) and 3-chloro-5-(chloromethyl)pyridine hydrochloride in Step A and (5-(trifluoromethyl)thiophen-2-yl)boronic acid in Step B. MS (ESI): mass calcd. for $C_{18}H_{12}ClF_3N_4OS$, 424.0; m/z found, 425.1 [M+H]$^+$. $^1$H NMR (500 MHz, DMSO-d$_6$) δ 8.62 (d, J=1.9 Hz, 1H), 8.57 (d, J=2.3 Hz, 1H), 8.42 (d, J=1.9 Hz, 1H), 8.02 (d, J=1.9 Hz, 1H), 7.95 (t, J=2.1 Hz, 1H), 7.78-7.75 (m, 1H), 7.63-7.60 (m, 1H), 5.20 (s, 2H), 3.39 (s, 3H).

Example 374: 1-[(5-Chloro-3-pyridyl)methyl]-3-methyl-6-(m-tolyl)imidazo[4,5-b]pyridin-2-one and its Trifluoroacetic Acid Salt

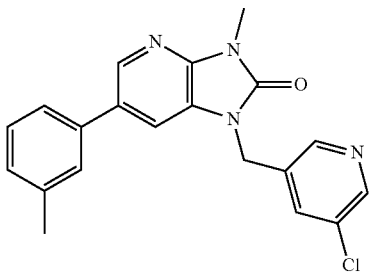 [SMILES: Cc1cccc(-c2cnc3c(c2)n(Cc2cncc(Cl)c2)c(=O)n3C)c1]

The title compound was prepared in a manner analogous to Example 33, Steps A-B, using 6-bromo-3-methyl-1,3-dihydro-2H-imidazo[4,5-b]pyridin-2-one (Intermediate 11) and 3-chloro-5-(chloromethyl)pyridine hydrochloride in Step A and m-tolylboronic acid in Step B. MS (ESI): mass calcd. for $C_{20}H_{17}ClN_4O$, 364.1; m/z found, 365.1 [M+H]$^+$. $^1$H NMR (500 MHz, DMSO-d$_6$) δ 8.61 (d, J=1.9 Hz, 1H), 8.56 (d, J=2.3 Hz, 1H), 8.31 (d, J=1.9 Hz, 1H), 7.95-7.94 (m, 1H), 7.93 (d, J=1.9 Hz, 1H), 7.50-7.48 (m, 1H), 7.47-7.44 (m, 1H), 7.36 (t, J=7.6 Hz, 1H), 7.21-7.17 (m, 1H), 5.22 (s, 2H), 3.40 (s, 3H), 2.38 (s, 3H).

Example 375: 1-[(5-Chloro-3-pyridyl)methyl]-6-(2,3-difluorophenyl)-3-methyl-imidazo[4,5-b]pyridin-2-one and its Trifluoroacetic Acid Salt

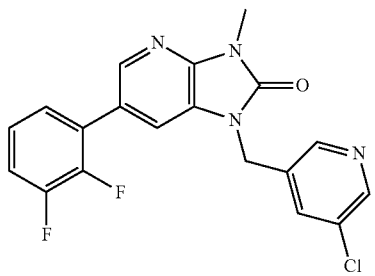 [SMILES: Cn1c(=O)n(Cc2cncc(Cl)c2)c2cc(-c3cccc(F)c3F)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-chloro-5-(chloromethyl)pyridine hydrochloride in Step A and (2,3-difluorophenyl)boronic acid in Step B. MS (ESI): mass calcd. for $C_{19}H_{13}ClF_2N_4O$, 386.1; m/z found, 387.1 [M+H]$^+$. $^1$H NMR (500 MHz, DMSO-d$_6$) δ 8.61 (d, J=1.9 Hz, 1H), 8.56 (d, J=2.4 Hz, 1H), 8.21 (t, J=1.6 Hz, 1H), 7.95 (t, J=2.1 Hz, 1H), 7.86 (t, J=1.6 Hz, 1H), 7.50-7.43 (m, 1H), 7.40-7.30 (m, 2H), 5.19 (s, 2H), 3.41 (s, 3H).

Example 376: 6-(3-Chlorophenyl)-3-methyl-1-(pyridazin-3-ylmethyl)imidazo[4,5-b]pyridin-2-one and its Trifluoroacetic Acid Salt

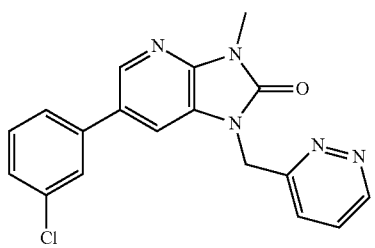 [SMILES: Cn1c(=O)n(Cc2cccnn2)c2cc(-c3cccc(Cl)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridazine hydrochloride in Step A and (3-chlorophenyl)boronic acid in Step B. MS (ESI): mass calcd. for $C_{18}H_{14}ClN_5O$, 351.1; m/z found, 352.1 [M+H]$^+$. $^1$H NMR (500 MHz, DMSO-d$_6$) δ 9.16 (dd, J=4.6, 2.0 Hz, 1H), 8.39 (d, J=1.9 Hz, 1H), 7.94 (d, J=2.0 Hz, 1H), 7.75 (t, J=1.9 Hz, 1H), 7.72-7.63 (m, 3H), 7.49 (t, J=7.9 Hz, 1H), 7.44-7.40 (m, 1H), 5.49 (s, 2H), 3.42 (s, 3H).

Example 377: 6-[3-(Difluoromethyl)phenyl]-3-methyl-1-(pyridazin-3-ylmethyl)imidazo[4,5-b]pyridin-2-one and its Trifluoroacetic Acid Salt The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridazine hydrochloride (Intermediate 2) in Step A and (3-(difluoromethyl)phenyl)boronic acid in Step B. MS (ESI): mass calcd. for $C_{19}H_{15}F_2N_5O$, 367.1; m/z found, 368.2 [M+H]$^+$. $^1$H NMR (500 MHz, DMSO-d$_6$) δ 9.16 (dd, J=4.5, 2.1 Hz, 1H), 8.38 (d, J=1.9 Hz, 1H), 7.93 (d, J=1.9 Hz, 1H), 7.86-7.82 (m, 2H), 7.72-7.66 (m, 2H), 7.65-7.55 (m, 2H), 7.08 (t, J=55.8 Hz, 1H), 5.50 (s, 2H), 3.43 (s, 3H).

Example 378: 3-Methyl-1-(pyridazin-3-ylmethyl)-6-[3-(trifluoromethyl)phenyl]imidazo[4,5-b]pyridin-2-one and its Trifluoroacetic Acid Salt The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridazine hydrochloride (Intermediate 2) in Step A and (3-(trifluoromethyl)phenyl)boronic acid in Step B. MS (ESI): mass calcd. for $C_{19}H_{14}F_3N_5O$, 385.1; m/z found, 386.2 [M+H]$^+$. $^1$H NMR (500 MHz, DMSO-d$_6$) δ 9.16 (dd, J=4.5, 2.1 Hz, 1H), 8.44 (d, J=1.9 Hz, 1H), 8.01-7.98 (m, 3H), 7.75-7.65 (m, 4H), 5.50 (s, 2H), 3.43 (s, 3H).

Example 379: 3-Methyl-6-(m-tolyl)-1-(pyridazin-3-ylmethyl)imidazo[4,5-b]pyridin-2-one and its Trifluoroacetic Acid Salt

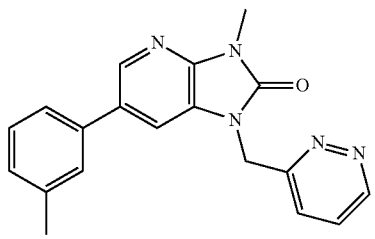 [SMILES: Cc1cccc(-c2cnc3c(c2)n(Cc2cccnn2)c(=O)n3C)c1]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridazine hydrochloride (Intermediate 2) in Step A and m-tolylboronic acid in Step B. MS (ESI): mass calcd. for $C_{19}H_{17}N_5O$, 331.1; m/z found, 332.2 [M+H]$^+$. $^1$H NMR (500 MHz, DMSO-d$_6$) δ 9.16 (dd, J=4.6, 2.0 Hz, 1H), 8.32 (d, J=1.9 Hz, 1H), 7.83 (d, J=1.9 Hz, 1H), 7.73-7.64 (m, 2H), 7.48-7.46 (m, 1H), 7.45-7.41 (m, 1H), 7.34 (t, J=7.6 Hz, 1H), 7.20-7.16 (m, 1H), 5.48 (s, 2H), 3.42 (s, 3H), 2.37 (s, 3H).

Example 381: 6-(3-Fluoro-5-methyl-phenyl)-3-methyl-1-(pyridazin-3-ylmethyl)imidazo[4,5-b]pyridin-2-one and its Trifluoroacetic Acid Salt

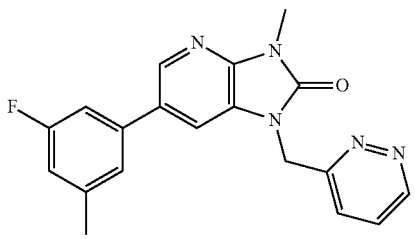 [SMILES: Cc1cc(F)cc(-c2cnc3c(c2)n(Cc2cccnn2)c(=O)n3C)c1]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridazine hydrochloride (Intermediate 2) in Step A and (3-fluoro-5-methylphenyl)boronic acid in Step B. MS (ESI): mass calcd. for $C_{19}H_{16}FN_5O$, 349.1; m/z found, 350.2 [M+H]$^+$. $^1$H NMR (500 MHz, DMSO-d$_6$) δ 9.16 (dd, J=4.6, 1.9 Hz, 1H), 8.38 (d, J=1.9 Hz, 1H), 7.90 (d, J=1.9 Hz, 1H), 7.72-7.65 (m, 2H), 7.37-7.34 (m, 1H), 7.34-7.30 (m, 1H), 7.05-7.00 (m, 1H), 5.48 (s, 2H), 3.42 (s, 3H), 2.38 (s, 3H).

Example 380: 6-(3-Chloro-4-fluoro-phenyl)-3-methyl-1-(pyridazin-3-ylmethyl)imidazo[4,5-b]pyridin-2-one and its Trifluoroacetic Acid Salt

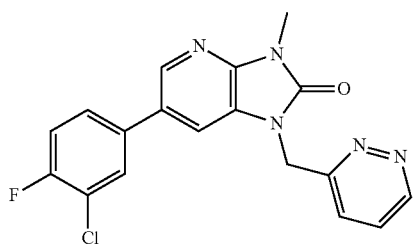

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridazine hydrochloride (Intermediate 2) in Step A and (3-chloro-4-fluorophenyl)boronic acid in Step B. MS (ESI): mass calcd. for $C_{18}H_{13}ClFN_5O$, 369.1; m/z found, 370.1 [M+H]$^+$. $^1$H NMR (500 MHz, DMSO-d$_6$) δ 9.16 (dd, J=4.6, 1.9 Hz, 1H), 8.38 (d, J=1.9 Hz, 1H), 7.93 (d, J=2.0 Hz, 1H), 7.91 (dd, J=7.1, 2.3 Hz, 1H), 7.72-7.65 (m, 3H), 7.51 (t, J=9.0 Hz, 1H), 5.48 (s, 2H), 3.42 (s, 3H).

Example 382: 6-[4-Fluoro-3-(trifluoromethyl)phenyl]-3-methyl-1-(pyridazin-3-ylmethyl)imidazo[4,5-b]pyridin-2-one

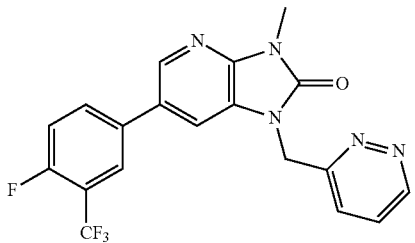 [SMILES: Cn1c(=O)n(Cc2cccnn2)c2cc(-c3ccc(F)c(C(F)(F)F)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridazine hydrochloride (Intermediate 2) in Step A and (4-fluoro-3-(trifluoromethyl)phenyl)boronic acid in Step B. MS (ESI): mass calcd. for $C_{19}H_{13}F_4N_5O$, 403.1; m/z found, 403.9 [M+H]$^+$. $^1$H NMR (400 MHz, DMSO-d$_6$) δ 9.15 (dd, J=4.4, 2.1 Hz, 1H), 8.41 (d, J=2.0 Hz, 1H), 8.08-7.96 (m, 3H), 7.72-7.59 (m, 3H), 5.49 (s, 2H), 3.42 (s, 3H).

Example 383: 6-[3-Fluoro-5-(trifluoromethyl)phenyl]-3-methyl-1-(pyridazin-3-ylmethyl)imidazo[4,5-b]pyridin-2-one

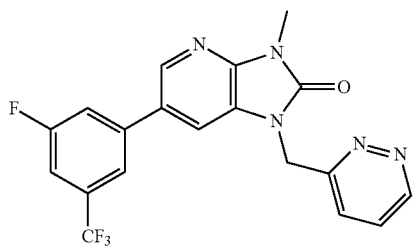 [SMILES: Cn1c(=O)n(Cc2cccnn2)c2cc(-c3cc(F)cc(C(F)(F)F)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridazine hydrochloride (Intermediate 2) in Step A and (3-fluoro-5-(trifluoromethyl)phenyl)boronic acid in Step B. MS (ESI): mass calcd. for $C_{19}H_{13}F_4N_5O$, 403.1; m/z found, 404.1 [M+H]$^+$. $^1$H NMR (500 MHz, DMSO-$d_6$) δ 9.15 (dd, J=4.6, 1.9 Hz, 1H), 8.51 (d, J=1.9 Hz, 1H), 8.07 (d, J=2.0 Hz, 1H), 7.96-7.92 (m, 1H), 7.91-7.89 (m, 1H), 7.71-7.64 (m, 3H), 5.50 (s, 2H), 3.43 (s, 3H).

Example 384: 6-[4-Chloro-3-(trifluoromethyl)phenyl]-3-methyl-1-(pyridazin-3-ylmethyl)imidazo[4,5-b]pyridin-2-one

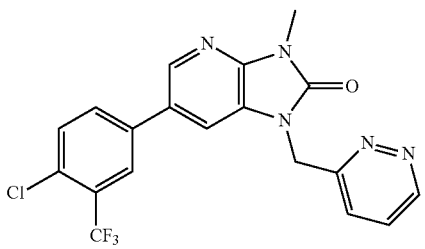 [SMILES: Cn1c(=O)n(Cc2cccnn2)c2cc(-c3ccc(Cl)c(C(F)(F)F)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridazine hydrochloride (Intermediate 2) in Step A and (4-chloro-3-(trifluoromethyl)phenyl)boronic acid in Step B. MS (ESI): mass calcd. for $C_{19}H_{13}ClF_3N_5O$, 419.1; m/z found, 419.9 [M+H]$^+$. $^1$H NMR (500 MHz, DMSO-$d_6$) δ 9.15 (dd, J=4.5, 2.0 Hz, 1H), 8.44 (d, J=1.9 Hz, 1H), 8.07 (d, J=2.2 Hz, 1H), 8.02-7.97 (m, 2H), 7.84-7.80 (m, 1H), 7.72-7.65 (m, 2H), 5.49 (s, 2H), 3.42 (s, 3H).

Example 385: 6-(5-(Difluoromethyl)-2-fluorophenyl)-3-methyl-1-(pyridazin-3-ylmethyl)-1,3-dihydro-2H-imidazo[4,5-b]pyridin-2-one and its Trifluoroacetic Acid Salt

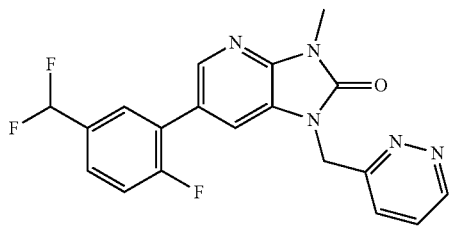 [SMILES: Cn1c(=O)n(Cc2cccnn2)c2cc(-c3cc(C(F)F)ccc3F)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridazine hydrochloride (Intermediate 2) in Step A and (5-(difluoromethyl)-2-fluorophenyl)boronic acid in Step B. MS (ESI): mass calcd. for $C_{19}H_{14}F_3N_5O$, 385.1; m/z found, 386.1 [M+H]$^+$. $^1$H NMR (400 MHz, DMSO-$d_6$) δ 9.16 (dd, J=4.2, 2.4 Hz, 1H), 8.23 (t, J=1.8 Hz, 1H), 7.77-7.62 (m, 5H), 7.53-7.46 (m, 1H), 7.08 (t, J=55.7 Hz, 1H), 5.47 (s, 2H), 3.43 (s, 3H).

Example 386: 6-(5-(Difluoromethyl)-2-fluorophenyl)-3-methyl-1-(pyridin-3-ylmethyl)-1,3-dihydro-2H-imidazo[4,5-b]pyridin-2-one and its Trifluoroacetic Acid Salt

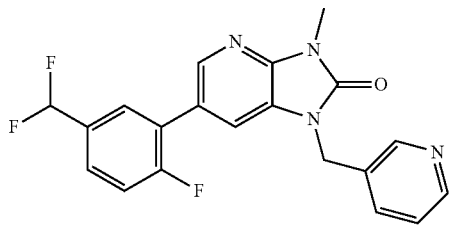 [SMILES: Cn1c(=O)n(Cc2cccnc2)c2cc(-c3cc(C(F)F)ccc3F)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridine hydrochloride in Step A and (5-(difluoromethyl)-2-fluorophenyl)boronic acid in Step B. MS (ESI): mass calcd. for $C_{20}H_{15}F_3N_4O$, 384.1; m/z found, 385.1 [M+H]$^+$. $^1$H NMR (400 MHz, DMSO-$d_6$) δ 8.80-8.77 (m, 1H), 8.66-8.63 (m, 1H), 8.22 (t, J=1.8 Hz, 1H), 8.09 (dt, J=8.1, 1.8 Hz, 1H), 7.85 (t, J=1.6 Hz, 1H), 7.78-7.73 (m, 1H), 7.70-7.62 (m, 2H), 7.54-7.47 (m, 1H), 7.09 (t, J=55.7 Hz, 1H), 5.27 (s, 2H), 3.42 (s, 3H).

Example 387: 6-[3,4-Difluoro-5-(trifluoromethyl)phenyl]-3-methyl-1-(pyridazin-3-ylmethyl)imidazo[4,5-b]pyridin-2-one

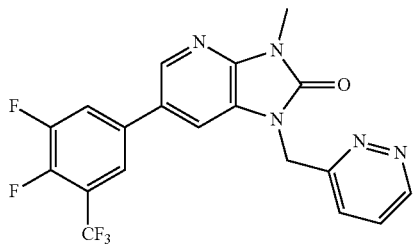 [SMILES: Cn1c(=O)n(Cc2cccnn2)c2cc(-c3cc(F)c(F)c(C(F)(F)F)c3)cnc21]

The title compound was prepared in a manner analogous to Example 33, Steps A-B, using 6-bromo-3-methyl-1,3-dihydro-2H-imidazo[4,5-b]pyridin-2-one (Intermediate 11) and 3-(chloromethyl)pyridazine hydrochloride (Intermediate 2) in Step A and (3,4-difluoro-5-(trifluoromethyl)phenyl)boronic acid in Step B. MS (ESI): mass calcd. for $C_{19}H_{12}F_5N_5O$, 421.1; m/z found, 429.1 [M+H]$^+$. $^1$H NMR (500 MHz, DMSO-d$_6$) δ 9.16 (dd, J=4.6, 1.9 Hz, 1H), 8.47 (d, J=2.0 Hz, 1H), 8.21 (ddd, J=11.7, 7.3, 2.2 Hz, 1H), 8.04 (d, J=2.0 Hz, 1H), 7.89-7.85 (m, 1H), 7.71-7.64 (m, 2H), 5.48 (s, 2H), 3.42 (s, 3H).

Example 388: 3-Methyl-1-(2-oxobutyl)-6-[3-(trifluoromethyl)phenyl]imidazo[4,5-b]pyridin-2-one

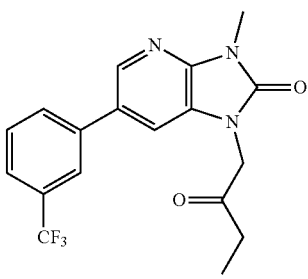 [SMILES: CCC(=O)Cn1c(=O)n(C)c2ncc(-c3cccc(C(F)(F)F)c3)cc21]

The title compound was prepared in a manner analogous to Example 33, Steps A-B, using 6-bromo-3-methyl-1,3-dihydro-2H-imidazo[4,5-b]pyridin-2-one (Intermediate 11) and 1-bromobutan-2-one in Step A; and (3-(trifluoromethyl)phenyl)boronic acid in Step B. MS (ESI): mass calcd. for $C_{18}H_{16}F_3N_3O_2$, 363.1; m/z found, 364.1 [M+H]$^+$. $^1$H NMR (500 MHz, DMSO-d$_6$) δ 8.41 (d, J=1.9 Hz, 1H), 8.01-7.96 (m, 2H), 7.89 (d, J=2.0 Hz, 1H), 7.77-7.70 (m, 2H), 4.92 (s, 2H), 3.41 (s, 3H), 2.63 (q, J=7.3 Hz, 2H), 0.99 (t, J=7.3 Hz, 3H).

Example 389: 6-(4-Fluoro-3-methyl-phenyl)-3-methyl-1-(2-oxobutyl)imidazo[4,5-b]pyridin-2-one and its Trifluoroacetic Acid Salt

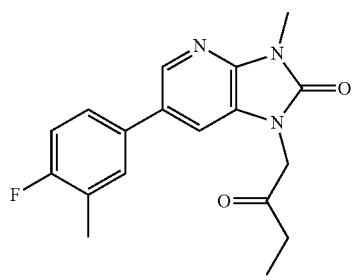 [SMILES: CCC(=O)Cn1c(=O)n(C)c2ncc(-c3ccc(F)c(C)c3)cc21]

The title compound was prepared in a manner analogous to Example 33, Steps A-B, using 6-bromo-3-methyl-1,3-dihydro-2H-imidazo[4,5-b]pyridin-2-one (Intermediate 11) and 1-bromobutan-2-one in Step A; and (4-fluoro-3-methylphenyl)boronic acid in Step B. MS (ESI): mass calcd. for $C_{18}H_{18}FN_3O_2$, 327.1; m/z found, 328.1[M+H]$^+$. $^1$H NMR (500 MHz, DMSO-d$_6$) δ 8.28 (d, J=1.9 Hz, 1H), 7.76 (d, J=1.9 Hz, 1H), 7.60-7.56 (m, 1H), 7.52-7.48 (m, 1H), 7.24 (dd, J=9.7, 8.5 Hz, 1H), 4.90 (s, 2H), 3.39 (s, 3H), 2.63 (q, J=7.3 Hz, 2H), 2.31 (d, J=1.9 Hz, 3H), 0.99 (t, J=7.3 Hz, 3H).

Example 390: 6-(3,4-Difluorophenyl)-3-methyl-1-(2-oxobutyl)imidazo[4,5-b]pyridin-2-one

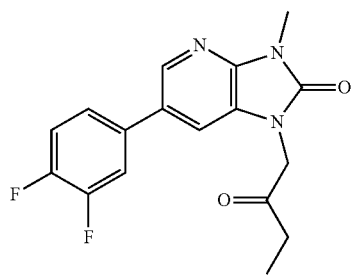 [SMILES: CCC(=O)Cn1c(=O)n(C)c2ncc(-c3ccc(F)c(F)c3)cc21]

The title compound was prepared in a manner analogous to Example 33, Steps A-B, using 6-bromo-3-methyl-1,3-dihydro-2H-imidazo[4,5-b]pyridin-2-one (Intermediate 11) and 1-bromobutan-2-one in Step A; and (3,4-difluorophenyl)boronic acid in Step B. MS (ESI): mass calcd. for $C_{17}H_{15}F_2N_3O_2$, 331.1; m/z found, 332.1 [M+H]$^+$. $^1$H NMR (500 MHz, DMSO-d$_6$) δ 8.36 (d, J=1.9 Hz, 1H), 7.82 (d, J=1.9 Hz, 1H), 7.81-7.75 (m, 1H), 7.59-7.51 (m, 2H), 4.89 (s, 2H), 3.39 (s, 3H), 2.63 (q, J=7.3 Hz, 2H), 0.99 (t, J=7.3 Hz, 3H).

Example 391: 6-(2,4-Difluoro-3-methyl-phenyl)-3-methyl-1-(2-oxobutyl)imidazo[4,5-b]pyridin-2-one and its Trifluoroacetic Acid Salt

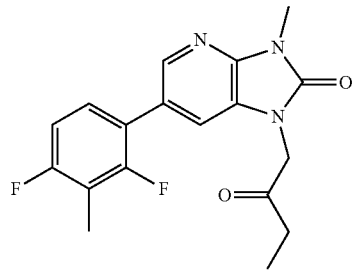 [SMILES: CCC(=O)Cn1c(=O)n(C)c2ncc(-c3ccc(F)c(C)c3F)cc21]

The title compound was prepared in a manner analogous to Example 33, Steps A-B, using 6-bromo-3-methyl-1,3-dihydro-2H-imidazo[4,5-b]pyridin-2-one (Intermediate 11) and 1-bromobutan-2-one in Step A; and (2,4-difluoro-3-methylphenyl)boronic acid in Step B. MS (ESI): mass calcd. for $C_{18}H_{17}F_2N_3O_2$, 345.1; m/z found, 346.1[M+H]$^+$. $^1$H NMR (500 MHz, DMSO-d$_6$) δ 8.12 (t, J=1.7 Hz, 1H), 7.63 (t, J=1.6 Hz, 1H), 7.39 (td, J=8.7, 6.5 Hz, 1H), 7.19 (td, J=8.7, 1.3 Hz, 1H), 4.89 (s, 2H), 3.40 (s, 3H), 2.61 (q, J=7.3 Hz, 2H), 2.22 (t, J=1.8 Hz, 3H), 0.97 (t, J=7.3 Hz, 3H).

Example 392: 6-(3-Cyclopropylphenyl)-3-methyl-1-(2-oxobutyl)imidazo[4,5-b]pyridin-2-one and its Trifluoroacetic Acid Salt

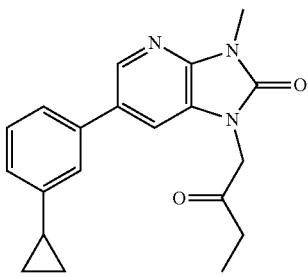 [SMILES: CCC(=O)Cn1c(=O)n(C)c2ncc(-c3cccc(C4CC4)c3)cc21]

The title compound was prepared in a manner analogous to Example 33, Steps A-B, using 6-bromo-3-methyl-1,3-dihydro-2H-imidazo[4,5-b]pyridin-2-one (Intermediate 11) and 1-bromobutan-2-one in Step A; and 2-(3-cyclopropylphenyl)-4,4,5,5-tetramethyl-1,3,2-dioxaborolane in Step B. MS (ESI): mass calcd. for $C_{20}H_{21}N_3O_2$, 335.2; m/z found, 336.1 [M+H]$^+$. $^1$H NMR (500 MHz, DMSO-d$_6$) δ 8.29 (d, J=1.9 Hz, 1H), 7.75 (d, J=1.9 Hz, 1H), 7.42-7.31 (m, 3H), 7.07-7.04 (m, 1H), 4.91 (s, 2H), 3.39 (s, 3H), 2.63 (q, J=7.3 Hz, 2H), 2.03-1.95 (m, 1H), 1.01-0.95 (m, 5H), 0.78-0.74 (m, 2H).

Example 393: (R/S)-6-(4-Fluoro-3-methyl-phenyl)-1-(2-hydroxy-4-methoxy-butyl)-3-methyl-imidazo[4,5-b]pyridin-2-one

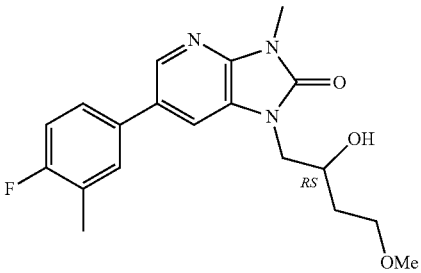 [SMILES: COCCC(O)Cn1c(=O)n(C)c2ncc(-c3ccc(F)c(C)c3)cc21]

The title compound was prepared in a manner analogous to Example 33, Step B; using 6-bromo-3-methyl-1-(oxetan-2-ylmethyl)-1,3-dihydro-2H-imidazo[4,5-b]pyridin-2-one (Intermediate 25) and (4-fluoro-3-methylphenyl)boronic acid. The title compound was isolated as a degraded product from the oxetane. MS (ESI): mass calcd. for $C_{19}H_{22}FN_3O_3$, 359.2; m/z found, 360.2 [M+H]$^+$. $^1$H NMR (400 MHz, DMSO-d$_6$) δ 8.25 (d, J=1.9 Hz, 1H), 7.79 (d, J=2.0 Hz, 1H), 7.63-7.59 (m, 1H), 7.55-7.49 (m, 1H), 7.30-7.22 (m, 1H), 4.93-4.88 (m, 1H), 3.98-3.77 (m, 3H), 3.47-3.42 (m, 2H), 3.40-3.37 (m, 3H), 3.22 (s, 3H), 2.37-2.30 (m, 3H), 1.77-1.67 (m, 1H), 1.63-1.53 (m, 1H).

Example 394: (R/S)-6-[3-(Difluoromethyl)phenyl]-3-methyl-1-(oxetan-2-ylmethyl)imidazo[4,5-b]pyridin-2-one

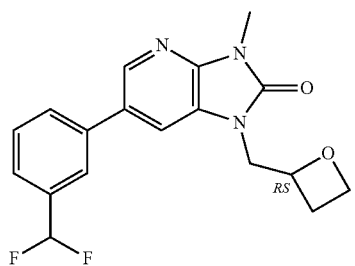 [SMILES: Cn1c(=O)n(CC2CCO2)c2cc(-c3cccc(C(F)F)c3)cnc21]

The title compound was prepared in a manner analogous to Example 33, Step B; using 6-bromo-3-methyl-1-(oxetan-2-ylmethyl)-1,3-dihydro-2H-imidazo[4,5-b]pyridin-2-one (Intermediate 25) and (3-(difluoromethyl)phenyl)boronic acid. MS (ESI): mass calcd. for $C_{18}H_{17}F_2N_3O_2$, 345.1; m/z found, 346.2 [M+H]$^+$. $^1$H NMR (500 MHz, DMSO-d$_6$) δ 8.35 (d, J=2.0 Hz, 1H), 7.94 (d, J=2.0 Hz, 1H), 7.90-7.85 (m, 2H), 7.67-7.56 (m, 2H), 7.11 (t, J=55.8 Hz, 1H), 5.10-5.02 (m, 1H), 4.49-4.42 (m, 1H), 4.36-4.30 (m, 1H), 4.19 (ddd, J=48.5, 14.9, 4.9 Hz, 2H), 3.41 (s, 3H), 2.71-2.62 (m, 1H).

Example 395: (R/S)-6-(4-Fluoro-3-methyl-phenyl)-3-methyl-1-(oxetan-2-ylmethyl)imidazo[4,5-b]pyridin-2-one

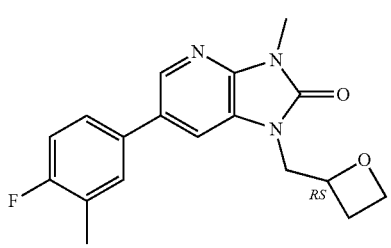 [SMILES: Cc1cc(-c2cnc3c(c2)n(CC2CCO2)c(=O)n3C)ccc1F]

The title compound was prepared in a manner analogous to Example 33, Step B; using 6-bromo-3-methyl-1-(oxetan-2-ylmethyl)-1,3-dihydro-2H-imidazo[4,5-b]pyridin-2-one (Intermediate 25) and (4-fluoro-3-methylphenyl)boronic acid. MS (ESI): mass calcd. for $C_{18}H_{18}FN_3O_2$, 327.1; m/z found, 328.2 $[M+H]^+$. $^1$H NMR (400 MHz, DMSO-$d_6$) δ 7.94 (d, J=1.8 Hz, 1H), 7.60 (d, J=1.9 Hz, 1H), 7.27 (dd, J=8.5, 6.1 Hz, 1H), 7.23-7.18 (m, 1H), 7.15-7.09 (m, 1H), 5.05-4.97 (m, 1H), 4.49-4.41 (m, 1H), 4.35-4.29 (m, 1H), 4.23-4.04 (m, 2H), 3.40 (s, 3H), 2.71-2.60 (m, 1H), 2.25 (s, 3H).

Example 396: (R/S)-6-[2-Fluoro-3-(trifluoromethyl)phenyl]-3-methyl-1-(oxetan-2-ylmethyl)imidazo[4,5-b]pyridin-2-one and its Trifluoroacetic Acid Salt

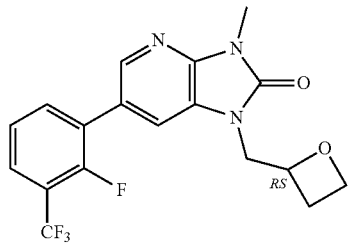 [SMILES: Cn1c(=O)n(CC2CCO2)c2cc(-c3cccc(C(F)(F)F)c3F)cnc21]

The title compound was prepared in a manner analogous to Example 33, Step B; using 6-bromo-3-methyl-1-(oxetan-2-ylmethyl)-1,3-dihydro-2H-imidazo[4,5-b]pyridin-2-one (Intermediate 25) and (4-fluoro-3-(trifluoromethyl)phenyl)boronic acid. MS (ESI): mass calcd. for $C_{18}H_{15}F_4N_3O_2$, 381.1; m/z found, 382.2 $[M+H]^+$. $^1$H NMR (400 MHz, DMSO-$d_6$) δ 8.21 (t, J=1.7 Hz, 1H), 7.91 (td, J=7.7, 1.7 Hz, 1H), 7.86-7.80 (m, 2H), 7.54 (t, J=7.8 Hz, 1H), 5.08-5.00 (m, 1H), 4.49-4.41 (m, 1H), 4.31 (dt, J=9.0, 6.0 Hz, 1H), 4.25-4.06 (m, 2H), 3.41 (s, 3H), 2.71-2.60 (m, 1H), 2.54-2.40 (m, 1H).

Example 397: (R/S)-6-(3-Chlorophenyl)-3-methyl-1-(oxetan-2-ylmethyl)imidazo[4,5-b]pyridin-2-one

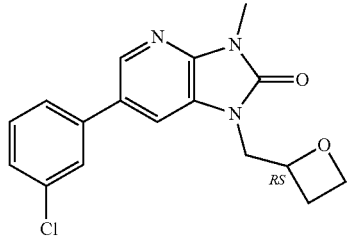 [SMILES: Cn1c(=O)n(CC2CCO2)c2cc(-c3cccc(Cl)c3)cnc21]

The title compound was prepared in a manner analogous to Example 33, Step B; using 6-bromo-3-methyl-1-(oxetan-2-ylmethyl)-1,3-dihydro-2H-imidazo[4,5-b]pyridin-2-one (Intermediate 25) and (3-chlorophenyl)boronic acid. MS (ESI): mass calcd. for $C_{17}H_{16}ClN_3O_2$, 329.1; m/z found, 330.1 $[M+H]^+$. $^1$H NMR (400 MHz, DMSO-$d_6$) δ 8.35 (d, J=2.0 Hz, 1H), 7.95 (d, J=2.0 Hz, 1H), 7.78 (t, J=1.9 Hz, 1H), 7.70-7.64 (m, 1H), 7.51 (t, J=7.8 Hz, 1H), 7.46-7.42 (m, 1H), 5.10-5.01 (m, 1H), 4.50-4.42 (m, 1H), 4.34 (dt, J=9.0, 5.9 Hz, 1H), 4.28-4.08 (m, 2H), 3.40 (s, 3H), 2.73-2.60 (m, 1H).

Example 398: (R/S)-3-Methyl-6-[2-methyl-3-(trifluoromethyl)phenyl]-1-(oxetan-2-ylmethyl)imidazo[4,5-b]pyridin-2-one

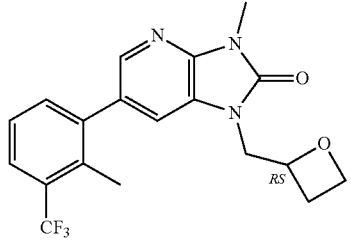 [SMILES: Cc1c(-c2cnc3c(c2)n(CC2CCO2)c(=O)n3C)cccc1C(F)(F)F]

The title compound was prepared in a manner analogous to Example 33, Step B; using 6-bromo-3-methyl-1-(oxetan-2-ylmethyl)-1,3-dihydro-2H-imidazo[4,5-b]pyridin-2-one (Intermediate 25) and (2-methyl-3-(trifluoromethyl)phenyl)boronic acid. MS (ESI): mass calcd. for $C_{19}H_{18}F_3N_3O_2$, 377.1; m/z found, 378.2 $[M+H]^+$. $^1$H NMR (400 MHz, DMSO-$d_6$) δ 7.97 (d, J=1.9 Hz, 1H), 7.78-7.73 (m, 1H), 7.64 (d, J=2.0 Hz, 1H), 7.57-7.47 (m, 2H), 5.05-4.97 (m, 1H), 4.49-4.40 (m, 1H), 4.36-4.28 (m, 1H), 4.24-4.03 (m, 2H), 3.41 (s, 3H), 2.71-2.59 (m, 1H), 2.35-2.28 (m, 3H).

Example 399: (R/S)-1-(2,4-Dihydroxybutyl)-3-methyl-6-[2-methyl-3-(trifluoromethyl)phenyl]imidazo[4,5-b]pyridin-2-one

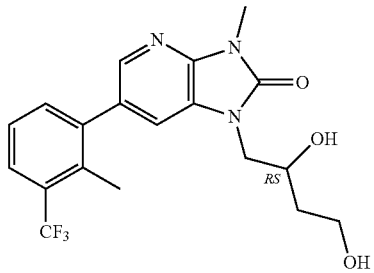 [SMILES: Cc1c(-c2cnc3c(c2)n(CC(O)CCO)c(=O)n3C)cccc1C(F)(F)F]

The title compound was prepared in a manner analogous to Example 33, Step B; using 6-bromo-3-methyl-1-(oxetan-2-ylmethyl)-1,3-dihydro-2H-imidazo[4,5-b]pyridin-2-one (Intermediate 25) and (2-methyl-3-(trifluoromethyl)phenyl)boronic acid, the oxetane decomposed to provide the title compound. MS (ESI): mass calcd. for $C_{19}H_{20}F_3N_3O_3$, 395.1; m/z found, 396.2 [M+H]$^+$. $^1$H NMR (500 MHz, DMSO-$d_6$) δ 7.94 (d, J=1.9 Hz, 1H), 7.78-7.73 (m, 1H), 7.59-7.47 (m, 3H), 4.83-4.77 (m, 1H), 4.41-4.34 (m, 1H), 3.97-3.89 (m, 1H), 3.88-3.76 (m, 2H), 3.57-3.45 (m, 2H), 2.35-2.30 (m, 3H), 1.64-1.55 (m, 1H), 1.54-1.46 (m, 1H).

Example 400: 6-(2,4-Difluoro-3-methyl-phenyl)-1-[2-(3-fluoroazetidin-1-yl)-2-oxo-ethyl]-3-methyl-imidazo[4,5-b]pyridin-2-one and its Trifluoroacetic Acid Salt

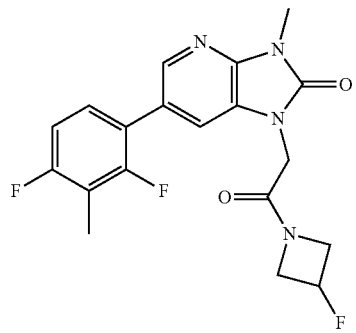 [SMILES: Cc1c(F)ccc(-c2cnc3c(c2)n(CC(=O)N2CC(F)C2)c(=O)n3C)c1F]

The title compound was prepared in a manner analogous to Example 34, using (2,4-difluoro-3-methylphenyl)boronic acid in Step B. MS (ESI): mass calcd. for $C_{19}H_{17}F_3N_4O_2$, 390.1; m/z found, 391.2 [M+H]$^+$. $^1$H NMR (400 MHz, DMSO-$d_6$) δ 8.12 (t, J=1.6 Hz, 1H), 7.64 (t, J=1.7 Hz, 1H), 7.44-7.35 (m, 1H), 7.24-7.15 (m, 1H), 5.57-5.33 (m, 1H), 4.74-4.54 (m, 3H), 4.46-4.33 (m, 1H), 4.30-4.17 (m, 1H), 4.03-3.88 (m, 1H), 3.39 (s, 3H), 2.23 (t, J=1.9 Hz, 3H).

Example 401: 1-[2-(3-Fluoroazetidin-1-yl)-2-oxo-ethyl]-6-(4-fluoro-3-methyl-phenyl)-3-methyl-imidazo[4,5-b]pyridin-2-one and its Trifluoroacetic Acid Salt

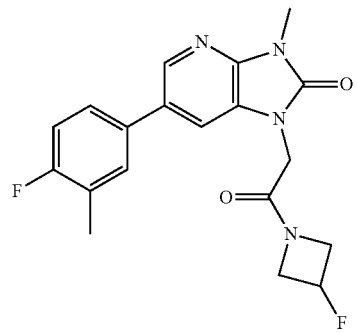 [SMILES: Cc1cc(-c2cnc3c(c2)n(CC(=O)N2CC(F)C2)c(=O)n3C)ccc1F]

The title compound was prepared in a manner analogous to Example 34, using (4-fluoro-3-methylphenyl)boronic acid in Step B.

MS (ESI): mass calcd. for $C_{19}H_{18}F_2N_4O_2$, 372.1; m/z found, 373.2 [M+H]$^+$. $^1$H NMR (500 MHz, DMSO-$d_6$) δ 8.28 (d, J=1.9 Hz, 1H), 7.76 (d, J=1.9 Hz, 1H), 7.61-7.57 (m, 1H), 7.52-7.48 (m, 1H), 7.28-7.23 (m, 1H), 5.56-5.37 (m, 1H), 4.74-4.58 (m, 3H), 4.46-4.35 (m, 1H), 4.29-4.19 (m, 1H), 4.03-3.90 (m, 1H), 3.38 (s, 3H), 2.32 (d, J=1.9 Hz, 3H).

Example 402: 1-[2-(3-Fluoroazetidin-1-yl)-2-oxo-ethyl]-3-methyl-6-(3,4,5-trifluorophenyl)imidazo[4,5-b]pyridin-2-one and its Trifluoroacetic Acid Salt

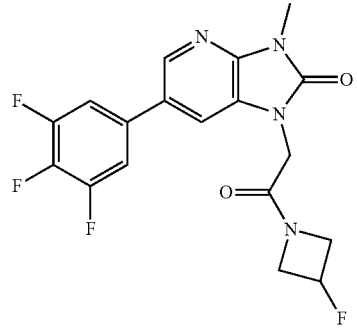 [SMILES: Cn1c(=O)n(CC(=O)N2CC(F)C2)c2cc(-c3cc(F)c(F)c(F)c3)cnc21]

The title compound was prepared in a manner analogous to Example 34, using (3,4,5-trifluorophenyl)boronic acid in Step B. MS (ESI): mass calcd. for $C_{18}H_{14}F_4N_4O_2$, 394.1; m/z found, 395.1 [M+H]$^+$. $^1$H NMR (400 MHz, DMSO-$d_6$) δ 8.41 (d, J=2.0 Hz, 1H), 7.87 (d, J=2.0 Hz, 1H), 7.77-7.67 (m, 2H), 5.60-5.36 (m, 1H), 4.73-4.58 (m, 3H), 4.48-4.34 (m, 1H), 4.32-4.19 (m, 1H), 4.04-3.90 (m, 1H), 3.39 (s, 3H).

Example 403: 6-(3,4-Difluorophenyl)-1-[2-(3-fluoroazetidin-1-yl)-2-oxo-ethyl]-3-methyl-imidazo[4,5-b]pyridin-2-one and its Trifluoroacetic Acid Salt

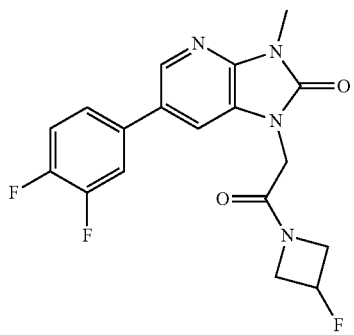 [SMILES: Cn1c(=O)n(CC(=O)N2CC(F)C2)c2cc(-c3ccc(F)c(F)c3)cnc21]

The title compound was prepared in a manner analogous to Example 34, using (3,4-difluorophenyl)boronic acid in Step B. MS (ESI): mass calcd. for $C_{18}H_{15}F_3N_4O_2$, 376.1; m/z found, 377.1 [M+H]$^+$. $^1$H NMR (400 MHz, DMSO-d$_6$) δ 8.35 (d, J=2.0 Hz, 1H), 7.84-7.75 (m, 2H), 7.61-7.51 (m, 2H), 5.59-5.35 (m, 1H), 4.74-4.57 (m, 3H), 4.47-4.34 (m, 1H), 4.31-4.18 (m, 1H), 4.04-3.91 (m, 1H), 3.39 (s, 3H).

Example 404: 1-[2-(3-Fluoroazetidin-1-yl)-2-oxo-ethyl]-3-methyl-6-(m-tolyl)imidazo[4,5-b]pyridin-2-one and its Trifluoroacetic Acid Salt

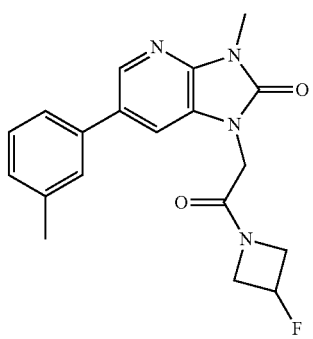

The title compound was prepared in a manner analogous to Example 34, using m-tolylboronic acid in Step B. MS (ESI): mass calcd. for $C_{19}H_{19}FN_4O_2$, 354.1; m/z found, 355.2 [M+H]$^+$. $^1$H NMR (400 MHz, DMSO-d$_6$) δ 8.29 (d, J=1.9 Hz, 1H), 7.77 (d, J=1.9 Hz, 1H), 7.51-7.42 (m, 2H), 7.37 (t, J=7.6 Hz, 1H), 7.22-7.18 (m, 1H), 5.58-5.36 (m, 1H), 4.75-4.57 (m, 3H), 4.48-4.34 (m, 1H), 4.31-4.18 (m, 1H), 4.04-3.89 (m, 1H), 3.39 (s, 3H), 2.39 (s, 3H).

Example 405: 1-[2-(3-Fluoroazetidin-1-yl)-2-oxo-ethyl]-6-(2-fluoro-3-methyl-phenyl)-3-methyl-imidazo[4,5-b]pyridin-2-one and its Trifluoroacetic Acid Salt

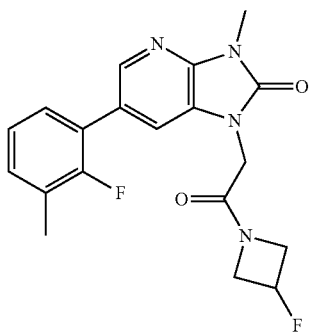 [SMILES: Cc1cccc(-c2cnc3c(c2)n(CC(=O)N2CC(F)C2)c(=O)n3C)c1F]

The title compound was prepared in a manner analogous to Example 34, using (2-fluoro-3-methylphenyl)boronic acid in Step B. MS (ESI): mass calcd. for $C_{19}H_{18}F_2N_4O_2$, 372.1; m/z found, 373.2 [M+H]$^+$. $^1$H NMR (400 MHz, DMSO-d$_6$) δ 8.14 (t, J=1.6 Hz, 1H), 7.65 (t, J=1.7 Hz, 1H), 7.36-7.30 (m, 2H), 7.24-7.17 (m, 1H), 5.57-5.33 (m, 1H), 4.73-4.56 (m, 3H), 4.46-4.33 (m, 1H), 4.30-4.17 (m, 1H), 4.02-3.90 (m, 1H), 3.40 (s, 3H), 2.31 (d, J=2.2 Hz, 3H).

Example 406: 6-(3-Chlorophenyl)-1-[2-(3-fluoro-azetidin-1-yl)-2-oxo-ethyl]-3-methyl-imidazo[4,5-b]pyridin-2-one and its Trifluoroacetic Acid Salt

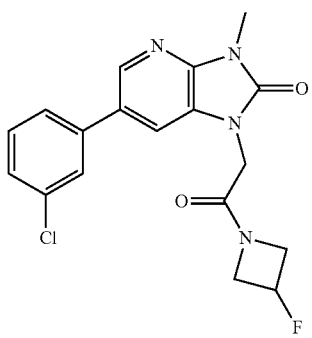 [SMILES: Cn1c(=O)n(CC(=O)N2CC(F)C2)c2cc(-c3cccc(Cl)c3)cnc21]

The title compound was prepared in a manner analogous to Example 34, using (3-chlorophenyl)boronic acid in Step B. MS (ESI): mass calcd. for $C_{18}H_{16}ClFN_4O_2$, 374.1; m/z found, 375.1 [M+H]$^+$. $^1$H NMR (400 MHz, DMSO-d$_6$) δ 8.36 (d, J=1.9 Hz, 1H), 7.85 (d, J=2.0 Hz, 1H), 7.75 (t, J=1.9 Hz, 1H), 7.69-7.64 (m, 1H), 7.52 (t, J=7.8 Hz, 1H), 7.47-7.42 (m, 1H), 5.58-5.36 (m, 1H), 4.76-4.57 (m, 3H), 4.48-4.34 (m, 1H), 4.33-4.17 (m, 1H), 4.06-3.90 (m, 1H), 3.39 (s, 3H).

Example 407: 1-[2-(3-Fluoroazetidin-1-yl)-2-oxo-ethyl]-6-[4-fluoro-3-(trifluoromethyl)phenyl]-3-methyl-imidazo[4,5-b]pyridin-2-one and its Trifluoroacetic Acid Salt

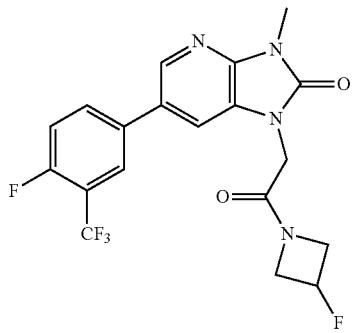 [SMILES: Cn1c(=O)n(CC(=O)N2CC(F)C2)c2cc(-c3ccc(F)c(C(F)(F)F)c3)cnc21]

The title compound was prepared in a manner analogous to Example 34, using (4-fluoro-3-(trifluoromethyl)phenyl)boronic acid in Step B. MS (ESI): mass calcd. for $C_{19}H_{15}F_5N_4O_2$, 426.1; m/z found, 427.1 [M+H]$^+$. $^1$H NMR (500 MHz, DMSO-$d_6$) δ 8.38 (d, J=1.9 Hz, 1H), 8.07-8.02 (m, 1H), 8.02-7.98 (m, 1H), 7.87 (d, J=2.0 Hz, 1H), 7.69-7.63 (m, 1H), 5.57-5.38 (m, 1H), 4.75-4.57 (m, 3H), 4.46-4.35 (m, 1H), 4.31-4.18 (m, 1H), 4.03-3.90 (m, 1H), 3.40 (s, 3H).

Example 408: 1-[2-(Azetidin-1-yl)-2-oxo-ethyl]-3-methyl-6-[3-(trifluoromethyl)phenyl]imidazo[4,5-b]pyridin-2-one and its Trifluoroacetic Acid Salt

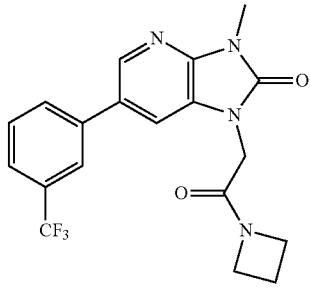 [SMILES: Cn1c(=O)n(CC(=O)N2CCC2)c2cc(-c3cccc(C(F)(F)F)c3)cnc21]

The title compound was prepared in a manner analogous to Example 34, using azetidine in Step A. MS (ESI): mass calcd. for $C_{19}H_{17}F_3N_4O_2$, 390.1; m/z found, 391.2 [M+H]$^+$. $^1$H NMR (500 MHz, DMSO-$d_6$) δ 8.40 (d, J=2.0 Hz, 1H), 8.04-7.97 (m, 2H), 7.90 (d, J=2.0 Hz, 1H), 7.78-7.69 (m, 2H), 4.63 (s, 2H), 4.29 (t, J=7.7 Hz, 2H), 3.91 (t, J=7.7 Hz, 2H), 3.40 (s, 3H), 2.33-2.24 (m, 2H).

Example 409: 1-[2-(Azetidin-1-yl)-2-oxo-ethyl]-6-(2,4-difluoro-3-methyl-phenyl)-3-methyl-imidazo[4,5-b]pyridin-2-one and its Trifluoroacetic Acid Salt

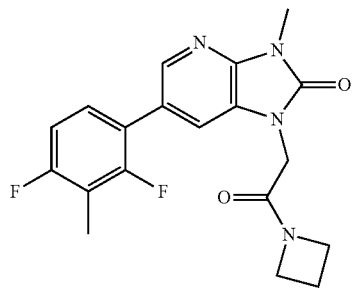 [SMILES: Cc1c(F)ccc(-c2cnc3c(c2)n(CC(=O)N2CCC2)c(=O)n3C)c1F]

The title compound was prepared in a manner analogous to Example 34, using azetidine in Step A and (2,4-difluoro-3-methylphenyl)boronic acid in Step B. MS (ESI): mass calcd. for $C_{19}H_{18}F_2N_4O_2$, 372.1; m/z found, 373.2 [M+H]$^+$. $^1$H NMR (500 MHz, DMSO-$d_6$) δ 8.12 (t, J=1.7 Hz, 1H), 7.63 (t, J=1.7 Hz, 1H), 7.43-7.37 (m, 1H), 7.22-7.17 (m, 1H), 4.59 (s, 2H), 4.27 (t, J=7.6 Hz, 2H), 3.89 (t, J=7.7 Hz, 2H), 3.39 (s, 3H), 2.33-2.21 (m, 5H).

Example 410: 1-[2-(Azetidin-1-yl)-2-oxo-ethyl]-6-(4-fluoro-3-methyl-phenyl)-3-methyl-imidazo[4,5-b]pyridin-2-one and its Trifluoroacetic Acid Salt

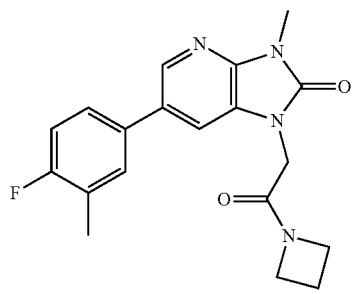 [SMILES: Cc1cc(-c2cnc3c(c2)n(CC(=O)N2CCC2)c(=O)n3C)ccc1F]

The title compound was prepared in a manner analogous to Example 34, using azetidine in Step A and (4-fluoro-3-methylphenyl)boronic acid in Step B. MS (ESI): mass calcd. for $C_{19}H_{19}FN_4O_2$, 354.1; m/z found, 355.2 [M+H]$^+$. $^1$H NMR (500 MHz, DMSO-$d_6$) δ 8.27 (d, J=1.9 Hz, 1H), 7.76 (d, J=1.9 Hz, 1H), 7.62-7.58 (m, 1H), 7.53-7.49 (m, 1H), 7.28-7.23 (m, 1H), 4.60 (s, 2H), 4.29 (t, J=7.6 Hz, 2H), 3.90 (t, J=7.7 Hz, 2H), 3.38 (s, 3H), 2.33-2.24 (m, 5H).

Example 411: 1-[2-(Azetidin-1-yl)-2-oxo-ethyl]-3-methyl-6-(3,4,5-trifluorophenyl)imidazo[4,5-b]pyridin-2-one and its Trifluoroacetic Acid Salt

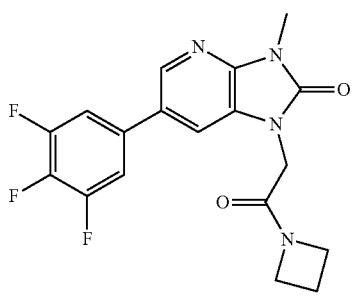 [SMILES: Cn1c(=O)n(CC(=O)N2CCC2)c2cc(-c3cc(F)c(F)c(F)c3)cnc21]

The title compound was prepared in a manner analogous to Example 34, using azetidine in Step A and (3,4,5-trifluorophenyl)boronic acid in Step B. MS (ESI): mass calcd. for $C_{18}H_{15}F_3N_4O_2$, 376.1; m/z found, 377.1 [M+H]$^+$. $^1$H NMR (500 MHz, DMSO-d$_6$) δ 8.41 (d, J=2.0 Hz, 1H), 7.88 (d, J=2.1 Hz, 1H), 7.77-7.69 (m, 2H), 4.59 (s, 2H), 4.29 (t, J=7.7 Hz, 2H), 3.91 (t, J=7.7 Hz, 2H), 3.38 (s, 3H), 2.34-2.24 (m, 2H).

Example 412: 1-[2-(Azetidin-1-yl)-2-oxo-ethyl]-6-(3,5-difluorophenyl)-3-methyl-imidazo[4,5-b]pyridin-2-one

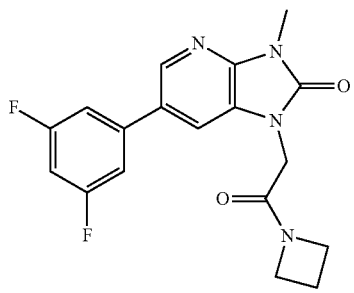 [SMILES: Cn1c(=O)n(CC(=O)N2CCC2)c2cc(-c3cc(F)cc(F)c3)cnc21]

The title compound was prepared in a manner analogous to Example 34, using azetidine in Step A and (3,5-difluorophenyl)boronic acid in Step B. MS (ESI): mass calcd. for $C_{18}H_{16}F_2N_4O_2$, 358.1; m/z found, 359.2 [M+H]$^+$. $^1$H NMR (500 MHz, DMSO-d$_6$) δ 8.43 (d, J=2.0 Hz, 1H), 7.90 (d, J=2.0 Hz, 1H), 7.53-7.46 (m, 2H), 7.29-7.22 (m, 1H), 4.60 (s, 2H), 4.29 (t, J=7.6 Hz, 2H), 3.91 (t, J=7.7 Hz, 2H), 3.39 (s, 3H), 2.34-2.25 (m, 2H).

Example 413: 1-(2-(3,3-Difluoroazetidin-1-yl)-2-oxoethyl)-6-(4-fluoro-3-methylphenyl)-3-methyl-1H-imidazo[4,5-b]pyridin-2(3H)-one

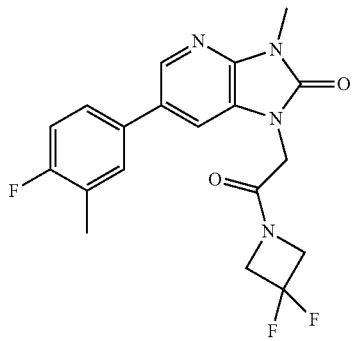 [SMILES: Cc1cc(-c2cnc3c(c2)n(CC(=O)N2CC(F)(F)C2)c(=O)n3C)ccc1F]

The title compound was prepared in a manner analogous to Example 34, using 3,3-difluoroazetidine hydrochloride in Step A and (4-fluoro-3-methylphenyl)boronic acid in Step B. MS (ESI): mass calcd. for $C_{19}H_{17}F_3N_4O_2$, 390.1; m/z found, 391.2 [M+H]$^+$. $^1$H NMR (500 MHz, DMSO-d$_6$) δ 8.28 (d, J=1.9 Hz, 1H), 7.76 (d, J=1.9 Hz, 1H), 7.60-7.56 (m, 1H), 7.52-7.47 (m, 1H), 7.28-7.24 (m, 1H), 4.82 (t, J=12.3 Hz, 2H), 4.75 (s, 2H), 4.38 (t, J=12.5 Hz, 2H), 3.39 (s, 3H), 2.32 (d, J=1.9 Hz, 3H).

Example 414: 1-[2-(3,3-Difluoroazetidin-1-yl)-2-oxo-ethyl]-6-(2,4-difluoro-3-methyl-phenyl)-3-methyl-imidazo[4,5-b]pyridin-2-one and its Trifluoroacetic Acid Salt

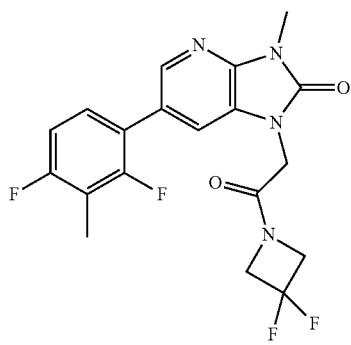 [SMILES: Cc1c(F)ccc(-c2cnc3c(c2)n(CC(=O)N2CC(F)(F)C2)c(=O)n3C)c1F]

The title compound was prepared in a manner analogous to Example 34, using 3,3-difluoroazetidine hydrochloride in Step A and (2,4-difluoro-3-methylphenyl)boronic acid in Step B. MS (ESI): mass calcd. for $C_{19}H_{16}F_4N_4O_2$, 408.1; m/z found, 409.2 [M+H]$^+$. $^1$H NMR (500 MHz, DMSO-d$_6$) δ 8.12 (t, J=1.6 Hz, 1H), 7.65 (t, J=1.6 Hz, 1H), 7.43-7.36 (m, 1H), 7.23-7.17 (m, 1H), 4.81 (t, J=12.4 Hz, 2H), 4.74 (s, 2H), 4.36 (t, J=12.5 Hz, 2H), 3.40 (s, 3H), 2.23 (t, J=1.9 Hz, 3H).

Example 415: 1-[2-(3,3-Difluoroazetidin-1-yl)-2-oxo-ethyl]-6-[2-fluoro-3-(trifluoromethyl)phenyl]-3-methyl-imidazo[4,5-b]pyridin-2-one and its Trifluoroacetic Acid Salt

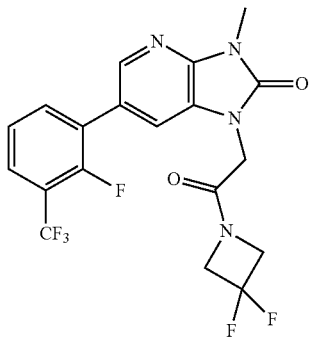 [SMILES: Cn1c(=O)n(CC(=O)N2CC(F)(F)C2)c2cc(-c3cccc(C(F)(F)F)c3F)cnc21]

The title compound was prepared in a manner analogous to Example 34, using 3,3-difluoroazetidine hydrochloride in Step A and (2-fluoro-3-(trifluoromethyl)phenyl)boronic acid in step B. MS (ESI): mass calcd. for $C_{19}H_{14}F_6N_4O_2$, 444.1; m/z found, 445.2 [M+H]$^+$. $^1$H NMR (400 MHz, DMSO-d$_6$)

δ 8.20 (t, J=1.6 Hz, 1H), 7.92-7.81 (m, 2H), 7.73 (t, J=1.7 Hz, 1H), 7.55 (t, J=7.8 Hz, 1H), 4.86-4.73 (m, 4H), 4.36 (t, J=12.5 Hz, 2H), 3.41 (s, 3H).

Example 416: 1-[2-(3,3-Difluoroazetidin-1-yl)-2-oxo-ethyl]-6-(3,4-difluorophenyl)-3-methyl-imidazo[4,5-b]pyridin-2-one and its Trifluoroacetic Acid Salt

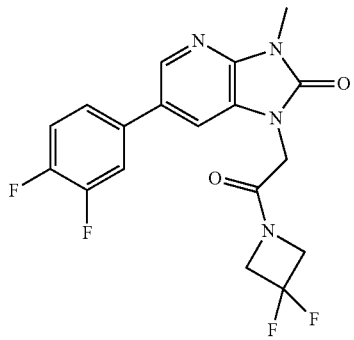 [SMILES: Cn1c(=O)n(CC(=O)N2CC(F)(F)C2)c2cc(-c3ccc(F)c(F)c3)cnc21]

The title compound was prepared in a manner analogous to Example 34, using 3,3-difluoroazetidine hydrochloride in Step A and (3,4-difluorophenyl)boronic acid in Step B. MS (ESI): mass calcd. for $C_{18}H_{14}F_4N_4O_2$, 394.1; m/z found, 395.2 [M+H]$^+$. $^1$H NMR (400 MHz, DMSO-d$_6$) δ 8.35 (d, J=1.9 Hz, 1H), 7.83 (d, J=2.0 Hz, 1H), 7.81-7.75 (m, 1H), 7.61-7.51 (m, 2H), 4.82 (t, J=12.4 Hz, 2H), 4.75 (s, 2H), 4.38 (t, J=12.5 Hz, 2H), 3.39 (s, 3H).

Example 417: 1-[2-(3,3-Difluoroazetidin-1-yl)-2-oxo-ethyl]-6-(3-fluorophenyl)-3-methyl-imidazo[4,5-b]pyridin-2-one and its Trifluoroacetic Acid Salt

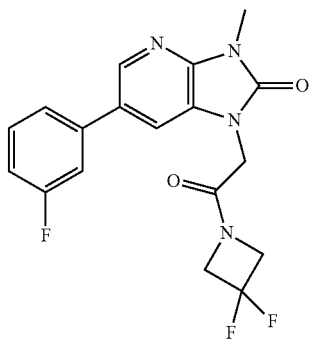

The title compound was prepared in a manner analogous to Example 34, using 3,3-difluoroazetidine hydrochloride in Step A and (3-fluorophenyl)boronic acid in step B. MS (ESI): mass calcd. for $C_{18}H_{15}F_3N_4O_2$, 376.1; m/z found, 377.2 [M+H]$^+$. $^1$H NMR (400 MHz, DMSO-d$_6$) δ 8.38 (d, J=1.9 Hz, 1H), 7.85 (d, J=2.0 Hz, 1H), 7.58-7.49 (m, 3H), 7.26-7.18 (m, 1H), 4.82 (t, J=12.4 Hz, 2H), 4.76 (s, 2H), 4.38 (t, J=12.5 Hz, 2H), 3.40 (s, 3H).

Example 418: 1-[2-(3,3-Difluoroazetidin-1-yl)-2-oxo-ethyl]-6-(2-fluoro-3-methyl-phenyl)-3-methyl-imidazo[4,5-b]pyridin-2-one

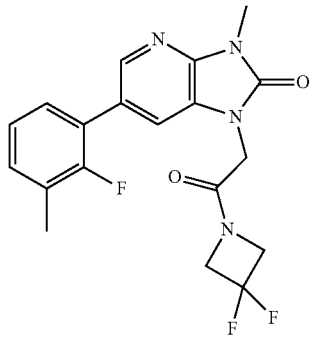 [SMILES: Cc1cccc(-c2cnc3c(c2)n(CC(=O)N2CC(F)(F)C2)c(=O)n3C)c1F]

The title compound was prepared in a manner analogous to Example 34, using 3,3-difluoroazetidine hydrochloride in Step A and (2-fluoro-3-methylphenyl)boronic acid in step B. MS (ESI): mass calcd. for $C_{19}H_{17}F_3N_4O_2$, 390.1; m/z found, 391.2 [M+H]$^+$. $^1$H NMR (400 MHz, DMSO-d$_6$) δ 8.15 (t, J=1.6 Hz, 1H), 7.67 (t, J=1.8 Hz, 1H), 7.36-7.29 (m, 2H), 7.25-7.18 (m, 1H), 4.87-4.69 (m, 4H), 4.36 (t, J=12.5 Hz, 2H), 3.40 (s, 3H), 2.31 (d, J=2.2 Hz, 3H).

Example 419: N,N-Dimethyl-2-[3-methyl-2-oxo-6-[3-(trifluoromethyl)phenyl]imidazo[4,5-b]pyridin-1-yl]acetamide and its Trifluoroacetic Acid Salt

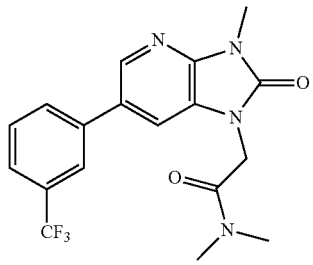 [SMILES: CN(C)C(=O)Cn1c(=O)n(C)c2ncc(-c3cccc(C(F)(F)F)c3)cc21]

The title compound was prepared in a manner analogous to Example 34, using dimethylamine hydrochloride in Step A. MS (ESI): mass calcd. for $C_{18}H_{17}F_3N_4O_2$, 378.1; m/z found, 379.2 [M+H]$^+$. $^1$H NMR (400 MHz, DMSO-d$_6$) δ 8.40 (d, J=2.0 Hz, 1H), 8.03-7.96 (m, 2H), 7.90 (d, J=2.0 Hz, 1H), 7.77-7.69 (m, 2H), 4.87 (s, 2H), 3.40 (s, 3H), 3.11 (s, 3H), 2.85 (s, 3H).

Example 420: 2-[6-(4-Fluoro-3-methyl-phenyl)-3-methyl-2-oxo-imidazo[4,5-b]pyridin-1-yl]-N,N-dimethyl-acetamide and its Trifluoroacetic Acid Salt

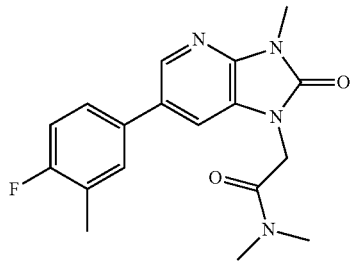

The title compound was prepared in a manner analogous to Example 34, using dimethylamine hydrochloride in Step A and (4-fluoro-3-methylphenyl)boronic acid in step B. MS (ESI): mass calcd. for $C_{18}H_{19}FN_4O_2$, 342.1; m/z found, 343.2 [M+H]$^+$. $^1$H NMR (400 MHz, DMSO-d$_6$) δ 8.27 (d, J=1.9 Hz, 1H), 7.76 (d, J=1.9 Hz, 1H), 7.61-7.57 (m, 1H), 7.53-7.47 (m, 1H), 7.24 (t, J=9.1 Hz, 1H), 4.85 (s, 2H), 3.38 (s, 3H), 3.10 (s, 3H), 2.84 (s, 3H), 2.31 (d, J=1.9 Hz, 3H).

Example 421: 2-[6-(3,4-Difluorophenyl)-3-methyl-2-oxo-imidazo[4,5-b]pyridin-1-yl]-N,N-dimethyl-acetamide and its Trifluoroacetic Acid Salt

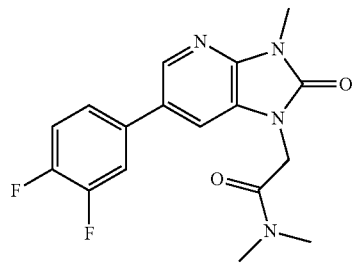 [SMILES: CN(C)C(=O)Cn1c(=O)n(C)c2ncc(-c3ccc(F)c(F)c3)cc21]

The title compound was prepared in a manner analogous to Example 34, using dimethylamine hydrochloride in Step A and (3,4-difluorophenyl)boronic acid in step B. MS (ESI): mass calcd. for $C_{17}H_{16}F_2N_4O_2$, 346.1; m/z found, 347.2 [M+H]$^+$. $^1$H NMR (400 MHz, DMSO-d$_6$) δ 8.35 (d, J=2.0 Hz, 1H), 7.84 (d, J=2.0 Hz, 1H), 7.83-7.75 (m, 1H), 7.60-7.50 (m, 2H), 4.84 (s, 2H), 3.39 (s, 3H), 3.11 (s, 3H), 2.85 (s, 3H).

Example 422: 1-[2-(Azetidin-1-yl)-2-oxo-ethyl]-6-(3,4-difluorophenyl)-3-methyl-imidazo[4,5-b]pyridin-2-one

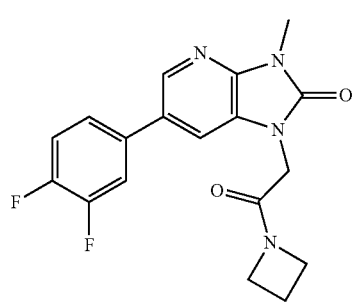 [SMILES: Cn1c(=O)n(CC(=O)N2CCC2)c2cc(-c3ccc(F)c(F)c3)cnc21]

The title compound was prepared in a manner analogous to Example 34, using azetidine in Step A and (3,4-difluorophenyl)boronic acid in Step B. MS (ESI): mass calcd. for $C_{18}H_{16}F_2N_4O_2$, 358.1; m/z found, 359.2 [M+H]$^+$. $^1$H NMR (400 MHz, DMSO-d$_6$) δ 8.35 (d, J=1.9 Hz, 1H), 7.84-7.76 (m, 2H), 7.61-7.52 (m, 2H), 4.60 (s, 2H), 4.29 (t, J=7.6 Hz, 2H), 3.91 (t, J=7.7 Hz, 2H), 3.38 (s, 3H), 2.35-2.23 (m, 2H).

Example 423: 2-[6-(2,4-Difluoro-3-methyl-phenyl)-3-methyl-2-oxo-imidazo[4,5-b]pyridin-1-yl]-N,N-dimethyl-acetamide and its Trifluoroacetic Acid Salt

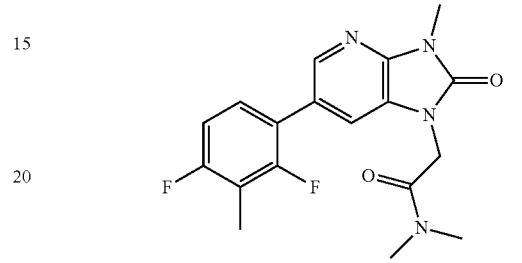

The title compound was prepared in a manner analogous to Example 34, using dimethylamine hydrochloride in Step A and (2,4-difluoro-3-methylphenyl)boronic acid in step B. MS (ESI): mass calcd. for $C_{18}H_{18}F_2N_4O_2$, 360.1; m/z found, 361.2 [M+H]$^+$. $^1$H NMR (400 MHz, DMSO-d$_6$) δ 8.11 (t, J=1.7 Hz, 1H), 7.64 (t, J=1.7 Hz, 1H), 7.43-7.35 (m, 1H), 7.19 (td, J=8.8, 1.4 Hz, 1H), 4.84 (s, 2H), 3.39 (s, 3H), 3.08 (s, 3H), 2.83 (s, 3H), 2.23 (t, J=1.9 Hz, 3H).

Example 424: 2-[6-[2-Fluoro-3-(trifluoromethyl)phenyl]-3-methyl-2-oxo-imidazo[4,5-b]pyridin-1-yl]-N,N-dimethyl-acetamide and its Trifluoroacetic Acid Salt

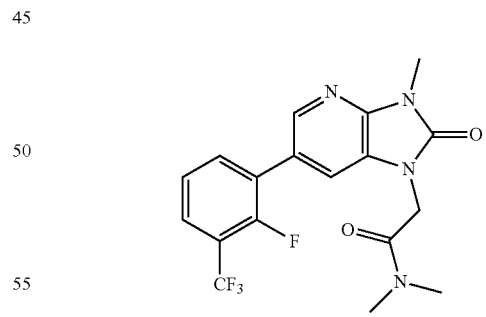

The title compound was prepared in a manner analogous to Example 34, using dimethylamine hydrochloride in Step A and (2-fluoro-3-(trifluoromethyl)phenyl)boronic acid in step B. MS (ESI): mass calcd. for $C_{18}H_{16}F_4N_4O_2$, 396.1; m/z found, 397.1[M+H]$^+$. $^1$H NMR (500 MHz, DMSO-d$_6$) δ 8.19 (t, J=1.6 Hz, 1H), 7.91-7.86 (m, 1H), 7.85-7.80 (m, 1H), 7.73 (t, J=1.7 Hz, 1H), 7.54 (t, J=7.8 Hz, 1H), 4.85 (s, 2H), 3.41 (s, 3H), 3.08 (s, 3H), 2.83 (s, 3H).

Example 425: 2-[6-(2,3-Difluorophenyl)-3-methyl-2-oxo-imidazo[4,5-b]pyridin-1-yl]-N,N-dimethyl-acetamide and its Trifluoroacetic Acid Salt

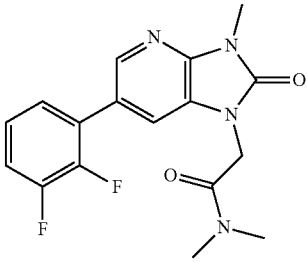 [SMILES: CN(C)C(=O)Cn1c(=O)n(C)c2ncc(-c3cccc(F)c3F)cc21]

The title compound was prepared in a manner analogous to Example 34, using dimethylamine hydrochloride in Step A and (2,3-difluorophenyl)boronic acid in step B. MS (ESI): mass calcd. for $C_{17}H_{16}F_2N_4O_2$, 346.1; m/z found, 347.2 [M+H]$^+$. $^1$H NMR (500 MHz, DMSO-d$_6$) δ 8.19 (t, J=1.7 Hz, 1H), 7.71 (t, J=1.6 Hz, 1H), 7.51-7.43 (m, 1H), 7.39-7.29 (m, 2H), 4.84 (s, 2H), 3.40 (s, 3H), 3.09 (s, 3H), 2.83 (s, 3H).

Example 426: 2-[6-[3-(Difluoromethyl)phenyl]-3-methyl-2-oxo-imidazo[4,5-b]pyridin-1-yl]-N,N-dimethyl-acetamide and its Trifluoroacetic Acid Salt

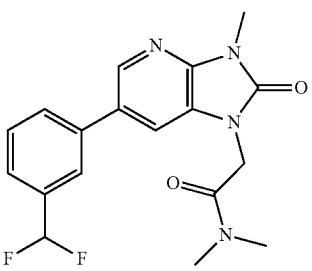 [SMILES: CN(C)C(=O)Cn1c(=O)n(C)c2ncc(-c3cccc(C(F)F)c3)cc21]

The title compound was prepared in a manner analogous to Example 34, using dimethylamine hydrochloride in Step A and (3-(difluoromethyl)phenyl)boronic acid in step B. MS (ESI): mass calcd. for $C_{18}H_{18}F_2N_4O_2$, 360.1; m/z found, 361.2 [M+H]$^+$. $^1$H NMR (500 MHz, DMSO-d$_6$) δ 8.35 (d, J=1.9 Hz, 1H), 7.90-7.80 (m, 3H), 7.67-7.56 (m, 2H), 7.11 (t, J=55.8 Hz, 1H), 4.87 (s, 2H), 3.40 (s, 3H), 3.11 (s, 3H), 2.85 (s, 3H).

Example 427: 2-[6-(2-Fluoro-3-methyl-phenyl)-3-methyl-2-oxo-imidazo[4,5-b]pyridin-1-yl]-N,N-dimethyl-acetamide and its Trifluoroacetic Acid Salt

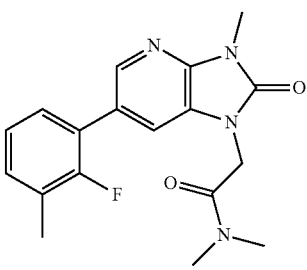 [SMILES: Cc1cccc(-c2cnc3c(c2)n(CC(=O)N(C)C)c(=O)n3C)c1F]

The title compound was prepared in a manner analogous to Example 34, using dimethylamine hydrochloride in Step A and (2-fluoro-3-methylphenyl)boronic acid in step B. MS (ESI): mass calcd. for $C_{18}H_{19}FN_4O_2$, 342.1; m/z found, 343.2 [M+H]$^+$. $^1$H NMR (500 MHz, DMSO-d$_6$) δ 8.14 (t, J=1.7 Hz, 1H), 7.65 (t, J=1.6 Hz, 1H), 7.36-7.29 (m, 2H), 7.22-7.18 (m, 1H), 4.84 (s, 2H), 3.40 (s, 3H), 3.08 (s, 3H), 2.83 (s, 3H), 2.31 (d, J=2.1 Hz, 3H).

Example 428: 2-[6-(3,5-Difluorophenyl)-3-methyl-2-oxo-imidazo[4,5-b]pyridin-1-yl]-N,N-dimethyl-acetamide and its Trifluoroacetic Acid Salt

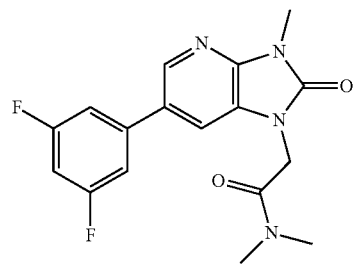 [SMILES: CN(C)C(=O)Cn1c(=O)n(C)c2ncc(-c3cc(F)cc(F)c3)cc21]

The title compound was prepared in a manner analogous to Example 34, using dimethylamine hydrochloride in Step A and (3,5-difluorophenyl)boronic acid in step B. MS (ESI): mass calcd. for $C_{17}H_{16}F_2N_4O_2$, 346.1; m/z found, 347.2 [M+H]$^+$. $^1$H NMR (500 MHz, DMSO-d$_6$) δ 8.43 (d, J=1.9 Hz, 1H), 7.91 (d, J=2.0 Hz, 1H), 7.52-7.46 (m, 2H), 7.24 (tt, J=9.2, 2.3 Hz, 1H), 4.84 (s, 2H), 3.39 (s, 3H), 3.11 (s, 3H), 2.85 (s, 3H).

Example 429: N,N-Dimethyl-2-[3-methyl-2-oxo-6-(3-pyridyl)imidazo[4,5-b]pyridin-1-yl]acetamide and its Trifluoroacetic Acid Salt

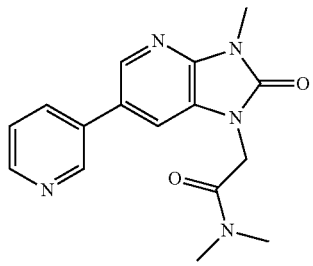 [SMILES: CN(C)C(=O)Cn1c(=O)n(C)c2ncc(-c3cccnc3)cc21]

The title compound was prepared in a manner analogous to Example 34, using dimethylamine hydrochloride in Step A and pyridin-3-ylboronic acid in step B. MS (ESI): mass calcd. for $C_{16}H_{17}N_5O_2$, 311.1; m/z found, 312.2 [M+H]$^+$. $^1$H NMR (500 MHz, DMSO-d$_6$) δ 9.03 (d, J=2.3 Hz, 1H), 8.69 (dd, J=5.0, 1.6 Hz, 1H), 8.43 (d, J=1.9 Hz, 1H), 8.37-8.32 (m, 1H), 7.94 (d, J=2.0 Hz, 1H), 7.72 (dd, J=8.1, 5.0 Hz, 1H), 4.85 (s, 2H), 3.41 (s, 3H), 3.11 (s, 3H), 2.85 (s, 3H).

Example 430: 1-[2-(3,3-Difluoroazetidin-1-yl)-2-oxo-ethyl]-3-methyl-6-[5-(trifluoromethyl)-2-thienyl]imidazo[4,5-b]pyridin-2-one and its Trifluoroacetic Acid Salt

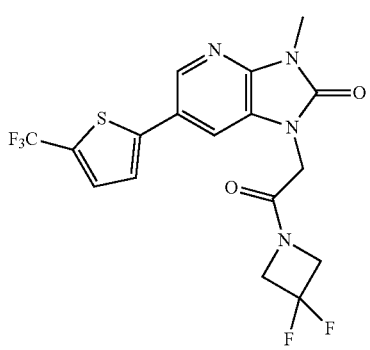 [SMILES: Cn1c(=O)n(CC(=O)N2CC(F)(F)C2)c2cc(-c3ccc(C(F)(F)F)s3)cnc21]

The title compound was prepared in a manner analogous to Example 34, using 3,3-difluoroazetidine hydrochloride in Step A and (5-(trifluoromethyl)thiophen-2-yl)boronic acid in step B. MS (ESI): mass calcd. for $C_{17}H_{13}F_5N_4O_2S$, 432.1; m/z found, 433.1[M+H]$^+$. $^1$H NMR (500 MHz, DMSO-d$_6$) δ 8.43 (d, J=1.9 Hz, 1H), 7.85 (d, J=2.0 Hz, 1H), 7.79-7.76 (m, 1H), 7.59-7.57 (m, 1H), 4.83 (t, J=12.4 Hz, 2H), 4.76 (s, 2H), 4.39 (t, J=12.4 Hz, 2H), 3.39 (s, 3H).

Example 431: 2-[6-[3,4-Difluoro-5-(trifluoromethyl)phenyl]-3-methyl-2-oxo-imidazo[4,5-b]pyridin-1-yl]-N,N-dimethyl-acetamide

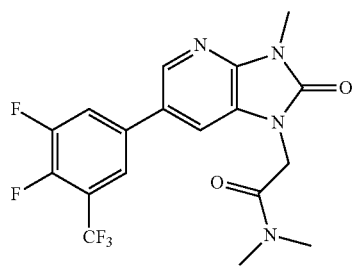 [SMILES: CN(C)C(=O)Cn1c(=O)n(C)c2ncc(-c3cc(F)c(F)c(C(F)(F)F)c3)cc21]

The title compound was prepared in a manner analogous to Example 34, using dimethylamine hydrochloride in Step A and (3,4-difluoro-5-(trifluoromethyl)phenyl)boronic acid in step B. MS (ESI): mass calcd. for $C_{18}H_{15}F_5N_4O_2$, 414.1; m/z found, 414.9 [M+H]$^+$. $^1$H NMR (500 MHz, DMSO-d$_6$) δ 8.44 (d, J=2.1 Hz, 1H), 8.23-8.17 (m, 1H), 7.92 (d, J=2.0 Hz, 1H), 7.88-7.85 (d, J=5.4 Hz, 1H), 4.85 (s, 2H), 3.40 (s, 3H), 3.12 (s, 3H), 2.85 (s, 3H).

Examples 434-525 were prepared in a manner described in the Examples above.

Example 432: 2-[2-Oxo-6-[3-(trifluoromethyl)phenyl]-3H-imidazo[4,5-b]pyridin-1-yl]acetamide

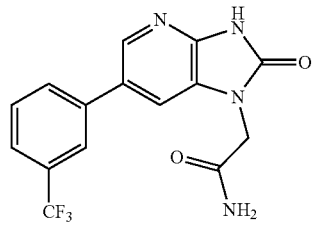 [SMILES: NC(=O)Cn1c(=O)[nH]c2ncc(-c3cccc(C(F)(F)F)c3)cc21]

MS (ESI): mass calcd. for $C_{15}H_{11}F_3N_4O_2$, 336.1; m/z found, 337.1 [M+H]$^+$.

Example 433: 2-[6-(4-Fluoro-2-methoxy-phenyl)-2-oxo-3H-imidazo[4,5-b]pyridin-1-yl]acetamide

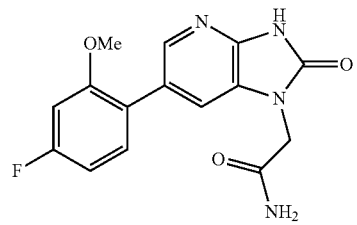 [SMILES: COc1cc(F)ccc1-c1cnc2[nH]c(=O)n(CC(N)=O)c2c1]

MS (ESI): mass calcd. for $C_{15}H_{13}FN_4O_3$, 316.1; m/z found, 317.1 [M+H]$^+$.

Example 434: 2-[6-(3-Chloro-4-fluoro-phenyl)-2-oxo-3H-imidazo[4,5-b]pyridin-1-yl]acetamide

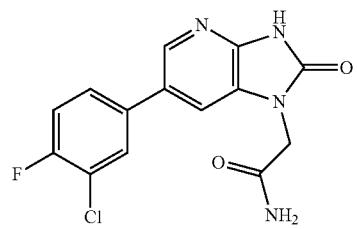 [SMILES: NC(=O)Cn1c(=O)[nH]c2ncc(-c3ccc(F)c(Cl)c3)cc21]

MS (ESI): mass calcd. for $C_{14}H_{10}ClFN_4O_2$, 320.0; m/z found, 321.1 [M+H]$^+$.

Example 435: N-Methyl-2-[2-oxo-6-[3-(trifluoromethyl)phenyl]-3H-imidazo[4,5-b]pyridin-1-yl]acetamide

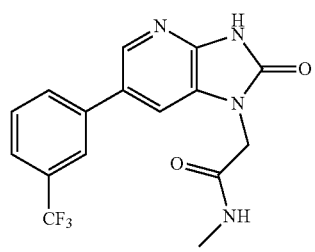 [SMILES: CNC(=O)Cn1c(=O)[nH]c2ncc(-c3cccc(C(F)(F)F)c3)cc21]

MS (ESI): mass calcd. for $C_{16}H_{13}F_3N_4O_2$, 350.1; m/z found, 351.1 [M+H]$^+$.

Example 436: 2-[6-(4-Chlorophenyl)-2-oxo-3H-imidazo[4,5-b]pyridin-1-yl]-N-methyl-acetamide

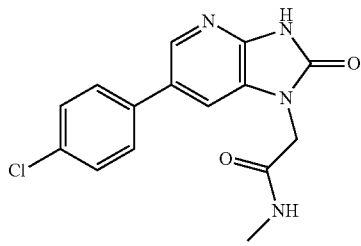 [SMILES: CNC(=O)Cn1c(=O)[nH]c2ncc(-c3ccc(Cl)cc3)cc21]

MS (ESI): mass calcd. for $C_{15}H_{13}ClN_4O_2$, 316.1; m/z found, 317.0 $[M+H]^+$.

Example 437: 2-[6-(4-Fluoro-2-methyl-phenyl)-2-oxo-3H-imidazo[4,5-b]pyridin-1-yl]-N-methyl-acetamide

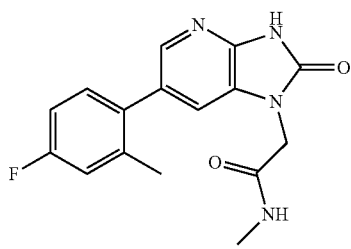 [SMILES: CNC(=O)Cn1c(=O)[nH]c2ncc(-c3ccc(F)cc3C)cc21]

MS (ESI): mass calcd. for $C_{16}H_{15}FN_4O_2$, 314.1; m/z found, 315.1 $[M+H]^+$.

Example 438: 2-[6-(3,5-Dimethylphenyl)-2-oxo-3H-imidazo[4,5-b]pyridin-1-yl]-N-methyl-acetamide

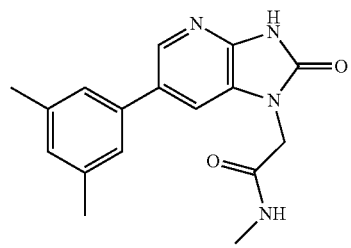 [SMILES: CNC(=O)Cn1c(=O)[nH]c2ncc(-c3cc(C)cc(C)c3)cc21]

MS (ESI): mass calcd. for $C_{17}H_{18}N_4O_2$, 310.1; m/z found, 311.1 $[M+H]^+$.

Example 439: 2-[6-(4-Methoxy-3-methyl-phenyl)-2-oxo-3H-imidazo[4,5-b]pyridin-1-yl]-N-methyl-acetamide

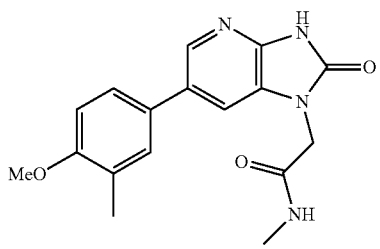 [SMILES: CNC(=O)Cn1c(=O)[nH]c2ncc(-c3ccc(OC)c(C)c3)cc21]

MS (ESI): mass calcd. for $C_{17}H_{18}N_4O_3$, 326.1; m/z found, 327.1 $[M+H]^+$.

Example 440: 2-[6-(4-Fluoro-2-methoxy-phenyl)-2-oxo-3H-imidazo[4,5-b]pyridin-1-yl]-N-methyl-acetamide

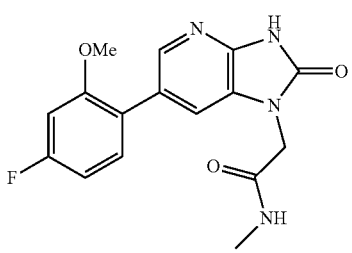 [SMILES: CNC(=O)Cn1c(=O)[nH]c2ncc(-c3ccc(F)cc3OC)cc21]

MS (ESI): mass calcd. for $C_{16}H_{15}FN_4O_3$, 330.1; m/z found, 331.1 $[M+H]^+$.

Example 441: 2-[6-(2-Ethoxyphenyl)-2-oxo-3H-imidazo[4,5-b]pyridin-1-yl]-N-methyl-acetamide

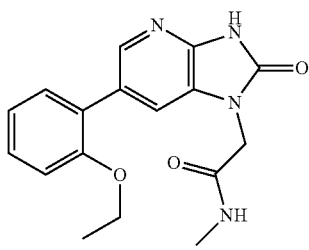 [SMILES: CCOc1ccccc1-c1cnc2[nH]c(=O)n(CC(=O)NC)c2c1]

MS (ESI): mass calcd. for $C_{17}H_{18}N_4O_3$, 326.1; m/z found, 327.1 $[M+H]^+$.

Example 442: N-(2-Methoxyethyl)-2-[2-oxo-6-[3-(trifluoromethyl)phenyl]-3H-imidazo[4,5-b]pyridin-1-yl]acetamide

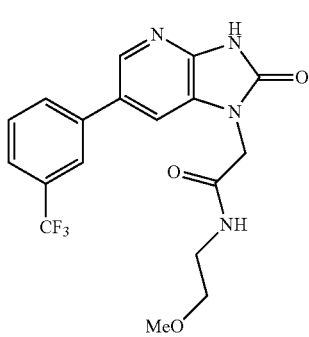 [SMILES: COCCNC(=O)Cn1c(=O)[nH]c2ncc(-c3cccc(C(F)(F)F)c3)cc21]

MS (ESI): mass calcd. for $C_{18}H_{17}F_3N_4O_3$, 394.1; m/z found, 395.0 $[M+H]^+$.

Example 443: 2-[6-(2-Ethoxy-5-fluoro-phenyl)-2-oxo-3H-imidazo[4,5-b]pyridin-1-yl]-N-(2-methoxyethyl)acetamide

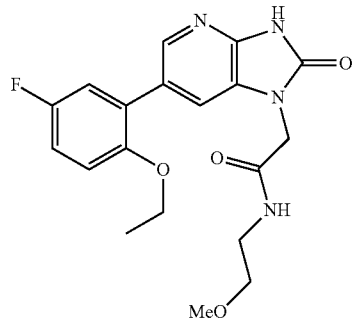 [SMILES: CCOc1ccc(F)cc1-c1cnc2[nH]c(=O)n(CC(=O)NCCOC)c2c1]

MS (ESI): mass calcd. for $C_{19}H_{21}FN_4O_4$, 388.2; m/z found, 389.2 $[M+H]^+$.

Example 444: N-(2-Methoxyethyl)-2-[6-(4-methoxyphenyl)-2-oxo-3H-imidazo[4,5-b]pyridin-1-yl]acetamide

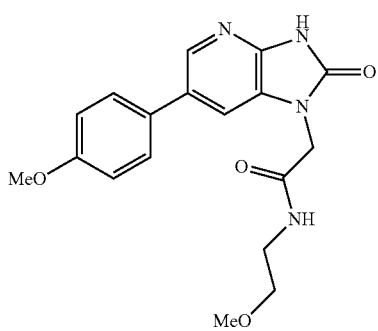 [SMILES: COCCNC(=O)Cn1c(=O)[nH]c2ncc(-c3ccc(OC)cc3)cc21]

MS (ESI): mass calcd. for $C_{18}H_{20}N_4O_4$, 356.1; m/z found, 357.1 $[M+H]^+$.

Example 445: N-(2-Methoxyethyl)-2-[2-oxo-6-(3-pyridyl)-3H-imidazo[4,5-b]pyridin-1-yl]acetamide

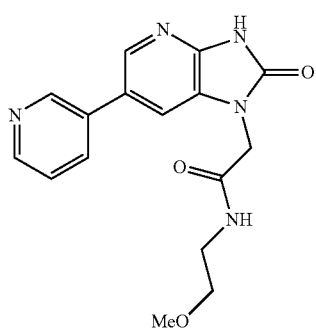 [SMILES: COCCNC(=O)Cn1c(=O)[nH]c2ncc(-c3cccnc3)cc21]

MS (ESI): mass calcd. for $C_{16}H_{17}N_5O_3$, 327.1; m/z found, 328.1 $[M+H]^+$.

Example 446: 2-[6-(4-Fluoro-2-methoxy-phenyl)-2-oxo-3H-imidazo[4,5-b]pyridin-1-yl]-N-(2-methoxyethyl)acetamide

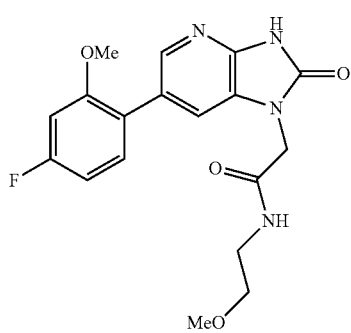 [SMILES: COCCNC(=O)Cn1c(=O)[nH]c2ncc(-c3ccc(F)cc3OC)cc21]

MS (ESI): mass calcd. for $C_{18}H_{19}FN_4O_4$, 374.1; m/z found, 375.1 $[M+H]^+$.

Example 447: N-Cyclopropyl-2-[6-(3,5-difluorophenyl)-2-oxo-3H-imidazo[4,5-b]pyridin-1-yl]acetamide

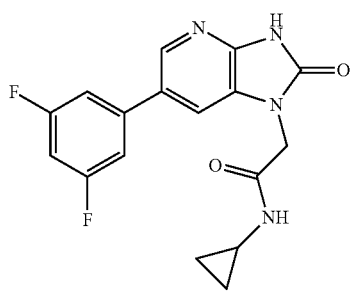 [SMILES: O=C(Cn1c(=O)[nH]c2ncc(-c3cc(F)cc(F)c3)cc21)NC1CC1]

MS (ESI): mass calcd. for $C_{17}H_{14}F_2N_4O_2$, 344.1; m/z found, 345.0 $[M+H]^+$.

Example 448: 2-[6-(3-Chloro-4-fluoro-phenyl)-2-oxo-3H-imidazo[4,5-b]pyridin-1-yl]-N-cyclopropylacetamide

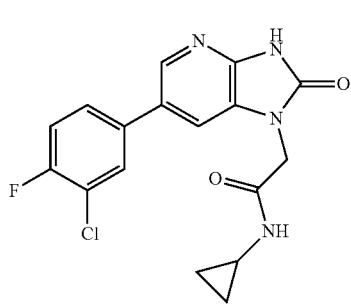 [SMILES: O=C(Cn1c(=O)[nH]c2ncc(-c3ccc(F)c(Cl)c3)cc21)NC1CC1]

MS (ESI): mass calcd. for $C_{17}H_{14}ClFN_4O_2$, 360.1; m/z found, 361.1 $[M+H]^+$.

Example 449: N-Cyclopropyl-2-[6-(3-ethoxyphenyl)-2-oxo-3H-imidazo[4,5-b]pyridin-1-yl]acetamide

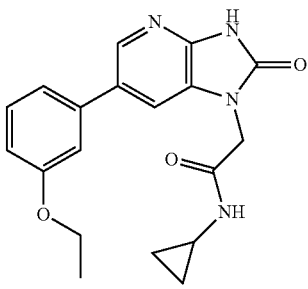 [SMILES: CCOc1cccc(-c2cnc3[nH]c(=O)n(CC(=O)NC4CC4)c3c2)c1]

MS (ESI): mass calcd. for $C_{19}H_{20}N_4O_3$, 352.2; m/z found, 353.1 $[M+H]^+$.

Example 450: N-Cyclopropyl-2-[6-(3-methoxyphenyl)-2-oxo-3H-imidazo[4,5-b]pyridin-1-yl]acetamide

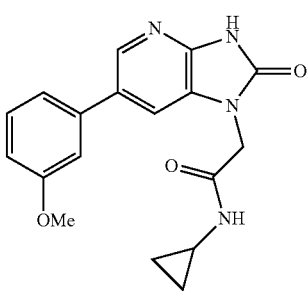 [SMILES: COc1cccc(-c2cnc3[nH]c(=O)n(CC(=O)NC4CC4)c3c2)c1]

MS (ESI): mass calcd. for $C_{18}H_{18}N_4O_3$, 338.1; m/z found, 339.1 $[M+H]^+$.

Example 451: N-Cyclopropyl-2-[6-(4-methoxy-3-methyl-phenyl)-2-oxo-3H-imidazo[4,5-b]pyridin-1-yl]acetamide

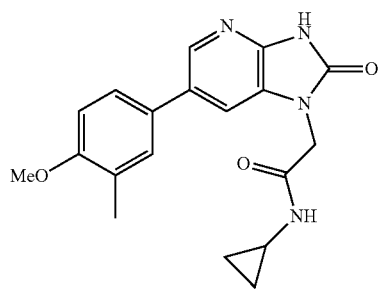 [SMILES: COc1ccc(-c2cnc3[nH]c(=O)n(CC(=O)NC4CC4)c3c2)cc1C]

MS (ESI): mass calcd. for $C_{19}H_{20}N_4O_3$, 352.2; m/z found, 353.1 $[M+H]^+$.

Example 452: N-Cyclopropyl-2-[6-(4-fluoro-2-methoxy-phenyl)-2-oxo-3H-imidazo[4,5-b]pyridin-1-yl]acetamide

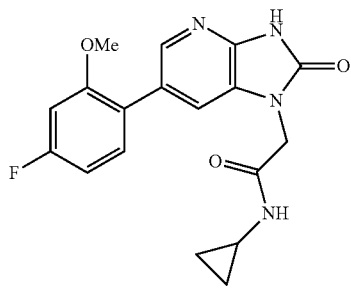 [SMILES: COc1cc(F)ccc1-c1cnc2[nH]c(=O)n(CC(=O)NC3CC3)c2c1]

MS (ESI): mass calcd. for $C_{18}H_{17}FN_4O_3$, 356.1; m/z found, 357.1 $[M+H]^+$.

Example 453: 2-[6-(4-Chlorophenyl)-2-oxo-3H-imidazo[4,5-b]pyridin-1-yl]-N-cyclopropyl-acetamide

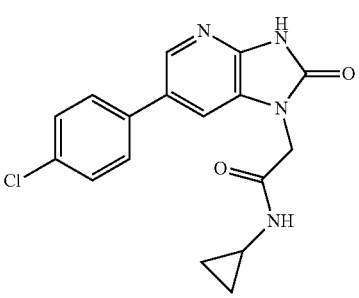 [SMILES: O=C(Cn1c(=O)[nH]c2ncc(-c3ccc(Cl)cc3)cc21)NC1CC1]

MS (ESI): mass calcd. for $C_{17}H_{15}ClN_4O_2$, 342.1; m/z found, 343.1 $[M+H]^+$.

Example 454: N-Cyclopropyl-2-[6-(2,4-dimethoxyphenyl)-2-oxo-3H-imidazo[4,5-b]pyridin-1-yl]acetamide

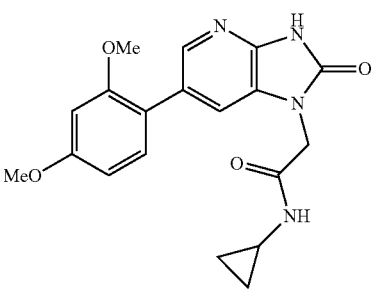 [SMILES: COc1ccc(-c2cnc3[nH]c(=O)n(CC(=O)NC4CC4)c3c2)c(OC)c1]

MS (ESI): mass calcd. for $C_{19}H_{20}N_4O_4$, 368.1; m/z found, 369.2 $[M+H]^+$.

Example 455: N-Cyclopropyl-2-[6-(2-fluoro-6-methoxy-phenyl)-2-oxo-3H-imidazo[4,5-b]pyridin-1-yl]acetamide

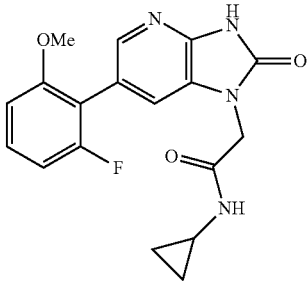 [SMILES: COc1cccc(F)c1-c1cnc2[nH]c(=O)n(CC(=O)NC3CC3)c2c1]

MS (ESI): mass calcd. for $C_{18}H_{17}FN_4O_3$, 356.1; m/z found, 357.1 [M+H]$^+$.

Example 456: N-Cyclopropyl-2-[6-(2-ethoxyphenyl)-2-oxo-3H-imidazo[4,5-b]pyridin-1-yl]acetamide

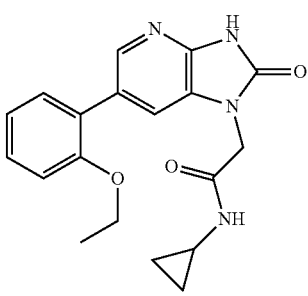 [SMILES: CCOc1ccccc1-c1cnc2[nH]c(=O)n(CC(=O)NC3CC3)c2c1]

MS (ESI): mass calcd. for $C_{19}H_{20}N_4O_3$, 352.2; m/z found, 353.1 [M+H]$^+$.

Example 457: 6-(3-Fluoro-4-methoxy-phenyl)-1-[2-oxo-2-(2-thienyl)ethyl]-3H-imidazo[4,5-b]pyridin-2-one

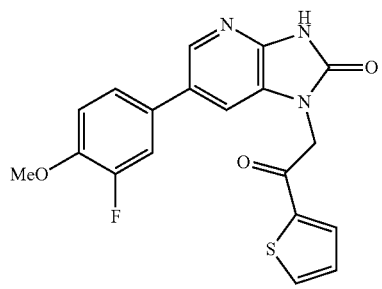 [SMILES: COc1ccc(-c2cnc3[nH]c(=O)n(CC(=O)c4cccs4)c3c2)cc1F]

MS (ESI): mass calcd. for $C_{19}H_{14}FN_3O_3S$, 383.1; m/z found, 384.1 [M+H]$^+$.

Example 458: 6-(2-Ethoxyphenyl)-1-[2-oxo-2-(2-thienyl)ethyl]-3H-imidazo[4,5-b]pyridin-2-one

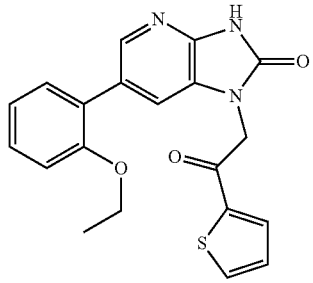 [SMILES: CCOc1ccccc1-c1cnc2[nH]c(=O)n(CC(=O)c3cccs3)c2c1]

MS (ESI): mass calcd. for $C_{20}H_{17}N_3O_3S$, 379.1; m/z found, 380.1 [M+H]$^+$.

Example 459: 6-(4-Chlorophenyl)-1-[2-oxo-2-(2-thienyl)ethyl]-3H-imidazo[4,5-b]pyridin-2-one

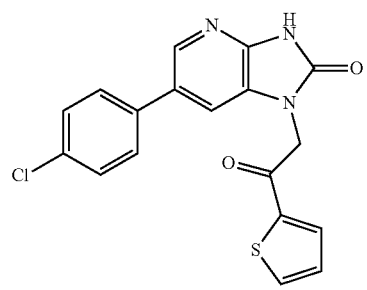 [SMILES: O=C(Cn1c(=O)[nH]c2ncc(-c3ccc(Cl)cc3)cc21)c1cccs1]

MS (ESI): mass calcd. for $C_{18}H_{12}ClN_3O_2S$, 369.0; m/z found, 370.0 [M+H]$^+$.

Example 460: 6-(2-Ethoxy-5-fluoro-phenyl)-1-[2-oxo-2-(2-thienyl)ethyl]-3H-imidazo[4,5-b]pyridin-2-one

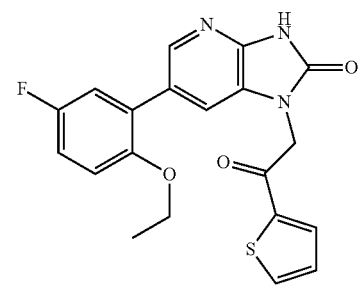 [SMILES: CCOc1ccc(F)cc1-c1cnc2[nH]c(=O)n(CC(=O)c3cccs3)c2c1]

MS (ESI): mass calcd. for $C_{20}H_{16}FN_3O_3S$, 397.1; m/z found, 398.1 [M+H]$^+$.

Example 461: 6-(4-Methoxyphenyl)-1-[2-oxo-2-(2-thienyl)ethyl]-3H-imidazo[4,5-b]pyridin-2-one

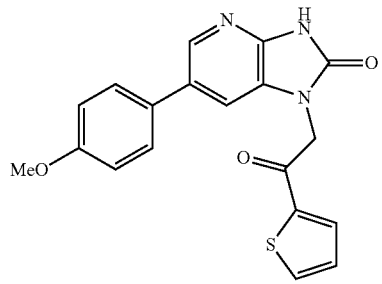 [SMILES: COc1ccc(-c2cnc3[nH]c(=O)n(CC(=O)c4cccs4)c3c2)cc1]

MS (ESI): mass calcd. for $C_{19}H_{15}N_3O_3S$, 365.1; m/z found, 366.1 [M+H]$^+$.

Example 462: 6-(4-Fluoro-2-methoxy-phenyl)-1-[2-oxo-2-(2-thienyl)ethyl]-3H-imidazo[4,5-b]pyridin-2-one

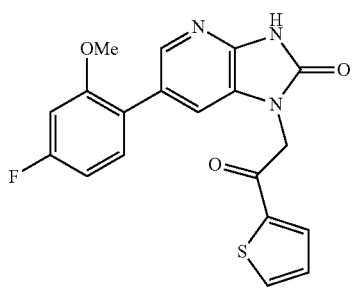 [SMILES: COc1cc(F)ccc1-c1cnc2[nH]c(=O)n(CC(=O)c3cccs3)c2c1]

MS (ESI): mass calcd. for $C_{19}H_{14}FN_3O_3S$, 383.1; m/z found, 384.1 [M+H]$^+$.

Example 463: 6-(3-Ethoxyphenyl)-1-[2-oxo-2-(2-thienyl)ethyl]-3H-imidazo[4,5-b]pyridin-2-one

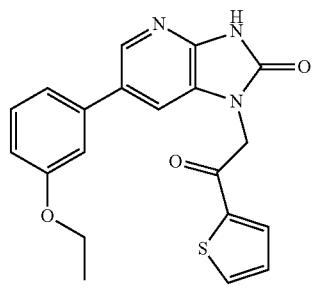 [SMILES: CCOc1cccc(-c2cnc3[nH]c(=O)n(CC(=O)c4cccs4)c3c2)c1]

MS (ESI): mass calcd. for $C_{20}H_{17}N_3O_3S$, 379.1; m/z found, 380.1 [M+H]$^+$.

Example 464: 6-(3-Chloro-4-fluoro-phenyl)-1-[2-oxo-2-(2-thienyl)ethyl]-3H-imidazo[4,5-b]pyridin-2-one

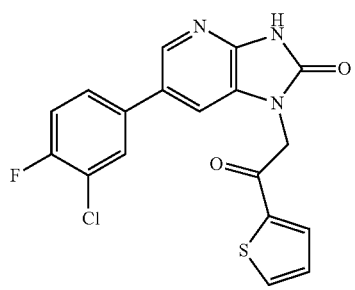 [SMILES: O=C(Cn1c(=O)[nH]c2ncc(-c3ccc(F)c(Cl)c3)cc21)c1cccs1]

MS (ESI): mass calcd. for $C_{18}H_{11}ClFN_3O_2S$, 387.0; m/z found, 388.0 [M+H]$^+$.

Example 465: 1-(Cyclopropylmethyl)-6-(2,4-dimethoxyphenyl)-3H-imidazo[4,5-b]pyridin-2-one

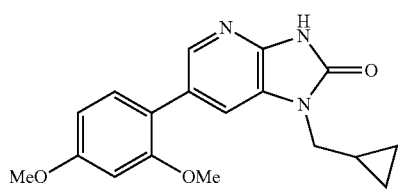 [SMILES: COc1ccc(-c2cnc3[nH]c(=O)n(CC4CC4)c3c2)c(OC)c1]

MS (ESI): mass calcd. for $C_{18}H_{19}N_3O_3$, 325.1; m/z found, 326.1 [M+H]$^+$.

Example 466: 1-(Cyclopropylmethyl)-6-(2-ethoxy-5-fluoro-phenyl)-3H-imidazo[4,5-b]pyridin-2-one

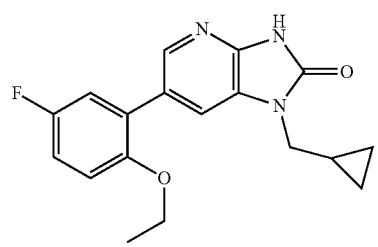 [SMILES: CCOc1ccc(F)cc1-c1cnc2[nH]c(=O)n(CC3CC3)c2c1]

MS (ESI): mass calcd. for $C_{18}H_{18}FN_3O_2$, 327.1; m/z found, 328.1 [M+H]$^+$.

Example 467: 1-(Cyclopropylmethyl)-6-(4-fluoro-2-methoxy-phenyl)-3H-imidazo[4,5-b]pyridin-2-one

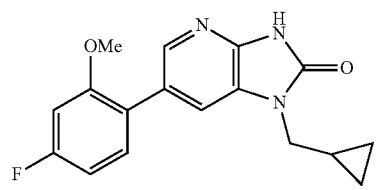 [SMILES: COc1cc(F)ccc1-c1cnc2[nH]c(=O)n(CC3CC3)c2c1]

MS (ESI): mass calcd. for $C_{17}H_{16}FN_3O_2$, 313.1; m/z found, 314.1 $[M+H]^+$.

Example 468: 1-(Cyclopropylmethyl)-6-(4-methoxy-3-methyl-phenyl)-3H-imidazo[4,5-b]pyridin-2-one

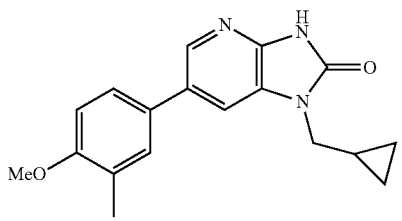 [SMILES: COc1ccc(-c2cnc3[nH]c(=O)n(CC4CC4)c3c2)cc1C]

MS (ESI): mass calcd. for $C_{18}H_{19}N_3O_2$, 309.1; m/z found, 310.1 $[M+H]^+$.

Example 469: 1-(Cyclopropylmethyl)-6-(3-fluoro-4-methoxy-phenyl)-3H-imidazo[4,5-b]pyridin-2-one

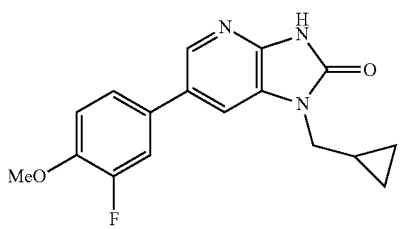 [SMILES: COc1ccc(-c2cnc3[nH]c(=O)n(CC4CC4)c3c2)cc1F]

MS (ESI): mass calcd. for $C_{17}H_{16}FN_3O_2$, 313.1; m/z found, 314.1 $[M+H]^+$.

Example 470: 1-(Cyclopropylmethyl)-6-(3,5-difluorophenyl)-3H-imidazo[4,5-b]pyridin-2-one

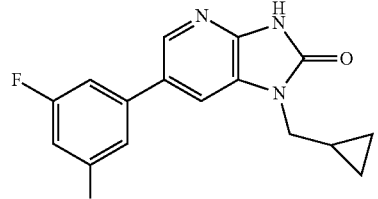

MS (ESI): mass calcd. for $C_{16}H_{13}F_2N_3O$, 301.1; m/z found, 302.1 $[M+H]^+$.

Example 471: 1-(Cyclopropylmethyl)-6-(4-methoxyphenyl)-3H-imidazo[4,5-b]pyridin-2-one

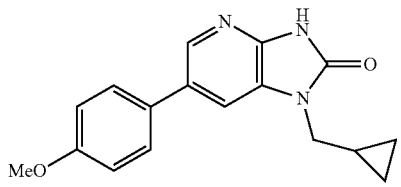 [SMILES: COc1ccc(-c2cnc3[nH]c(=O)n(CC4CC4)c3c2)cc1]

MS (ESI): mass calcd. for $C_{17}H_{17}N_3O_2$, 295.1; m/z found, 296.1 $[M+H]^+$.

Example 472: 1-(Cyclopropylmethyl)-6-(2-thienyl)-3H-imidazo[4,5-b]pyridin-2-one

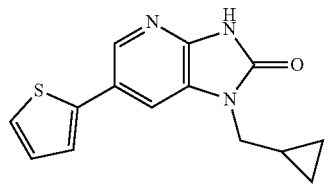 [SMILES: O=c1[nH]c2ncc(-c3cccs3)cc2n1CC1CC1]

MS (ESI): mass calcd. for $C_{14}H_{13}N_3OS$, 271.1; m/z found, 272.1 $[M+H]^+$.

Example 473: 1-(Cyclopropylmethyl)-6-[3-(dimethylamino)phenyl]-3H-imidazo[4,5-b]pyridin-2-one

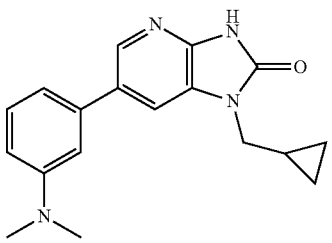 [SMILES: CN(C)c1cccc(-c2cnc3[nH]c(=O)n(CC4CC4)c3c2)c1]

MS (ESI): mass calcd. for $C_{18}H_{20}N_4O$, 308.2; m/z found, 309.2 $[M+H]^+$.

Example 474: 1-(Cyclopropylmethyl)-6-(3,5-dimethylphenyl)-3H-imidazo[4,5-b]pyridin-2-one

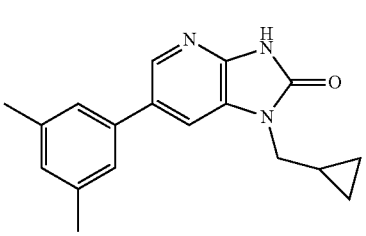 [SMILES: Cc1cc(C)cc(-c2cnc3[nH]c(=O)n(CC4CC4)c3c2)c1]

MS (ESI): mass calcd. for $C_{18}H_{19}N_3O$, 293.2; m/z found, 294.2 $[M+H]^+$.

Example 475: 6-(3-Methoxyphenyl)-1-(tetrahydrofuran-2-ylmethyl)-3H-imidazo[4,5-b]pyridin-2-one

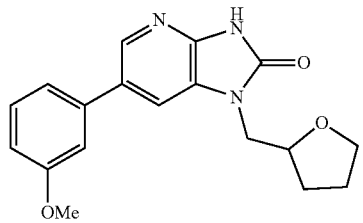 [SMILES: COc1cccc(-c2cnc3[nH]c(=O)n(CC4CCCO4)c3c2)c1]

MS (ESI): mass calcd. for $C_{18}H_{19}N_3O_3$, 325.1; m/z found, 326.1 $[M+H]^+$.

Example 476: 4-[[6-(4-Methoxyphenyl)-2-oxo-3H-imidazo[4,5-b]pyridin-1-yl]methyl]benzonitrile

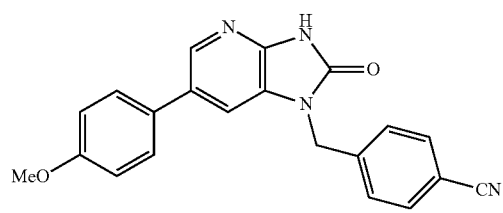 [SMILES: COc1ccc(-c2cnc3[nH]c(=O)n(Cc4ccc(C#N)cc4)c3c2)cc1]

MS (ESI): mass calcd. for $C_{21}H_{16}N_4O_2$, 356.1; m/z found, 357.1 $[M+H]^+$.

Example 477: 3-[[6-(4-Methoxyphenyl)-2-oxo-3H-imidazo[4,5-b]pyridin-1-yl]methyl]benzonitrile

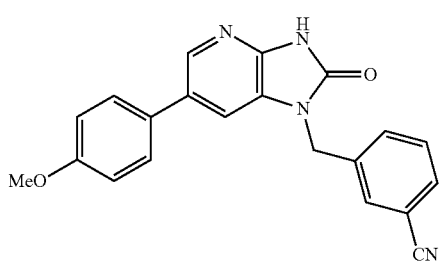 [SMILES: COc1ccc(-c2cnc3[nH]c(=O)n(Cc4cccc(C#N)c4)c3c2)cc1]

MS (ESI): mass calcd. for $C_{21}H_{16}N_4O_2$, 356.1; m/z found, 357.1 $[M+H]^+$.

Example 478: 3-[[6-(4-Fluoro-2-methoxy-phenyl)-2-oxo-3H-imidazo[4,5-b]pyridin-1-yl]methyl]benzonitrile

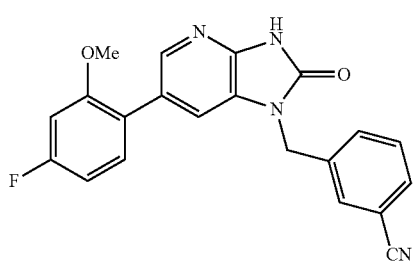 [SMILES: COc1cc(F)ccc1-c1cnc2[nH]c(=O)n(Cc3cccc(C#N)c3)c2c1]

MS (ESI): mass calcd. for $C_{21}H_{15}FN_4O_2$, 374.1; m/z found, 375.1 $[M+H]^+$.

Example 479: 3-[[6-(4-Fluoro-2-methyl-phenyl)-2-oxo-3H-imidazo[4,5-b]pyridin-1-yl]methyl]benzonitrile

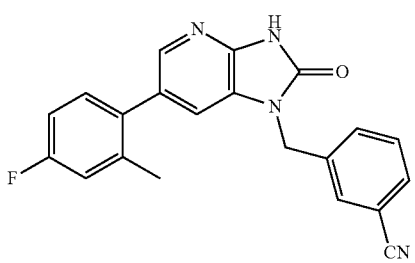 [SMILES: Cc1cc(F)ccc1-c1cnc2[nH]c(=O)n(Cc3cccc(C#N)c3)c2c1]

MS (ESI): mass calcd. for $C_{21}H_{15}FN_4O$, 358.1; m/z found, 359.1 $[M+H]^+$.

Example 480: 3-[[6-(3-Chloro-4-fluoro-phenyl)-2-oxo-3H-imidazo[4,5-b]pyridin-1-yl]methyl]benzonitrile

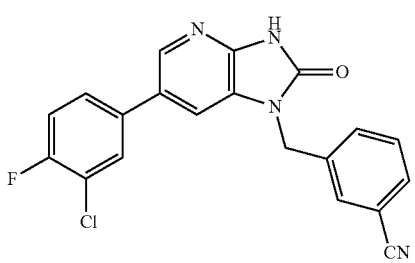 [SMILES: N#Cc1cccc(Cn2c(=O)[nH]c3ncc(-c4ccc(F)c(Cl)c4)cc32)c1]

MS (ESI): mass calcd. for $C_{20}H_{12}ClFN_4O$, 378.1; m/z found, 379.1 $[M+H]^+$.

Example 481: 2-[[6-(2-Fluoro-6-methoxy-phenyl)-2-oxo-3H-imidazo[4,5-b]pyridin-1-yl]methyl]benzonitrile

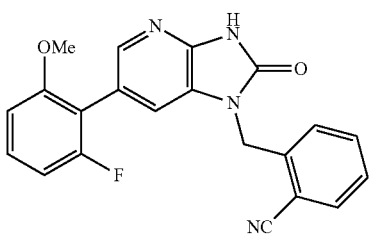 [SMILES: COc1cccc(F)c1-c1cnc2[nH]c(=O)n(Cc3ccccc3C#N)c2c1]

MS (ESI): mass calcd. for $C_{21}H_{15}FN_4O_2$, 374.1; m/z found, 375.1 $[M+H]^+$.

Example 482: 2-[[6-(4-Chlorophenyl)-2-oxo-3H-imidazo[4,5-b]pyridin-1-yl]methyl]benzonitrile

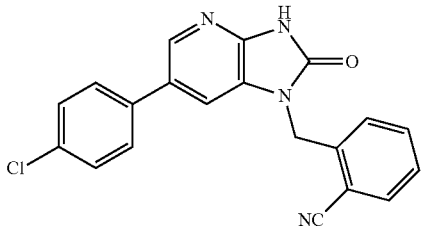 [SMILES: N#Cc1ccccc1Cn1c(=O)[nH]c2ncc(-c3ccc(Cl)cc3)cc21]

MS (ESI): mass calcd. for C$_{20}$H$_{13}$ClN$_4$O, 360.1; m/z found, 361.1 [M+H]$^+$.

Example 483: 2-[[6-(4-Fluoro-2-methyl-phenyl)-2-oxo-3H-imidazo[4,5-b]pyridin-1-yl]methyl]benzonitrile

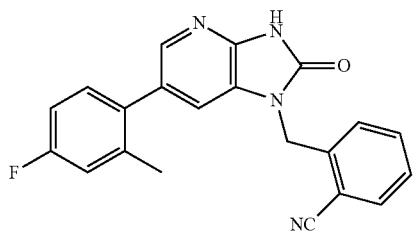 [SMILES: Cc1cc(F)ccc1-c1cnc2[nH]c(=O)n(Cc3ccccc3C#N)c2c1]

MS (ESI): mass calcd. for C$_{21}$H$_{15}$FN$_4$O, 358.1; m/z found, 359.2 [M+H]$^+$.

Example 484: 2-[[6-(2-Ethoxyphenyl)-2-oxo-3H-imidazo[4,5-b]pyridin-1-yl]methyl]benzonitrile

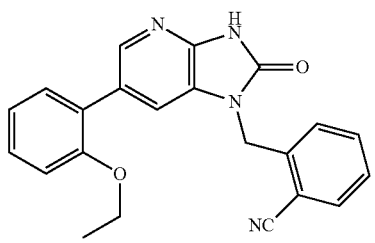 [SMILES: CCOc1ccccc1-c1cnc2[nH]c(=O)n(Cc3ccccc3C#N)c2c1]

MS (ESI): mass calcd. for C$_{22}$H$_{18}$N$_4$O$_2$, 370.1; m/z found, 371.1 [M+H]$^+$.

Example 485: 2-[[6-(3-Methoxyphenyl)-2-oxo-3H-imidazo[4,5-b]pyridin-1-yl]methyl]benzonitrile

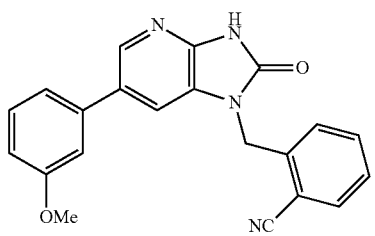 [SMILES: COc1cccc(-c2cnc3[nH]c(=O)n(Cc4ccccc4C#N)c3c2)c1]

MS (ESI): mass calcd. for C$_{21}$H$_{16}$N$_4$O$_2$, 356.1; m/z found, 357.1 [M+H]$^+$.

Example 486: 2-[[6-(3-Cyanophenyl)-2-oxo-3H-imidazo[4,5-b]pyridin-1-yl]methyl]benzonitrile

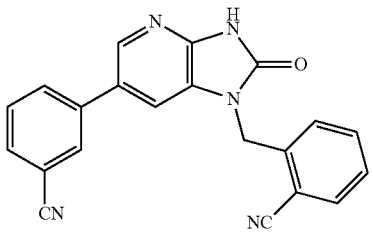 [SMILES: N#Cc1cccc(-c2cnc3[nH]c(=O)n(Cc4ccccc4C#N)c3c2)c1]

MS (ESI): mass calcd. for C$_{21}$H$_{13}$N$_5$O, 351.1; m/z found, 352.1 [M+H]$^+$.

Example 487: 2-[[6-(2,4-Dimethoxyphenyl)-2-oxo-3H-imidazo[4,5-b]pyridin-1-yl]methyl]benzonitrile

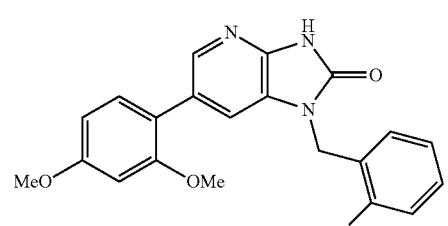

MS (ESI): mass calcd. for C$_{22}$H$_{18}$N$_4$O$_3$, 386.1; m/z found, 387.1 [M+H]$^+$.

Example 488: 2-[[6-(3,5-Dimethylphenyl)-2-oxo-3H-imidazo[4,5-b]pyridin-1-yl]methyl]benzonitrile

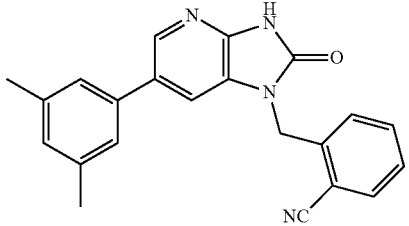 [SMILES: Cc1cc(C)cc(-c2cnc3[nH]c(=O)n(Cc4ccccc4C#N)c3c2)c1]

MS (ESI): mass calcd. for C$_{22}$H$_{18}$N$_4$O, 354.1; m/z found, 355.2 [M+H]$^+$.

Example 489: 2-[[6-(2-Ethoxy-5-fluoro-phenyl)-2-oxo-3H-imidazo[4,5-b]pyridin-1-yl]methyl]benzonitrile

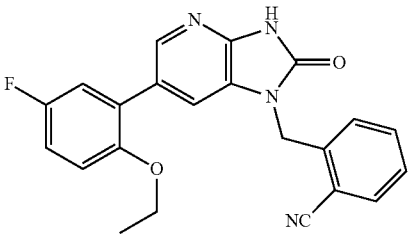 [SMILES: CCOc1ccc(F)cc1-c1cnc2[nH]c(=O)n(Cc3ccccc3C#N)c2c1]

MS (ESI): mass calcd. for $C_{22}H_{17}FN_4O_2$, 388.1; m/z found, 389.1 $[M+H]^+$.

Example 490: 2-[[6-(4-Fluoro-2-methoxy-phenyl)-2-oxo-3H-imidazo[4,5-b]pyridin-1-yl]methyl]benzonitrile

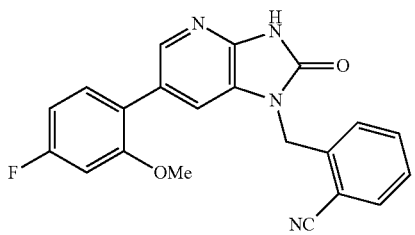 [SMILES: COc1cc(F)ccc1-c1cnc2[nH]c(=O)n(Cc3ccccc3C#N)c2c1]

MS (ESI): mass calcd. for $021H_{15}FN_4O_2$, 374.1; m/z found, 375.1 $[M+H]^+$.

Example 491: 2-[[6-(3-Fluoro-4-methoxy-phenyl)-2-oxo-3H-imidazo[4,5-b]pyridin-1-yl]methyl]benzonitrile

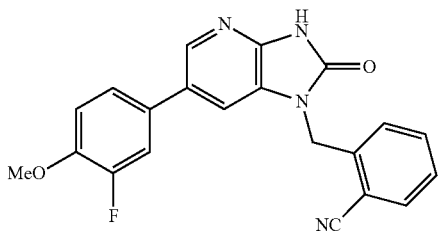 [SMILES: COc1ccc(-c2cnc3[nH]c(=O)n(Cc4ccccc4C#N)c3c2)cc1F]

MS (ESI): mass calcd. for $021H_{15}FN_4O_2$, 374.1; m/z found, 375.1 $[M+H]^+$.

Example 492: 6-(4-Fluoro-2-methyl-phenyl)-1-[(4-fluorophenyl)methyl]-3H-imidazo[4,5-b]pyridin-2-one

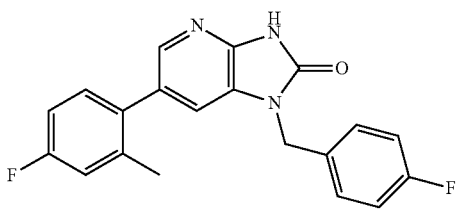 [SMILES: Cc1cc(F)ccc1-c1cnc2[nH]c(=O)n(Cc3ccc(F)cc3)c2c1]

MS (ESI): mass calcd. for $C_{20}H_{15}F_2N_3O$, 351.1; m/z found, 352.1 $[M+H]^+$.

Example 493: 6-(2,3-Dimethoxyphenyl)-1-[(4-fluorophenyl)methyl]-3H-imidazo[4,5-b]pyridin-2-one

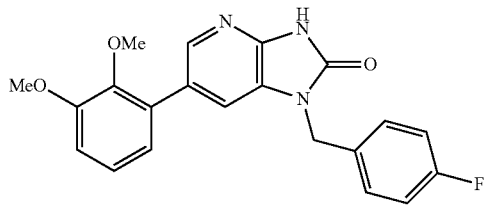 [SMILES: COc1cccc(-c2cnc3[nH]c(=O)n(Cc4ccc(F)cc4)c3c2)c1OC]

MS (ESI): mass calcd. for $021H_{18}FN_3O_3$, 379.1; m/z found, 380.1 $[M+H]^+$.

Example 494: 6-(2-Ethoxy-5-fluoro-phenyl)-1-[(3-fluorophenyl)methyl]-3H-imidazo[4,5-b]pyridin-2-one

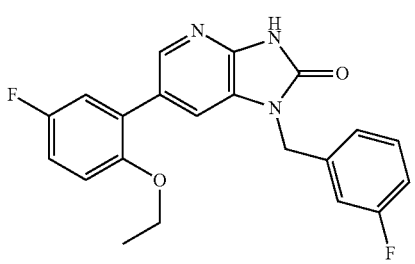 [SMILES: CCOc1ccc(F)cc1-c1cnc2[nH]c(=O)n(Cc3cccc(F)c3)c2c1]

MS (ESI): mass calcd. for $C_{21}H_{17}F_2N_3O_2$, 381.1; m/z found, 382.1 $[M+H]^+$.

Example 495: 6-(3,5-Dimethyl phenyl)-1-[(3-fluorophenyl)methyl]-3H-imidazo[4,5-b]pyridin-2-one

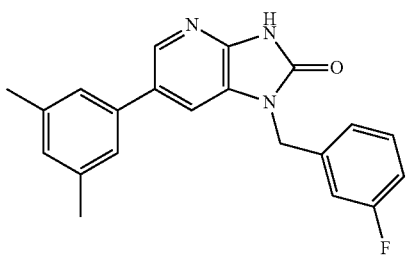 [SMILES: Cc1cc(C)cc(-c2cnc3[nH]c(=O)n(Cc4cccc(F)c4)c3c2)c1]

MS (ESI): mass calcd. for $C_{21}H_{18}FN_3O$, 347.1; m/z found, 348.1 $[M+H]^+$.

Example 496: 6-(2,4-Dimethoxyphenyl)-1-[(3-fluorophenyl)methyl]-3H-imidazo[4,5-b]pyridin-2-one

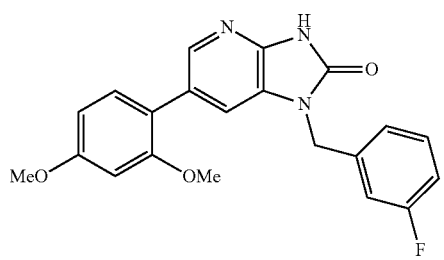 [SMILES: COc1ccc(-c2cnc3[nH]c(=O)n(Cc4cccc(F)c4)c3c2)c(OC)c1]

MS (ESI): mass calcd. for $C_{21}H_{18}FN_3O_3$, 379.1; m/z found, 380.1 $[M+H]^+$.

Example 497: 6-(2-Ethoxyphenyl)-1-[(3-fluorophenyl)methyl]-3H-imidazo[4,5-b]pyridin-2-one

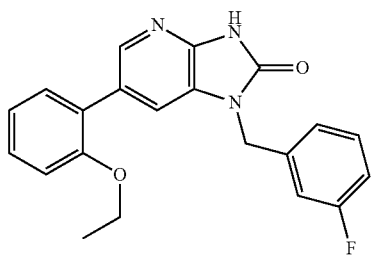 [SMILES: CCOc1ccccc1-c1cnc2[nH]c(=O)n(Cc3cccc(F)c3)c2c1]

MS (ESI): mass calcd. for $C_{21}H_{18}FN_3O_2$, 363.1; m/z found, 364.1 $[M+H]^+$.

Example 498: 1-[(3-Fluorophenyl)methyl]-6-(4-methoxy-3-methyl-phenyl)-3H-imidazo[4,5-b]pyridin-2-one

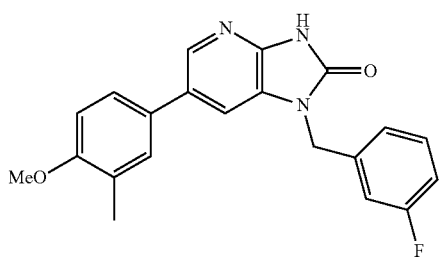 [SMILES: COc1ccc(-c2cnc3[nH]c(=O)n(Cc4cccc(F)c4)c3c2)cc1C]

MS (ESI): mass calcd. for $C_{21}H_{18}FN_3O_2$, 363.1; m/z found, 364.1 $[M+H]^+$.

Example 499: 6-(4-Fluoro-2-methoxy-phenyl)-1-[(3-fluorophenyl)methyl]-3H-imidazo[4,5-b]pyridin-2-one

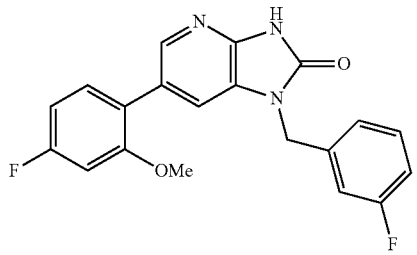 [SMILES: COc1cc(F)ccc1-c1cnc2[nH]c(=O)n(Cc3cccc(F)c3)c2c1]

MS (ESI): mass calcd. for $C_{20}H_{15}F_2N_3O_2$, 367.1; m/z found, 368.1 $[M+H]^+$.

Example 500: 6-[3-(Dimethylamino)phenyl]-1-[(3-fluorophenyl)methyl]-3H-imidazo[4,5-b]pyridin-2-one

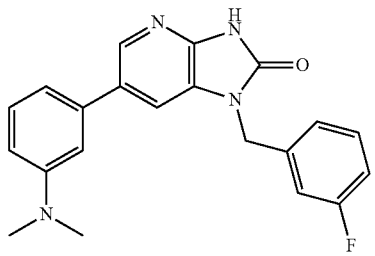 [SMILES: CN(C)c1cccc(-c2cnc3[nH]c(=O)n(Cc4cccc(F)c4)c3c2)c1]

MS (ESI): mass calcd. for $C_{21}H_{19}FN_4O$, 362.2; m/z found, 363.1 $[M+H]^+$.

Example 501: 6-(4-Fluoro-2-methoxy-phenyl)-1-[(4-fluorophenyl)methyl]-3H-imidazo[4,5-b]pyridin-2-one

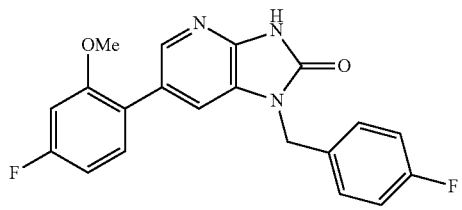 [SMILES: COc1cc(F)ccc1-c1cnc2[nH]c(=O)n(Cc3ccc(F)cc3)c2c1]

MS (ESI): mass calcd. for $C_{20}H_{15}F_2N_3O_2$, 367.1; m/z found, 368.1 $[M]^+$.

Example 502: 6-(3-Chloro-4-fluoro-phenyl)-1-[(4-fluorophenyl)methyl]-3H-imidazo[4,5-b]pyridin-2-one

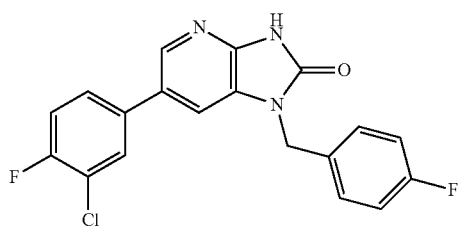 [SMILES: O=c1[nH]c2ncc(-c3ccc(F)c(Cl)c3)cc2n1Cc1ccc(F)cc1]

MS (ESI): mass calcd. for $C_{19}H_{12}ClF_2N_3O$, 371.1; m/z found, 372.1 $[M+H]^+$.

Example 503: 6-(2-Ethoxyphenyl)-1-[(2-fluorophenyl)methyl]-3H-imidazo[4,5-b]pyridin-2-one

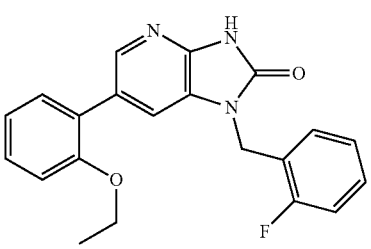 [SMILES: CCOc1ccccc1-c1cnc2[nH]c(=O)n(Cc3ccccc3F)c2c1]

MS (ESI): mass calcd. for $021H_{18}FN_3O_2$, 363.1; m/z found, 364.1 $[M+H]^+$.

Example 504: 1-[(3-Chlorophenyl)methyl]-6-(3,5-difluorophenyl)-3H-imidazo[4,5-b]pyridin-2-one

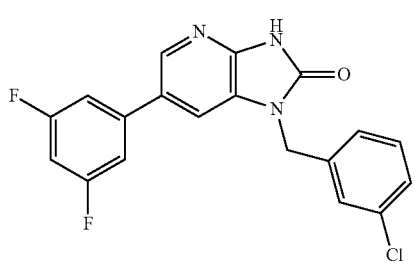 [SMILES: O=c1[nH]c2ncc(-c3cc(F)cc(F)c3)cc2n1Cc1cccc(Cl)c1]

MS (ESI): mass calcd. for $C_{19}H_{12}ClF_2N_3O$, 371.1; m/z found, 372.1 [M+H]$^+$.

Example 505: 6-(4-Fluoro-2-methoxy-phenyl)-1-[(3-methoxyphenyl)methyl]-3H-imidazo[4,5-b]pyridin-2-one

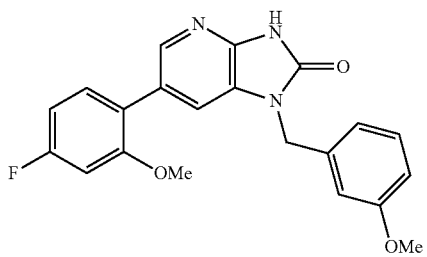 [SMILES: COc1cccc(Cn2c(=O)[nH]c3ncc(-c4ccc(F)cc4OC)cc32)c1]

MS (ESI): mass calcd. for $C_{21}H_{18}FN_3O_3$, 379.1; m/z found, 380.1 [M+H]$^+$.

Example 506: 1-[(3-Methoxyphenyl)methyl]-6-(3-pyridyl)-3H-imidazo[4,5-b]pyridin-2-one

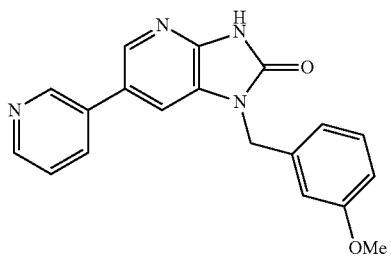 [SMILES: COc1cccc(Cn2c(=O)[nH]c3ncc(-c4cccnc4)cc32)c1]

MS (ESI): mass calcd. for $C_{19}H_{16}N_4O_2$, 332.1; m/z found, 333.1 [M+H]$^+$.

Example 507: 1-[(3-Methoxyphenyl)methyl]-6-(4-methyl-2-thienyl)-3H-imidazo[4,5-b]pyridin-2-one

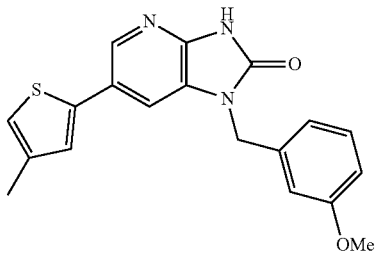 [SMILES: COc1cccc(Cn2c(=O)[nH]c3ncc(-c4cc(C)cs4)cc32)c1]

MS (ESI): mass calcd. for $C_{19}H_{17}N_3O_2S$, 351.1; m/z found, 352.1 [M+H]$^+$.

Example 508: 6-(3,5-Difluorophenyl)-1-[(4-methoxyphenyl)methyl]-3H-imidazo[4,5-b]pyridin-2-one

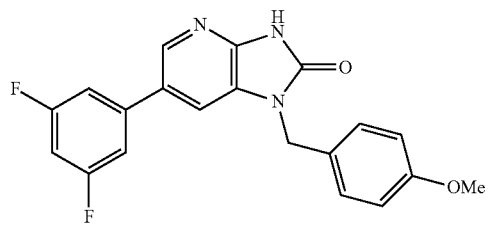 [SMILES: COc1ccc(Cn2c(=O)[nH]c3ncc(-c4cc(F)cc(F)c4)cc32)cc1]

MS (ESI): mass calcd. for $C_{20}H_{15}F_2N_3O_2$, 367.1; m/z found, 368.1 [M+H]$^+$.

Example 509: 1-[(3,5-Dimethoxyphenyl)methyl]-6-(2-fluoro-6-methoxy-phenyl)-3H-imidazo[4,5-b]pyridin-2-one

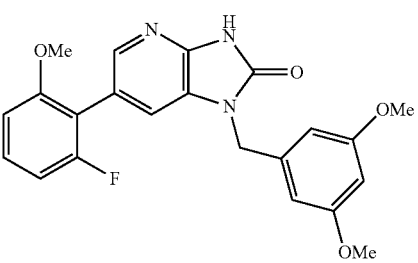 [SMILES: COc1cc(Cn2c(=O)[nH]c3ncc(-c4c(F)cccc4OC)cc32)cc(OC)c1]

MS (ESI): mass calcd. for $C_{22}H_{20}FN_3O_4$, 409.1; m/z found, 410.1 [M+H]$^+$.

Example 510: 1-[(3,5-Dimethoxyphenyl)methyl]-6-[3-(trifluoromethyl)phenyl]-3H-imidazo[4,5-b]pyridin-2-one

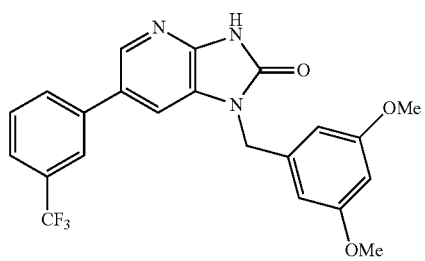 [SMILES: COc1cc(Cn2c(=O)[nH]c3ncc(-c4cccc(C(F)(F)F)c4)cc32)cc(OC)c1]

MS (ESI): mass calcd. for $C_{22}H_{18}F_3N_3O_3$, 429.1; m/z found, 430.1 [M+H]$^+$.

Example 511: 6-(4-Chlorophenyl)-1-[(4-isopropylphenyl)methyl]-3H-imidazo[4,5-b]pyridin-2-one

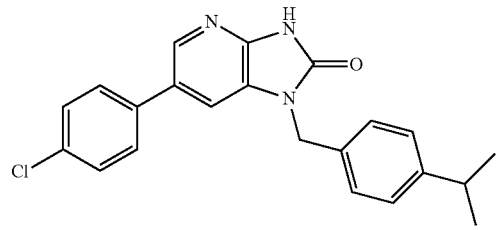 [SMILES: CC(C)c1ccc(Cn2c(=O)[nH]c3ncc(-c4ccc(Cl)cc4)cc32)cc1]

MS (ESI): mass calcd. for $C_{22}H_{20}ClN_3O$, 377.1; m/z found, 378.1 [M+H]$^+$.

Example 512: 6-(4-tert-Butylphenyl)-1-[(3,4-dimethoxy-2-pyridyl)methyl]-3H-imidazo[4,5-b]pyridin-2-one

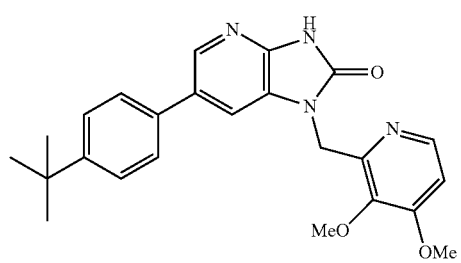 [SMILES: COc1ccnc(Cn2c(=O)[nH]c3ncc(-c4ccc(C(C)(C)C)cc4)cc32)c1OC]

MS (ESI): mass calcd. for $C_{24}H_{26}N_4O_3$, 418.2; m/z found, 419.2 [M+H]$^+$.

Example 513: 3-[1-[(3,5-Dimethylisoxazol-4-yl)methyl]-2-oxo-3H-imidazo[4,5-b]pyridin-6-yl]benzonitrile

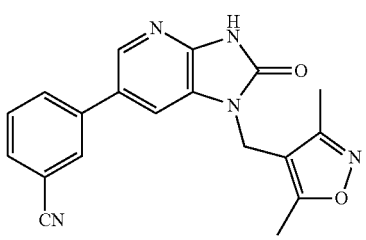 [SMILES: Cc1noc(C)c1Cn1c(=O)[nH]c2ncc(-c3cccc(C#N)c3)cc21]

MS (ESI): mass calcd. for $C_{19}H_{15}N_5O_2$, 345.1; m/z found, 346.1 [M+H]$^+$.

Example 514: 1-[(3,5-Dimethylisoxazol-4-yl)methyl]-6-(2-ethoxy-5-fluoro-phenyl)-3H-imidazo[4,5-b]pyridin-2-one

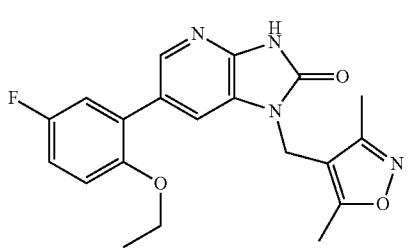 [SMILES: CCOc1ccc(F)cc1-c1cnc2[nH]c(=O)n(Cc3c(C)noc3C)c2c1]

MS (ESI): mass calcd. for $C_{20}H_{19}FN_4O_3$, 382.1; m/z found, 383.0 [M+H]$^+$.

Example 515: 6-(4-Methoxy-3-methyl-phenyl)-1-[(5-methyl isoxazol-3-yl)methyl]-3H-imidazo[4,5-b]pyridin-2-one

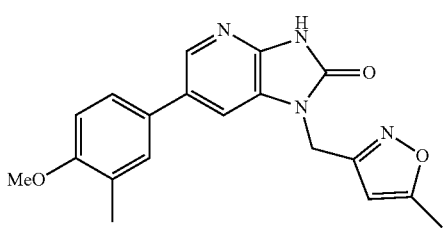 [SMILES: COc1ccc(-c2cnc3[nH]c(=O)n(Cc4cc(C)on4)c3c2)cc1C]

MS (ESI): mass calcd. for $C_{19}H_{18}N_4O_3$, 350.1; m/z found, 351.1 [M+H]$^+$.

Example 516: 6-(3,5-Dimethyl phenyl)-1-[(5-methyl isoxazol-3-yl)methyl]-3H-imidazo[4,5-b]pyridin-2-one

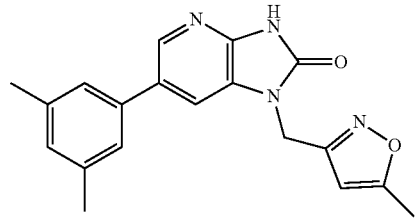

MS (ESI): mass calcd. for $C_{19}H_{18}N_4O_2$, 334.1; m/z found, 335.1 [M+H]$^+$.

Example 517: 6-(2-Ethoxyphenyl)-1-[(5-methyl isoxazol-3-yl)methyl]-3H-imidazo[4,5-b]pyridin-2-one

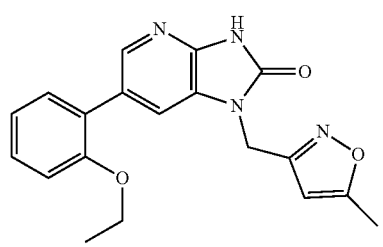 [SMILES: CCOc1ccccc1-c1cnc2[nH]c(=O)n(Cc3cc(C)on3)c2c1]

MS (ESI): mass calcd. for $C_{19}H_{18}N_4O_3$, 350.1; m/z found, 351.1 [M+H]$^+$.

Example 518: 6-(2,4-Dimethoxyphenyl)-1-[(5-methyl isoxazol-3-yl)methyl]-3H-imidazo[4,5-b]pyridin-2-one

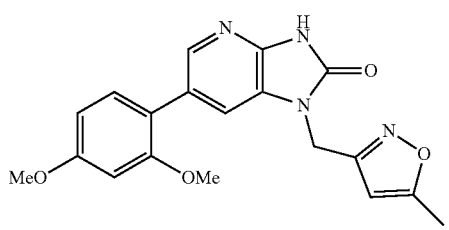 [SMILES: COc1ccc(-c2cnc3[nH]c(=O)n(Cc4cc(C)on4)c3c2)c(OC)c1]

MS (ESI): mass calcd. for $C_{19}H_{18}N_4O_4$, 366.1; m/z found, 367.1 [M+H]$^+$.

Example 519: 6-(3-Fluoro-4-methoxy-phenyl)-1-[(5-methylisoxazol-3-yl)methyl]-3H-imidazo[4,5-b]pyridin-2-one

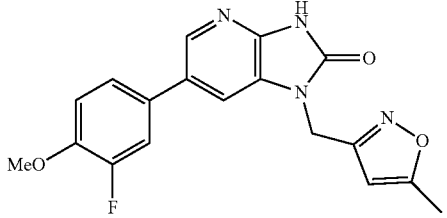 [SMILES: COc1ccc(-c2cnc3[nH]c(=O)n(Cc4cc(C)on4)c3c2)cc1F]

MS (ESI): mass calcd. for $C_{18}H_{15}FN_4O_3$, 354.1; m/z found, 355.1 [M+H]$^+$.

Example 520: 6-(4-Fluoro-2-methoxy-phenyl)-1-[(5-methylisoxazol-3-yl)methyl]-3H-imidazo[4,5-b]pyridin-2-one

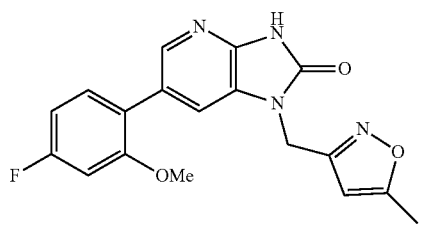 [SMILES: COc1cc(F)ccc1-c1cnc2[nH]c(=O)n(Cc3cc(C)on3)c2c1]

MS (ESI): mass calcd. for $C_{18}H_{15}FN_4O_3$, 354.1; m/z found, 355.1 [M+H]$^+$.

Example 521: 6-(2-Ethoxy-5-fluoro-phenyl)-1-[(5-methylisoxazol-3-yl)methyl]-3H-imidazo[4,5-b]pyridin-2-one

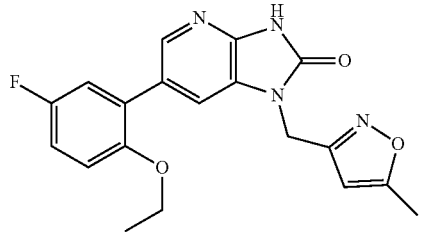 [SMILES: CCOc1ccc(F)cc1-c1cnc2[nH]c(=O)n(Cc3cc(C)on3)c2c1]

MS (ESI): mass calcd. for $C_{19}H_{17}FN_4O_3$, 368.1; m/z found, 369.1 [M+H]$^+$.

Example 522: 6-(4-Fluoro-2-methyl-phenyl)-1-[(5-methylisoxazol-3-yl)methyl]-3H-imidazo[4,5-b]pyridin-2-one

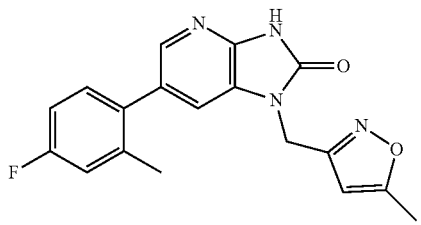 [SMILES: Cc1cc(Cn2c(=O)[nH]c3ncc(-c4ccc(F)cc4C)cc32)no1]

MS (ESI): mass calcd. for $C_{18}H_{15}FN_4O_2$, 338.1; m/z found, 339.1 [M+H]$^+$.

Example 523: 6-(3,5-Difluorophenyl)-1-[(5-methylisoxazol-3-yl)methyl]-3H-imidazo[4,5-b]pyridin-2-one

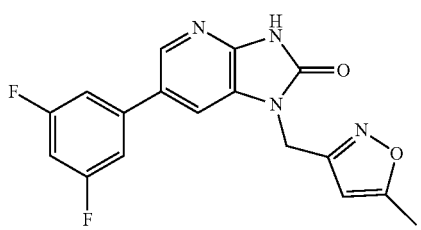 [SMILES: Cc1cc(Cn2c(=O)[nH]c3ncc(-c4cc(F)cc(F)c4)cc32)no1]

MS (ESI): mass calcd. for $C_{17}H_{12}F_2N_4O_2$, 342.1.

The following compounds may be prepared in a manner analogous to the methods as described above.

Example 524: 1-(2-Oxo-2-(pyrrolidin-1-yl)ethyl)-6-(thiazol-5-yl)-1H-imidazo[4,5-b]pyridin-2(3H)-one

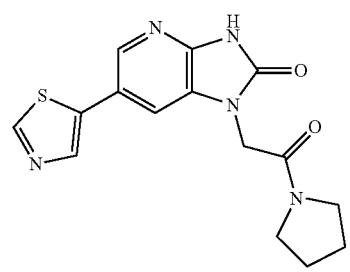 [SMILES: O=C(Cn1c(=O)[nH]c2ncc(-c3cncs3)cc21)N1CCCC1]

MS (ESI): mass calcd. for $C_{15}H_{15}N_5O_2S$, 329.1.

Example 525: 1-(2-(3-hydroxy-3-methylazetidin-1-yl)-2-oxoethyl)-6-(5-methyl pyridin-3-yl)-1H-imidazo[4,5-b]pyridin-2(3H)-one

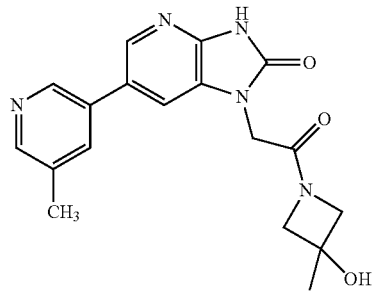 [SMILES: Cc1cncc(-c2cnc3[nH]c(=O)n(CC(=O)N4CC(C)(O)C4)c3c2)c1]

MS (ESI): mass calcd. for $C_{18}H_{19}N_5O_3$, 353.2.

Example 526: 1-(2-(Azetidin-1-yl)-2-oxoethyl)-6-(6-fluoropyridin-3-yl)-1H-imidazo[4,5-b]pyridin-2(3H)-one

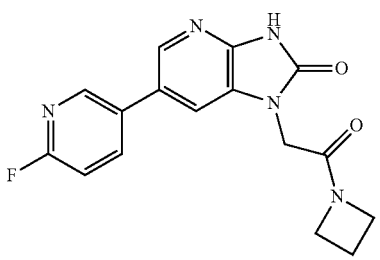 [SMILES: O=C(Cn1c(=O)[nH]c2ncc(-c3ccc(F)nc3)cc21)N1CCC1]

MS (ESI): mass calcd. for $C_{16}H_{14}FN_5O_2$, 327.1.

Example 527: 1-(2-(2-Oxo-6-(3-(trifluoromethyl)phenyl)-2,3-dihydro-1H-imidazo[4,5-b]pyridin-1-yl)acetyl)azetidine-3-carbonitrile

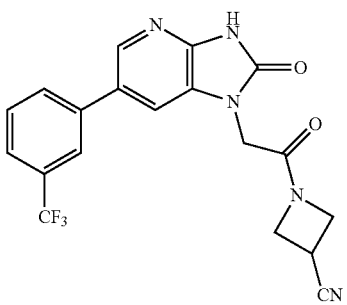 [SMILES: N#CC1CN(C(=O)Cn2c(=O)[nH]c3ncc(-c4cccc(C(F)(F)F)c4)cc32)C1]

MS (ESI): mass calcd. for $C_{19}H_{14}F_3N_5O_2$, 401.1.

Example 528: 1-Benzyl-6-(4-fluoro-3-(trifluoromethyl)phenyl)-1H-imidazo[4,5-b]pyridin-2(3H)-one

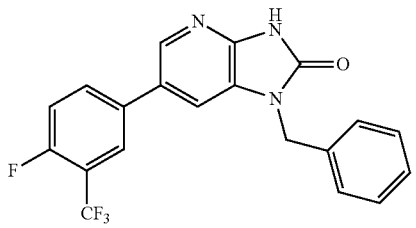

MS (ESI): mass calcd. for $C_{20}H_{13}F_4N_3O$, 387.1.

Example 529: 1-(2-(3-Methylazetidin-1-yl)-2-oxoethyl)-6-(3-(trifluoromethyl) phenyl)-1H-imidazo[4,5-b]pyridin-2(3H)-one

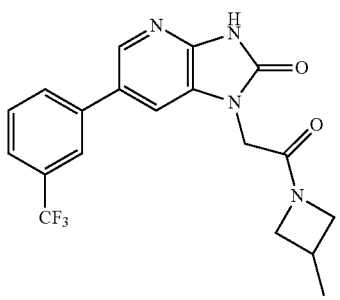 [SMILES: CC1CN(C(=O)Cn2c(=O)[nH]c3ncc(-c4cccc(C(F)(F)F)c4)cc32)C1]

MS (ESI): mass calcd. for $C_{19}H_{17}F_3N_4O_2$, 390.1.

Example 530: 1-(2-(3-(Methoxymethyl)azetidin-1-yl)-2-oxoethyl)-6-(3-(trifluoromethyl)phenyl)-1H-imidazo[4,5-b]pyridin-2(3H)-one

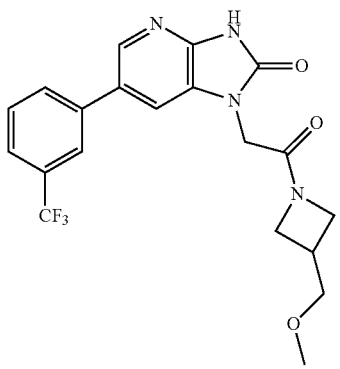 [SMILES: COCC1CN(C(=O)Cn2c(=O)[nH]c3ncc(-c4cccc(C(F)(F)F)c4)cc32)C1]

MS (ESI): mass calcd. for $C_{20}H_{19}F_3N_4O_3$, 420.1.

Example 531: 6-(2-Fluoro-3-methyl phenyl)-1-(2-oxo-2-(3-(trifluoromethyl)azetidin-1-yl)ethyl)-1H-imidazo[4,5-b]pyridin-2(3H)-one

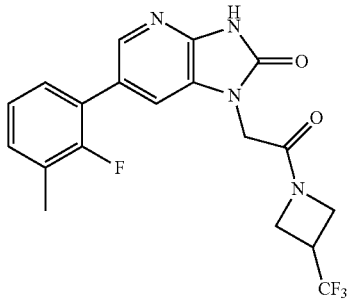 [SMILES: Cc1cccc(-c2cnc3[nH]c(=O)n(CC(=O)N4CC(C(F)(F)F)C4)c3c2)c1F]

MS (ESI): mass calcd. for $C_{19}H_{16}F_4N_4O_2$, 408.1.

Example 532: N-(3-Chloropropyl)-2-[3-methyl-2-oxo-6-[5-(trifluoromethyl)-2-thienyl]imidazo[4,5-b]pyridin-1-yl]acetamide

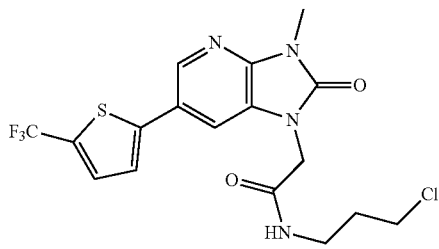 [SMILES: Cn1c(=O)n(CC(=O)NCCCCl)c2cc(-c3ccc(C(F)(F)F)s3)cnc21]

To a suspension of 2-(3-methyl-2-oxo-6-(5-(trifluoromethyl)thiophen-2-yl)-2,3-dihydro-1H-imidazo[4,5-b]pyridin-1-yl)acetic acid (Intermediate 67, 300 mg, 0.84 mmol) and benzotriazol-1-yloxy-tris(dimethylamino)phosphonium hexafluorophosphate (371.3 mg, 0.84 mmol) in DCM (3 mL) was added TEA (0.35 mL, 2.5 mmol) followed by 3-chloropropan-1-amine hydrochloride (218.3 mg, 1.67 mmol). The reaction mixture was stirred at room temperature overnight. To the reaction mixture was added water and the reaction mixture was extracted with DCM. The organics were separated, combined, dried, concentrated under reduced pressure. Purification (via HPLC Method A) afforded the title compound (140 mg, 38%). MS (ESI): mass calcd. for $C_{17}H_{16}ClF_3N_4O_2S$, 432.1; m/z found, [M+H]$^+$. $^1$H NMR (500 MHz, DMSO-d$_6$) δ 8.43 (d, J=2.0 Hz, 1H), 8.27 (t, J=5.6 Hz, 1H), 7.91 (d, J=2.0 Hz, 1H), 7.77 (dq, J=3.7, 1.2 Hz, 1H), 7.60 (dt, J=3.8, 1.3 Hz, 1H), 4.56 (s, 2H), 3.64 (t, J=6.6 Hz, 2H), 3.41 (s, 3H), 3.21 (q, J=6.5 Hz, 2H), 1.87 (p, J=6.6 Hz, 2H).

Example 533: 2-[6-[3-(Difluoromethyl)-4-fluoro-phenyl]-3-methyl-2-oxo-imidazo[4,5-b]pyridin-1-yl]-N,N-dimethyl-acetamide

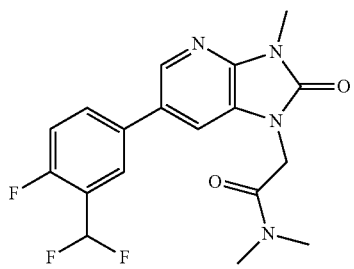 [SMILES: CN(C)C(=O)Cn1c(=O)n(C)c2ncc(-c3ccc(F)c(C(F)F)c3)cc21]

DIPEA (133 µL, 0.8 mmol) and HBtU (147 mg, 0.4 mmol) were added to a solution of 2-(6-(3-(difluoromethyl)-4-fluorophenyl)-3-methyl-2-oxo-2,3-dihydro-1H-imidazo[4,5-b]pyridin-1-yl)acetic acid (Intermediate 59, 100 mg, 0.3 mmol) in DMF (5 mL) in a sealed tube. The mixture was stirred 10 minutes and dimethylamine was added (2M in THF, 130 µL, 0.3 mmol). The reaction was stirred at room temperature overnight. Saturated solution of NaHCO$_3$ was added and the mixture was extracted with EtOAc (×3). The organic layers were dried over MgSO$_4$ and concentrated. The crude product was purified (FCC, SiO$_2$, 0-100% EtOAc in heptane) to provide the title compound (61.5 mg, 0.16 mmol, 61%). MS (ESI): mass calcd. for $C_{18}H_{17}F_3N_4O_2$, 378.1; m/z found, [M+H]$^+$. $^1$H NMR (300 MHz, DMSO-d$_6$) δ 8.31 (s, 1H), 7.88 (d, J=6.1 Hz, 2H), 7.83 (s, 1H), 7.50 (t, J=9.7 Hz, 1H), 7.26 (t, J=54.2 Hz, 1H), 4.86 (s, 2H), 3.39 (s, 3H), 3.10 (s, 3H), 2.84 (s, 3H).

Example 534: 1-[2-(Azetidin-1-yl)-2-oxo-ethyl]-3-(fluoromethyl)-6-[5-(trifluoromethyl)-2-thienyl]imidazo[4,5-b]pyridin-2-one

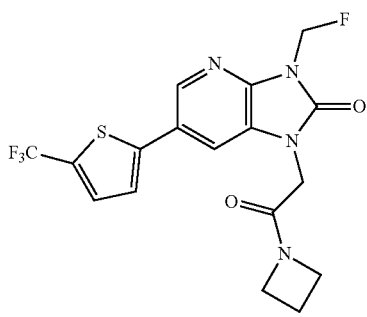 [SMILES: O=C(Cn1c(=O)n(CF)c2ncc(-c3ccc(C(F)(F)F)s3)cc21)N1CCC1]

To a mixture of 1-[2-(azetidin-1-yl)-2-oxo-ethyl]-6-[5-(trifluoromethyl)-2-thienyl]-3H-imidazo[4,5-b]pyridin-2-one (Example 323, 66 mg, 0.173 mmol) in DMF (3 mL) was added NaH (8 mg, 0.21 mmol). The solution was stirred at rt for 1.5 h then fluoroiodomethane was added (0.017 mL, 0.26 mmol). After stirring 2 h additional at rt, MeOH was added (0.5 mL) and the solution was loaded directly onto silica gel (24 g) and purified by FCC (0-10% (2N NH$_3$-MeOH)/DCM gradient). The solvents were removed in vacuo. The residue was dissolved in MeCN/water (20 mL, 1:1) and solvents were removed by lyophilization to give the title compound as a white powder (24 mg, 34%). MS (ESI): mass calcd. for $C_{17}H_{14}F_4N_4O_2S$, 414.1; m/z found, 415.2 [M+H]$^+$. $^1$H NMR (600 MHz, CDCl$_3$-d) δ 8.34 (d, J=1.9 Hz, 1H), 7.51 (d, J=1.9 Hz, 1H), 7.42 (dq, J=3.4, 1.1 Hz, 1H), 7.22 (dq, J=3.6, 1.1 Hz, 1H), 6.08 (d, J=52.5 Hz, 2H), 4.49 (s, 2H), 4.35 (t, J=7.8 Hz, 2H), 4.10 (t, J=7.8 Hz, 2H), 2.42-2.35 (m, 2H).

Example 535: 1-[2-(Azetidin-1-yl)-2-oxo-ethyl]-3-(2-fluoroethyl)-6-[5-(trifluoromethyl)-2-thienyl]imidazo[4,5-b]pyridin-2-one

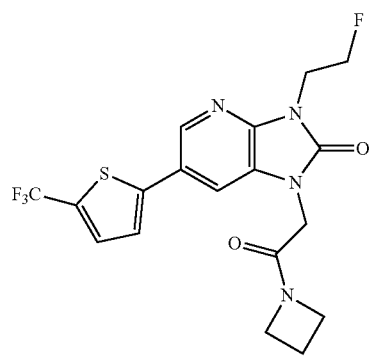 [SMILES: O=C(Cn1c(=O)n(CCF)c2ncc(-c3ccc(C(F)(F)F)s3)cc21)N1CCC1]

To a solution of 1-[2-(azetidin-1-yl)-2-oxo-ethyl]-6-[5-(trifluoromethyl)-2-thienyl]-3H-imidazo[4,5-b]pyridin-2-one (Example 323, 7 mg, 0.018 mmol) in dry DMF (0.3 mL) at rt was added sodium hydride (60% dispersion in mineral oil, 3 mg, 0.073 mmol). The reaction mixture was stirred at rt for 10 min followed by addition of 1-fluoro-2-iodoethane (6.4 mg, 0.073 mmol). The reaction mixture was stirred at rt for 1 h. The reaction mixture was cooled to 0° C. and quenched by adding two drops of methanol. The reaction mixture was diluted with EtOAc (10 mL) and washed with brine (20 mL). The organic phase was separated, dried (Na$_2$SO$_4$), and concentrated under reduced pressure. Purification (reversed phase HPLC; TFA 0.05% buffered water/MeCN) afforded the title compound which was suspended in EtOAc and neutralized with saturated NaHCO$_3$ solution. The compound was further dried under high vacuum to afford the tittle compound as a white solid. MS (ESI): mass calcd. for $C_{18}H_{16}F_4N_4O_2S$, 428.1; m/z found, [M+H]$^+$. $^1$H NMR (500 MHz, CDCl$_3$) δ 8.32 (d, J=1.8 Hz, 1H), 7.55 (d, J=1.9 Hz, 1H), 7.45 (dd, J=3.7, 1.2 Hz, 1H), 7.30-7.26 (m, 1H), 4.84 (t, J=5.0 Hz, 1H), 4.75 (t, J=5.0 Hz, 1H), 4.40-4.30 (m, 5H), 2.41 (dt, J=15.5, 7.8 Hz, 2H).

Example 536: 1-[2-[3-(2-Fluoroethyl)azetidin-1-yl]-2-oxo-ethyl]-6-[3-(trifluoromethyl)phenyl]-3H-imidazo[4,5-b]pyridin-2-one

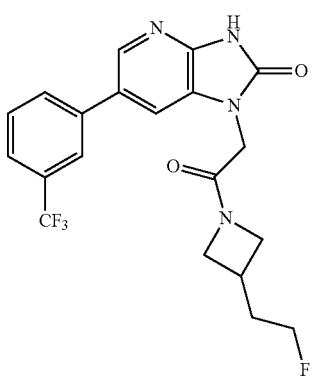 [SMILES: O=C(Cn1c(=O)[nH]c2ncc(-c3cccc(C(F)(F)F)c3)cc21)N1CC(CCF)C1]

Step A: 1-(2-(3-(2-Fluoroethyl)azetidin-1-yl)-2-oxo-ethyl)-6-(3-(trifluoromethyl)phenyl)-3-trityl-1,3-dihydro-2H-imidazo[4,5-b]pyridin-2-one To a vial containing Pd(PPh$_3$)$_4$ (4.43 mg, 0.0038 mmol) and K$_2$CO$_3$ (15.9 mg, 0.115 mmol) was added 6-bromo-1-(2-(3-(2-fluoroethyl)azetidin-1-yl)-2-oxoethyl)-3-trityl-1,3-dihydro-2H-imidazo[4,5-b]pyridin-2-one (Intermediate 68, 23 mg, 0.038 mmol) and 3-(trifluoromethyl)phenylboronic acid (14.5 mg, 0.076 mmol) under nitrogen. DMF was added (0.15 mL) and the reaction mixture was heated to 110° C. for 2 h. The reaction mixture was cooled, diluted with EtOAc and NaHCO$_3$ (aq). The organic layer was separated, washed with brine, separated, dried, and concentrated under reduced pressure. The title compound was used crude in the next step without further purification.

Step B: 1-[2-[3-(2-Fluoroethyl)azetidin-1-yl]-2-oxo-ethyl]-6-[3-(trifluoromethyl)phenyl]-3H-imidazo[4,5-b]pyridin-2-one The title compound was prepared in a manner analogous to Example 24, Step C using 1-(2-(3-(2-fluoroethyl)azetidin-1-yl)-2-oxoethyl)-6-(3-(trifluoromethyl)phenyl)-3-trityl-1,3-dihydro-2H-imidazo[4,5-b]pyridin-2-one. MS (ESI): mass calcd. for C$_{20}$H$_{18}$F$_4$N$_4$O$_2$, 422.1; m/z found, 423.1 [M+H]$^+$. $^1$H NMR (400 MHz, CDCl$_3$) δ 8.21 (d, J=1.9 Hz, 1H), 7.80-7.61 (m, 2H), 7.61-7.46 (m, 2H), 7.44 (d, J=1.9 Hz, 1H), 4.59-4.27 (m, 3H), 4.41 (s, 2H), 4.14 (t, J=9.5 Hz, 1H), 3.97 (dd, J=8.7, 5.8 Hz, 1H), 3.70 (dd, J=10.2, 5.9 Hz, 1H), 2.82 (t, J=7.9 Hz, 1H), 2.11-1.86 (m, 2H).

Example 537: 6-(6-Fluoro-2-pyridyl)-1-(2-oxobutyl)-3H-imidazo[4,5-b]pyridin-2-one

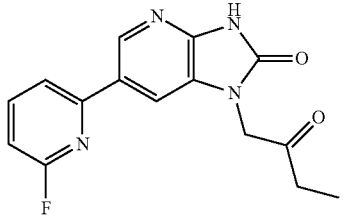 [SMILES: CCC(=O)Cn1c(=O)[nH]c2ncc(-c3cccc(F)n3)cc21]

Step A: 6-Bromo-1-(2-oxobutyl)-3-trityl-1,3-dihydro-2H-imidazo[4,5-b]pyridin-2-one The title compound was prepared in a manner analogous to Example 330, Step A, using 1-chlorobutan-2-one instead of 1-bromo-2-butanone.

Step B: 6-(6-fluoropyridin-2-yl)-1-(2-oxobutyl)-3-trityl-1,3-dihydro-2H-imidazo[4,5-b]pyridin-2-one The title compound was prepared in a manner analogous to Example 330, Step B, using 6-bromo-1-(2-oxobutyl)-3-trityl-1,3-dihydro-2H-imidazo[4,5-b]pyridin-2-one and using (6-fluoropyridin-2-yl)boronic acid instead of (3,4-difluorophenyl)boronic acid.

Step C. 6-(6-Fluoro-2-pyridyl)-1-(2-oxobutyl)-3H-imidazo[4,5-b]pyridin-2-one The title compound was prepared in a manner analogous to Example 11, Step C. MS (ESI): mass calcd. for C$_{15}$H$_{13}$FN$_4$O$_2$, 300.1; m/z found, 301.1 [M+H]$^+$. $^1$H NMR (400 MHz, CD$_3$CN) δ 8.66 (d, J=2.1 Hz, 1H), 8.11-7.91 (m, 1H), 7.87 (d, J=1.8 Hz, 1H), 7.79 (dd, J=7.5, 2.7 Hz, 1H), 7.01 (dd, J=8.0, 2.8 Hz, 1H), 4.78 (s, 2H), 2.65 (d, J=7.2 Hz, 2H), 1.09 (t, J=7.3 Hz, 3H).

Example 538: 1-[2-(Azetidin-1-yl)-2-oxo-ethyl]-6-[4-(2-fluoroethoxy)-3-(trifluoromethyl)phenyl]-3H-imidazo[4,5-b]pyridin-2-one

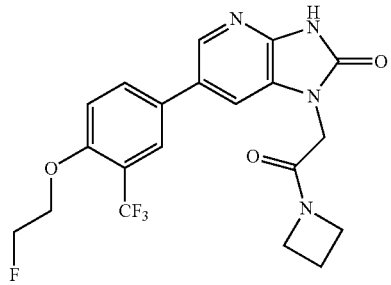 [SMILES: O=C(Cn1c(=O)[nH]c2ncc(-c3ccc(OCCF)c(C(F)(F)F)c3)cc21)N1CCC1]

Step A: 1-(2-(Azetidin-1-yl)-2-oxoethyl)-6-(4-hydroxy-3-(trifluoromethyl)phenyl)-3-trityl-1,3-dihydro-2H-imidazo[4,5-b]pyridin-2-one The title compound was prepared in a manner analogous to Example 330, Steps A-B, using 1-(2-(azetidin-1-yl)-2-oxoethyl)-6-bromo-3-trityl-1,3-dihydro-2H-imidazo[4,5-b]pyridin-2-one (Intermediate 38) in Step A; and (4-hydroxy-3-(trifluoromethyl)phenyl)boronic acid, K$_2$CO$_3$ instead of Cs$_2$CO$_3$, and DMF instead of dioxane in Step B. MS (ESI): mass calcd. for C$_{37}$H$_{29}$F$_3$N$_4$O$_3$, 634.2. m/z found, 626.2 [M+Na]$^+$.

Step B: 1-(2-(Azetidin-1-yl)-2-oxoethyl)-6-(4-(2-fluoroethoxy)-3-(trifluoromethyl)phenyl)-3-trityl-1,3-dihydro-2H-imidazo[4,5-b]pyridin-2-one To a solution of 1-(2-(azetidin-1-yl)-2-oxoethyl)-6-(4-hydroxy-3-(trifluoromethyl)phenyl)-3-trityl-1,3-dihydro-2H-imidazo[4,5-b]pyridin-2-one (30 mg, 0.047 mmol) in DMF (0.073 mL) was added 1-fluoro-2-iodoethane (20.55 mg, 0.118 mmol) and potassium carbonate (13 mg, 0.09 mmol). The reaction mixture was stirred at rt for 5 h. The mixture was diluted with EtOAc (25 mL) and NaHCO$_3$ (aq. 20 mL). The organic layers were washed with brine (20 mL), dried over Na$_2$SO$_4$ and concentrated. The residue (20 mg, yield 62%) was used in next step directly. MS (ESI): mass calcd. for C$_{39}$H$_{32}$F$_4$N$_4$O$_3$, 680.2. m/z found, 703.2 [M+Na]$^+$.

Step C. 1-[2-(Azetidin-1-yl)-2-oxo-ethyl]-6-[4-(2-fluoroethoxy)-3-(trifluoromethyl)phenyl]-3H-imidazo[4,5-b]pyridin-2-one To a solution of 1-(2-(azetidin-1-yl)-2-oxoethyl)-6-(4-(2-fluoroethoxy)-3-(trifluoromethyl)phenyl)-3-trityl-1,3-dihydro-2H-imidazo[4,5-b]pyridin-2-one (20 mg, 0.029 mmol) in DCM (5.6 mL), was added the mixed solution of TFA and TIPS (20:1, 250 μL). The reaction mixture was stirred at rt overnight. The solvents were removed under vacuum. The residue was purified on a RP-HPLC (C18, MeCN in Water 35% to 60%) to afford the title compound (6.5 mg, yield 51%). MS (ESI): mass calcd. for $C_{20}H_{18}F_4N_4O_3$, 438.1; m/z found, 439.1 [M+H]$^+$. $^1$H NMR (400 MHz, CDCl$_3$) δ 8.16 (s, 1H), 7.68 (d, J=2.2 Hz, 1H), 7.61 (dd, J=8.7, 2.3 Hz, 1H), 7.39 (d, J=1.6 Hz, 1H), 7.03 (d, J=8.6 Hz, 1H), 5.23 (s, 1H), 4.90-4.59 (m, 2H), 4.45 (s, 2H), 4.40-4.20 (m, 3H), 4.10-3.95 (m, 3H), 2.30 (t, J=7.8 Hz, 2H).

Example 539: 1-[2-(Azetidin-1-yl)-2-oxo-ethyl]-6-[3-(2-fluoroethoxy)-5-(trifluoromethyl)phenyl]-3H-imidazo[4,5-b]pyridin-2-one

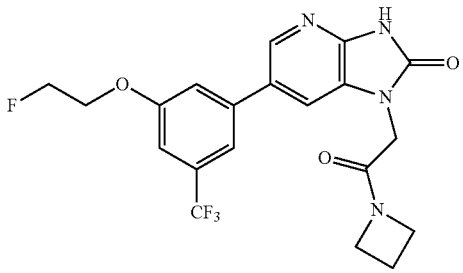 [SMILES: O=C(Cn1c(=O)[nH]c2ncc(-c3cc(OCCF)cc(C(F)(F)F)c3)cc21)N1CCC1]

Step A: 1-Bromo-3-(2-fluoroethoxy)-5-(trifluoromethyl)benzene

To a solution of 3-bromo-5-(trifluoromethyl)phenol (500 mg, 2.1 mmol) in DMF (3.2 mL) was added potassium carbonate (573 mg, 4.1 mmol). 1-fluoro-2-iodoethane was added dropwise at rt. The reaction was stirred overnight. The reaction mixture was diluted with EtOAc (50 mL) and brine (30 mL). The organic layer was collected, dried over Na$_2$SO$_4$ and concentrated. The residue was purified (FCC EtOAc in Hexanes 0% to 50%) to afford colorless oil (380 mg, yield 64%) MS (ESI): mass calcd. for $C_9H_7BrF_4O$, 286.0; m/z found, 287.1 [M+H]$^+$. $^1$H NMR (400 MHz, CDCl$_3$) δ 7.43 (d, J=0.7 Hz, 1H), 7.38-7.24 (s, 1H), 7.15 (d, J=0.7 Hz, 1H), 4.92-4.69 (m, 2H), 4.37-4.24 (m, 2H).

Step B: 1-(2-(Azetidin-1-yl)-2-oxoethyl)-6-(3-(2-fluoroethoxy)-5-(trifluoromethyl)phenyl)-3-trityl-1,3-dihydro-2H-imidazo[4,5-b]pyridin-2-one To a vial charged with a stirring bar, 1-bromo-3-(2-fluoroethoxy)-5-(trifluoromethyl)benzene (250 mg, 0.87 mmol), bis(pinacolato)diboron (266 mg, 1.0 mmol), potassium acetate (256 mg, 2.6 mmol) and palladium acetate (10 mg, 0.04 mmol), was added DMF (10 mL). The mixture was degassed with nitrogen for 10 mins. The vial was sealed and heated at 90° C. for 2 h. The reaction was allowed to rt, filtered. To the solution, were added intermediate 38 (240 mg, 0.44 mmol), Pd(PPh$_3$)$_4$ (25 mg, 0.04 mmol), and potassium carbonate (180 mmol). The mixture was heated overnight at 110° C. The mixture was diluted with EtOAc and Brine after cooling down. The organic layer was collected, dried and concentrated. The residue was purified (FCC, EtOAc in Hexanes 10% to 80%) to afford the desired product (180 mg, yield 30%) MS (ESI): mass calcd. for $C_{39}H_{32}F_4ON_4O_3$, 680.2; m/z found, 703.2 [M+H]$^+$.

Step C: 1-[2-(Azetidin-1-yl)-2-oxo-ethyl]-6-[3-(2-fluoroethoxy)-5-(trifluoromethyl)phenyl]-3H-imidazo[4,5-b]pyridin-2-one The title compound was prepared in a manner analogous to Example 24, Step C using 1-(2-(azetidin-1-yl)-2-oxo-ethyl)-6-(3-(2-fluoroethoxy)-5-(trifluoromethyl)phenyl)-3-trityl-1,3-dihydro-2H-imidazo[4,5-b]pyridin-2-one. MS (ESI): mass calcd. for $C_{20}H_{18}F_4N_4O_3$, 438.1; m/z found, 439.1 [M+H]$^+$. $^1$H NMR (400 MHz, DMSO) δ 11.83 (s, 1H), 8.42 (d, J=2.0 Hz, 1H), 7.90 (d, J=2.1 Hz, 1H), 7.64 (d, J=6.5 Hz, 2H), 7.35 (s, 1H), 4.85 (dt, J=47.9, 3.6 Hz, 2H), 4.70-4.41 (m, 4H), 4.33 (s, 2H), 3.96 (s, 2H), 2.34 (s, 2H).

Example 540: 1-[2-(3-$^{18}$F-Fluoranylazetidin-1-yl)-2-oxo-ethyl]-6-(4-fluoro-3-methyl-phenyl)-3-methyl-imidazo[4,5-b]pyridin-2-one

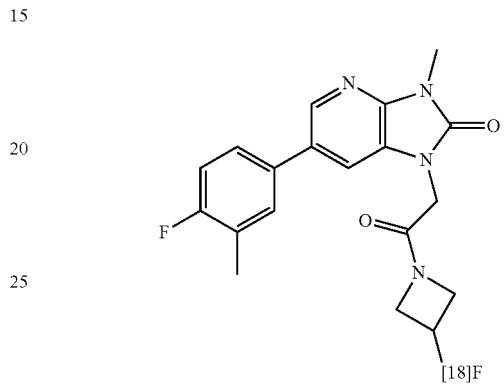

Fluoride-18 ([$^{18}$F]F$^-$) was purchased from PETNET Solutions (PETNET Solutions, USA). The process was performed in Synthra RNPlus (Synthra GmbH). The aqueous solution of [$^{18}$F]fluoride ([$^{18}$F]F$^-$) was trapped on a SepPak Light Accell plus QMA anion exchange cartridge (CO$_3^{2-}$ form, Waters, Milford, Mass., U.S.A.) and eluted with a mixture of Kryptofix 2.2.2 (K-222, 7.2 mg) and KHCO$_3$ (1.1 mg) dissolved in CH$_3$CN/H$_2$O (0.8 mL; 3:1 v/v). After evaporation of the solvent with a stream of nitrogen at 85° C. and vacuum, anhydrous CH$_3$CN (0.5 mL) was added, and [$^{18}$F]F$^-$ was further dried under the same conditions before drying temperature was changed to 110° C. for 10 min. The reaction vial was then cooled to 70° C. before a solution of 1-(2-(6-(4-fluoro-3-methylphenyl)-3-methyl-2-oxo-2,3-dihydro-1H-imidazo[4,5-b]pyridin-1-yl)acetyl)azetidin-3-yl 4-methylbenzenesulfonate (1.50 mg) in anhydrous MeCN (0.7 mL) was added to the dried [$^{18}$F]F$^-$/KHCO$_3$/K-222 complex and the mixture was heated at 100° C. for 10 min. The crude radiolabeling mixture was diluted with water (4.3 mL) and purified using reverse phase HPLC (RP-HPLC) on an Eclipse XDB-C$_{18}$ column (5 μm, 9.4 mm×250 mm; Agilent, Santa Clara, Calif., U.S.A.) eluted with a mixture of 10 mM NH$_4$OAc and MeCN (62:38 v/v) at a flow rate of 4 mL/min and with UV detection at 254 nm. The purified radiotracer solution was diluted with water (30 mL) and passed through a SepPak Light C-18 cartridge. The C-18 cartridge was further washed by water (10 mL) before EtOH (0.5 mL) was used to elute the tracer and diluted by saline (4.5 mL) and formulated as an ethanol concentration 10%, suitable for intravenous injection (IV). Quality control was performed using RP-HPLC on an Eclipse XDB-C$_{18}$ column (5 μm, 4.6 mm×150 mm m, Agilent, Santa Clara, Calif., U.S.A.) eluted with a mixture of 0.05% TFA solution and MeCN at a flow rate of 1.0 mL/min. UV detection was performed at 254 nm.

Example 541: 6-[3-(Difluoromethyl)-4-fluoro-phenyl]-3-methyl-1-(pyridazin-3-ylmethyl)imidazo[4,5-b]pyridin-2-one

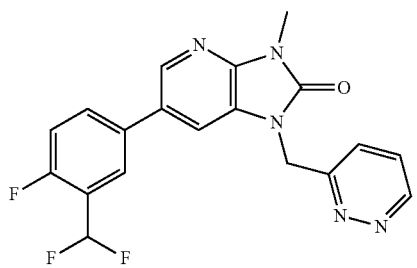 [SMILES: Cn1c(=O)n(Cc2cccnn2)c2cc(-c3ccc(F)c(C(F)F)c3)cnc21]

The title compound was prepared in a manner analogous to Example 6, using 6-(3-(difluoromethyl)-4-fluorophenyl)-3-methyl-1,3-dihydro-2H-imidazo[4,5-b]pyridin-2-one (Intermediate 56) and 3-(chloromethyl)pyridazine (Intermediate 2, Method B). MS (ESI): mass calcd. for $C_{19}H_{14}F_3N_5O$, 385.1; m/z found, 386 [M+H]$^+$. $^1$H NMR (300 MHz, DMSO-d$_6$) δ 9.15 (s, 1H), 8.36 (s, 1H), 7.96-7.84 (m, 3H), 7.73-7.63 (m, 2H), 7.49 (t, J=9.8 Hz, 1H), 7.24 (t, J=54.2 Hz, 1H), 5.49 (s, 2H), 3.42 (s, 3H).

Example 542: 6-[3-(Difluoromethoxy)-4-fluoro-phenyl]-3-methyl-1-(pyridazin-3-ylmethyl)imidazo[4,5-b]pyridin-2-one

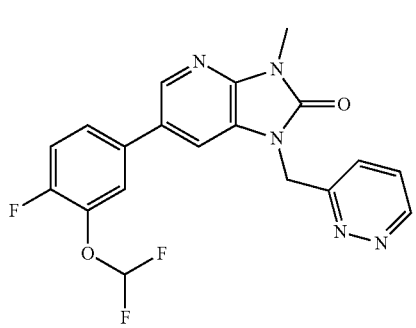 [SMILES: Cn1c(=O)n(Cc2cccnn2)c2cc(-c3ccc(F)c(OC(F)F)c3)cnc21]

The title compound was prepared in a manner analogous to Example 6, using 6-(3-(difluoromethoxy)-4-fluorophenyl)-3-methyl-1,3-dihydro-2H-imidazo[4,5-b]pyridin-2-one (Intermediate 58) and 3-(chloromethyl)pyridazine (Intermediate 2). MS (ESI): mass calcd. for $C_{19}H_{14}F_3N_5O_2$, 401.1; m/z found 402 [M+H]$^+$. $^1$H NMR (300 MHz, DMSO-d$_6$) δ 9.15 (s, 1H), 8.35 (s, 1H), 7.88 (s, 1H), 7.72-7.04 (m, 6H), 5.48 (s, 2H), 3.41 (s, 3H).

Example 543: 6-[4-Chloro-3-(difluoromethoxy)phenyl]-3-methyl-1-(pyridazin-3-ylmethyl)imidazo[4,5-b]pyridin-2-one

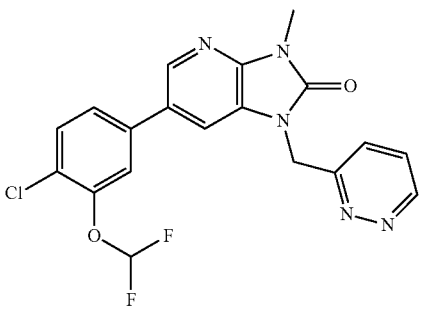 [SMILES: Cn1c(=O)n(Cc2cccnn2)c2cc(-c3ccc(Cl)c(OC(F)F)c3)cnc21]

The title compound was prepared in a manner analogous to Example 6, using 6-(4-chloro-3-(difluoromethoxy)phenyl)-3-methyl-1,3-dihydro-2H-imidazo[4,5-b]pyridin-2-one (Intermediate 57) and 3-(chloromethyl)pyridazine (Intermediate 2). MS (ESI): mass calcd. for $C_{19}H_{14}ClF_2N_5O_2$, 417.1; m/z found, 418 [M+H]$^+$. $^1$H NMR (300 MHz, DMSO-d$_6$) δ 9.15 (s, 1H), 8.39 (s, 1H), 7.90 (s, 1H), 7.72-7.10 (m, 6H), 5.48 (s, 2H), 3.40 (s, 3H).

Example 544: 6-[4-Chloro-3-(difluoromethoxy)phenyl]-1-[(5-fluoro-3-pyridyl)methyl]-3-methyl-imidazo[4,5-b]pyridin-2-one

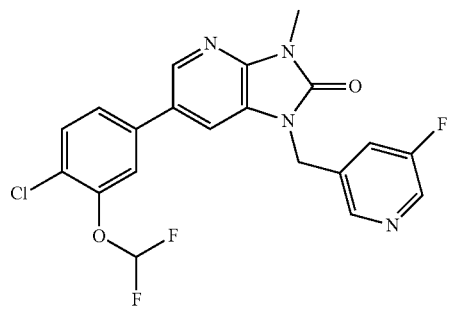 [SMILES: Cn1c(=O)n(Cc2cncc(F)c2)c2cc(-c3ccc(Cl)c(OC(F)F)c3)cnc21]

The title compound was prepared in a manner analogous to Example 6, using 6-(4-chloro-3-(difluoromethoxy)phenyl)-3-methyl-1,3-dihydro-2H-imidazo[4,5-b]pyridin-2-one (Intermediate 57) and 3-(chloromethyl)-5-fluoropyridine (Intermediate 64). The halide was added as a solution of DMF (5 mL) and DIPEA (1 equivalent). MS (ESI): mass calcd. for $C_{20}H_{14}ClF_3N_4O_2$, 434.1; m/z found, 435 [M+H]$^-$. $^1$H NMR (300 MHz, DMSO-d$_6$) δ 8.53 (s, 1H), 8.50 (s, 1H), 8.38 (s, 1H), 7.97 (s, 1H), 7.77-7.11 (m, 5H), 5.24 (s, 2H), 3.40 (s, 3H).

Example 545: 6-(3,4-Difluorophenyl)-3-methyl-1-(thiadiazol-4-ylmethyl)imidazo[4,5-b]pyridin-2-one

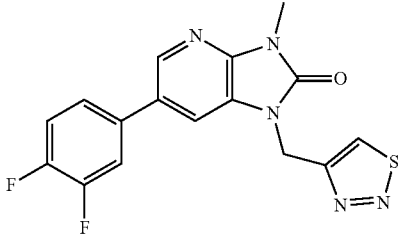 [SMILES: Cn1c(=O)n(Cc2csnn2)c2cc(-c3ccc(F)c(F)c3)cnc21]

The title compound was prepared in a manner analogous to Example 6, using 6-(3,4-difluorophenyl)-3-methyl-1,3-dihydro-2H-imidazo[4,5-b]pyridin-2-one (Intermediate 29) and 4-(chloromethyl)-1,2,3-thiadiazole. MS (ESI): mass calcd. for $C_{16}H_{11}F_2N_5OS$, 359.1; m/z found, 360 [M+H]$^+$. $^1$H NMR (300 MHz, CDCl$_3$) δ 8.66 (s, 1H), 8.21 (d, J=1.5 Hz, 1H), 7.61 (d, J=1.5 Hz, 1H), 7.34 (dd, J=11.0, 7.6 Hz, 1H), 7.23 (br s, 2H), 5.62 (s, 2H), 3.54 (s, 3H).

Example 546: 6-[3-(Difluoromethyl)-4-fluoro-phenyl]-1-[(5-fluoro-3-pyridyl)methyl]-3-methyl-imidazo[4,5-b]pyridin-2-one

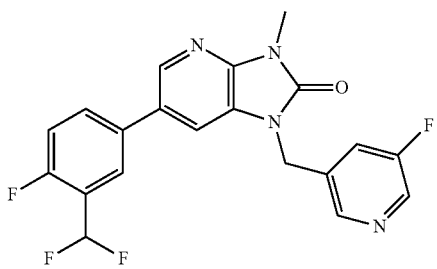 [SMILES: Cn1c(=O)n(Cc2cncc(F)c2)c2cc(-c3ccc(F)c(C(F)F)c3)cnc21]

The title compound was prepared in a manner analogous to Example 6, using 6-(3-(difluoromethyl)-4-fluorophenyl)-3-methyl-1,3-dihydro-2H-imidazo[4,5-b]pyridin-2-one (Intermediate 56) and 3-(chloromethyl)-5-fluoropyridine (Intermediate 64). MS (ESI): mass calcd. for $C_{20}H_{14}F_4N_4O$, 402.1; m/z found, 403 [M+H]$^+$. $^1$H NMR (300 MHz, DMSO-d$_6$) δ 8.54 (s, 1H), 8.50 (d, J=2.0 Hz, 1H), 8.33 (s, 1H), 7.98 (s, 1H), 7.90 (d, J=4.4 Hz, 2H), 7.73 (d, J=9.6 Hz, 1H), 7.50 (t, J=9.7 Hz, 1H), 7.25 (t, J=54.2 Hz, 1H), 5.24 (s, 2H), 3.40 (s, 3H).

Example 547: 6-[3-(Difluoromethoxy)-4-fluoro-phenyl]-1-[(5-fluoro-3-pyridyl)methyl]-3-methyl-imidazo[4,5-b]pyridin-2-one

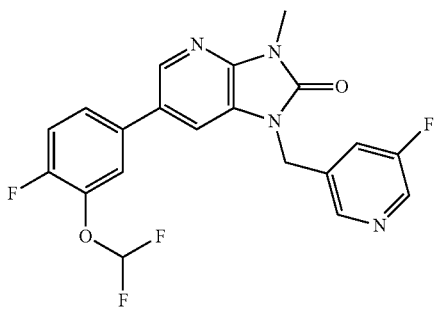 [SMILES: Cn1c(=O)n(Cc2cncc(F)c2)c2cc(-c3ccc(F)c(OC(F)F)c3)cnc21]

The title compound was prepared in a manner analogous to Example 6, using 6-(3-(difluoromethoxy)-4-fluorophenyl)-3-methyl-1,3-dihydro-2H-imidazo[4,5-b]pyridin-2-one (Intermediate 58) and 3-(chloromethyl)-5-fluoropyridine (Intermediate 64). The halide was added as a solution of DMF (5 mL) and DIPEA (1 equivalent). MS (ESI): mass calcd. for $C_{20}H_{14}F_4N_4O_2$, 418.1; m/z found, 419 [M+H]$^+$. $^1$H NMR (300 MHz, DMSO-d$_6$) δ 8.53 (s, 1H), 8.50 (d, J=2.2 Hz, 1H), 8.34 (s, 1H), 7.94 (s, 1H), 7.70 (dd, J=17.3, 8.6 Hz, 2H), 7.65-7.06 (m, 3H), 5.23 (s, 2H), 3.40 (s, 3H).

Example 548: 3-Methyl-1-(thiadiazol-4-ylmethyl)-6-[3-(trifluoromethyl)phenyl]imidazo[4,5-b]pyridin-2-one

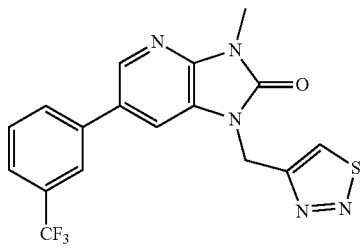 [SMILES: Cn1c(=O)n(Cc2csnn2)c2cc(-c3cccc(C(F)(F)F)c3)cnc21]

The title compound was prepared in a manner analogous to Example 6, using 3-methyl-6-(3-(trifluoromethyl)phenyl)-1,3-dihydro-2H-imidazo[4,5-b]pyridin-2-one (Intermediate 26) and 4-(chloromethyl)-1,2,3-thiadiazole. MS (ESI): mass calcd. for $C_{17}H_{12}F_3N_5OS$, 391.1; m/z found 392 [M+H]$^+$. $^1$H NMR (300 MHz, CDCl$_3$) δ 8.66 (s, 1H), 8.27 (d, J=1.5 Hz, 1H), 7.77 (s, 1H), 7.72 (d, J=7.4 Hz, 1H), 7.68-7.58 (m, 3H), 5.64 (s, 2H), 3.56 (s, 3H).

Example 549: 6-(3,4-Difluorophenyl)-3-methyl-1-[(1-methyltriazol-4-yl)methyl]imidazo[4,5-b]pyridin-2-one

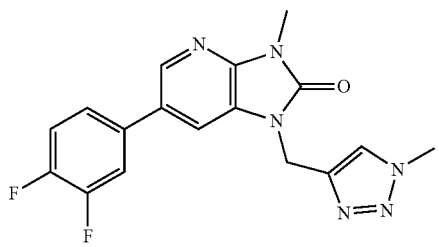 [SMILES: Cn1cc(Cn2c(=O)n(C)c3ncc(-c4ccc(F)c(F)c4)cc32)nn1]

The title compound was prepared in a manner analogous to Example 6, using 6-(3,4-difluorophenyl)-3-methyl-1,3-dihydro-2H-imidazo[4,5-b]pyridin-2-one (Intermediate 29) and 4-(chloromethyl)-1-methyl-1H-1,2,3 triazole hydrochloride. The halide was added as a solution of DMF (5 mL) and DIPEA (1 equivalent). MS (ESI): mass calcd. for $C_{17}H_{14}F_2N_6O$, 356.1; m/z found, 357 [M+H]$^+$. $^1$H NMR (300 MHz, DMSO-d$_6$) δ 8.34 (d, J=1.7 Hz, 1H), 8.05 (s, 1H), 7.93 (d, J=1.7 Hz, 1H), 7.86-7.76 (m, 1H), 7.59-7.51 (m, 2H), 5.19 (s, 2H), 3.97 (s, 3H), 3.38 (s, 3H).

Example 550: 6-(3,4-Difluorophenyl)-3-methyl-1-[(1-methylpyrazol-4-yl)methyl]imidazo[4,5-b]pyridin-2-one

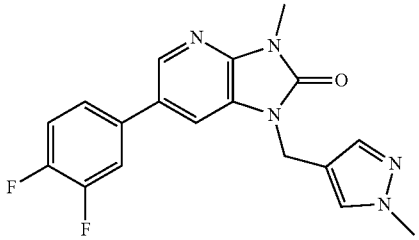 [SMILES: Cn1cc(Cn2c(=O)n(C)c3ncc(-c4ccc(F)c(F)c4)cc32)cn1]

The title compound was prepared in a manner analogous to Example 6, using 6-(3,4-difluorophenyl)-3-methyl-1,3-dihydro-2H-imidazo[4,5-b]pyridin-2-one (Intermediate 29) and 4-(chloromethyl)-1-methyl-1H-pyrazole hydrochloride. The halide was added as a solution of DMF (5 mL) and DIPEA (1 equivalent). MS (ESI): mass calcd. for $C_{18}H_{15}F_2N_5O$, 355.1; m/z found, 356 [M+H]$^+$. $^1$H NMR (300 MHz, CDCl$_3$) δ 8.17 (d, J=1.7 Hz, 1H), 7.49 (s, 1H), 7.41 (s, 1H), 7.36-7.28 (m, 1H), 7.25-7.17 (m, 3H), 4.98 (s, 2H), 3.85 (s, 3H), 3.53 (s, 3H).

Example 551: 3-Methyl-1-[(1-methylpyrazol-4-yl)methyl]-6-[3-(trifluoromethyl)phenyl]imidazo[4,5-b]pyridin-2-one

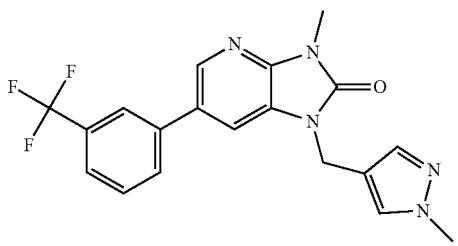 [SMILES: Cn1cc(Cn2c(=O)n(C)c3ncc(-c4cccc(C(F)(F)F)c4)cc32)cn1]

The title compound was prepared in a manner analogous to Example 6, using 3-methyl-6-(3-(trifluoromethyl)phenyl)-1,3-dihydro-2H-imidazo[4,5-b]pyridin-2-one (Intermediate 26) and 4-(chloromethyl)-1-methyl-1H-pyrazole hydrochloride. The halide was added as a solution of DMF (5 mL) and DIPEA (1 equivalent) at 0° C. MS (ESI): mass calcd. for $C_{19}H_{16}F_3N_5O$, 387.1; m/z found, 388 [M+H]$^+$. $^1$H NMR (300 MHz, CDCl$_3$) δ 8.23 (d, J=1.5 Hz, 1H), 7.73 (s, 1H), 7.72-7.54 (m, 3H), 7.50 (s, 1H), 7.42 (s, 1H), 7.29 (d, J=1.4 Hz, 1H), 4.99 (s, 2H), 3.84 (s, 3H), 3.54 (s, 3H).

Example 552: 3-Methyl-1-[(1-methyltriazol-4-yl)methyl]-6-[3-(trifluoromethyl)phenyl]imidazo[4,5-b]pyridin-2-one

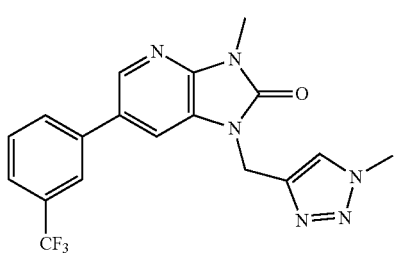 [SMILES: Cn1cc(Cn2c(=O)n(C)c3ncc(-c4cccc(C(F)(F)F)c4)cc32)nn1]

The title compound was prepared in a manner analogous to Example 6, using 3-methyl-6-(3-(trifluoromethyl)phenyl)-1,3-dihydro-2H-imidazo[4,5-b]pyridin-2-one (Intermediate 26) and 4-(chloromethyl)-1-methyl-1H-1,2,3 triazole hydrochloride. The halide was added as a solution of DMF (5 mL) and DIPEA (1 equivalent). MS (ESI): mass calcd. for $C_{18}H_{15}F_3N_6O$, 388.1; m/z found, 389 [M+H]$^+$. $^1$H NMR (300 MHz, CDCl$_3$) δ 8.24 (d, J=1.7 Hz, 1H), 7.78 (s, 1H), 7.76-7.67 (m, 2H), 7.67-7.53 (m, 3H), 5.23 (s, 2H), 4.05 (s, 3H), 3.53 (s, 3H).

Example 553: 3-Methyl-6-(5-methyl-2-thienyl)-1-[(1-methyltriazol-4-yl)methyl]imidazo[4,5-b]pyridin-2-one

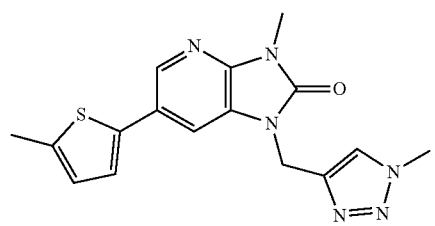

The title compound was prepared in a manner analogous to Example 8, using 6-bromo-3-methyl-1-((1-methyl-1H-1,2,3-triazol-4-yl)methyl)-1,3-dihydro-2H-imidazo[4,5-b]pyridin-2-one (Intermediate 50) in Step A; and 2-bromo-5-methylthiophene (Intermediate 48) in Step B. MS (ESI): mass calcd. for $C_{16}H_{16}N_6OS$, 340.1; m/z found, 341 [M+H]$^+$. $^1$H NMR (300 MHz, CDCl$_3$) δ 8.23 (s, 1H), 7.59 (s, 2H), 7.06 (d, J=3.4 Hz, 1H), 6.73 (d, J=2.3 Hz, 1H), 5.19 (s, 2H), 4.05 (s, 3H), 3.50 (s, 3H), 2.51 (s, 3H).

Example 554: 3-Methyl-1-[(5-methyl-1,3,4-oxadiazol-2-yl)methyl]-6-(5-methyl-2-thienyl)imidazo[4,5-b]pyridin-2-one

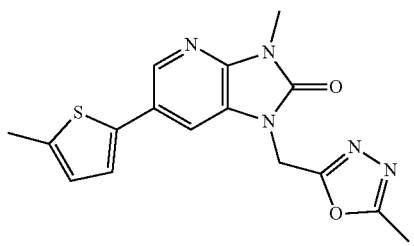

The title compound was prepared in a manner analogous to Example 8, using 6-bromo-3-methyl-1-((5-methyl-1,3,4-oxadiazol-2-yl)methyl)-1,3-dihydro-2H-imidazo[4,5-b]pyridin-2-one (Intermediate 51) in Step A; and 2-bromo-5-methylthiophene (Intermediate 48) in Step B. MS (ESI): mass calcd. for $C_{16}H_{15}N_5O_2S$, 341.1; m/z found, 342 [M+H]$^+$. $^1$H NMR (300 MHz, CDCl$_3$) δ 8.28 (d, J=1.3 Hz, 1H), 7.41 (d, J=1.3 Hz, 1H), 7.04 (d, J=3.4 Hz, 1H), 6.74 (d, J=2.4 Hz, 1H), 5.30 (s, 2H), 3.53 (s, 3H), 2.51 (s, 6H).

Example 555: 3-Methyl-1-[(1-methylpyrazol-4-yl)methyl]-6-(5-methyl-2-thienyl)imidazo[4,5-b]pyridin-2-one

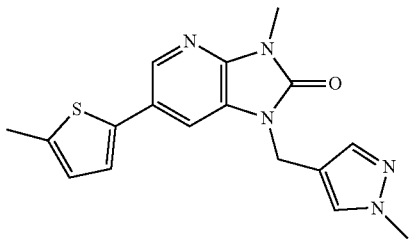

The title compound was prepared in a manner analogous to Example 8, using 6-bromo-3-methyl-1-((1-methyl-1H-pyrazol-4-yl)methyl)-1,3-dihydro-2H-imidazo[4,5-b]pyridin-2-one (Intermediate 52) in Step A; and 2-bromo-5-methylthiophene (Intermediate 48) in Step B. MS (ESI): mass calcd. for $C_{17}H_{17}N_5OS$, 339.1; m/z found, 340 [M+H]$^+$. $^1$H NMR (300 MHz, CDCl$_3$) δ 8.23 (s, 1H), 7.50 (s, 1H), 7.40 (s, 1H), 7.25 (s, 1H), 7.01 (d, J=2.8 Hz, 1H), 6.75 (s, 1H), 4.95 (s, 2H), 3.84 (s, 3H), 3.50 (s, 3H), 2.52 (s, 3H).

Example 556: 3-Methyl-6-(5-methyl-2-thienyl)-1-(thiadiazol-4-ylmethyl)imidazo[4,5-b]pyridin-2-one

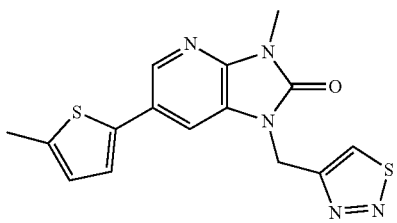 [SMILES: Cc1ccc(-c2cnc3c(c2)n(Cc2csnn2)c(=O)n3C)s1]

The title compound was prepared in a manner analogous to Example 8, using 1-((1,2,3-thiadiazol-4-yl)methyl)-6-bromo-3-methyl-1,3-dihydro-2H-imidazo[4,5-b]pyridin-2-one (Intermediate 53) in Step A; and 2-bromo-5-methylthiophene (Intermediate 48) in Step B. MS (ESI): mass calcd. for $C_{15}H_{13}N_5OS_2$, 343.1; m/z found, 344 [M+H]$^+$. $^1$H NMR (300 MHz, CDCl$_3$) δ 8.62 (s, 1H), 8.26 (d, J=1.5 Hz, 1H), 7.55 (d, J=1.5 Hz, 1H), 7.05 (d, J=3.4 Hz, 1H), 6.74 (d, J=2.3 Hz, 1H), 5.61 (s, 2H), 3.52 (s, 3H), 2.51 (s, 3H).

Example 557: 3-Methyl-1-[(3-methyl-1,2,4-oxadiazol-5-yl)methyl]-6-(5-methyl-2-thienyl)imidazo[4,5-b]pyridin-2-one

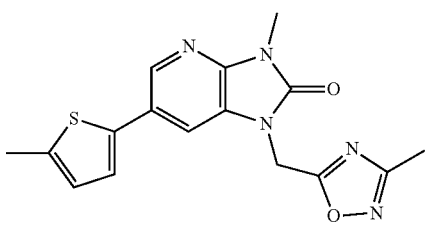

The title compound was prepared in a manner analogous to Example 8, using 6-bromo-3-methyl-1-((3-methyl-1,2,4-oxadiazol-5-yl)methyl)-1,3-dihydro-2H-imidazo[4,5-b]pyridin-2-one (Intermediate 55) in Step A; and 2-bromo-5-methylthiophene (Intermediate 48) in Step B. MS (ESI): mass calcd. for $C_{16}H_{15}N_5O_2S$, 341.1; m/z found, 342 [M+H]$^+$. $^1$H NMR (300 MHz, CDCl$_3$) δ 8.29 (d, J=1.4 Hz, 1H), 7.29 (d, J=1.5 Hz, 1H), 7.04 (d, J=3.4 Hz, 1H), 6.74 (d, J=2.5 Hz, 1H), 5.31 (s, 2H), 3.54 (s, 3H), 2.51 (s, 3H), 2.38 (s, 3H).

Example 558: 3-Methyl-1-[(5-methylisoxazol-3-yl)methyl]-6-(5-methyl-2-thienyl)imidazo[4,5-b]pyridin-2-one

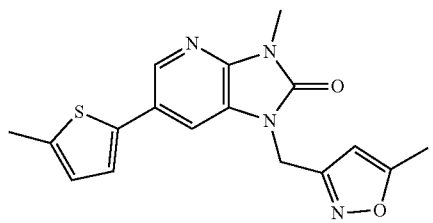

The title compound was prepared in a manner analogous to Example 8, using 6-bromo-3-methyl-1-((5-methylisoxazol-3-yl)methyl)-1,3-dihydro-2H-imidazo[4,5-b]pyridin-2-one (Intermediate 54) in Step A, and 2-bromo-5-methylthiophene (Intermediate 48) in Step B. MS (ESI): mass calcd. for $C_{17}H_{16}N_4O_2S$, 340.1; m/z found, 341[M+H]$^+$. $^1$H NMR (300 MHz, CDCl$_3$) δ 8.24 (s, 1H), 7.39 (s, 1H), 7.03 (s, 1H), 6.73 (s, 1H), 6.00 (s, 1H), 5.10 (s, 2H), 3.52 (s, 3H), 2.50 (s, 3H), 2.37 (s, 3H).

Example 559: 6-[5-(Difluoromethyl)-2-thienyl]-3-methyl-1-[(1-methyltriazol-4-yl)methyl]imidazo[4,5-b]pyridin-2-one

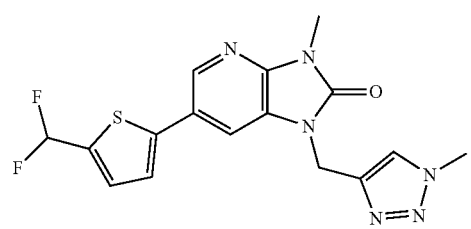 [SMILES: Cn1cc(Cn2c(=O)n(C)c3ncc(-c4ccc(C(F)F)s4)cc32)nn1]

The title compound was prepared in a manner analogous to Example 8, using 6-bromo-3-methyl-1-((1-methyl-1H-1,2,3-triazol-4-yl)methyl)-1,3-dihydro-2H-imidazo[4,5-b]pyridin-2-one (Intermediate 50) in Step A; and 2-bromo-5-(difluoromethyl)thiophene (Intermediate 49) in Step B. MS (ESI): mass calcd. for $C_{16}H_{14}F_2N_6OS$, 376.1; m/z found, 377 [M+H]$^+$. $^1$H NMR (300 MHz, CDCl$_3$) δ 8.34 (s, 1H), 7.74 (s, 1H), 7.67 (s, 1H), 7.31 (s, 2H), 6.89 (t, J=56.0 Hz, 1H), 5.26 (s, 2H), 4.11 (s, 3H), 3.56 (s, 3H).

Example 560: 6-[5-(Difluoromethyl)-2-thienyl]-3-methyl-1-[(5-methyl-1,3,4-oxadiazol-2-yl)methyl]imidazo[4,5-b]pyridin-2-one

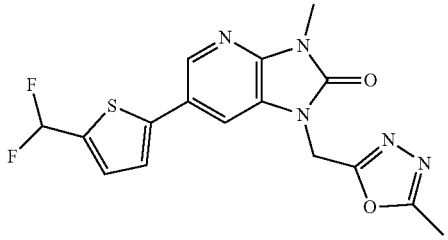 [SMILES: Cc1nnc(Cn2c(=O)n(C)c3ncc(-c4ccc(C(F)F)s4)cc32)o1]

The title compound was prepared in a manner analogous to Example 8, using 6-bromo-3-methyl-1-((5-methyl-1,3,4-oxadiazol-2-yl)methyl)-1,3-dihydro-2H-imidazo[4,5-b]pyridin-2-one (Intermediate 51) in Step A; using 2-bromo-5-(difluoromethyl)thiophene (Intermediate 49) in Step B. MS (ESI): mass calcd. for $C_{16}H_{13}F_2N_5O_2S$, 377.1; m/z found 378 [M+H]$^+$. $^1$H NMR (300 MHz, CDCl$_3$) δ 8.33 (d, J=1.2 Hz, 1H), 7.47 (d, J=1.3 Hz, 1H), 7.18 (d, J=3.5 Hz, 1H), 6.83 (t, J=56.0 Hz, 1H), 5.32 (s, 2H), 3.55 (s, 3H), 2.52 (s, 3H).

Example 561: 6-[5-(Difluoromethyl)-2-thienyl]-3-methyl-1-[(1-methylpyrazol-4-yl)methyl]imidazo[4,5-b]pyridin-2-one

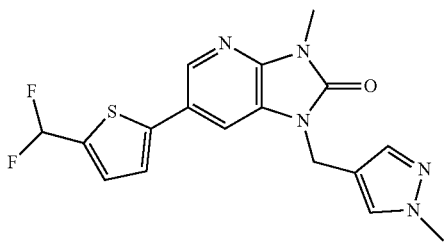 [SMILES: Cn1cc(Cn2c(=O)n(C)c3ncc(-c4ccc(C(F)F)s4)cc32)cn1]

The title compound was prepared in a manner analogous to Example 8, using 6-bromo-3-methyl-1-((1-methyl-1H-pyrazol-4-yl)methyl)-1,3-dihydro-2H-imidazo[4,5-b]pyridin-2-one (Intermediate 52) in Step A; and 2-bromo-5-(difluoromethyl)thiophene (Intermediate 49) in Step B. MS (ESI): mass calcd. for $C_{17}H_{15}F_2N_5OS$, 375.1; m/z found, 376 [M+H]$^+$. $^1$H NMR (300 MHz, CDCl$_3$) δ 8.27 (s, 1H), 7.49 (s, 1H), 7.40 (s, 1H), 7.26 (s, 2H), 7.14 (s, 1H), 6.83 (t, J=56.0 Hz, 1H), 4.95 (s, 2H), 3.84 (s, 3H), 3.51 (s, 3H).

Example 562: 6-[5-(Difluoromethyl)-2-thienyl]-3-methyl-1-(thiadiazol-4-ylmethyl)imidazo[4,5-b]pyridin-2-one

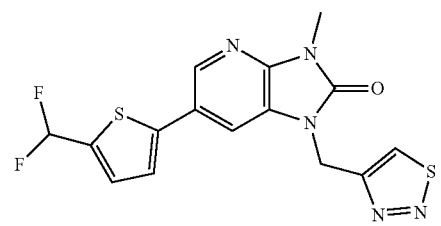 [SMILES: Cn1c(=O)n(Cc2csnn2)c2cc(-c3ccc(C(F)F)s3)cnc21]

The title compound was prepared in a manner analogous to Example 8, using 1-((1,2,3-thiadiazol-4-yl)methyl)-6-bromo-3-methyl-1,3-dihydro-2H-imidazo[4,5-b]pyridin-2-one (Intermediate 53) in Step A; and 2-bromo-5-(difluoromethyl)thiophene (Intermediate 49) in Step B. MS (ESI): mass calcd. for $C_{15}H_{11}F_2N_5OS_2$, 379.0; m/z found, 380 [M+H]$^+$. $^1$H NMR (300 MHz, CDCl$_3$) δ 8.65 (s, 1H), 8.31 (s, 1H), 7.64 (s, 1H), 7.26 (s, 1H), 7.22-7.17 (m, 1H), 6.84 (t, J=56.0 Hz, 1H), 5.61 (s, 2H), 3.53 (s, 3H).

Example 563: 6-[5-(Difluoromethyl)-2-thienyl]-3-methyl-1-[(3-methyl-1,2,4-oxadiazol-5-yl)methyl]imidazo[4,5-b]pyridin-2-one

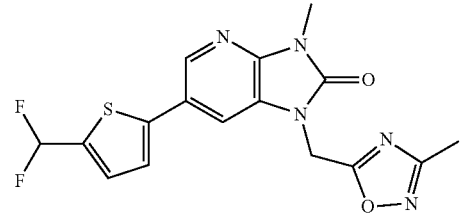 [SMILES: Cc1noc(Cn2c(=O)n(C)c3ncc(-c4ccc(C(F)F)s4)cc32)n1]

The title compound was prepared in a manner analogous to Example 8, using bromo-3-methyl-1-((5-methyl-1,3,4-oxadiazol-2-yl)methyl)-1,3-dihydro-2H-imidazo[4,5-b]pyridin-2-one (Intermediate 55) in Step A and 2-bromo-5-(difluoromethyl)thiophene (Intermediate 49) in Step B. MS (ESI): mass calcd. for $C_{16}H_{13}F_2N_5O_2S$, 377.1; m/z found, 378 [M+H]$^+$. $^1$H NMR (300 MHz, CDCl$_3$) δ 8.35 (d, J=1.4 Hz, 1H), 7.34 (d, J=1.4 Hz, 1H), 7.26-7.27 (m, 1H), 7.18 (d, J=3.5 Hz, 1H), 6.84 (t, J=56.0 Hz, 1H), 5.33 (s, 2H), 3.55 (s, 3H), 2.39 (s, 3H).

Example 564: 6-[5-(Difluoromethyl)-2-thienyl]-3-methyl-1-[(5-methylisoxazol-3-yl)methyl]imidazo[4,5-b]pyridin-2-one

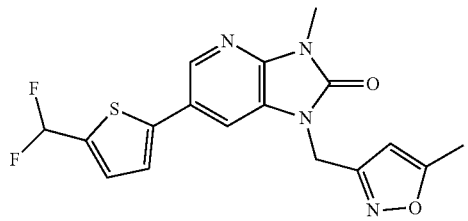 [SMILES: Cc1cc(Cn2c(=O)n(C)c3ncc(-c4ccc(C(F)F)s4)cc32)no1]

The title compound was prepared in a manner analogous to Example 8, using 6-bromo-3-methyl-1-((5-methylisoxazol-3-yl)methyl)-1,3-dihydro-2H-imidazo[4,5-b]pyridin-2-one (Intermediate 54) in Step A; and 2-bromo-5-(difluoromethyl)thiophene (Intermediate 49) in Step B. MS (ESI): mass calcd. for $C_{17}H_{14}F_2N_4O_2S$, 376.1; m/z found 377 [M+H]$^+$. $^1$H NMR (300 MHz, CDCl$_3$) δ 8.30 (s, 1H), 7.45 (s, 1H), 7.18 (s, 1H), 6.83 (t, J=56.0 Hz, 1H), 6.02 (s, 1H), 5.12 (s, 2H), 3.54 (s, 3H), 2.38 (s, 3H).

Example 565: 3-Methyl-1-[(1-methylpyrazol-4-yl)methyl]-6-[5-(trifluoromethyl)-2-thienyl]imidazo[4,5-b]pyridin-2-one

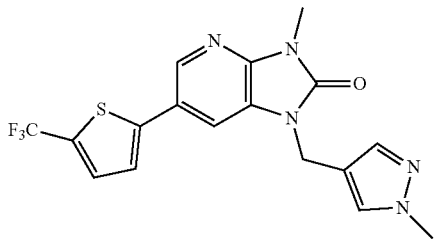 [SMILES: Cn1cc(Cn2c(=O)n(C)c3ncc(-c4ccc(C(F)(F)F)s4)cc32)cn1]

The title compound was prepared in a manner analogous to Example 8, using 6-bromo-3-methyl-1-((1-methyl-1H-pyrazol-4-yl)methyl)-1,3-dihydro-2H-imidazo[4,5-b]pyridin-2-one (Intermediate 52) in Step A; and 2-bromo-5-trifluoromethylthiophene in Step B. MS (ESI): mass calcd. for $C_{17}H_{14}F_3N_5OS$, 393.1; m/z found, 394 [M+H]$^+$. $^1$H NMR (300 MHz, CDCl$_3$) δ 8.28 (d, J=1.4 Hz, 1H), 7.50 (s, 1H), 7.41 (s, 2H), 7.26 (s, 1H), 7.15 (d, J=2.9 Hz, 1H), 4.97 (s, 2H), 3.85 (s, 3H), 3.52 (s, 3H).

Example 566: 3-Methyl-1-[(1-methyltriazol-4-yl)methyl]-6-[5-(trifluoromethyl)-2-thienyl]imidazo[4,5-b]pyridin-2-one

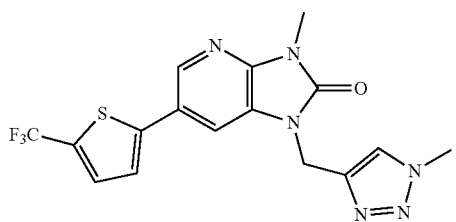 [SMILES: Cn1cc(Cn2c(=O)n(C)c3ncc(-c4ccc(C(F)(F)F)s4)cc32)nn1]

The title compound was prepared in a manner analogous to Example 8, using 6-bromo-3-methyl-1-((1-methyl-1H-1,2,3-triazol-4-yl)methyl)-1,3-dihydro-2H-imidazo[4,5-b]pyridin-2-one (Intermediate 50) in Step A; and 2-bromo-5-trifluoromethylthiophene in Step B. MS (ESI): mass calcd. for $C_{16}H_{13}F_3N_6OS$, 394.1; m/z found 395 [M+H]$^+$. $^1$H NMR (300 MHz, CDCl$_3$) δ 8.27 (s, 1H), 7.69 (s, 1H), 7.62 (s, 1H), 7.41 (s, 1H), 7.21 (s, 1H), 5.20 (s, 2H), 4.06 (s, 3H), 3.51 (s, 3H).

Example 567: 3-Methyl-1-[(5-methyl-1,3,4-oxadiazol-2-yl)methyl]-6-[5-(trifluoromethyl)-2-thienyl]imidazo[4,5-b]pyridin-2-one

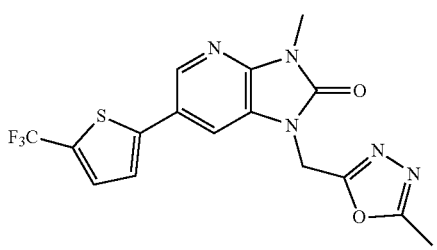 [SMILES: Cc1nnc(Cn2c(=O)n(C)c3ncc(-c4ccc(C(F)(F)F)s4)cc32)o1]

The title compound was prepared in a manner analogous to Example 8, using 6-bromo-3-methyl-1-((5-methyl-1,3,4-oxadiazol-2-yl)methyl)-1,3-dihydro-2H-imidazo[4,5-b]pyridin-2-one (Intermediate 51) in Step A; and 2-bromo-5-trifluoromethylthiophene in Step B. MS (ESI): mass calcd. for $C_{16}H_{12}F_3N_5O_2S$, 395.1; m/z found, 396 [M+H]$^+$. $^1$H NMR (300 MHz, CDCl$_3$) δ 8.33 (d, J=1.5 Hz, 1H), 7.47 (d, J=1.4 Hz, 1H), 7.42 (d, J=3.0 Hz, 1H), 7.19 (d, J=2.9 Hz, 1H), 5.32 (s, 2H), 3.55 (s, 3H), 2.52 (s, 3H).

Example 568: 3-Methyl-1-(thiadiazol-4-ylmethyl)-6-[5-(trifluoromethyl)-2-thienyl]imidazo[4,5-b]pyridin-2-one

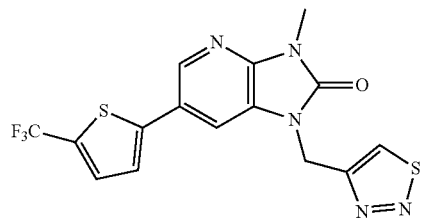 [SMILES: Cn1c(=O)n(Cc2csnn2)c2cc(-c3ccc(C(F)(F)F)s3)cnc21]

The title compound was prepared in a manner analogous to Example 8, using 1-((1,2,3-thiadiazol-4-yl)methyl)-6-bromo-3-methyl-1,3-dihydro-2H-imidazo[4,5-b]pyridin-2-one (Intermediate 53) in Step A; and 2-bromo-5-trifluoromethylthiophene in Step B. MS (ESI): mass calcd. for $C_{15}H_{10}F_3N_5OS_2$, 397.0; m/z found, 398 [M+H]$^+$. $^1$H NMR (300 MHz, CDCl$_3$) δ 8.66 (s, 1H), 8.31 (s, 1H), 7.65 (d, J=1.4 Hz, 1H), 7.43 (d, J=2.8 Hz, 1H), 7.21 (d, J=2.8 Hz, 1H), 5.61 (s, 2H), 3.53 (s, 3H).

Example 569: 3-Methyl-1-[(3-methyl-1,2,4-oxadiazol-5-yl)methyl]-6-[5-(trifluoromethyl)-2-thienyl]imidazo[4,5-b]pyridin-2-one

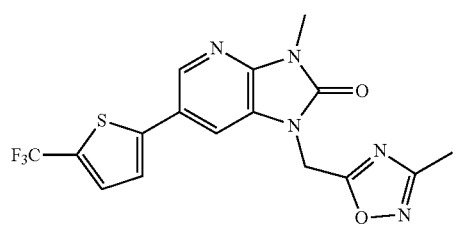 [SMILES: Cc1noc(Cn2c(=O)n(C)c3ncc(-c4ccc(C(F)(F)F)s4)cc32)n1]

The title compound was prepared in a manner analogous to Example 8, using 6-bromo-3-methyl-1-((3-methyl-1,2,4-oxadiazol-5-yl)methyl)-1,3-dihydro-2H-imidazo[4,5-b]pyridin-2-one (Intermediate 55) in Step A; and 2-bromo-5-trifluoromethylthiophene in Step B. MS (ESI): mass calcd. for $C_{16}H_{12}F_3N_5O_2S$, 395.1; m/z found, 396 [M+H]$^+$. $^1$H NMR (300 MHz, CDCl$_3$) δ 8.35 (s, 1H), 7.43 (s, 1H), 7.34 (s, 1H), 7.19 (s, 1H), 5.33 (s, 2H), 3.56 (s, 3H), 2.39 (s, 3H).

Example 570: 3-Methyl-1-[(5-methylisoxazol-3-yl)methyl]-6-[5-(trifluoromethyl)-2-thienyl]imidazo[4,5-b]pyridin-2-one

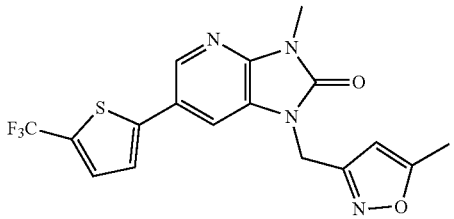 [SMILES: Cc1cc(Cn2c(=O)n(C)c3ncc(-c4ccc(C(F)(F)F)s4)cc32)no1]

The title compound was prepared in a manner analogous to Example 8, using 6-bromo-3-methyl-1-((5-methylisoxazol-3-yl)methyl)-1,3-dihydro-2H-imidazo[4,5-b]pyridin-2-one (Intermediate 54) in Step A, and 2-bromo-5-trifluoromethylthiophene in Step B. MS (ESI): mass calcd. for $C_{17}H_{13}F_3N_4O_2S$, 394.1; m/z found, 395 [M+H]$^+$. $^1$H NMR (300 MHz, CDCl$_3$) δ 8.29 (s, 1H), 7.43 (d, J=8.6 Hz, 2H), 7.18 (s, 1H), 6.02 (s, 1H), 5.12 (s, 2H), 3.54 (s, 3H), 2.38 (s, 3H).

Example 571: 6-(2,4-Difluoro-3-methyl-phenyl)-3-methyl-1-[(5-methylisoxazol-3-yl)methyl]imidazo[4,5-b]pyridin-2-one

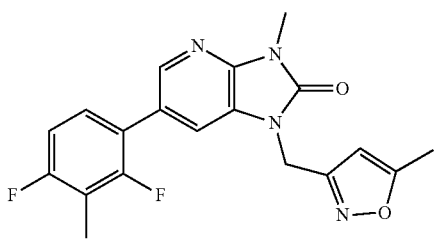 [SMILES: Cc1cc(Cn2c(=O)n(C)c3ncc(-c4ccc(F)c(C)c4F)cc32)no1]

The title compound was prepared in a manner analogous to Example 8, using 6-bromo-3-methyl-1-((5-methylisoxazol-3-yl)methyl)-1,3-dihydro-2H-imidazo[4,5-b]pyridin-2-one (Intermediate 54) in Step A, using 1-bromo-2,4-difluoro-3-methyl-benzene in Step B. MS (ESI): mass calcd. for $C_{19}H_{16}F_2N_4O_2$, 370.1; m/z found, 371 [M+H]$^+$. $^1$H NMR (300 MHz, CDCl$_3$) δ 8.14 (s, 1H), 7.40 (s, 1H), 7.21-7.10 (m, 1H), 6.99-6.87 (m, 1H), 6.02 (s, 1H), 5.12 (s, 2H), 3.55 (s, 3H), 2.37 (s, 3H), 2.26 (s, 3H).

Example 572: 6-(2,4-Difluoro-3-methyl-phenyl)-3-methyl-1-[(1-methylpyrazol-4-yl)methyl]imidazo[4,5-b]pyridin-2-one

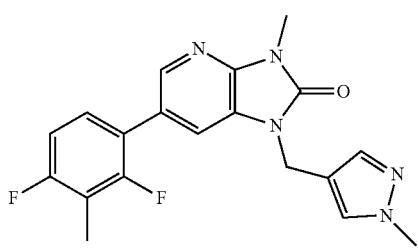 [SMILES: Cc1c(F)ccc(-c2cnc3c(c2)n(Cc2cnn(C)c2)c(=O)n3C)c1F]

The title compound was prepared in a manner analogous to Example 8, using 6-bromo-3-methyl-1-((1-methyl-1H-pyrazol-4-yl)methyl)-1,3-dihydro-2H-imidazo[4,5-b]pyridin-2-one (Intermediate 52) in Step A; and 1-bromo-2,4-difluoro-3-methyl-benzene in Step B. MS (ESI): mass calcd. for $C_{19}H_{17}F_2N_5O$, 369.1; m/z found, 370 [M+H]$^+$. $^1$H NMR (300 MHz, CDCl$_3$) δ 8.11 (s, 1H), 7.49 (s, 1H), 7.41 (s, 1H), 7.30 (s, 1H), 7.17 (dd, J=15.1, 8.4 Hz, 1H), 6.94 (t, J=8.6 Hz, 1H), 4.96 (s, 2H), 3.84 (s, 3H), 3.53 (s, 3H), 2.27 (s, 3H).

Example 573: 6-(2,4-Difluoro-3-methyl-phenyl)-3-methyl-1-[(3-methyl-1,2,4-oxadiazol-5-yl)methyl]imidazo[4,5-b]pyridin-2-one

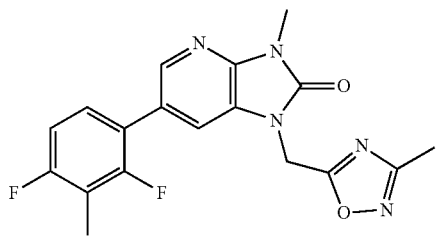 [SMILES: Cc1noc(Cn2c(=O)n(C)c3ncc(-c4ccc(F)c(C)c4F)cc32)n1]

The title compound was prepared in a manner analogous to Example 8, using 6-bromo-3-methyl-1-((3-methyl-1,2,4-oxadiazol-5-yl)methyl)-1,3-dihydro-2H-imidazo[4,5-b]pyridin-2-one (Intermediate 55) in Step A; and 1-bromo-2,4-difluoro-3-methyl-benzene in Step B. MS (ESI): mass calcd. for $C_{18}H_{15}F_2N_5O_2$, 371.1; m/z found 372.1 [M+H]$^+$. $^1$H NMR (300 MHz, CDCl$_3$) δ 8.19 (s, 1H), 7.32 (s, 1H), 7.18 (dd, J=15.1, 8.5 Hz, 1H), 6.94 (t, J=9.0 Hz, 1H), 5.32 (s, 2H), 3.57 (s, 3H), 2.37 (s, 3H), 2.26 (s, 3H).

Example 574: 6-(2,4-Difluoro-3-methyl-phenyl)-3-methyl-1-[(1-methyltriazol-4-yl)methyl]imidazo[4,5-b]pyridin-2-one

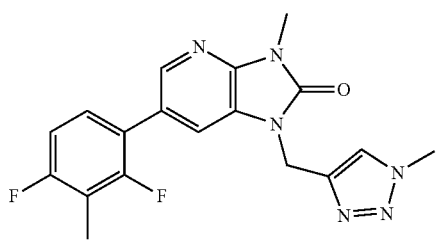 [SMILES: Cc1c(F)ccc(-c2cnc3c(c2)n(Cc2cn(C)nn2)c(=O)n3C)c1F]

The title compound was prepared in a manner analogous to Example 8, using 6-bromo-3-methyl-1-((1-methyl-1H-1,2,3-triazol-4-yl)methyl)-1,3-dihydro-2H-imidazo[4,5-b]pyridin-2-one (Intermediate 50) in Step A; and 1-bromo-2,4-difluoro-3-methyl-benzene in Step B. MS (ESI): mass calcd. for $C_{18}H_{16}F_2N_6O$, 370.1; m/z found, 371[M+H]$^+$. $^1$H NMR (300 MHz, CDCl$_3$) δ 8.16 (s, 1H), 7.64 (d, J=3.0 Hz, 2H), 7.26-7.16 (m, 1H), 6.96 (t, J=8.3 Hz, 1H), 5.24 (s, 2H), 4.08 (s, 3H), 3.56 (s, 3H), 2.29 (s, 3H).

Example 575: 6-(2,4-Difluoro-3-methyl-phenyl)-3-methyl-1-[(5-methyl-1,3,4-oxadiazol-2-yl)methyl]imidazo[4,5-b]pyridin-2-one

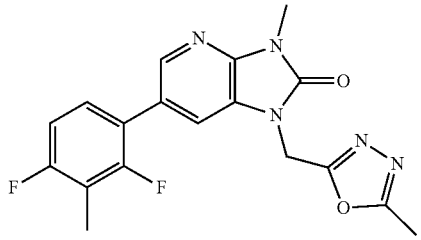 [SMILES: Cc1nnc(Cn2c(=O)n(C)c3ncc(-c4ccc(F)c(C)c4F)cc32)o1]

The title compound was prepared in a manner analogous to Example 8, using 6-bromo-3-methyl-1-((5-methyl-1,3,4-oxadiazol-2-yl)methyl)-1,3-dihydro-2H-imidazo[4,5-b]pyridin-2-one (Intermediate 51) in Step A; and 1-bromo-2,4-difluoro-3-methyl-benzene in Step B. MS (ESI): mass calcd. for $C_{18}H_{15}F_2N_5O_2$, 371.1; m/z found, 372, [M+H]$^+$. $^1$H NMR (300 MHz, CDCl$_3$) δ 8.18 (s, 1H), 7.44 (s, 1H), 7.16 (dd, J=15.0, 8.4 Hz, 1H), 6.93 (t, J=8.4 Hz, 1H), 5.32 (s, 2H), 3.56 (s, 3H), 2.51 (s, 3H), 2.26 (s, 3H).

Example 576: 6-(2,4-Difluoro-3-methyl-phenyl)-3-methyl-1-(thiadiazol-4-ylmethyl)imidazo[4,5-b]pyridin-2-one

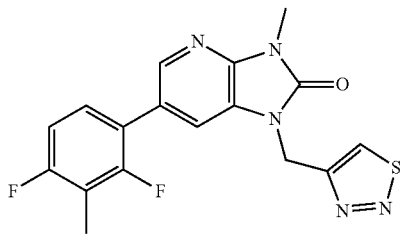 [SMILES: Cc1c(F)ccc(-c2cnc3c(c2)n(Cc2csnn2)c(=O)n3C)c1F]

The title compound was prepared in a manner analogous to Example 8, using 1-((1,2,3-thiadiazol-4-yl)methyl)-6-bromo-3-methyl-1,3-dihydro-2H-imidazo[4,5-b]pyridin-2-one (Intermediate 53) in Step A; and 1-bromo-2,4-difluoro-3-methyl-benzene in Step B. MS (ESI): mass calcd. for $C_{17}H_{13}F_2N_5OS$, 373.1; m/z found, 374 [M+H]$^+$. $^1$H NMR (300 MHz, CDCl$_3$) δ 8.63 (s, 1H), 8.16 (s, 1H), 7.58 (s, 1H), 7.18 (dd, J=15.1, 8.4 Hz, 1H), 6.94 (t, J=8.5 Hz, 1H), 5.62 (s, 2H), 3.55 (s, 3H), 2.26 (s, 3H).

Example 577: N-(2-Fluoroethyl)-N-methyl-2-[3-methyl-2-oxo-6-[5-(trifluoromethyl)-2-thienyl]imidazo[4,5-b]pyridin-1-yl]acetamide

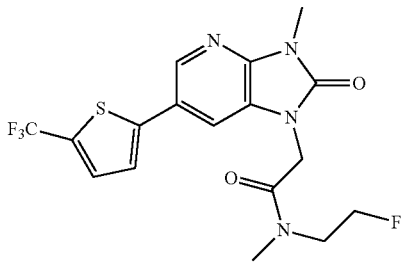 [SMILES: CN(CCF)C(=O)Cn1c(=O)n(C)c2ncc(-c3ccc(C(F)(F)F)s3)cc21]

The title compound was prepared in a manner analogous to Example 11, Step B: using 2-(6-bromo-3-methyl-2-oxo-2,3-dihydro-1H-imidazo[4,5-b]pyridin-1-yl)-N-(2-fluoroethyl)-N-methylacetamide (Intermediate 66) and 4,4,5,5-tetramethyl-2-(5-(trifluoromethyl)thiophen-2-yl)-1,3,2-dioxaborolane. MS (ESI): mass calcd. for $C_{17}H_{16}F_4N_4O_2$, 416.1; m/z found, 417.1 [M+H]$^+$. $^1$H NMR (400 MHz, CDCl$_3$) δ 8.24 (t, J=2.27 Hz, 1H), 7.34 (m, 1H), 7-29-7.23 (m, 1H), 7.11 (dt, J=1.17, 3.91 Hz, 1H), 5.23 (s, 2H), 4.62-4.52 (m, 2H), 3.81-3.57 (m, 2H), 3.50-3.40 (m, 3H), 3.21 (d, J=0.70 Hz, 3H).

Example 578: 1-[2-(3-Fluoroazetidin-1-yl)-2-oxo-ethyl]-6-[5-(trifluoromethyl)-2-thienyl]-3H-imidazo[4,5-b]pyridin-2-one

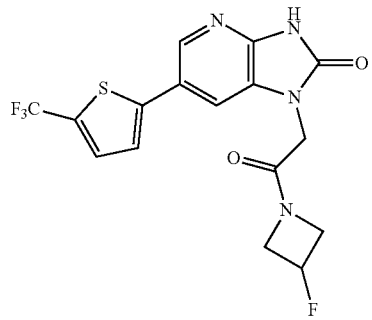 [SMILES: O=C(Cn1c(=O)[nH]c2ncc(-c3ccc(C(F)(F)F)s3)cc21)N1CC(F)C1]

The title compound was prepared in a manner analogous to Example 25, using 1-(2-(3-fluoroazetidin-1-yl)-2-oxoethyl)-6-bromo-3-trityl-1,3-dihydro-2H-imidazo[4,5-b]pyridin-2-one (Intermediate 40) in place of 1-(2-(azetidin-1-yl)-2-oxoethyl)-6-bromo-3-trityl-1,3-dihydro-2H-imidazo[4,5-b]pyridin-2-one (Intermediate 38) and (5-(trifluoromethyl)thiophen-2-yl)boronic acid in place of (3-(trifluoromethyl)phenyl)boronic acid in Step A. MS (ESI): mass calcd. for $C_{16}H_{12}F_4N_4O_2S$, 400.1; m/z found, 401.1 [M+H]$^+$.

Example 579: 1-[2-(Azetidin-1-yl)-2-oxo-ethyl]-6-(2,4-difluoro-3-methyl-phenyl)-3H-imidazo[4,5-b]pyridin-2-one

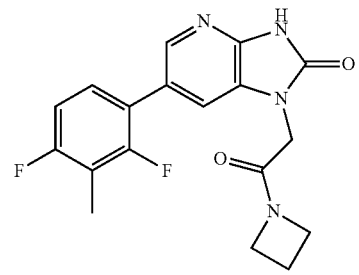 [SMILES: Cc1c(F)ccc(-c2cnc3[nH]c(=O)n(CC(=O)N4CCC4)c3c2)c1F]

The title compound was prepared in a manner analogous to Example 26, Method A, using (2,4-difluoro-3-methylphenyl)boronic acid instead of 4,4,5,5-tetramethyl-2-(5-(trifluoromethyl)thiophen-2-yl)-1,3,2-dioxaborolane in Step A; and azetidine instead of dimethylamine hydrochloride in Step C. MS (ESI): mass calcd. for $C_{18}H_{16}F_2N_4O_2$, 358.1; m/z found, [M+H]$^+$.

Example 580: 1-[2-(3,3-Difluoroazetidin-1-yl)-2-oxo-ethyl]-6-(m-tolyl)-3H-imidazo[4,5-b]pyridin-2-one

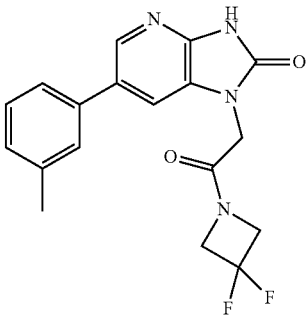 [SMILES: Cc1cccc(-c2cnc3[nH]c(=O)n(CC(=O)N4CC(F)(F)C4)c3c2)c1]

Step A: 6-Bromo-1-(2-(3,3-difluoroazetidin-1-yl)-2-oxoethyl)-3-trityl-1,3-dihydro-2H-imidazo[4,5-b]pyridin-2-one The title compound was prepared in a manner analogous to Intermediate 38 using 3,3-difluoroazetidine in place of azetidine in Step B.

Step B: 1-[2-(3,3-Difluoroazetidin-1-yl)-2-oxo-ethyl]-6-(m-tolyl)-3H-imidazo[4,5-b]pyridin-2-one The title compound was prepared in a manner analogous to Example 25, using 6-bromo-1-(2-(3,3-difluoroazetidin-1-yl)-2-oxoethyl)-3-trityl-1,3-dihydro-2H-imidazo[4,5-b]pyridin-2-one in place of intermediate 38. MS (ESI): mass calcd. for $C_{18}H_{16}F_2N_4O_2$, 358.1; m/z found, 359.1 [M+H]$^+$. $^1$H NMR (400 MHz, CDCl$_3$) δ 8.07 (d, J=2.0 Hz, 1H), 7.34-7.13 (m, 5H), 4.53 (s, 2H), 4.25 (t, J=12.0 Hz, 2H), 3.79 (t, J=11.6 Hz, 2H), 2.39 (s, 3H).

Example 581: 1-[2-(3,3-Difluoroazetidin-1-yl)-2-oxo-ethyl]-3-methyl-6-(m-tolyl)imidazo[4,5-b]pyridin-2-one

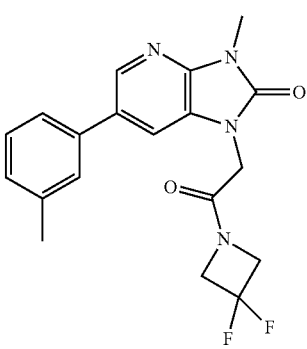

The title compound was prepared in a manner analogous to Example 14 Step B, using 1-[2-(3,3-difluoroazetidin-1-yl)-2-oxo-ethyl]-6-(m-tolyl)-3H-imidazo[4,5-b]pyridin-2-one (Example 580) in place of 1-((5-methylisoxazol-3-yl)methyl)-6-(4-methylthiophen-2-yl)-1,3-dihydro-2H-imidazo[4,5-b]pyridin-2-one. MS (ESI): mass calcd. for $C_{19}H_{18}F_2N_4O_2$, 372.1; m/z found, [M+H]$^+$. $^1$H NMR (500 MHz, CDCl$_3$) δ 8.29 (d, J=1.8 Hz, 1H), 7.44 (d, J=1.8 Hz, 1H), 7.42-7.39 (m, 1H), 7.36-7.31 (m, 2H), 7.22-7.17 (m, 1H), 4.59 (d, J=28.0 Hz, 4H), 4.43-4.33 (m, 2H), 3.54 (s, 3H), 2.42 (s, 3H).

Example 582: 1-[2-(Azetidin-1-yl)-2-oxo-ethyl]-6-[3-(2-fluoroethoxy)-5-(trifluoromethyl)phenyl]-3-methyl-imidazo[4,5-b]pyridin-2-one

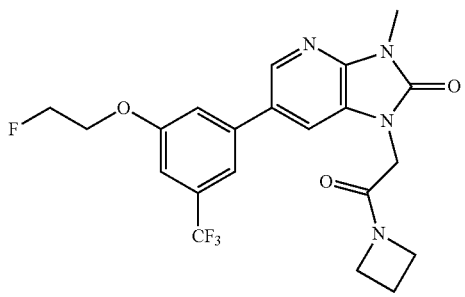 [SMILES: Cn1c(=O)n(CC(=O)N2CCC2)c2cc(-c3cc(OCCF)cc(C(F)(F)F)c3)cnc21]

The title compound was prepared in a manner analogous to Example 14 Step B, using 1-[2-(azetidin-1-yl)-2-oxo-ethyl]-6-[3-(2-fluoroethoxy)-5-(trifluoromethyl)phenyl]-3H-imidazo[4,5-b]pyridin-2-one (Example 539). MS (ESI): mass calcd. for $C_{20}H_{18}F_4N_4O_3$, 438.1; m/z found, 439.1 [M+H]$^+$. $^1$H NMR (400 MHz, CD$_3$CN) δ 8.37 (d, J=1.9 Hz, 1H), 7.59 (d, J=1.9 Hz, 2H), 7.48 (s, 1H), 7.27 (s, 1H), 4.98-4.66 (m, 1H), 4.52 (s, 2H), 4.48-4.25 (m, 4H), 3.99 (t, J=7.7 Hz, 2H), 3.45 (s, 3H), 2.35 (t, J=7.7 Hz, 2H).

Example 583: N,N-Dimethyl-2-[3-methyl-6-(m-tolyl)-2-oxo-imidazo[4,5-b]pyridin-1-yl]acetamide

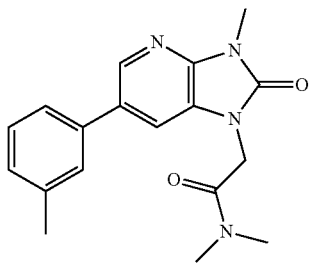 [SMILES: Cc1cccc(-c2cnc3c(c2)n(CC(=O)N(C)C)c(=O)n3C)c1]

Step A: N,N-Dimethyl-2-(2-oxo-6-(m-tolyl)-2,3-dihydro-1H-imidazo[4,5-b]pyridin-1-yl)acetamide The title compound was prepared in a manner analogous to Example 26 Method A using m-tolylboronic acid instead of 4,4,5,5-tetramethyl-2-(5-(trifluoromethyl)thiophen-2-yl)-1,3,2-dioxaborolane in Step A.

Step B: N,N-Dimethyl-2-[3-methyl-6-(m-tolyl)-2-oxo-imidazo[4,5-b]pyridin-1-yl]acetamide The title compound was prepared in a manner analogous to Example 14 Step B using N,N-dimethyl-2-(2-oxo-6-(m- tolyl)-2,3-dihydro-1H-imidazo[4,5-b]pyridin-1-yl)acetamide. MS (ESI): mass calcd. for $C_{18}H_{20}N_4O_2$, 324.2; m/z found, 325.2 [M+H]$^+$. $^1$H NMR (400 MHz, CDCl$_3$-d) δ 8.25 (d, J=1.9 Hz, 1H), 7.38-7.31 (m, 4H), 7.20-7.15 (m, 1H), 4.73 (s, 2H), 3.54 (s, 3H), 3.16 (s, 3H), 2.98 (s, 3H), 2.42 (s, 3H).

Example 584: 1-[2-(Azetidin-1-yl)-2-oxo-ethyl]-6-[3-(difluoromethyl)-4-fluoro-phenyl]-3-methyl-imidazo[4,5-b]pyridin-2-one

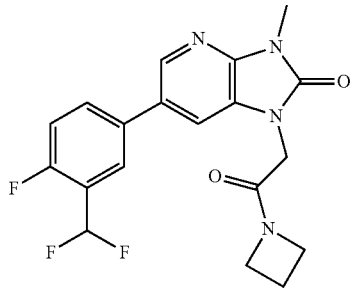 [SMILES: Cn1c(=O)n(CC(=O)N2CCC2)c2cc(-c3ccc(F)c(C(F)F)c3)cnc21]

The title compound was prepared in a manner analogous to Example 533, using azetidine. MS (ESI): mass calcd. for $C_{19}H_{17}F_3N_4O_2$, 390.1; m/z found 391[M+H]$^+$. $^1$H NMR (300 MHz, DMSO-d$_6$) δ 8.32 (s, 1H), 7.90 (d, J=6.1 Hz, 2H), 7.83 (s, 1H), 7.51 (t, J=9.7 Hz, 1H), 7.27 (t, J=54.2 Hz, 1H), 4.61 (s, 2H), 4.29 (t, J=7.5 Hz, 2H), 3.90 (t, J=7.6 Hz, 2H), 3.39 (s, 3H), 2.36-2.21 (m, 2H).

Example 585: 6-[3-(Difluoromethyl)-4-fluoro-phenyl]-1-[2-(3-fluoroazetidin-1-yl)-2-oxo-ethyl]-3-methyl-imidazo[4,5-b]pyridin-2-one

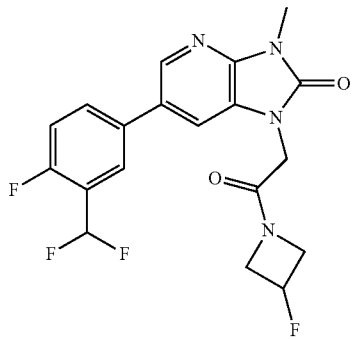 [SMILES: Cn1c(=O)n(CC(=O)N2CC(F)C2)c2cc(-c3ccc(F)c(C(F)F)c3)cnc21]

The title compound was prepared in a manner analogous to Example 533, using 3-fluoroazetidine hydrochloride. MS (ESI): mass calcd. for $C_{19}H_{16}F_4N_4O_2$, 408.1; m/z found, 409 [M+H]$^+$. $^1$H NMR (300 MHz, DMSO-d$_6$) δ 8.32 (s, 1H), 7.89 (d, J=6.2 Hz, 2H), 7.82 (s, 1H), 7.51 (t, J=9.7 Hz, 1H), 7.27 (t, J=54.2 Hz, 1H), 5.47 (d, J=57.1 Hz, 1H), 4.69 (s, 2H), 4.66-4.54 (m, 1H), 4.40 (dd, J=24.4, 10.6 Hz, 1H), 4.33-4.16 (m, 1H), 3.97 (dd, J=25.0, 11.5 Hz, 1H), 3.39 (s, 3H).

Example 586: 1-[2-(3,3-Difluoroazetidin-1-yl)-2-oxo-ethyl]-6-[3-(difluoromethyl)-4-fluoro-phenyl]-3-methyl-imidazo[4,5-b]pyridin-2-one

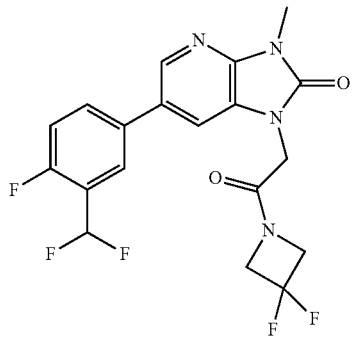 [SMILES: Cn1c(=O)n(CC(=O)N2CC(F)(F)C2)c2cc(-c3ccc(F)c(C(F)F)c3)cnc21]

The title compound was prepared in a manner analogous to Example 533, using 3,3-difluoroazetidine hydrochloride. MS (ESI): mass calcd. for $C_{19}H_{15}F_5N_4O_2$, 426.1; m/z found, 427 [M+H]$^+$. $^1$H NMR (300 MHz, DMSO-d$_6$) δ 8.32 (s, 1H), 7.88 (d, J=6.1 Hz, 2H), 7.82 (s, 1H), 7.52 (t, J=9.7 Hz, 1H), 7.27 (t, J=54.2 Hz, 1H), 4.90-4.72 (m, 4H), 4.37 (t, J=12.5 Hz, 2H), 3.40 (s, 3H).

Example 587: 2-[6-[3-(Difluoromethoxy)-4-fluoro-phenyl]-3-methyl-2-oxo-imidazo[4,5-b]pyridin-1-yl]-N,N-dimethyl-acetamide

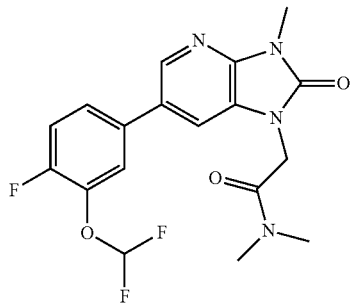 [SMILES: CN(C)C(=O)Cn1c(=O)n(C)c2ncc(-c3ccc(F)c(OC(F)F)c3)cc21]

The title compound was prepared in a manner analogous to Example 533, using 2-(6-(3-(difluoromethoxy)-4-fluorophenyl)-3-methyl-2-oxo-2,3-dihydro-1H-imidazo[4,5-b]pyridin-1-yl)acetic acid (Intermediate 60). MS (ESI): mass calcd. for $C_{18}H_{17}F_3N_4O_3$, 394.1; m/z found, 395 [M+H]$^+$. $^1$H NMR (300 MHz, DMSO-d$_6$) δ 8.32 (s, 1H), 7.80 (s, 1H), 7.69-7.08 (m, 4H), 4.85 (s, 2H), 3.39 (s, 3H), 3.11 (s, 3H), 2.84 (s, 3H).

Example 588: 1-[2-(Azetidin-1-yl)-2-oxo-ethyl]-6-[3-(difluoromethoxy)-4-fluoro-phenyl]-3-methyl-imidazo[4,5-b]pyridin-2-one

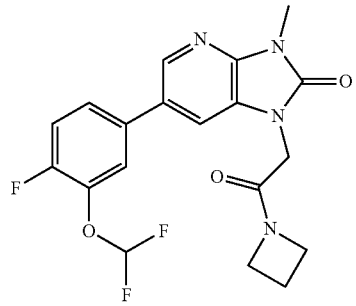 [SMILES: Cn1c(=O)n(CC(=O)N2CCC2)c2cc(-c3ccc(F)c(OC(F)F)c3)cnc21]

The title compound was prepared in a manner analogous to Example 533, using 2-(6-(3-(difluoromethoxy)-4-fluorophenyl)-3-methyl-2-oxo-2,3-dihydro-1H-imidazo[4,5-b]pyridin-1-yl)acetic acid (Intermediate 60) and azetidine. MS (ESI): mass calcd. for $C_{19}H_{17}F_3N_4O_3$, 406.1; m/z found 407 [M+H]$^+$. $^1$H NMR (300 MHz, CDCl$_3$) δ 8.24-8.16 (m, 1H), 7.44-7.32 (m, 3H), 7.29-7.19 (m, 1H), 6.61 (t, J=73.5 Hz, 1H), 4.50 (s, 2H), 4.34 (t, J=7.7 Hz, 2H), 4.09 (t, J=7.8 Hz, 2H), 3.54 (s, 3H), 2.44-2.28 (m, 2H).

Example 589: 6-[3-(Difluoromethoxy)-4-fluoro-phenyl]-1-[2-(3-fluoroazetidin-1-yl)-2-oxo-ethyl]-3-methyl-imidazo[4,5-b]pyridin-2-one

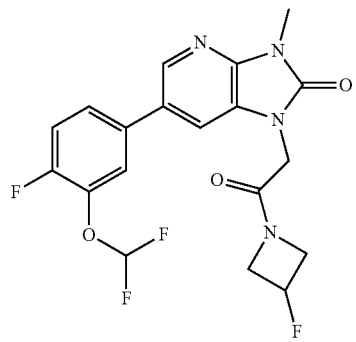 [SMILES: Cn1c(=O)n(CC(=O)N2CC(F)C2)c2cc(-c3ccc(F)c(OC(F)F)c3)cnc21]

The title compound was prepared in a manner analogous to Example 533, using 2-(6-(3-(difluoromethoxy)-4-fluorophenyl)-3-methyl-2-oxo-2,3-dihydro-1H-imidazo[4,5-b]pyridin-1-yl)acetic acid (Intermediate 60) and 3-fluoroazetidine hydrochloride. MS (ESI): mass calcd. for $C_{19}H_{16}F_4N_4O_3$, 424.1; m/z found, 425 [M+H]$^+$. $^1$H NMR (300 MHz, DMSO-d$_6$) δ 8.33 (s, 1H), 7.80 (s, 1H), 7.70-7.03 (m, 4H), 5.47 (d, J=57.1 Hz, 1H), 4.68 (s, 2H), 4.65-4.55 (m, 1H), 4.48-4.33 (m, 1H), 4.31-4.17 (m, 1H), 4.05-3.89 (m, 1H), 3.39 (s, 3H).

Example 590: 1-[2-(3,3-Difluoroazetidin-1-yl)-2-oxo-ethyl]-6-[3-(difluoromethoxy)-4-fluoro-phenyl]-3-methyl-imidazo[4,5-b]pyridin-2-one

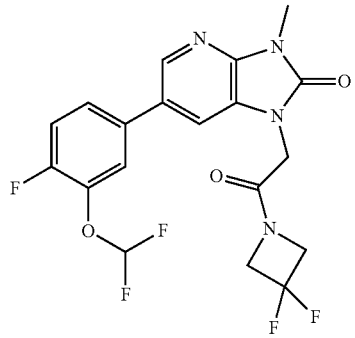 [SMILES: Cn1c(=O)n(CC(=O)N2CC(F)(F)C2)c2cc(-c3ccc(F)c(OC(F)F)c3)cnc21]

The title compound was prepared in a manner analogous to Example 533, using 2-(6-(3-(difluoromethoxy)-4-fluorophenyl)-3-methyl-2-oxo-2,3-dihydro-1H-imidazo[4,5-b]pyridin-1-yl)acetic acid (Intermediate 60) and 3,3-difluoroazetidine hydrochloride. MS (ESI): mass calcd. for $C_{19}H_{15}F_5N_4O_3$, 442.1; m/z found, 443 [M+H]$^+$. $^1$H NMR (300 MHz, DMSO-d$_6$) δ 8.33 (s, 1H), 7.80 (s, 1H), 7.68-7.07 (m, 4H), 4.89-4.71 (m, 4H), 4.38 (t, J=12.4 Hz, 2H), 3.40 (s, 3H).

Example 591: 2-[6-[4-Chloro-3-(difluoromethoxy)phenyl]-3-methyl-2-oxo-imidazo[4,5-b]pyridin-1-yl]-N,N-dimethyl-acetamide

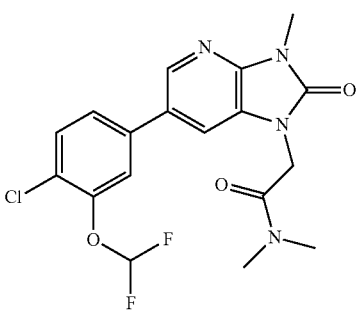 [SMILES: CN(C)C(=O)Cn1c(=O)n(C)c2ncc(-c3ccc(Cl)c(OC(F)F)c3)cc21]

The title compound was prepared in a manner analogous to Example 533, using 2-(6-(4-chloro-3-(difluoromethoxy)phenyl)-3-methyl-2-oxo-2,3-dihydro-1H-imidazo[4,5-b]pyridin-1-yl)acetic acid (Intermediate 65). MS (ESI): mass calcd. for $C_{18}H_{17}ClF_2N_4O_3$, 410.1; m/z found, 411[M+H]$^+$. $^1$H NMR (300 MHz, CDCl$_3$) δ 8.21 (d, J=1.4 Hz, 1H), 7.51 (d, J=8.2 Hz, 1H), 7.39 (s, 1H), 7.38-7.32 (m, 1H), 7.30 (d, J=1.4 Hz, 1H), 6.59 (t, J=73.5 Hz, 1H), 4.74 (s, 2H), 3.54 (s, 3H), 3.18 (s, 3H), 2.99 (s, 3H).

Example 592: 1-[2-(Azetidin-1-yl)-2-oxo-ethyl]-6-[4-chloro-3-(difluoromethoxy)phenyl]-3-methyl-imidazo[4,5-b]pyridin-2-one

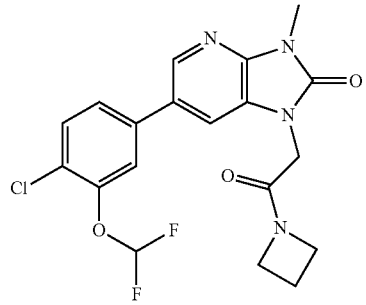 [SMILES: Cn1c(=O)n(CC(=O)N2CCC2)c2cc(-c3ccc(Cl)c(OC(F)F)c3)cnc21]

The title compound was prepared in a manner analogous to Example 533, using 2-(6-(4-chloro-3-(difluoromethoxy)phenyl)-3-methyl-2-oxo-2,3-dihydro-1H-imidazo[4,5-b]pyridin-1-yl)acetic acid (Intermediate 65) and azetidine. MS (ESI): mass calcd. for $C_{19}H_{17}ClF_2N_4O_3$, 422.1; m/z found, 423 [M+H]$^+$. $^1$H NMR (300 MHz, DMSO-d$_6$) δ 8.35 (s, 1H), 7.81 (s, 1H), 7.71 (d, J=8.3 Hz, 1H), 7.68-7.59 (m, 2H), 7.37 (t, J=65.6 Hz, 1H), 4.60 (s, 2H), 4.28 (t, J=7.5 Hz, 2H), 3.90 (t, J=7.6 Hz, 2H), 3.38 (s, 3H), 2.35-2.22 (m, 2H).

Example 593: 6-[4-Chloro-3-(difluoromethoxy)phenyl]-1-[2-(3-fluoroazetidin-1-yl)-2-oxo-ethyl]-3-methyl-imidazo[4,5-b]pyridin-2-one

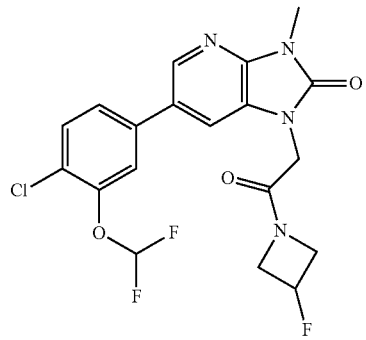 [SMILES: Cn1c(=O)n(CC(=O)N2CC(F)C2)c2cc(-c3ccc(Cl)c(OC(F)F)c3)cnc21]

The title compound was prepared in a manner analogous to Example 533, using 2-(6-(4-chloro-3-(difluoromethoxy)phenyl)-3-methyl-2-oxo-2,3-dihydro-1H-imidazo[4,5-b]pyridin-1-yl)acetic acid (Intermediate 65) and 3-fluoroazetidine hydrochloride. MS (ESI): mass calcd. for $C_{19}H_{16}ClF_3N_4O_3$, 440.1; m/z found, 441[M+H]$^+$. $^1$H NMR (300 MHz, DMSO-d$_6$) δ 8.36 (s, 1H), 7.82 (s, 1H), 7.71 (d, J=8.3 Hz, 1H), 7.62 (d, J=12.5 Hz, 2H), 7.36 (t, J=65.2 Hz, 1H), 5.46 (d, J=56.8 Hz, 1H), 4.76-4.53 (m, 3H), 4.40 (dd, J=24.4, 10.7 Hz, 1H), 4.33-4.16 (m, 1H), 3.96 (dd, J=24.9, 11.5 Hz, 1H), 3.39 (s, 3H).

Example 594: 6-[4-Chloro-3-(difluoromethoxy)phenyl]-1-[2-(3,3-difluoroazetidin-1-yl)-2-oxo-ethyl]-3-methyl-imidazo[4,5-b]pyridin-2-one

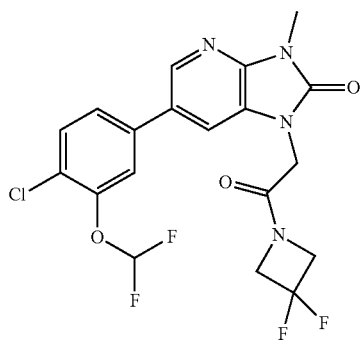 [SMILES: Cn1c(=O)n(CC(=O)N2CC(F)(F)C2)c2cc(-c3ccc(Cl)c(OC(F)F)c3)cnc21]

The title compound was prepared in a manner analogous to Example 533, using 2-(6-(4-chloro-3-(difluoromethoxy)phenyl)-3-methyl-2-oxo-2,3-dihydro-1H-imidazo[4,5-b]pyridin-1-yl)acetic acid (Intermediate 65) and 3,3-difluoroazetidine hydrochloride. MS (ESI): mass calcd. for $C_{19}H_{15}ClF_4N_4O_3$, 458.1; m/z found, 459 [M+H]$^+$. $^1$H NMR (300 MHz, DMSO-d$_6$) δ 8.36 (s, 1H), 7.82 (s, 1H), 7.72 (d, J=8.4 Hz, 1H), 7.67-7.59 (m, 2H), 7.37 (t, J=64.7 Hz, 1H), 4.91-4.70 (m, 4H), 4.37 (t, J=12.4 Hz, 2H), 3.40 (s, 3H).

Example 595: 1-[2-(Azetidin-1-yl)-2-oxo-ethyl]-6-(2,4-difluoro-3-methyl-phenyl)-3-(fluoromethyl)imidazo[4,5-b]pyridin-2-one

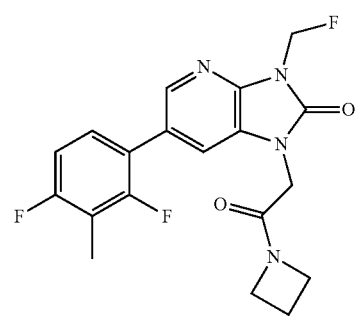 [SMILES: Cc1c(F)ccc(-c2cnc3c(c2)n(CC(=O)N2CCC2)c(=O)n3CF)c1F]

The title compound was prepared in a manner analogous to Example 534, using 1-[2-(azetidin-1-yl)-2-oxo-ethyl]-6-(2,4-difluoro-3-methyl-phenyl)-3H-imidazo[4,5-b]pyridin-2-one (Example 579). MS (ESI): mass calcd. for $C_{19}H_{17}F_3N_4O_2$, 390.1; m/z found, 391.2 [M+H]$^+$.

Example 596: 2-[3-(Fluoromethyl)-2-oxo-6-[5-(trifluoromethyl)-2-thienyl]imidazo[4,5-b]pyridin-1-yl]-N,N-dimethyl-acetamide

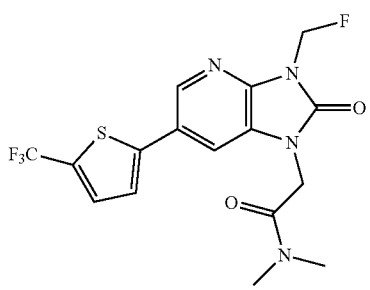 [SMILES: CN(C)C(=O)Cn1c(=O)n(CF)c2ncc(-c3ccc(C(F)(F)F)s3)cc21]

The title compound was prepared in a manner analogous to Example 534 using N,N-dimethyl-2-[2-oxo-6-[5-(trifluoromethyl)-2-thienyl]-3H-imidazo[4,5-b]pyridin-1-yl]acetamide (Example 26) in place of 1-[2-(azetidin-1-yl)-2-oxo-ethyl]-6-[5-(trifluoromethyl)-2-thienyl]-3H-imidazo[4,5-b]pyridin-2-one (Example 323). MS (ESI): mass calcd. for $C_{16}H_{14}F_4N_4O_2S$, 402.1; m/z found, 403.1 $[M+H]^+$. $^1H$ NMR (500 MHz, CDCl$_3$-d) δ 8.36 (d, J=1.9 Hz, 1H), 7.46-7.42 (m, 1H), 7.41 (d, J=1.9 Hz, 1H), 7.24-7.20 (m, 1H), 6.11 (d, J=52.6 Hz, 2H), 4.75 (s, 2H), 3.20 (s, 3H), 3.02 (s, 3H).

Example 597: 1-[2-(3-Fluoroazetidin-1-yl)-2-oxo-ethyl]-3-(fluoromethyl)-6-[5-(trifluoromethyl)-2-thienyl]imidazo[4,5-b]pyridin-2-one

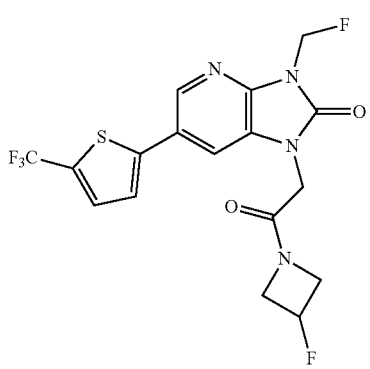 [SMILES: O=C(Cn1c(=O)n(CF)c2ncc(-c3ccc(C(F)(F)F)s3)cc21)N1CC(F)C1]

The title compound was prepared in a manner analogous to Example 534, using 1-[2-(3-fluoroazetidin-1-yl)-2-oxo-ethyl]-6-[5-(trifluoromethyl)-2-thienyl]-3H-imidazo[4,5-b]pyridin-2-one (Example 578). MS (ESI): mass calcd. for $C_{17}H_{13}F_5N_4O_2S$, 432.1; m/z found, 433.1 $[M+H]^+$. $^1H$ NMR (600 MHz, DMSO-d$_6$) δ 8.49 (d, J=1.9 Hz, 1H), 7.97 (d, J=2.0 Hz, 1H), 7.80-7.78 (m, 1H), 7.65-7.62 (m, 1H), 6.03 (d, J=53.3 Hz, 2H), 5.57-5.51 (m, 0.5H), 5.47-5.41 (m, 0.5H), 4.79-4.61 (m, 3H), 4.49-4.37 (m, 1H), 4.34-4.23 (m, 1H), 4.05-3.94 (m, 1H).

Example 598: 3-(Fluoromethyl)-1-(2-oxo-2-pyrrolidin-1-yl-ethyl)-6-[5-(trifluoromethyl)-2-thienyl]imidazo[4,5-b]pyridin-2-one

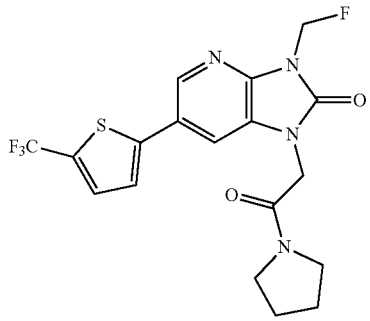 [SMILES: O=C(Cn1c(=O)n(CF)c2ncc(-c3ccc(C(F)(F)F)s3)cc21)N1CCCC1]

Step A: 1-(2-Oxo-2-pyrrolidin-1-yl-ethyl)-6-[5-(trifluoromethyl)-2-thienyl]imidazo[4,5-b]pyridin-2-one The title compound was prepared in a manner analogous to Example 26, Method A, using pyrrolidine in place of dimethylamine hydrochloride in Step C. MS (ESI): mass calcd. for $C_{17}H_{15}F_3N_4O_2S$, 396.1; m/z found, 397.1 $[M+H]^+$.

Step B: 3-(Fluoromethyl)-1-(2-oxo-2-pyrrolidin-1-yl-ethyl)-6-[5-(trifluoromethyl)-2-thienyl]imidazo[4,5-b]pyridin-2-one The title compound was prepared in a manner analogous to Example 534 using 1-(2-oxo-2-pyrrolidin-1-yl-ethyl)-6-[5-(trifluoromethyl)-2-thienyl]imidazo[4,5-b]pyridin-2-one. MS (ESI): mass calcd. for $C_{18}H_{16}F_4N_4O_2S$, 428.1; m/z found, 429.1 $[M+H]^+$. $^1H$ NMR (500 MHz, CDCl$_3$) δ 8.35 (d, J=1.9 Hz, 1H), 7.46 (d, J=1.9 Hz, 1H), 7.45-7.42 (m, 1H), 7.24-7.21 (m, 1H), 6.11 (d, J=52.5 Hz, 2H), 4.68 (s, 2H), 3.64 (t, J=6.8 Hz, 2H), 3.53 (t, J=7.0 Hz, 2H), 2.09 (p, J=6.9 Hz, 2H), 1.94 (p, J=6.9 Hz, 2H).

Example 599: 2-[6-(2,4-Difluoro-3-methyl-phenyl)-3-(fluoromethyl)-2-oxo-imidazo[4,5-b]pyridin-1-yl]-N,N-dimethyl-acetamide

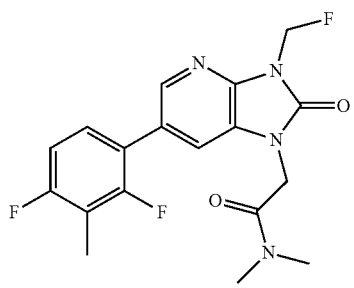 [SMILES: Cc1c(F)ccc(-c2cnc3c(c2)n(CC(=O)N(C)C)c(=O)n3CF)c1F]

Step A: 2-[6-(2,4-Difluoro-3-methyl-phenyl)-2-oxo-imidazo[4,5-b]pyridin-1-yl]-N,N-dimethyl-acetamide The title compound was prepared in a manner analogous to Example 26 using (2,4-difluoro-3-methylphenyl)boronic acid in Step A. MS (ESI): mass calcd. for $C_{17}H_{16}F_2N_4O_2S$, 346.1; m/z found, 347.2 [M+H]$^+$.

Step B: 2-[6-(2,4-Difluoro-3-methyl-phenyl)-3-(fluoromethyl)-2-oxo-imidazo[4,5-b]pyridin-1-yl]-N,N-dimethyl-acetamide The title compound was prepared in a manner analogous to Example 534. MS (ESI): mass calcd. for $C_{18}H_{17}F_3N_4O_2$, 378.1; m/z found, 379.2 [M+H]$^+$. $^1$H NMR (400 MHz, DMSO-d$_6$) δ 8.20-8.17 (m, 1H), 7.79-7.76 (m, 1H), 7.47-7.39 (m, 1H), 7.25-7.18 (m, 1H), 6.05 (d, J=53.3 Hz, 2H), 4.89 (s, 2H), 3.09 (s, 3H), 2.84 (s, 3H), 2.25-2.22 (m, 3H).

Example 600: 6-(2,4-Difluoro-3-methyl-phenyl)-1-[2-(3-fluoroazetidin-1-yl)-2-oxo-ethyl]-3-(fluoromethyl)imidazo[4,5-b]pyridin-2-one

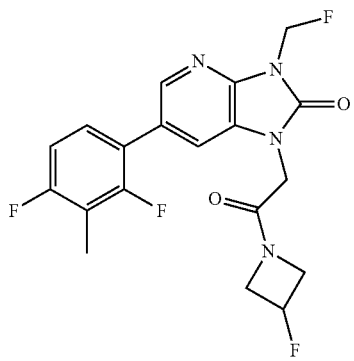 [SMILES: Cc1c(F)ccc(-c2cnc3c(c2)n(CC(=O)N2CC(F)C2)c(=O)n3CF)c1F]

Step A: 6-(2,4-Difluoro-3-methylphenyl)-1-(2-(3-fluoroazetidin-1-yl)-2-oxoethyl)-1,3-dihydro-2H-imidazo[4,5-b]pyridin-2-one The title compound was prepared in a manner analogous to Example 25, using 1-(2-(3-fluoroazetidin-1-yl)-2-oxoethyl)-6-bromo-3-trityl-1,3-dihydro-2H-imidazo[4,5-b]pyridin-2-one (Intermediate 40) in place of 1-(2-(azetidin-1-yl)-2-oxoethyl)-6-bromo-3-trityl-1,3-dihydro-2H-imidazo[4,5-b]pyridin-2-one (Intermediate 38) and (2,4-difluoro-3-methylphenyl)boronic acid in place of (3-(trifluoromethyl)phenyl)boronic acid in Step A.

Step B: 6-(2,4-Difluoro-3-methyl-phenyl)-1-[2-(3-fluoroazetidin-1-yl)-2-oxo-ethyl]-3-(fluoromethyl)imidazo[4,5-b]pyridin-2-one The title compound was prepared in a manner analogous to Example 534. MS (ESI): mass calcd. for $C_{19}H_{16}F_4N_4O_2$, 408.1; m/z found, 409.2 [M+H]$^+$. $^1$H NMR (500 MHz, CDCl$_3$) δ 8.24-8.21 (m, 1H), 7.51-7.49 (m, 1H), 7.25-7.19 (m, 1H), 6.99-6.93 (m, 1H), 6.12 (d, J=52.7 Hz, 2H), 5.47-5.41 (m, 0.5H), 5.36-5.29 (m, 0.5H), 4.69-4.57 (m, 2H), 4.53-4.32 (m, 3H), 4.26-4.15 (m, 1H), 2.30-2.27 (m, 3H).

Examples 601-612 were prepared in a manner described in the Examples above.

Example 601: 1-(3,3-Dimethyl-2-oxo-butyl)-6-(4-methoxyphenyl)-3H-imidazo[4,5-b]pyridin-2-one

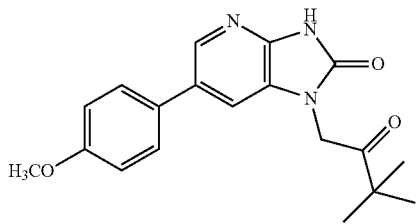 [SMILES: COc1ccc(-c2cnc3[nH]c(=O)n(CC(=O)C(C)(C)C)c3c2)cc1]

MS (ESI): mass calcd. for $C_{19}H_{21}N_3O_3$, 339.2; m/z found, [M+H]$^+$.

Example 602: 6-(3-Methoxyphenyl)-1-[2-oxo-2-(2-thienyl)ethyl]-3H-imidazo[4,5-b]pyridin-2-one

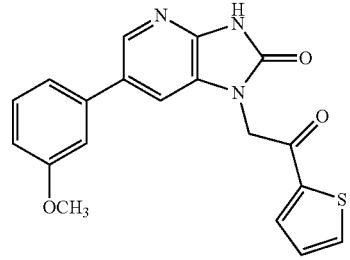 [SMILES: COc1cccc(-c2cnc3[nH]c(=O)n(CC(=O)c4cccs4)c3c2)c1]

MS (ESI): mass calcd. for $C_{19}H_{15}N_3O_3S$, 365.1; m/z found, [M+H]$^+$.

Example 603: 1-(3,3-Dimethyl-2-oxo-butyl)-6-(4-methoxy-3-methyl-phenyl)-3H-imidazo[4,5-b]pyridin-2-one

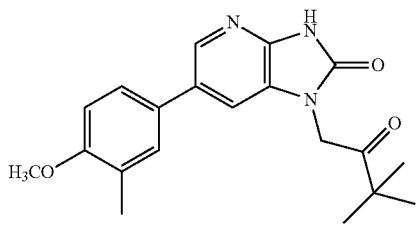 [SMILES: COc1ccc(-c2cnc3[nH]c(=O)n(CC(=O)C(C)(C)C)c3c2)cc1C]

MS (ESI): mass calcd. for $C_{20}H_{23}N_3O_3$, 353.2; m/z found, [M+H]$^+$.

Example 604: 1-Isobutyl-6-(4-methoxyphenyl)-3H-imidazo[4,5-b]pyridin-2-one

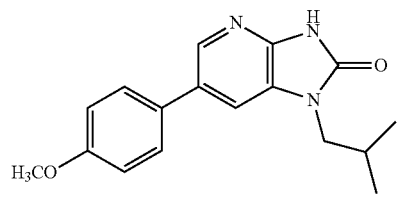 [SMILES: COc1ccc(-c2cnc3[nH]c(=O)n(CC(C)C)c3c2)cc1]

MS (ESI): mass calcd. for $C_{17}H_{19}N_3O_2$, 297.1; m/z found, 39676416 [M+H]+.

Example 605: 6-(2-Ethoxyphenyl)-1-[(3-methoxy-phenyl)methyl]-3H-imidazo[4,5-b]pyridin-2-one

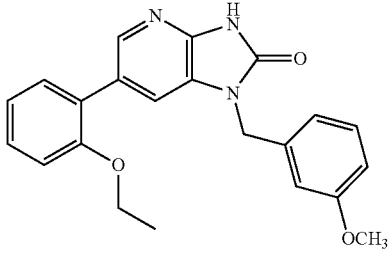 [SMILES: CCOc1ccccc1-c1cnc2[nH]c(=O)n(Cc3cccc(OC)c3)c2c1]

MS (ESI): mass calcd. for $C_{22}H_{21}N_3O_3$, 375.2; m/z found, [M+H]+.

Example 606: 6-(2-Ethoxyphenyl)-1-[(4-fluorophenyl)methyl]-3H-imidazo[4,5-b]pyridin-2-one

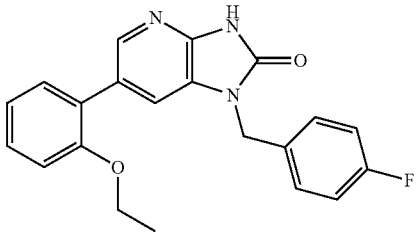 [SMILES: CCOc1ccccc1-c1cnc2[nH]c(=O)n(Cc3ccc(F)cc3)c2c1]

MS (ESI): mass calcd. for $C_{21}H_{18}FN_3O_2$, 363.1; m/z found, [M+H]+.

Example 607: N-Cyclopropyl-2-[6-(2-ethoxy-5-fluoro-phenyl)-2-oxo-3H-imidazo[4,5-b]pyridin-1-yl]acetamide

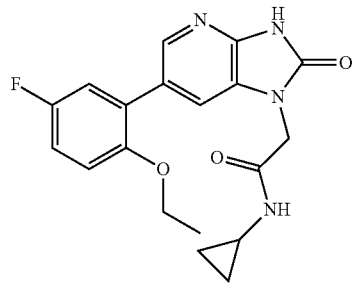 [SMILES: CCOc1ccc(F)cc1-c1cnc2[nH]c(=O)n(CC(=O)NC3CC3)c2c1]

MS (ESI): mass calcd. for $C_{19}H_{19}FN_4O_3$, 370.1; m/z found, [M+H]+.

Example 608: 2-[[6-(4-Methoxy-3-methyl-phenyl)-2-oxo-3H-imidazo[4,5-b]pyridin-1-yl]methyl]benzonitrile

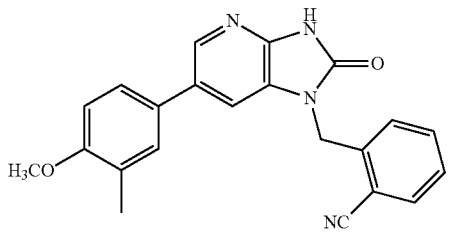 [SMILES: COc1ccc(-c2cnc3[nH]c(=O)n(Cc4ccccc4C#N)c3c2)cc1C]

MS (ESI): mass calcd. for $C_{22}H_{18}N_4O_2$, 370.1; m/z found, [M+H]+.

Example 609: 1-(3,3-Dimethyl-2-oxo-butyl)-6-(3-fluoro-4-methoxy-phenyl)-3H-imidazo[4,5-b]pyridin-2-one

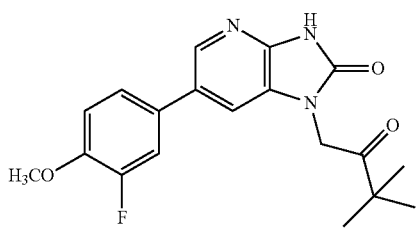

MS (ESI): mass calcd. for $C_{19}H_{20}FN_3O_3$, 357.1; m/z found, 39686582 [M+H]+.

Example 610: 2-[6-(3,5-Difluorophenyl)-2-oxo-3H-imidazo[4,5-b]pyridin-1-yl]-N-(2-methoxyethyl)acetamide

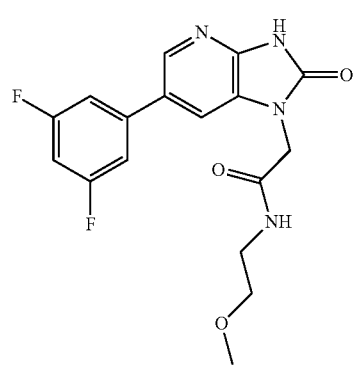 [SMILES: COCCNC(=O)Cn1c(=O)[nH]c2ncc(-c3cc(F)cc(F)c3)cc21]

MS (ESI): mass calcd. for $C_{17}H_{16}F_2N_4O_3$, 362.1; m/z found, [M+H]+.

Example 611: 1-(3,3-Dimethyl-2-oxo-butyl)-6-[3-(trifluoromethyl)phenyl]-3H-imidazo[4,5-b]pyridin-2-one

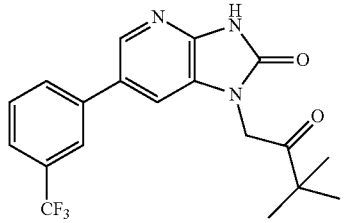 [SMILES: CC(C)(C)C(=O)Cn1c(=O)[nH]c2ncc(-c3cccc(C(F)(F)F)c3)cc21]

MS (ESI): mass calcd. for $C_{19}H_{18}F_3N_3O_2$, 377.1; m/z found, [M+H]$^+$.

Example 612: 2-[6-(3-Chloro-4-fluoro-phenyl)-2-oxo-3H-imidazo[4,5-b]pyridin-1-yl]-N-(2-m ethoxy-ethyl)acetamide

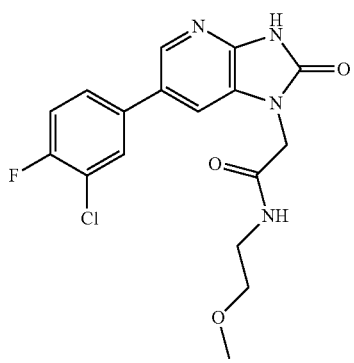 [SMILES: COCCNC(=O)Cn1c(=O)[nH]c2ncc(-c3ccc(F)c(Cl)c3)cc21]

MS (ESI): mass calcd. for $C_{17}H_{16}ClFN_4O_3$, 378.1; m/z found, [M+H]$^+$.

Biological Assays

Effects of Test Articles on Cloned Human NR1/NR2B Ion Channels Expressed in Mammalian Cells NMDA receptors are ion channels that are highly permeable to $Ca^{2+}$ ions, rendering it possible to monitor NMDA receptor function using cell-based calcium flux assay. In this assay, co-agonists glutamate and glycine are added to cells heterologously expressing human GluN1/GluN2B NMDA receptors to initiate cellular $Ca^{2+}$ influx. The time course of the changes in intracellular calcium is measured using a fluorescent dye and a FLIPR (Fluorometric Imaging Plate Reader) device.

Twenty four hours before measurements, the expression of the NMDA receptors in the stable cell line is induced with Tet-On inducible system in the presence of a non-selective NMDA receptor blocker. On the day of the experiment, cell culture media is carefully washed and the cells are loaded with Calcium 5 Dye Kit (Molecular Devices) in dye loading buffer containing 137 mM NaCl, 4 mM KCl, 2 mM $CaCl_2$), 0.5 mM $MgCl_2$ (standard assay) or 1.5 mM $MgCl_2$ (HTS assay), 10 mM HEPES and 5 mM D-glucose; pH 7.4. After 1 h incubation at the room temperature, the dye is washed away with the assay buffer (137 mM NaCl (standard assay) or 150 mM (HTS assay), 4 mM KCl (standard assay) or 3 mM (HTS assay), 2 mM $CaCl_2$), 0.01 mM EDTA, 10 mM HEPES and 5 mM D-glucose; pH 7.4) In the FLIPR TETRA reader, various concentrations of the test compounds are added to the cells for 5 min while fluorescence is monitored to detect potential agonist activity. Next, co-agonists, glutamate and glycine are added for another 5 minutes. The concentration of glutamate corresponding to ~$EC_{40}$ (standard assay) or $EC_{40}$ (HTS assay) is used to maximize the assay's signal window and ability to detect NMDA receptor antagonists and negative allosteric modulators. A saturating concentration (10 µM) of glycine is also present in the assay. A non-selective NMDA receptor antagonist, (+)MK-801 is used as a positive control for antagonist activity. The fluorescent signal in the presence of test compounds is quantified and normalized to the signal defined by the appropriate control wells.

TABLE 3

| Ex # | Compound Name | NR2B IC$_{50}$ (µM) standard assay | NR2B IC$_{50}$ (µM) HTS assay |
|---|---|---|---|
| 1 | 6-(4-Methoxyphenyl)-1-(2-morpholino-2-oxo-ethyl)-3H-imidazo[4,5-b]pyridin-2-one; | 2.740 | |
| 2 | 6-(4-Fluoro-2-methyl-phenyl)-1-(2-methoxyethyl)-3H-imidazo[4,5-b]pyridin-2-one; | | 2.062 |
| 3 | N-Ethyl-2-[6-(4-fluoro-2-methyl-phenyl)-2-oxo-3H-imidazo[4,5-b]pyridin-1-yl]acetamide; | 0.088 | |
| 4 | (S*)-1-(2-Hydroxybutyl)-6-(4-methoxyphenyl)-3H-imidazo[4,5-b]pyridin-2-one; | 0.320 | |
| 5 | (R*)-1-(2-Hydroxybutyl)-6-(4-methoxyphenyl)-3H-imidazo[4,5-b]pyridin-2-one; | NT | |
| 6 | 6-(4-Fluoro-3-methyl-phenyl)-3-methyl-1-(2-pyridylmethyl)imidazo[4,5-b]pyridin-2-one; | 0.048 | |
| 7 | 6-(3-Fluorophenyl)-3-methyl-1-(pyrimidin-4-ylmethyl)imidazo[4,5-b]pyridin-2-one; | 6.770 | |
| 8 | 6-(3,4-Difluorophenyl)-3-methyl-1-[(5-methylisoxazol-3-yl)methyl]imidazo[4,5-b]pyridin-2-one; | 0.104 | |
| 9 | 2-[6-(5-Chloro-2-thienyl)-3-methyl-2-oxo-imidazo[4,5-b]pyridin-1-yl]-N,N-dimethyl-acetamide; | 0.005 | |

TABLE 3-continued

| Ex # | Compound Name | NR2B IC$_{50}$ (μM) standard assay | NR2B IC$_{50}$ (μM) HTS assay |
|---|---|---|---|
| 10 | 6-[5-(Difluoromethyl)-2-thienyl]-1-[2-(3-fluoroazetidin-1-yl)-2-oxo-ethyl]-3-methyl-imidazo[4,5-b]pyridin-2-one; | 0.010 | |
| 11 | 1-[(5-Methylisoxazol-3-yl)methyl]-6-phenyl-3H-imidazo[4,5-b]pyridin-2-one; | 0.088 | |
| 12 | 6-(4-Fluorophenyl)-1-[(5-methylisoxazol-3-yl)methyl]-3H-imidazo[4,5-b]pyridin-2-one; | 0.029 | |
| 13 | 6-(4-Fluorophenyl)-1-[(5-methyl-1,3,4-oxadiazol-2-yl)methyl]-3H-imidazo[4,5-b]pyridin-2-one; | 0.076 | |
| 14 | 3-Methyl-1-[(5-methylisoxazol-3-yl)methyl]-6-(4-methyl-2-thienyl)imidazo[4,5-b]pyridin-2-one; | 0.097 | |
| 15 | 6-(4-Fluorophenyl)-1-[(1-methylpyrazol-4-yl)methyl]-3H-imidazo[4,5-b]pyridin-2-one; | 0.204 | |
| 16 | 1-[(1,5-Dimethylpyrazol-3-yl)methyl]-6-(4-fluorophenyl)-3H-imidazo[4,5-b]pyridin-2-one; | 8.900 | |
| 17 | 1-[2-(Azetidin-1-yl)ethyl]-6-[3-(trifluoromethyl)phenyl]-3H-imidazo[4,5-b]pyridin-2-one; | 0.146 | |
| 18 | 1-[2-(Azetidin-1-yl)ethyl]-3-methyl-6-[3-(trifluoromethyl)phenyl]imidazo[4,5-b]pyridin-2-one; | 0.700 | |
| 19 | 1-[(5-Methylisoxazol-3-yl)methyl]-6-[3-(trifluoromethyl)phenyl]-3H-imidazo[4,5-b]pyridin-2-one; | 0.124 | |
| 20 | N-Cyclopropyl-2-[2-oxo-6-[3-(trifluoromethyl)phenyl]-3H-imidazo[4,5-b]pyridin-1-yl]acetamide; | 0.022 | |
| 21 | 1-[(3-Chlorophenyl)methyl]-6-[3-(trifluoromethyl)phenyl]-3H-imidazo[4,5-b]pyridin-2-one; | 1.340 | |
| 22 | 1-[(2-Methoxy-3-pyridyl)methyl]-6-[3-(trifluoromethyl)phenyl]-3H-imidazo[4,5-b]pyridin-2-one; | 26.699 | |
| 23 | 1-(Pyrimidin-4-ylmethyl)-6-[3-(trifluoromethyl)phenyl]-3H-imidazo[4,5-b]pyridin-2-one; | 0.220 | |
| 24 | (R/S)-1-(Tetrahydrofuran-2-ylmethyl)-6-[3-(trifluoromethyl)phenyl]-3H-imidazo[4,5-b]pyridin-2-one; | 0.127 | |
| 25 | 1-[2-(Azetidin-1-yl)-2-oxo-ethyl]-6-[3-(trifluoromethyl)phenyl]-3H-imidazo[4,5-b]pyridin-2-one; | 0.070 | |
| 26 | N,N-Dimethyl-2-[2-oxo-6-[5-(trifluoromethyl)-2-thienyl]-3H-imidazo[4,5-b]pyridin-1-yl]acetamide; | 0.012 | |
| 27 | 1-[2-(Azetidin-1-yl)-2-oxo-ethyl]-3-methyl-6-[5-(trifluoromethyl)-2-thienyl]imidazo[4,5-b]pyridin-2-one; | 0.031 | |
| 28 | N,N-Dimethyl-2-[3-methyl-2-oxo-6-[5-(trifluoromethyl)-2-thienyl]imidazo[4,5-b]pyridin-1-yl]acetamide; | 0.034 | |
| 29 | 1-[2-(Azetidin-1-yl)-2-oxo-ethyl]-6-[2-methyl-5-(trifluoromethyl)phenyl]-3H-imidazo[4,5-b]pyridin-2-one; | 0.396 | |
| 30 | 6-(2,4-Difluoro-3-methyl-phenyl)-1-(2-oxobutyl)-3H-imidazo[4,5-b]pyridin-2-one; | 0.011 | |
| 31 | (R/S)-1-(2-Cyclopropyl-2-hydroxy-ethyl)-6-[3-(trifluoromethyl)phenyl]-3H-imidazo[4,5-b]pyridin-2-one; | 0.151 | |
| 32 | 1-[(2-Oxo-1H-pyridin-3-yl)methyl]-6-[3-(trifluoromethyl)phenyl]-3H-imidazo[4,5-b]pyridin-2-one; | 8.329 | |
| 33 | (R/S)-6-(4-Fluoro-2-methyl-phenyl)-3-methyl-1-(oxetan-2-ylmethyl)imidazo[4,5-b]pyridin-2-one; | 1.230 | |
| 34 | 1-[2-(3-Fluoroazetidin-1-yl)-2-oxo-ethyl]-3-methyl-6-[3-(trifluoromethyl)phenyl]imidazo[4,5-b]pyridin-2-one; | 0.065 | |
| 35 | 6-(4-Methoxyphenyl)-1-(2-oxo-2-pyrrolidin-1-yl-ethyl)-3H-imidazo[4,5-b]pyridin-2-one; | | 2.139 |
| 36 | N-Cyclopropyl-2-[6-(4-fluoro-2-methyl-phenyl)-2-oxo-3H-imidazo[4,5-b]pyridin-1-yl]acetamide; | 0.159 | |
| 37 | 2-[6-(2-Chloro-4-methoxy-phenyl)-2-oxo-3H-imidazo[4,5-b]pyridin-1-yl]-N-cyclopropyl-acetamide; | | 1.376 |

TABLE 3-continued

| Ex # | Compound Name | NR2B IC$_{50}$ (μM) standard assay | NR2B IC$_{50}$ (μM) HTS assay |
|---|---|---|---|
| 38 | N-Cyclopropyl-2-[6-(4-methoxyphenyl)-2-oxo-3H-imidazo[4,5-b]pyridin-1-yl]acetamide; | | 1.013 |
| 39 | N-Cyclopropyl-2-[6-(3,5-dimethylphenyl)-2-oxo-3H-imidazo[4,5-b]pyridin-1-yl]acetamide; | | 1.026 |
| 40 | N-Cyclopropyl-2-[6-(4-fluoro-2-methyl-phenyl)-2-oxo-3H-imidazo[4,5-b]pyridin-1-yl]-N-methyl-acetamide; | | 1.822 |
| 41 | N-Cyclopropyl-2-[6-(4-methoxyphenyl)-2-oxo-3H-imidazo[4,5-b]pyridin-1-yl]-N-methyl-acetamide; | | 8.718 |
| 42 | N-Cyclopropyl-2-[6-(4-fluoro-2-methyl-phenyl)-3-methyl-2-oxo-imidazo[4,5-b]pyridin-1-yl]acetamide; | | 2.707 |
| 43 | (R*)-6-(4-Fluoro-2-methyl-phenyl)-1-(2-hydroxybutyl)-3H-imidazo[4,5-b]pyridin-2-one; | | 3.487 |
| 44 | (S*)-6-(4-Fluoro-2-methyl-phenyl)-1-(2-hydroxybutyl)-3H-imidazo[4,5-b]pyridin-2-one; | | 0.325 |
| 45 | 6-(4-Fluoro-3-methyl-phenyl)-3-methyl-1-(3-pyridylmethyl)imidazo[4,5-b]pyridin-2-one; | 0.038 | |
| 46 | 6-(4-Fluoro-3-methyl-phenyl)-3-methyl-1-(4-pyridylmethyl)imidazo[4,5-b]pyridin-2-one; | 0.600 | |
| 47 | 6-(4-Fluoro-3-methyl-phenyl)-3-methyl-1-(pyrazin-2-ylmethyl)imidazo[4,5-b]pyridin-2-one; | 0.113 | |
| 48 | 6-(4-Fluoro-3-methyl-phenyl)-3-methyl-1-(pyrimidin-5-ylmethyl)imidazo[4,5-b]pyridin-2-one; | 0.072 | |
| 49 | 6-(4-Fluoro-3-methyl-phenyl)-3-methyl-1-(pyrimidin-2-ylmethyl)imidazo[4,5-b]pyridin-2-one; | 0.486 | |
| 50 | 6-(4-Fluoro-3-methyl-phenyl)-3-methyl-1-(pyridazin-3-ylmethyl)imidazo[4,5-b]pyridin-2-one; | 0.009 | |
| 51 | 6-(3-Fluorophenyl)-3-methyl-1-(3-pyridylmethyl)imidazo[4,5-b]pyridin-2-one; | 22.600 | |
| 52 | 6-(3-Fluorophenyl)-3-methyl-1-(4-pyridylmethyl)imidazo[4,5-b]pyridin-2-one; | 3.330 | |
| 53 | 6-(3-Fluorophenyl)-3-methyl-1-(2-pyridylmethyl)imidazo[4,5-b]pyridin-2-one; | 1.400 | |
| 54 | 6-(3-Fluorophenyl)-3-methyl-1-(pyrimidin-5-ylmethyl)imidazo[4,5-b]pyridin-2-one; | 0.610 | |
| 55 | 6-(3-Fluorophenyl)-3-methyl-1-(pyrazin-2-ylmethyl)imidazo[4,5-b]pyridin-2-one; | 3.030 | |
| 56 | 6-(3-Fluorophenyl)-3-methyl-1-(pyrimidin-2-ylmethyl)imidazo[4,5-b]pyridin-2-one; | 8.710 | |
| 57 | 6-(3-Fluorophenyl)-3-methyl-1-(pyridazin-3-ylmethyl)imidazo[4,5-b]pyridin-2-one; | 0.200 | |
| 58 | 6-(3,4-Difluorophenyl)-3-methyl-1-(4-pyridylmethyl)imidazo[4,5-b]pyridin-2-one; | 1.900 | |
| 59 | 6-(3,4-Difluorophenyl)-3-methyl-1-(3-pyridylmethyl)imidazo[4,5-b]pyridin-2-one; | 0.246 | |
| 60 | 6-(3,4-Difluorophenyl)-3-methyl-1-(pyrimidin-5-ylmethyl)imidazo[4,5-b]pyridin-2-one; | 0.450 | |
| 61 | 6-(3,4-Difluorophenyl)-3-methyl-1-(pyridazin-3-ylmethyl)imidazo[4,5-b]pyridin-2-one; | 0.223 | |
| 62 | 6-(3,4-difluorophenyl)-3-methyl-1-(2-pyridylmethyl)imidazo[4,5-b]pyridin-2-one; | 2.000 | |
| 63 | 6-(3,4-Difluorophenyl)-3-methyl-1-(pyrazin-2-ylmethyl)imidazo[4,5-b]pyridin-2-one; | 2.300 | |
| 64 | 6-(3,4-Difluorophenyl)-3-methyl-1-(pyrimidin-2-ylmethyl)imidazo[4,5-b]pyridin-2-one; | 3.590 | |
| 65 | 6-(2,4-Difluoro-3-methyl-phenyl)-3-methyl-1-(pyrimidin-2-ylmethyl)imidazo[4,5-b]pyridin-2-one; | 0.810 | |
| 66 | 6-(2,4-Difluoro-3-methyl-phenyl)-3-methyl-1-(4-pyridylmethyl)imidazo[4,5-b]pyridin-2-one; | 0.725 | |
| 67 | 6-(2,4-Difluoro-3-methyl-phenyl)-3-methyl-1-(pyridazin-3-ylmethyl)imidazo[4,5-b]pyridin-2-one; | 0.009 | |
| 68 | 6-(2,4-Difluoro-3-methyl-phenyl)-3-methyl-1-(2-pyridylmethyl)imidazo[4,5-b]pyridin-2-one; | 0.310 | |
| 69 | 6-(2,4-Difluoro-3-methyl-phenyl)-3-methyl-1-(pyrimidin-5-ylmethyl)imidazo[4,5-b]pyridin-2-one; | 0.033 | |
| 70 | 6-(3,4-Difluorophenyl)-3-methyl-1-(pyrimidin-4-ylmethyl)imidazo[4,5-b]pyridin-2-one; | 2.210 | |
| 71 | 6-(4-Fluoro-3-methyl-phenyl)-3-methyl-1-(pyrimidin-4-ylmethyl)imidazo[4,5-b]pyridin-2-one; | 0.278 | |
| 72 | 6-(2,4-Difluoro-3-methyl-phenyl)-3-methyl-1-(pyrimidin-4-ylmethyl)imidazo[4,5-b]pyridin-2-one; | 0.482 | |

TABLE 3-continued

| Ex # | Compound Name | NR2B IC$_{50}$ (μM) standard assay | NR2B IC$_{50}$ (μM) HTS assay |
|---|---|---|---|
| 73 | 6-(3,4-Difluorophenyl)-3-methyl-1-[(5-methyl-1,3,4-oxadiazol-2-yl)methyl]imidazo[4,5-b]pyridin-2-one; | 0.314 | |
| 74 | 3-Methyl-1-[(5-methylisoxazol-3-yl)methyl]-6-[3-(trifluoromethyl)phenyl]imidazo[4,5-b]pyridin-2-one; | 0.057 | |
| 75 | 3-Methyl-1-[(5-methyl-1,3,4-oxadiazol-2-yl)methyl]-6-[3-(trifluoromethyl)phenyl]imidazo[4,5-b]pyridin-2-one; | 0.093 | |
| 76 | 3-Methyl-1-[(3-methyl-1,2,4-oxadiazol-5-yl)methyl]-6-[3-(trifluoromethyl)phenyl]imidazo[4,5-b]pyridin-2-one; | 0.218 | |
| 77 | 6-(3,4-Difluorophenyl)-3-methyl-1-[(3-methyl-1,2,4-oxadiazol-5-yl)methyl]imidazo[4,5-b]pyridin-2-one; | 0.457 | |
| 78 | N,N-Dimethyl-2-[3-methyl-6-(5-methyl-2-thienyl)-2-oxo-imidazo[4,5-b]pyridin-1-yl]acetamide; | 0.043 | |
| 79 | 2-[6-(5-Ethyl-2-thienyl)-3-methyl-2-oxo-imidazo[4,5-b]pyridin-1-yl]-N,N-dimethyl-acetamide; | 0.031 | |
| 80 | N,N-Dimethyl-2-[3-methyl-6-(4-methyl-2-thienyl)-2-oxo-imidazo[4,5-b]pyridin-1-yl]acetamide; | 0.030 | |
| 81 | 1-[2-(Azetidin-1-yl)-2-oxo-ethyl]-6-(5-fluoro-2-thienyl)-3-methyl-imidazo[4,5-b]pyridin-2-one; | 0.031 | |
| 82 | 2-[6-(5-Fluoro-2-thienyl)-3-methyl-2-oxo-imidazo[4,5-b]pyridin-1-yl]-N,N-dimethyl-acetamide; | 0.154 | |
| 83 | 1-[2-(3-Fluoroazetidin-1-yl)-2-oxo-ethyl]-6-(5-fluoro-2-thienyl)-3-methyl-imidazo[4,5-b]pyridin-2-one; | 0.033 | |
| 84 | 3-Methyl-1-(pyridazin-3-ylmethyl)-6-[5-(trifluoromethyl)-2-thienyl]imidazo[4,5-b]pyridin-2-one; | 0.030 | |
| 85 | 6-(5-Fluoro-2-thienyl)-3-methyl-1-(pyridazin-3-ylmethyl)imidazo[4,5-b]pyridin-2-one; | 0.157 | |
| 86 | 1-[2-(3-Fluoroazetidin-1-yl)-2-oxo-ethyl]-3-methyl-6-(4-methylthiazol-2-yl)imidazo[4,5-b]pyridin-2-one; | 1.600 | |
| 87 | 1-[2-(Azetidin-1-yl)-2-oxo-ethyl]-6-(5-ethyl-2-thienyl)-3-methyl-imidazo[4,5-b]pyridin-2-one; | 0.021 | |
| 88 | 6-(5-Ethyl-2-thienyl)-1-[2-(3-fluoroazetidin-1-yl)-2-oxo-ethyl]-3-methyl-imidazo[4,5-b]pyridin-2-one; | 0.020 | |
| 89 | 1-[2-(Azetidin-1-yl)-2-oxo-ethyl]-6-[5-(hydroxymethyl)-2-thienyl]-3-methyl-imidazo[4,5-b]pyridin-2-one; | 0.549 | |
| 90 | 1-[2-(3-Fluoroazetidin-1-yl)-2-oxo-ethyl]-6-[5-(hydroxymethyl)-2-thienyl]-3-methyl-imidazo[4,5-b]pyridin-2-one; | 0.915 | |
| 91 | 2-[6-[5-(Hydroxymethyl)-2-thienyl]-3-methyl-2-oxo-imidazo[4,5-b]pyridin-1-yl]-N,N-dimethyl-acetamide; | 1.700 | |
| 92 | 1-[2-(3-Fluoroazetidin-1-yl)-2-oxo-ethyl]-3-methyl-6-[2-(trifluoromethyl)-3-thienyl]imidazo[4,5-b]pyridin-2-one; | 0.249 | |
| 93 | 1-[2-(Azetidin-1-yl)-2-oxo-ethyl]-6-[5-(difluoromethyl)-2-thienyl]-3-methyl-imidazo[4,5-b]pyridin-2-one; | 0.006 | |
| 94 | 2-[6-[5-(Difluoromethyl)-2-thienyl]-3-methyl-2-oxo-imidazo[4,5-b]pyridin-1-yl]-N,N-dimethyl-acetamide; | 0.017 | |
| 95 | 1-[2-(Azetidin-1-yl)-2-oxo-ethyl]-3-methyl-6-[2-(trifluoromethyl)-3-thienyl]imidazo[4,5-b]pyridin-2-one; | 0.096 | |
| 96 | N,N-Dimethyl-2-[3-methyl-2-oxo-6-[2-(trifluoromethyl)-3-thienyl]imidazo[4,5-b]pyridin-1-yl]acetamide; | 0.522 | |
| 97 | 2-[6-[5-(Difluoromethyl)-3-thienyl]-3-methyl-2-oxo-imidazo[4,5-b]pyridin-1-yl]-N,N-dimethyl-acetamide; | 0.015 | |
| 98 | 1-[2-(Azetidin-1-yl)-2-oxo-ethyl]-6-[5-(difluoromethyl)-3-thienyl]-3-methyl-imidazo[4,5-b]pyridin-2-one; | 0.013 | |

TABLE 3-continued

| Ex # | Compound Name | NR2B IC$_{50}$ (µM) standard assay | NR2B IC$_{50}$ (µM) HTS assay |
|---|---|---|---|
| 99 | 6-[5-(Difluoromethyl)-3-thienyl]-1-[2-(3-fluoroazetidin-1-yl)-2-oxo-ethyl]-3-methyl-imidazo[4,5-b]pyridin-2-one; | 0.007 | |
| 100 | 6-[5-(Difluoromethyl)-2-thienyl]-3-methyl-1-(pyridazin-3-ylmethyl)imidazo[4,5-b]pyridin-2-one; | 0.033 | |
| 101 | N,N-Dimethyl-2-[3-methyl-2-oxo-6-[5-(trifluoromethyl)-3-thienyl]imidazo[4,5-b]pyridin-1-yl]acetamide; | 0.019 | |
| 102 | 1-[2-(3-Fluoroazetidin-1-yl)-2-oxo-ethyl]-3-methyl-6-[5-(trifluoromethyl)-3-thienyl]imidazo[4,5-b]pyridin-2-one; | 0.018 | |
| 103 | 3-Methyl-1-(pyridazin-3-ylmethyl)-6-[5-(trifluoromethyl)-3-thienyl]imidazo[4,5-b]pyridin-2-one; | 0.017 | |
| 104 | 1-[2-(Azetidin-1-yl)-2-oxo-ethyl]-3-methyl-6-[5-(trifluoromethyl)-3-thienyl]imidazo[4,5-b]pyridin-2-one; | 0.048 | |
| 105 | 1-[2-(Azetidin-1-yl)-2-oxo-ethyl]-6-(5-cyclopropyl-2-thienyl)-3-methyl-imidazo[4,5-b]pyridin-2-one; | 0.081 | |
| 106 | 6-(5-Cyclopropyl-2-thienyl)-1-[2-(3-fluoroazetidin-1-yl)-2-oxo-ethyl]-3-methyl-imidazo[4,5-b]pyridin-2-one; | 0.039 | |
| 107 | 1-[2-(Azetidin-1-yl)-2-oxo-ethyl]-3-methyl-6-[2-(trifluoromethyl)thiazol-4-yl]imidazo[4,5-b]pyridin-2-one; | 0.087 | |
| 108 | N,N-Dimethyl-2-[3-methyl-2-oxo-6-[2-(trifluoromethyl)thiazol-4-yl]imidazo[4,5-b]pyridin-1-yl]acetamide; | 0.047 | |
| 109 | 1-[2-(3-Fluoroazetidin-1-yl)-2-oxo-ethyl]-3-methyl-6-[2-(trifluoromethyl)thiazol-4-yl]imidazo[4,5-b]pyridin-2-one; | 0.040 | |
| 110 | 2-[6-(5-Cyclopropyl-2-thienyl)-3-methyl-2-oxo-imidazo[4,5-b]pyridin-1-yl]-N,N-dimethyl-acetamide; | 0.040 | |
| 111 | 1-[2-(Azetidin-1-yl)-2-oxo-ethyl]-3-methyl-6-[5-(1,1,2,2,2-pentafluoroethyl)-2-thienyl]imidazo[4,5-b]pyridin-2-one; | 0.037 | |
| 112 | 1-[2-(Azetidin-1-yl)-2-oxo-ethyl]-3-methyl-6-(2-methylthiazol-5-yl)imidazo[4,5-b]pyridin-2-one; | 5.104 | |
| 113 | 1-[2-(3-Fluoroazetidin-1-yl)-2-oxo-ethyl]-3-methyl-6-(2-methylthiazol-5-yl)imidazo[4,5-b]pyridin-2-one; | 5.359 | |
| 114 | N,N-Dimethyl-2-[3-methyl-6-(2-methylthiazol-5-yl)-2-oxo-imidazo[4,5-b]pyridin-1-yl]acetamide; | 11.700 | |
| 115 | 1-[2-(Azetidin-1-yl)-2-oxo-ethyl]-3-methyl-6-[2-(trifluoromethyl)thiazol-5-yl]imidazo[4,5-b]pyridin-2-one; | 0.820 | |
| 116 | 1-[2-(3-Fluoroazetidin-1-yl)-2-oxo-ethyl]-3-methyl-6-[2-(trifluoromethyl)thiazol-5-yl]imidazo[4,5-b]pyridin-2-one; | 0.705 | |
| 117 | 1-[2-(Azetidin-1-yl)-2-oxo-ethyl]-6-[4-(difluoromethyl)-2-thienyl]-3-methyl-imidazo[4,5-b]pyridin-2-one; | 0.038 | |
| 118 | 6-[4-(Difluoromethyl)-2-thienyl]-1-[2-(3-fluoroazetidin-1-yl)-2-oxo-ethyl]-3-methyl-imidazo[4,5-b]pyridin-2-one; | 0.020 | |
| 119 | N,N-Dimethyl-2-[3-methyl-2-oxo-6-[2-(trifluoromethyl)thiazol-5-yl]imidazo[4,5-b]pyridin-1-yl]acetamide; | NT | |
| 120 | 1-(2-(Azetidin-1-yl)-2-oxoethyl)-3-methyl-6-(5-(trifluoromethyl)thiophen-2-yl)-1,3-dihydro-2H-imidazo[4,5-b]pyridin-2-one-7-D; | 0.010 | |
| 121 | N,N-Dimethyl-2-[3-methyl-2-oxo-6-[5-(trideuteriomethoxymethyl)-2-thienyl]imidazo[4,5-b]pyridin-1-yl]acetamide; | 2.960 | |
| 122 | 1-[2-(Azetidin-1-yl)-2-oxo-ethyl]-3-methyl-6-[5-(trideuteriomethoxymethyl)-2-thienyl]imidazo[4,5-b]pyridin-2-one; | 1.220 | |
| 123 | 1-[2-(3-Fluoroazetidin-1-yl)-2-oxo-ethyl]-3-methyl-6-[5-(trideuteriomethoxymethyl)-2-thienyl]imidazo[4,5-b]pyridin-2-one; | 1.820 | |
| 124 | 1-(2-(Azetidin-1-yl)-2-oxoethyl)-3-methyl-6-(5-(trifluoromethyl)thiophen-2-yl)-1,3-dihydro-2H-imidazo[4,5-b]pyridin-2-one-7-T; | NT | |

TABLE 3-continued

| Ex # | Compound Name | NR2B IC$_{50}$ (μM) standard assay | NR2B IC$_{50}$ (μM) HTS assay |
|---|---|---|---|
| 125 | 1-[(5-Methylisoxazol-3-yl)methyl]-6-(4-methyl-2-thienyl)-3H-imidazo[4,5-b]pyridin-2-one; | 0.082 | |
| 126 | 1-[(5-Methylisoxazol-3-yl)methyl]-6-(o-tolyl)-3H-imidazo[4,5-b]pyridin-2-one; | 0.038 | |
| 127 | 1-[(3-Methyl-1,2,4-oxadiazol-5-yl)methyl]-6-(4-methyl-2-thienyl)-3H-imidazo[4,5-b]pyridin-2-one; | 0.095 | |
| 128 | 6-(4-Fluorophenyl)-1-[(1-methylpyrazol-3-yl)methyl]-3H-imidazo[4,5-b]pyridin-2-one; | 5.159 | |
| 129 | 6-(4-Fluoro-3-methyl-phenyl)-1-[(1-methylpyrazol-3-yl)methyl]-3H-imidazo[4,5-b]pyridin-2-one; | 0.394 | |
| 130 | 6-(3-Chloro-4-fluoro-phenyl)-1-[(1-methylpyrazol-3-yl)methyl]-3H-imidazo[4,5-b]pyridin-2-one; | 4.726 | |
| 131 | 6-(3,4-Difluorophenyl)-1-[(1-methylpyrazol-3-yl)methyl]-3H-imidazo[4,5-b]pyridin-2-one; | 3.560 | |
| 132 | 6-(2,4-Difluorophenyl)-1-[(1-methylpyrazol-3-yl)methyl]-3H-imidazo[4,5-b]pyridin-2-one; | 6.759 | |
| 133 | (R/S)-3-methyl-1-(oxetan-2-ylmethyl)-6-[3-(trifluoromethyl)phenyl]imidazo[4,5-b]pyridin-2-one; | 0.211 | |
| 134 | Ethyl 2-[2-oxo-6-[3-(trifluoromethyl)phenyl]-3H-imidazo[4,5-b]pyridin-1-yl]acetate; | 0.035 | |
| 135 | 2-[2-Oxo-6-[3-(trifluoromethyl)phenyl]-3H-imidazo[4,5-b]pyridin-1-yl]acetic acid; | 5.999 | |
| 136 | Ethyl 2-[3-methyl-2-oxo-6-[3-(trifluoromethyl)phenyl]imidazo[4,5-b]pyridin-1-yl]acetate; | 0.159 | |
| 137 | 2-[3-Methyl-2-oxo-6-[3-(trifluoromethyl)phenyl]imidazo[4,5-b]pyridin-1-yl]acetic acid; | >10 | |
| 138 | 1-[2-(3,3-difluoroazetidin-1-yl)-2-oxo-ethyl]-3-methyl-6-[3-(trifluoromethyl)phenyl]imidazo[4,5-b]pyridin-2-one; | 0.089 | |
| 139 | 6-(2,4-Difluoro-3-methyl-phenyl)-3-methyl-1-(pyrazin-2-ylmethyl)imidazo[4,5-b]pyridin-2-one; | 0.084 | |
| 140 | 6-(4-Fluorophenyl)-1-[(3-methyl-1,2,4-oxadiazol-5-yl)methyl]-3H-imidazo[4,5-b]pyridin-2-one; | 0.105 | |
| 141 | 6-(4-Fluorophenyl)-1-[(1-methyl-1,2,4-triazol-3-yl)methyl]-3H-imidazo[4,5-b]pyridin-2-one; | 1.181 | |
| 142 | 6-(4-Fluorophenyl)-1-[(1-methyltriazol-4-yl)methyl]-3H-imidazo[4,5-b]pyridin-2-one; | 0.208 | |
| 143 | 6-(3,4-Difluorophenyl)-1-[(3-methyl-1,2,4-oxadiazol-5-yl)methyl]-3H-imidazo[4,5-b]pyridin-2-one; | 0.075 | |
| 144 | 6-(3,4-Difluorophenyl)-1-[(5-methyl-1,2,4-oxadiazol-3-yl)methyl]-3H-imidazo[4,5-b]pyridin-2-one; | 0.107 | |
| 145 | 6-(3,4-Difluorophenyl)-1-[[3-(methoxymethyl)-1,2,4-oxadiazol-5-yl]methyl]-3H-imidazo[4,5-b]pyridin-2-one; | 1.310 | |
| 146 | 1-(2-Pyrrolidin-1-ylethyl)-6-[3-(trifluoromethyl)phenyl]-3H-imidazo[4,5-b]pyridin-2-one; | 0.506 | |
| 147 | 1-[2-(3-Hydroxyazetidin-1-yl)ethyl]-6-[3-(trifluoromethyl)phenyl]-3H-imidazo[4,5-b]pyridin-2-one; | 0.365 | |
| 148 | 1-[2-(Cyclopropylamino)ethyl]-6-[3-(trifluoromethyl)phenyl]-3H-imidazo[4,5-b]pyridin-2-one; | 0.505 | |
| 149 | 1-[2-(3-Methoxyazetidin-1-yl)ethyl]-6-[3-(trifluoromethyl)phenyl]-3H-imidazo[4,5-b]pyridin-2-one; | 0.756 | |
| 150 | 1-[2-(Cyclobutylamino)ethyl]-6-[3-(trifluoromethyl)phenyl]-3H-imidazo[4,5-b]pyridin-2-one; | 0.277 | |
| 151 | 1-[2-(Azetidin-1-yl)ethyl]-6-(4-fluoro-2-methyl-phenyl)-3H-imidazo[4,5-b]pyridin-2-one; | 0.115 | |
| 152 | 1-[2-(Azetidin-1-yl)ethyl]-6-(o-tolyl)-3H-imidazo[4,5-b]pyridin-2-one; | 0.127 | |
| 153 | 1-[2-(Azetidin-1-yl)ethyl]-6-phenyl-3H-imidazo[4,5-b]pyridin-2-one; | 0.283 | |
| 154 | 1-[2-(Azetidin-1-yl)ethyl]-6-(m-tolyl)-3H-imidazo[4,5-b]pyridin-2-one; | 0.077 | |
| 155 | 1-[2-(Azetidin-1-yl)ethyl]-6-[2-(trifluoromethyl)-4-pyridyl]-3H-imidazo[4,5-b]pyridin-2-one; | 1.750 | |

TABLE 3-continued

| Ex # | Compound Name | NR2B IC$_{50}$ (μM) standard assay | NR2B IC$_{50}$ (μM) HTS assay |
|---|---|---|---|
| 156 | 1-[2-(Azetidin-1-yl)ethyl]-6-(4-fluoro-3-methyl-phenyl)-3H-imidazo[4,5-b]pyridin-2-one; | 0.039 | |
| 157 | 1-[2-(Azetidin-1-yl)ethyl]-6-(2,6-dimethylphenyl)-3H-imidazo[4,5-b]pyridin-2-one; | 1.970 | |
| 158 | 1-[2-(Azetidin-1-yl)ethyl]-6-(3-chlorophenyl)-3H-imidazo[4,5-b]pyridin-2-one; | 0.201 | |
| 159 | 1-[2-(Azetidin-1-yl)ethyl]-6-(3,5-difluorophenyl)-3H-imidazo[4,5-b]pyridin-2-one; | 0.211 | |
| 160 | 1-[2-(Azetidin-1-yl)ethyl]-6-[3-(trifluoromethoxy)phenyl]-3H-imidazo[4,5-b]pyridin-2-one; | 0.311 | |
| 161 | 1-[2-(1-Piperidyl)ethyl]-6-[3-(trifluoromethyl)phenyl]-3H-imidazo[4,5-b]pyridin-2-one; | 1.430 | |
| 162 | 1-[2-(4-Fluoro-1-piperidyl)ethyl]-6-[3-(trifluoromethyl)phenyl]-3H-imidazo[4,5-b]pyridin-2-one; | 1.100 | |
| 163 | 1-[2-(3-Fluoroazetidin-1-yl)ethyl]-6-[3-(trifluoromethyl)phenyl]-3H-imidazo[4,5-b]pyridin-2-one; | 0.246 | |
| 164 | 1-[2-(3-Methylpyrrolidin-1-yl)ethyl]-6-[3-(trifluoromethyl)phenyl]-3H-imidazo[4,5-b]pyridin-2-one; | 1.220 | |
| 165 | 1-[2-(4-Hydroxy-1-piperidyl)ethyl]-6-[3-(trifluoromethyl)phenyl]-3H-imidazo[4,5-b]pyridin-2-one; | NT | |
| 166 | 1-[2-[3-(Trifluoromethyl)azetidin-1-yl]ethyl]-6-[3-(trifluoromethyl)phenyl]-3H-imidazo[4,5-b]pyridin-2-one; | 3.480 | |
| 167 | 1-[2-(3,3-Difluoroazetidin-1-yl)ethyl]-6-[3-(trifluoromethyl)phenyl]-3H-imidazo[4,5-b]pyridin-2-one; | 0.158 | |
| 168 | 1-[2-(Azetidin-1-yl)ethyl]-6-[2-methyl-3-(trifluoromethyl)phenyl]-3H-imidazo[4,5-b]pyridin-2-one; | 4.230 | |
| 169 | 1-[2-(Azetidin-1-yl)ethyl]-6-(2,3-dimethylphenyl)-3H-imidazo[4,5-b]pyridin-2-one; | 0.217 | |
| 170 | 1-[2-(Azetidin-1-yl)ethyl]-6-(3,5-dimethylphenyl)-3H-imidazo[4,5-b]pyridin-2-one; | 0.581 | |
| 171 | 1-[2-(Azetidin-1-yl)ethyl]-6-(4-fluoro-2,3-dimethyl-phenyl)-3H-imidazo[4,5-b]pyridin-2-one; | 0.210 | |
| 172 | 1-[2-(Azetidin-1-yl)ethyl]-6-[2-methyl-5-(trifluoromethyl)phenyl]-3H-imidazo[4,5-b]pyridin-2-one; | 0.326 | |
| 173 | 6-(3,5-Difluorophenyl)-1-[2-(2-hydroxyethylamino)ethyl]-3H-imidazo[4,5-b]pyridin-2-one; | 4.260 | |
| 174 | 6-(3,5-Difluorophenyl)-1-(2-pyrrolidin-1-ylethyl)-3H-imidazo[4,5-b]pyridin-2-one; | 1.248 | |
| 175 | 6-(3,5-Difluorophenyl)-1-[2-(3-hydroxypyrrolidin-1-yl)ethyl]-3H-imidazo[4,5-b]pyridin-2-one; | 2.108 | |
| 176 | 6-(3,5-Difluorophenyl)-1-[2-(3-methoxypyrrolidin-1-yl)ethyl]-3H-imidazo[4,5-b]pyridin-2-one; | 4.368 | |
| 177 | 6-(4-Fluoro-2-methyl-phenyl)-1-(2-pyrrolidin-1-ylethyl)-3H-imidazo[4,5-b]pyridin-2-one; | 0.502 | |
| 178 | 6-(2,6-Dimethylphenyl)-1-(2-pyrrolidin-1-ylethyl)-3H-imidazo[4,5-b]pyridin-2-one; | 20.701 | |
| 179 | 6-(o-Tolyl)-1-(2-pyrrolidin-1-ylethyl)-3H-imidazo[4,5-b]pyridin-2-one; | 0.707 | |
| 180 | 6-Phenyl-1-(2-pyrrolidin-1-ylethyl)-3H-imidazo[4,5-b]pyridin-2-one; | 0.539 | |
| 181 | 1-[2-(3-Fluoroazetidin-1-yl)ethyl]-6-[2-methyl-3-(trifluoromethyl)phenyl]-3H-imidazo[4,5-b]pyridin-2-one; | 9.350 | |
| 182 | 6-(2,3-Dimethylphenyl)-1-[2-(3-fluoroazetidin-1-yl)ethyl]-3H-imidazo[4,5-b]pyridin-2-one; | 1.740 | |
| 183 | 6-(3,5-Dimethylphenyl)-1-[2-(3-fluoroazetidin-1-yl)ethyl]-3H-imidazo[4,5-b]pyridin-2-one; | 2.080 | |
| 184 | 1-[2-(3-Fluoroazetidin-1-yl)ethyl]-6-(4-fluoro-2,3-dimethyl-phenyl)-3H-imidazo[4,5-b]pyridin-2-one; | 2.570 | |
| 185 | 1-[2-(3-Fluoroazetidin-1-yl)ethyl]-6-[2-methyl-5-(trifluoromethyl)phenyl]-3H-imidazo[4,5-b]pyridin-2-one; | 2.130 | |

TABLE 3-continued

| Ex # | Compound Name | NR2B IC$_{50}$ (μM) standard assay | NR2B IC$_{50}$ (μM) HTS assay |
|---|---|---|---|
| 186 | 1-[2-(3-Fluoroazetidin-1-yl)ethyl]-6-(o-tolyl)-3H-imidazo[4,5-b]pyridin-2-one; | 1.340 | |
| 187 | 1-[2-(3-Fluoroazetidin-1-yl)ethyl]-6-(4-fluoro-2-methyl-phenyl)-3H-imidazo[4,5-b]pyridin-2-one; | 1.190 | |
| 188 | 1-[2-(3-Fluoroazetidin-1-yl)ethyl]-6-phenyl-3H-imidazo[4,5-b]pyridin-2-one; | 1.435 | |
| 189 | 6-(3,5-Difluorophenyl)-1-[2-(propylamino)ethyl]-3H-imidazo[4,5-b]pyridin-2-one; | 2.570 | |
| 190 | N-Cyclobutyl-2-[2-oxo-6-[3-(trifluoromethyl)phenyl]-3H-imidazo[4,5-b]pyridin-1-yl]acetamide; | 0.070 | |
| 191 | 1-[2-(3-Methoxyazetidin-1-yl)-2-oxo-ethyl]-6-[3-(trifluoromethyl)phenyl]-3H-imidazo[4,5-b]pyridin-2-one; | 0.132 | |
| 192 | N-(Oxetan-3-yl)-2-[2-oxo-6-[3-(trifluoromethyl)phenyl]-3H-imidazo[4,5-b]pyridin-1-yl]acetamide; | 0.052 | |
| 193 | 1-[2-(4-Methylpiperazin-1-yl)-2-oxo-ethyl]-6-[3-(trifluoromethyl)phenyl]-3H-imidazo[4,5-b]pyridin-2-one; | 0.587 | |
| 194 | 1-[2-(3,3-Difluoroazetidin-1-yl)-2-oxo-ethyl]-6-[3-(trifluoromethyl)phenyl]-3H-imidazo[4,5-b]pyridin-2-one; | 0.047 | |
| 195 | N-(3,3-Difluorocyclobutyl)-2-[2-oxo-6-[3-(trifluoromethyl)phenyl]-3H-imidazo[4,5-b]pyridin-1-yl]acetamide; | 0.007 | |
| 196 | 1-[2-(3,3-Difluoropyrrolidin-1-yl)-2-oxo-ethyl]-3-methyl-6-[3-(trifluoromethyl)phenyl]imidazo[4,5-b]pyridin-2-one; | 0.182 | |
| 197 | 3-Methyl-1-(2-oxo-2-pyrrolidin-1-yl-ethyl)-6-[3-(trifluoromethyl)phenyl]imidazo[4,5-b]pyridin-2-one; | 0.205 | |
| 198 | N-(3,3-Difluoro-1-methyl-cyclobutyl)-2-[3-methyl-2-oxo-6-[3-(trifluoromethyl)phenyl]imidazo[4,5-b]pyridin-1-yl]acetamide; | 5.010 | |
| 199 | N-(3-Methyloxetan-3-yl)-2-[3-methyl-2-oxo-6-[3-(trifluoromethyl)phenyl]imidazo[4,5-b]pyridin-1-yl]acetamide; | 2.660 | |
| 200 | N-(3,3-Difluorocyclobutyl)-2-[3-methyl-2-oxo-6-[3-(trifluoromethyl)phenyl]imidazo[4,5-b]pyridin-1-yl]acetamide; | 0.174 | |
| 201 | 1-(2-Oxo-2-pyrrolidin-1-yl-ethyl)-6-[3-(trifluoromethyl)phenyl]-3H-imidazo[4,5-b]pyridin-2-one; | 0.033 | |
| 202 | (R/S)-N-Cyclopropyl-2-[2-oxo-6-[3-(trifluoromethyl)phenyl]-3H-imidazo[4,5-b]pyridin-1-yl]propanamide; | 7.318 | |
| 203 | (R/S)-1-[2-(Azetidin-1-yl)-1-methyl-2-oxo-ethyl]-6-[3-(trifluoromethyl)phenyl]-3H-imidazo[4,5-b]pyridin-2-one; | 1.102 | |
| 204 | 1-(2-Morpholino-2-oxo-ethyl)-6-[3-(trifluoromethyl)phenyl]-3H-imidazo[4,5-b]pyridin-2-one; | 0.037 | |
| 205 | N-Cyclopentyl-2-[2-oxo-6-[3-(trifluoromethyl)phenyl]-3H-imidazo[4,5-b]pyridin-1-yl]acetamide; | 0.523 | |
| 206 | 1-[2-Oxo-2-(1-piperidyl)ethyl]-6-[3-(trifluoromethyl)phenyl]-3H-imidazo[4,5-b]pyridin-2-one; | 0.163 | |
| 207 | 1-[2-(2,6-Diazaspiro[3.3]heptan-6-yl)-2-oxo-ethyl]-6-[3-(trifluoromethyl)phenyl]-3H-imidazo[4,5-b]pyridin-2-one; | 0.453 | |
| 208 | 2-[2-Oxo-6-[3-(trifluoromethyl)phenyl]-3H-imidazo[4,5-b]pyridin-1-yl]-N-(2-pyridyl)acetamide; | >10 | |
| 209 | N-(3,3-Difluoro-1-methyl-cyclobutyl)-2-[2-oxo-6-[3-(trifluoromethyl)phenyl]-3H-imidazo[4,5-b]pyridin-1-yl]acetamide; | 0.443 | |
| 210 | 1-[(6-Methoxy-3-pyridyl)methyl]-6-[3-(trifluoromethyl)phenyl]-3H-imidazo[4,5-b]pyridin-2-one; | 1.620 | |
| 211 | 1-(Cyclopropylmethyl)-6-[3-(trifluoromethyl)phenyl]-3H-imidazo[4,5-b]pyridin-2-one; | 0.115 | |

TABLE 3-continued

| Ex # | Compound Name | NR2B IC$_{50}$ (μM) standard assay | NR2B IC$_{50}$ (μM) HTS assay |
|---|---|---|---|
| 212 | 3-[[2-Oxo-6-[3-(trifluoromethyl)phenyl]-3H-imidazo[4,5-b]pyridin-1-yl]methyl]benzonitrile; | 0.123 | |
| 213 | 2-[[2-Oxo-6-[3-(trifluoromethyl)phenyl]-3H-imidazo[4,5-b]pyridin-1-yl]methyl]benzonitrile; | 0.375 | |
| 214 | 1-[2-Oxo-2-(2-thienyl)ethyl]-6-[3-(trifluoromethyl)phenyl]-3H-imidazo[4,5-b]pyridin-2-one; | >10 | |
| 215 | 1-(2-Oxo-2-thiazol-2-yl-ethyl)-6-[3-(trifluoromethyl)phenyl]-3H-imidazo[4,5-b]pyridin-2-one; | 0.365 | |
| 216 | (R/S)-1-(Oxetan-2-ylmethyl)-6-[3-(trifluoromethyl)phenyl]-3H-imidazo[4,5-b]pyridin-2-one; | 0.034 | |
| 217 | (R/S)-1-(Morpholin-2-ylmethyl)-6-[3-(trifluoromethyl)phenyl]-3H-imidazo[4,5-b]pyridin-2-one; | 6.489 | |
| 218 | (R/S)-1-(Tetrahydropyran-2-ylmethyl)-6-[3-(trifluoromethyl)phenyl]-3H-imidazo[4,5-b]pyridin-2-one; | 0.552 | |
| 219 | 6-[3-(Trifluoromethyl)phenyl]-1-[[4-(trifluoromethyl)phenyl]methyl]-3H-imidazo[4,5-b]pyridin-2-one; | >10 | |
| 220 | 1-[(3-Fluoro-4-methoxy-phenyl)methyl]-6-[3-(trifluoromethyl)phenyl]-3H-imidazo[4,5-b]pyridin-2-one; | 1.650 | |
| 221 | 1-[(4-Fluoro-3-methyl-phenyl)methyl]-6-[3-(trifluoromethyl)phenyl]-3H-imidazo[4,5-b]pyridin-2-one; | 8.714 | |
| 222 | 1-[(3-Fluorophenyl)methyl]-6-[3-(trifluoromethyl)phenyl]-3H-imidazo[4,5-b]pyridin-2-one; | 0.479 | |
| 223 | (R*)-1-(Oxetan-2-ylmethyl)-6-[3-(trifluoromethyl)phenyl]-3H-imidazo[4,5-b]pyridin-2-one; | 0.036 | |
| 224 | (S*)-1-(Oxetan-2-ylmethyl)-6-[3-(trifluoromethyl)phenyl]-3H-imidazo[4,5-b]pyridin-2-one; | 0.054 | |
| 225 | (R/S)-1-[(2,2-Difluorocyclopropyl)methyl]-6-[3-(trifluoromethyl)phenyl]-3H-imidazo[4,5-b]pyridin-2-one; | 0.400 | |
| 226 | 1-[(3-Fluorooxetan-3-yl)methyl]-6-[3-(trifluoromethyl)phenyl]-3H-imidazo[4,5-b]pyridin-2-one; | 0.800 | |
| 227 | 1-(Pyrimidin-2-ylmethyl)-6-[3-(trifluoromethyl)phenyl]-3H-imidazo[4,5-b]pyridin-2-one; | 0.096 | |
| 228 | 1-(2-Pyridylmethyl)-6-[3-(trifluoromethyl)phenyl]-3H-imidazo[4,5-b]pyridin-2-one; | 0.083 | |
| 229 | 1-(4-Pyridylmethyl)-6-[3-(trifluoromethyl)phenyl]-3H-imidazo[4,5-b]pyridin-2-one; | 0.194 | |
| 230 | 1-(3-Pyridylmethyl)-6-[3-(trifluoromethyl)phenyl]-3H-imidazo[4,5-b]pyridin-2-one; | 0.017 | |
| 231 | 1-[(2-Methylpyrimidin-5-yl)methyl]-6-[3-(trifluoromethyl)phenyl]-3H-imidazo[4,5-b]pyridin-2-one; | 0.094 | |
| 232 | 1-(Pyridazin-3-ylmethyl)-6-[3-(trifluoromethyl)phenyl]-3H-imidazo[4,5-b]pyridin-2-one; | 0.017 | |
| 233 | 1-[(3-Methoxy-2-pyridyl)methyl]-6-[3-(trifluoromethyl)phenyl]-3H-imidazo[4,5-b]pyridin-2-one; | 2.825 | |
| 234 | 1-[(3-Fluoro-5-methyl-2-pyridyl)methyl]-6-[3-(trifluoromethyl)phenyl]-3H-imidazo[4,5-b]pyridin-2-one; | 1.980 | |
| 235 | 1-[(6-Methyl-3-pyridyl)methyl]-6-[3-(trifluoromethyl)phenyl]-3H-imidazo[4,5-b]pyridin-2-one; | 0.256 | |
| 236 | 1-(2H-Tetrazol-5-ylmethyl)-6-[3-(trifluoromethyl)phenyl]-3H-imidazo[4,5-b]pyridin-2-one; | >5 | |
| 237 | 1-[Difluoro(3-pyridyl)methyl]-6-[3-(trifluoromethyl)phenyl]-3H-imidazo[4,5-b]pyridin-2-one; | >10 | |

TABLE 3-continued

| Ex # | Compound Name | NR2B IC$_{50}$ (µM) standard assay | NR2B IC$_{50}$ (µM) HTS assay |
|---|---|---|---|
| 238 | 1-[(6-Fluoro-3-pyridyl)methyl]-6-[3-(trifluoromethyl)phenyl]-3H-imidazo[4,5-b]pyridin-2-one; | 0.088 | |
| 239 | 1-(2-Cyclopropyl-2-oxo-ethyl)-6-[3-(trifluoromethyl)phenyl]-3H-imidazo[4,5-b]pyridin-2-one; | 0.034 | |
| 240 | 1-(2-Oxobutyl)-6-[3-(trifluoromethyl)phenyl]-3H-imidazo[4,5-b]pyridin-2-one; | 0.022 | |
| 241 | 1-(3-Methyl-2-oxo-butyl)-6-[3-(trifluoromethyl)phenyl]-3H-imidazo[4,5-b]pyridin-2-one; | 0.093 | |
| 242 | 1-[(5-Methyl-3-pyridyl)methyl]-6-[3-(trifluoromethyl)phenyl]-3H-imidazo[4,5-b]pyridin-2-one; | 0.150 | |
| 243 | 1-(Thiadiazol-4-ylmethyl)-6-[3-(trifluoromethyl)phenyl]-3H-imidazo[4,5-b]pyridin-2-one; | 0.065 | |
| 244 | 1-[(6-Oxo-1H-pyridin-3-yl)methyl]-6-[3-(trifluoromethyl)phenyl]-3H-imidazo[4,5-b]pyridin-2-one; | 1.890 | |
| 245 | (R/S)-1-(Azetidin-2-ylmethyl)-3-methyl-6-[3-(trifluoromethyl)phenyl]imidazo[4,5-b]pyridin-2-one; | 0.409 | |
| 246 | 3-Methyl-1-(pyrimidin-4-ylmethyl)-6-[3-(trifluoromethyl)phenyl]imidazo[4,5-b]pyridin-2-one; | 0.349 | |
| 247 | 3-Methyl-1-(pyrimidin-5-ylmethyl)-6-[3-(trifluoromethyl)phenyl]imidazo[4,5-b]pyridin-2-one; | 0.133 | |
| 248 | 3-Methyl-1-[(2-methylpyrimidin-4-yl)methyl]-6-[3-(trifluoromethyl)phenyl]imidazo[4,5-b]pyridin-2-one; | 2.050 | |
| 249 | 3-Methyl-1-(pyrazin-2-ylmethyl)-6-[3-(trifluoromethyl)phenyl]imidazo[4,5-b]pyridin-2-one; | 0.253 | |
| 250 | 3-Methyl-1-(4-pyridylmethyl)-6-[3-(trifluoromethyl)phenyl]imidazo[4,5-b]pyridin-2-one; | 1.999 | |
| 251 | 3-Methyl-1-(2-pyridylmethyl)-6-[3-(trifluoromethyl)phenyl]imidazo[4,5-b]pyridin-2-one; | 0.800 | |
| 252 | 1-[(6-Methoxypyridazin-3-yl)methyl]-6-[3-(trifluoromethyl)phenyl]-3H-imidazo[4,5-b]pyridin-2-one; | >10 | |
| 253 | 1-(Pyrazin-2-ylmethyl)-6-[3-(trifluoromethyl)phenyl]-3H-imidazo[4,5-b]pyridin-2-one; | 0.066 | |
| 254 | 1-[(2-Methylpyrimidin-4-yl)methyl]-6-[3-(trifluoromethyl)phenyl]-3H-imidazo[4,5-b]pyridin-2-one; | 0.824 | |
| 255 | 1-(Pyrimidin-5-ylmethyl)-6-[3-(trifluoromethyl)phenyl]-3H-imidazo[4,5-b]pyridin-2-one; | 0.043 | |
| 256 | 1-[(5-Fluoropyrimidin-2-yl)methyl]-6-[3-(trifluoromethyl)phenyl]-3H-imidazo[4,5-b]pyridin-2-one; | 0.134 | |
| 257 | 6-[3-(Trifluoromethyl)phenyl]-1-[[6-(trifluoromethyl)-3-pyridyl]methyl]-3H-imidazo[4,5-b]pyridin-2-one; | 1.460 | |
| 258 | 1-[(5-Fluoro-3-pyridyl)methyl]-6-[3-(trifluoromethyl)phenyl]-3H-imidazo[4,5-b]pyridin-2-one; | 0.077 | |
| 259 | 6-[3-(Trifluoromethyl)phenyl]-1-[[5-(trifluoromethyl)-3-pyridyl]methyl]-3H-imidazo[4,5-b]pyridin-2-one; | 1.030 | |
| 260 | 6-[3-(Trifluoromethyl)phenyl]-1-[[4-(trifluoromethyl)-3-pyridyl]methyl]-3H-imidazo[4,5-b]pyridin-2-one; | 2.860 | |
| 261 | 3-Methyl-1-(pyrimidin-2-ylmethyl)-6-[3-(trifluoromethyl)phenyl]imidazo[4,5-b]pyridin-2-one; | 0.573 | |
| 262 | 1-(2-cyclobutyl-2-oxo-ethyl)-6-[3-(trifluoromethyl)phenyl]-3H-imidazo[4,5-b]pyridin-2-one; | 0.308 | |

TABLE 3-continued

| Ex # | Compound Name | NR2B IC$_{50}$ (μM) standard assay | NR2B IC$_{50}$ (μM) HTS assay |
|---|---|---|---|
| 263 | (R/S)-1-(Azetidin-2-ylmethyl)-6-[3-(trifluoromethyl)phenyl]-3H-imidazo[4,5-b]pyridin-2-one; | 0.063 | |
| 264 | (R/S)-1-(Azetidin-2-ylmethyl)-6-[2-fluoro-3-(trifluoromethyl)phenyl]-3H-imidazo[4,5-b]pyridin-2-one; | 0.044 | |
| 265 | (R/S)-1-(Azetidin-2-ylmethyl)-6-phenyl-3H-imidazo[4,5-b]pyridin-2-one; | 0.397 | |
| 266 | (R/S)-1-(Azetidin-2-ylmethyl)-6-(4-fluorophenyl)-3H-imidazo[4,5-b]pyridin-2-one; | 0.173 | |
| 267 | (R/S)-1-(Azetidin-2-ylmethyl)-6-[4-fluoro-3-(trifluoromethyl)phenyl]-3H-imidazo[4,5-b]pyridin-2-one; | 0.442 | |
| 268 | (R/S)-1-(Azetidin-2-ylmethyl)-6-(2,3-dichlorophenyl)-3H-imidazo[4,5-b]pyridin-2-one; | 0.041 | |
| 269 | 6-(4-Fluoro-3-methyl-phenyl)-1-[(5-methyl-3-pyridyl)methyl]-3H-imidazo[4,5-b]pyridin-2-one; | 0.128 | |
| 270 | 6-(2,4-Difluoro-3-methyl-phenyl)-1-[(5-methyl-3-pyridyl)methyl]-3H-imidazo[4,5-b]pyridin-2-one; | 0.115 | |
| 271 | (R/S)-6-[4-Fluoro-3-(trifluoromethyl)phenyl]-1-(oxetan-2-ylmethyl)-3H-imidazo[4,5-b]pyridin-2-one; | 0.046 | |
| 272 | 6-(3,4-Difluorophenyl)-1-[(5-methyl-3-pyridyl)methyl]-3H-imidazo[4,5-b]pyridin-2-one; | 0.034 | |
| 273 | 6-(3-Chlorophenyl)-1-[(5-methyl-3-pyridyl)methyl]-3H-imidazo[4,5-b]pyridin-2-one; | 0.096 | |
| 274 | 6-(3-Fluorophenyl)-1-[(5-methyl-3-pyridyl)methyl]-3H-imidazo[4,5-b]pyridin-2-one; | 0.057 | |
| 275 | 6-(3,4-Difluorophenyl)-1-[(4-methyl-3-pyridyl)methyl]-3H-imidazo[4,5-b]pyridin-2-one; | 0.009 | |
| 276 | 6-(3-Fluorophenyl)-1-[(4-methyl-3-pyridyl)methyl]-3H-imidazo[4,5-b]pyridin-2-one; | 0.034 | |
| 277 | 6-(4-Fluoro-3-methyl-phenyl)-1-[(4-methyl-3-pyridyl)methyl]-3H-imidazo[4,5-b]pyridin-2-one; | 0.077 | |
| 278 | 6-(2,4-Difluoro-3-methyl-phenyl)-1-[(4-methyl-3-pyridyl)methyl]-3H-imidazo[4,5-b]pyridin-2-one; | 0.111 | |
| 279 | 6-(3,4-Difluorophenyl)-1-(2-pyridylmethyl)-3H-imidazo[4,5-b]pyridin-2-one; | 5.030 | |
| 280 | 6-(2,4-Difluoro-3-methyl-phenyl)-1-(2-pyridylmethyl)-3H-imidazo[4,5-b]pyridin-2-one; | 0.576 | |
| 281 | 6-(3-Fluorophenyl)-1-(2-pyridylmethyl)-3H-imidazo[4,5-b]pyridin-2-one; | 0.932 | |
| 282 | 6-(3-Chlorophenyl)-1-(2-pyridylmethyl)-3H-imidazo[4,5-b]pyridin-2-one; | 2.610 | |
| 283 | 6-(4-Fluoro-3-methyl-phenyl)-1-(2-pyridylmethyl)-3H-imidazo[4,5-b]pyridin-2-one; | 0.079 | |
| 284 | 6-(3,4-Difluorophenyl)-1-[(3-methyl-2-pyridyl)methyl]-3H-imidazo[4,5-b]pyridin-2-one; | >10 | |
| 285 | 6-(3-Fluorophenyl)-1-[(3-methyl-2-pyridyl)methyl]-3H-imidazo[4,5-b]pyridin-2-one; | >10 | |
| 286 | 6-(4-Fluorophenyl)-1-(2-pyridylmethyl)-3H-imidazo[4,5-b]pyridin-2-one; | 1.980 | |
| 287 | 6-[3-(Difluoromethyl)phenyl]-1-(2-pyridylmethyl)-3H-imidazo[4,5-b]pyridin-2-one; | 0.107 | |
| 288 | 6-(3-Methoxyphenyl)-1-(2-pyridylmethyl)-3H-imidazo[4,5-b]pyridin-2-one; | 4.050 | |
| 289 | 6-(p-Tolyl)-1-(2-pyridylmethyl)-3H-imidazo[4,5-b]pyridin-2-one; | 7.079 | |
| 290 | 6-(3-fluorophenyl)-1-(3-pyridylmethyl)-3H-imidazo[4,5-b]pyridin-2-one; | 0.065 | |
| 291 | 6-[3-(Difluoromethyl)phenyl]-1-(3-pyridylmethyl)-3H-imidazo[4,5-b]pyridin-2-one; | 0.022 | |
| 292 | 6-(3,4-Difluorophenyl)-1-(3-pyridylmethyl)-3H-imidazo[4,5-b]pyridin-2-one; | 0.060 | |
| 293 | 6-(2,4-Difluoro-3-methyl-phenyl)-1-(3-pyridylmethyl)-3H-imidazo[4,5-b]pyridin-2-one; | 0.017 | |
| 294 | 6-(4-Fluoro-3-methyl-phenyl)-1-(3-pyridylmethyl)-3H-imidazo[4,5-b]pyridin-2-one; | 0.023 | |
| 295 | 6-(4-Fluorophenyl)-1-(3-pyridylmethyl)-3H-imidazo[4,5-b]pyridin-2-one; | 0.098 | |
| 296 | 6-(3-Chlorophenyl)-1-(3-pyridylmethyl)-3H-imidazo[4,5-b]pyridin-2-one; | 0.029 | |
| 297 | 6-(m-Tolyl)-1-(3-pyridylmethyl)-3H-imidazo[4,5-b]pyridin-2-one; | 0.027 | |

TABLE 3-continued

| Ex # | Compound Name | NR2B IC$_{50}$ (μM) standard assay | NR2B IC$_{50}$ (μM) HTS assay |
|---|---|---|---|
| 298 | 6-(3,4-Difluorophenyl)-1-[(5-fluoro-3-pyridyl)methyl]-3H-imidazo[4,5-b]pyridin-2-one; | 0.032 | |
| 299 | 6-(4-Fluoro-3-methyl-phenyl)-1-[(5-fluoro-3-pyridyl)methyl]-3H-imidazo[4,5-b]pyridin-2-one; | 0.019 | |
| 300 | 6-[3-(Difluoromethoxy)phenyl]-1-(3-pyridylmethyl)-3H-imidazo[4,5-b]pyridin-2-one; | 0.030 | |
| 301 | 6-(2,4-Difluoro-3-methyl-phenyl)-1-[(5-fluoro-3-pyridyl)methyl]-3H-imidazo[4,5-b]pyridin-2-one; | 0.045 | |
| 302 | 6-[3-(Difluoromethyl)phenyl]-1-[(5-fluoro-3-pyridyl)methyl]-3H-imidazo[4,5-b]pyridin-2-one; | 0.022 | |
| 303 | 6-(2,3-Difluorophenyl)-1-[(5-fluoro-3-pyridyl)methyl]-3H-imidazo[4,5-b]pyridin-2-one; | 0.030 | |
| 304 | 6-[3-(Difluoromethoxy)phenyl]-1-[(5-fluoro-3-pyridyl)methyl]-3H-imidazo[4,5-b]pyridin-2-one; | 0.021 | |
| 305 | 6-(3-Chlorophenyl)-1-[(5-fluoro-3-pyridyl)methyl]-3H-imidazo[4,5-b]pyridin-2-one; | 0.013 | |
| 306 | 6-(4-Chloro-3-methyl-phenyl)-1-[(5-fluoro-3-pyridyl)methyl]-3H-imidazo[4,5-b]pyridin-2-one; | 0.086 | |
| 307 | 1-[(5-Fluoro-3-pyridyl)methyl]-6-[3-(trifluoromethoxy)phenyl]-3H-imidazo[4,5-b]pyridin-2-one; | 0.088 | |
| 308 | 1-[(5-Methyl-3-pyridyl)methyl]-6-(3,4,5-trifluorophenyl)-3H-imidazo[4,5-b]pyridin-2-one; | 0.030 | |
| 309 | 6-[4-Fluoro-3-(trifluoromethyl)phenyl]-1-[(5-methyl-3-pyridyl)methyl]-3H-imidazo[4,5-b]pyridin-2-one; | 0.316 | |
| 310 | 6-(2,3-Difluorophenyl)-1-[(5-methyl-3-pyridyl)methyl]-3H-imidazo[4,5-b]pyridin-2-one; | 0.088 | |
| 311 | 6-(3,5-Difluorophenyl)-1-[(5-methyl-3-pyridyl)methyl]-3H-imidazo[4,5-b]pyridin-2-one; | 0.028 | |
| 312 | 1-[(4-Methyl-3-pyridyl)methyl]-6-(3,4,5-trifluorophenyl)-3H-imidazo[4,5-b]pyridin-2-one; | 0.002 | |
| 313 | 1-[(4-Methyl-3-pyridyl)methyl]-6-[3-(trifluoromethyl)phenyl]-3H-imidazo[4,5-b]pyridin-2-one; | 0.018 | |
| 314 | 6-[4-Fluoro-3-(trifluoromethyl)phenyl]-1-[(4-methyl-3-pyridyl)methyl]-3H-imidazo[4,5-b]pyridin-2-one; | 0.049 | |
| 315 | 1-[(3-Methyl-2-pyridyl)methyl]-6-[3-(trifluoromethyl)phenyl]-3H-imidazo[4,5-b]pyridin-2-one; | >10 | |
| 316 | 6-(4-Fluoro-3-methyl-phenyl)-1-[(3-methyl-2-pyridyl)methyl]-3H-imidazo[4,5-b]pyridin-2-one; | 0.114 | |
| 317 | 6-(2,4-Difluoro-3-methyl-phenyl)-1-[(3-methyl-2-pyridyl)methyl]-3H-imidazo[4,5-b]pyridin-2-one; | 0.046 | |
| 318 | 6-(3,5-Difluorophenyl)-1-[(3-methyl-2-pyridyl)methyl]-3H-imidazo[4,5-b]pyridin-2-one; | >10 | |
| 319 | 6-(2,3-Difluorophenyl)-1-[(3-methyl-2-pyridyl)methyl]-3H-imidazo[4,5-b]pyridin-2-one; | >10 | |
| 320 | 1-[2-(Azetidin-1-yl)-2-oxo-ethyl]-6-(4-fluoro-2-methyl-phenyl)-3H-imidazo[4,5-b]pyridin-2-one; | 0.075 | |
| 321 | 2-[6-(5-Chloro-4-methyl-2-thienyl)-2-oxo-3H-imidazo[4,5-b]pyridin-1-yl]-N,N-dimethyl-acetamide; | 0.014 | |
| 322 | 2-[6-(5-Chloro-4-methyl-2-thienyl)-3-methyl-2-oxo-imidazo[4,5-b]pyridin-1-yl]-N,N-dimethyl-acetamide; | 0.023 | |
| 323 | 1-[2-(Azetidin-1-yl)-2-oxo-ethyl]-6-[5-(trifluoromethyl)-2-thienyl]-3H-imidazo[4,5-b]pyridin-2-one; | 0.041 | |
| 324 | 1-[2-(Azetidin-1-yl)-2-oxo-ethyl]-6-(5-chloro-4-methyl-2-thienyl)-3H-imidazo[4,5-b]pyridin-2-one; | 0.015 | |
| 325 | 1-[2-(Azetidin-1-yl)-2-oxo-ethyl]-6-(5-chloro-4-methyl-2-thienyl)-3-methyl-imidazo[4,5-b]pyridin-2-one; | NT | |
| 326 | 1-[2-(Azetidin-1-yl)-2-oxo-ethyl]-3-methyl-6-(5-methyl-2-thienyl)imidazo[4,5-b]pyridin-2-one; | 0.022 | |
| 327 | 1-[2-(3-Fluoroazetidin-1-yl)-2-oxo-ethyl]-3-methyl-6-[5-(trifluoromethyl)-2-thienyl]imidazo[4,5-b]pyridin-2-one; | 0.071 | |
| 328 | 3-Methyl-1-(2-oxo-2-pyrrolidin-1-yl-ethyl)-6-[5-(trifluoromethyl)-2-thienyl]imidazo[4,5-b]pyridin-2-one; | 0.079 | |
| 329 | 1-[2-(Azetidin-1-yl)-2-oxo-ethyl]-6-[2-methyl-3-(trifluoromethyl)phenyl]-3H-imidazo[4,5-b]pyridin-2-one; | 0.750 | |

TABLE 3-continued

| Ex # | Compound Name | NR2B IC$_{50}$ (μM) standard assay | NR2B IC$_{50}$ (μM) HTS assay |
|---|---|---|---|
| 330 | 6-(3,4-Difluorophenyl)-1-(2-oxobutyl)-3H-imidazo[4,5-b]pyridin-2-one; | 0.004 | |
| 331 | 6-(4-Fluoro-3-methyl-phenyl)-1-(2-oxobutyl)-3H-imidazo[4,5-b]pyridin-2-one; | 0.012 | |
| 332 | 6-(m-Tolyl)-1-(2-oxobutyl)-3H-imidazo[4,5-b]pyridin-2-one; | 0.036 | |
| 333 | (R/S)-6-(3,4-Difluorophenyl)-1-(2-hydroxybutyl)-3-methyl-imidazo[4,5-b]pyridin-2-one; | 1.900 | |
| 334 | (R/S)-6-(4-Fluoro-3-methyl-phenyl)-1-(2-hydroxybutyl)-3H-imidazo[4,5-b]pyridin-2-one; | 0.031 | |
| 335 | (R/S)-1-(2-Hydroxybutyl)-6-(m-tolyl)-3H-imidazo[4,5-b]pyridin-2-one; | 0.054 | |
| 336 | (R/S)-6-(2,4-difluoro-3-methyl-phenyl)-1-(2-hydroxybutyl)-3H-imidazo[4,5-b]pyridin-2-one; | 0.015 | |
| 337 | (R/S)-1-(2-Hydroxybutyl)-6-[3-(trifluoromethyl)phenyl]-3H-imidazo[4,5-b]pyridin-2-one; | 0.119 | |
| 338 | (R/S)-1-(2-Hydroxy-3-methyl-butyl)-6-[3-(trifluoromethyl)phenyl]-3H-imidazo[4,5-b]pyridin-2-one; | 0.687 | |
| 339 | 6-(2,4-Difluoro-3-methyl-phenyl)-3-methyl-1-(3-pyridylmethyl)imidazo[4,5-b]pyridin-2-one; | 0.034 | |
| 340 | 6-(4-Fluoro-3-methyl-phenyl)-1-[(5-fluoro-3-pyridyl)methyl]-3-methyl-imidazo[4,5-b]pyridin-2-one; | 0.052 | |
| 341 | 6-(2,4-Difluoro-3-methyl-phenyl)-1-[(5-fluoro-3-pyridyl)methyl]-3-methyl-imidazo[4,5-b]pyridin-2-one; | 0.081 | |
| 342 | 6-[3-(Difluoromethoxy)phenyl]-1-[(5-fluoro-3-pyridyl)methyl]-3-methyl-imidazo[4,5-b]pyridin-2-one; | 0.138 | |
| 343 | 6-(3,4-Difluorophenyl)-1-[(5-fluoro-3-pyridyl)methyl]-3-methyl-imidazo[4,5-b]pyridin-2-one; | 0.256 | |
| 344 | 1-[(5-Fluoro-3-pyridyl)methyl]-3-methyl-6-(3,4,5-trifluorophenyl)imidazo[4,5-b]pyridin-2-one; | 0.518 | |
| 345 | 1-[(5-Fluoro-3-pyridyl)methyl]-3-methyl-6-[3-(trifluoromethoxy)phenyl]imidazo[4,5-b]pyridin-2-one; | 0.778 | |
| 346 | 6-(2,3-Difluorophenyl)-1-[(5-fluoro-3-pyridyl)methyl]-3-methyl-imidazo[4,5-b]pyridin-2-one; | 0.225 | |
| 347 | 1-[(5-Fluoro-3-pyridyl)methyl]-3-methyl-6-(2,3,4-trifluorophenyl)imidazo[4,5-b]pyridin-2-one; | 0.621 | |
| 348 | 6-(3-Chlorophenyl)-1-[(5-fluoro-3-pyridyl)methyl]-3-methyl-imidazo[4,5-b]pyridin-2-one; | 0.213 | |
| 349 | 6-(3-Chloro-2-fluoro-phenyl)-1-[(5-fluoro-3-pyridyl)methyl]-3-methyl-imidazo[4,5-b]pyridin-2-one; | 0.107 | |
| 350 | 1-[(5-Fluoro-3-pyridyl)methyl]-3-methyl-6-(m-tolyl)imidazo[4,5-b]pyridin-2-one; | 0.029 | |
| 351 | 6-(3,4-Dichlorophenyl)-1-[(5-fluoro-3-pyridyl)methyl]-3-methyl-imidazo[4,5-b]pyridin-2-one; | 0.251 | |
| 352 | 6-(2-Fluoro-3-methyl-phenyl)-1-[(5-fluoro-3-pyridyl)methyl]-3-methyl-imidazo[4,5-b]pyridin-2-one; | 0.052 | |
| 353 | 3-Methyl-1-(3-pyridylmethyl)-6-(3,4,5-trifluorophenyl)imidazo[4,5-b]pyridin-2-one; | 0.144 | |
| 354 | 6-(3,5-Difluorophenyl)-3-methyl-1-(3-pyridylmethyl)imidazo[4,5-b]pyridin-2-one; | 1.030 | |
| 355 | 6-(3-Chloro-4-fluoro-phenyl)-3-methyl-1-(3-pyridylmethyl)imidazo[4,5-b]pyridin-2-one; | 0.044 | |
| 356 | 3-Methyl-6-(m-tolyl)-1-(3-pyridylmethyl)imidazo[4,5-b]pyridin-2-one; | 0.070 | |
| 357 | 6-(2-Fluoro-3-methyl-phenyl)-3-methyl-1-(3-pyridylmethyl)imidazo[4,5-b]pyridin-2-one; | 0.118 | |
| 358 | 6-[2-Fluoro-3-(trifluoromethyl)phenyl]-3-methyl-1-(3-pyridylmethyl)imidazo[4,5-b]pyridin-2-one; | 0.049 | |
| 359 | 6-(3-Chloro-2-fluoro-phenyl)-3-methyl-1-(3-pyridylmethyl)imidazo[4,5-b]pyridin-2-one; | 0.096 | |
| 360 | 6-[4-Fluoro-3-(trifluoromethyl)phenyl]-3-methyl-1-(3-pyridylmethyl)imidazo[4,5-b]pyridin-2-one; | 0.034 | |

TABLE 3-continued

| Ex # | Compound Name | NR2B IC$_{50}$ (μM) standard assay | NR2B IC$_{50}$ (μM) HTS assay |
|---|---|---|---|
| 361 | 3-Methyl-1-(3-pyridylmethyl)-6-(2,3,4-trifluorophenyl)imidazo[4,5-b]pyridin-2-one; | 1.540 | |
| 362 | 3-Methyl-1-(3-pyridylmethyl)-6-[3-(trifluoromethyl)phenyl]imidazo[4,5-b]pyridin-2-one; | 0.105 | |
| 363 | 6-[3-(Difluoromethyl)phenyl]-3-methyl-1-(3-pyridylmethyl)imidazo[4,5-b]pyridin-2-one; | 0.053 | |
| 364 | 3-Methyl-1-(3-pyridylmethyl)-6-[5-(trifluoromethyl)-2-thienyl]imidazo[4,5-b]pyridin-2-one; | 0.168 | |
| 365 | 6-(5-Chloro-4-methyl-2-thienyl)-3-methyl-1-(3-pyridylmethyl)imidazo[4,5-b]pyridin-2-one; | 0.063 | |
| 366 | 1-[(5-Chloro-3-pyridyl)methyl]-3-methyl-6-[3-(trifluoromethyl)phenyl]imidazo[4,5-b]pyridin-2-one; | 0.433 | |
| 367 | 1-[(5-Chloro-3-pyridyl)methyl]-6-(4-fluoro-3-methyl-phenyl)-3-methyl-imidazo[4,5-b]pyridin-2-one; | 0.117 | |
| 368 | 1-[(5-Chloro-3-pyridyl)methyl]-6-(2,4-difluoro-3-methyl-phenyl)-3-methyl-imidazo[4,5-b]pyridin-2-one; | 0.356 | |
| 369 | 1-[(5-Chloro-3-pyridyl)methyl]-6-(3,4-difluorophenyl)-3-methyl-imidazo[4,5-b]pyridin-2-one; | 0.096 | |
| 370 | 1-[(5-Chloro-3-pyridyl)methyl]-3-methyl-6-(3,4,5-trifluorophenyl)imidazo[4,5-b]pyridin-2-one; | 0.131 | |
| 371 | 1-[(5-Chloro-3-pyridyl)methyl]-6-(2-fluoro-3-methyl-phenyl)-3-methyl-imidazo[4,5-b]pyridin-2-one; | 0.190 | |
| 372 | 6-(5-Chloro-4-methyl-2-thienyl)-1-[(5-chloro-3-pyridyl)methyl]-3-methyl-imidazo[4,5-b]pyridin-2-one; | 6.640 | |
| 373 | 1-[(5-Chloro-3-pyridyl)methyl]-3-methyl-6-[5-(trifluoromethyl)-2-thienyl]imidazo[4,5-b]pyridin-2-one; | 9.721 | |
| 374 | 1-[(5-Chloro-3-pyridyl)methyl]-3-methyl-6-(m-tolyl)imidazo[4,5-b]pyridin-2-one; | 0.416 | |
| 375 | 1-[(5-Chloro-3-pyridyl)methyl]-6-(2,3-difluorophenyl)-3-methyl-imidazo[4,5-b]pyridin-2-one; | 1.510 | |
| 376 | 6-(3-Chlorophenyl)-3-methyl-1-(pyridazin-3-ylmethyl)imidazo[4,5-b]pyridin-2-one; | 0.056 | |
| 377 | 6-[3-(Difluoromethyl)phenyl]-3-methyl-1-(pyridazin-3-ylmethyl)imidazo[4,5-b]pyridin-2-one; | 0.030 | |
| 378 | 3-Methyl-1-(pyridazin-3-ylmethyl)-6-[3-(trifluoromethyl)phenyl]imidazo[4,5-b]pyridin-2-one; | 0.031 | |
| 379 | 3-Methyl-6-(m-tolyl)-1-(pyridazin-3-ylmethyl)imidazo[4,5-b]pyridin-2-one; | 0.033 | |
| 380 | 6-(3-Chloro-4-fluoro-phenyl)-3-methyl-1-(pyridazin-3-ylmethyl)imidazo[4,5-b]pyridin-2-one; | 0.016 | |
| 381 | 6-(3-Fluoro-5-methyl-phenyl)-3-methyl-1-(pyridazin-3-ylmethyl)imidazo[4,5-b]pyridin-2-one; | 0.037 | |
| 382 | 6-[4-Fluoro-3-(trifluoromethyl)phenyl]-3-methyl-1-(pyridazin-3-ylmethyl)imidazo[4,5-b]pyridin-2-one; | 0.016 | |
| 383 | 6-[3-Fluoro-5-(trifluoromethyl)phenyl]-3-methyl-1-(pyridazin-3-ylmethyl)imidazo[4,5-b]pyridin-2-one; | 0.041 | |
| 384 | 6-[4-Chloro-3-(trifluoromethyl)phenyl]-3-methyl-1-(pyridazin-3-ylmethyl)imidazo[4,5-b]pyridin-2-one; | 0.206 | |
| 385 | 6-(5-(Difluoromethyl)-2-fluorophenyl)-3-methyl-1-(pyridazin-3-ylmethyl)-1,3-dihydro-2H-imidazo[4,5-b]pyridin-2-one; | 0.653 | |
| 386 | 6-(5-(Difluoromethyl)-2-fluorophenyl)-3-methyl-1-(pyridin-3-ylmethyl)-1,3-dihydro-2H-imidazo[4,5-b]pyridin-2-one; | 1.110 | |
| 387 | 6-[3,4-Difluoro-5-(trifluoromethyl)phenyl]-3-methyl-1-(pyridazin-3-ylmethyl)imidazo[4,5-b]pyridin-2-one; | 0.022 | |
| 388 | 3-Methyl-1-(2-oxobutyl)-6-[3-(trifluoromethyl)phenyl]imidazo[4,5-b]pyridin-2-one; | 0.050 | |
| 389 | 6-(4-Fluoro-3-methyl-phenyl)-3-methyl-1-(2-oxobutyl)imidazo[4,5-b]pyridin-2-one; | 0.017 | |
| 390 | 6-(3,4-Difluorophenyl)-3-methyl-1-(2-oxobutyl)imidazo[4,5-b]pyridin-2-one; | 0.019 | |

TABLE 3-continued

| Ex # | Compound Name | NR2B IC$_{50}$ (μM) standard assay | NR2B IC$_{50}$ (μM) HTS assay |
|---|---|---|---|
| 391 | 6-(2,4-Difluoro-3-methyl-phenyl)-3-methyl-1-(2-oxobutyl)imidazo[4,5-b]pyridin-2-one; | 0.026 | |
| 392 | 6-(3-Cyclopropylphenyl)-3-methyl-1-(2-oxobutyl)imidazo[4,5-b]pyridin-2-one; | 0.324 | |
| 393 | (R/S)-6-(4-Fluoro-3-methyl-phenyl)-1-(2-hydroxy-4-methoxy-butyl)-3-methyl-imidazo[4,5-b]pyridin-2-one; | 0.486 | |
| 394 | (R/S)-6-[3-(Difluoromethyl)phenyl]-3-methyl-1-(oxetan-2-ylmethyl)imidazo[4,5-b]pyridin-2-one; | 0.128 | |
| 395 | (R/S)-6-(4-Fluoro-3-methyl-phenyl)-3-methyl-1-(oxetan-2-ylmethyl)imidazo[4,5-b]pyridin-2-one; | 1.200 | |
| 396 | (R/S)-6-[2-Fluoro-3-(trifluoromethyl)phenyl]-3-methyl-1-(oxetan-2-ylmethyl)imidazo[4,5-b]pyridin-2-one; | 0.135 | |
| 397 | (R/S)-6-(3-Chlorophenyl)-3-methyl-1-(oxetan-2-ylmethyl)imidazo[4,5-b]pyridin-2-one; | 0.228 | |
| 398 | (R/S)-3-Methyl-6-[2-methyl-3-(trifluoromethyl)phenyl]-1-(oxetan-2-ylmethyl)imidazo[4,5-b]pyridin-2-one; | 2.840 | |
| 399 | (R/S)-1-(2,4-Dihydroxybutyl)-3-methyl-6-[2-methyl-3-(trifluoromethyl)phenyl]imidazo[4,5-b]pyridin-2-one; | 5.100 | |
| 400 | 6-(2,4-Difluoro-3-methyl-phenyl)-1-[2-(3-fluoroazetidin-1-yl)-2-oxo-ethyl]-3-methyl-imidazo[4,5-b]pyridin-2-one; | 0.017 | |
| 401 | 1-[2-(3-Fluoroazetidin-1-yl)-2-oxo-ethyl]-6-(4-fluoro-3-methyl-phenyl)-3-methyl-imidazo[4,5-b]pyridin-2-one; | 0.016 | |
| 402 | 1-[2-(3-Fluoroazetidin-1-yl)-2-oxo-ethyl]-3-methyl-6-(3,4,5-trifluorophenyl)imidazo[4,5-b]pyridin-2-one; | 0.016 | |
| 403 | 6-(3,4-Difluorophenyl)-1-[2-(3-fluoroazetidin-1-yl)-2-oxo-ethyl]-3-methyl-imidazo[4,5-b]pyridin-2-one; | 0.042 | |
| 404 | 1-[2-(3-Fluoroazetidin-1-yl)-2-oxo-ethyl]-3-methyl-6-(m-tolyl)imidazo[4,5-b]pyridin-2-one; | 0.050 | |
| 405 | 1-[2-(3-Fluoroazetidin-1-yl)-2-oxo-ethyl]-6-(2-fluoro-3-methyl-phenyl)-3-methyl-imidazo[4,5-b]pyridin-2-one; | 0.022 | |
| 406 | 6-(3-Chlorophenyl)-1-[2-(3-fluoroazetidin-1-yl)-2-oxo-ethyl]-3-methyl-imidazo[4,5-b]pyridin-2-one; | 0.016 | |
| 407 | 1-[2-(3-Fluoroazetidin-1-yl)-2-oxo-ethyl]-6-[4-fluoro-3-(trifluoromethyl)phenyl]-3-methyl-imidazo[4,5-b]pyridin-2-one; | 0.031 | |
| 408 | 1-[2-(Azetidin-1-yl)-2-oxo-ethyl]-3-methyl-6-[3-(trifluoromethyl)phenyl]imidazo[4,5-b]pyridin-2-one; | 0.042 | |
| 409 | 1-[2-(Azetidin-1-yl)-2-oxo-ethyl]-6-(2,4-difluoro-3-methyl-phenyl)-3-methyl-imidazo[4,5-b]pyridin-2-one; | 0.008 | |
| 410 | 1-[2-(Azetidin-1-yl)-2-oxo-ethyl]-6-(4-fluoro-3-methyl-phenyl)-3-methyl-imidazo[4,5-b]pyridin-2-one; | 0.013 | |
| 411 | 1-[2-(Azetidin-1-yl)-2-oxo-ethyl]-3-methyl-6-(3,4,5-trifluorophenyl)imidazo[4,5-b]pyridin-2-one; | 0.014 | |
| 412 | 1-[2-(Azetidin-1-yl)-2-oxo-ethyl]-6-(3,5-difluorophenyl)-3-methyl-imidazo[4,5-b]pyridin-2-one; | 0.027 | |
| 413 | 1-(2-(3,3-Difluoroazetidin-1-yl)-2-oxoethyl)-6-(4-fluoro-3-methylphenyl)-3-methyl-1H-imidazo[4,5-b]pyridin-2(3H)-one; | 0.009 | |
| 414 | 1-[2-(3,3-Difluoroazetidin-1-yl)-2-oxo-ethyl]-6-(2,4-difluoro-3-methyl-phenyl)-3-methyl-imidazo[4,5-b]pyridin-2-one; | 0.013 | |
| 415 | 1-[2-(3,3-Difluoroazetidin-1-yl)-2-oxo-ethyl]-6-[2-fluoro-3-(trifluoromethyl)phenyl]-3-methyl-imidazo[4,5-b]pyridin-2-one; | 0.015 | |
| 416 | 1-[2-(3,3-Difluoroazetidin-1-yl)-2-oxo-ethyl]-6-(3,4-difluorophenyl)-3-methyl-imidazo[4,5-b]pyridin-2-one; | 0.010 | |
| 417 | 1-[2-(3,3-Difluoroazetidin-1-yl)-2-oxo-ethyl]-6-(3-fluorophenyl)-3-methyl-imidazo[4,5-b]pyridin-2-one; | 0.031 | |

TABLE 3-continued

| Ex # | Compound Name | NR2B IC$_{50}$ (μM) standard assay | NR2B IC$_{50}$ (μM) HTS assay |
|---|---|---|---|
| 418 | 1-[2-(3,3-Difluoroazetidin-1-yl)-2-oxo-ethyl]-6-(2-fluoro-3-methyl-phenyl)-3-methyl-imidazo[4,5-b]pyridin-2-one; | 0.019 | |
| 419 | N,N-Dimethyl-2-[3-methyl-2-oxo-6-[3-(trifluoromethyl)phenyl]imidazo[4,5-b]pyridin-1-yl]acetamide; | 0.047 | |
| 420 | 2-[6-(4-Fuoro-3-methyl-phenyl)-3-methyl-2-oxo-imidazo[4,5-b]pyridin-1-yl]-N,N-dimethyl-acetamide; | 0.017 | |
| 421 | 2-[6-(3,4-Difluorophenyl)-3-methyl-2-oxo-imidazo[4,5-b]pyridin-1-yl]-N,N-dimethyl-acetamide; | 0.053 | |
| 422 | 1-[2-(Azetidin-1-yl)-2-oxo-ethyl]-6-(3,4-difluorophenyl)-3-methyl-imidazo[4,5-b]pyridin-2-one; | 0.010 | |
| 423 | 2-[6-(2,4-Difluoro-3-methyl-phenyl)-3-methyl-2-oxo-imidazo[4,5-b]pyridin-1-yl]-N,N-dimethyl-acetamide; | 0.006 | |
| 424 | 2-[6-[2-Fluoro-3-(trifluoromethyl)phenyl]-3-methyl-2-oxo-imidazo[4,5-b]pyridin-1-yl]-N,N-dimethyl-acetamide; | 0.028 | |
| 425 | 2-[6-(2,3-Difluorophenyl)-3-methyl-2-oxo-imidazo[4,5-b]pyridin-1-yl]-N,N-dimethyl-acetamide; | 0.408 | |
| 426 | 2-[6-[3-(Difluoromethyl)phenyl]-3-methyl-2-oxo-imidazo[4,5-b]pyridin-1-yl]-N,N-dimethyl-acetamide; | 0.019 | |
| 427 | 2-[6-(2-Fluoro-3-methyl-phenyl)-3-methyl-2-oxo-imidazo[4,5-b]pyridin-1-yl]-N,N-dimethyl-acetamide; | 0.041 | |
| 428 | 2-[6-(3,5-Difluorophenyl)-3-methyl-2-oxo-imidazo[4,5-b]pyridin-1-yl]-N,N-dimethyl-acetamide; | 0.126 | |
| 429 | N,N-Dimethyl-2-[3-methyl-2-oxo-6-(3-pyridyl)imidazo[4,5-b]pyridin-1-yl]acetamide; | >10 | |
| 430 | 1-[2-(3,3-Difluoroazetidin-1-yl)-2-oxo-ethyl]-3-methyl-6-[5-(trifluoromethyl)-2-thienyl]imidazo[4,5-b]pyridin-2-one; | 0.028 | |
| 431 | 2-[6-[3,4-Difluoro-5-(trifluoromethyl)phenyl]-3-methyl-2-oxo-imidazo[4,5-b]pyridin-1-yl]-N,N-dimethyl-acetamide; | 0.095 | |
| 432 | 2-[2-Oxo-6-[3-(trifluoromethyl)phenyl]-3H-imidazo[4,5-b]pyridin-1-yl]acetamide; | 0.962 | |
| 433 | 2-[6-(4-Fluoro-2-methoxy-phenyl)-2-oxo-3H-imidazo[4,5-b]pyridin-1-yl]acetamide; | | 0.867 |
| 434 | 2-[6-(3-Chloro-4-fluoro-phenyl)-2-oxo-3H-imidazo[4,5-b]pyridin-1-yl]acetamide; | 0.583 | |
| 435 | N-Methyl-2-[2-oxo-6-[3-(trifluoromethyl)phenyl]-3H-imidazo[4,5-b]pyridin-1-yl]acetamide; | 0.264 | |
| 436 | 2-[6-(4-Chlorophenyl)-2-oxo-3H-imidazo[4,5-b]pyridin-1-yl]-N-methyl-acetamide; | | 4.700 |
| 437 | 2-[6-(4-Fluoro-2-methyl-phenyl)-2-oxo-3H-imidazo[4,5-b]pyridin-1-yl]-N-methyl-acetamide; | 0.219 | |
| 438 | 2-[6-(3,5-Dimethylphenyl)-2-oxo-3H-imidazo[4,5-b]pyridin-1-yl]-N-methyl-acetamide; | | 0.394 |
| 439 | 2-[6-(4-Methoxy-3-methyl-phenyl)-2-oxo-3H-imidazo[4,5-b]pyridin-1-yl]-N-methyl-acetamide; | | 3.371 |
| 440 | 2-[6-(4-Fluoro-2-methoxy-phenyl)-2-oxo-3H-imidazo[4,5-b]pyridin-1-yl]-N-methyl-acetamide; | 0.358 | |
| 441 | 2-[6-(2-Ethoxyphenyl)-2-oxo-3H-imidazo[4,5-b]pyridin-1-yl]-N-methyl-acetamide; | | 2.444 |
| 442 | N-(2-Methoxyethyl)-2-[2-oxo-6-[3-(trifluoromethyl)phenyl]-3H-imidazo[4,5-b]pyridin-1-yl]acetamide; | | 0.197 |
| 443 | 2-[6-(2-Ethoxy-5-fluoro-phenyl)-2-oxo-3H-imidazo[4,5-b]pyridin-1-yl]-N-(2-methoxyethyl)acetamide; | | 1.322 |
| 444 | N-(2-Methoxyethyl)-2-[6-(4-methoxyphenyl)-2-oxo-3H-imidazo[4,5-b]pyridin-1-yl]acetamide; | | 0.747 |
| 445 | N-(2-Methoxyethyl)-2-[2-oxo-6-(3-pyridyl)-3H-imidazo[4,5-b]pyridin-1-yl]acetamide; | | >29.0001 |
| 446 | 2-[6-(4-Fluoro-2-methoxy-phenyl)-2-oxo-3H-imidazo[4,5-b]pyridin-1-yl]-N-(2-methoxyethyl)acetamide; | 0.204 | |

TABLE 3-continued

| Ex # | Compound Name | NR2B IC$_{50}$ (μM) standard assay | NR2B IC$_{50}$ (μM) HTS assay |
|---|---|---|---|
| 447 | N-Cyclopropyl-2-[6-(3,5-difluorophenyl)-2-oxo-3H-imidazo[4,5-b]pyridin-1-yl]acetamide; | 0.184 | |
| 448 | 2-[6-(3-Chloro-4-fluoro-phenyl)-2-oxo-3H-imidazo[4,5-b]pyridin-1-yl]-N-cyclopropyl-acetamide; | 0.008 | |
| 449 | N-Cyclopropyl-2-[6-(3-ethoxyphenyl)-2-oxo-3H-imidazo[4,5-b]pyridin-1-yl]acetamide; | | 0.638 |
| 450 | N-Cyclopropyl-2-[6-(3-methoxyphenyl)-2-oxo-3H-imidazo[4,5-b]pyridin-1-yl]acetamide; | | 1.763 |
| 451 | N-Cyclopropyl-2-[6-(4-methoxy-3-methyl-phenyl)-2-oxo-3H-imidazo[4,5-b]pyridin-1-yl]acetamide; | | 1.031 |
| 452 | N-Cyclopropyl-2-[6-(4-fluoro-2-methoxy-phenyl)-2-oxo-3H-imidazo[4,5-b]pyridin-1-yl]acetamide; | | 0.071 |
| 453 | 2-[6-(4-Chlorophenyl)-2-oxo-3H-imidazo[4,5-b]pyridin-1-yl]-N-cyclopropyl-acetamide; | | 0.100 |
| 454 | N-Cyclopropyl-2-[6-(2,4-dimethoxyphenyl)-2-oxo-3H-imidazo[4,5-b]pyridin-1-yl]acetamide; | | 1.938 |
| 455 | N-Cyclopropyl-2-[6-(2-fluoro-6-methoxy-phenyl)-2-oxo-3H-imidazo[4,5-b]pyridin-1-yl]acetamide; | 0.416 | |
| 456 | N-Cyclopropyl-2-[6-(2-ethoxyphenyl)-2-oxo-3H-imidazo[4,5-b]pyridin-1-yl]acetamide; | 0.146 | |
| 457 | 6-(3-Fluoro-4-methoxy-phenyl)-1-[2-oxo-2-(2-thienyl)ethyl]-3H-imidazo[4,5-b]pyridin-2-one; | 0.330 | |
| 458 | 6-(2-Ethoxyphenyl)-1-[2-oxo-2-(2-thienyl)ethyl]-3H-imidazo[4,5-b]pyridin-2-one; | 0.135 | |
| 459 | 6-(4-Chlorophenyl)-1-[2-oxo-2-(2-thienyl)ethyl]-3H-imidazo[4,5-b]pyridin-2-one; | | 1.422 |
| 460 | 6-(2-Ethoxy-5-fluoro-phenyl)-1-[2-oxo-2-(2-thienyl)ethyl]-3H-imidazo[4,5-b]pyridin-2-one; | | 1.770 |
| 461 | 6-(4-Methoxyphenyl)-1-[2-oxo-2-(2-thienyl)ethyl]-3H-imidazo[4,5-b]pyridin-2-one; | 0.054 | |
| 462 | 6-(4-Fluoro-2-methoxy-phenyl)-1-[2-oxo-2-(2-thienyl)ethyl]-3H-imidazo[4,5-b]pyridin-2-one; | 0.255 | |
| 463 | 6-(3-Ethoxyphenyl)-1-[2-oxo-2-(2-thienyl)ethyl]-3H-imidazo[4,5-b]pyridin-2-one; | | 0.360 |
| 464 | 6-(3-Chloro-4-fluoro-phenyl)-1-[2-oxo-2-(2-thienyl)ethyl]-3H-imidazo[4,5-b]pyridin-2-one; | 0.359 | |
| 465 | 1-(Cyclopropylmethyl)-6-(2,4-dimethoxyphenyl)-3H-imidazo[4,5-b]pyridin-2-one; | | 14.401 |
| 466 | 1-(Cyclopropylmethyl)-6-(2-ethoxy-5-fluoro-phenyl)-3H-imidazo[4,5-b]pyridin-2-one; | | 15.754 |
| 467 | 1-(Cyclopropylmethyl)-6-(4-fluoro-2-methoxy-phenyl)-3H-imidazo[4,5-b]pyridin-2-one; | | 0.305 |
| 468 | 1-(Cyclopropylmethyl)-6-(4-methoxy-3-methyl-phenyl)-3H-imidazo[4,5-b]pyridin-2-one; | | 4.174 |
| 469 | 1-(Cyclopropylmethyl)-6-(3-fluoro-4-methoxy-phenyl)-3H-imidazo[4,5-b]pyridin-2-one; | | 0.944 |
| 470 | 1-(Cyclopropylmethyl)-6-(3,5-difluorophenyl)-3H-imidazo[4,5-b]pyridin-2-one; | | 0.509 |
| 471 | 1-(Cyclopropylmethyl)-6-(4-methoxyphenyl)-3H-imidazo[4,5-b]pyridin-2-one; | 1.803 | |
| 472 | 1-(Cyclopropylmethyl)-6-(2-thienyl)-3H-imidazo[4,5-b]pyridin-2-one; | 1.556 | |
| 473 | 1-(Cyclopropylmethyl)-6-[3-(dimethylamino)phenyl]-3H-imidazo[4,5-b]pyridin-2-one; | | 15.668 |
| 474 | 1-(Cyclopropylmethyl)-6-(3,5-dimethylphenyl)-3H-imidazo[4,5-b]pyridin-2-one; | 3.570 | |
| 475 | 6-(3-Methoxyphenyl)-1-(tetrahydrofuran-2-ylmethyl)-3H-imidazo[4,5-b]pyridin-2-one; | | 0.157 |
| 476 | 4-[[6-(4-Methoxyphenyl)-2-oxo-3H-imidazo[4,5-b]pyridin-1-yl]methyl]benzonitrile; | | 4.534 |
| 477 | 3-[[6-(4-Methoxyphenyl)-2-oxo-3H-imidazo[4,5-b]pyridin-1-yl]methyl]benzonitrile; | | 3.156 |
| 478 | 3-[[6-(4-Fluoro-2-methoxy-phenyl)-2-oxo-3H-imidazo[4,5-b]pyridin-1-yl]methyl]benzonitrile; | | 3.044 |
| 479 | 3-[[6-(4-Fluoro-2-methyl-phenyl)-2-oxo-3H-imidazo[4,5-b]pyridin-1-yl]methyl]benzonitrile; | 0.778 | |
| 480 | 3-[[6-(3-Chloro-4-fluoro-phenyl)-2-oxo-3H-imidazo[4,5-b]pyridin-1-yl]methyl]benzonitrile; | | 4.222 |
| 481 | 2-[[6-(2-Fluoro-6-methoxy-phenyl)-2-oxo-3H-imidazo[4,5-b]pyridin-1-yl]methyl]benzonitrile; | 2.250 | |
| 482 | 2-[[6-(4-Chlorophenyl)-2-oxo-3H-imidazo[4,5-b]pyridin-1-yl]methyl]benzonitrile; | | 1.410 |

TABLE 3-continued

| Ex # | Compound Name | NR2B IC$_{50}$ (µM) standard assay | NR2B IC$_{50}$ (µM) HTS assay |
|---|---|---|---|
| 483 | 2-[[6-(4-Fluoro-2-methyl-phenyl)-2-oxo-3H-imidazo[4,5-b]pyridin-1-yl]methyl]benzonitrile; | | 1.801 |
| 484 | 2-[[6-(2-Ethoxyphenyl)-2-oxo-3H-imidazo[4,5-b]pyridin-1-yl]methyl]benzonitrile; | 1.390 | |
| 485 | 2-[[6-(3-Methoxyphenyl)-2-oxo-3H-imidazo[4,5-b]pyridin-1-yl]methyl]benzonitrile; | 0.031 | |
| 486 | 2-[[6-(3-Cyanophenyl)-2-oxo-3H-imidazo[4,5-b]pyridin-1-yl]methyl]benzonitrile; | | 3.839 |
| 487 | 2-[[6-(2,4-Dimethoxyphenyl)-2-oxo-3H-imidazo[4,5-b]pyridin-1-yl]methyl]benzonitrile; | | 2.566 |
| 488 | 2-[[6-(3,5-Dimethylphenyl)-2-oxo-3H-imidazo[4,5-b]pyridin-1-yl]methyl]benzonitrile; | | 4.949 |
| 489 | 2-[[6-(2-Ethoxy-5-fluoro-phenyl)-2-oxo-3H-imidazo[4,5-b]pyridin-1-yl]methyl]benzonitrile; | | 1.283 |
| 490 | 2-[[6-(4-Fluoro-2-methoxy-phenyl)-2-oxo-3H-imidazo[4,5-b]pyridin-1-yl]methyl]benzonitrile; | 0.046 | |
| 491 | 2-[[6-(3-Fluoro-4-methoxy-phenyl)-2-oxo-3H-imidazo[4,5-b]pyridin-1-yl]methyl]benzonitrile; | 0.053 | |
| 492 | 6-(4-Fluoro-2-methyl-phenyl)-1-[(4-fluorophenyl)methyl]-3H-imidazo[4,5-b]pyridin-2-one; | | 6.121 |
| 493 | 6-(2,3-Dimethoxyphenyl)-1-[(4-fluorophenyl)methyl]-3H-imidazo[4,5-b]pyridin-2-one; | | 1.012 |
| 494 | 6-(2-Ethoxy-5-fluoro-phenyl)-1-[(3-fluorophenyl)methyl]-3H-imidazo[4,5-b]pyridin-2-one; | | 5.643 |
| 495 | 6-(3,5-Dimethylphenyl)-1-[(3-fluorophenyl)methyl]-3H-imidazo[4,5-b]pyridin-2-one; | | 2.813 |
| 496 | 6-(2,4-Dimethoxyphenyl)-1-[(3-fluorophenyl)methyl]-3H-imidazo[4,5-b]pyridin-2-one; | | 2.795 |
| 497 | 6-(2-Ethoxyphenyl)-1-[(3-fluorophenyl)methyl]-3H-imidazo[4,5-b]pyridin-2-one; | | 1.946 |
| 498 | 1-[(3-Fluorophenyl)methyl]-6-(4-methoxy-3-methyl-phenyl)-3H-imidazo[4,5-b]pyridin-2-one; | 2.220 | |
| 499 | 6-(4-Fluoro-2-methoxy-phenyl)-1-[(3-fluorophenyl)methyl]-3H-imidazo[4,5-b]pyridin-2-one; | 0.090 | |
| 500 | 6-[3-(Dimethylamino)phenyl]-1-[(3-fluorophenyl)methyl]-3H-imidazo[4,5-b]pyridin-2-one; | 6.080 | |
| 501 | 6-(4-Fluoro-2-methoxy-phenyl)-1-[(4-fluorophenyl)methyl]-3H-imidazo[4,5-b]pyridin-2-one; | | 0.790 |
| 502 | 6-(3-Chloro-4-fluoro-phenyl)-1-[(4-fluorophenyl)methyl]-3H-imidazo[4,5-b]pyridin-2-one; | | 4.858 |
| 503 | 6-(2-Ethoxyphenyl)-1-[(2-fluorophenyl)methyl]-3H-imidazo[4,5-b]pyridin-2-one; | | 5.492 |
| 504 | 1-[(3-Chlorophenyl)methyl]-6-(3,5-difluorophenyl)-3H-imidazo[4,5-b]pyridin-2-one; | | 4.132 |
| 505 | 6-(4-Fluoro-2-methoxy-phenyl)-1-[(3-methoxyphenyl)methyl]-3H-imidazo[4,5-b]pyridin-2-one; | 1.640 | |
| 506 | 1-[(3-Methoxyphenyl)methyl]-6-(3-pyridyl)-3H-imidazo[4,5-b]pyridin-2-one; | | >29 |
| 507 | 1-[(3-Methoxyphenyl)methyl]-6-(4-methyl-2-thienyl)-3H-imidazo[4,5-b]pyridin-2-one; | | 8.100 |
| 508 | 6-(3,5-Difluorophenyl)-1-[(4-methoxyphenyl)methyl]-3H-imidazo[4,5-b]pyridin-2-one; | | 0.463 |
| 509 | 1-[(3,5-Dimethoxyphenyl)methyl]-6-(2-fluoro-6-methoxy-phenyl)-3H-imidazo[4,5-b]pyridin-2-one; | | 0.884 |
| 510 | 1-[(3,5-Dimethoxyphenyl)methyl]-6-[3-(trifluoromethyl)phenyl]-3H-imidazo[4,5-b]pyridin-2-one; | | 17.434 |
| 511 | 6-(4-Chlorophenyl)-1-[(4-isopropylphenyl)methyl]-3H-imidazo[4,5-b]pyridin-2-one; | | >29 |
| 512 | 6-(4-tert-Butylphenyl)-1-[(3,4-dimethoxy-2-pyridyl)methyl]-3H-imidazo[4,5-b]pyridin-2-one; | | >29 |
| 513 | 3-[1-[(3,5-Dimethylisoxazol-4-yl)methyl]-2-oxo-3H-imidazo[4,5-b]pyridin-6-yl]benzonitrile; | | >29 |

TABLE 3-continued

| Ex # | Compound Name | NR2B IC$_{50}$ (µM) standard assay | NR2B IC$_{50}$ (µM) HTS assay |
|---|---|---|---|
| 514 | 1-[(3,5-Dimethylisoxazol-4-yl)methyl]-6-(2-ethoxy-5-fluoro-phenyl)-3H-imidazo[4,5-b]pyridin-2-one; | | >29 |
| 515 | 6-(4-Methoxy-3-methyl-phenyl)-1-[(5-methylisoxazol-3-yl)methyl]-3H-imidazo[4,5-b]pyridin-2-one; | | 0.156 |
| 516 | 6-(3,5-Dimethylphenyl)-1-[(5-methylisoxazol-3-yl)methyl]-3H-imidazo[4,5-b]pyridin-2-one; | 0.491 | |
| 517 | 6-(2-Ethoxyphenyl)-1-[(5-methylisoxazol-3-yl)methyl]-3H-imidazo[4,5-b]pyridin-2-one; | 0.709 | |
| 518 | 6-(2,4-Dimethoxyphenyl)-1-[(5-methylisoxazol-3-yl)methyl]-3H-imidazo[4,5-b]pyridin-2-one; | 0.808 | |
| 519 | 6-(3-Fluoro-4-methoxy-phenyl)-1-[(5-methylisoxazol-3-yl)methyl]-3H-imidazo[4,5-b]pyridin-2-one; | 0.139 | |
| 520 | 6-(4-Fluoro-2-methoxy-phenyl)-1-[(5-methylisoxazol-3-yl)methyl]-3H-imidazo[4,5-b]pyridin-2-one; | 0.019 | |
| 521 | 6-(2-Ethoxy-5-fluoro-phenyl)-1-[(5-methylisoxazol-3-yl)methyl]-3H-imidazo[4,5-b]pyridin-2-one; | 0.132 | |
| 522 | 6-(4-Fluoro-2-methyl-phenyl)-1-[(5-methylisoxazol-3-yl)methyl]-3H-imidazo[4,5-b]pyridin-2-one; | 0.034 | |
| 523 | 6-(3,5-Difluorophenyl)-1-[(5-methylisoxazol-3-yl)methyl]-3H-imidazo[4,5-b]pyridin-2-one; | 0.133 | |
| 532 | N-(3-Chloropropyl)-2-[3-methyl-2-oxo-6-[5-(trifluoromethyl)-2-thienyl]imidazo[4,5-b]pyridin-1-yl]acetamide; | 0.862 | |
| 533 | 2-[6-[3-(Difluoromethyl)-4-fluoro-phenyl]-3-methyl-2-oxo-imidazo[4,5-b]pyridin-1-yl]-N,N-dimethyl-acetamide; | 0.025 | |
| 534 | 1-[2-(Azetidin-1-yl)-2-oxo-ethyl]-3-(fluoromethyl)-6-[5-(trifluoromethyl)-2-thienyl]imidazo[4,5-b]pyridin-2-one; | 0.036 | |
| 535 | 1-[2-(Azetidin-1-yl)-2-oxo-ethyl]-3-(2-fluoroethyl)-6-[5-(trifluoromethyl)-2-thienyl]imidazo[4,5-b]pyridin-2-one; | 0.106 | |
| 536 | 1-[2-[3-(2-Fluoroethyl)azetidin-1-yl]-2-oxo-ethyl]-6-[3-(trifluoromethyl)phenyl]-3H-imidazo[4,5-b]pyridin-2-one; | 0.163 | |
| 537 | 6-(6-Fluoro-2-pyridyl)-1-(2-oxobutyl)-3H-imidazo[4,5-b]pyridin-2-one; | 0.273 | |
| 538 | 1-[2-(Azetidin-1-yl)-2-oxo-ethyl]-6-[4-(2-fluoroethoxy)-3-(trifluoromethyl)phenyl]-3H-imidazo[4,5-b]pyridin-2-one; | 0.240 | |
| 539 | 1-[2-(Azetidin-1-yl)-2-oxo-ethyl]-6-[3-(2-fluoroethoxy)-5-(trifluoromethyl)phenyl]-3H-imidazo[4,5-b]pyridin-2-one; | 0.333 | |
| 541 | 6-[3-(Difluoromethyl)-4-fluoro-phenyl]-3-methyl-1-(pyridazin-3-ylmethyl)imidazo[4,5-b]pyridin-2-one; | 0.022 | |
| 542 | 6-[3-(Difluoromethoxy)-4-fluoro-phenyl]-3-methyl-1-(pyridazin-3-ylmethyl)imidazo[4,5-b]pyridin-2-one; | 0.016 | |
| 543 | 6-[4-Chloro-3-(difluoromethoxy)phenyl]-3-methyl-1-(pyridazin-3-ylmethyl)imidazo[4,5-b]pyridin-2-one; | 0.028 | |
| 544 | 6-[4-Chloro-3-(difluoromethoxy)phenyl]-1-[(5-fluoro-3-pyridyl)methyl]-3-methyl-imidazo[4,5-b]pyridin-2-one; | 0.090 | |
| 545 | 6-(3,4-Difluorophenyl)-3-methyl-1-(thiadiazol-4-ylmethyl)imidazo[4,5-b]pyridin-2-one; | 0.512 | |
| 546 | 6-[3-(Difluoromethyl)-4-fluoro-phenyl]-1-[(5-fluoro-3-pyridyl)methyl]-3-methyl-imidazo[4,5-b]pyridin-2-one; | 0.024 | |
| 547 | 6-[3-(Difluoromethoxy)-4-fluoro-phenyl]-1-[(5-fluoro-3-pyridyl)methyl]-3-methyl-imidazo[4,5-b]pyridin-2-one; | 0.036 | |
| 548 | 3-Methyl-1-(thiadiazol-4-ylmethyl)-6-[3-(trifluoromethyl)phenyl]imidazo[4,5-b]pyridin-2-one; | 0.185 | |
| 549 | 6-(3,4-Difluorophenyl)-3-methyl-1-[(1-methyltriazol-4-yl)methyl]imidazo[4,5-b]pyridin-2-one; | 0.467 | |
| 550 | 6-(3,4-Difluorophenyl)-3-methyl-1-[(1-methylpyrazol-4-yl)methyl]imidazo[4,5-b]pyridin-2-one; | 0.697 | |

TABLE 3-continued

| Ex # | Compound Name | NR2B IC$_{50}$ (μM) standard assay | NR2B IC$_{50}$ (μM) HTS assay |
|---|---|---|---|
| 551 | 3-Methyl-1-[(1-methylpyrazol-4-yl)methyl]-6-[3-(trifluoromethyl)phenyl]imidazo[4,5-b]pyridin-2-one; | 0.190 | |
| 552 | 3-Methyl-1-[(1-methyltriazol-4-yl)methyl]-6-[3-(trifluoromethyl)phenyl]imidazo[4,5-b]pyridin-2-one; | 0.130 | |
| 553 | 3-Methyl-6-(5-methyl-2-thienyl)-1-[(1-methyltriazol-4-yl)methyl]imidazo[4,5-b]pyridin-2-one; | 0.726 | |
| 554 | 3-Methyl-1-[(5-methyl-1,3,4-oxadiazol-2-yl)methyl]-6-(5-methyl-2-thienyl)imidazo[4,5-b]pyridin-2-one; | 0.533 | |
| 555 | 3-Methyl-1-[(1-methylpyrazol-4-yl)methyl]-6-(5-methyl-2-thienyl)imidazo[4,5-b]pyridin-2-one; | 1.310 | |
| 556 | 3-Methyl-6-(5-methyl-2-thienyl)-1-(thiadiazol-4-ylmethyl)imidazo[4,5-b]pyridin-2-one; | 0.363 | |
| 557 | 3-Methyl-1-[(3-methyl-1,2,4-oxadiazol-5-yl)methyl]-6-(5-methyl-2-thienyl)imidazo[4,5-b]pyridin-2-one; | 0.671 | |
| 558 | 3-Methyl-1-[(5-methylisoxazol-3-yl)methyl]-6-(5-methyl-2-thienyl)imidazo[4,5-b]pyridin-2-one; | 0.216 | |
| 559 | 6-[5-(Difluoromethyl)-2-thienyl]-3-methyl-1-[(1-methyltriazol-4-yl)methyl]imidazo[4,5-b]pyridin-2-one; | 0.280 | |
| 560 | 6-[5-(Difluoromethyl)-2-thienyl]-3-methyl-1-[(5-methyl-1,3,4-oxadiazol-2-yl)methyl]imidazo[4,5-b]pyridin-2-one; | 0.304 | |
| 561 | 6-[5-(Difluoromethyl)-2-thienyl]-3-methyl-1-[(1-methylpyrazol-4-yl)methyl]imidazo[4,5-b]pyridin-2-one; | 0.354 | |
| 562 | 6-[5-(Difluoromethyl)-2-thienyl]-3-methyl-1-(thiadiazol-4-ylmethyl)imidazo[4,5-b]pyridin-2-one; | 0.166 | |
| 563 | 6-[5-(Difluoromethyl)-2-thienyl]-3-methyl-1-[(3-methyl-1,2,4-oxadiazol-5-yl)methyl]imidazo[4,5-b]pyridin-2-one; | 0.316 | |
| 564 | 6-[5-(Difluoromethyl)-2-thienyl]-3-methyl-1-[(5-methylisoxazol-3-yl)methyl]imidazo[4,5-b]pyridin-2-one; | 0.087 | |
| 565 | 3-Methyl-1-[(1-methylpyrazol-4-yl)methyl]-6-[5-(trifluoromethyl)-2-thienyl]imidazo[4,5-b]pyridin-2-one; | 0.374 | |
| 566 | 3-Methyl-1-[(1-methyltriazol-4-yl)methyl]-6-[5-(trifluoromethyl)-2-thienyl]imidazo[4,5-b]pyridin-2-one; | 0.349 | |
| 567 | 3-Methyl-1-[(5-methyl-1,3,4-oxadiazol-2-yl)methyl]-6-[5-(trifluoromethyl)-2-thienyl]imidazo[4,5-b]pyridin-2-one; | 0.146 | |
| 568 | 3-Methyl-1-(thiadiazol-4-ylmethyl)-6-[5-(trifluoromethyl)-2-thienyl]imidazo[4,5-b]pyridin-2-one; | 0.305 | |
| 569 | 3-Methyl-1-[(3-methyl-1,2,4-oxadiazol-5-yl)methyl]-6-[5-(trifluoromethyl)-2-thienyl]imidazo[4,5-b]pyridin-2-one; | 0.412 | |
| 570 | 3-Methyl-1-[(5-methylisoxazol-3-yl)methyl]-6-[5-(trifluoromethyl)-2-thienyl]imidazo[4,5-b]pyridin-2-one; | 0.139 | |
| 571 | 6-(2,4-Difluoro-3-methyl-phenyl)-3-methyl-1-[(5-methylisoxazol-3-yl)methyl]imidazo[4,5-b]pyridin-2-one; | 0.037 | |
| 572 | 6-(2,4-Difluoro-3-methyl-phenyl)-3-methyl-1-[(1-methylpyrazol-4-yl)methyl]imidazo[4,5-b]pyridin-2-one; | 0.150 | |
| 573 | 6-(2,4-Difluoro-3-methyl-phenyl)-3-methyl-1-[(3-methyl-1,2,4-oxadiazol-5-yl)methyl]imidazo[4,5-b]pyridin-2-one; | 0.043 | |
| 574 | 6-(2,4-Difluoro-3-methyl-phenyl)-3-methyl-1-[(1-methyltriazol-4-yl)methyl]imidazo[4,5-b]pyridin-2-one; | 0.046 | |
| 575 | 6-(2,4-Difluoro-3-methyl-phenyl)-3-methyl-1-[(5-methyl-1,3,4-oxadiazol-2-yl)methyl]imidazo[4,5-b]pyridin-2-one; | 0.028 | |
| 576 | 6-(2,4-Difluoro-3-methyl-phenyl)-3-methyl-1-(thiadiazol-4-ylmethyl)imidazo[4,5-b]pyridin-2-one; | 0.050 | |

TABLE 3-continued

| Ex # | Compound Name | NR2B IC$_{50}$ (μM) standard assay | NR2B IC$_{50}$ (μM) HTS assay |
|---|---|---|---|
| 577 | N-(2-Fluoroethyl)-N-methyl-2-[3-methyl-2-oxo-6-[5-(trifluoromethyl)-2-thienyl]imidazo[4,5-b]pyridin-1-yl]acetamide; | 0.064 | |
| 578 | 1-[2-(3-Fluoroazetidin-1-yl)-2-oxo-ethyl]-6-[5-(trifluoromethyl)-2-thienyl]-3H-imidazo[4,5-b]pyridin-2-one; | 0.014 | |
| 579 | 1-[2-(Azetidin-1-yl)-2-oxo-ethyl]-6-(2,4-difluoro-3-methyl-phenyl)-3H-imidazo[4,5-b]pyridin-2-one; | 0.015 | |
| 580 | 1-[2-(3,3-Difluoroazetidin-1-yl)-2-oxo-ethyl]-6-(m-tolyl)-3H-imidazo[4,5-b]pyridin-2-one; | 0.026 | |
| 581 | 1-[2-(3,3-Difluoroazetidin-1-yl)-2-oxo-ethyl]-3-methyl-6-(m-tolyl)imidazo[4,5-b]pyridin-2-one; | 0.032 | |
| 582 | 1-[2-(Azetidin-1-yl)-2-oxo-ethyl]-6-[3-(2-fluoroethoxy)-5-(trifluoromethyl)phenyl]-3-methyl-imidazo[4,5-b]pyridin-2-one; | 1.290 | |
| 583 | N,N-Dimethyl-2-[3-methyl-6-(m-tolyl)-2-oxo-imidazo[4,5-b]pyridin-1-yl]acetamide; | 0.051 | |
| 584 | 1-[2-(Azetidin-1-yl)-2-oxo-ethyl]-6-[3-(difluoromethyl)-4-fluoro-phenyl]-3-methyl-imidazo[4,5-b]pyridin-2-one; | 0.024 | |
| 585 | 6-[3-(Difluoromethyl)-4-fluoro-phenyl]-1-[2-(3-fluoroazetidin-1-yl)-2-oxo-ethyl]-3-methyl-imidazo[4,5-b]pyridin-2-one; | 0.018 | |
| 586 | 1-[2-(3,3-Difluoroazetidin-1-yl)-2-oxo-ethyl]-6-[3-(difluoromethyl)-4-fluoro-phenyl]-3-methyl-imidazo[4,5-b]pyridin-2-one; | 0.051 | |
| 587 | 2-[6-[3-(Difluoromethoxy)-4-fluoro-phenyl]-3-methyl-2-oxo-imidazo[4,5-b]pyridin-1-yl]-N,N-dimethyl-acetamide; | 0.035 | |
| 588 | 1-[2-(Azetidin-1-yl)-2-oxo-ethyl]-6-[3-(difluoromethoxy)-4-fluoro-phenyl]-3-methyl-imidazo[4,5-b]pyridin-2-one; | 0.023 | |
| 589 | 6-[3-(Difluoromethoxy)-4-fluoro-phenyl]-1-[2-(3-fluoroazetidin-1-yl)-2-oxo-ethyl]-3-methyl-imidazo[4,5-b]pyridin-2-one; | 0.028 | |
| 590 | 1-[2-(3,3-Difluoroazetidin-1-yl)-2-oxo-ethyl]-6-[3-(difluoromethoxy)-4-fluoro-phenyl]-3-methyl-imidazo[4,5-b]pyridin-2-one; | 0.025 | |
| 591 | 2-[6-[4-Chloro-3-(difluoromethoxy)phenyl]-3-methyl-2-oxo-imidazo[4,5-b]pyridin-1-yl]-N,N-dimethyl-acetamide; | 0.034 | |
| 592 | 1-[2-(Azetidin-1-yl)-2-oxo-ethyl]-6-[4-chloro-3-(difluoromethoxy)phenyl]-3-methyl-imidazo[4,5-b]pyridin-2-one; | 0.071 | |
| 593 | 6-[4-Chloro-3-(difluoromethoxy)phenyl]-1-[2-(3-fluoroazetidin-1-yl)-2-oxo-ethyl]-3-methyl-imidazo[4,5-b]pyridin-2-one; | 0.053 | |
| 594 | 6-[4-Chloro-3-(difluoromethoxy)phenyl]-1-[2-(3,3-difluoroazetidin-1-yl)-2-oxo-ethyl]-3-methyl-imidazo[4,5-b]pyridin-2-one; | 0.082 | |
| 595 | 1-[2-(Azetidin-1-yl)-2-oxo-ethyl]-6-(2,4-difluoro-3-methyl-phenyl)-3-(fluoromethyl)imidazo[4,5-b]pyridin-2-one; | 0.974 | |
| 596 | 2-[3-(Fluoromethyl)-2-oxo-6-[5-(trifluoromethyl)-2-thienyl]imidazo[4,5-b]pyridin-1-yl]-N,N-dimethyl-acetamide; | 0.066 | |
| 597 | 1-[2-(3-Fluoroazetidin-1-yl)-2-oxo-ethyl]-3-(fluoromethyl)-6-[5-(trifluoromethyl)-2-thienyl]imidazo[4,5-b]pyridin-2-one; | 0.063 | |
| 598 | 3-(Fluoromethyl)-1-(2-oxo-2-pyrrolidin-1-yl-ethyl)-6-[5-(trifluoromethyl)-2-thienyl]imidazo[4,5-b]pyridin-2-one; | 0.173 | |
| 599 | 2-[6-(2,4-Difluoro-3-methyl-phenyl)-3-(fluoromethyl)-2-oxo-imidazo[4,5-b]pyridin-1-yl]-N,N-dimethyl-acetamide; | 0.025 | |
| 600 | 6-(2,4-Difluoro-3-methyl-phenyl)-1-[2-(3-fluoroazetidin-1-yl)-2-oxo-ethyl]-3-(fluoromethyl)imidazo[4,5-b]pyridin-2-one; | 0.017 | |
| 601 | 1-(3,3-Dimethyl-2-oxo-butyl)-6-(4-methoxyphenyl)-3H-imidazo[4,5-b]pyridin-2-one; | 1.634 | |
| 602 | 6-(3-Methoxyphenyl)-1-[2-oxo-2-(2-thienyl)ethyl]-3H-imidazo[4,5-b]pyridin-2-one; | 0.204 | |
| 603 | 1-(3,3-Dimethyl-2-oxo-butyl)-6-(4-methoxy-3-methyl-phenyl)-3H-imidazo[4,5-b]pyridin-2-one; | 1.290 | |

TABLE 3-continued

| Ex # | Compound Name | NR2B IC$_{50}$ (μM) standard assay | NR2B IC$_{50}$ (μM) HTS assay |
|---|---|---|---|
| 604 | 1-Isobutyl-6-(4-methoxyphenyl)-3H-imidazo[4,5-b]pyridin-2-one; | 1.824 | |
| 605 | 6-(2-Ethoxyphenyl)-1-[(3-methoxyphenyl)methyl]-3H-imidazo[4,5-b]pyridin-2-one; | 2.090 | |
| 606 | 6-(2-Ethoxyphenyl)-1-[(4-fluorophenyl)methyl]-3H-imidazo[4,5-b]pyridin-2-one; | 2.180 | |
| 607 | N-Cyclopropyl-2-[6-(2-ethoxy-5-fluoro-phenyl)-2-oxo-3H-imidazo[4,5-b]pyridin-1-yl]acetamide; | 0.336 | |
| 608 | 2-[[6-(4-Methoxy-3-methyl-phenyl)-2-oxo-3H-imidazo[4,5-b]pyridin-1-yl]methyl]benzonitrile; | 1.020 | |
| 609 | 1-(3,3-Dimethyl-2-oxo-butyl)-6-(3-fluoro-4-methoxy-phenyl)-3H-imidazo[4,5-b]pyridin-2-one; | 0.263 | |
| 610 | 2-[6-(3,5-Difluorophenyl)-2-oxo-3H-imidazo[4,5-b]pyridin-1-yl]-N-(2-methoxyethyl)acetamide; | 1.790 | |
| 611 | 1-(3,3-Dimethyl-2-oxo-butyl)-6-[3-(trifluoromethyl)phenyl]-3H-imidazo[4,5-b]pyridin-2-one; and | 0.204 | |
| 612 | 2-[6-(3-Chloro-4-fluoro-phenyl)-2-oxo-3H-imidazo[4,5-b]pyridin-1-yl]-N-(2-methoxyethyl)acetamide. | 0.116 | |

What is claimed:

1. A compound having the structure of Formula (I):

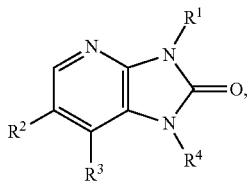

(I)

or a pharmaceutically acceptable salt, solvate, stereoisomer, isotopic variant, or N-oxide thereof, wherein:

$R^1$ is H; $CH_2F$; or $CH_3$;

$R^2$ is selected from the group consisting of: phenyl; phenyl substituted with one, two, or three members each independently selected from the group consisting of: halo, $C_{1-6}$alkyl, $C_{1-6}$haloalkyl, CN, $OC_{1-6}$alkyl, $OC_{1-6}$haloalkyl, $N(CH_3)_2$, and cyclopropyl; pyridinyl; pyridinyl substituted with F, $C_{1-4}$alkyl, or $C_{1-4}$haloalkyl; thiazolyl; thiazolyl substituted with $C_{1-6}$alkyl or $C_{1-6}$haloalkyl; thienyl; and thienyl substituted with one or two members each independently selected from the group consisting of: halo, $C_{1-6}$alkyl, $C_{1-6}$haloalkyl, $CH_2OH$, $CH_2OCH_3$, and cyclopropyl;

$R^3$ is H;

$R^4$ is:

(a)

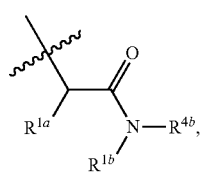

wherein $R^{4b}$ is selected from the group consisting of: H; $C_{1-6}$alkyl; $CH_2CH_2OCH_3$; $C_{3-6}$cycloalkyl; $C_{3-6}$cycloalkyl substituted with two or three members independently selected from the group consisting of F and $CH_3$; oxetanyl; oxetanyl substituted with $CH_3$; and pyridinyl; or (b)

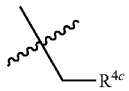

wherein $R^{4c}$ is selected from the group consisting of: cyclopropyl substituted with one or two F members; CH(OH) cyclopropyl; azetidinyl; $CH_2$-azetidinyl; $CH_2$-azetidinyl substituted with one or two members independently selected from: F, OH, $OCH_3$, and $CF_3$; oxetanyl; oxetanyl substituted with F or $CH_3$; tetrahydrofuranyl; $CH_2$pyrrolidinyl; $CH_2$pyrrolidinyl substituted with $CH_3$, OH, or $OCH_3$; $CH_2$piperidinyl; $CH_2$piperidinyl substituted with OH, or F; morpholinyl; pyrazolyl substituted with one or two CHs members; triazolyl substituted with $CH_3$; tetrazolyl; isoxazolyl substituted with one or two CHs members; oxadiazolyl substituted with $CH_3$, or $CH_2OCH_3$; thiadiazolyl; pyridinyl; pyridinyl substituted with one or two members independently selected from the group consisting of: Cl, F, $CH_3$, $OCH_3$, and $CF_3$; 2-oxo-1H-pyridin-3-yl; 6-oxo-1H-pyridin-3-yl; pyrimidinyl; pyrimidinyl substituted with F or $CH_3$; pyrazinyl; pyridazinyl; pyridazinyl substituted with $OCH_3$; phenyl; and phenyl substituted with one or two members independently selected from the group consisting of: halo, CN, $OCH_3$, $C_{1-6}$alkyl, and $CF_3$;

and $R^{1a}$ and $R^{1b}$ are each independently H or $CH_3$.

2. The compound of claim 1 or a pharmaceutically acceptable salt, solvate, stereoisomer, isotopic variant, or N-oxide thereof, wherein $R^1$ is H.

3. The compound of claim 1 or a pharmaceutically acceptable salt, solvate, stereoisomer, isotopic variant, or N-oxide thereof, wherein $R^1$ is $CH_3$ or $CH_2F$.

4. The compound of claim 1 or a pharmaceutically acceptable salt, solvate, stereoisomer, isotopic variant, or N-oxide thereof, wherein $R^{1a}$ is H.

5. The compound of claim 1 or a pharmaceutically acceptable salt, solvate, stereoisomer, isotopic variant, or N-oxide thereof, wherein $R^2$ is phenyl; phenyl substituted with one, two, or three members each independently selected from the group consisting of: Cl, F, $C_{1-6}$alkyl, $C_{1-6}$haloalkyl, CN, $OC_{1-6}$alkyl, $OC_{1-6}$haloalkyl, $N(CH_3)_2$, and cyclopropyl; pyridinyl; or pyridinyl substituted with $CF_3$.

6. The compound of claim 1 or a pharmaceutically acceptable salt, solvate, stereoisomer, isotopic variant, or N-oxide thereof, wherein $R^2$ is thiazolyl substituted with $C_{1-6}$alkyl or $CF_3$; thienyl; or thienyl substituted with one or two members each independently selected from the group consisting of: Cl, F, $C_{1-6}$alkyl, $C_{1-6}$haloalkyl, $CH_2OH$, $CH_2OCD_3$, and cyclopropyl.

7. The compound of claim 1 or a pharmaceutically acceptable salt, solvate, stereoisomer, isotopic variant, or N-oxide thereof, wherein $R^1$ is H or $CH_3$, $R^2$ is phenyl, wherein the phenyl is optionally substituted with one, two, or three members independently selected from: halo, $C_{1-6}$alkyl, and $C_{1-6}$haloalkyl; or thienyl, wherein the thienyl is optionally substituted with one or two members independently selected from: halo, $C_{1-6}$alkyl, and $C_{1-6}$haloalkyl; $R^3$ is H, and $R^4$ is

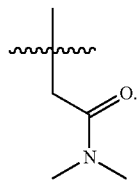

8. The compound of claim 1 or a pharmaceutically acceptable salt, solvate, stereoisomer, isotopic variant, or N-oxide thereof, wherein $R^2$ is phenyl; o-tolyl; m-tolyl; p-tolyl; 4-tert-butylphenyl; 3-(trifluoromethyl)phenyl; 4-fluorophenyl; 3-fluorophenyl; 3-cyanophenyl; 3-chlorophenyl; 4-chlorophenyl; 3-(difluoromethyl)phenyl; 3-methoxyphenyl; 3-(difluoromethoxy) phenyl; 4-methoxyphenyl; 3-(trifluoromethoxy)phenyl; 2-ethoxyphenyl; 3-ethoxyphenyl; 3-cyclopropylphenyl; 3-(dimethylamino) phenyl; 2,3-dichlorophenyl; 2,3-difluorophenyl; 2,3-dimethylphenyl; 2-fluoro-3-(trifluoromethyl)phenyl; 2,4-dimethoxyphenyl; 2,3-dimethoxyphenyl; 2,4-difluorophenyl; 3,4-difluorophenyl; 3,4-dichlorophenyl; 3-(difluoromethyl)-4-fluoro-phenyl; 5-(difluoromethyl)-2-fluorophenyl; 2,6-di methyl phenyl; 3,5-dimethylphenyl; 3,5-difluorophenyl; 3-fluoro-5-(trifluoromethyl)phenyl; 2-methyl-5-(trifluoromethyl)phenyl; 2-methyl-3-(trifluoromethyl)phenyl; 4-chloro-3-methyl-phenyl; 4-fluoro-3-(trifluoromethyl)phenyl; 4-chloro-3-(trifluoromethyl)phenyl; 2-ethoxy-5-fluoro-phenyl; 3-chloro-2-fluoro-phenyl; 3-chloro-4-fluoro-phenyl; 2-chloro-4-methoxy-phenyl; 4-fluoro-2-methyl-phenyl; 4-fluoro-2-methoxy-phenyl; 2-fluoro-6-methoxy-phenyl; 3-fluoro-4-methoxy-phenyl; 3-fluoro-5-methyl-phenyl; 2-fluoro-3-methyl-phenyl; 4-fluoro-3-methyl-phenyl; 4-methoxy-3-methyl-phenyl; 4-fluoro-2,3-dimethyl-phenyl; 2,4-difluoro-3-methyl-phenyl; 2,3,4-trifluorophenyl; 3,4,5-trifluorophenyl; 3,4-difluoro-5-(trifluoromethyl)phenyl; 3-pyridyl; 2-(trifluoromethyl)-4-pyridyl; 2-thienyl; 5-methyl-2-thienyl; 5-ethyl-2-thienyl; 4-methyl-2-thienyl; 5-(trideuteriomethoxymethyl; 5-(hydroxymethyl)-2-thienyl; 5-fluoro-2-thienyl; 5-chloro-2-thienyl; 5-cyclopropyl-2-thienyl; 5-chloro-4-methyl-2-thienyl; 5-(difluoromethyl)-2-thienyl; 5-(difluoromethyl)-3-thienyl; 5-(trifluoromethyl)-2-thienyl; 5-(trifluoromethyl)-3-thienyl; 2-(trifluoromethyl)-3-thienyl; 4-(difluoromethyl)-2-thienyl; 5-(1,1,2,2,2-pentafluoroethyl)-2-thienyl; 4-methylthiazol-2-yl; 2-methylthiazol-5-yl; 2-(trifluoromethyl)thiazol-5-yl; or 2-(trifluoromethyl)thiazol-4-yl.

9. The compound of claim 1 or a pharmaceutically acceptable salt, solvate, stereoisomer, isotopic variant, or N-oxide thereof, wherein $R^3$ is $^1H$.

10. The compound of claim 1 or a pharmaceutically acceptable salt, solvate, stereoisomer, isotopic variant, or N-oxide thereof, wherein $R^3$ is $^2H$ or $^3H$.

11. The compound of claim 1 or a pharmaceutically acceptable salt, solvate, stereoisomer, isotopic variant, or N-oxide thereof, wherein $R^4$ is

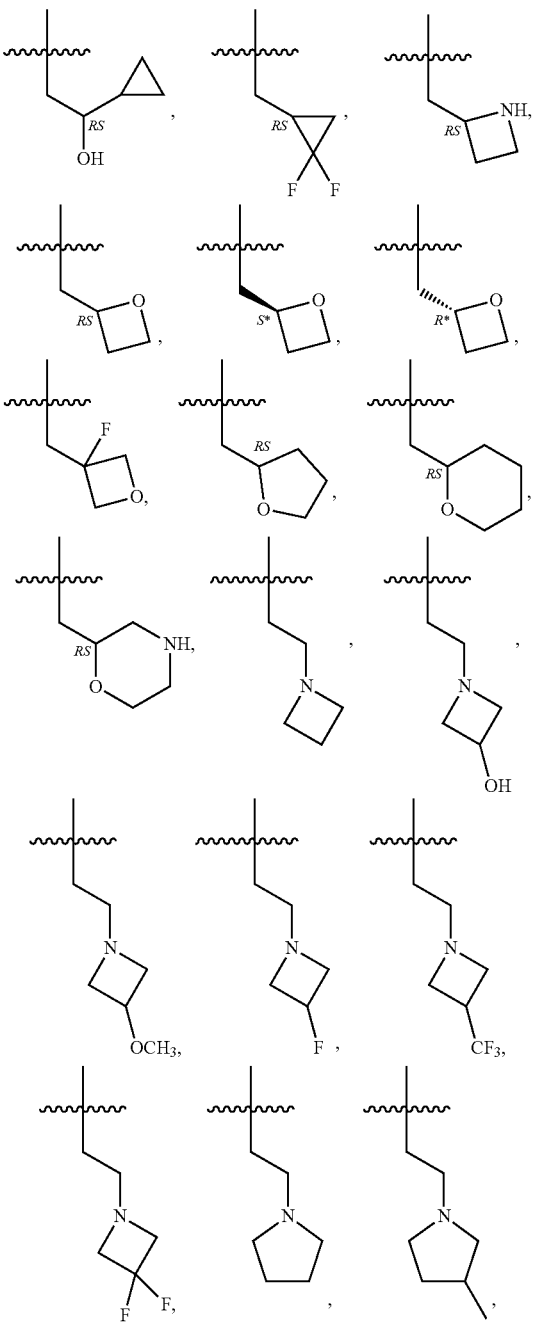

-continued

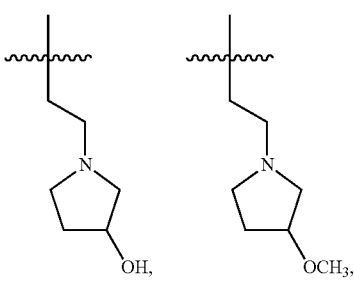

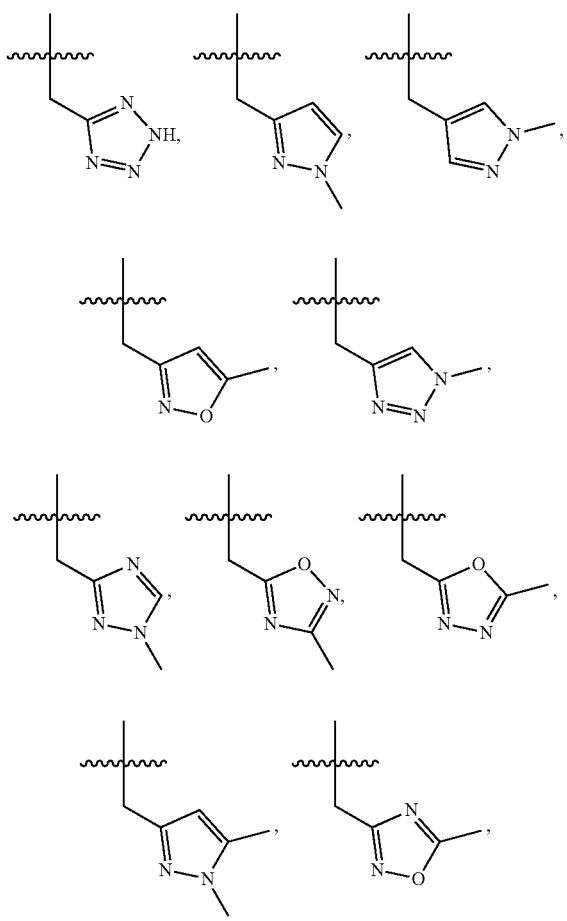

12. The compound of claim 1 or a pharmaceutically acceptable salt, solvate, stereoisomer, isotopic variant, or N-oxide thereof, wherein $R^4$ is -continued

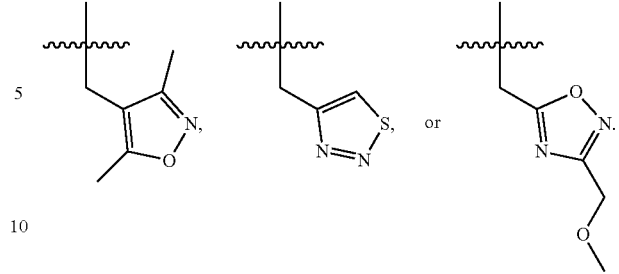

13. The compound of claim 1 or a pharmaceutically acceptable salt, solvate, stereoisomer, isotopic variant, or N-oxide thereof, wherein $R^4$ is

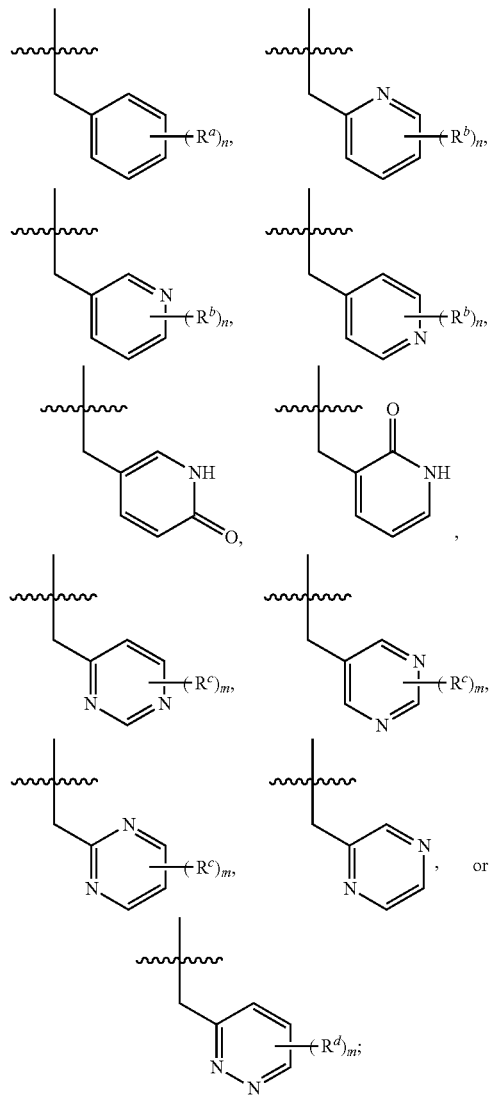

wherein
  $R^a$ is independently selected from: halo, CN, $OCH_3$, $C_{1-6}$alkyl, and $CF_3$;
  $R^b$ is independently selected from: Cl, F, $CH_3$, $OCH_3$, and $CF_3$;
  $R^c$ is F or $CH_3$;
  $R^d$ is $OCH_3$;
  M is 0 or 1; and
  n is 0, 1, or 2.

14. The compound of claim 1, having the structure of Formula (IB):

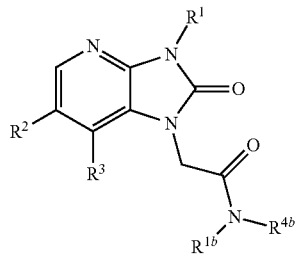

(IB)

or a pharmaceutically acceptable salt, solvate, stereoisomer, isotopic variant, or N-oxide thereof, wherein:

$R^1$ and $R^{1b}$ are each independently H or $CH_3$;

$R^2$ is selected from the group consisting of: phenyl substituted with one, two, or three members each independently selected from the group consisting of: halo, $C_{1-6}$alkyl, $C_{1-6}$haloalkyl, and $OC_{1-6}$alkyl; pyridinyl; thiazolyl substituted with $C_{1-6}$alkyl; and thienyl substituted with one or two members each independently selected from the group consisting of: halo, $C_{1-6}$alkyl, $C_{1-6}$haloalkyl, $CH_2OH$, and cyclopropyl;

$R^3$ is H; and $R^{4b}$ is H, $C_{1-6}$alkyl, 2-methoxyethyl, $C_{3-6}$cycloalkyl, 3,3-difluorocyclobutyl, 3,3-difluoro-1-methyl-cyclobutyl, cyclopentyl, oxetan-3-yl, 3-methyloxetan-3-yl, or 2-pyridyl.

15. The compound of claim 14 or a pharmaceutically acceptable salt, solvate, stereoisomer, isotopic variant, or N-oxide thereof, wherein $R^1$ is H; or $CH_3$;

$R^{1b}$ is $CH_3$;

$R^2$ is 3-(trifluoromethyl)phenyl, 4-fluoro-3-methyl-phenyl, 2,4-difluoro-3-methyl-phenyl, 5-(trifluoromethyl)-2-thienyl, 5-(difluoromethyl)-2-thienyl, or 5-chloro-4-methyl-2-thienyl;

$R^3$ is H; and $R^{4b}$ is $CH_3$.

16. The compound of claim 14 or a pharmaceutically acceptable salt, solvate, stereoisomer, isotopic variant, or N-oxide thereof, wherein $R^2$ is 3-pyridyl, 5-methyl-2-thienyl, 4-methyl-2-thienyl, 5-cyclopropyl-2-thienyl, 5-ethyl-2-thienyl, 5-chloro-2-thienyl, 5-(hydroxymethyl)-2-thienyl, 5-(trifluoromethyl)-2-thienyl, 5-(trifluoromethyl)-3-thienyl, 2-(trifluoromethyl)-3-thienyl, 5-(difluoromethyl)-2-thienyl, 5-(difluoromethyl)-3-thienyl, 5-chloro-4-methyl-2-thienyl, 5-fluoro-2-thienyl, 5-fluoro-2-thienyl, 2-methylthiazol-5-yl, 3,5-dimethylphenyl, 3-methoxyphenyl, 4-methoxyphenyl, 4-fluoro-2-methyl-phenyl, 2-fluoro-3-methyl-phenyl, 4-fluoro-3-methyl-phenyl, 4-chlorophenyl, 2,3-difluorophenyl, 3,5-difluorophenyl, 3,4-difluorophenyl, 2-ethoxyphenyl, 3-ethoxyphenyl, 4-methoxy-3-methyl-phenyl, 4-fluoro-2-methoxy-phenyl, 2-fluoro-6-methoxy-phenyl, 2,4-difluoro-3-methyl-phenyl, 3-(difluoromethyl)phenyl, 3-chloro-4-fluoro-phenyl, 2,4-dimethoxyphenyl, 2-ethoxy-5-fluoro-phenyl, 2-chloro-4-methoxy-phenyl, 3-(trifluoromethyl)phenyl, 2-(trifluoromethyl)thiazol-5-yl, 2-(trifluoromethyl)thiazol-4-yl, 2-fluoro-3-(trifluoromethyl)phenyl, or 3,4-difluoro-5-(trifluoromethyl)phenyl.

17. The compound of claim 1 having the structure of Formula (IC):

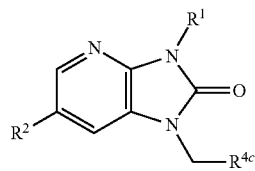

(IC)

or a pharmaceutically acceptable salt, solvate, stereoisomer, isotopic variant, or N-oxide thereof, wherein:

$R^1$ is H or $CH_3$;

$R^2$ is selected from the group consisting of: phenyl; phenyl substituted with one, two, or three members each independently selected from the group consisting of: halo, $C_{1-6}$alkyl, $C_{1-6}$haloalkyl, CN, $OC_{1-6}$alkyl, $OC_{1-6}$haloalkyl, and $N(CH_3)_2$; pyridinyl substituted with $CF_3$; and thienyl substituted with one or two members each independently selected from the group consisting of: halo, $C_{1-6}$alkyl, and $C_{1-6}$haloalkyl; and $R^{4c}$ is selected from the group consisting of: cyclopropyl substituted with one or two F members; CH(OH)cyclopropyl; azetidinyl; $CH_2$-azetidinyl; $CH_2$-azetidinyl substituted with one or two members independently selected from: F, OH, $OCH_3$, and $CF_3$; oxetanyl; oxetanyl substituted with F or $CH_3$; tetrahydrofuranyl; $CH_2$pyrrolidinyl; $CH_2$pyrrolidinyl substituted with $CH_3$, OH, or $OCH_3$; $CH_2$piperidinyl; $CH_2$piperidinyl substituted with OH, or F; morpholinyl; pyrazolyl substituted with one or two $CH_3$ members; triazolyl substituted with $CH_3$; tetrazolyl; isoxazolyl substituted with one or two $CH_3$ members; oxadiazolyl substituted with $CH_3$, or $CH_2OCH_3$; thiadiazolyl; pyridinyl; pyridinyl substituted with one or two members independently selected from the group consisting of: Cl, F, $CH_3$, $OCH_3$, and $CF_3$; (2-oxo-1H-pyridin-3-yl); 6-oxo-1H-pyridin-3-yl; pyrimidinyl; pyrimidinyl substituted with F or $CH_3$; pyrazinyl; pyridazinyl; pyridazinyl substituted with $OCH_3$; phenyl; and phenyl substituted with one or two members independently selected from the group consisting of: halo, CN, $OCH_3$, $C_{1-6}$alkyl, and $CF_3$.

18. The compound of claim 1 or a pharmaceutically acceptable salt thereof.

19. The compound of claim 14 or a pharmaceutically acceptable salt thereof.

20. The compound of claim 17 or a pharmaceutically acceptable salt thereof.

21. A compound having the structure of Formula (I):

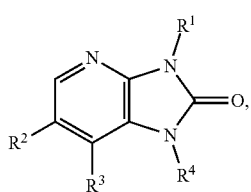

(I)

or a pharmaceutically acceptable salt, solvate, stereoisomer, isotopic variant, or N-oxide thereof, wherein:

$R^1$ is H; $CH_2F$; or $CH_3$;

$R^2$ is selected from the group consisting of: phenyl; phenyl substituted with one, two, or three members each independently selected from the group consisting of: halo, $C_{1-6}$alkyl, $C_{1-6}$haloalkyl, CN, $OC_{1-6}$alkyl, $OC_{1-6}$haloalkyl, $N(CH_3)_2$, and cyclopropyl; pyridinyl; pyridinyl substituted with F, $C_{1-4}$alkyl, or $C_{1-4}$haloalkyl; thiazolyl; thiazolyl substituted with $C_{1-6}$alkyl or $C_{1-6}$haloalkyl; thienyl; and thienyl substituted with one or two members each independently selected from the group consisting of: halo, $C_{1-6}$alkyl, $C_{1-6}$haloalkyl, $CH_2OH$, $CH_2OCH_3$, and cyclopropyl;

$R^3$ is H; and
$R^4$ is

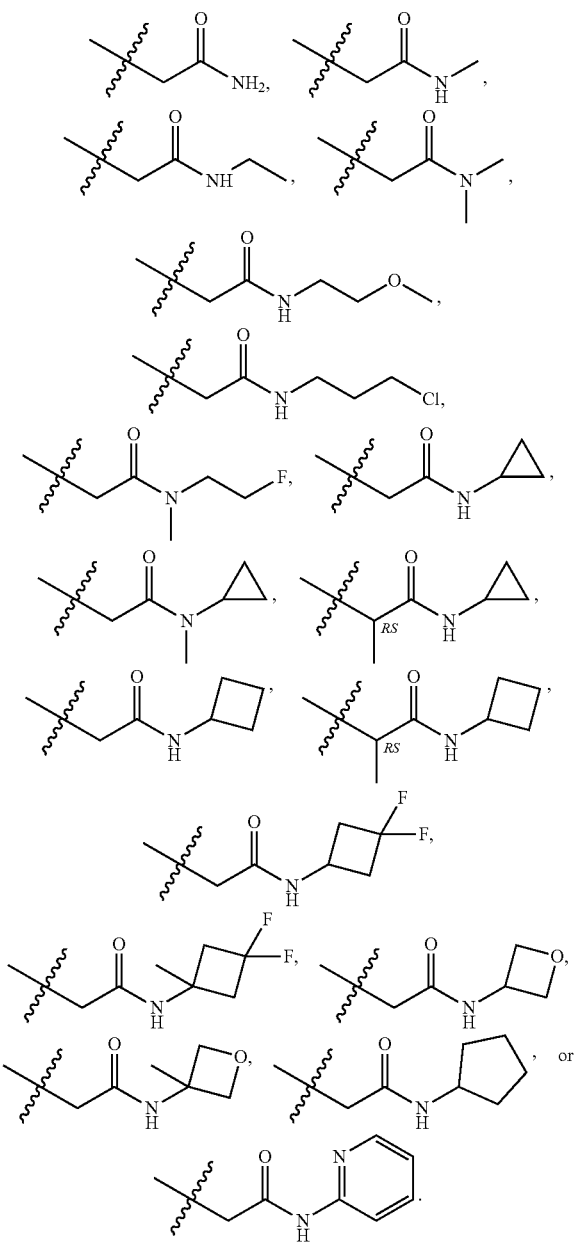

22. A compound selected from the group consisting of:
N-Ethyl-2-[6-(4-fluoro-2-methyl-phenyl)-2-oxo-3H-imidazo[4,5-b]pyridin-1-yl]acetamide;
6-(4-Fluoro-3-methyl-phenyl)-3-methyl-1-(2-pyridylmethyl)imidazo[4,5-b]pyridin-2-one;
6-(3-Fluorophenyl)-3-methyl-1-(pyrimidin-4-ylmethyl)imidazo[4,5-b]pyridin-2-one;
6-(3,4-Difluorophenyl)-3-methyl-1-[(5-methylisoxazol-3-yl)methyl]imidazo[4,5-b]pyridin-2-one;
2-[6-(5-Chloro-2-thienyl)-3-methyl-2-oxo-imidazo[4,5-b]pyridin-1-yl]-N,N-dimethyl-acetamide;
1-[(5-Methylisoxazol-3-yl)methyl]-6-phenyl-3H-imidazo[4,5-b]pyridin-2-one;
6-(4-Fluorophenyl)-1-[(5-methylisoxazol-3-yl)methyl]-3H-imidazo[4,5-b]pyridin-2-one;
6-(4-Fluorophenyl)-1-[(5-methyl-1,3,4-oxadiazol-2-yl)methyl]-3H-imidazo[4,5-b]pyridin-2-one;
3-Methyl-1-[(5-methylisoxazol-3-yl)methyl]-6-(4-methyl-2-thienyl)imidazo[4,5-b]pyridin-2-one;
6-(4-Fluorophenyl)-1-[(1-methylpyrazol-4-yl)methyl]-3H-imidazo[4,5-b]pyridin-2-one;
1-[(1,5-Dimethylpyrazol-3-yl)methyl]-6-(4-fluorophenyl)-3H-imidazo[4,5-b]pyridin-2-one;
1-[2-(Azetidin-1-yl)ethyl]-6-[3-(trifluoromethyl)phenyl]-3H-imidazo[4,5-b]pyridin-2-one;
1-[2-(Azetidin-1-yl)ethyl]-3-methyl-6-[3-(trifluoromethyl)phenyl]imidazo[4,5-b]pyridin-2-one;
1-[(5-Methylisoxazol-3-yl)methyl]-6-[3-(trifluoromethyl)phenyl]-3H-imidazo[4,5-b]pyridin-2-one;
N-Cyclopropyl-2-[2-oxo-6-[3-(trifluoromethyl)phenyl]-3H-imidazo[4,5-b]pyridin-1-yl]acetamide;
1-[(3-Chlorophenyl)methyl]-6-[3-(trifluoromethyl)phenyl]-3H-imidazo[4,5-b]pyridin-2-one;
1-[(2-Methoxy-3-pyridyl)methyl]-6-[3-(trifluoromethyl)phenyl]-3H-imidazo[4,5-b]pyridin-2-one;
1-(Pyrimidin-4-ylmethyl)-6-[3-(trifluoromethyl)phenyl]-3H-imidazo[4,5-b]pyridin-2-one;
(R/S)-1-(Tetrahydrofuran-2-ylmethyl)-6-[3-(trifluoromethyl)phenyl]-3H-imidazo[4,5-b]pyridin-2-one;
N,N-Dimethyl-2-[2-oxo-6-[5-(trifluoromethyl)-2-thienyl]-3H-imidazo[4,5-b]pyridin-1-yl]acetamide;
N,N-Dimethyl-2-[3-methyl-2-oxo-6-[5-(trifluoromethyl)-2-thienyl]imidazo[4,5-b]pyridin-1-yl]acetamide;
(R/S)-1-(2-Cyclopropyl-2-hydroxy-ethyl)-6-[3-(trifluoromethyl)phenyl]-3H-imidazo[4,5-b]pyridin-2-one;
1-[(2-Oxo-1H-pyridin-3-yl)methyl]-6-[3-(trifluoromethyl)phenyl]-3H-imidazo[4,5-b]pyridin-2-one;
(R/S)-6-(4-Fluoro-2-methyl-phenyl)-3-methyl-1-(oxetan-2-ylmethyl)imidazo[4,5-b]pyridin-2-one;
N-Cyclopropyl-2-[6-(4-fluoro-2-methyl-phenyl)-2-oxo-3H-imidazo[4,5-b]pyridin-1-yl]acetamide;
2-[6-(2-Chloro-4-methoxy-phenyl)-2-oxo-3H-imidazo[4,5-b]pyridin-1-yl]-N-cyclopropyl-acetamide;
N-Cyclopropyl-2-[6-(4-methoxyphenyl)-2-oxo-3H-imidazo[4,5-b]pyridin-1-yl]acetamide;
N-Cyclopropyl-2-[6-(3,5-dimethylphenyl)-2-oxo-3H-imidazo[4,5-b]pyridin-1-yl]acetamide;
N-Cyclopropyl-2-[6-(4-fluoro-2-methyl-phenyl)-2-oxo-3H-imidazo[4,5-b]pyridin-1-yl]-N-methyl-acetamide;
N-Cyclopropyl-2-[6-(4-methoxyphenyl)-2-oxo-3H-imidazo[4,5-b]pyridin-1-yl]-N-methyl-acetamide;
N-Cyclopropyl-2-[6-(4-fluoro-2-methyl-phenyl)-3-methyl-2-oxo-imidazo[4,5-b]pyridin-1-yl]acetamide;
6-(4-Fluoro-3-methyl-phenyl)-3-methyl-1-(3-pyridylmethyl)imidazo[4,5-b]pyridin-2-one;
6-(4-Fluoro-3-methyl-phenyl)-3-methyl-1-(4-pyridylmethyl)imidazo[4,5-b]pyridin-2-one;
6-(4-Fluoro-3-methyl-phenyl)-3-methyl-1-(pyrazin-2-ylmethyl)imidazo[4,5-b]pyridin-2-one;
6-(4-Fluoro-3-methyl-phenyl)-3-methyl-1-(pyrimidin-5-ylmethyl)imidazo[4,5-b]pyridin-2-one;
6-(4-Fluoro-3-methyl-phenyl)-3-methyl-1-(pyrimidin-2-ylmethyl)imidazo[4,5-b]pyridin-2-one;

6-(4-Fluoro-3-methyl-phenyl)-3-methyl-1-(pyridazin-3-ylmethyl)imidazo[4,5-b]pyridin-2-one;
6-(3-Fluorophenyl)-3-methyl-1-(3-pyridylmethyl)imidazo[4,5-b]pyridin-2-one;
6-(3-Fluorophenyl)-3-methyl-1-(4-pyridylmethyl)imidazo[4,5-b]pyridin-2-one;
6-(3-Fluorophenyl)-3-methyl-1-(2-pyridylmethyl)imidazo[4,5-b]pyridin-2-one;
6-(3-Fluorophenyl)-3-methyl-1-(pyrimidin-5-ylmethyl)imidazo[4,5-b]pyridin-2-one;
6-(3-Fluorophenyl)-3-methyl-1-(pyrazin-2-ylmethyl)imidazo[4,5-b]pyridin-2-one;
6-(3-Fluorophenyl)-3-methyl-1-(pyrimidin-2-ylmethyl)imidazo[4,5-b]pyridin-2-one;
6-(3-Fluorophenyl)-3-methyl-1-(pyridazin-3-ylmethyl)imidazo[4,5-b]pyridin-2-one;
6-(3,4-Difluorophenyl)-3-methyl-1-(4-pyridylmethyl)imidazo[4,5-b]pyridin-2-one;
6-(3,4-Difluorophenyl)-3-methyl-1-(3-pyridylmethyl)imidazo[4,5-b]pyridin-2-one;
6-(3,4-Difluorophenyl)-3-methyl-1-(pyrimidin-5-ylmethyl)imidazo[4,5-b]pyridin-2-one;
6-(3,4-Difluorophenyl)-3-methyl-1-(pyridazin-3-ylmethyl)imidazo[4,5-b]pyridin-2-one;
6-(3,4-difluorophenyl)-3-methyl-1-(2-pyridylmethyl)imidazo[4,5-b]pyridin-2-one;
6-(3,4-Difluorophenyl)-3-methyl-1-(pyrazin-2-ylmethyl)imidazo[4,5-b]pyridin-2-one;
6-(3,4-Difluorophenyl)-3-methyl-1-(pyrimidin-2-ylmethyl)imidazo[4,5-b]pyridin-2-one;
6-(2,4-Difluoro-3-methyl-phenyl)-3-methyl-1-(pyrimidin-2-ylmethyl)imidazo[4,5-b]pyridin-2-one;
6-(2,4-Difluoro-3-methyl-phenyl)-3-methyl-1-(4-pyridylmethyl)imidazo[4,5-b]pyridin-2-one;
6-(2,4-Difluoro-3-methyl-phenyl)-3-methyl-1-(pyridazin-3-ylmethyl)imidazo[4,5-b]pyridin-2-one;
6-(2,4-Difluoro-3-methyl-phenyl)-3-methyl-1-(2-pyridylmethyl)imidazo[4,5-b]pyridin-2-one;
6-(2,4-Difluoro-3-methyl-phenyl)-3-methyl-1-(pyrimidin-5-ylmethyl)imidazo[4,5-b]pyridin-2-one;
6-(3,4-Difluorophenyl)-3-methyl-1-(pyrimidin-4-ylmethyl)imidazo[4,5-b]pyridin-2-one;
6-(4-Fluoro-3-methyl-phenyl)-3-methyl-1-(pyrimidin-4-ylmethyl)imidazo[4,5-b]pyridin-2-one;
6-(2,4-Difluoro-3-methyl-phenyl)-3-methyl-1-(pyrimidin-4-ylmethyl)imidazo[4,5-b]pyridin-2-one;
6-(3,4-Difluorophenyl)-3-methyl-1-[(5-methyl-1,3,4-oxadiazol-2-yl)methyl]imidazo[4,5-b]pyridin-2-one;
3-Methyl-1-[(5-methylisoxazol-3-yl)methyl]-6-[3-(trifluoromethyl)phenyl]imidazo[4,5-b]pyridin-2-one;
3-Methyl-1-[(5-methyl-1,3,4-oxadiazol-2-yl)methyl]-6-[3-(trifluoromethyl)phenyl]imidazo[4,5-b]pyridin-2-one;
3-Methyl-1-[(3-methyl-1,2,4-oxadiazol-5-yl)methyl]-6-[3-(trifluoromethyl)phenyl]imidazo[4,5-b]pyridin-2-one;
6-(3,4-Difluorophenyl)-3-methyl-1-[(3-methyl-1,2,4-oxadiazol-5-yl)methyl]imidazo[4,5-b]pyridin-2-one;
N,N-Dimethyl-2-[3-methyl-6-(5-methyl-2-thienyl)-2-oxo-imidazo[4,5-b]pyridin-1-yl]acetamide;
2-[6-(5-Ethyl-2-thienyl)-3-methyl-2-oxo-imidazo[4,5-b]pyridin-1-yl]-N,N-dimethyl-acetamide;
N,N-Dimethyl-2-[3-methyl-6-(4-methyl-2-thienyl)-2-oxo-imidazo[4,5-b]pyridin-1-yl]acetamide;
2-[6-(5-Fluoro-2-thienyl)-3-methyl-2-oxo-imidazo[4,5-b]pyridin-1-yl]-N,N-dimethyl-acetamide;
3-Methyl-1-(pyridazin-3-ylmethyl)-6-[5-(trifluoromethyl)-2-thienyl]imidazo[4,5-b]pyridin-2-one;
6-(5-Fluoro-2-thienyl)-3-methyl-1-(pyridazin-3-ylmethyl)imidazo[4,5-b]pyridin-2-one;
2-[6-[5-(Hydroxymethyl)-2-thienyl]-3-methyl-2-oxo-imidazo[4,5-b]pyridin-1-yl]-N,N-dimethyl-acetamide;
2-[6-[5-(Difluoromethyl)-2-thienyl]-3-methyl-2-oxo-imidazo[4,5-b]pyridin-1-yl]-N,N-dimethyl-acetamide;
N,N-Dimethyl-2-[3-methyl-2-oxo-6-[2-(trifluoromethyl)-3-thienyl]imidazo[4,5-b]pyridin-1-yl]acetamide;
2-[6-[5-(Difluoromethyl)-3-thienyl]-3-methyl-2-oxo-imidazo[4,5-b]pyridin-1-yl]-N,N-dimethyl-acetamide;
6-[5-(Difluoromethyl)-2-thienyl]-3-methyl-1-(pyridazin-3-ylmethyl)imidazo[4,5-b]pyridin-2-one;
N,N-Dimethyl-2-[3-methyl-2-oxo-6-[5-(trifluoromethyl)-3-thienyl]imidazo[4,5-b]pyridin-1-yl]acetamide;
3-Methyl-1-(pyridazin-3-ylmethyl)-6-[5-(trifluoromethyl)-3-thienyl]imidazo[4,5-b]pyridin-2-one;
N,N-Dimethyl-2-[3-methyl-2-oxo-6-[2-(trifluoromethyl)thiazol-4-yl]imidazo[4,5-b]pyridin-1-yl]acetamide;
2-[6-(5-Cyclopropyl-2-thienyl)-3-methyl-2-oxo-imidazo[4,5-b]pyridin-1-yl]-N,N-dimethyl-acetamide;
N,N-Dimethyl-2-[3-methyl-6-(2-methylthiazol-5-yl)-2-oxo-imidazo[4,5-b]pyridin-1-yl]acetamide;
N,N-Dimethyl-2-[3-methyl-2-oxo-6-[2-(trifluoromethyl)thiazol-5-yl]imidazo[4,5-b]pyridin-1-yl]acetamide;
N,N-Dimethyl-2-[3-methyl-2-oxo-6-[5-(trideuteriomethoxymethyl)-2-thienyl]imidazo[4,5-b]pyridin-1-yl]acetamide;
1-[(5-Methylisoxazol-3-yl)methyl]-6-(4-methyl-2-thienyl)-3H-imidazo[4,5-b]pyridin-2-one;
1-[(5-Methylisoxazol-3-yl)methyl]-6-(o-tolyl)-3H-imidazo[4,5-b]pyridin-2-one;
1-[(3-Methyl-1,2,4-oxadiazol-5-yl)methyl]-6-(4-methyl-2-thienyl)-3H-imidazo[4,5-b]pyridin-2-one;
6-(4-Fluorophenyl)-1-[(1-methylpyrazol-3-yl)methyl]-3H-imidazo[4,5-b]pyridin-2-one;
6-(4-Fluoro-3-methyl-phenyl)-1-[(1-methylpyrazol-3-yl)methyl]-3H-imidazo[4,5-b]pyridin-2-one;
6-(3-Chloro-4-fluoro-phenyl)-1-[(1-methylpyrazol-3-yl)methyl]-3H-imidazo[4,5-b]pyridin-2-one;
6-(3,4-Difluorophenyl)-1-[(1-methylpyrazol-3-yl)methyl]-3H-imidazo[4,5-b]pyridin-2-one;
6-(2,4-Difluorophenyl)-1-[(1-methylpyrazol-3-yl)methyl]-3H-imidazo[4,5-b]pyridin-2-one;
(R/S)-3-methyl-1-(oxetan-2-ylmethyl)-6-[3-(trifluoromethyl)phenyl]imidazo[4,5-b]pyridin-2-one;
6-(2,4-Difluoro-3-methyl-phenyl)-3-methyl-1-(pyrazin-2-ylmethyl)imidazo[4,5-b]pyridin-2-one;
6-(4-Fluorophenyl)-1-[(3-methyl-1,2,4-oxadiazol-5-yl)methyl]-3H-imidazo[4,5-b]pyridin-2-one;
6-(4-Fluorophenyl)-1-[(1-methyl-1,2,4-triazol-3-yl)methyl]-3H-imidazo[4,5-b]pyridin-2-one;
6-(4-Fluorophenyl)-1-[(1-methyltriazol-4-yl)methyl]-3H-imidazo[4,5-b]pyridin-2-one;
6-(3,4-Difluorophenyl)-1-[(3-methyl-1,2,4-oxadiazol-5-yl)methyl]-3H-imidazo[4,5-b]pyridin-2-one;
6-(3,4-Difluorophenyl)-1-[(5-methyl-1,2,4-oxadiazol-3-yl)methyl]-3H-imidazo[4,5-b]pyridin-2-one;
6-(3,4-Difluorophenyl)-1-[[3-(methoxymethyl)-1,2,4-oxadiazol-5-yl]methyl]-3H-imidazo[4,5-b]pyridin-2-one;
1-(2-Pyrrolidin-1-ylethyl)-6-[3-(trifluoromethyl)phenyl]-3H-imidazo[4,5-b]pyridin-2-one;

1-[2-(3-Hydroxyazetidin-1-yl)ethyl]-6-[3-(trifluoromethyl)phenyl]-3H-imidazo[4,5-b]pyridin-2-one;
1-[2-(3-Methoxyazetidin-1-yl)ethyl]-6-[3-(trifluoromethyl)phenyl]-3H-imidazo[4,5-b]pyridin-2-one;
1-[2-(Azetidin-1-yl)ethyl]-6-(4-fluoro-2-methyl-phenyl)-3H-imidazo[4,5-b]pyridin-2-one;
1-[2-(Azetidin-1-yl)ethyl]-6-(o-tolyl)-3H-imidazo[4,5-b]pyridin-2-one;
1-[2-(Azetidin-1-yl)ethyl]-6-phenyl-3H-imidazo[4,5-b]pyridin-2-one;
1-[2-(Azetidin-1-yl)ethyl]-6-(m-tolyl)-3H-imidazo[4,5-b]pyridin-2-one;
1-[2-(Azetidin-1-yl)ethyl]-6-[2-(trifluoromethyl)-4-pyridyl]-3H-imidazo[4,5-b]pyridin-2-one;
1-[2-(Azetidin-1-yl)ethyl]-6-(4-fluoro-3-methyl-phenyl)-3H-imidazo[4,5-b]pyridin-2-one;
1-[2-(Azetidin-1-yl)ethyl]-6-(2,6-dimethylphenyl)-3H-imidazo[4,5-b]pyridin-2-one;
1-[2-(Azetidin-1-yl)ethyl]-6-(3-chlorophenyl)-3H-imidazo[4,5-b]pyridin-2-one;
1-[2-(Azetidin-1-yl)ethyl]-6-(3,5-difluorophenyl)-3H-imidazo[4,5-b]pyridin-2-one;
1-[2-(Azetidin-1-yl)ethyl]-6-[3-(trifluoromethoxy)phenyl]-3H-imidazo[4,5-b]pyridin-2-one;
1-[2-(1-Piperidyl)ethyl]-6-[3-(trifluoromethyl)phenyl]-3H-imidazo[4,5-b]pyridin-2-one;
1-[2-(4-Fluoro-1-piperidyl)ethyl]-6-[3-(trifluoromethyl)phenyl]-3H-imidazo[4,5-b]pyridin-2-one;
1-[2-(3-Fluoroazetidin-1-yl)ethyl]-6-[3-(trifluoromethyl)phenyl]-3H-imidazo[4,5-b]pyridin-2-one;
1-[2-(3-Methylpyrrolidin-1-yl)ethyl]-6-[3-(trifluoromethyl)phenyl]-3H-imidazo[4,5-b]pyridin-2-one;
1-[2-(4-Hydroxy-1-piperidyl)ethyl]-6-[3-(trifluoromethyl)phenyl]-3H-imidazo[4,5-b]pyridin-2-one;
1-[2-[3-(Trifluoromethyl)azetidin-1-yl]ethyl]-6-[3-(trifluoromethyl)phenyl]-3H-imidazo[4,5-b]pyridin-2-one;
1-[2-(3,3-Difluoroazetidin-1-yl)ethyl]-6-[3-(trifluoromethyl)phenyl]-3H-imidazo[4,5-b]pyridin-2-one;
1-[2-(Azetidin-1-yl)ethyl]-6-[2-methyl-3-(trifluoromethyl)phenyl]-3H-imidazo[4,5-b]pyridin-2-one;
1-[2-(Azetidin-1-yl)ethyl]-6-(2,3-dimethylphenyl)-3H-imidazo[4,5-b]pyridin-2-one;
1-[2-(Azetidin-1-yl)ethyl]-6-(3,5-dimethylphenyl)-3H-imidazo[4,5-b]pyridin-2-one;
1-[2-(Azetidin-1-yl)ethyl]-6-(4-fluoro-2,3-dimethyl-phenyl)-3H-imidazo[4,5-b]pyridin-2-one;
1-[2-(Azetidin-1-yl)ethyl]-6-[2-methyl-5-(trifluoromethyl)phenyl]-3H-imidazo[4,5-b]pyridin-2-one;
6-(3,5-Difluorophenyl)-1-(2-pyrrolidin-1-ylethyl)-3H-imidazo[4,5-b]pyridin-2-one;
6-(3,5-Difluorophenyl)-1-[2-(3-hydroxypyrrolidin-1-yl)ethyl]-3H-imidazo[4,5-b]pyridin-2-one;
6-(3,5-Difluorophenyl)-1-[2-(3-methoxypyrrolidin-1-yl)ethyl]-3H-imidazo[4,5-b]pyridin-2-one;
6-(4-Fluoro-2-methyl-phenyl)-1-(2-pyrrolidin-1-ylethyl)-3H-imidazo[4,5-b]pyridin-2-one;
6-(2,6-Dimethylphenyl)-1-(2-pyrrolidin-1-ylethyl)-3H-imidazo[4,5-b]pyridin-2-one;
6-(o-Tolyl)-1-(2-pyrrolidin-1-ylethyl)-3H-imidazo[4,5-b]pyridin-2-one;
6-Phenyl-1-(2-pyrrolidin-1-ylethyl)-3H-imidazo[4,5-b]pyridin-2-one;
1-[2-(3-Fluoroazetidin-1-yl)ethyl]-6-[2-methyl-3-(trifluoromethyl)phenyl]-3H-imidazo[4,5-b]pyridin-2-one;
6-(2,3-Dimethylphenyl)-1-[2-(3-fluoroazetidin-1-yl)ethyl]-3H-imidazo[4,5-b]pyridin-2-one;
6-(3,5-Dimethylphenyl)-1-[2-(3-fluoroazetidin-1-yl)ethyl]-3H-imidazo[4,5-b]pyridin-2-one;
1-[2-(3-Fluoroazetidin-1-yl)ethyl]-6-(4-fluoro-2,3-dimethyl-phenyl)-3H-imidazo[4,5-b]pyridin-2-one;
1-[2-(3-Fluoroazetidin-1-yl)ethyl]-6-[2-methyl-5-(trifluoromethyl)phenyl]-3H-imidazo[4,5-b]pyridin-2-one;
1-[2-(3-Fluoroazetidin-1-yl)ethyl]-6-(o-tolyl)-3H-imidazo[4,5-b]pyridin-2-one;
1-[2-(3-Fluoroazetidin-1-yl)ethyl]-6-(4-fluoro-2-methyl-phenyl)-3H-imidazo[4,5-b]pyridin-2-one;
1-[2-(3-Fluoroazetidin-1-yl)ethyl]-6-phenyl-3H-imidazo[4,5-b]pyridin-2-one;
N-Cyclobutyl-2-[2-oxo-6-[3-(trifluoromethyl)phenyl]-3H-imidazo[4,5-b]pyridin-1-yl]acetamide;
N-(Oxetan-3-yl)-2-[2-oxo-6-[3-(trifluoromethyl)phenyl]-3H-imidazo[4,5-b]pyridin-1-yl]acetamide;
N-(3,3-Difluorocyclobutyl)-2-[2-oxo-6-[3-(trifluoromethyl)phenyl]-3H-imidazo[4,5-b]pyridin-1-yl]acetamide;
N-(3,3-Difluoro-1-methyl-cyclobutyl)-2-[3-methyl-2-oxo-6-[3-(trifluoromethyl)phenyl]imidazo[4,5-b]pyridin-1-yl]acetamide;
N-(3-Methyloxetan-3-yl)-2-[3-methyl-2-oxo-6-[3-(trifluoromethyl)phenyl]imidazo[4,5-b]pyridin-1-yl]acetamide;
N-(3,3-Difluorocyclobutyl)-2-[3-methyl-2-oxo-6-[3-(trifluoromethyl)phenyl]imidazo[4,5-b]pyridin-1-yl]acetamide;
(R/S)—N-Cyclopropyl-2-[2-oxo-6-[3-(trifluoromethyl)phenyl]-3H-imidazo[4,5-b]pyridin-1-yl]propanamide;
N-Cyclopentyl-2-[2-oxo-6-[3-(trifluoromethyl)phenyl]-3H-imidazo[4,5-b]pyridin-1-yl]acetamide;
2-[2-Oxo-6-[3-(trifluoromethyl)phenyl]-3H-imidazo[4,5-b]pyridin-1-yl]-N-(2-pyridyl)acetamide;
N-(3,3-Difluoro-1-methyl-cyclobutyl)-2-[2-oxo-6-[3-(trifluoromethyl)phenyl]-3H-imidazo[4,5-b]pyridin-1-yl]acetamide;
1-[(6-Methoxy-3-pyridyl)methyl]-6-[3-(trifluoromethyl)phenyl]-3H-imidazo[4,5-b]pyridin-2-one;
1-(Cyclopropylmethyl)-6-[3-(trifluoromethyl)phenyl]-3H-imidazo[4,5-b]pyridin-2-one;
3-[[2-Oxo-6-[3-(trifluoromethyl)phenyl]-3H-imidazo[4,5-b]pyridin-1-yl]methyl]benzonitrile;
2-[[2-Oxo-6-[3-(trifluoromethyl)phenyl]-3H-imidazo[4,5-b]pyridin-1-yl]methyl]benzonitrile;
(R/S)-1-(Oxetan-2-ylmethyl)-6-[3-(trifluoromethyl)phenyl]-3H-imidazo[4,5-b]pyridin-2-one;
(R/S)-1-(Morpholin-2-ylmethyl)-6-[3-(trifluoromethyl)phenyl]-3H-imidazo[4,5-b]pyridin-2-one;
(R/S)-1-(Tetrahydropyran-2-ylmethyl)-6-[3-(trifluoromethyl)phenyl]-3H-imidazo[4,5-b]pyridin-2-one;
6-[3-(Trifluoromethyl)phenyl]-1-[[4-(trifluoromethyl)phenyl]methyl]-3H-imidazo[4,5-b]pyridin-2-one;
1-[(3-Fluoro-4-methoxy-phenyl)methyl]-6-[3-(trifluoromethyl)phenyl]-3H-imidazo[4,5-b]pyridin-2-one;
1-[(4-Fluoro-3-methyl-phenyl)methyl]-6-[3-(trifluoromethyl)phenyl]-3H-imidazo[4,5-b]pyridin-2-one;
1-[(3-Fluorophenyl)methyl]-6-[3-(trifluoromethyl)phenyl]-3H-imidazo[4,5-b]pyridin-2-one;
(R*)-1-(Oxetan-2-ylmethyl)-6-[3-(trifluoromethyl)phenyl]-3H-imidazo[4,5-b]pyridin-2-one;
(S*)-1-(Oxetan-2-ylmethyl)-6-[3-(trifluoromethyl)phenyl]-3H-imidazo[4,5-b]pyridin-2-one;
(R/S)-1-[(2,2-Difluorocyclopropyl)methyl]-6-[3-(trifluoromethyl)phenyl]-3H-imidazo[4,5-b]pyridin-2-one;
1-[(3-Fluorooxetan-3-yl)methyl]-6-[3-(trifluoromethyl)phenyl]-3H-imidazo[4,5-b]pyridin-2-one;

1-(Pyrimidin-2-ylmethyl)-6-[3-(trifluoromethyl)phenyl]-3H-imidazo[4,5-b]pyridin-2-one;
1-(2-Pyridylmethyl)-6-[3-(trifluoromethyl)phenyl]-3H-imidazo[4,5-b]pyridin-2-one;
1-(4-Pyridylmethyl)-6-[3-(trifluoromethyl)phenyl]-3H-imidazo[4,5-b]pyridin-2-one;
1-(3-Pyridylmethyl)-6-[3-(trifluoromethyl)phenyl]-3H-imidazo[4,5-b]pyridin-2-one;
1-[(2-M ethylpyrimidin-5-yl)methyl]-6-[3-(trifluoromethyl)phenyl]-3H-imidazo[4,5-b]pyridin-2-one;
1-(Pyridazin-3-ylmethyl)-6-[3-(trifluoromethyl)phenyl]-3H-imidazo[4,5-b]pyridin-2-one;
1-[(3-M ethoxy-2-pyridyl) methyl]-6-[3-(trifluoromethyl)phenyl]-3H-imidazo[4,5-b]pyridin-2-one;
1-[(3-Fluoro-5-methyl-2-pyridyl)methyl]-6-[3-(trifluoromethyl)phenyl]-3H-imidazo[4,5-b]pyridin-2-one;
1-[(6-Methyl-3-pyridyl)methyl]-6-[3-(trifluoromethyl)phenyl]-3H-imidazo[4,5-b]pyridin-2-one;
1-(2H-Tetrazol-5-ylmethyl)-6-[3-(trifluoromethyl)phenyl]-3H-imidazo[4,5-b]pyridin-2-one;
1-[Difluoro(3-pyridyl)methyl]-6-[3-(trifluoromethyl)phenyl]-3H-imidazo[4,5-b]pyridin-2-one;
1-[(6-Fluoro-3-pyridyl)methyl]-6-[3-(trifluoromethyl)phenyl]-3H-imidazo[4,5-b]pyridin-2-one;
1-[(5-Methyl-3-pyridyl)methyl]-6-[3-(trifluoromethyl)phenyl]-3H-imidazo[4,5-b]pyridin-2-one;
1-(Thiadiazol-4-ylmethyl)-6-[3-(trifluoromethyl)phenyl]-3H-imidazo[4,5-b]pyridin-2-one;
1-[(6-Oxo-1H-pyridin-3-yl)methyl]-6-[3-(trifluoromethyl)phenyl]-3H-imidazo[4,5-b]pyridin-2-one;
(R/S)-1-(Azetidin-2-ylmethyl)-3-methyl-6-[3-(trifluoromethyl)phenyl]imidazo[4,5-b]pyridin-2-one;
3-Methyl-1-(pyrimidin-4-ylmethyl)-6-[3-(trifluoromethyl)phenyl]imidazo[4,5-b]pyridin-2-one;
3-Methyl-1-(pyrimidin-5-ylmethyl)-6-[3-(trifluoromethyl)phenyl]imidazo[4,5-b]pyridin-2-one;
3-Methyl-1-[(2-methylpyrimidin-4-yl)methyl]-6-[3-(trifluoromethyl)phenyl]imidazo[4,5-b]pyridin-2-one;
3-Methyl-1-(pyrazin-2-ylmethyl)-6-[3-(trifluoromethyl)phenyl]imidazo[4,5-b]pyridin-2-one;
3-Methyl-1-(4-pyridylmethyl)-6-[3-(trifluoromethyl)phenyl]imidazo[4,5-b]pyridin-2-one;
3-Methyl-1-(2-pyridylmethyl)-6-[3-(trifluoromethyl)phenyl]imidazo[4,5-b]pyridin-2-one;
1-[(6-M ethoxypyridazin-3-yl)methyl]-6-[3-(trifluoromethyl)phenyl]-3H-imidazo[4,5-b]pyridin-2-one;
1-(Pyrazin-2-ylmethyl)-6-[3-(trifluoromethyl)phenyl]-3H-imidazo[4,5-b]pyridin-2-one;
1-[(2-M ethylpyrimidin-4-yl)methyl]-6-[3-(trifluoromethyl)phenyl]-3H-imidazo[4,5-b]pyridin-2-one;
1-(Pyrimidin-5-ylmethyl)-6-[3-(trifluoromethyl)phenyl]-3H-imidazo[4,5-b]pyridin-2-one;
1-[(5-Fluoropyrimidin-2-yl)methyl]-6-[3-(trifluoromethyl)phenyl]-3H-imidazo[4,5-b]pyridin-2-one;
6-[3-(Trifluoromethyl)phenyl]-1-[[6-(trifluoromethyl)-3-pyridyl]methyl]-3H-imidazo[4,5-b]pyridin-2-one;
1-[(5-Fluoro-3-pyridyl)methyl]-6-[3-(trifluoromethyl)phenyl]-3H-imidazo[4,5-b]pyridin-2-one;
6-[3-(Trifluoromethyl)phenyl]-1-[[5-(trifluoromethyl)-3-pyridyl]methyl]-3H-imidazo[4,5-b]pyridin-2-one;
6-[3-(Trifluoromethyl)phenyl]-1-[[4-(trifluoromethyl)-3-pyridyl]methyl]-3H-imidazo[4,5-b]pyridin-2-one;
3-Methyl-1-(pyrimidin-2-ylmethyl)-6-[3-(trifluoromethyl)phenyl]imidazo[4,5-b]pyridin-2-one;
(R/S)-1-(Azetidin-2-ylmethyl)-6-[3-(trifluoromethyl)phenyl]-3H-imidazo[4,5-b]pyridin-2-one;
(R/S)-1-(Azetidin-2-ylmethyl)-6-[2-fluoro-3-(trifluoromethyl)phenyl]-3H-imidazo[4,5-b]pyridin-2-one;
(R/S)-1-(Azetidin-2-ylmethyl)-6-phenyl-3H-imidazo[4,5-b]pyridin-2-one;
(R/S)-1-(Azetidin-2-ylmethyl)-6-(4-fluorophenyl)-3H-imidazo[4,5-b]pyridin-2-one;
(R/S)-1-(Azetidin-2-ylmethyl)-6-[4-fluoro-3-(trifluoromethyl)phenyl]-3H-imidazo[4,5-b]pyridin-2-one;
(R/S)-1-(Azetidin-2-ylmethyl)-6-(2,3-dichlorophenyl)-3H-imidazo[4,5-b]pyridin-2-one;
6-(4-Fluoro-3-methyl-phenyl)-1-[(5-methyl-3-pyridyl)methyl]-3H-imidazo[4,5-b]pyridin-2-one;
6-(2,4-Difluoro-3-methyl-phenyl)-1-[(5-methyl-3-pyridyl)methyl]-3H-imidazo[4,5-b]pyridin-2-one;
(R/S)-6-[4-Fluoro-3-(trifluoromethyl)phenyl]-1-(oxetan-2-ylmethyl)-3H-imidazo[4,5-b]pyridin-2-one;
6-(3,4-Difluorophenyl)-1-[(5-methyl-3-pyridyl)methyl]-3H-imidazo[4,5-b]pyridin-2-one;
6-(3-Chlorophenyl)-1-[(5-methyl-3-pyridyl)methyl]-3H-imidazo[4,5-b]pyridin-2-one;
6-(3-Fluorophenyl)-1-[(5-methyl-3-pyridyl)methyl]-3H-imidazo[4,5-b]pyridin-2-one;
6-(3,4-Difluorophenyl)-1-[(4-methyl-3-pyridyl)methyl]-3H-imidazo[4,5-b]pyridin-2-one;
6-(3-Fluorophenyl)-1-[(4-methyl-3-pyridyl)methyl]-3H-imidazo[4,5-b]pyridin-2-one;
6-(4-Fluoro-3-methyl-phenyl)-1-[(4-methyl-3-pyridyl)methyl]-3H-imidazo[4,5-b]pyridin-2-one;
6-(2,4-Difluoro-3-methyl-phenyl)-1-[(4-methyl-3-pyridyl)methyl]-3H-imidazo[4,5-b]pyridin-2-one;
6-(3,4-Difluorophenyl)-1-(2-pyridylmethyl)-3H-imidazo[4,5-b]pyridin-2-one;
6-(2,4-Difluoro-3-methyl-phenyl)-1-(2-pyridylmethyl)-3H-imidazo[4,5-b]pyridin-2-one;
6-(3-Fluorophenyl)-1-(2-pyridylmethyl)-3H-imidazo[4,5-b]pyridin-2-one;
6-(3-Chlorophenyl)-1-(2-pyridylmethyl)-3H-imidazo[4,5-b]pyridin-2-one;
6-(4-Fluoro-3-methyl-phenyl)-1-(2-pyridylmethyl)-3H-imidazo[4,5-b]pyridin-2-one;
6-(3,4-Difluorophenyl)-1-[(3-methyl-2-pyridyl)methyl]-3H-imidazo[4,5-b]pyridin-2-one;
6-(3-Fluorophenyl)-1-[(3-methyl-2-pyridyl)methyl]-3H-imidazo[4,5-b]pyridin-2-one;
6-(4-Fluorophenyl)-1-(2-pyridylmethyl)-3H-imidazo[4,5-b]pyridin-2-one;
6-[3-(Difluoromethyl)phenyl]-1-(2-pyridylmethyl)-3H-imidazo[4,5-b]pyridin-2-one;
6-(3-Methoxyphenyl)-1-(2-pyridylmethyl)-3H-imidazo[4,5-b]pyridin-2-one;
6-(p-Tolyl)-1-(2-pyridylmethyl)-3H-imidazo[4,5-b]pyridin-2-one;
6-(3-fluorophenyl)-1-(3-pyridylmethyl)-3H-imidazo[4,5-b]pyridin-2-one;
6-[3-(Difluoromethyl)phenyl]-1-(3-pyridylmethyl)-3H-imidazo[4,5-b]pyridin-2-one;
6-(3,4-Difluorophenyl)-1-(3-pyridylmethyl)-3H-imidazo[4,5-b]pyridin-2-one;
6-(2,4-Difluoro-3-methyl-phenyl)-1-(3-pyridylmethyl)-3H-imidazo[4,5-b]pyridin-2-one;
6-(4-Fluoro-3-methyl-phenyl)-1-(3-pyridylmethyl)-3H-imidazo[4,5-b]pyridin-2-one;
6-(4-Fluorophenyl)-1-(3-pyridylmethyl)-3H-imidazo[4,5-b]pyridin-2-one;
6-(3-Chlorophenyl)-1-(3-pyridylmethyl)-3H-imidazo[4,5-b]pyridin-2-one;

6-(m-Tolyl)-1-(3-pyridylmethyl)-3H-imidazo[4,5-b]pyridin-2-one;
6-(3,4-Difluorophenyl)-1-[(5-fluoro-3-pyridyl)methyl]-3H-imidazo[4,5-b]pyridin-2-one;
6-(4-Fluoro-3-methyl-phenyl)-1-[(5-fluoro-3-pyridyl)methyl]-3H-imidazo[4,5-b]pyridin-2-one;
6-[3-(Difluoromethoxy)phenyl]-1-(3-pyridylmethyl)-3H-imidazo[4,5-b]pyridin-2-one;
6-(2,4-Difluoro-3-methyl-phenyl)-1-[(5-fluoro-3-pyridyl)methyl]-3H-imidazo[4,5-b]pyridin-2-one;
6-[3-(Difluoromethyl)phenyl]-1-[(5-fluoro-3-pyridyl)methyl]-3H-imidazo[4,5-b]pyridin-2-one;
6-(2,3-Difluorophenyl)-1-[(5-fluoro-3-pyridyl)methyl]-3H-imidazo[4,5-b]pyridin-2-one;
6-[3-(Difluoromethoxy)phenyl]-1-[(5-fluoro-3-pyridyl)methyl]-3H-imidazo[4,5-b]pyridin-2-one;
6-(3-Chlorophenyl)-1-[(5-fluoro-3-pyridyl)methyl]-3H-imidazo[4,5-b]pyridin-2-one;
6-(4-Chloro-3-methyl-phenyl)-1-[(5-fluoro-3-pyridyl)methyl]-3H-imidazo[4,5-b]pyridin-2-one;
1-[(5-Fluoro-3-pyridyl)methyl]-6-[3-(trifluoromethoxy)phenyl]-3H-imidazo[4,5-b]pyridin-2-one;
1-[(5-Methyl-3-pyridyl)methyl]-6-(3,4,5-trifluorophenyl)-3H-imidazo[4,5-b]pyridin-2-one;
6-[4-Fluoro-3-(trifluoromethyl)phenyl]-1-[(5-methyl-3-pyridyl)methyl]-3H-imidazo[4,5-b]pyridin-2-one;
6-(2,3-Difluorophenyl)-1-[(5-methyl-3-pyridyl)methyl]-3H-imidazo[4,5-b]pyridin-2-one;
6-(3,5-Difluorophenyl)-1-[(5-methyl-3-pyridyl)methyl]-3H-imidazo[4,5-b]pyridin-2-one;
1-[(4-Methyl-3-pyridyl)methyl]-6-(3,4,5-trifluorophenyl)-3H-imidazo[4,5-b]pyridin-2-one;
1-[(4-Methyl-3-pyridyl)methyl]-6-[3-(trifluoromethyl)phenyl]-3H-imidazo[4,5-b]pyridin-2-one;
6-[4-Fluoro-3-(trifluoromethyl)phenyl]-1-[(4-methyl-3-pyridyl)methyl]-3H-imidazo[4,5-b]pyridin-2-one;
1-[(3-Methyl-2-pyridyl)methyl]-6-[3-(trifluoromethyl)phenyl]-3H-imidazo[4,5-b]pyridin-2-one;
6-(4-Fluoro-3-methyl-phenyl)-1-[(3-methyl-2-pyridyl)methyl]-3H-imidazo[4,5-b]pyridin-2-one;
6-(2,4-Difluoro-3-methyl-phenyl)-1-[(3-methyl-2-pyridyl)methyl]-3H-imidazo[4,5-b]pyridin-2-one;
6-(3,5-Difluorophenyl)-1-[(3-methyl-2-pyridyl)methyl]-3H-imidazo[4,5-b]pyridin-2-one;
6-(2,3-Difluorophenyl)-1-[(3-methyl-2-pyridyl)methyl]-3H-imidazo[4,5-b]pyridin-2-one;
2-[6-(5-Chloro-4-methyl-2-thienyl)-2-oxo-3H-imidazo[4,5-b]pyridin-1-yl]-N,N-dimethyl-acetamide;
2-[6-(5-Chloro-4-methyl-2-thienyl)-3-methyl-2-oxo-imidazo[4,5-b]pyridin-1-yl]-N,N-dimethyl-acetamide;
6-(2,4-Difluoro-3-methyl-phenyl)-3-methyl-1-(3-pyridylmethyl)imidazo[4,5-b]pyridin-2-one;
6-(4-Fluoro-3-methyl-phenyl)-1-[(5-fluoro-3-pyridyl)methyl]-3-methyl-imidazo[4,5-b]pyridin-2-one;
6-(2,4-Difluoro-3-methyl-phenyl)-1-[(5-fluoro-3-pyridyl)methyl]-3-methyl-imidazo[4,5-b]pyridin-2-one;
6-[3-(Difluoromethoxy)phenyl]-1-[(5-fluoro-3-pyridyl)methyl]-3-methyl-imidazo[4,5-b]pyridin-2-one;
6-(3,4-Difluorophenyl)-1-[(5-fluoro-3-pyridyl)methyl]-3-methyl-imidazo[4,5-b]pyridin-2-one;
1-[(5-Fluoro-3-pyridyl)methyl]-3-methyl-6-(3,4,5-trifluorophenyl)imidazo[4,5-b]pyridin-2-one;
1-[(5-Fluoro-3-pyridyl)methyl]-3-methyl-6-[3-(trifluoromethoxy)phenyl]imidazo[4,5-b]pyridin-2-one;
6-(2,3-Difluorophenyl)-1-[(5-fluoro-3-pyridyl)methyl]-3-methyl-imidazo[4,5-b]pyridin-2-one;
1-[(5-Fluoro-3-pyridyl)methyl]-3-methyl-6-(2,3,4-trifluorophenyl)imidazo[4,5-b]pyridin-2-one;
6-(3-Chlorophenyl)-1-[(5-fluoro-3-pyridyl)methyl]-3-methyl-imidazo[4,5-b]pyridin-2-one;
6-(3-Chloro-2-fluoro-phenyl)-1-[(5-fluoro-3-pyridyl)methyl]-3-methyl-imidazo[4,5-b]pyridin-2-one;
1-[(5-Fluoro-3-pyridyl)methyl]-3-methyl-6-(m-tolyl)imidazo[4,5-b]pyridin-2-one;
6-(3,4-Dichlorophenyl)-1-[(5-fluoro-3-pyridyl)methyl]-3-methyl-imidazo[4,5-b]pyridin-2-one;
6-(2-Fluoro-3-methyl-phenyl)-1-[(5-fluoro-3-pyridyl)methyl]-3-methyl-imidazo[4,5-b]pyridin-2-one;
3-Methyl-1-(3-pyridylmethyl)-6-(3,4,5-trifluorophenyl)imidazo[4,5-b]pyridin-2-one;
6-(3,5-Difluorophenyl)-3-methyl-1-(3-pyridylmethyl)imidazo[4,5-b]pyridin-2-one;
6-(3-Chloro-4-fluoro-phenyl)-3-methyl-1-(3-pyridylmethyl)imidazo[4,5-b]pyridin-2-one;
3-Methyl-6-(m-tolyl)-1-(3-pyridylmethyl)imidazo[4,5-b]pyridin-2-one;
6-(2-Fluoro-3-methyl-phenyl)-3-methyl-1-(3-pyridylmethyl)imidazo[4,5-b]pyridin-2-one;
6-[2-Fluoro-3-(trifluoromethyl)phenyl]-3-methyl-1-(3-pyridylmethyl)imidazo[4,5-b]pyridin-2-one;
6-(3-Chloro-2-fluoro-phenyl)-3-methyl-1-(3-pyridylmethyl)imidazo[4,5-b]pyridin-2-one;
6-[4-Fluoro-3-(trifluoromethyl)phenyl]-3-methyl-1-(3-pyridylmethyl)imidazo[4,5-b]pyridin-2-one;
3-Methyl-1-(3-pyridylmethyl)-6-(2,3,4-trifluorophenyl)imidazo[4,5-b]pyridin-2-one;
3-Methyl-1-(3-pyridylmethyl)-6-[3-(trifluoromethyl)phenyl]imidazo[4,5-b]pyridin-2-one;
6-[3-(Difluoromethyl)phenyl]-3-methyl-1-(3-pyridylmethyl)imidazo[4,5-b]pyridin-2-one;
3-Methyl-1-(3-pyridylmethyl)-6-[5-(trifluoromethyl)-2-thienyl]imidazo[4,5-b]pyridin-2-one;
6-(5-Chloro-4-methyl-2-thienyl)-3-methyl-1-(3-pyridylmethyl)imidazo[4,5-b]pyridin-2-one;
1-[(5-Chloro-3-pyridyl)methyl]-3-methyl-6-[3-(trifluoromethyl)phenyl]imidazo[4,5-b]pyridin-2-one;
1-[(5-Chloro-3-pyridyl)methyl]-6-(4-fluoro-3-methyl-phenyl)-3-methyl-imidazo[4,5-b]pyridin-2-one;
1-[(5-Chloro-3-pyridyl)methyl]-6-(2,4-difluoro-3-methyl-phenyl)-3-methyl-imidazo[4,5-b]pyridin-2-one;
1-[(5-Chloro-3-pyridyl)methyl]-6-(3,4-difluorophenyl)-3-methyl-imidazo[4,5-b]pyridin-2-one;
1-[(5-Chloro-3-pyridyl)methyl]-3-methyl-6-(3,4,5-trifluorophenyl)imidazo[4,5-b]pyridin-2-one;
1-[(5-Chloro-3-pyridyl)methyl]-6-(2-fluoro-3-methyl-phenyl)-3-methyl-imidazo[4,5-b]pyridin-2-one;
6-(5-Chloro-4-methyl-2-thienyl)-1-[(5-chloro-3-pyridyl)methyl]-3-methyl-imidazo[4,5-b]pyridin-2-one;
1-[(5-Chloro-3-pyridyl)methyl]-3-methyl-6-[5-(trifluoromethyl)-2-thienyl]imidazo[4,5-b]pyridin-2-one;
1-[(5-Chloro-3-pyridyl)methyl]-3-methyl-6-(m-tolyl)imidazo[4,5-b]pyridin-2-one;
1-[(5-Chloro-3-pyridyl)methyl]-6-(2,3-difluorophenyl)-3-methyl-imidazo[4,5-b]pyridin-2-one;
6-(3-Chlorophenyl)-3-methyl-1-(pyridazin-3-ylmethyl)imidazo[4,5-b]pyridin-2-one;
6-[3-(Difluoromethyl)phenyl]-3-methyl-1-(pyridazin-3-ylmethyl)imidazo[4,5-b]pyridin-2-one;
3-Methyl-1-(pyridazin-3-ylmethyl)-6-[3-(trifluoromethyl)phenyl]imidazo[4,5-b]pyridin-2-one;
3-Methyl-6-(m-tolyl)-1-(pyridazin-3-ylmethyl)imidazo[4,5-b]pyridin-2-one;

6-(3-Chloro-4-fluoro-phenyl)-3-methyl-1-(pyridazin-3-ylmethyl)imidazo[4,5-b]pyridin-2-one;
6-(3-Fluoro-5-methyl-phenyl)-3-methyl-1-(pyridazin-3-ylmethyl)imidazo[4,5-b]pyridin-2-one;
6-[4-Fluoro-3-(trifluoromethyl)phenyl]-3-methyl-1-(pyridazin-3-ylmethyl)imidazo[4,5-b]pyridin-2-one;
6-[3-Fluoro-5-(trifluoromethyl)phenyl]-3-methyl-1-(pyridazin-3-ylmethyl)imidazo[4,5-b]pyridin-2-one;
6-[4-Chloro-3-(trifluoromethyl)phenyl]-3-methyl-1-(pyridazin-3-ylmethyl)imidazo[4,5-b]pyridin-2-one;
6-[3,4-Difluoro-5-(trifluoromethyl)phenyl]-3-methyl-1-(pyridazin-3-ylmethyl)imidazo[4,5-b]pyridin-2-one;
(R/S)-6-[3-(Difluoromethyl)phenyl]-3-methyl-1-(oxetan-2-ylmethyl)imidazo[4,5-b]pyridin-2-one;
(R/S)-6-(4-Fluoro-3-methyl-phenyl)-3-methyl-1-(oxetan-2-ylmethyl)imidazo[4,5-b]pyridin-2-one;
(R/S)-6-[2-Fluoro-3-(trifluoromethyl)phenyl]-3-methyl-1-(oxetan-2-ylmethyl)imidazo[4,5-b]pyridin-2-one;
(R/S)-6-(3-Chlorophenyl)-3-methyl-1-(oxetan-2-ylmethyl)imidazo[4,5-b]pyridin-2-one;
(R/S)-3-Methyl-6-[2-methyl-3-(trifluoromethyl)phenyl]-1-(oxetan-2-ylmethyl)imidazo[4,5-b]pyridin-2-one;
N,N-Dimethyl-2-[3-methyl-2-oxo-6-[3-(trifluoromethyl)phenyl]imidazo[4,5-b]pyridin-1-yl]acetamide;
2-[6-(4-Fluoro-3-methyl-phenyl)-3-methyl-2-oxo-imidazo[4,5-b]pyridin-1-yl]-N,N-dimethyl-acetamide;
2-[6-(3,4-Difluorophenyl)-3-methyl-2-oxo-imidazo[4,5-b]pyridin-1-yl]-N,N-dimethyl-acetamide;
2-[6-(2,4-Difluoro-3-methyl-phenyl)-3-methyl-2-oxo-imidazo[4,5-b]pyridin-1-yl]-N,N-dimethyl-acetamide;
2-[6-[2-Fluoro-3-(trifluoromethyl)phenyl]-3-methyl-2-oxo-imidazo[4,5-b]pyridin-1-yl]-N,N-dimethyl-acetamide;
2-[6-(2,3-Difluorophenyl)-3-methyl-2-oxo-imidazo[4,5-b]pyridin-1-yl]-N,N-dimethyl-acetamide;
2-[6-[3-(Difluoromethyl)phenyl]-3-methyl-2-oxo-imidazo[4,5-b]pyridin-1-yl]-N,N-dimethyl-acetamide;
2-[6-(2-Fluoro-3-methyl-phenyl)-3-methyl-2-oxo-imidazo[4,5-b]pyridin-1-yl]-N,N-dimethyl-acetamide;
2-[6-(3,5-Difluorophenyl)-3-methyl-2-oxo-imidazo[4,5-b]pyridin-1-yl]-N,N-dimethyl-acetamide;
N,N-Dimethyl-2-[3-methyl-2-oxo-6-(3-pyridyl)imidazo[4,5-b]pyridin-1-yl]acetamide;
2-[6-[3,4-Difluoro-5-(trifluoromethyl)phenyl]-3-methyl-2-oxo-imidazo[4,5-b]pyridin-1-yl]-N,N-dimethyl-acetamide;
2-[2-Oxo-6-[3-(trifluoromethyl)phenyl]-3H-imidazo[4,5-b]pyridin-1-yl]acetamide;
2-[6-(4-Fluoro-2-methoxy-phenyl)-2-oxo-3H-imidazo[4,5-b]pyridin-1-yl]acetamide;
2-[6-(3-Chloro-4-fluoro-phenyl)-2-oxo-3H-imidazo[4,5-b]pyridin-1-yl]acetamide;
N-Methyl-2-[2-oxo-6-[3-(trifluoromethyl)phenyl]-3H-imidazo[4,5-b]pyridin-1-yl]acetamide;
2-[6-(4-Chlorophenyl)-2-oxo-3H-imidazo[4,5-b]pyridin-1-yl]-N-methyl-acetamide;
2-[6-(4-Fluoro-2-methyl-phenyl)-2-oxo-3H-imidazo[4,5-b]pyridin-1-yl]-N-methyl-acetamide;
2-[6-(3,5-Dimethylphenyl)-2-oxo-3H-imidazo[4,5-b]pyridin-1-yl]-N-methyl-acetamide;
2-[6-(4-Methoxy-3-methyl-phenyl)-2-oxo-3H-imidazo[4,5-b]pyridin-1-yl]-N-methyl-acetamide;
2-[6-(4-Fluoro-2-methoxy-phenyl)-2-oxo-3H-imidazo[4,5-b]pyridin-1-yl]-N-methyl-acetamide;
2-[6-(2-Ethoxyphenyl)-2-oxo-3H-imidazo[4,5-b]pyridin-1-yl]-N-methyl-acetamide;
N-(2-Methoxyethyl)-2-[2-oxo-6-[3-(trifluoromethyl)phenyl]-3H-imidazo[4,5-b]pyridin-1-yl]acetamide;
2-[6-(2-Ethoxy-5-fluoro-phenyl)-2-oxo-3H-imidazo[4,5-b]pyridin-1-yl]-N-(2-methoxyethyl)acetamide;
N-(2-Methoxyethyl)-2-[6-(4-methoxyphenyl)-2-oxo-3H-imidazo[4,5-b]pyridin-1-yl]acetamide;
N-(2-Methoxyethyl)-2-[2-oxo-6-(3-pyridyl)-3H-imidazo[4,5-b]pyridin-1-yl]acetamide;
2-[6-(4-Fluoro-2-methoxy-phenyl)-2-oxo-3H-imidazo[4,5-b]pyridin-1-yl]-N-(2-methoxyethyl)acetamide;
N-Cyclopropyl-2-[6-(3,5-difluorophenyl)-2-oxo-3H-imidazo[4,5-b]pyridin-1-yl]acetamide;
2-[6-(3-Chloro-4-fluoro-phenyl)-2-oxo-3H-imidazo[4,5-b]pyridin-1-yl]-N-cyclopropyl-acetamide;
N-Cyclopropyl-2-[6-(3-ethoxyphenyl)-2-oxo-3H-imidazo[4,5-b]pyridin-1-yl]acetamide;
N-Cyclopropyl-2-[6-(3-methoxyphenyl)-2-oxo-3H-imidazo[4,5-b]pyridin-1-yl]acetamide;
N-Cyclopropyl-2-[6-(4-methoxy-3-methyl-phenyl)-2-oxo-3H-imidazo[4,5-b]pyridin-1-yl]acetamide;
N-Cyclopropyl-2-[6-(4-fluoro-2-methoxy-phenyl)-2-oxo-3H-imidazo[4,5-b]pyridin-1-yl]acetamide;
2-[6-(4-Chlorophenyl)-2-oxo-3H-imidazo[4,5-b]pyridin-1-yl]-N-cyclopropyl-acetamide;
N-Cyclopropyl-2-[6-(2,4-dimethoxyphenyl)-2-oxo-3H-imidazo[4,5-b]pyridin-1-yl]acetamide;
N-Cyclopropyl-2-[6-(2-fluoro-6-methoxy-phenyl)-2-oxo-3H-imidazo[4,5-b]pyridin-1-yl]acetamide;
N-Cyclopropyl-2-[6-(2-ethoxyphenyl)-2-oxo-3H-imidazo[4,5-b]pyridin-1-yl]acetamide;
1-(Cyclopropylmethyl)-6-(2,4-dimethoxyphenyl)-3H-imidazo[4,5-b]pyridin-2-one;
1-(Cyclopropylmethyl)-6-(2-ethoxy-5-fluoro-phenyl)-3H-imidazo[4,5-b]pyridin-2-one;
1-(Cyclopropylmethyl)-6-(4-fluoro-2-methoxy-phenyl)-3H-imidazo[4,5-b]pyridin-2-one;
1-(Cyclopropylmethyl)-6-(4-methoxy-3-methyl-phenyl)-3H-imidazo[4,5-b]pyridin-2-one;
1-(Cyclopropylmethyl)-6-(3-fluoro-4-methoxy-phenyl)-3H-imidazo[4,5-b]pyridin-2-one;
1-(Cyclopropylmethyl)-6-(3,5-difluorophenyl)-3H-imidazo[4,5-b]pyridin-2-one;
1-(Cyclopropylmethyl)-6-(4-methoxyphenyl)-3H-imidazo[4,5-b]pyridin-2-one;
1-(Cyclopropylmethyl)-6-(2-thienyl)-3H-imidazo[4,5-b]pyridin-2-one;
1-(Cyclopropylmethyl)-6-[3-(dimethylamino)phenyl]-3H-imidazo[4,5-b]pyridin-2-one;
1-(Cyclopropylmethyl)-6-(3,5-dimethylphenyl)-3H-imidazo[4,5-b]pyridin-2-one;
6-(3-Methoxyphenyl)-1-(tetrahydrofuran-2-ylmethyl)-3H-imidazo[4,5-b]pyridin-2-one;
4-[[6-(4-Methoxyphenyl)-2-oxo-3H-imidazo[4,5-b]pyridin-1-yl]methyl]benzonitrile;
3-[[6-(4-Methoxyphenyl)-2-oxo-3H-imidazo[4,5-b]pyridin-1-yl]methyl]benzonitrile;
3-[[6-(4-Fluoro-2-methoxy-phenyl)-2-oxo-3H-imidazo[4,5-b]pyridin-1-yl]methyl]benzonitrile;
3-[[6-(4-Fluoro-2-methyl-phenyl)-2-oxo-3H-imidazo[4,5-b]pyridin-1-yl]methyl]benzonitrile;
3-[[6-(3-Chloro-4-fluoro-phenyl)-2-oxo-3H-imidazo[4,5-b]pyridin-1-yl]methyl]benzonitrile;
2-[[6-(2-Fluoro-6-methoxy-phenyl)-2-oxo-3H-imidazo[4,5-b]pyridin-1-yl]methyl]benzonitrile;
2-[[6-(4-Chlorophenyl)-2-oxo-3H-imidazo[4,5-b]pyridin-1-yl]methyl]benzonitrile;

2-[[6-(4-Fluoro-2-methyl-phenyl)-2-oxo-3H-imidazo[4,5-b]pyridin-1-yl]methyl]benzonitrile;
2-[[6-(2-Ethoxyphenyl)-2-oxo-3H-imidazo[4,5-b]pyridin-1-yl]methyl]benzonitrile;
2-[[6-(3-Methoxyphenyl)-2-oxo-3H-imidazo[4,5-b]pyridin-1-yl]methyl]benzonitrile;
2-[[6-(3-Cyanophenyl)-2-oxo-3H-imidazo[4,5-b]pyridin-1-yl]methyl]benzonitrile;
2-[[6-(2,4-Dimethoxyphenyl)-2-oxo-3H-imidazo[4,5-b]pyridin-1-yl]methyl]benzonitrile;
2-[[6-(3,5-Dimethylphenyl)-2-oxo-3H-imidazo[4,5-b]pyridin-1-yl]methyl]benzonitrile;
2-[[6-(2-Ethoxy-5-fluoro-phenyl)-2-oxo-3H-imidazo[4,5-b]pyridin-1-yl]methyl]benzonitrile;
2-[[6-(4-Fluoro-2-methoxy-phenyl)-2-oxo-3H-imidazo[4,5-b]pyridin-1-yl]methyl]benzonitrile;
2-[[6-(3-Fluoro-4-methoxy-phenyl)-2-oxo-3H-imidazo[4,5-b]pyridin-1-yl]methyl]benzonitrile;
6-(4-Fluoro-2-methyl-phenyl)-1-[(4-fluorophenyl)methyl]-3H-imidazo[4,5-b]pyridin-2-one;
6-(2,3-Dimethoxyphenyl)-1-[(4-fluorophenyl)methyl]-3H-imidazo[4,5-b]pyridin-2-one;
6-(2-Ethoxy-5-fluoro-phenyl)-1-[(3-fluorophenyl)methyl]-3H-imidazo[4,5-b]pyridin-2-one;
6-(3,5-Dimethylphenyl)-1-[(3-fluorophenyl)methyl]-3H-imidazo[4,5-b]pyridin-2-one;
6-(2,4-Dimethoxyphenyl)-1-[(3-fluorophenyl)methyl]-3H-imidazo[4,5-b]pyridin-2-one;
6-(2-Ethoxyphenyl)-1-[(3-fluorophenyl)methyl]-3H-imidazo[4,5-b]pyridin-2-one;
1-[(3-Fluorophenyl)methyl]-6-(4-methoxy-3-methyl-phenyl)-3H-imidazo[4,5-b]pyridin-2-one;
6-(4-Fluoro-2-methoxy-phenyl)-1-[(3-fluorophenyl)methyl]-3H-imidazo[4,5-b]pyridin-2-one;
6-[3-(Dimethylamino)phenyl]-1-[(3-fluorophenyl)methyl]-3H-imidazo[4,5-b]pyridin-2-one;
6-(4-Fluoro-2-methoxy-phenyl)-1-[(4-fluorophenyl)methyl]-3H-imidazo[4,5-b]pyridin-2-one;
6-(3-Chloro-4-fluoro-phenyl)-1-[(4-fluorophenyl)methyl]-3H-imidazo[4,5-b]pyridin-2-one;
6-(2-Ethoxyphenyl)-1-[(2-fluorophenyl)methyl]-3H-imidazo[4,5-b]pyridin-2-one;
1-[(3-Chlorophenyl)methyl]-6-(3,5-difluorophenyl)-3H-imidazo[4,5-b]pyridin-2-one;
6-(4-Fluoro-2-methoxy-phenyl)-1-[(3-methoxyphenyl)methyl]-3H-imidazo[4,5-b]pyridin-2-one;
1-[(3-Methoxyphenyl)methyl]-6-(3-pyridyl)-3H-imidazo[4,5-b]pyridin-2-one;
1-[(3-Methoxyphenyl)methyl]-6-(4-methyl-2-thienyl)-3H-imidazo[4,5-b]pyridin-2-one;
6-(3,5-Difluorophenyl)-1-[(4-methoxyphenyl)methyl]-3H-imidazo[4,5-b]pyridin-2-one;
1-[(3,5-Dimethoxyphenyl)methyl]-6-(2-fluoro-6-methoxy-phenyl)-3H-imidazo[4,5-b]pyridin-2-one;
1-[(3,5-Dimethoxyphenyl)methyl]-6-[3-(trifluoromethyl)phenyl]-3H-imidazo[4,5-b]pyridin-2-one;
6-(4-Chlorophenyl)-1-[(4-isopropylphenyl)methyl]-3H-imidazo[4,5-b]pyridin-2-one;
6-(4-tert-Butylphenyl)-1-[(3,4-dimethoxy-2-pyridyl)methyl]-3H-imidazo[4,5-b]pyridin-2-one;
3-[1-[(3,5-Dimethylisoxazol-4-yl)methyl]-2-oxo-3H-imidazo[4,5-b]pyridin-6-yl]benzonitrile;
1-[(3,5-Dimethylisoxazol-4-yl)methyl]-6-(2-ethoxy-5-fluoro-phenyl)-3H-imidazo[4,5-b]pyridin-2-one;
6-(4-Methoxy-3-methyl-phenyl)-1-[(5-methylisoxazol-3-yl)methyl]-3H-imidazo[4,5-b]pyridin-2-one;
6-(3,5-Dimethylphenyl)-1-[(5-methylisoxazol-3-yl)methyl]-3H-imidazo[4,5-b]pyridin-2-one;
6-(2-Ethoxyphenyl)-1-[(5-methylisoxazol-3-yl)methyl]-3H-imidazo[4,5-b]pyridin-2-one;
6-(2,4-Dimethoxyphenyl)-1-[(5-methylisoxazol-3-yl)methyl]-3H-imidazo[4,5-b]pyridin-2-one;
6-(3-Fluoro-4-methoxy-phenyl)-1-[(5-methylisoxazol-3-yl)methyl]-3H-imidazo[4,5-b]pyridin-2-one;
6-(4-Fluoro-2-methoxy-phenyl)-1-[(5-methylisoxazol-3-yl)methyl]-3H-imidazo[4,5-b]pyridin-2-one;
6-(2-Ethoxy-5-fluoro-phenyl)-1-[(5-methylisoxazol-3-yl)methyl]-3H-imidazo[4,5-b]pyridin-2-one;
6-(4-Fluoro-2-methyl-phenyl)-1-[(5-methylisoxazol-3-yl)methyl]-3H-imidazo[4,5-b]pyridin-2-one;
6-(3,5-Difluorophenyl)-1-[(5-methylisoxazol-3-yl)methyl]-3H-imidazo[4,5-b]pyridin-2-one;
and
pharmaceutically acceptable salts, solvates, stereoisomers, isotopic variants, and N-oxides thereof.

23. The compound of claim 22, wherein the compound is N,N-Dimethyl-2-[3-methyl-2-oxo-6-[5-(trifluoromethyl)-2-thienyl]imidazo[4,5-b]pyridin-1-yl]acetamide or a pharmaceutically acceptable salt, solvate, stereoisomer, isotopic variant, or N-oxide thereof.

24. 1-Benzyl-6-(4-fluoro-3-(trifluoromethyl)phenyl)-1H-imidazo[4,5-b]pyridin-2(3H)-one or a pharmaceutically acceptable salt, solvate, stereoisomer, isotopic variant, or N-oxide thereof.

25. A compound selected from the group consisting of:
6-(5-(Difluoromethyl)-2-fluorophenyl)-3-methyl-1-(pyridazin-3-ylmethyl)-1,3-dihydro-2H-imidazo[4,5-b]pyridin-2-one;
6-(5-(Difluoromethyl)-2-fluorophenyl)-3-methyl-1-(pyridin-3-ylmethyl)-1,3-dihydro-2H-imidazo[4,5-b]pyridin-2-one;
N-(3-Chloropropyl)-2-[3-methyl-2-oxo-6-[5-(trifluoromethyl)-2-thienyl]imidazo[4,5-b]pyridin-1-yl]acetamide;
2-[6-[3-(Difluoromethyl)-4-fluoro-phenyl]-3-methyl-2-oxo-imidazo[4,5-b]pyridin-1-yl]-N,N-dimethyl-acetamide;
6-[3-(Difluoromethyl)-4-fluoro-phenyl]-3-methyl-1-(pyridazin-3-ylmethyl)imidazo[4,5-b]pyridin-2-one;
6-[3-(Difluoromethoxy)-4-fluoro-phenyl]-3-methyl-1-(pyridazin-3-ylmethyl)imidazo[4,5-b]pyridin-2-one;
6-[4-Chloro-3-(difluoromethoxy)phenyl]-3-methyl-1-(pyridazin-3-ylmethyl)imidazo[4,5-b]pyridin-2-one;
6-[4-Chloro-3-(difluoromethoxy)phenyl]-1-[(5-fluoro-3-pyridyl)methyl]-3-methyl-imidazo[4,5-b]pyridin-2-one;
6-(3,4-Difluorophenyl)-3-methyl-1-(thiadiazol-4-ylmethyl)imidazo[4,5-b]pyridin-2-one;
6-[3-(Difluoromethyl)-4-fluoro-phenyl]-1-[(5-fluoro-3-pyridyl)methyl]-3-methyl-imidazo[4,5-b]pyridin-2-one;
6-[3-(Difluoromethoxy)-4-fluoro-phenyl]-1-[(5-fluoro-3-pyridyl)methyl]-3-methyl-imidazo[4,5-b]pyridin-2-one;
3-Methyl-1-(thiadiazol-4-ylmethyl)-6-[3-(trifluoromethyl)phenyl]imidazo[4,5-b]pyridin-2-one;
6-(3,4-Difluorophenyl)-3-methyl-1-[(1-methyltriazol-4-yl)methyl]imidazo[4,5-b]pyridin-2-one;
6-(3,4-Difluorophenyl)-3-methyl-1-[(1-methylpyrazol-4-yl)methyl]imidazo[4,5-b]pyridin-2-one;
3-Methyl-1-[(1-methylpyrazol-4-yl)methyl]-6-[3-(trifluoromethyl)phenyl]imidazo[4,5-b]pyridin-2-one;

3-Methyl-1-[(1-methyltriazol-4-yl)methyl]-6-[3-(trifluoromethyl)phenyl]imidazo[4,5-b]pyridin-2-one;
3-Methyl-6-(5-methyl-2-thienyl)-1-[(1-methyltriazol-4-yl)methyl]imidazo[4,5-b]pyridin-2-one;
3-Methyl-1-[(5-methyl-1,3,4-oxadiazol-2-yl)methyl]-6-(5-methyl-2-thienyl)imidazo[4,5-b]pyridin-2-one;
3-Methyl-1-[(1-methylpyrazol-4-yl)methyl]-6-(5-methyl-2-thienyl)imidazo[4,5-b]pyridin-2-one;
3-Methyl-6-(5-methyl-2-thienyl)-1-(thiadiazol-4-ylmethyl)imidazo[4,5-b]pyridin-2-one;
3-Methyl-1-[(3-methyl-1,2,4-oxadiazol-5-yl)methyl]-6-(5-methyl-2-thienyl)imidazo[4,5-b]pyridin-2-one;
3-Methyl-1-[(5-methylisoxazol-3-yl)methyl]-6-(5-methyl-2-thienyl)imidazo[4,5-b]pyridin-2-one;
6-[5-(Difluoromethyl)-2-thienyl]-3-methyl-1-[(1-methyltriazol-4-yl)methyl]imidazo[4,5-b]pyridin-2-one;
6-[5-(Difluoromethyl)-2-thienyl]-3-methyl-1-[(5-methyl-1,3,4-oxadiazol-2-yl)methyl]imidazo[4,5-b]pyridin-2-one;
6-[5-(Difluoromethyl)-2-thienyl]-3-methyl-1-[(1-methylpyrazol-4-yl)methyl]imidazo[4,5-b]pyridin-2-one;
6-[5-(Difluoromethyl)-2-thienyl]-3-methyl-1-(thiadiazol-4-ylmethyl)imidazo[4,5-b]pyridin-2-one;
6-[5-(Difluoromethyl)-2-thienyl]-3-methyl-1-[(3-methyl-1,2,4-oxadiazol-5-yl)methyl]imidazo[4,5-b]pyridin-2-one;
6-[5-(Difluoromethyl)-2-thienyl]-3-methyl-1-[(5-methylisoxazol-3-yl)methyl]imidazo[4,5-b]pyridin-2-one;
3-Methyl-1-[(1-methylpyrazol-4-yl)methyl]-6-[5-(trifluoromethyl)-2-thienyl]imidazo[4,5-b]pyridin-2-one;
3-Methyl-1-[(1-methyltriazol-4-yl)methyl]-6-[5-(trifluoromethyl)-2-thienyl]imidazo[4,5-b]pyridin-2-one;
3-Methyl-1-[(5-methyl-1,3,4-oxadiazol-2-yl)methyl]-6-[5-(trifluoromethyl)-2-thienyl]imidazo[4,5-b]pyridin-2-one;
3-Methyl-1-(thiadiazol-4-ylmethyl)-6-[5-(trifluoromethyl)-2-thienyl]imidazo[4,5-b]pyridin-2-one;
3-Methyl-1-[(3-methyl-1,2,4-oxadiazol-5-yl)methyl]-6-[5-(trifluoromethyl)-2-thienyl]imidazo[4,5-b]pyridin-2-one;
3-Methyl-1-[(5-methylisoxazol-3-yl)methyl]-6-[5-(trifluoromethyl)-2-thienyl]imidazo[4,5-b]pyridin-2-one;
6-(2,4-Difluoro-3-methyl-phenyl)-3-methyl-1-[(5-methylisoxazol-3-yl)methyl]imidazo[4,5-b]pyridin-2-one;
6-(2,4-Difluoro-3-methyl-phenyl)-3-methyl-1-[(1-methylpyrazol-4-yl)methyl]imidazo[4,5-b]pyridin-2-one;
6-(2,4-Difluoro-3-methyl-phenyl)-3-methyl-1-[(3-methyl-1,2,4-oxadiazol-5-yl)methyl]imidazo[4,5-b]pyridin-2-one;
6-(2,4-Difluoro-3-methyl-phenyl)-3-methyl-1-[(1-methyltriazol-4-yl)methyl]imidazo[4,5-b]pyridin-2-one;
6-(2,4-Difluoro-3-methyl-phenyl)-3-methyl-1-[(5-methyl-1,3,4-oxadiazol-2-yl)methyl]imidazo[4,5-b]pyridin-2-one;
6-(2,4-Difluoro-3-methyl-phenyl)-3-methyl-1-(thiadiazol-4-ylmethyl)imidazo[4,5-b]pyridin-2-one;
N-(2-Fluoroethyl)-N-methyl-2-[3-methyl-2-oxo-6-[5-(trifluoromethyl)-2-thienyl]imidazo[4,5-b]pyridin-1-yl]acetamide;
N,N-Dimethyl-2-[3-methyl-6-(m-tolyl)-2-oxo-imidazo[4,5-b]pyridin-1-yl]acetamide;
2-[6-[3-(Difluoromethoxy)-4-fluoro-phenyl]-3-methyl-2-oxo-imidazo[4,5-b]pyridin-1-yl]-N,N-dimethyl-acetamide;
2-[6-[4-Chloro-3-(difluoromethoxy)phenyl]-3-methyl-2-oxo-imidazo[4,5-b]pyridin-1-yl]-N,N-dimethyl-acetamide;
2-[3-(Fluoromethyl)-2-oxo-6-[5-(trifluoromethyl)-2-thienyl]imidazo[4,5-b]pyridin-1-yl]-N,N-dimethyl-acetamide;
2-[6-(2,4-Difluoro-3-methyl-phenyl)-3-(fluoromethyl)-2-oxo-imidazo[4,5-b]pyridin-1-yl]-N,N-dimethyl-acetamide;
6-(2-Ethoxyphenyl)-1-[(3-methoxyphenyl)methyl]-3H-imidazo[4,5-b]pyridin-2-one;
6-(2-Ethoxyphenyl)-1-[(4-fluorophenyl)methyl]-3H-imidazo[4,5-b]pyridin-2-one;
N-Cyclopropyl-2-[6-(2-ethoxy-5-fluoro-phenyl)-2-oxo-3H-imidazo[4,5-b]pyridin-1-yl]acetamide;
2-[[6-(4-Methoxy-3-methyl-phenyl)-2-oxo-3H-imidazo[4,5-b]pyridin-1-yl]methyl]benzonitrile;
2-[6-(3,5-Difluorophenyl)-2-oxo-3H-imidazo[4,5-b]pyridin-1-yl]-N-(2-methoxyethyl)acetamide;
2-[6-(3-Chloro-4-fluoro-phenyl)-2-oxo-3H-imidazo[4,5-b]pyridin-1-yl]-N-(2-methoxyethyl)acetamide;
and
pharmaceutically acceptable salts, solvates, stereiosomers, isotopic variants, and N-oxides thereof.

26. The compound of claim 22 or a pharmaceutically acceptable salt thereof.

27. The compound of claim 25 or a pharmaceutically acceptable salt thereof.

28. A pharmaceutical composition comprising:
(A) an effective amount of at least one compound selected from compounds of Formula (I):

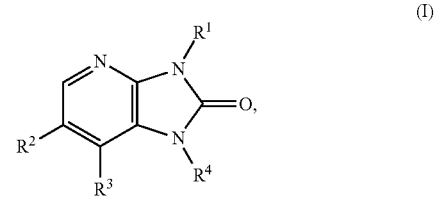

and pharmacuetically acceptable salts, solvates, steroisomers, isotopic variants, and N-oxides thereof, wherein:
$R^1$ is H; $CH_2F$; or $CH_3$;
$R^2$ is selected from the group consisting of: phenyl; phenyl substituted with one, two, or three members each independently selected from the group consisting of: halo, $C_{1-6}$alkyl, $C_{1-6}$haloalkyl, CN, $OC_{1-6}$alkyl, $OC_{1-6}$haloalkyl, $N(CH_3)_2$, and cyclopropyl; pyridinyl; pyridinyl substituted with F, $C_{1-4}$alkyl, or $C_{1-4}$haloalkyl; thiazolyl; thiazolyl substituted with $C_{1-6}$alkyl or $C_{1-6}$haloalkyl; thienyl; and thienyl substituted with one or two members each independently selected from the group consisting of: halo, $C_{1-6}$alkyl, $C_{1-6}$haloalkyl, $CH_2OH$, $CH_2OCH_3$, and cyclopropyl;
$R^3$ is H;
$R^4$ is:
(a)

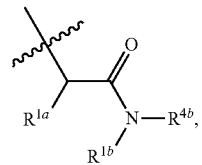

wherein $R^{4b}$ is selected from the group consisting of: H; $C_{1-6}$alkyl; $CH_2CH_2OCH_3$; $C_{3-6}$cycloalkyl; $C_{3-6}$cycloalkyl substituted with two or three members independently selected from the group consisting of F and CH₃; oxetanyl; oxetanyl substituted with CH₃; and pyridinyl; or
(b)

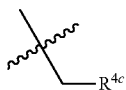

wherein R⁴ᶜ is selected from the group consisting of: cyclopropyl; cyclopropyl substituted with one or two F members; CH(OH)cyclopropyl; azetidinyl; CH₂-azetidinyl; CH₂-azetidinyl substituted with one or two members independently selected from: F, OH, OCH₃, and CF₃; oxetanyl; oxetanyl substituted with F or CH₃; tetrahydrofuranyl; tetrahydropyranyl; CH₂pyrrolidinyl; CH₂pyrrolidinyl substituted with CH₃, OH, or OCH₃; CH₂piperidinyl; CH₂piperidinyl substituted with OH, or F; morpholinyl; pyrazolyl substituted with one or two CH₃ members; triazolyl substituted with CH₃; tetrazolyl; isoxazolyl substituted with one or two CH₃ members; oxadiazolyl substituted with CH₃, or CH₂OCH₃; thiadiazolyl; pyridinyl; pyridinyl substituted with one or two members independently selected from the group consisting of: Cl, F, CH₃, OCH₃, and CF₃; (2-oxo-1H-pyridin-3-yl); 6-oxo-1H-pyridin-3-yl; pyrimidinyl; pyrimidinyl substituted with F or CH₃; pyrazinyl; pyridazinyl; pyridazinyl substituted with OCH₃; phenyl; and phenyl substituted with one or two members independently selected from the group consisting of: halo, CN, OCH₃, C₁₋₆alkyl, and CF₃;
and
R¹ᵃ and R¹ᵇ are each independently H or CH₃;
and
(B) at least one pharmaceutically acceptable excipient.

29. A pharmaceutical composition comprising an effective amount of at least one compound of claim 22 or a pharmaceutically acceptable salt, solvates or N-oxide thereof and at least one pharmaceutically acceptable excipient.

30. A method of treating a subject suffering from or diagnosed with a disease, disorder, or medical condition mediated by NR2B receptor activity, comprising administering to a subject in need of such treatment an effective amount of at least one compound selected from compounds of Formula (I):

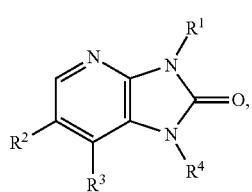

and pharamceutically acceptable salts, solvates, stereoisomers, isotopic variants, and N-oxides thereof, wherein:
R¹ is H; CH₂F; or CH₃;
R² is selected from the group consisting of: phenyl; phenyl substituted with one, two, or three members each independently selected from the group consisting of: halo, C₁₋₆alkyl, C₁₋₆haloalkyl, CN, OC₁₋₆alkyl, OC₁₋₆haloalkyl, N(CH₃)₂, and cyclopropyl; pyridinyl; pyridinyl substituted with F, C₁₋₄alkyl, or C₁₋₄haloalkyl; thiazolyl; thiazolyl substituted with C₁₋₆alkyl or C₁₋₆haloalkyl; thienyl; and thienyl substituted with one or two members each independently selected from the group consisting of: halo, C₁₋₆alkyl, C₁₋₆haloalkyl, CH₂OH, CH₂OCH₃, and cyclopropyl;
R³ is H;
R⁴ is:
(a)

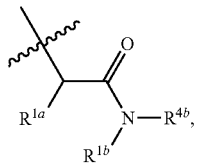

wherein R⁴ᵇ is selected from the group consisting of: H; C₁₋₆alkyl; CH₂CH₂OCH₃; C₃₋₆cycloalkyl; C₃₋₆cycloalkyl substituted with two or three members independently selected from the group consisting of F and CH₃; oxetanyl; oxetanyl substituted with CH₃; and pyridinyl; or
(b)

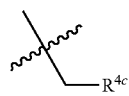

wherein R⁴ᶜ is selected from the group consisting of: cyclopropyl substituted with one or two F members; CH(OH)cyclopropyl; azetidinyl; CH₂-azetidinyl; CH₂-azetidinyl substituted with one or two members independently selected from: F, OH, OCH₃, and CF₃; oxetanyl; oxetanyl substituted with F or CH₃; tetrahydrofuranyl; tetrahydropyranyl; CH₂pyrrolidinyl; CH₂pyrrolidinyl substituted with CH₃, OH, or OCH₃; CH₂piperidinyl; CH₂piperidinyl substituted with OH, or F; morpholinyl; pyrazolyl substituted with one or two CHs members; triazolyl substituted with CH₃; tetrazolyl; isoxazolyl substituted with one or two CHs members; oxadiazolyl substituted with CH₃, or CH₂OCH₃; thiadiazolyl; pyridinyl; pyridinyl substituted with one or two members independently selected from the group consisting of: Cl, F, CH₃, OCH₃, and CF₃; (2-oxo-1H-pyridin-3-yl); 6-oxo-1H-pyridin-3-yl; pyrimidinyl; pyrimidinyl substituted with F or CH₃; pyrazinyl; pyridazinyl; pyridazinyl substituted with OCH₃; phenyl; and phenyl substituted with one or two members independently selected from the group consisting of: halo, CN, OCH₃, C₁₋₆alkyl, and CF₃;
and
R¹ᵃ and R¹ᵇ are each independently H or CH₃.

31. The method of claim 30, wherein the disease, disorder, or medical condition mediated by NR2B receptor activity is selected from the group consisting of: bipolar disorder, major depressive disorder, treatment-resistant depression, post-partum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with bacterial or chronic infections, pain, diabetic neuropathy, migraine, cerebral ischemia, schizophrenia, encephalitis, autism and autism spectrum disorders, memory and learning disorders, obsessive compulsive disorder, attention deficit hyperactivity disorder (ADHD), and an addictive illness.

32. The method of claim 31, wherein the disease, disorder, or medical condition is selected from the group consisting of treatment-resistant depression, major depressive disorder and bipolar disorder.

* * * * *